(12) United States Patent
Michelmore et al.

(10) Patent No.: US 6,350,933 B1
(45) Date of Patent: Feb. 26, 2002

(54) RG POLYNUCLEOTIDES FOR CONFERRING POWDERY MILDEW RESISTANCE IN PLANTS

(75) Inventors: Richard W. Michelmore, Davis; Kathy A. Shen, El Macero; Blake C. Meyers, Davis, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/004,838

(22) Filed: Jan. 9, 1998

Related U.S. Application Data

(63) Continuation-in-part of application No. 08/781,734, filed on Jan. 10, 1997, now abandoned.

(51) Int. Cl.[7] ........................ A01H 3/00; C07H 21/04; C07K 14/415; C12N 5/14
(52) U.S. Cl. ........................ 800/279; 800/278; 435/6; 435/69.1; 435/69.7; 435/410; 435/418; 435/419; 435/320.1; 530/370; 536/23.1; 536/23.4; 536/23.6; 536/24.1; 536/24.32; 536/24.33
(58) Field of Search ................... 800/278, 279; 435/6, 69.1, 69.7, 410, 418, 419, 320.1; 530/370; 536/23.1, 23.4, 23.6, 24.1, 24.32, 24.33

(56) References Cited

FOREIGN PATENT DOCUMENTS

EP          03 22712      *   7/1989

OTHER PUBLICATIONS

Brown et al. Science, vol. 282, p. 131–133, Nov. 13, 1988.*
Bork. Genome Research. vol. 10, p 398–400, 2000.*
Ochoa et al. Mol. Plant Microbe Interact., 1997, vol. 10, No. 8, p 970–977.*
Mindrinos, et al., *Cell,* 78:1089–1099 (1994).
Bent et al., *Science* 265:1856–1860 (1994).
Grant, et al., *Science* 269:843–846 (1995).
Lawrence, et al., *The Plant Cell* 7:1195–1206 (1995).
Whitham, et al., *Cell* 78:1101–1115 (1994).
Michelmore, Richard, "Flood warning — resistance genes unleashed", *nature genetics,* 14:376–378 (1996).
Jones, David A., et al., "Isolation of the Tomato Cf–9 Gene for Resistance to *Cladosporium fulvum* by Transposon Tagging", *Science,* 266:789–793 (1994).
Yu, Yong G., et al., "Isolation of a superfamily of candidate disease–resistance genes in soybean based on a conserved nucleotide–binding site", *Proc. Natl. Acad. Sci. USA,* 93:11751–11756 (1996).
Kanazin, Vladimir, et al., "Resistance gene analogs are conserved and clustered in soybean", *Proc. Natl. Acad. Sci. USA,* 93:11746–11750 (1996).

* cited by examiner

*Primary Examiner*—Phuong T. Bui
(74) *Attorney, Agent, or Firm*—Townsend & Townsend & Crew LLP

(57) ABSTRACT

RG nucleic acids and proteins which confer powdery mildew disease resistance to plants are provided. The nucleic acids can be used to produce transgenic plants resistant to pests. Antibodies to proteins of the invention are also provided.

18 Claims, No Drawings

US 6,350,933 B1

RG POLYNUCLEOTIDES FOR CONFERRING POWDERY MILDEW RESISTANCE IN PLANTS

The present application is a continuation-in-part application ("CIP") of U.S. patent application Ser. No. ("USSN") 08/781,734, filed Jan. 10, 1997, now abandoned, which is explicitly incorporated herein by reference in its entirety and for all purposes.

This invention was made with Government support under Grant Nos. 92-37300-7547 and 95-37300-1571, awarded by the United States Department of Agriculture. The Government has certain rights in this invention.

FIELD OF THE INVENTION

The present invention relates generally to plant molecular biology. In particular, it relates to nucleic acids and methods for conferring pest resistance in plants, particularly lettuce.

BACKGROUND OF THE INVENTION

Recently, several resistance genes have been cloned by several groups from several plants. Many of these genes are sequence related. The derived amino acid sequences of the most common class, RPS2, RPM1 (bacterial resistances in *Arabidopsis* (Mindrinos et al. *Cell* 78:1089–1099 (1994)); Bent et al. *Science* 265:1856–1860 (1994); Grant et al., *Science* 269:843–846 (1995)), L6 (fungal resistance in flax; Lawrence, et al., *The Plant Cell* 7:1195–1206 (1995)), and N, (virus resistance in tobacco; Whitham, et al., *Cell* 78:1101–1115 (1994); and U.S. Pat. No. 5,571,706), all contain leucine-rich repeats (LRR) and nucleotide binding sites (NBS).

The NBS is a common motif in several mammalian gene families encoding signal transduction components (e.g., Ras) and is associated with ATP/GTP-binding sites.

The NBS is a common motif in several mammalian gene families encoding signal transduction components (e.g., Ras) and is associated with ATP/GTP-binding sites.

LRR domains can mediate protein-protein interactions and are found in a variety of proteins involved in signal transduction, cell adhesion and various other functions. LRRs are leucine rich regions often comprising 20–30 amino acid repeats where leucine and other aliphatic residues occur periodically. LRRs can function extracellularly or intracellularly.

Since the onset of civilization, plant diseases have had catastrophic effects on crops and the well-being of the human population. Plant diseases continue to effect enormous human and economic costs. An increasing human population and decreasing amounts of arable land make all approaches to preventing and treating plant pathogen destruction critical. The ability to control and enhance a plant's protective responses against pathogens would be of enormous benefit. Tissue-specific and temporal control of mechanisms responsible for plant cell death would also be of great practical and economic value. The present invention fulfills these and other needs.

What is needed in the art are plant disease resistance genes and means to create transgenic disease resistance plants, particularly in lettuce. Further, what is needed in the art is a means to DNA fingerprint cultivars and germplasm with respect to their disease resistance haplotypes for use in plant breeding programs. The present invention provides these and other advantages.

SUMMARY OF THE INVENTION

The present invention provides isolated nucleic acid constructs. These constructs comprise an RG (resistance gene) polynucleotide which encodes an RG polypeptide having at least 60% sequence identity to an RG polypeptide selected from the group consisting of: an RG1 polypeptide, an RG2 polypeptide, an RG3 polypeptide, and an RG4 polypeptide. RG1, RG2, RG3, RG4, and the like, represent individual "RG families." Each "RG family," as defined herein, is a group of polypeptide sequences that have at least 60% amino acid sequence identity. Individual members of an RG family, i.e., individual species of the genus, typically map to the same genomic locus. The invention provides for constructs comprising nucleotides encoding the RG families of the invention, which can include sequences encoding a leucine rich region (LRR), and/or a nucleotide binding site (NBS), or both.

The invention provides for an isolated nucleic acid construct comprising an RG polynucleotide which encodes an RG polypeptide having at least 60% sequence identity to an RG polypeptide from an RG family selected from the group consisting of: an RG1 polypeptide, an RG2 polypeptide, an RG3 polypeptide, an RG4 polypeptide, an RG5 polypeptide, and an RG7 polypeptide. In alternative embodiments, the nucleic acid construct comprises an RG polynucleotide which encodes an RG polypeptide comprising an leucine rich region (LRR), or, an RG polypeptide comprising a nucleotide binding site (NBS). The nucleic acid construct can comprise a polynucleotide which is a full length gene. In another embodiment, the nucleic acid construct encodes a fusion protein.

In one embodiment, the nucleic acid construct comprises a sequence encoding an RG1 polypeptide. The RG1 polypeptide can be encoded by a polynucleotide sequence selected from the group consisting of SEQ ID NO:1 (RG1A), SEQ ID NO:2 and SEQ ID NO:137 (RG1B), SEQ ID NO:3 (RG1C), SEQ ID NO:4 (RG1D), SEQ ID NO:5 (RG1E), SEQ ID NO:6 (RG1F), SEQ ID NO:7 (RG1G), SEQ ID NO:8 (RG1H), SEQ ID NO:9 (RG1I), and SEQ ID NO:10 (RG1J).

In another embodiment, the nucleic acid construct comprises a sequence encoding an RG2 polypeptide. The RG2 polypeptide can be encoded by a polynucleotide sequence selected from the group consisting of: SEQ ID NO:21 and SEQ ID NO:27 (RG2A); SEQ ID NO:23 and SEQ ID NO:28 (RG2B); SEQ ID NO:29 (RG2C); SEQ ID NO:30 (RG2D); SEQ ID NO:31 (RG2E); SEQ ID NO:32 (RG2F); SEQ ID NO:33 (RG2G); SEQ ID NO:34 (RG2H); SEQ ID NO:35 (RG2I); SEQ ID NO:36 (RG2J); SEQ ID NO:37 (RG2K); SEQ ID NO:38 (RG2L); SEQ ID NO:39 (RG2M); SEQ ID NO:87 (RG2A); SEQ ID NO:89 (RG2B); SEQ ID NO:91 (RG2C); SEQ ID NO:93 (RG2D) and SEQ ID NO:94 (RG2D); SEQ ID NO:96 (RG2E); SEQ ID NO:98 (RG2F); SEQ ID NO:100 (RG2G); SEQ ID NO:102 (RG2H); SEQ ID NO:104 (RG2I); SEQ ID NO:106 (RG2J) and SEQ ID NO:107 (RG2J); SEQ ID NO:109 and SEQ ID NO:110 (RG2K); SEQ ID NO:112 (RG2L); SEQ ID NO:114 (RG2M); SEQ ID NO:116 (RG2N); SEQ ID NO:118 (RG2O); SEQ ID NO:120 (RG2P); SEQ ID NO:122 (RG2Q); SEQ ID NO:124 (RG2S); SEQ ID NO:126 (RG2T); SEQ ID NO:128 (RG2U); SEQ ID NO:130 (RG2V); and, SEQ ID NO:132 (RG2W).

In other embodiments, the nucleic acid construct comprises a RG3 sequence (SEQ ID NO:68) encoding an RG3 polypeptide (SEQ ID NO:138) (RG3). In other embodiments, the nucleic acid construct comprises an RG4 sequence (SEQ ID NO:69) encoding an RG4 polypeptide (SEQ ID NO:139) (RG4).

In other embodiments, the nucleic acid construct comprises a RG5 sequence (SEQ ID NO:134) encoding an RG5 polypeptide (SEQ ID NO:135). The RG5 polypeptide can be encoded by a polynucleotide sequence as set forth in SEQ ID NO:134.

The invention also provides for a nucleic acid construct which comprises an RG7 sequence encoding an RG7 polypeptide. The RG7 polypeptide can be encoded by a polynucleotide sequence as set forth in SEQ ID NO:136.

In further embodiments, the nucleic acid construct can further comprise a promoter operably linked to the RG polynucleotide. In alternative embodiments, the promoter can be a plant promoter; a disease resistance promoter; a lettuce promoter; a constitutive promoter; an inducible promoter; or, a tissue-specific promoter. The nucleic acid construct can comprise a promoter sequence from an RG gene linked to a heterologous polynucleotide.

The invention also provides for a transgenic plant comprising a recombinant expression cassette comprising a promoter operably linked to an RG polynucleotide. The expression cassette can comprise a plant promoter or a viral promoter; the plant promoter can be a heterologous promoter. In one embodiment, the transgenic plant is lettuce. In alternative embodiments, the transgenic plant comprises an expression cassette which includes an RG polynucleotide selected from the group consisting of SEQ ID NO:1 (RG1A); SEQ ID NO:2 and SEQ ID NO:137 (RG1B); SEQ ID NO: 3 (RG1C); SEQ ID NO:4 (RG1D); SEQ ID NO:5 (RG1E); SEQ ID NO:6 (RG1F); SEQ ID NO:7 (RG1G); SEQ ID NO:8 (RG1H); SEQ ID NO:9 (RG1I) and SEQ ID NO:10 (RG1J); SEQ ID NO:21 and SEQ ID NO:27 (RG2A); SEQ ID NO:23 and SEQ ID NO:28 (RG2B); SEQ ID NO:29 (RG2C); SEQ ID NO:30 (RG2D); SEQ ID NO:31 (RG2E); SEQ ID NO:32 (RG2F); SEQ ID NO:33 (RG2G); SEQ ID NO:34 (RG2H); SEQ ID NO:35 (RG2I); SEQ ID NO:36 (RG2J); SEQ ID NO:37 (RG2K); SEQ ID NO:38 (RG2L); SEQ ID NO:39 (RG2M); SEQ ID NO:87 (RG2A); SEQ ID NO:89 (RG2B); SEQ ID NO:91 (RG2C); SEQ ID NO:93 (RG2D) and SEQ ID NO:94 (RG2D); SEQ ID NO:96 (RG2E); SEQ ID NO:98 (RG2F); SEQ ID NO: 100 (RG2G); SEQ ID NO:102 (RG2H); SEQ ID NO:104 (RG2I); SEQ ID NO:106 (RG2J) and SEQ ID NO: 107 (RG2J); SEQ ID NO:109 and SEQ ID NO:110(RG2K); SEQ ID NO:112 (RG2L); SEQ ID NO:114 (RG2M); SEQ ID NO:116 (RG2N); SEQ ID NO:118 (RG20); SEQ ID NO:120 (RG2P); SEQ ID NO:122 (RG2Q); SEQ ID NO:124 (RG2S); SEQ ID NO:126 (RG2T); SEQ ID NO:128 (RG2U); SEQ ID NO:130 (RG2V); and, SEQ ID NO:132 (RG2W); SEQ ID NO:68 (RG3); SEQ ID NO:69 (RG4); SEQ ID NO:134 (RG5); or SEQ ID NO:136 (RG7).

The invention provide for a transgenic plant comprising an expression cassette comprising an RG polynucleotide which can encode an RG1 polypeptide selected from the group consisting of SEQ ID NO:11 (RG1A), SEQ ID NO:12 (RG1B), SEQ ID NO:13 (RG1C), SEQ ID NO:14 (RG1D), SEQ ID NO:15 (RG1E), SEQ ID NO:16 (RG1F), SEQ ID NO:17 (RG1G), SEQ ID NO:18 (RG1H), SEQ ID NO:19 (RG1I), or SEQ ID NO:20 (RG1J); or, an RG2 polypeptide selected from the group consisting of SEQ ID NO:22 and SEQ ID NO:41 (RG2A); SEQ ID NO:24 and SEQ ID NO:42 (RG2B); SEQ ID NO:43 (RG2C); SEQ ID NO:44 (RG2D); SEQ ID NO:45 (RG2E); SEQ ID NO:46 (RG2F); SEQ ID NO:47 (RG2G); SEQ ID NO:48 (RG2H); SEQ ID NO:49 (RG2I); SEQ ID NO:50 (RG2J); SEQ ID NO:51 (RG2K); SEQ ID NO:52 (RG2L); SEQ ID NO:53 (RG2M); SEQ ID NO:88 (RG2A); SEQ ID NO:90 (RG2B); SEQ ID NO:92 (RG2C); SEQ ID NO:95 (RG2D); SEQ ID NO:97 (RG2E); SEQ ID NO:99 (RG2F); SEQ ID NO:101 (RG2G); SEQ ID NO:103 (RG2H); SEQ ID NO:105 (RG2I); SEQ ID NO:108 (RG2J); SEQ ID NO:111 (RG2K); SEQ ID NO:113 (RG2L); SEQ ID NO:115 (RG2M); SEQ ID NO:117 (RG2N); SEQ ID NO:119 (RG20); SEQ ID NO:121 (RG2P); SEQ ID NO:123 (RG2Q); SEQ ID NO:125 (RG2S); SEQ ID NO:127 (RG2T); SEQ ID NO:129 (RG2U); SEQ ID NO:131 (RG2V); and, SEQ ID NO:133 (RG2W); an RG4 polypeptide as set forth by SEQ ID NO:72; an RG5 polypeptide with a sequence as set forth by SEQ ID NO:135; or, an RG7 polypeptide.

The invention also provides for a method of enhancing disease resistance in a plant, the method comprising introducing into the plant a recombinant expression cassette comprising a promoter functional in the plant and operably linked to an RG polynucleotide sequence. In this method, the plant can be a lettuce plant; and, the RG polynucleotide can encode an RG polypeptide selected from the group consisting of an RG1 polypeptide selected from the group consisting of SEQ ID NO:11 (RG1A), SEQ ID NO:12 (RG1B), SEQ ID NO:13 (RG1C), SEQ ID NO:14 (RG1D), SEQ ID NO:15 (RG1E), SEQ ID NO:16 (RG1F), SEQ ID NO:17 (RG1G), SEQ ID NO:18 (RG1H), SEQ ID NO:19 (RG1I), or SEQ ID NO:20 (RG1J); or, an RG2 polypeptide selected from the group consisting of SEQ ID NO:22 and SEQ ID NO:41 (RG2A); SEQ ID NO:24 and SEQ ID NO:42 (RG2B); SEQ ID NO:43 (RG2C); SEQ ID NO:44 (RG2D); SEQ ID NO:45 (RG2E); SEQ ID NO:46 (RG2F); SEQ ID NO:47 (RG2G); SEQ ID NO:48 (RG2H); SEQ ID NO:49 (RG2I); SEQ ID NO:50 (RG2J); SEQ ID NO:51 (RG2K); SEQ ID NO:52 (RG2L); SEQ ID NO:53 (RG2M); SEQ ID NO:72; SEQ ID NO:74; SEQ ID NO:88 (RG2A); SEQ ID NO:90 (RG2B); SEQ ID NO:92 (RG2C); SEQ ID NO:95 (RG2D); SEQ ID NO:97 ( RG2E); SEQ ID NO:99 (RG2F); SEQ ID NO:101 (RG2G); SEQ ID NO:103 (RG2H); SEQ ID NO:105 (RG2I); SEQ ID NO:108 (RG2J); SEQ ID NO:111 (RG2K); SEQ ID NO:113 (RG2L); SEQ ID NO:115 (RG2M); SEQ ID NO:117 (RG2N); SEQ ID NO:119 (RG20); SEQ ID NO:121 (RG2P); SEQ ID NO:123 (RG2Q); SEQ ID NO:125 (RG2S); SEQ ID NO:127 (RG2T); SEQ ID NO:129 (RG2U); SEQ ID NO:131 (RG2V); and, SEQ ID NO:133 (RG2W). In this method, the promoter can be a plant disease resistance promoter, a tissue-specific promoter, a constitutive promoter, or an inducible promoter.

The invention also provides for a method of detecting RG resistance genes in a nucleic acid sample, the method comprising: contacting the nucleic acid sample with an RG polynucleotide to form a hybridization complex; and, wherein the formation of the hybridization complex is used to detect the RG resistance gene in the nucleic acid sample. In this method, the RG polynucleotide can be an RG1 polynucleotide, an RG2 polynucleotide, an RG3 polynucleotide, an RG4 polynucleotide, an RG5 polynucleotide or an RG7 polynucleotide. In this method, the RG resistance gene can be amplified prior to the step of contacting the nucleic acid sample with the RG polynucleotide, and, the RG resistance gene can be amplified by the polymerase chain reaction. In one embodiment, the RG polynucleotide is labeled.

The invention further provides for an RG polypeptide having at least 60% sequence identity to a polypeptide selected from the group consisting of: an RG1 polypeptide, an RG2 polypeptide, an RG3 polypeptide, an RG4 polypeptide, an RG5 polypeptide, and an RG7 polypeptide.

A further understanding of the nature and advantages of the present invention may be realized by reference to the remaining portions of the specification, the figures and claims.

All publications, patents and patent applications cited herein are hereby expressly incorporated by reference for all purposes.

DETAILED DESCRIPTION OF THE INVENTION

This invention relates to families of RG genes, particularly from *Lactuca sativa*. Nucleic acid sequences of the present invention can be used to confer resistance in plants to a variety of pests including viruses, fungi, nematodes, insects, and bacteria. Sequences from within the RG genes can be used to fingerprint cultivars or germplasm for the presence of desired resistance genes. Promoters of RG genes can be used to drive heterologous gene expression under conditions in which RG genes are expressed. Further, the present invention provides RG proteins and antibodies specifically reactive to RG proteins. Antibodies to RG proteins can be used to detect the type and amount of RG protein expressed in a plant sample.

The present invention has use over a broad range of types of plants, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, and, Sorghum. In particularly preferred embodiments, species from the family Compositae and in particular the genus Lactuca are employed such as *L. sativa* and such subspecies as crispa, longifolia, and asparagina.

The nucleic acids of the present invention can be used in marker-aided selection. Marker-aided selection does not require the complete sequence of the gene or precise knowledge of which sequence confers which specificity. Instead, partial sequences can be used as hybridization probes or as the basis for oligonucleotide primers to amplify nucleic acid, e.g., by PCR. Partial sequences can be used in other methods, such as to follow the segregation of chromosome segments containing resistance genes in plants. Because the RG marker is the gene itself, there can be negligible recombination between the marker and the resistance phenotype. Thus, RG polynucleotides of the present invention provide an optimal means to DNA fingerprint cultivars and wild germplasm with respect to their disease resistance haplotypes. This can be used to indicate which germplasm accessions and cultivars carry the same resistance genes. At present, selection of plants (e.g., lettuce) for resistance to some diseases is slow and difficult. But linked markers allow indirect selection for such resistance genes. Moreover, RG markers also allow resistance genes to be identified and combined in a manner that would not otherwise be possible. Numerous accessions have been identified that provide resistance to all isolates of downy mildew (*Bremia lactucae*). However, without molecular markers it is impossible to combine such resistances from different sources. The nucleic acid sequences of the invention provide for a fast and convenient means to identify and combine resistances from different sources. The RG markers of the invention can also be used to identify recombinants that have new combinations of resistance genes in cis on the same chromosome.

In addition, RG markers may allow the identification of the Mendelian factors determining traits, such as field resistance to downy mildew. Once such markers have been identified, they will greatly increase the ease with which field resistance can be transferred between lines and combined with other resistances.

In another application, primers to RG sequences can be also designed to amplify sequences that are conserved in multiple RG family members. This gives genetic information on multiple RG family members. Alternatively, one or more primers can be made to sequences unique to a single resistance gene genus or a single RG specie. This allows an analysis of individual family groups (an RG genus) or an individual family member (a specie). Primers made to individual RGs at the edge of each cluster can be used to select for recombinants within the cluster. This minimizes the amount of linkage drag during introgression. Classical and molecular genetics has shown that pest resistance genes tend to be clustered in the genome. Pest resistance loci comprise arrays of genes and exhibit a variety of complex haplotypes rather than being simple alternate allelic forms. Pest resistance is conferred by families, or genuses, of related RG sequences, individual members, or species, of which have evolved to have a different specificity. Oligonucleotide primers can be designed that amplify members from multiple haplotypes, or genuses, or amplify only members of one genus, or only amplify an individual specie. This will provide codominant information and allow heterozygotes to be distinguished from homozygotes.

Further, comparison of RG sequences will allow a determination of which sequences are critical for resistance and will ultimately lead to engineering resistance genes with new specificities. Resistance gene sequences were not previously available for lettuce. Marker-aided selection will greatly increase the precision and speed of breeding for disease resistance. Transgenic approaches will allow pyramiding of resistance genes into a single Mendelian unit, transfer between sexually-incompatible species, substitute for conventional backcrossing procedures, and allow expression of other genes in parallel with resistance genes.

The RG polynucleotides also have utility in the construction of disease resistant transgenic plants. This avoids lengthy and sometimes difficult backcrossing programs currently necessary for introgression of resistance. It is also possible to transfer resistance polynucleotides between sexually-incompatible species, thereby greatly increasing the germplasm pool that can be used as a source of resistance genes. Cloning of multiple RG sequences in a single cassette will allow pyramiding of genes for resistance against multiple isolates of a single pathogen such as downy mildew or against multiple pathogens. Once introduced, such a cassette can be manipulated by classical breeding methods as a single Mendelian unit.

Transgenic plants of the present invention can also be constructed using an RG promoter. The promoter sequences from RG sequences of the invention can be used with RG genes or heterologous genes. Thus, RG promoters can be used to express a variety of genes in the same temporal and spatial patterns and at similar levels to resistance genes.

Nucleic Acids Of The Invention and Their Preparation

RG Polynucleotide Families

The present invention provides isolated nucleic acid constructs which comprise an RG polynucleotide. In alternative embodiments, the RG polynucleotide is at least 18 nucleotides in length, typically at least 20, 25, or 30 nucleotides in length, more typically at least 100 nucleotides in length, generally at least 200 nucleotides in length, preferably at least 300 nucleotides in length, more preferably at least 400 nucleotides in length, and most preferably at least 500 nucleotides in length.

In particularly preferred embodiments, the RG polynucleotide encodes a RG protein which confers resistance to plant pests. This RG protein can be longer, equivalent, or shorter than the RG protein encoded by an RG gene. In various embodiments, an RG polynucleotide can hybridize under stringent conditions to members of an RG family (an RG genus); e.g., it can hybridize to a member of the RG1 RG family, such as an RG1 polynucleotide selected from the group consisting of: SEQ ID NO:1 (RG1A); SEQ ID NO:2 and SEQ ID NO:137 (RG1B); SEQ ID NO:3 (RG1C); SEQ ID NO:4 (RG1D); SEQ ID NO:5 (RG1E); SEQ ID NO:6 (RG1F); SEQ ID NO:7 (RG1G); SEQ ID NO:8 (RG1H); SEQ ID NO:9 (RG1I) and SEQ ID NO:10 (RG1J).

In other embodiments, the polynucleotide can also hybridize under stringent conditions to a member of the RG2 family; such as an RG2 polynucleotide selected from the group consisting of: SEQ ID NO:21 and SEQ ID NO:27 (RG2A); SEQ ID NO:23 and SEQ ID NO:28 (RG2B); SEQ ID NO:29 (RG2C); SEQ ID NO:30 (RG2D); SEQ ID NO:31 (RG2E); SEQ ID NO:32 (RG2F); SEQ ID NO:33 (RG2G); SEQ ID NO:34 (RG2H); SEQ ID NO:35 (RG2I); SEQ ID NO:36 (RG2J); SEQ ID NO:37 (RG2K); SEQ ID NO:38 (RG2L); SEQ ID NO:39 (RG2M); SEQ ID NO:87 (RG2A); SEQ ID NO:89 (RG2B); SEQ ID NO:91 (RG2C); SEQ ID NO:93 (RG2D) and SEQ ID NO:94 (RG2D); SEQ ID NO:96 (RG2E); SEQ ID NO:98 (RG2F); SEQ ID NO:100 (RG2G); SEQ ID NO:102 (RG2H); SEQ ID NO:104 (RG2I); SEQ ID NO:106 (RG2J) and SEQ ID NO:107 (RG2J); SEQ ID NO:109 and SEQ ID NO:110(RG2K); SEQ ID NO:112 (RG2L); SEQ ID NO:114 (RG2M); SEQ ID NO:116 (RG2N); SEQ ID NO:118 (RG2O); SEQ ID NO:120 (RG2P); SEQ ID NO:122 (RG2Q); SEQ ID NO:124 (RG2S); SEQ ID NO:126 (RG2T); SEQ ID NO:128 (RG2U); SEQ ID NO:130 (RG2V); and, SEQ ID NO:132 (RG2W).

In alternative embodiments, each RG2 gene can also include an AC15 sequence which hybridizes under stringent conditions to a polynucleotide selected from the group consisting of: SEQ ID NO:56 (AC15-2A); SEQ ID NO:57 (AC15-2B); SEQ ID NO:58 (AC15-2C); SEQ ID NO:59 (AC15-2D); SEQ ID NO:60 (AC15-2E); SEQ ID NO:61 (AC15-2G); SEQ ID NO:62 (AC15-2H); SEQ ID NO:63 (AC15-2I); SEQ ID NO:64 (AC15-2J); SEQ ID NO:65 (AC15-2L); SEQ ID NO:66 (AC15-2N); SEQ ID NO:67 (AC15-2O).

In other embodiments, an RG polynucleotide can hybridize under stringent conditions to an RG3 (SEQ ID NO:68), an RG4 (SEQ ID NO:69), and RG5 (SEQ ID NO:135), and an RG7 (SEQ ID NO:137), RG family member.

The present invention further provides nucleic acid constructs which comprise an RG polynucleotide which encodes RG polypeptides from various RG families; such as an RG polypeptide having at least 60% sequence identity to an RG polypeptide selected from the group consisting of: an RG1 polypeptide, an RG2 polypeptide, an RG3 polypeptide, and RG4 polypeptide, and RG5 polypeptide, and an RG7 polypeptide.

Exemplary RG1 polypeptides have the sequences shown in SEQ ID NO:2 (RG1A), SEQ ID NO:4 (RG1B), SEQ ID NO:6 (RG1C), SEQ ID NO:8 (RG1D), SEQ ID NO:10 (RG1E), SEQ ID NO:12 (RG1F), SEQ ID NO:14 (RG1G), SEQ ID NO:16 (RG1H), SEQ ID NO:20 (RG1J). Exemplary RG2 polypeptides have the sequences shown in SEQ ID NO:22 and SEQ ID NO:41 (RG2A); SEQ ID NO:24 and SEQ ID NO:42 (RG2B); SEQ ID NO:43 (RG2C); SEQ ID NO:44 (RG2D); SEQ ID NO:45 (RG2E); SEQ ID NO:46 (RG2F); SEQ ID NO:47 (RG2G); SEQ ID NO:48 (RG2H); SEQ ID NO:49 (RG2I); SEQ ID NO:50 (RG2J); SEQ ID NO:51 (RG2K); SEQ ID NO:52 (RG2L); SEQ ID NO:53 (RG2M); SEQ ID NO:88 (RG2A); SEQ ID NO:90 (RG2B); SEQ ID NO:92 (RG2C); SEQ ID NO:95 (RG2D); SEQ ID NO:97 (RG2E); SEQ ID NO:99 (RG2F); SEQ ID NO:101 (RG2G); SEQ ID NO:103 (RG2H); SEQ ID NO:105 (RG2I); SEQ ID NO:108 (RG2J); SEQ ID NO:111 (RG2K); SEQ ID NO:113 (RG2L); SEQ ID NO:115 (RG2M); SEQ ID NO:117 (RG2N); SEQ ID NO:119 (RG2O); SEQ ID NO:121 (RG2P); SEQ ID NO:123 (RG2Q); SEQ ID NO:125 (RG2S); SEQ ID NO:127 (RG2T); SEQ ID NO:129 (RG2U); SEQ ID NO:131 (RG2V); and, SEQ ID NO:133 (RG2W).

An exemplary RG3 polypeptide has the sequence shown in SEQ ID NO:138. An exemplary RG4 polypeptide has the sequence shown in SEQ ID NO:139. RG polynucleotides will have at least 60% identity, more typically at least 65% identity, generally at least 70% identity, and preferably at least 75% identity, more preferably at least 80% identity, and most preferably at least 85%, 90%, or 95% identity at the deduced amino acid level. The regions where substantial identity is assessed can be inclusive or exclusive of the nucleotide binding site or the leucine rich region.

Vectors and Transcriptional Control Elements

The invention, providing methods and reagents for making novel species and genuses of RG nucleic acids described herein, further provides methods and reagents for expressing these nucleic acids using novel expression cassettes, vectors, transgenic plants and animals, using constitutive and inducible transcriptional and translational cis-(e.g., promoters and enhancers) and trans-acting control elements.

The expression of natural, recombinant or synthetic plant disease resistance polypeptide-encoding or other (i.e., antisense, ribozyme) nucleic acids can be achieved by operably linking the coding region a promoter (that can be plant-specific or not, constitutive or inducible), incorporating the construct into an expression cassette (such as an expression vector), and introducing the resultant construct into an in vitro reaction system or a suitable host cell or organism. Synthetic procedures may also be used. Typical expression systems contain, in addition to coding or antisense sequence, transcription and translation terminators, polyadenylation sequences, transcription and translation initiation sequences, and promoters useful for transcribing DNA into RNA. The expression systems optionally at least one independent terminator sequence, sequences permitting replication of the cassette in vivo, e.g., plants, eukaryotes, or prokaryotes, or a combination thereof, (e.g., shuttle vectors) and selection markers for the selected expression system, e.g., plant, prokaryotic or eukaryotic systems. To ensure proper polypeptide expression under varying conditions, a polyadenylation region at the 3'-end of the coding region can be included (see Li (1997) *Plant Physiol.* 115:321–325, for a review of the polyadenylation of RNA in plants). The polyadenylation region can be derived from the natural gene, from a variety of other plant genes, or from T-DNA (e.g., using *Agrobacterium tumefaciens* T-DNA replacement vectors, see e.g., Thykjaer (1997) *Plant Mol Biol.* 35:523–530; using a plasmid containing a gene of interest flanked by Agrobacterium T-DNA border repeat sequences; Hansen (1997) "T-strand integration in maize protoplasts after codelivery of a T-DNA substrate and virulence genes," *Proc. Natl. Acad. Sci. USA* 94:11726–11730.

To identify the promoters, the 5' portions of the clones described here are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G (see, e.g., Messing, in *Genetic Engineering in Plants*, pp. 221–227, Kosage, Meredith and Hollaender, eds. 1983). If proper polypeptide expression is desired, a polyadenylation region at the 3'-end of the RG coding region should be included. The polyadenylation region can be derived from the natural gene, from a variety of other plant genes, or from viral genes, such as T-DNA.

The nucleic acids of the invention can be expressed in expression cassettes, vectors or viruses which are transiently expressed in cells using, for example, episomal expression systems (e.g., cauliflower mosaic virus (CAMV) viral RNA is generated in the nucleus by transcription of an episomal minichromosome containing supercoiled DNA, Covey (1990) *Proc. Natl. Acad. Sci. USA* 87:1633–1637). Alternatively, coding sequences can be inserted into the host cell genome becoming an integral part of the host chromosomal DNA.

Selection markers can be incorporated into expression cassettes and vectors to confer a selectable phenotype on transformed cells and sequences coding for episomal maintenance and replication such that integration into the host genome is not required. For example, the marker may encode biocide resistance, such as antibiotic resistance, particularly resistance to chloramphenicol, kanamycin, G418, bleomycin, hygromycin, or herbicide resistance, such as resistance to chlorosulfuron or Basta, to permit selection of those cells transformed with the desired DNA sequences, see for example, Blondelet-Rouault (1997) *Gene* 190:315–317; Aubrecht (1997) *J. Pharmacol. Exp. Ther.* 281:992–997. Because selectable marker genes conferring resistance to substrates like neomycin or hygromycin can only be utilized in tissue culture, chemoresistance genes are also used as selectable markers in vitro and in vivo. See also, Mengiste (1997) "High-efficiency transformation of *Arabidopsis thaliana* with a selectable marker gene regulated by the T-DNA 1' promoter," *Plant J.* 12:945–948, showing that the 1' promoter is an attractive alternative to the cauliflower mosaic virus (CaMV) 35S promoter for the generation of T-DNA insertion lines, the 1' promoter may be especially beneficial for the secondary transformation of transgenic strains containing the 35S promoter to exclude homology-mediated gene silencing.

The endogenous promoters from the RG genes of the present invention can be used to direct expression of the genes. These promoters can also be used to direct expression of heterologous structural genes. The promoters can be used, for example, in recombinant expression cassettes to drive expression of genes conferring resistance to any number of pathogens or pests, including fungi, bacteria, and the like.

Constitutive Promoters

In construction of recombinant expression cassettes, vectors, transgenics, of the invention, a promoter fragment can be employed to direct expression of the desired gene in all tissues of a plant or animal. Promoters that drive expression continuously under physiological conditions are referred to as "constitutive" promoters and are active under most environmental conditions and states of development or cell differentiation. Examples of constitutive promoters include those from viruses which infect plants, such as the cauliflower mosaic virus (CaMV) 35S transcription initiation region; the 1'- or 2'-promoter derived from T-DNA of *Agrobacterium tumafaciens*; the promoter of the tobacco mosaic virus; and, other transcription initiation regions from various plant genes known to those of skill. See also Holtorf (1995) "Comparison of different constitutive and inducible promoters for the overexpression of transgenes in *Arabidopsis thaliana*," *Plant Mol. Biol.* 29:637–646.

Inducible Promoters

Alternatively, a plant promoter may direct expression of the plant disease resistance nucleic acid of the invention under the influence of changing environmental conditions or developmental conditions. Examples of environmental conditions that may effect transcription by inducible promoters include pathogenic attack, anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897–909).

Embodiments of the invention also incorporate use of plant promoters which are inducible upon injury or infection to express the invention's plant disease resistance (RG) polypeptides. Various embodiments include use of, e.g., the promoter for a tobacco (*Nicotiana tabacum*) sesquiterpene cyclase gene (EAS4 promoter), which is expressed in wounded leafs, roots, and stem tissues, and upon infection with microbial pathogens (Yin (1997) *Plant Physiol.* 115(2) :437–451); the ORF13 promoter from *Agrobacteinum rhizogenes* 8196, which is wound inducible in a limited area adjacent to the wound site (Hansen (1997) Mol. Gen. Genet. 254:337–343); the Shpx6b gene promoter, which is a plant peroxidase gene promoter induced by microbial pathogens (demonstrated using a fungal pathogen, see Curtis (1997) *Mol. Plant Microbe Interact.* 10:326–338); the wound-inducible gene promoter wun1, derived from potato (Siebertz (1989) *Plant Cell* 1:961–968); the wound-inducible *Agrobacterium pmas* gene (mannopine synthesis gene) promoter (Guevara-Garcia (1993) *Plant J.* 4:495–505).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine mar L.*) (Liu (1997) Plant Physiol. 115:397–407); the auxin-responsive Arabidopsis GST6 promoter (also responsive to salicylic acid and hydrogen peroxide) (Chen (1996) *Plant J.* 10: 955–966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900–1902).

Plant promoters which are inducible upon exposure to chemicals reagents which can be applied to the plant, such as herbicides or antibiotics, are also used to express the nucleic acids of the invention. For example, the maize In2—2 promoter, activated by benzenesulfonamide herbicide safeners, can be used (De Veylder (1997) Plant Cell Physiol. 38:568–577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa L.* (oat) arginine decarboxylase gene (Masgrau (1997) *Plant J.* 11:465–473); or, a salicylic acid-responsive element (Stange (1997) *Plant J.* 11:1315–1324. Using chemically- (e.g., hormone- or pesticide-) induced promoters, harvesting of fruits and plant parts would be greatly facilitated. A chemical which can be applied to the transgenic plant in the field and induce expression of a polypeptide of the invention throughout all or most of the plant would make a environmentally safe defoliant or herbicide. Thus, the invention also provides for transgenic plants containing an inducible gene encoding for the RG polypeptides of the invention whose host range is limited to target plant species, such as weeds or crops before, during or after harvesting.

Abcission promoters are activated upon plant ripening, such as fruit ripening, and are especially useful incorporated in the expression systems (e.g., expression cassettes, vectors) of the invention. In some embodiments, when a plant disease resistant polypeptide-encoding nucleic acid is under the control of such a promoter, rapid cell death, induced by expression of the invention's polypeptide, can accelerate and/or accentuate abcission, increasing the efficiency of the harvesting of fruits or other plant parts, such as cotton, and the like. Induction of rapid cell death at this time would accelerate separation of the fruit from the plant, greatly augmenting harvesting procedures. See, e.g., Kalaitzis (1997) *Plant Physiol.* 113:1303–1308, discussing tomato leaf and flower abscission; Payton (1996) *Plant Mol. Biol.* 31:1227–1231, discussing ethylene receptor expression regulation during fruit ripening, flower senescence and abscission; Koehler (1996) *Plant Mol. Biol.* 31:595–606, discussing the gene promoter for a bean abscission cellulase; Kalaitzis (1995) *Plant Mol. Biol.*28: 647–656, discussing cloning of a tomato polygalacturonase expressed in abscission; del Campillo (1996) *Plant Physiol.* 111:813–820, discussing pedicel breakstrength and cellulase gene expression during tomato flower abscission.

Tissue-Specific Promoters

Tissue specific promoters are transcriptional control elements that are only active in particular cells or tissues. Plant promoters which are active only in specific tissues or at specific times during plant development are used to express the nucleic acids of the invention. Examples of promoters under developmental control include promoters that initiate transcription only in certain tissues, such as leaves, roots, fruit, seeds, ovules, pollen, pistols, or flowers. Such promoters are referred to as "tissue specific". The operation of a promoter may also vary depending on its location in the genome. Thus, an inducible promoter may become fully or partially constitutive in certain locations.

For example, a seed-specific promoter directs expression in seed tissues. Such promoters may be, for example, ovule-specific, embryo-specific, endosperm-specific, integument-specific, seed coat-specific, or some combination thereof. A leaf-specific promoter has been identified in maize, Busk (1997) *Plant J.* 11: 1285–1295. The ORF13 promoter from *Agrobacterium rhizogenes* exhibits high activity in roots (Hansen (1997) supra). A maize pollen-specific promoter has been identified in maize (Guerrero (1990) *Mol. Gen. Genet.* 224:161–168). A tomato promoter active during fruit ripening, senescence and abscission of leaves and, to a lesser extent, of flowers can be used (Blume (1997) *Plant J.* 12:731–746). A pistol specific promoter has been identified in the potato (*Solanum tuberosum* L.) SK2 gene, encoding a pistil-specific basic endochitinase (Ficker (1997) *Plant Mol. Biol.* 35:425–431). The Blec4 gene from pea (*Pisum sativum cv. Alaska*) is active in epidermal tissue of vegetative and floral shoot apices of transgenic alfalfa, making it a useful tool to target the expression of foreign genes to the epidermal layer of actively growing shoots. The activity of the Blec4 promoter in the epidermis of the shoot apex makes it particularly suitable for genetically engineering defense against insects and diseases that attack the growing shoot apex (Mandaci (1997) *Plant Mol Biol.* 34:961–965).

The invention also provides for use of tissue-specific plant promoters include a promoter from the ovule-specific BELI gene described in Reiser (1995) *Cell* 83:735–742, GenBank No. U39944. Suitable seed specific promoters are derived from the following genes: MAC1 from maize, Sheridan (1996) *Genetics* 142:1009–1020; Cat3 from maize, GenBank No. L05934, Abler (1993)

Plant Mol. Biol. 22:10131–1038; the gene encoding oleosin 18 kD from maize, GenBank No. J05212, Lee (1994) *Plant Mol. Biol.* 26:1981–1987; vivparous-1 from Arabidopsis, Genbank No. U93215; the gene encoding oleosin from Arabidopsis, Genbank No. Z17657; Atmyc1 from Arabidopsis, Urao (1996) *Plant Mol. Biol.* 32:571–576; the 2s seed storage protein gene family from Arabidopsis, Conceicao (1994) *Plant* 5:493–505; the gene encoding oleosin 20 kD from *Brassica napus*, GenBank No. M63985; napA from *Brassica napus*, GenBank No. J02798, Josefsson (1987) JBL 26:12196–1301; the napin gene family from *Brassica napus*, Sjodahl (1995) *Planta* 197:264–271; the gene encoding the 2S storage protein from *Brassica napus*, Dasgupta (1993) *Gene* 133:301–302; the genes encoding oleosin a, Genbank No. U09118, and, oleosin B, Genbank No. U09119, from soybean; and, the gene encoding low molecular weight sulphur rich protein from soybean, Choi (1995) *Mol Gen, Genet.* 246:266–268. The tissue specific E8 promoter from tomato is particularly useful for directing gene expression so that a desired gene product is located in fruits. Other suitable promoters include those from genes encoding embryonic storage proteins.

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

The invention also provides for use of tissue-specific promoters derived from viruses which can include, e.g., the tobamovirus subgenomic promoter (Kumagai (1995) *Proc. Natl. Acad. Sci. USA* 92:1679–1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129–1139).

In some embodiments, the nucleic acid construct will comprise a promoter functional in a specific plant cell, such as in a species of *Lactuca*, operably linked to an RG polynucleotide. Promoters useful in these embodiments include RG promoters. In additional embodiments, the nucleic acid construct will comprise a RG promoter operably linked to a heterologous polynucleotide. The heterologous polynucleotide is chosen to provide a plant with a desired phenotype. For example, the heterologous polynucleotide can be a structural gene which encodes a polypeptide which imparts a desired resistance phenotype. Alternatively, the heterologous polynucleotide may be a regulatory gene which might play a role in transcriptional and/or translational control to suppress, enhance, or otherwise modify the transcription and/or expression of an endogenous gene within the plant. The heterologous polynucleotide of the nucleic acid construct of the present invention can be expressed in either sense or anti-sense orientation as desired. It will be appreciated that control of gene expression in either sense or anti-sense orientation can have a direct impact on the observable plant characteristics.

Modifying and Inhibiting RG Gene Expression

The invention also provides for RG nucleic acid sequences which are complementary to the RG polypeptide-encoding sequences of the invention; i.e., antisense RG nucleic acids. Antisense technology can be conveniently used to modify gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy (1988) *Proc. Nat. Acad. Sci. USA* 85:8805–8809; Hiatt et al., U.S. Pat. No. 4,801,340.

Antisense sequences are capable of inhibiting the transport, splicing or transcription of RG-encoding genes. The inhibition can be effected through the targeting of genomic DNA or messenger RNA. The transcription or function of targeted nucleic acid can be inhibited, e.g., by hybridization and/or cleavage. One particularly useful set of inhibitors provided by the present invention includes oligonucleotides which are able to either bind RG gene or message, in either case preventing or inhibiting the production or function of RG. The association can be though sequence specific hybridization. Such inhibitory nucleic acid sequences can, for example, be used to completely inhibit a plant disease resistance response. Another useful class of inhibitors includes oligonucleotides which cause inactivation or cleavage of RG message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Antisense Oligonucleotides

The invention provides for with antisense oligonucleotides capable of binding RG message which can inhibit RG activity by targeting mRNA. Strategies for designing antisense oligonucleotides are well described in the scientific and patent literature, and the skilled artisan can design such RG oligonucleotides using the novel reagents of the invention. In some situations, naturally occurring nucleic acids used as antisense oligonucleotides may need to be relatively long (18 to 40 nucleotides) and present at high concentrations. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) *Toxicol Appl Pharmacol* 144:189–197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids, as described herein.

Combinatorial chemistry methodology can be used to create vast numbers of oligonucleotides that can be rapidly screened for specific oligonucleotides that have appropriate binding affinities and specificities toward any target, such as the sense and antisense RG sequences of the invention (for general background information, see, e.g., Gold (1995) *J. of Biol. Chem.* 270:13581–13584).

Inhibitory Ribozymes

The invention provides for with ribozymes capable of binding RG message which can inhibit RG activity by targeting mRNA. Strategies for designing ribozymes and selecting the RG-specific antisense sequence for targeting are well described in the scientific and patent literature, and the skilled artisan can design such RG ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence, or, preventing transport of the message from the nucleus to the cytoplasm. After a ribozyme has bound and cleaved its RNA target, it is typically released from that RNA and so can bind and cleave new targets repeatedly.

Catalytic RNA molecules or ribozymes can also be used to inhibit expression of any plant gene. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described, e.g., in Haseloff (1988) *Nature* 334:585–591.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) *Aids Research and Human Retroviruses* 8:183;

hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

Sense Supression

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990), and U.S. Pat. No. 5,034,323.

Cloning of RG Polypeptides

Synthesis and/or cloning of RG polynucleotides and isolated nucleic acid constructs of the present invention are provided by methods well known to those of ordinary skill in the art. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of RG genes may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as roots and a cDNA library which contains the RG gene transcript is prepared from the mRNA. Alternatively, cDNA may be prepared from mRNA extracted from other tissues in which RG genes or homologs are expressed.

The cDNA or genomic library can then be screened using a probe based upon the sequence of a cloned RG gene such as the genes disclosed herein. Probes may be used to hybridize with genomic DNA or cDNA sequences to isolate homologous genes in the same or different plant species.

Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

Alternatively, the RG nucleic acids of the invention can be amplified from nucleic acid samples using a variety of amplification techniques, such as polymerase chain reaction (PCR) technology, to amplify the sequences of the RG and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Oligonucleotides can be used to identify and detect additional RG families and RG family species using a variety of hybridization techniques and conditions. Suitable amplification methods include, but are not limited to: polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. (Innis )), ligase chain reaction (LCR) (Wu (1989) *Genomics* 4:560; Landegren (1988) *Science* 241:1077; Barringer (1990) *Gene* 89:117); transcription amplification (Kwoh (1989) *Proc. Natl. Acad. Sci. USA* 86:1173); and, self-sustained sequence replication (Guatelli (1990) *Proc. Natl. Acad. Sci. USA,* 87:1874); Q Beta replicase amplification and other RNA polymerase mediated techniques (e.g., NASBA, Cangene, Mississauga, Ontario); see Berger (1987) Methods Enzymol. 152:307–316, Sambrook, and Ausubel, as well as Mullis (1987) U.S. Pat. Nos. 4,683,195 and 4,683,202; Arnheim (1990) *C&EN* 36–47; Lomell *J. Clin. Chem.,* 35:1826 (1989); Van Brunt, *Biotechnology,* 8:291–294 (1990); Wu (1989) *Gene* 4:560; Sooknanan (1995) *Biotechnology* 13:563–564. Methods for cloning in vitro amplified nucleic acids are described in Wallace, U.S. Pat. No. 5,426,039.

The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium as described earlier.

In some preferred embodiments, members of this class of pest resistance genes can be identified by their ability to be amplified by PCR primers based on the sequences disclosed here. Appropriate primers and probes for identifying RG sequences from plant tissues are generated from comparisons of the sequences provided herein. See, e.g., Table 1. For a general overview of PCR see PCR *Protocols: A Guide to Methods and Applications.* (Innis, M, Gelfand, D., Sninsky, J. and White, T., eds.), *Academic Press*, San Diego (1990), incorporated herein by reference.

Briefly, the first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965, 188). Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

RG Proteins

The present invention further provides isolated RG proteins encoded by the RG polynucleotides disclosed herein. One of skill will recognize that the nucleic acid encoding a functional RG protein need not have a sequence identical to the exemplified genes disclosed here. For example, because of codon degeneracy a large number of nucleic acid sequences can encode the same polypeptide. In addition, the polypeptides encoded by the RG genes, like other proteins, have different domains which perform different functions. Thus, the RG gene sequences need not be full length, so long as the desired functional domain of the protein is expressed.

The resistance proteins are at least 25 amino acid residues in length. Typically, the RG proteins are at least 50 amino acid residues, generally at least 100, preferably at least 150, more preferably at least 200 amino acids in length. In particularly preferred embodiments, the RG proteins are of sufficient length to provide resistance to pests when expressed in the desired plants. Generally then, the RG proteins will be the length encoded by an RG gene of the present invention. However, those of ordinary skill will appreciate that minor deletions, substitutions, or additions to an RG protein will typically yield a protein with pest resistance characteristics similar or identical to that of the full length sequence. Thus, full-length RG proteins modified by 1, 2, 3, 4, or 5 deletions, substitutions, or additions, generally provide an effective degree of pest resistance relative to the full-length protein.

The RG proteins which provide pest resistance will typically comprise at least one of an LRR or an NBS. Preferably, both are present. LRR and/or NBS regions present in the RG proteins of the present invention can be provided by RG genes of the present invention. In some embodiments, the LRR and/or NBS regions are obtained from other pest resistance genes. See, e.g., Yu et al., *Proc. Natl. Acad. Sci. USA*, 93: 11751–11756 (1996); Bent et al., *Science*, 265: 1856–1860 (1994).

Modified protein chains can also be readily designed utilizing various recombinant DNA techniques well known to those skilled in the art. For example, the chains can vary from the naturally occurring sequence at the primary structure level by amino acid substitutions, additions, deletions, and the like. Modification can also include swapping domains from the proteins of the invention with related domains from other pest resistance genes.

Pests that can be targeted by RG genes and proteins of the present invention include such bacterial pests as *Erwinia carotovora* and *Pseudomonas marginalis*. Fungal pests which can be targeted by the present invention include *Bremia lactucae, Marssonina panattoniana, Rhizoctonia solani, Olpidium brassicae*, root aphid, *Sclerotinia sclerotiorum* and *S. minor*, and *Botrytis cinerea* which causes gray mold. RG genes also provide resistance to viral diseases such as lettuce and turnip mosaic viruses.

Fusion Proteins

RG polypeptides can also be expressed as recombinant proteins with one or more additional polypeptide domains linked thereto to facilitate protein detection, purification, or other applications. Such detection and purification facilitating domains include, but are not limited to, metal chelating peptides such as polyhistidine tracts and histidine-tryptophan modules that allow purification on immobilized metals, protein a domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and plant disease resistant polypeptide may be useful to facilitate purification. One such expression vector provides for expression of a fusion protein comprising the sequence encoding a plant disease resistant polypeptide of the invention and nucleic acid sequence encoding six histidine residues followed by thioredoxin and an enterokinase cleavage site (e.g., see Williams (1995) *Biochemistry* 34:1787–1797). The histidine residues facilitate detection and purification while the enterokinase cleavage site provides a means for purifying the desired protein(s) from the remainder of the fusion protein. Technology pertaining to vectors encoding fusion proteins and application of fusion proteins are well described, see e.g., Kroll (1993) DNA *Cell. Biol.,* 12:441–53.

Antibodies Reactive to RG Polypeptides and Immunological Assays

The present invention also provides antibodies which specifically react with RG proteins of the present invention under immunologically reactive conditions. An antibody immunologically reactive with a particular antigen can be generated in vivo or by recombinant methods such as selection of libraries of recombinant antibodies in phage or similar vectors. "Immunologically reactive conditions" includes reference to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols.

"Antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG). See, Pierce Catalog and Handbook, 1994–1995 (Pierce Chemical Co., Rockford, Ill.). An antibody immunologically reactive with a particular antigen can be generated in vivo or by recombinant methods such as selection of libraries of recombinant antibodies in phage or similar vectors. See, e.g., Huse et al. (1989) *Science* 246:1275–1281; and Ward, et al. (1989) *Nature* 341:544–546; and Vaughan et al. (1996) *Nature Biotechnology*, 14:309–314.

Many methods of making antibodies are known to persons of skill. A number of immunogens are used to produce antibodies specifically reactive to an isolated RG protein of the present invention under immunologically reactive conditions. An isolated recombinant, synthetic, or native RG protein of the present invention is the preferred immunogens (antigen) for the production of monoclonal or polyclonal antibodies.

The RG protein is then injected into an animal capable of producing antibodies. Either monoclonal or polyclonal antibodies can be generated for subsequent use in immunoassays to measure the presence and quantity of the RG protein. Methods of producing monoclonal or polyclonal antibodies are known to those of skill in the art. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.); Goding (1986) *Monoclonal Antibodies: Principles and Practice* (2d ed.) Academic Press, New York, N.Y.

Frequently, the RG proteins and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

The antibodies of the present invention can be used to screen plants for the expression of RG proteins of the present invention. The antibodies of this invention are also used for affinity chromatography in isolating RG protein.

The present invention further provides RG polypeptides that specifically bind, under immunologically reactive conditions, to an antibody generated against a defined immunogen, such as an immunogen consisting of the RG polypeptides of the present invention. Immunogens will generally be at least 10 contiguous amino acids from an RG polypeptide of the present invention. Optionally, immunogens can be from regions exclusive of the NBS and/or LRR regions of the RG polypeptides. Nucleic acids which encode such cross-reactive RG polypeptides are also provided by the present invention. The RG polypeptides can be isolated from any number plants as discussed earlier. Preferred are species from the family Compositae and in particular the genus Lactuca such as *L. sativa* and such subspecies as crispa, longifolia, and asparagina.

"Specifically binds" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between a ligand and a non-target molecule. Nevertheless, specific binding, may be distinguished as mediated through specific recognition of the target molecule. Typically specific binding results in a much stronger association between the ligand and the target molecule than between the ligand and non-target molecule. Specific binding by an antibody to a protein under such conditions requires an antibody that is selected for its specificity for a particular protein. The affinity constant of the antibody binding site for its cognate monovalent antigen is at least $10^7$, usually at least $10^8$, preferably at least $10^9$, more preferably at least $10^{10}$, and most preferably at least $10^{11}$ liters/mole. A variety of immunoassay formats are appropriate for selecting antibodies specifically reactive with a particular protein. For example, solid-phase ELISA immunoassays are routinely used to select monoclonal antibodies specifically reactive with a protein. See Harlow and Lane (1988) Antibodies, A Laboratory Manual, Cold Spring Harbor Publications, New York, for a description of immunoassay formats and conditions that can be used to determine specific reactivity. The antibody may be polyclonal but preferably is monoclonal. Generally, antibodies cross-reactive to such proteins as RPS2, RPM1 (bacterial resistances in Arabidopsis, L6 (fungal resistance in flax, PRF (resistance to *Pseudomonas syringae* in tomator), and N, (virus resistance in tobacco), are removed by immunoabsorbtion.

Immunoassays in the competitive binding format are typically used for cross-reactivity determinations. For example, an immunogenic RG polypeptide is immobilized to a solid support. Polypeptides added to the assay compete with the binding of the antisera to the immobilized antigen. The ability of the above polypeptides to compete with the binding of the antisera to the immobilized RG polypeptide is compared to the immunogenic RG polypeptide. The percent cross-reactivity for the above proteins is calculated, using standard calculations. Those antisera with less than 10% cross-reactivity with such proteins as RPS2, RPM1, L6, PRF, and N, are selected and pooled. The cross-reacting antibodies are then removed from the pooled antisera by immunoabsorbtion with these non-RG resistance proteins.

The immunoabsorbed and pooled antisera are then used in a competitive binding immunoassay to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

Production Of Transgenic Plants Of The Invention

Isolated nucleic acid constructs prepared as described herein can be introduced into plants according techniques known in the art. In some embodiments, the introduced nucleic acid is used to provide RG gene expression and therefore pest resistance in desired plants. In some embodiments, RG promoters are used to drive expression of desired heterologous genes in plants. Finally, in some embodiments, the constructs can be used to suppress expression of a target endogenous gene, including RG genes.

To use isolated RG sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988).

A DNA sequence coding for the desired RG polypeptide, for example a cDNA or a genomic sequence encoding a full length protein, will be used to construct a recombinant expression cassette which can be introduced into the desired plant. An expression cassette will typically comprise the RG polynucleotide operably linked to transcriptional and translational initiation regulatory sequences which will direct the transcription of the sequence from the RG gene in the intended tissues of the transformed plant.

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Transformation techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-meditated transformation techniques are well described in the scientific literature. See, for example Horsch et al. *Science* 233:496–498 (1984), and Fraley et al. *Proc. Natl. Acad. Sci. USA* 80:4803 (1983). Although *Agrobacterium* is useful primarily in dicots, certain monocots can be transformed by *Agrobacterium*. For instance, *Agrobacterium* transformation of rice is described by Hiei et al, *Plant J.* 6:271–282 (1994). A particularly preferred means of transforming lettuce is described in Michelmore et al., *Plant Cell Reports,* 6:439–442 (1987).

Transformed plant cells which are derived by any of the above transformation techniques can be cultured to regenerate a whole plant which possesses the transformed genotype and thus the desired RG-controlled phenotype. Such regeneration techniques rely on manipulation of certain phytohormones in a tissue culture growth medium, typically relying on a biocide and/or herbicide marker which has been introduced together with the RG nucleotide sequences. Plant regeneration from cultured protoplasts is described in Evans et al., *Protoplasts Isolation and Culture, Handbook of Plant Cell Culture*, pp. 124–176, Macmillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the RG polynucleotides into transformed plants in ways and under circumstances which are not found naturally. In particular, the RG polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Detection of RG Resistance Genes

The present invention further provides methods for detecting RG resistance genes in a nucleic acid sample suspected of comprising an RG resistance gene. The means by which the RG resistance gene is detected is not a critical aspect of the invention. For example, RG resistance genes can be detected by the presence of amplicons using RG resistance gene specific primers. Additionally, RG resistance genes can be detected by assaying for specific hybridization of an RG polynucleotide to an RG resistance gene. In some embodiments, the RG resistance gene can be amplified prior to the step of contacting the nucleic acid sample with the RG polynucleotide.

In a typical detection method, the nucleic acid sample is contacted with an RG polynucleotide to form a hybridization complex. The hybridization complex may be detected directly (e.g., in Southern or northern blots), or indirectly (e.g., by subsequent primer extension during PCR amplification). The RG polynucleotide hybridizes under stringent conditions to an RG polynucleotide of the invention. Formation of the hybridization complex is directly or indirectly used to indicate the presence of the RG resistance gene in the nucleic acid sample.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3):230–250 (1986); Haase et al., *Methods in Virology*, Vol. VII, pp. 189–226 (1984); Wilkinson, "The theory and practice of in situ hybridization" In: In situ Hybridization, Ed. D. G. Wilkinson. IRL Press, Oxford University Press, Oxford; and *Nucleic Acid Hybridization: A Practical Approach*, Ed. Hames, B. D. and Higgins, S. J., IRL Press (1987).

The effect of the modification of RG gene expression can be measured by detection of increases or decreases in mRNA levels using, for instance, Northern blots. In addition, the phenotypic effects of gene expression can be detected by measuring nematode, fungal, bacterial, viral, or other pest resistance in plants. Suitable assays for determining pest resistance are well known. Michelmore and Crute, *Trans. Br. mycol. Soc,* 79(3):542–546 (1982).

The means by which hybridization complexes are detected is not a critical aspect of the present invention and can be accomplished by any number of methods currently known or later developed. RG polynucleotides can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the RG polynucleotide is readily achieved such as by the use of labeled PCR primers.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation with DNA polymerase I, by tailing radioactive DNA bases to the 3' end of probes with terminal deoxynucleotidyl transferase, by treating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., 32P phosphate or 14C organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K. (1984) A Colorimetric Method for DNA Hybridization. *Nucl. Acids Res.* 12: 3435–3444) and synthetic oligonucleotides have been coupled directly with alkaline phosphatase (Jablonski, E., et al. (1986) Preparation of Oligodeoxynucleotide-Alkaline Phosphatase Conjugates and Their Use as Hybridization Probes. *Nuc. Acids. Res.* 14: 6115–6128; and Li P., et al. (1987) Enzyme-linked Synthetic Oligonucleotide probes: Non-Radioactive Detection of Enterotoxigenic *Escherichia Coli* in Faeca Specimens. *Nucl. Acids Res.* 15:5275–5287).

Definitions

Units, prefixes, and symbols can be denoted in their SI accepted form. Numeric ranges are inclusive of the numbers defining the range. Unless otherwise indicated, nucleic acids are written left to right in 5' to 3' orientation, respectively. The headings provided herein are not limitations of the various aspects or embodiments of the invention which can be had by reference to the specification as a whole. Accordingly, the terms defined immediately below are more fully defined by reference to the specification as a whole.

As used herein, the term "plant" includes reference to whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

As used herein, "pest" includes, but is not limited to, viruses, fungi, nematodes, insects, and bacteria.

As used herein, "heterologous" is a nucleic acid that originates from a foreign species, or, if from the same species, is substantially modified from its original form. For example, a promoter operably linked to a heterologous structural gene is from a species different from that from which the structural gene was derived, or, if from the same species, one or both are substantially modified from their original form.

As used herein, "RG gene," alternatively referred to as "RLG gene," is a gene encoding resistance to plant pests, such as viruses, fungi, nematodes, insects, and bacteria, and which hybridizes under stringent conditions and/or has at least 60% sequence identity at the deduced amino acid level to the exemplified sequences provided herein. RG genes encode "RG polypeptides," alternatively referred to as "RLG polypeptides," which can comprise LRR motifs and/or NBS motifs. The RG polypeptides encoded by RG genes have at least 55% or 60% sequence identity, typically at least 65% sequence identity, preferably at least 70% sequence identity, often at least 75% sequence identity, more preferably at least 80% sequence identity, and most preferably at least 90% sequence identity at the deduced amino acid level relative to the exemplary RG sequences provided herein. The term "RG family" or "RG family genus" or "genus" includes reference to a group of RG polypeptide sequence species that have at least 60% amino acid sequence identity, and, the nucleic acids encoding these polypeptides. The individual species of a genus, i.e., the members of a family, typically are genetically mapped to the same locus.

As used herein, "RG polynucleotide" includes reference to a contiguous sequence from an RG gene of at least 18, 20, 25, 30, 40, or 50 nucleotides in length, up to at least about 100 or at least about 200 nucleotides in length. In some embodiments, the polynucleotide is preferably at least 100 nucleotides in length, more preferably at least 200 nucleotides in length, most preferably at least 500 nucleotides in length. Thus, RG polynucleotide may be a RG gene or a subsequence thereof.

As used herein, "isolated," when referring to a molecule or composition, such as, for example, an RG polypeptide or nucleic acid, means that the molecule or composition is separated from at least one other compound, such as a protein, other nucleic acids (e.g., RNAS), or other contaminants with which it is associated in vivo or in its naturally occurring state. Thus, an RG polypeptide or nucleic acid is considered isolated when it has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC).

The term "nucleic acid" or "nucleic acid molecule" or "nucleic acid sequence" refers to a deoxyribonucleotide or ribonucleotide oligonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol Appl Pharmacol* 144:189–197. Other synthetic backbones encompasses by the term include methylphosphonate linkages or alternating methylphosphonate and phosphodiester linkages (Strauss-Soukup (1997) *Biochemistry* 36:8692–8698), and benzylphosphonate linkages (Samstag (1996) *Antisense Nucleic Acid Drug Dev* 6:153–156). The term nucleic acid is used interchangeably with gene, cDNA, mRNA, oligonucleotide primer, probe and amplification product. Unless otherwise indicated, a particular nucleic acid sequence includes the complementary sequence thereof.

The term "exogenous nucleic acid" refers to a nucleic acid that has been isolated, synthesized, cloned, ligated, excised in conjunction with another nucleic acid, in a manner that is not found in nature, and/or introduced into and/or expressed in a cell or cellular environment other than or at levels or forms different than the cell or cellular environment in which said nucleic acid or protein is be found in nature. The term encompasses both nucleic acids originally obtained from a different organism or cell type than the cell type in which it is expressed, and also nucleic acids that are obtained from the same cell line as the cell line in which it is expressed invention.

The term "recombinant," when used with reference to a cell, or to the nucleic acid, protein or vector refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell or express native genes that are otherwise expressed at a different level, typically, under-expressed or not expressed at all. The term "recombinant means" encompasses all means of expressing, i.e., transcription or translation of, an isolated and/or cloned nucleic acid in vitro or in vivo. For example, the term "recombinant means" encompasses techniques where a recombinant nucleic acid, such as a cDNA encoding a protein, is inserted into an expression vector, the vector is introduced into a cell and the cell expresses the protein. "Recombinant means" also encompass the ligation of nucleic acids having coding or promoter sequences from different sources into one vector for expression of a fusion protein, constitutive expression of a protein, or inducible expression of a protein, such as the plant disease resistant, or RG, polypeptides of the invention.

The term "specifically hybridizes" refers to a nucleic acid that hybridizes, duplexes or binds to a particular target DNA or RNA sequence. The target sequences can be present in a preparation of total cellular DNA or RNA. Proper annealing conditions depend, for example, upon a nucleic acid's, such as a probe's length, base composition, and the number of mismatches and their position on the probe, and can be readily determined empirically providing the appropriate reagents are available. For discussions of nucleic acid probe design and annealing conditions, see, e.g., Sambrook and Ausubel.

The terms "stringent hybridization," "stringent conditions," or "specific hybridization conditions" refers to conditions under which an oligonucleotide (when used, for example, as a probe or primer) will hybridize to its target subsequence, such as an RG nucleic acid in an expression vector of the invention but not to a non-RG sequence. Stringent conditions are sequence-dependent. Thus, in one set of stringent conditions an oligonucleotide probe will hybridize to only one specie of the genus of RG nucleic acids of the invention. In another set of stringent conditions (less stringent) an oligonucleotide probe will hybridize to all species of the invention's genus but not to non-RG nucleic acids. Longer sequences hybridize specifically at higher temperatures. Stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium (if the target sequences are present in excess, at $T_m$, 50% of the probes are occupied at equilibrium). Typically, stringent conditions will be those in which the salt concentration is less than about 1.0 M sodium ion, i.e., about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Often, high stringency wash conditions preceded by low stringency wash conditions to remove background probe signal. An example of medium stringency wash conditions for a duplex of, e.g., more than 100 nucleotides, is 1×SSC at 45° C. for 15 minutes (see Sambrook for a description of SSC buffer). An example low stringency wash for a duplex of, e.g., more than 100 nucleotides, is 4×SSC at 40° C. for 15 minutes, a signal to noise ratio of 2× (or higher) than that observed for an unrelated probe in the particular hybridization assay indicates detection of a "specific hybridization." Nucleic acids which do not hybridize to each other under stringent conditions can still be substantially identical if the polypeptides which they encode are substantially identical.

This can occur, e.g., when a nucleic acid is created that encodes for conservative substitutions. Stringent hybridization and stringent hybridization wash conditions are different under different environmental parameters, such as for Southern and Northern hybridizations. An extensive guide to the hybridization of nucleic acids is found in, e.g., Sambrook, Tijssen (1993) supra.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

In the expression of transgenes one of skill will recognize that the inserted polynucleotide sequence need not be identical and may be "substantially identical" to a sequence of the gene from which it was derived. As explained herein, these variants are specifically covered by this term.

In the case where the inserted polynucleotide sequence is transcribed and translated to produce a functional RG polypeptide, one of skill will recognize that because of codon degeneracy, a number of polynucleotide sequences will encode the same polypeptide. These variants are specifically covered by the term "RG polynucleotide sequence". In addition, the term specifically includes those full length sequences substantially identical (determined as described herein) with an RG gene sequence which encode proteins that retain the function of the RG protein. Thus, in the case of RG genes disclosed here, the term includes variant polynucleotide sequences which have substantial identity with the sequences disclosed here and which encode proteins capable of conferring resistance to nematodes, bacteria, viruses, fungi, insects or other pests on a transgenic plant comprising the sequence.

Two polynucleotides or polypeptides are said to be "identical" if the sequence of nucleotides or amino acid residues, respectively, in the two sequences is the same when aligned for maximum correspondence, as described below. The term "complementary to" is used herein to mean that the complementary sequence is identical to all or a specified contiguous portion of a reference polynucleotide sequence.

The terms "sequence identity," "sequence similarity" and "homology" refer to when two sequences, such as the nucleic acid and amino acid sequences or the polypeptides of the invention, when optimally aligned, as with, for example, the programs PILEUP, BLAST, GAP, FASTA or BESTFIT (see discussion, supra). "Percentage amino acid/ nucleic acid sequence identity" refers to a comparison of the sequences of two polypeptides/nucleic acids which, when optimally aligned, have approximately the designated percentage of the same amino acids/nucleic acids, respectively. For example, "60% sequence identity" and "60% homology" refer to a comparison of the sequences of two RG nucleic acids or polypeptides which, when optimally aligned, have 60% identity. For example, in one embodiment, nucleic acids encoding RG polypeptides of the invention comprise a sequence with at least 50% nucleic acid sequence identity to SEQ ID NO:1. In other embodiments, the RG polypeptides of the invention are encoded by nucleic acids comprising a sequence with at least 50% sequence identity to SEQ ID NO:1, or, are encoded by nucleic acids comprising SEQ ID NO:1, or, have at least 60% amino acid sequence identity to the polypeptide of SEQ ID NO:2.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 55% or 60% sequence identity, generally at least 65%, preferably at least 70%, often at least 75%, more preferably at least 80% and most preferably at least 90%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 55% or 60%, preferably at least 70%, more preferably at least 80%, and most preferably at least 95%. Polypeptides having "sequence similarity" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under appropriate conditions. Appropriate conditions can be high or low stringency and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

Nucleic acids of the invention can be identified from a cDNA or genomic library prepared according to standard procedures and the nucleic acids disclosed here used as a probe. Thus, for example, stringent hybridization conditions will typically include at least one low stringency wash using 0.3 molar salt (e.g., 2×SSC) at 65° C. The washes are preferably followed by one or more subsequent washes using 0.03 molar salt (e.g., 0.2×SSC) at 50°C., usually 60° C., or more usually 65° C. Nucleic acid probes used to identify the nucleic acids are preferably at least 100 nucleotides in length.

As used herein, "nucleotide binding site" or "nucleotide binding domain" ("NBS") includes reference to highly conserved nucleotide-, i.e., ATP/GTP-, binding domains, typically included in the "kinase domain" of kinase polypeptides, such as a kinase-1a, kinase 2, or a kinase 3a motif, as described herein. For example, the tobacco N and Arabidopsis RPS2 genes, among several recently cloned disease-resistance genes, share highly conserved NBS sequence. Kinase NBS subdomains further consist of three subdomain motifs: the P-loop, kinase-2, and kinase-3a subdomains (Yu (1996) Proc. Acad. Sci. USA 93:11751–11756). As discussed in detail herein, examples include the Arabidopsis RPP5 gene (Parker (1997) supra), the A. thaliana RPS2 gene (Mindrinos (1997) supra), and the flax L6 rust resistance gene (Lawrence (1995) supra) which all encode proteins containing an NBS; and Mindrinos (1994) Cell 78:1089–1099; and Shen (1993) FEBS 335:380–385. Using the teachings disclosed and incorporated herein and standard nucleic acid hybridization and/or amplification techniques, one of skill can identify members having NBS domains, including any of the genus of NBS-containing plant disease resistant polypeptides of the invention.

As used herein, "leucine rich region" ("LRR") includes reference to a region that has a leucine content of at least 20% leucine or isoleucine, or 30% of the aliphatic residues: leucine, isoleucine, methionine, valine, and phenylalanine, and arranged with approximate repeated periodicity. The length of the repeat may vary in length but is generally about 20 to 30 amino acids. An LRR-containing polypeptide typically will have the canonical 24 amino acid leucine-rich repeat (LRR) sequence, which is present in different proteins that mediates molecular recognition and/or interaction processes; as described in Bent (1994) Science 265:1856–1860; Parker (1997) Plant Cell. 9:879–894; Hong (1997) Plant Physiol. 113:1203–1212; Schmitz (1997) Nucleic Acids Res. 25:756–763; Hipskind (1996) Mol. Plant Microbe Interact. 9:819–825; Tornero (1996) Plant J. 10:315–330; Dixon (1996) Cell 84:451–459; Jones (1994) Science 266:789–793; Lawrence (1995) Plant Cell 7:1195–1206; Song (1995) Science 270:1804–1806; as discussed in further detail supra. Using the teachings disclosed and incorporated herein and standard nucleic acid hybridization and/or amplification techniques, one of skill can identify polypeptides having LRR domains, including any member of the genus of LRR-containing RG polypeptides of the invention.

The term "promoter" refers to a region or sequence determinants located upstream or downstream from the start of transcription and which are involved in recognition and binding of RNA polymerase and other proteins to initiate transcription. A "plant promoter" is a promoter capable of initiating and/or regulating transcription in plant cells; see also discussion on plant promoters, supra.

The term "constitutive promoter" refers to a promoter that initiates and helps control transcription in all tissues. Promoters that drive expression continuously under physiological conditions are referred to herein as "constitutive" promoters and are active under most environmental conditions and states of development or cell differentiation; see also detailed discussion, supra.

The term "inducible promoter" refers to a promoter which directs transcription under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters; see also detailed discussion, supra.

The term "abscission-induced promoter" or "abcission promoter" refers to a class of promoters which are activated upon plant ripening, such as fruit ripening, and are especially useful incorporated in the expression systems (e.g., expression cassettes, vectors) of the invention. When the plant disease resistant polypeptide-encoding nucleic acid is under the control of an abcission promoter, rapid cell death, induced by expression of the invention's polypeptide, accelerates and/or accentuates abcission of the plant part, increasing the efficiency of the harvesting of fruits or other plant parts, such as cotton, and the like; see also detailed discussion, supra.

The term "tissue-specific promoter" refers to a class of transcriptional control elements that are only active in particular cells or tissues. Examples of plant promoters under developmental control include promoters that initiate transcription only (or primarily only) in certain tissues, such as roots, leaves, fruit, ovules, seeds, pollen, pistols, or flowers; see also detailed discussion, supra.

As used herein "recombinant" includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, a "recombinant expression cassette" or "expression cassette" is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter.

As used herein, "transgenic plant" includes reference to a plant modified by introduction of a heterologous polynucleotide. Generally, the heterologous polynucleotide is an RG structural or regulatory gene or subsequences thereof.

As used herein, "hybridization complex" includes reference to a duplex nucleic acid sequence formed by selective hybridization of two single-stranded nucleic acids with each other.

As used herein, "amplified" includes reference to an increase in the molarity of a specified sequence. Amplification methods include the polymerase chain reaction (PCR), the ligase chain reaction (LCR), the transcription-based amplification system (TAS), the self-sustained sequence replication system (SSR). A wide variety of cloning methods, host cells, and in vitro amplification methodologies are well-known to persons of skill.

As used herein, "nucleic acid sample" includes reference to a specimen suspected of comprising RG resistance genes. Such specimens are generally derived, directly or indirectly, from lettuce tissue.

The term "antibody" refers to a polypeptide substantially encoded by an immunoglobulin gene or immunoglobulin genes, or fragments or synthetic or recombinant analogues thereof which specifically bind and recognize analytes and antigens, such as a genus or subgenus of polypeptides of the invention, as described supra.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Example 1 describes the use of PCR to amplify RG genes from lettuce.

Multiple primers with low degeneracy, particularly at the 3' end, were designed based on the sequences of two known resistance genes from tobacco and flax.

DNA Templates

Lettuce genomic DNA was extracted from cultivar Diana and a mutant line derived from cultivar Diana using a standard CTAB protocol. To generate cDNA templates, RNA was isolated from cultivar Diana and the mutant following standard procedures; first strand cDNA was synthesized using Superscript reverse transcriptase from 1 Φ g total RNA as specified by the manufacturer (Life Technologies). BAC (bacterial artificial chromosome) clones from the Dm3 region were isolated from a BAC library of over 53,000 clones using marker AC15 that was known to be closely linked to Dm3. Bacterial plasmids containing clones of L6 and RPS2 were used as positive controls.

PCR with degenerate oligonucleotide primers

Oligonucleotide primers were designed based on conserved motifs in the nucleotide binding sites (NBS) of L6, RPS2, and N. Eight primers were made corresponding to the GVGKTT (SEQ ID NO:71) motif in the sense direction; each had 64-fold degeneracy. Six primers were made to the GLPLAL (SEQ ID NO:72) motif in the anti-sense direction; with either 16 or 256-fold degeneracy (Table 1).

Oligonucleotides included 14-mer adaptors of $(CUA)_4$ (SEQ ID NO:139)at the 5' end of the sense primers and $(CAU)_4$ (SEQ ID NO:140) at the 5' end of the antisense primers to allow rapid cloning of the PCR products into pAMP1 (Life Technologies).

PCR amplification was performed in 50 Φl reaction volume with 1 ΦM of each of a pair of sense and antisense primers. The templates were denatured by heating to 94EC for 2 min. This was followed by 35 cycles of 30 sec at 94EC, 1 min at 50EC, 2 min at 72EC, with a single final extension of 5 min at 72EC. 25 ng of genomic DNA or cDNA was used. BAC clones as templates required less. The final dNTP concentration was 0.2 mM; $MgCl_2$ was 1.5 mM.

Forty-eight combinations of sense and antisense primers were tested on a panel of nine templates consisting of two genomic DNA samples, two cDNA preparations, three BAC clones and plasmids containing L6 and RPS2 as positive controls. Amplification from L6 and RPS2 resulted in fragments of 516 and 513 respectively. Seven combinations of primers resulted in fragments of approximately this size with multiple templates (Table 2). Primers that gave RLG products were: PLOOPAA, PLOOPAG, PLOOPGA, PLOOPGG, PLOOPAC, GLPL3, GLPL4.

TABLE 1

DEGENERATE PRIMER SEQUENCES for NBS PCR

Sense primers based on GVGKTT (SEQ ID NO: 71) amino acid sequence from L6, N and rps2 PLOOP motif:

| | | |
|---|---|---|
| PLOOPAG | 5'GGN GTN GGN AAA ACG AC 3' | (SEQ ID NO: 73) |
| PLOOPAA | 5'GGN GTN GGN AAA ACA AC 3' | (SEQ ID NO: 74) |
| PLOOPAT | 5'GGN GTN GGN AAA ACT AC 3' | (SEQ ID NO: 75) |
| PLOOPAC | 5'GGN GTN GGN AAA ACC AC 3' | (SEQ ID NO: 76) |
| PLOOPGG | 5'GGN GTN GGN AAG ACG AC 3' | (SEQ ID NO: 77) |

TABLE 1-continued

DEGENERATE PRIMER SEQUENCES for NBS PCR

| | | |
|---|---|---|
| PLOOPGA | 5'GGN GTN GGN AAG ACA AC 3' | (SEQ ID NO: 78) |
| PLOOPGT | 5'GGN GTN GGN AAG ACT AC 3' | (SEQ ID NO: 79) |
| PLOOPGC | 5'GGN GTN GGN AAG ACC AC 3' | (SEQ ID NO: 80) |

Antisense primers based on GLPLAL (SEQ ID NO: 72) amino acid sequence:

| | | |
|---|---|---|
| GLPL1 | 5'AGN GCN AGN GGN AGG CC 3' | (SEQ ID NO: 81) |
| GLPL2 | 5'AGN GCN AGN GGN AGA CC 3' | (SEQ ID NO: 82) |
| GLPL3 | 5'AGN GCN AGN GGN AGT CC 3' | (SEQ ID NO: 83) |
| GLPL4 | 5'AGN GCN AGN GGN AGC CC 3' | (SEQ ID NO: 84) |
| GLPL5 | 5'AAN GCC AAN GGC AAA CC 3' | (SEQ ID NO: 85) |
| GLPL6 | 5'AAN GCC AAN GGC AAT CC 3' | (SEQ ID NO: 86) |

TABLE 2

Characteristics of RLGs isolated from lettuce.

| | Template | Primers | Number[a] | Size[b] (bp) | Copy number[c] | Dm linkage |
|---|---|---|---|---|---|---|
| RLG1 | genomic | PLOOPGA + GLPL6 | 6/6 | 522 | | DM4, DM13 |
| | cDNA | PLOOPGA + GLPL6 | 1/5 | | | |
| | genomic DNA | PLOOPAA + GLPL6 | 5/5 | | | |
| | cDNA | PLOOPAA + GLPL6 | 1/1 | | | |
| RLG2 | BACH8 | PLOOPGG + GLPL3 | 3/3 | 510 | | DM1, Dm3 |
| RLG3 | genomic DNA | PLOOPGA + GLPL4 | 3/6 | 461 | | Dm5 Dm8 |
| RLG4 | genomic DNA | PLOOPGA + GLPL4 | 1/6 | 524 | | |

[a]Number of RLG sequences out of total number of clones sequenced.
[b]Size of fragment amplified from the nucleotide bindind domain.
[c]Estimated copy number from genomic Southern blot analysis and numbers of clones in the BAC library.

Example 2

Example 2 describes the genetic analysis used to obtain a preliminary indication of the linkage relationships of the amplified products and known clusters of resistance genes.

Bulked segregant analysis was performed to obtain a preliminary indication of the linkage relationships of the amplified products and known clusters of resistance genes. DNA from individuals were pooled for each susceptible and resistant bulk. Amplified products were then mapped by RFLP analysis from our intraspecific mapping population. Resistances from four clusters of resistance genes as well as over six hundred markers have now been mapped on this population. Linkage analysis was done using JIONMAP or MAPMAKER mapping programs. Due to a suppression of recombination in the Dm3 region, sequences were mapped relative to Dm3 using a panel of deletion mutants that provided greater genetic resolution than the mapping population (Anderson et al. 1996). All blots were washed twice at 63EC in 2xSSC/1% SDS for 20 min, followed by one wash at 63EC in 1xSSC/0.1% SDS for 10 or 30 min.

Most of the RLG sequences were analyzed by bulked segregant analysis (BSA) using pools of resistant and susceptible individuals for each of the four clusters of resistance genes. In genomic Southern analyses, all the RLGs revealed numerous fragments of varying intensity. The numbers of bands was highly dependent of the stringency of hybridization. BSA demonstrated that RLG1 was linked to the Dm4, 7 and Dm13 clusters. Segregation analysis confirmed this linkage.

RLG2 was derived from BAC H8 that was known to be from the Dm3 region. BSA with RLG2 demonstrated that the polymorphic bands that distinguished the parents of our mapping population mapped to the Dm1,Dm3 cluster. Several bands absolutely cosegregated with Dm1 or Dm3. To provide finer genetic resolution, RLG2 was also mapped using a panel of Dm3 deletion mutants. A number of fragments were missing in largest deletion mutant demonstrating that several RLG2 family members are physically located very close to Dm3. No fragment was missing in all deletion mutants; however, this is not unexpected as there is extensive duplication within the region.

Example 3

Example 3 describes the screening of a bacterial artificial chromosome library.

Over 53,000 BAC clones containing lettuce genomic DNA were screened with two of the amplified products. High density filters each containing 1536 clones were hybridized to $^{32}P$ labelled probes. Filters were washed at 65EC with 40 mM $Na_2PO_4$/0.1% SDS for 5 min followed by 20 min in the same solution.

To isolate additional RLG sequences we screened our genomic BAC library. Clones were identified that hybridized to RLG1 and RLG2. Nearly all the clones that hybridized to RLG2 also hybridized to marker AC15 that had already been shown by deletion mutant analysis to be clustered around Dm3. This provided further evidence for clustering of RLG2 sequences.

Using primers conserved within each family, part of the NBS was amplified from each unique BAC clone and sequenced. This revealed that members within each family varied from 64% identical at the deduced amino acid level. The most divergent members only weakly cross-hybridized to each other. Currently, RLG sequences are considered to be part of the same family of sequences if they are at least 55% identical at the deduced amino acid level and map to the same region of the chromosome.

Example 4

Example 4 describes the cloning, identification, sequencing and characterization of RG polynucleotide sequences; including use of RG sequences from plasmid and PCR products.

Doubled stranded plasmid DNA clones and PCR products were sequenced using an ABI377 automated sequencer and fluorescently labelled di-deoxy terminators. Sequences were assembled using Sequencher (Genecodes), DNAStar (DNAStar) and Genetics Computer Group (GCG, Madison, Wis.) software. Database searches were performed using BLASTX and FASTA (GCG) algorithms.

Sequences flanking the NBS region for RLG2 and for some of RLG1 were obtained by a series of IPCR and the products sequenced directly. IPCR worked less well for RLG1. Therefore RLG1 was subcloned from a BAC clone into pBSK (Stratagene) and the double stranded plasmid sequenced by long range sequencing.

Initially, a total of 30 clones were sequenced. Three of these seven primer combinations yielded sequences that comprised continuous open reading frames with sequence identity to the NBS of known resistance genes. Seven out of 10 clones amplified from genomic DNA with the primer pair PLOOPGA/GLP6 were 522 bp long; they were identical to each other and named RLG1. All six clones amplified from genomic DNA or cDNA using the primers PLOOPAA/GLP6 were similar/the same as RLG1. All three clones sequenced from BAC clone H8 were 510 bp long, identical to each other but different from RLG1 and were therefore designated RLG2. The 11 clones sequenced from four other primer combinations had no similarity to any NBS motifs and therefore were not studied further. Therefore, sequencing resulted in the identification of clones containing NBS motifs representing four RLG sequences.

Comparison of the deduced amino acid sequences of RLG1 and RLG2 to those of known resistance genes revealed that RLG1 and RLG2 are as similar to each other as they are to resistance genes from other species and that this is the same level of identity shown between the known resistance genes (Table 3). The percent identity (upper quadrant) and percent identity (lower quadrant) were determined using the MEGALIGN routine of the DNASTAR package. Identity refers to the proportion of identical amino acids; identity refers to the proportion of identical and similar amino acids and takes into account substitutions of amino acids with similar chemical characteristics. RG1 and RG2 are as similar to each other and to cloned resistance genes as cloned resistance genes from a variety of species are to each other. L6, resistance to *Melampsora lini* in flax (Lawrence et al., 1995). N, resistance to tobacco mosaic virus in tobacco (Whitham et al., 1994). PRF, required for resistance to *Pseudomonas syringae* in tomato. RPS2, resistance to *Pseudomonas syringae* in *Arabidopsis thaliana* (Bent et al., 1994; Mindrinos et al., 1994). RPM1, resistance to *Pseudomonas syringae* pv. maculicola in *A. thaliana* (Grant et al., 1995). The initial RG1 and RG2, sequences were amplified from lettuce using degenerate primers.

TABLE 3

IDENTITIES OF RESISTANCE GENE HOMOLOGUES

| | | RG1 | RG2 | RG3 | RG4 | N gene | RPS2 |
|---|---|---|---|---|---|---|---|
| Lettuce | RG1 | *** | 22.7 | 15.0 | 29.2 | 25.4 | 23.8 |
| Lettuce | RG2 | | *** | 32.2 | 21.6 | 22.7 | 33.0 |
| Lettuce | RG3 | | | *** | 17.2 | 15.0 | 32.8 |
| Lettuce | RG4 | | | | *** | 44.3 | 22.7 |
| Tobacco | N gene | | | | | *** | 21.6 |
| Arabidopsis | RPS2 | | | | | | *** |

The regions homologous to the primers are included in this analysis as the genomic sequences for RLG1 and RLG2 were determined by IPCR. Interestingly, the genomic sequences for RLG1 exactly matched that of the primers used.

To obtain further evidence that we had amplified resistance genes, we amplified the regions flanking the NBSs of RLG1a and RLG2a by IPCR of BAC clones. These products were then directly sequenced without cloning to minimize the introduction of PCR artifacts. Sequence analysis of the 5' regions failed to detect any homology to known resistance genes. However, the sequence of the 3' region contained leucine-rich repeats (LRRs). When this sequence was used to search GENBANK using BLASTX, it detected identity to the Arabidopsis resistance gene, RPS2. This region does not contain as regular LRRs as in some resistance genes; however, the repeat structure seems to be consistent with that of the flax resistance gene, L6. Therefore, the presence of an LRR region is further evidence that the sequences we amplified using degenerate oligonucleotide primers are probably resistance genes.

The sequences of the IPCR products also provided the genomic sequences of the regions complementary to the sequences of the degenerate oligonucleotide primers. The genomic sequences for RLGL were identical to one of the primers in the mixture. The RLG sequences are resistance genes as supported by three criteria: the presence of multiple sequence motifs characteristic of resistance genes, genetic cosegregation with known resistance genes, and their existence as clustered multi-gene families. The presence of LRR regions in a similar position relative to the NBS as in cloned resistance genes provides stronger evidence than relying solely sequence similarity between NBS regions. The clustering of RLG sequences at the same position as the known clusters of resistance genes make them strong candidates for encoding resistance genes. The hybridization patterns and genetic distribution of the RLG sequences are similar to that of cloned resistance genes in other species. Most of these hybridize to small multigene families and preliminary genetic evidence indicates that they are clustered in the genome. Therefore, the degenerate primers that we designed from other resistance genes seemed to have been specific enough to amplify resistance genes rather than P-loop containing proteins in general.

What is claimed is:

1. An isolated nucleic acid molecule comprising an RG2B polynucleotide that encodes a polypeptide conferring resistance to downy mildew on a plant and hybridizes to SEQ ID NO: 89 under hybridization conditions that include a wash with 0.2×SSC at 65° C.

2. The nucleic acid molecule of claim 1, further comprising a promoter operably linked to the RG2B polynucleotide.

3. The nucleic acid molecule of claim 2, wherein the promoter is a constitutive promoter.

4. The nucleic acid molecule of claim 2, wherein the promoter is an inducible promoter.

5. The nucleic acid molecule of claim 2, wherein the promoter is a tissue-specific promoter.

6. The nucleic acid molecule of claim 1, wherein the RG2B polynucleotide is SEQ ID NO: 89.

7. The nucleic acid molecule of claim 1, wherein the RG2B polynucleotide encodes a RG2B polypeptide comprising a sequence with at least 80% sequence identity to SEQ ID NO:90.

8. The nucleic acid molecule of claim 7, wherein the RG2B polypeptide is SEQ ID NO: 90.

9. A transgenic plant comprising a heterologous expression cassette comprising a promoter operably linked to an RG2B polynucleotide that encodes a polypeptide conferring resistance to downy mildew on a plant and hybridizes to SEQ ID NO:89 under hybridization conditions that include a wash with 0.2×SSC at 65° C.

10. The transgenic plant of claim 9, wherein the plant is lettuce.

11. The transgenic plant of claim 9, wherein the RG2B polynucleotide is SEQ ID NO: 89.

12. The transgenic plant of claim 1, wherein the RG2B polynucleotide encodes an RG2B polypeptide with at least 80% sequence identity to SEQ ID NO:90.

13. The transgenic plant of claim 12, wherein the RG2B polypeptide comprises a sequence as shown in SEQ ID NO: 90.

14. The method of conferring resistance to downy mildew on a plant, the method comprising introducing into the plant an expression cassette comprising a promoter operably linked to an RG2B polynucleotide that hybridizes to SEQ ID NO: 89 under hybridization conditions that include a wash with 0.2×SSC at 65° C., thereby inducing expression of the RG2B polynucleotide sufficient to confer resistance to downy mildew.

15. The transgenic plant of claim 14, wherein the plant is lettuce.

16. The method of claim 14, wherein the RG2B polynucleotide is SEQ ID NO: 89.

17. The method of claim 14, wherein the RG2B polypeptide comprises a sequence with at least 80% sequence identity to SEQ ID NO: 90.

18. The method of claim 14, wherein the RG2B polypeptide comprises a sequence as shown in SEQ ID NO: 90.

* * * * *

SEQUENCE LISTING (1) GENERAL INFORMATION:

(iii) NUMBER OF SEQUENCES: 140

(2) INFORMATION FOR SEQ ID NO:1:

(i) SEQUENCE CHARACTERISTICS:
      (A) LENGTH: 4208 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..4208
      (D) OTHER INFORMATION: /note= "RLG1A"

(xi) SEQUENCE DESCRIPTION: SEQ ID NO:1:

```
ATCGTAACCG TTCGTACGAG ANCGCTGTCC CTCCTTCATC TTTTGTCATA TGTCATATTC      60

TCATNNATTN TGCCACATNT AATTTTGTGG TTATTTTAAA TTAATTTTTA TTCCACATGT     120

CATTTTATGA GTTTTTCTAT TTTATTGAGT TTCACATAAT ATTTAAATGT AATAACAATA     180

AATGCATATT TATTTTTCTT TAAATAAACG CATATAATAT ATAGATTAAA ATCATATAAT     240

ACATAGGTTA AACTCATATA ATACATATGT TCATCCCCAG TTTATTTATA TGTCTCATCC     300

TTAATTTATT TATTATTTAT TTATTAGAGT AGATGATCTT TGTGATATTA AAAATTTAAT     360

TTGTTCAAAA TTTAAAATTA TTAATAATCC CACAATTTGA ATAAAATTAA AAAAAATGGN     420

CCCACCATTA GTCCATCACT TTTTCAGCTC ATCAATATCG TGAGTATTCT CCTTCGTTTC     480

CACCCTAATC AATATTTCCA GCGAATGACA GACTCCTACG GCGTTTCTGA ATTTGCGTTC     540

CGACACTGTT CATTGAAGGA GATAATAAAT CAAATGGAGC TGCTCCAATG TTCATTGCTG     600

ATGAAAGGTG AATTGTATGT GAAGANAATG TCAGCGATCN ATCTCCATCC GGAACCCACC     660

ACATTATCAG TGTACCACCA AACCACTCAA AACGGYGGAA GTAGRRAKAC WRKAAAGTCA     720

TGAAGAATAG ATTATTTTTG TCCTCATGGG CTGACTGAGG AGCGGGTTTA GTTCATCATT     780

TTTCTTTGAN CAAAGAATTA TCGGTCCATC GAATTTTTAC ATCGACAAAG AAGTTTCACT     840

TCGCAATGTT TTGTTAAACA ATTTTTAATC TTTTTATCTT TTCGTTGAAA CTCCTCAATT     900

GCAACTTGCA ACTTGCAACT TTTGGGCCCA CAAATTTGTG GTGGGCGTTA ATTTAATCCA     960

CATATTCACT GTAAACAATA ATTCAAATCG ATCTCTGTTC ATCCAATTCA TCAACATCTC    1020
```

```
TTGATAATTG AAATCATTCA CGCTTCATCC ATTTCATCCA CATCTATACT ATATTCTCTG    1080

CTCTTATCAT ATTAAACGAT GGCTGAAATC GTTCTTTCTG CCTTCTTGAC AGTGGTGTTT    1140

GAAAAGCTGG CATYTGAAGC CTTGAAGAAG ATTGTTCGCT CCAAAAGAAT TGAATCTGAG    1200

CTTAAGAAAT TGAAGGAGAC ATTAGACCAA ATCCAAGATC TGCTTAACGA TGCTTCCCAG    1260

AAGGAAGTAA CTAATGAAGC CGTTAAAAGA TGGCTGAATG ATCTCCAACA TTTGGCTTAT    1320

GACATAGACG ACCTACTTGA TGATYTTGCA ACTGAAGCTG TTCAWCGTGA GTTGACCGAG    1380

GAGGGTGGAG CCTCCTCCAG TATGGTAAGA AAACTAATCC CAAGTTGTTG CACAAGTTTC    1440

TCACAAAGTA ATAGGATGCA TGCCAAGTTA GATGATATTG CCACCAGGTT ACAAGAACTG    1500

GTAGAGGCAA AAAATAATCT TGGTTTAAGT GTGATAACAT ATGAAAAGCC AAAAATTGAA    1560

AGGTATGAGG CGTCTTTGGT AGATGAAAGC GGTACTGTCG GACGTGAAGA TGATAAGAAA    1620

AAATTGCTGG AGAAGCTGTT GGGGGATAAA GATGAATCAG GGAGTCAAAA CTTCAGCATC    1680

GTGCCCATAG TTGGTATGGG TGGAGTTGGT AAAACAACTC TAGCTAGACT TTTGTATGAT    1740

GAAAAGAAAG TGAAGGATCA CTTCGAACTC AGGGCTTGGG TTTGTGTTTC TGATGAGTTC    1800

AGTGTTCCCA ATATAAGCAG AGTTATTTAT CAATCTGTGA CTGGGAAAAA GAAGGAGTTT    1860

GAAGACTTAA ATCTGCTTCA AGAAGCTCTT AAAGAGAAAC TTAGGAACCA GCTATTTCTA    1920

ATAGTTTTGG ATGATGTGTG GTCTGAAAGC TATGGTGATT GGGAGAAATT AGTGGGCCCA    1980

TTCCTTGCGG GGTCTCCTGG AAGTAGAATA ATCATGACAA CTCGGAAGGA GCAATTGCTC    2040

AGAAAGCTGG GCTTTTCTCA TCAAGACCCT CTGGAGGGTC TATCACAAGA TGATGCTTTG    2100

TCTTTGTTTG CTCAACACGC ATTTGGTGTA CCAAACTTTG ATTCACATCC AACACTAAGG    2160

CCACATGGAG AACTGTTTGT GAAGAAATGT GATGGCTTAC CTCTAGCYTT AAGAACACTT    2220

GGAAGGTTAT TAAGGACAAA AACAGACGAG GAACAATGGA AGGAGCTGTT GGATAGTGAG    2280

ATATGGAGGT TAGGAAAGAG CGATGAGATT GTTCCGGCTC TTAGACTAAG CTACAATGAT    2340

CTTTCTGCCW CTTTGAAGCT RTTRTTTGCA TAYTGCTCCT TGTTTCCCAA GGACTATGAG    2400

TTTGACAAGG AGGAGTTGAT TCTATTGTGG ATGGCAGAAG GGTTTTTGCA CCAACCAACT    2460

AYAAACAAGT CAAAGCAACG KTTGGGTCTT GAATATTTTR AAGAGTTRTT GTCAAGRTCR    2520

TTTTTTCAAC ATGCTCCTAA TRRCAAATCS TTGTTTGTGA TGCATGACCT AATGAATGAT    2580

TTGGCTACAT TTGTTGCTGG AGAATTTTTT TCAAGGTTAG ACATAGAGAT GAAGAAGGAA    2640

TTTAGGATGS AATCTTTGGA RAAGCACCGM CATATGTCAT TTGTATGTGA GRATTACATA    2700

GGTTACAAAA RGTTCGAGCC ATTTAGAGGA GCTAAAAATT TGAGAACATT TTTAGCATTG    2760

TCTGTTGGGG TGGTAGAAGA TTGGAAGATG TTTTACTTAT CAAACAAGGT CTTGAATGAC    2820

WTACTTCARG ATTTACCATT GTTAAGGGTC CTRAKTTTGA TTRRTCTTAY AATAASYRAG    2880

GTACCARAAK TCGTSGGTAG TATGAACCAC TTGCGGTATC TTAATCTATC WGRAACTTWA    2940

ATCACMCATT TACCGGAAWA TKTCTGCAAT CTTTATAATT TACARACCCT GATTGTKTCT    3000

GGCTGTGAMT ATTTAGTTAA KTTGCCCAAR ACCTTCTCAA ASCTTAAAAA TTTGCASCAT    3060

TTTGACATGA GGGRTACTCC KAAKTTRAAR AACATGCCCT TARGGATTGG TGARTTGAAA    3120

ARTCTACAAA CTCTCTTYMG TAACATTGGC ATAGCAATAA CCGAGCTTAA GAACTTGCAM    3180

AAYCTCCATG GGAAARTTTG TATTGGCGGG CTGGGAAAAA TGGAAAATGC MGTKGGATGC    3240

ACGTTAAGCG AACTTGTCTC AAAAAAGGTT WAATGARTTA NAAACTGGRW TKGGGGGTGA    3300

TRAATTTAAT GTTTTCCGAA ATGGGAACAC TTGAAAAAGA AGTCCTCAAT GAAGTGATGC    3360

CTCATAATGG TACTCTANAA AAACCCANA ATTATGTCTA TAGGGGGTAT AGAGTTTCCA    3420
```

```
AATTGGGTTG GTTNCACTAA GGGTTTCTGA AACTAGAGAT GTGTTCATGG TGTATGAAAA      3480

AGANTGTTTT ACGTAGTTTC ATCAATCACC AAGTGGGAAA TAGATGATAT TTTCAGGGCY      3540

TACTGATGAG ATGTGGAGAG GTATGATAGG GTNTCTTGGG GCGGTAGAAG AAATAAGCAT      3600

CCATTCTTGT AATGAAATAA GATATYTGTG GGAATCAGAA GCAGAGGCAA GTAAGGTTCT      3660

TATGAATTTA AAGAAGTTGG ATTTAGGTGA ATGTGAAAAT TTGGTGAGTT TAGGGGAGAA      3720

AAAGGAGGAT AATCATAATA TTAATAGTGG GAGCAGCCTA ACATCTTTTA GGAGGTTGAA      3780

TGTATGGAGA TGTAACAGCT TGGAGCATTG CAGGTGTCCA GATAGCATGG AGAATTTGTA      3840

TATGCACATG TGTGATTCAA TNACATCCGT CTCCTTCCCA ACAGGAGGAG GACAGAAGAT      3900

CAAGTCACTT ACCATCACTG ATTGCAAGAA GCTTTCGGAA GAGGAGTTGG GAGGACGAGA      3960

GAGGACAAGA GTGCTTATAA ACTCAAAAAT GCAGATGCTT GAATCAGTAG ATATACGTAA      4020

TTGGCCAAAT CTGAAATCTA TCAGTGAATT GAGTTGCTTC ATTCACCTGA ACAGATTATA      4080

TATATCAAAC TGTCCGAGTR TGGAGTCATT TCCTGACCAT GAGTTGCCAA ATCTCACCTC      4140

CTTAACAGAT CGAAGGAGAG GACAGCGATT TTCGTACGAA CGGTTACGAT TCGACTGGCC      4200

GTCGTTTT                                                              4208
```

(2) INFORMATION FOR SEQ ID NO:2:

(i) SEQUENCE CHARACTERISTICS:
        (A) LENGTH: 2353 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..2353
        (D) OTHER INFORMATION: /note= "RLG1B"

(xi) SEQUENCE DESCRIPTION: SEQ ID NO:2:

```
AACCGTTCGT ACGAGAATCG CTGTCCTCTC CTTCCTGTAA TATAATGATA AGAAAAAATA       60

TGATTAAAGG TTTAAATCCA AAATCCATTA TTCCACCGGT GATATGATGC ACTAGCTGTA      120

GTATGCAAAA ACAGTATTAT AAATGCTAAC CAAAACAGCA GCTAAGAAAC AATATAAATA      180

ATGGTTTGAA TCGTCCTTTC TCCGTACACT CATTTCTTCC AAATCCCTAT CATTCATACA      240

TACAAGTGCT CCCATATTAG GTTTTCACTA TAAGCAATGG CTGAAATCCT TGGTTCTGCG      300

TTCTTTGCGG TGTTCTTTGA AAAGCTTGCT TCTGAAGCCT TGAAGAGGGT TGCTTGCTCC      360

AAAGTAATTG ACAAGGAGCT CGAGAAATTG AATAGCTCAT GAATCAATAT AAAAGCTCTG      420

CTCAATGATG CTTCTCAGAA GGAAATAAGT AAGGAAGCTG TTAAAGAATG GTTGAATGCT      480

CTTCAACATT TGCCTTACGA CATAGATGAT CTACTTGGCG ATTTGGCAAC CAAAGCTATC      540

CATCGTAAGT TCTCTGAGGA ATACGGGGCC ACCATCAACA AGGTACGAAA GTTAATTCCA      600

TCTTGTTTCT CTAGTTTGTC AAGTACTAAG ATGCGCAACA AGATACATAA TATTACCAGC      660

AAGTTACAAG AACTATTAGA AGAGAGAAAT AATCTTGGAT TATGTGAAAT TGGTGAAAGC      720

CGAAAACTTC GAAATAGAAA ATCAGAGACC TCTNTGCTAG ATCCATCTAG TATTGTTGGA      780

CGCACAGATG ATAAGGAAGC GTTGCTTCTC AAGCTATATG AACCATGTGA TAGAAACTTT      840

AGCATCTTGC CNATAGTTGG TATGGGTGGG TTAGATAAGA CCACTTTAGG TAGACTTTTG      900

TATGATNAAA TGCAAGTGAA GGATCACTTC GAACTCAAGG CGTGGGTTTG TGTTTCTGAT      960
```

```
GAGTTTGATA TCTTCGGTAT AAGCAAAACC ATTTTCGAAT CGATAGAGGG GGGAAACCAA    1020

GAGTTTAAGG ATTTAAATCT GCTTCAGGTG GCTTTAAAGG AGAAAATCTC AAAGAAACGA    1080

TTTCTTGTTG TTCTTGATGA TGTATGGAGC GAGAGCTATA CTGATTGGGA AATTCTAGAA    1140

CGTCCATTTC TAGCAGGAGC ACCAGGAAGT AAAGTAATCA TCACAACCCG CAAGTTGTCG    1200

TTGCTAAACC AATTGGGTCA TGATCAACCA TACCAATTGT CTGATTTGTC ACATGACAAT    1260

GCTCTATCCT TATTTTGTCA ACACGCATTT GGTGTAAATA GCTTTGATTC ACATCCGATA    1320

CTTAAACCAC ATGGTGAAGG TATTGTTGAA AAATGTGATG GTTTGCCATT GGCTTTGATT    1380

GCACTTGGGA GGTTATTGAG GACAAAAAGA GATGAGGAAG AATGGAAGGA ACTATTGAAT    1440

AGTGAGATAT GGAGGTTAGG AAAGAGAGAT GAGATTATTC CGGYTCTTAG ACTAAGCTAT    1500

AATGATCTTT CTGCCTCTTT GAAGCAGTTG TTTGCATATT GCTCCTTGTT CCCCAAAGAC    1560

TATGTGTTCA ACAAGGAGAA GTTGATTTTA TTATGGATGG CAGAAGGGTT TTTGCACAAT    1620

GAAAATACAA ACAAGTCAAT GGAACGCTTA GNTCTTGAAT ATTTTGACGA CTTGTTGTCA    1680

AGGTCATTTT TTCAACATGC ACTCGATGAC AAATCGTTGT TTGTGGTGCA CGACCTCATG    1740

AATGACTTGG CCACATCTGT TGCTGGAGAT TATTTTTTAA GATTAGACAT TGAAATGAAA    1800

AAGGAAGCTT TGGAAAAATA CCGACATATG TCATTTGTTT GTGAGAGTTA CATGGTTTAC    1860

AAAAGGTTCG AACCATTTAA AGGAGCTAAA AAATTGAGAA CTTTCTTAGC AATGCCTGTT    1920

GGGATGATAA AAAGTTGGAC AACATTTTAC TTATCAAATA AGGTCCTTGA TGACTTACTT    1980

CACGAATTAC CATTGTTGAG AGTTCTAAGT TTGAGTTATC TTAGCATCAA GGAGGTACCT    2040

GAAATAATAG GCAATTTGAA ACACTTGCGG TATCTTAATT TATCACACAC GAGTATCACA    2100

CATTTACCAG AAAATGTCTG CAATCTTTAC AACTTACAAA CATTGATCCT TTGTGGCTGT    2160

TGTTTTATAA CCAAGTTTCC CAACAACTTC TTAAAGCTTA GAAATTTACG GCATTTGGAC    2220

ATTAGCGATA CTCCCGGTTT GAAGAAGATG TCCTCGGGGA TTGGTGAATT GAAGAACCTA    2280

CACACYCTCT CCAAGCTCAT TATTGGAGGT GAAAATAGAC TAAACGAGCT AAGAACTTA     2340

CAAAATCTCC ATG                                                      2353

(2) INFORMATION FOR SEQ ID NO:3:

(i) SEQUENCE CHARACTERISTICS:
        (A) LENGTH: 1036 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1036
        (D) OTHER INFORMATION: /note= "RLG1C"

(xi) SEQUENCE DESCRIPTION: SEQ ID NO:3:

TCCCGTGCAA CGTNTATCAT TCAGAAGNGC CCAAAGACCA NAGATNTGTT TAANGNTGNT      60

TNTCAGAAGG AAGTAATTGA TGAAGCTGTN AAAAGATGGC TGATTGATNT CCAACAATTG     120

GCTTACGACA CTGANGACNA ACTTGATGAT NTCGCAACAG AAGCTATTCA TCGTGAGTTG     180

ATCCGTGAAA CTGGAGCTTC CNCCAGCATG GTAAGAAAGC TAATCCCAAG TTGTTGCACA     240

AGTTTCTCAC AAAGTAATAG GATGCATGCC AGGTTAGATG ATATTGCCGC TAAGTNACAA     300

GAACTGGTAG AGGCGAAAAA TAATCTTGGT TTAAGTGTGA TAACATACGA AAAACCCAAA     360

ATTGAAAGAG ATGAGGCGTN TTTGGTAGAT GCAAGTGGTA TCATTGGACG TGAAGATGAT     420
```

```
AAGAAAAAAT TGCTTCAGAA GCTGTTGGGG GATACTTATG AATCAAGTAG TCAAAACTTC      480

AACATCGTGC CCATAGTTGG TATGGGTGGG GTAGGTAAAA CAACTCTAGC TAGACTTTTG      540

TATGATGAAA AAAAGTGAA GGATCACTTC GAACTCAGGG TTTGGGTTTG TGTTTCTGAT       600

GAGTTCAGTG TTCCCAATAT AAGCAGAGTT ATCTATCAAT CTGTGACTGG TGAAAACAAA      660

GAATTTGCAG ATTTAAATCT GCTTCAAGAA GCCCTTAAAG AGAAACTTCA GAACAAACTA      720

TTTCTAATAG TTTTAGATGA TGTATGGTCT GAAAGCTATG GTGATTGGGA GAAATTAGTG      780

GGCCCATTTC ATGCTGGGAC TTCTGGAAGT AGAATAATCA TGACTACTCG GAAGGAGCAA      840

TTACTCAAAC AGCTGGGTTT TTCTCATGAA GACCCTCTGC ATAGTATAGA CTCCCTGCAA      900

CGTCTATCAC AAGAAGATGC TTTGTCTTTG TTTTCTCAAC ACGCATTTGG TGTACCTAAC      960

TTTGATTCAC ATCCAACACT AAGGCCATAT GGGGAACAGT TTGTGAAAAA ATGTGGGGGA     1020

TTGCCTTTGG CCTTGT                                                     1036

(2) INFORMATION FOR SEQ ID NO:4:

(i) SEQUENCE CHARACTERISTICS:
        (A) LENGTH: 946 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..946
        (D) OTHER INFORMATION: /note= "RLG1D"

(xi) SEQUENCE DESCRIPTION: SEQ ID NO:4:

CNTACCNTTC TACGAGATCG CTGTCCCTCC TCGATCTGCT TAACGATGCT TCCCAGAAGG       60

AAGTNACTAA TGAAGCCGTT AAAAGATGGC TGAATGATCT CCAACATTTG GCTTATGACA      120

TANACGACCT ACTTGATGAT CTTGCAACAS AAAGCTATTC NTCSTGAGTT GACCGANGAA      180

GGTGGAGCCT CCACCAGTAT GGTAAGAAAA CTAATCCCAA GTTGTTGCAC AAGTTTCTCA      240

CAAAGTTATA GGATGCATGC CAAGTTAGAT GATATTGCCA CCAGGTTACA AGAACTGGTA      300

GAGGCAAAAA ATAATCTTGG TTTAAGTGTG ATAACATATG AAAAGCCCAA AATTGAAAGG      360

TATGAGGCAT CTTTGGTAGA CGAAAGTGGT ATTTTTGGAC GTTNAGATGA TNAGAAAAAA      420

TTGATGGAGA AGCTGTTGGA GGATAAAGAT GAATCCGGAG TCNAAACTTC AGCATCCTGC      480

CCATAATTGG TATGGGTGGA GTTGGCNAAA CAACTCTAGC TAGACTCTTG TTTGATGAAA      540

AGACAGTGAA GGATCACTTC GAACTCAGGG CTTGGGTTTG TGTTTCTGAT GAATTCAGTA      600

TTCTCAACAT AAGCAAAGTT ATCTATCAAT CTGTGACCGG GGAAAAGAAA GAGTTTGAAG      660

ACTTAAATCT GCTTCAAGAA GCTCTTAGAG GGAAACTACA AAACAAACTA TTTCTAATAG      720

TTTTGGATGA TGTATGGTCG GAAAGCTATG GTGATTGGGA GAAATTAGTG GGCCCATTTC      780

ATGCTGGGAC TTCTGGAAGT AGAATAATCA TGACTACTCG GAAGGAGCAA TTACTCAAAC      840

AGTTGGGTTT TTCTCATCAA GACCCTCTGC GTTGTATAGA CTCCCTGCAA CGTCTATCAC      900

AAGATGATGC TTTGTCTTTG TTTGCTCAAC ACGCATTTGG TGWCCA                    946

(2) INFORMATION FOR SEQ ID NO:5:

(i) SEQUENCE CHARACTERISTICS:
        (A) LENGTH: 475 base pairs
        (B) TYPE: nucleic acid
```

(C) STRANDEDNESS: single
        (D) TOPOLOGY: linear (ii) MOLECULE TYPE: DNA (ix) FEATURE:
        (A) NAME/KEY: -
        (B) LOCATION: 1..475
        (D) OTHER INFORMATION: /note= "RLG1E"

(xi) SEQUENCE DESCRIPTION: SEQ ID NO:5:

```
TCTAGCTAGA CTTTTGTATG ACGAGATGCA AGAGAAGGAT CACTTCGAAC TCAAGGCGTG     60

GGTTTGTGTT TCTGATGAGT TTGATATATT CAATATAAGC AAAATTATTT TCCAATCGAT    120

AGGAGGTGGA AACCAAGAAT TTAAGGACTT AAATCTCCTT CAAGTAGCTG TAAAAGAGAA    180

GATTTCAAAG AAACGATTTC TACTTGTTCT TGATGATGTT TGGAGTGAAA GCTATGCGGA    240

TTGGGAAATT CTGGAACGCC CATTTCTTGC AGGGGCAGCC GGAAGTAAAA TTATCATGAC    300

GACCCGGAAG CAGTCATTGC TAACCAAACT CGGTTACAAG CAACCTTACA ACCTTTCCGT    360

TTTGTCACAT GACAGTGCTC TCTCTTTATT CTGTCAGCAT GCATTGGGTG AAGATAACTT    420

CGATTCACAT CCAACACTTA AACCACATGG CGAAGGCATT GTTGAAAAAT GTGCT         475
```

(2) INFORMATION FOR SEQ ID NO:6:

(i) SEQUENCE CHARACTERISTICS:
        (A) LENGTH: 1662 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1662
        (D) OTHER INFORMATION: /note= "RLG1F"

(xi) SEQUENCE DESCRIPTION: SEQ ID NO:6:

```
ATTTTCNGCT CNAAACAAAN AAAAGCAATG GCTGAAATCT TTCTTTCNGC ATTCTAGACC     60

AGTATTCTTT GAAAAGNTGG CTTCTGAAGC CTTGAAGAAG ATCGCTCGCT TCCATCGGAT    120

TGATTCTGAG CTCAAGAAAC TGAAGAGGTC ATTAATCCAG ATCAGATCTG TGCTTAATGA    180

TGCTTCTGAG AAGGAAATAA GTGATGAAGC TGTTAAAGAA TGGCTGAATG GTCTCCAACA    240

TTTGTCTTAC GACATAGACG ACCTACTTGA TGATTTGGCA ACCGAAACTA TGCATCGTGA    300

GTTGACCCAC GGATCTGGAG CCTCCACCAG CTTGTAAGAA AGATAATCCC AACTTGTTGC    360

ACAGATTTCT CACTAAGTAG TAAGATGCGT AACAAGTTAG ATAATATTAC CATCAAGTTA    420

CAAGAACTGG TAGAGGAAAA AGATAATCTT GGCTTAAGTG TGAAAGGTGA AGCCCAAAA    480

CATACCAACA GAAGATTACA GACCTCTTTG GTAGATGCAT CTAGCATTAT TGGTCGTGAA    540

GGTGATAAGG ATGCATTGCT CCATAAGCTG CTGGAGGATG AACCAAGTGA TAGAAACTTT    600

AGCATCGTGC AATAGTTGG TATGGGTGGT GTGGGTAAGA CGACTCTAGC TAGACTTTTG    660

TATGACGAGA TGCAAGAGAA GGATCACTTC GAACTCAAGG CGTGGGTTTG TGTTTCTGAT    720

GAGTTTGATA TCTTCAATAT AAGCAAAGTT ATCTTCCAAT CGATAGGTGG TGGARACCAA    780

GAATTTAAGG ACTTAAATCT CCTTCAAGTA GCTGTAAAAG AGAAGATTTC AAAGAAACGA    840

TTTCTWYTTG TTCTGGATGA TGTTTGGAGT GAAAGCTATA CAGAATGGGA AATTCTAGCA    900

CGTCCATTTC TTGCAGGGGC ACCAGGAAGT AAGATTATCA TGACGACCCG GAAGTTGTCG    960

TTGCTAACCA AACTCGGTTA CAATCAACCT TACAACCTTT CSGTTTTGTC ACATGATAAT   1020
```

```
GCTYTGTCTT TATTCTGTCA GCAYGCATTG GGTGAAGATA ACTTCGATTC ACATCCAACA    1080

CTTAAACCAC ASGGTGAAAG TATTGTTGAA AAATGTGACG GTTTACCATT GGCTTTRATT    1140

GCACTTGGGA GRTTGTTGAR GACAAAAACA GATGAGGAAG AATGGAARGA AGTGTTGAAT    1200

AGTGAAATAT GGGGGTCAGG AAAGGGAGAT GAGATTGTTC CGGCTCTTAA ACTAAGCTAC    1260

AATGATCTCT CTGCCTCTTT GAAGAAGTTG TTTGCATACT GCTCCTTGTT CCCAAAAGAC    1320

TATGTGTTCG ATAAGGAGGA GTTGATTTTG TTGTGGATGG CAGAAGGGTT TTTGCACCAA    1380

TCAACCACAA GCAAGTCBAT GGAACGCTTG GGHCATGAAG GTTTTGATGA ATTGTTGTCA    1440

AGATCATTTT TTCAACATGC CCCTGATGCC AAATCGATGT TTGTGATGCA TGACCTGATG    1500

AATGACTTGG CHACATCTGT TGCTGGAGAT TTTTTTTCAA GGATGGACAT TGAGATGAAG    1560

AARGAATTTA GGAAGGAAGC TTTGSAAAAG YAYCGCCATA TGTCAWTTGT TTGTGAKGAT    1620

TACATGGTKK ACAAAAGGTT CRAGCCATTS ACAAGGAGCT AG                      1662
```

(2) INFORMATION FOR SEQ ID NO:7:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..384
        (D) OTHER INFORMATION: /note= "RLG1G"

(xi) SEQUENCE DESCRIPTION: SEQ ID NO:7:

```
GTGAAGGATC ACTTCGAACT CAGGGCTTGG GTTTGTGTTT CTGATGAATT TAATATCCTC      60

AATATAAGCA AAGTAATTTA TCAATCTGTA ACCGGGGAAA AAAAGGAGTT TGAAGACTTA     120

AATCTGCTTC AAGAAGCTCT TAAAGAAAAA CTTTGGAATC AGTTATTTCT AATAGTTCTG     180

GATGATGTGT GGTCTGAAAG CTATCGTGAT TGGGAGAAAT TAGTGGGCCC ATTTTTTTCG     240

GGGTCTCCTG GAAGTATGAT TATCATGACA ACTCGGAAGG AGCAATTGCC AAGAAAGCTG     300

GGTTTTCCTC ATCAAGACCC TTTGCAAGGT CTATCACATG ACGATGCTTT GTCTTTGTTT     360

GCTCAACACG CATTTGGTGT ACCA                                            384
```

(2) INFORMATION FOR SEQ ID NO:8:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..475
        (D) OTHER INFORMATION: /note= "RLG1H"

(xi) SEQUENCE DESCRIPTION: SEQ ID NO:8:

```
TCTAGCTAGA CTTTTGTATG AGGAAATGCA AGGGAAGGAT CACTTCGAAC TCAAGGCGTG      60

GGTATGTGTT TCTGATGAGT TTGATATCTT CAATATAAGC AAAATTATCT TACAATCGAT     120

AGGTGGTGGA AACCAAGAAT TTACGGACTT AAACCTGCTT CAAGTAGCTT TAAAAGAGAA     180
```

```
GATCTCAAAG AAAAGATTTC TTCTTGTTCT TGATGATGTT TGGAGTGAAA GCTATACCGA      240

TTGGGAAATT CTAGAACGCC CATTTCTTGC AGGGGCACCT GGAAGTAAGA TTATTATCAC      300

CACCCGGAAG CTGTCATTGT TAAACAAACT CGGTTACAAT CAACCTTACA ACCTTTCGGT      360

TTTGTCACAT GAGAATGCTT TGTCTTTATT CTGTCAGCAT GCATTGGGTG AAGATAACTT      420

CAATTCACAT CCAACACTTA AACCACATGG CGAAGGTATT GTTGAAAAAT GTGAT          475

(2) INFORMATION FOR SEQ ID NO:9:

(i) SEQUENCE CHARACTERISTICS:
          (A) LENGTH: 499 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..499
          (D) OTHER INFORMATION: /note= "RLG1I"

(xi) SEQUENCE DESCRIPTION: SEQ ID NO:9:

TCTAGCTAGA CTTGTGTATG ATGAGATGCA AGAGAAGGAT CACTTTGAAC TCAAGGCGTG       60

GGTATGTGTT TCTGATGAGT TTGATATATT CAATATAAGC AAAATTATTT TCCAATCGAT      120

AGGAGGTGGA AACCAAGAAT TTAAGGACTT AAACCTCCTT CAAGTAGCTG TAAAAGAGAA      180

GATTTTAAAG AAACGATTTC TTCTTGTTCT TGACGACGTT TGGAGTGAAA GCTATGCCGA      240

TTGGGAAATT NTGGAACGCC CATTTCTTGC AGGGGCAGCC GGAAGTAAAA TTATCATGAC      300

AACCCGAAAG CAGTCATTGC TAACCAAACT CGGTTACAAG CAACCTTACA ACCTTTCCGT      360

TTTGTCACAT GACAGTGCTC TGTCTTTATT CTGTCAGCAT GCATTGGGTG AAGGTAACTT      420

CGATTCACAT CCAACACTTA AACCACATGG CGAAGGCATT GTTGAAAAAT GTGCTGGATT      480

GCCATTGGCA TTGTCGACA                                                  499

(2) INFORMATION FOR SEQ ID NO:10:

(i) SEQUENCE CHARACTERISTICS:
          (A) LENGTH: 544 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..544
          (D) OTHER INFORMATION: /note= "RLG1J"

(xi) SEQUENCE DESCRIPTION: SEQ ID NO:10:

TACTACTACT AGAATTCGGT GTTGGTAAGA CGACTCTAGC TAGACTTTTG TATGAGGAAA       60

TGCAAGGGAA GGATCACTTC GAACTTAAGG CGTGGGTATG TGTTTCTGAT GAGTTTGATA      120

TCTTCAATAT AAGCAAAATT ATCTTACAAT CGATAGGTGG TGGAAACCAA GAATTTACGG      180

ACTTAAACCT GCTTCGAGTA GCTTTAAAAG AGAAGATCTC AAAGAAAAGA TTTCTTCTTG      240

TTCTTGATGA TGTTTGGAGT GAAAGCTATA CCGATTGGGA AATTNTAGAA CGCCCATTTC      300

TTGCAGGGGC ACCTGGAAGT AAGATTATTA TCACCACCCG GAAGCTGTCA TTGTTAAACA      360

AACTCGGTTA CAATCAACCT TACAACCTTT CGGTTTTGTC ACATGAGAAT GCTTTGTCTT      420

TATTCTGTCA GCATGCATTG GGTGAAGATA ACTTCAATTC ACATCCAACA CTTAAACCAC      480
```

```
ATGGCGNAGG TATTGTTGAA AAATGTGATG GATTGCCATT GGCATTGTCG ACATGATGAT      540

GATG                                                                 544
```

(2) INFORMATION FOR SEQ ID NO:11:

(i) SEQUENCE CHARACTERISTICS:
        (A) LENGTH: 1402 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1402
        (D) OTHER INFORMATION: /note= "RLG1A amino acids"

(xi) SEQUENCE DESCRIPTION: SEQ ID NO:11:

```
Ile Val Thr Val Arg Thr Arg Xaa Leu Ser Leu Leu His Leu Leu Ser
1               5                   10                  15

Tyr Val Ile Phe Ser Xaa Ile Xaa Pro His Xaa Ile Leu Trp Leu Phe
            20                  25                  30

Xaa Ile Asn Phe Tyr Ser Thr Cys His Phe Met Ser Phe Ser Ile Leu
        35                  40                  45

Leu Ser Phe Thr Xaa Tyr Leu Asn Val Ile Thr Ile Asn Ala Tyr Leu
    50                  55                  60

Phe Phe Phe Lys Xaa Thr His Ile Ile Tyr Arg Leu Lys Ser Tyr Asn
65                  70                  75                  80

Thr Xaa Val Lys Leu Ile Xaa Tyr Ile Cys Ser Ser Pro Val Tyr Leu
                85                  90                  95

Tyr Val Ser Ser Leu Ile Tyr Leu Leu Phe Ile Tyr Xaa Ser Arg Xaa
            100                 105                 110

Ser Leu Xaa Tyr Xaa Lys Phe Asn Leu Phe Lys Ile Xaa Asn Tyr Xaa
        115                 120                 125

Xaa Ser His Asn Leu Asn Lys Ile Lys Lys Asn Gly Pro Thr Ile Ser
    130                 135                 140

Pro Ser Leu Phe Gln Leu Ile Asn Ile Val Ser Ile Leu Leu Arg Phe
145                 150                 155                 160

His Pro Asn Gln Tyr Phe Gln Arg Met Thr Asp Ser Tyr Gly Val Ser
                165                 170                 175

Glu Phe Ala Phe Arg His Cys Ser Leu Lys Glu Ile Ile Asn Gln Met
            180                 185                 190

Glu Leu Leu Gln Cys Ser Leu Leu Met Lys Gly Glu Leu Tyr Val Lys
        195                 200                 205

Xaa Met Ser Ala Ile Xaa Leu His Pro Glu Pro Thr Thr Leu Ser Val
    210                 215                 220

Tyr His Gln Thr Thr Gln Asn Gly Gly Ser Arg Xaa Thr Xaa Lys Ser
225                 230                 235                 240

Xaa Arg Ile Asp Tyr Phe Cys Pro His Gly Leu Thr Glu Glu Arg Val
                245                 250                 255

Xaa Phe Ile Ile Phe Leu Xaa Xaa Lys Asn Tyr Arg Ser Ile Glu Phe
            260                 265                 270

Leu His Arg Gln Arg Ser Phe Thr Ser Gln Cys Phe Val Lys Gln Phe
        275                 280                 285

Leu Ile Phe Leu Ser Phe Arg Xaa Asn Ser Ser Ile Ala Thr Cys Asn
    290                 295                 300
```

-continued

Leu Gln Leu Leu Gly Pro Gln Ile Cys Gly Gly Arg Xaa Phe Asn Pro
305                 310                 315                 320

His Ile His Cys Lys Gln Xaa Phe Lys Ser Ile Ser Val His Pro Ile
            325                 330                 335

His Gln His Leu Leu Ile Ile Glu Ile Ile His Ala Ser Ser Ile Ser
            340                 345                 350

Ser Thr Ser Ile Leu Tyr Ser Leu Leu Leu Ser Tyr Xaa Thr Met Ala
            355                 360                 365

Glu Ile Val Leu Ser Ala Phe Leu Thr Val Val Phe Glu Lys Leu Ala
    370                 375                 380

Xaa Glu Ala Leu Lys Lys Ile Val Arg Ser Lys Arg Ile Glu Ser Glu
385                 390                 395                 400

Leu Lys Lys Leu Lys Glu Thr Leu Asp Gln Ile Gln Asp Leu Leu Asn
                405                 410                 415

Asp Ala Ser Gln Lys Glu Val Thr Asn Glu Ala Val Lys Arg Trp Leu
            420                 425                 430

Asn Asp Leu Gln His Leu Ala Tyr Asp Ile Asp Leu Leu Asp Asp
            435                 440                 445

Xaa Ala Thr Glu Ala Val Xaa Arg Glu Leu Thr Glu Glu Gly Gly Ala
450                 455                 460

Ser Ser Ser Met Val Arg Lys Leu Ile Pro Ser Cys Cys Thr Ser Phe
465                 470                 475                 480

Ser Gln Ser Asn Arg Met His Ala Lys Leu Asp Asp Ile Ala Thr Arg
            485                 490                 495

Leu Gln Glu Leu Val Glu Ala Lys Asn Asn Leu Gly Leu Ser Val Ile
            500                 505                 510

Thr Tyr Glu Lys Pro Lys Ile Glu Arg Tyr Glu Ala Ser Leu Val Asp
            515                 520                 525

Glu Ser Gly Thr Val Gly Arg Glu Asp Lys Lys Lys Leu Leu Glu
            530                 535                 540

Lys Leu Leu Gly Asp Lys Asp Glu Ser Gly Ser Gln Asn Phe Ser Ile
545                 550                 555                 560

Val Pro Ile Val Gly Met Gly Gly Val Gly Lys Thr Thr Leu Ala Arg
            565                 570                 575

Leu Leu Tyr Asp Glu Lys Lys Val Lys Asp His Phe Glu Leu Arg Ala
            580                 585                 590

Trp Val Cys Val Ser Asp Glu Phe Ser Val Pro Asn Ile Ser Arg Val
            595                 600                 605

Ile Tyr Gln Ser Val Thr Gly Glu Lys Lys Glu Phe Glu Asp Leu Asn
    610                 615                 620

Leu Leu Gln Glu Ala Leu Lys Glu Lys Leu Arg Asn Gln Leu Phe Leu
625                 630                 635                 640

Ile Val Leu Asp Asp Val Trp Ser Glu Ser Tyr Gly Asp Trp Glu Lys
                645                 650                 655

Leu Val Gly Pro Phe Leu Ala Gly Ser Pro Gly Ser Arg Ile Ile Met
            660                 665                 670

Thr Thr Arg Lys Glu Gln Leu Leu Arg Lys Leu Gly Phe Ser His Gln
            675                 680                 685

Asp Pro Leu Glu Gly Leu Ser Gln Asp Ala Leu Ser Leu Phe Ala
            690                 695                 700

Gln His Ala Phe Gly Val Pro Asn Phe Asp Ser His Pro Thr Leu Arg
705                 710                 715                 720

-continued

```
Pro His Gly Glu Leu Phe Val Lys Lys Cys Asp Gly Leu Pro Leu Ala
            725                 730                 735

Leu Arg Thr Leu Gly Arg Leu Leu Arg Thr Lys Thr Asp Glu Glu Gln
            740                 745                 750

Trp Lys Glu Leu Leu Asp Ser Glu Ile Trp Arg Leu Gly Lys Ser Asp
            755                 760                 765

Glu Ile Val Pro Ala Leu Arg Leu Ser Tyr Asn Asp Leu Ser Ala Xaa
            770                 775                 780

Leu Lys Leu Leu Phe Ala Tyr Cys Ser Leu Phe Pro Lys Asp Tyr Glu
785                 790                 795                 800

Phe Asp Lys Glu Glu Leu Ile Leu Leu Trp Met Ala Glu Gly Phe Leu
            805                 810                 815

His Gln Pro Thr Xaa Asn Lys Ser Lys Gln Arg Leu Gly Leu Glu Tyr
            820                 825                 830

Phe Xaa Glu Leu Leu Ser Arg Ser Phe Phe Gln His Ala Pro Asn Xaa
            835                 840                 845

Lys Ser Leu Phe Val Met His Asp Leu Met Asn Asp Leu Ala Thr Phe
            850                 855                 860

Val Ala Gly Glu Phe Phe Ser Arg Leu Asp Ile Glu Met Lys Lys Glu
865                 870                 875                 880

Phe Arg Met Xaa Ser Leu Glu Lys His Arg His Met Ser Phe Val Cys
            885                 890                 895

Glu Xaa Tyr Ile Gly Tyr Lys Xaa Phe Glu Pro Phe Arg Gly Ala Lys
            900                 905                 910

Asn Leu Arg Thr Phe Leu Ala Leu Ser Val Gly Val Val Glu Asp Trp
            915                 920                 925

Lys Met Phe Tyr Leu Ser Asn Lys Val Leu Asn Asp Xaa Leu Gln Asp
            930                 935                 940

Leu Pro Leu Leu Arg Val Leu Xaa Leu Ile Xaa Leu Xaa Ile Xaa Xaa
945                 950                 955                 960

Val Pro Xaa Xaa Val Gly Ser Met Xaa His Leu Arg Tyr Leu Asn Leu
            965                 970                 975

Ser Xaa Thr Xaa Ile Thr His Leu Pro Glu Xaa Xaa Cys Asn Leu Tyr
            980                 985                 990

Asn Leu Gln Thr Leu Ile Val Ser Gly Cys Xaa Tyr Leu Val Xaa Leu
            995                 1000                1005

Pro Lys Thr Phe Ser Xaa Leu Lys Asn Leu Xaa His Phe Asp Met Arg
            1010                1015                1020

Xaa Thr Pro Xaa Leu Lys Asn Met Pro Leu Xaa Ile Gly Glu Leu Lys
1025                1030                1035                1040

Xaa Leu Gln Thr Leu Phe Xaa Asn Ile Gly Ile Ala Ile Thr Glu Leu
            1045                1050                1055

Lys Asn Leu Xaa Asn Leu His Gly Lys Xaa Cys Ile Gly Gly Leu Gly
            1060                1065                1070

Lys Met Glu Asn Ala Val Gly Cys Thr Leu Ser Glu Leu Val Ser Lys
            1075                1080                1085

Lys Val Xaa Xaa Xaa Xaa Asn Trp Xaa Xaa Gly Xaa Xaa Ile Xaa Cys
            1090                1095                1100

Phe Pro Lys Trp Glu His Leu Lys Lys Ser Ser Met Lys Xaa Cys
1105                1110                1115                1120

Leu Ile Met Val Leu Xaa Lys Lys Pro Xaa Ile Met Ser Ile Gly Gly
            1125                1130                1135

Ile Glu Phe Pro Asn Trp Val Gly Ser Leu Arg Val Ser Glu Thr Arg
```

```
                    1140              1145              1150

Asp Val Phe Met Val Tyr Glu Lys Xaa Cys Phe Thr Xaa Phe His Gln
           1155              1160              1165

Ser Pro Ser Gly Lys Xaa Met Ile Phe Ser Gly Xaa Thr Asp Glu Met
       1170              1175              1180

Trp Arg Gly Met Ile Gly Xaa Leu Gly Ala Val Glu Glu Ile Ser Ile
1185              1190              1195              1200

His Ser Cys Asn Glu Ile Arg Tyr Leu Trp Glu Ser Glu Ala Glu Ala
               1205              1210              1215

Ser Lys Val Leu Met Asn Leu Lys Lys Leu Asp Leu Gly Glu Cys Glu
           1220              1225              1230

Asn Leu Val Ser Leu Gly Glu Lys Lys Glu Asp Asn His Asn Ile Asn
       1235              1240              1245

Ser Gly Ser Ser Leu Thr Ser Phe Arg Arg Leu Asn Val Trp Arg Cys
   1250              1255              1260

Asn Ser Leu Glu His Cys Arg Cys Pro Asp Ser Met Glu Asn Leu Tyr
1265              1270              1275              1280

Met His Met Cys Asp Ser Xaa Thr Ser Val Ser Phe Pro Thr Gly Gly
               1285              1290              1295

Gly Gln Lys Ile Lys Ser Leu Thr Ile Thr Asp Cys Lys Lys Leu Ser
           1300              1305              1310

Glu Glu Glu Leu Gly Gly Arg Glu Arg Thr Arg Val Leu Ile Asn Ser
       1315              1320              1325

Lys Met Gln Met Leu Glu Ser Val Asp Ile Arg Asn Trp Pro Asn Leu
   1330              1335              1340

Lys Ser Ile Ser Glu Leu Ser Cys Phe Ile His Leu Asn Arg Leu Tyr
1345              1350              1355              1360

Ile Ser Asn Cys Pro Ser Xaa Glu Ser Phe Pro Asp His Glu Leu Pro
               1365              1370              1375

Asn Leu Thr Ser Leu Thr Asp Arg Arg Arg Gly Gln Arg Phe Ser Tyr
           1380              1385              1390

Glu Arg Leu Arg Phe Asp Trp Pro Ser Phe
       1395              1400

(2) INFORMATION FOR SEQ ID NO:12:

(i) SEQUENCE CHARACTERISTICS:
        (A) LENGTH: 784 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..784
        (D) OTHER INFORMATION: /note= "RLG1B amino acids"

(xi) SEQUENCE DESCRIPTION: SEQ ID NO:12:

Asn Arg Ser Tyr Glu Asn Arg Cys Pro Leu Leu Pro Val Ile Xaa Xaa
1               5                  10                  15

Xaa Glu Lys Ile Xaa Leu Lys Val Xaa Ile Gln Asn Pro Leu Phe His
               20                  25                  30

Arg Xaa Tyr Asp Ala Leu Ala Val Val Cys Lys Asn Ser Ile Ile Asn
           35                  40                  45

Ala Asn Gln Asn Ser Ser Xaa Glu Thr Ile Xaa Ile Met Val Xaa Ile
       50                  55                  60
```

-continued

```
Val Leu Ser Pro Tyr Thr His Phe Phe Gln Ile Pro Ile Ile His Thr
 65                  70                  75                  80

Tyr Lys Cys Ser His Ile Arg Phe Ser Leu Xaa Ala Met Ala Glu Ile
                 85                  90                  95

Leu Gly Ser Ala Phe Phe Ala Val Phe Phe Glu Lys Leu Ala Ser Glu
                100                 105                 110

Ala Leu Lys Arg Val Ala Cys Ser Lys Val Ile Asp Lys Glu Leu Glu
                115                 120                 125

Lys Leu Asn Ser Ser Xaa Ile Asn Ile Lys Ala Leu Leu Asn Asp Ala
130                 135                 140

Ser Gln Lys Glu Ile Ser Lys Glu Ala Val Lys Glu Trp Leu Asn Ala
145                 150                 155                 160

Leu Gln His Leu Pro Tyr Asp Ile Asp Asp Leu Leu Gly Asp Leu Ala
                165                 170                 175

Thr Lys Ala Ile His Arg Lys Phe Ser Glu Glu Tyr Gly Ala Thr Ile
                180                 185                 190

Asn Lys Val Arg Lys Leu Ile Pro Ser Cys Phe Ser Ser Leu Ser Ser
                195                 200                 205

Thr Lys Met Arg Asn Lys Ile His Asn Ile Thr Ser Lys Leu Gln Glu
                210                 215                 220

Leu Leu Glu Glu Arg Asn Asn Leu Gly Leu Cys Glu Ile Gly Glu Ser
225                 230                 235                 240

Arg Lys Leu Arg Asn Arg Lys Ser Glu Thr Ser Xaa Leu Asp Pro Ser
                245                 250                 255

Ser Ile Val Gly Arg Thr Asp Asp Lys Glu Ala Leu Leu Leu Lys Leu
                260                 265                 270

Tyr Glu Pro Cys Asp Arg Asn Phe Ser Ile Leu Pro Ile Val Gly Met
                275                 280                 285

Gly Gly Leu Asp Lys Thr Thr Leu Gly Arg Leu Leu Tyr Asp Xaa Met
                290                 295                 300

Gln Val Lys Asp His Phe Glu Leu Lys Ala Trp Val Cys Val Ser Asp
305                 310                 315                 320

Glu Phe Asp Ile Phe Gly Ile Ser Lys Thr Ile Phe Glu Ser Ile Glu
                325                 330                 335

Gly Gly Asn Gln Glu Phe Lys Asp Leu Asn Leu Leu Gln Val Ala Leu
                340                 345                 350

Lys Glu Lys Ile Ser Lys Lys Arg Phe Leu Val Val Leu Asp Asp Val
                355                 360                 365

Trp Ser Glu Ser Tyr Thr Asp Trp Glu Ile Leu Glu Arg Pro Phe Leu
370                 375                 380

Ala Gly Ala Pro Gly Ser Lys Val Ile Ile Thr Thr Arg Lys Leu Ser
385                 390                 395                 400

Leu Leu Asn Gln Leu Gly His Asp Gln Pro Tyr Gln Leu Ser Asp Leu
                405                 410                 415

Ser His Asp Asn Ala Leu Ser Leu Phe Cys Gln His Ala Phe Gly Val
                420                 425                 430

Asn Ser Phe Asp Ser His Pro Ile Leu Lys Pro His Gly Glu Gly Ile
                435                 440                 445

Val Glu Lys Cys Asp Gly Leu Pro Leu Ala Leu Ile Ala Leu Gly Arg
                450                 455                 460

Leu Leu Arg Thr Lys Arg Asp Glu Glu Glu Trp Lys Glu Leu Leu Asn
465                 470                 475                 480
```

-continued

```
Ser Glu Ile Trp Arg Leu Gly Lys Arg Asp Glu Ile Ile Pro Xaa Leu
                485                 490                 495

Arg Leu Ser Tyr Asn Asp Leu Ser Ala Ser Leu Lys Gln Leu Phe Ala
            500                 505                 510

Tyr Cys Ser Leu Phe Pro Lys Asp Tyr Val Phe Asn Lys Glu Lys Leu
        515                 520                 525

Ile Leu Leu Trp Met Ala Glu Gly Phe Leu His Asn Glu Asn Thr Asn
    530                 535                 540

Lys Ser Met Glu Arg Leu Xaa Leu Glu Tyr Phe Asp Asp Leu Leu Ser
545                 550                 555                 560

Arg Ser Phe Phe Gln His Ala Leu Asp Asp Lys Ser Leu Phe Val Val
                565                 570                 575

His Asp Leu Met Asn Asp Leu Ala Thr Ser Val Ala Gly Asp Tyr Phe
            580                 585                 590

Leu Arg Leu Asp Ile Glu Met Lys Lys Glu Ala Leu Glu Lys Tyr Arg
        595                 600                 605

His Met Ser Phe Val Cys Glu Ser Tyr Met Val Tyr Lys Arg Phe Glu
    610                 615                 620

Pro Phe Lys Gly Ala Lys Lys Leu Arg Thr Phe Leu Ala Met Pro Val
625                 630                 635                 640

Gly Met Ile Lys Ser Trp Thr Thr Phe Tyr Leu Ser Asn Lys Val Leu
                645                 650                 655

Asp Asp Leu Leu His Glu Leu Pro Leu Leu Arg Val Leu Ser Leu Ser
            660                 665                 670

Tyr Leu Ser Ile Lys Glu Val Pro Glu Ile Ile Gly Asn Leu Lys His
        675                 680                 685

Leu Arg Tyr Leu Asn Leu Ser His Thr Ser Ile Thr His Leu Pro Glu
    690                 695                 700

Asn Val Cys Asn Leu Tyr Asn Leu Gln Thr Leu Ile Leu Cys Gly Cys
705                 710                 715                 720

Cys Phe Ile Thr Lys Phe Pro Asn Asn Phe Leu Lys Leu Arg Asn Leu
                725                 730                 735

Arg His Leu Asp Ile Ser Asp Thr Pro Gly Leu Lys Lys Met Ser Ser
            740                 745                 750

Gly Ile Gly Glu Leu Lys Asn Leu His Thr Leu Ser Lys Leu Ile Ile
        755                 760                 765

Gly Gly Glu Asn Arg Leu Asn Glu Leu Lys Asn Leu Gln Asn Leu His
    770                 775                 780
```

(2) INFORMATION FOR SEQ ID NO:13:

(i) SEQUENCE CHARACTERISTICS:
        (A) LENGTH: 345 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..345
        (D) OTHER INFORMATION: /note= "RLG1C amino acids"

(xi) SEQUENCE DESCRIPTION: SEQ ID NO:13:

```
Ser Arg Ala Thr Xaa Ile Ile Gln Lys Xaa Pro Lys Thr Xaa Asp Xaa
1               5                   10                  15

Phe Xaa Xaa Xaa Xaa Gln Lys Glu Val Ile Asp Glu Ala Val Lys Arg
```

```
                    20                  25                  30
Trp Leu Ile Asp Xaa Gln Gln Leu Ala Tyr Asp Thr Xaa Asp Xaa Leu
                35                  40                  45

Asp Asp Xaa Ala Thr Glu Ala Ile His Arg Glu Leu Ile Arg Glu Thr
 50                  55                  60

Gly Ala Ser Xaa Ser Met Val Arg Lys Leu Ile Pro Ser Cys Cys Thr
 65                  70                  75                  80

Ser Phe Ser Gln Ser Asn Arg Met His Ala Arg Leu Asp Asp Ile Ala
                85                  90                  95

Ala Lys Xaa Gln Glu Leu Val Glu Ala Lys Asn Asn Leu Gly Leu Ser
               100                 105                 110

Val Ile Thr Tyr Glu Lys Pro Lys Ile Glu Arg Asp Glu Ala Xaa Leu
               115                 120                 125

Val Asp Ala Ser Gly Ile Ile Gly Arg Glu Asp Asp Lys Lys Lys Leu
 130                 135                 140

Leu Gln Lys Leu Leu Gly Asp Thr Tyr Glu Ser Ser Gln Asn Phe
145                 150                 155                 160

Asn Ile Val Pro Ile Val Gly Met Gly Gly Val Gly Lys Thr Thr Leu
               165                 170                 175

Ala Arg Leu Leu Tyr Asp Glu Lys Lys Val Lys Asp His Phe Glu Leu
               180                 185                 190

Arg Val Trp Val Cys Val Ser Asp Glu Phe Ser Val Pro Asn Ile Ser
               195                 200                 205

Arg Val Ile Tyr Gln Ser Val Thr Gly Glu Asn Lys Glu Phe Ala Asp
               210                 215                 220

Leu Asn Leu Leu Gln Glu Ala Leu Lys Glu Lys Leu Gln Asn Lys Leu
225                 230                 235                 240

Phe Leu Ile Val Leu Asp Asp Val Trp Ser Glu Ser Tyr Gly Asp Trp
               245                 250                 255

Glu Lys Leu Val Gly Pro Phe His Ala Gly Thr Ser Gly Ser Arg Ile
               260                 265                 270

Ile Met Thr Thr Arg Lys Glu Gln Leu Leu Lys Gln Leu Gly Phe Ser
               275                 280                 285

His Glu Asp Pro Leu His Ser Ile Asp Ser Leu Gln Arg Leu Ser Gln
               290                 295                 300

Glu Asp Ala Leu Ser Leu Phe Ser Gln His Ala Phe Gly Val Pro Asn
305                 310                 315                 320

Phe Asp Ser His Pro Thr Leu Arg Pro Tyr Gly Glu Gln Phe Val Lys
               325                 330                 335

Lys Cys Gly Gly Leu Pro Leu Ala Leu
               340                 345
```

(2) INFORMATION FOR SEQ ID NO:14:

(i) SEQUENCE CHARACTERISTICS:
        (A) LENGTH: 314 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..314
        (D) OTHER INFORMATION: /note= "RLG1D amino acids"

(xi) SEQUENCE DESCRIPTION: SEQ ID NO:14:

Xaa Thr Xaa Leu Arg Asp Arg Cys Pro Ser Ser Ile Cys Leu Thr Met
1               5                   10                  15

Leu Pro Arg Arg Lys Xaa Leu Met Lys Pro Leu Lys Asp Gly Xaa Met
            20                  25                  30

Ile Ser Asn Ile Trp Leu Met Thr Xaa Thr Thr Tyr Leu Met Ile Leu
            35                  40                  45

Gln Xaa Lys Ala Ile Xaa Xaa Glu Leu Thr Xaa Glu Gly Gly Ala Ser
        50                  55                  60

Thr Ser Met Val Arg Lys Leu Ile Pro Ser Cys Cys Thr Ser Phe Ser
65                  70                  75                  80

Gln Ser Tyr Arg Met His Ala Lys Leu Asp Asp Ile Ala Thr Arg Leu
                85                  90                  95

Gln Glu Leu Val Glu Ala Lys Asn Asn Leu Gly Leu Ser Val Ile Thr
                100                 105                 110

Tyr Glu Lys Pro Lys Ile Glu Arg Tyr Glu Ala Ser Leu Val Asp Glu
                115                 120                 125

Ser Gly Ile Phe Gly Arg Xaa Asp Asp Xaa Lys Lys Leu Met Glu Lys
130                 135                 140

Leu Leu Glu Asp Lys Asp Glu Ser Gly Val Lys Leu Gln His Leu Pro
145                 150                 155                 160

Ile Ile Gly Met Gly Gly Val Gly Xaa Thr Thr Leu Ala Arg Leu Leu
                165                 170                 175

Phe Asp Glu Lys Thr Val Lys Asp His Phe Glu Leu Arg Ala Trp Val
                180                 185                 190

Cys Val Ser Asp Glu Phe Ser Ile Leu Asn Ile Ser Lys Val Ile Tyr
                195                 200                 205

Gln Ser Val Thr Gly Glu Lys Lys Glu Phe Glu Asp Leu Asn Leu Leu
210                 215                 220

Gln Glu Ala Leu Arg Gly Lys Leu Gln Asn Lys Leu Phe Leu Ile Val
225                 230                 235                 240

Leu Asp Asp Val Trp Ser Glu Ser Tyr Gly Asp Trp Glu Lys Leu Val
                245                 250                 255

Gly Pro Phe His Ala Gly Thr Ser Gly Ser Arg Ile Ile Met Thr Thr
                260                 265                 270

Arg Lys Glu Gln Leu Leu Lys Gln Leu Gly Phe Ser His Gln Asp Pro
                275                 280                 285

Leu Arg Cys Ile Asp Ser Leu Gln Arg Leu Ser Gln Asp Asp Ala Leu
                290                 295                 300

Ser Leu Phe Ala Gln His Ala Phe Gly Xaa
305                 310

(2) INFORMATION FOR SEQ ID NO:15:

(i) SEQUENCE CHARACTERISTICS:
        (A) LENGTH: 158 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..158
        (D) OTHER INFORMATION: /note= "RLG1E amino acids"

(xi) SEQUENCE DESCRIPTION: SEQ ID NO:15:

```
Leu Ala Arg Leu Leu Tyr Asp Glu Met Gln Glu Lys Asp His Phe Glu
1               5                   10                  15

Leu Lys Ala Trp Val Cys Val Ser Asp Glu Phe Asp Ile Phe Asn Ile
            20                  25                  30

Ser Lys Ile Ile Phe Gln Ser Ile Gly Gly Gly Asn Gln Glu Phe Lys
        35                  40                  45

Asp Leu Asn Leu Gln Val Ala Val Lys Glu Lys Ile Ser Lys Lys
    50                  55                  60

Arg Phe Leu Leu Val Leu Asp Asp Val Trp Ser Glu Ser Tyr Ala Asp
65                  70                  75                  80

Trp Glu Ile Leu Glu Arg Pro Phe Leu Ala Gly Ala Ala Gly Ser Lys
                85                  90                  95

Ile Ile Met Thr Thr Arg Lys Gln Ser Leu Leu Thr Lys Leu Gly Tyr
                100                 105                 110

Lys Gln Pro Tyr Asn Leu Ser Val Leu Ser His Asp Ser Ala Leu Ser
            115                 120                 125

Leu Phe Cys Gln His Ala Leu Gly Glu Asp Asn Phe Asp Ser His Pro
    130                 135                 140

Thr Leu Lys Pro His Gly Glu Gly Ile Val Glu Lys Cys Ala
145                 150                 155
```

(2) INFORMATION FOR SEQ ID NO:16:

(i) SEQUENCE CHARACTERISTICS:
        (A) LENGTH: 553 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..553
        (D) OTHER INFORMATION: /note= "RLG1F amino acids"

(xi) SEQUENCE DESCRIPTION: SEQ ID NO:16:

```
Phe Ser Ala Xaa Asn Lys Xaa Lys Gln Trp Leu Lys Ser Phe Phe Xaa
1               5                   10                  15

His Ser Arg Pro Val Phe Phe Glu Lys Xaa Ala Ser Glu Ala Leu Lys
            20                  25                  30

Lys Ile Ala Arg Phe His Arg Ile Asp Ser Glu Leu Lys Lys Leu Lys
        35                  40                  45

Arg Ser Leu Ile Gln Ile Arg Ser Val Leu Asn Asp Ala Ser Glu Lys
50                  55                  60

Glu Ile Ser Asp Glu Ala Val Lys Glu Trp Leu Asn Gly Leu Gln His
65                  70                  75                  80

Leu Ser Tyr Asp Ile Asp Asp Leu Leu Asp Leu Ala Thr Glu Thr
            85                  90                  95

Met His Arg Glu Leu Thr Thr Asp Leu Glu Pro Pro Ala Cys Lys
                100                 105                 110

Lys Asp Asn Pro Thr Cys Cys Thr Asp Phe Ser Leu Ser Ser Lys Met
            115                 120                 125

Arg Asn Lys Leu Asp Asn Ile Thr Ile Lys Leu Gln Glu Leu Val Glu
        130                 135                 140

Glu Lys Asp Asn Leu Gly Leu Ser Val Lys Gly Glu Ser Pro Lys His
145                 150                 155                 160

Thr Asn Arg Arg Leu Gln Thr Ser Leu Val Asp Ala Ser Ser Ile Ile
```

```
                          165                 170                 175
Gly Arg Glu Gly Asp Lys Asp Ala Leu Leu His Lys Leu Leu Glu Asp
                    180                 185                 190

Glu Pro Ser Asp Arg Asn Phe Ser Ile Val Pro Ile Val Gly Met Gly
                195                 200                 205

Gly Val Gly Lys Thr Thr Leu Ala Arg Leu Leu Tyr Asp Glu Met Gln
            210                 215                 220

Glu Lys Asp His Phe Glu Leu Lys Ala Trp Val Cys Val Ser Asp Glu
225                 230                 235                 240

Phe Asp Ile Phe Asn Ile Ser Lys Val Ile Phe Gln Ser Ile Gly Gly
                    245                 250                 255

Gly Xaa Gln Glu Phe Lys Asp Leu Asn Leu Leu Gln Val Ala Val Lys
                260                 265                 270

Glu Lys Ile Ser Lys Lys Arg Phe Leu Xaa Val Leu Asp Asp Val Trp
            275                 280                 285

Ser Glu Ser Tyr Thr Glu Trp Glu Ile Leu Ala Arg Pro Phe Leu Ala
        290                 295                 300

Gly Ala Pro Gly Ser Lys Ile Ile Met Thr Thr Arg Lys Leu Ser Leu
305                 310                 315                 320

Leu Thr Lys Leu Gly Tyr Asn Gln Pro Tyr Asn Leu Ser Val Leu Ser
                    325                 330                 335

His Asp Asn Ala Leu Ser Leu Phe Cys Gln His Ala Leu Gly Glu Asp
                340                 345                 350

Asn Phe Asp Ser His Pro Thr Leu Lys Pro Xaa Gly Glu Ser Ile Val
            355                 360                 365

Glu Lys Cys Asp Gly Leu Pro Leu Ala Leu Ile Ala Leu Gly Arg Leu
        370                 375                 380

Leu Xaa Thr Lys Thr Asp Glu Glu Glu Trp Lys Glu Val Leu Asn Ser
385                 390                 395                 400

Glu Ile Trp Gly Ser Gly Lys Gly Asp Glu Ile Val Pro Ala Leu Lys
                    405                 410                 415

Leu Ser Tyr Asn Asp Leu Ser Ala Ser Leu Lys Lys Leu Phe Ala Tyr
                420                 425                 430

Cys Ser Leu Phe Pro Lys Asp Tyr Val Phe Asp Lys Glu Glu Leu Ile
            435                 440                 445

Leu Leu Trp Met Ala Glu Gly Phe Leu His Gln Ser Thr Thr Ser Lys
        450                 455                 460

Ser Met Glu Arg Leu Gly His Glu Gly Phe Asp Glu Leu Leu Ser Arg
465                 470                 475                 480

Ser Phe Phe Gln His Ala Pro Asp Ala Lys Ser Met Phe Val Met His
                    485                 490                 495

Asp Leu Met Asn Asp Leu Ala Thr Ser Val Ala Gly Asp Phe Phe Ser
                500                 505                 510

Arg Met Asp Ile Glu Met Lys Lys Glu Phe Arg Lys Glu Ala Leu Xaa
            515                 520                 525

Lys Xaa Arg His Met Ser Xaa Val Cys Xaa Asp Tyr Met Val Xaa Lys
        530                 535                 540

Arg Phe Xaa Pro Xaa Thr Arg Ser Xaa
545                 550
```

(2) INFORMATION FOR SEQ ID NO:17:

(i) SEQUENCE CHARACTERISTICS:
       (A) LENGTH: 128 amino acids (B) TYPE: amino acid
(C) STRANDEDNESS:
(D) TOPOLOGY: linear (ii) MOLECULE TYPE: protein (ix) FEATURE:
(A) NAME/KEY: -
(B) LOCATION: 1..128
(D) OTHER INFORMATION: /note= "RLG1G amino acids"

(xi) SEQUENCE DESCRIPTION: SEQ ID NO:17:

```
Val Lys Asp His Phe Glu Leu Arg Ala Trp Val Cys Val Ser Asp Glu
1               5                  10                  15

Phe Asn Ile Leu Asn Ile Ser Lys Val Ile Tyr Gln Ser Val Thr Gly
            20                  25                  30

Glu Lys Lys Glu Phe Glu Asp Leu Asn Leu Leu Gln Glu Ala Leu Lys
        35                  40                  45

Glu Lys Leu Trp Asn Gln Leu Phe Leu Ile Val Leu Asp Asp Val Trp
    50                  55                  60

Ser Glu Ser Tyr Arg Asp Trp Glu Lys Leu Val Gly Pro Phe Phe Ser
65                  70                  75                  80

Gly Ser Pro Gly Ser Met Ile Ile Met Thr Thr Arg Lys Glu Gln Leu
                85                  90                  95

Pro Arg Lys Leu Gly Phe Pro His Gln Asp Pro Leu Gln Gly Leu Ser
            100                 105                 110

His Asp Asp Ala Leu Ser Leu Phe Ala Gln His Ala Phe Gly Val Pro
        115                 120                 125
```

(2) INFORMATION FOR SEQ ID NO:18:

(i) SEQUENCE CHARACTERISTICS:
(A) LENGTH: 158 amino acids
(B) TYPE: amino acid
(C) STRANDEDNESS:
(D) TOPOLOGY: linear (ii) MOLECULE TYPE: protein (ix) FEATURE:
(A) NAME/KEY: -
(B) LOCATION: 1..158
(D) OTHER INFORMATION: /note= "RLG1H amino acids"

(xi) SEQUENCE DESCRIPTION: SEQ ID NO:18:

```
Leu Ala Arg Leu Leu Tyr Glu Glu Met Gln Gly Lys Asp His Phe Glu
1               5                  10                  15

Leu Lys Ala Trp Val Cys Val Ser Asp Glu Phe Asp Ile Phe Asn Ile
            20                  25                  30

Ser Lys Ile Ile Leu Gln Ser Ile Gly Gly Gly Asn Gln Glu Phe Thr
        35                  40                  45

Asp Leu Asn Leu Leu Gln Val Ala Leu Lys Glu Lys Ile Ser Lys Lys
    50                  55                  60

Arg Phe Leu Leu Val Leu Asp Asp Val Trp Ser Glu Ser Tyr Thr Asp
65                  70                  75                  80

Trp Glu Ile Leu Glu Arg Pro Phe Leu Ala Gly Ala Pro Gly Ser Lys
                85                  90                  95

Ile Ile Ile Thr Thr Arg Lys Leu Ser Leu Leu Asn Lys Leu Gly Tyr
            100                 105                 110

Asn Gln Pro Tyr Asn Leu Ser Val Leu Ser His Glu Asn Ala Leu Ser
        115                 120                 125
```

```
Leu Phe Cys Gln His Ala Leu Gly Glu Asp Asn Phe Asn Ser His Pro
    130                 135                 140
Thr Leu Lys Pro His Gly Glu Gly Ile Val Glu Lys Cys Asp
145                 150                 155
```

(2) INFORMATION FOR SEQ ID NO:19:

(i) SEQUENCE CHARACTERISTICS:
        (A) LENGTH: 166 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..166
        (D) OTHER INFORMATION: /note= "RLG1I amino acids"

(xi) SEQUENCE DESCRIPTION: SEQ ID NO:19:

```
Leu Ala Arg Leu Val Tyr Asp Glu Met Gln Glu Lys Asp His Phe Glu
1               5                   10                  15
Leu Lys Ala Trp Val Cys Val Ser Asp Glu Phe Asp Ile Phe Asn Ile
                20                  25                  30
Ser Lys Ile Ile Phe Gln Ser Ile Gly Gly Asn Gln Glu Phe Lys
            35                  40                  45
Asp Leu Asn Leu Leu Gln Val Ala Val Lys Glu Lys Ile Leu Lys Lys
    50                  55                  60
Arg Phe Leu Leu Val Leu Asp Asp Val Trp Ser Glu Ser Tyr Ala Asp
65                  70                  75                  80
Trp Glu Ile Xaa Glu Arg Pro Phe Leu Ala Gly Ala Ala Gly Ser Lys
                85                  90                  95
Ile Ile Met Thr Thr Arg Lys Gln Ser Leu Leu Thr Lys Leu Gly Tyr
                100                 105                 110
Lys Gln Pro Tyr Asn Leu Ser Val Leu Ser His Asp Ser Ala Leu Ser
            115                 120                 125
Leu Phe Cys Gln His Ala Leu Gly Glu Gly Asn Phe Asp Ser His Pro
    130                 135                 140
Thr Leu Lys Pro His Gly Glu Gly Ile Val Glu Lys Cys Ala Gly Leu
145                 150                 155                 160
Pro Leu Ala Leu Ser Thr
                165
```

(2) INFORMATION FOR SEQ ID NO:20:

(i) SEQUENCE CHARACTERISTICS:
        (A) LENGTH: 173 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..173
        (D) OTHER INFORMATION: /note= "RLG1J amino acids"

(xi) SEQUENCE DESCRIPTION: SEQ ID NO:20:

```
Glu Phe Gly Val Gly Lys Thr Thr Leu Ala Arg Leu Leu Tyr Glu Glu
1               5                   10                  15
Met Gln Gly Lys Asp His Phe Glu Leu Lys Ala Trp Val Cys Val Ser
```

```
                    20                  25                  30
Asp Glu Phe Asp Ile Phe Asn Ile Ser Lys Ile Ile Leu Gln Ser Ile
                35                  40                  45
Gly Gly Gly Asn Gln Glu Phe Thr Asp Leu Asn Leu Leu Arg Val Ala
        50                  55                  60
Leu Lys Glu Lys Ile Ser Lys Lys Arg Phe Leu Leu Val Leu Asp Asp
65                  70                  75                  80
Val Trp Ser Glu Ser Tyr Thr Asp Trp Glu Ile Xaa Glu Arg Pro Phe
                85                  90                  95
Leu Ala Gly Ala Pro Gly Ser Lys Ile Ile Thr Thr Arg Lys Leu
                100                 105                 110
Ser Leu Leu Asn Lys Leu Gly Tyr Asn Gln Pro Tyr Asn Leu Ser Val
            115                 120                 125
Leu Ser His Glu Asn Ala Leu Ser Leu Phe Cys Gln His Ala Leu Gly
            130                 135                 140
Glu Asp Asn Phe Asn Ser His Pro Thr Leu Lys Pro His Gly Xaa Gly
145                 150                 155                 160
Ile Val Glu Lys Cys Asp Gly Leu Pro Leu Ala Leu Ser
                165                 170
```

(2) INFORMATION FOR SEQ ID NO:21:

(i) SEQUENCE CHARACTERISTICS:
        (A) LENGTH: 10815 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..10815
        (D) OTHER INFORMATION: /note= "RLG2A"

(xi) SEQUENCE DESCRIPTION: SEQ ID NO:21:

```
TTNACACCAT AAATTCTCNA CCTGNGGGGA CAAAAACCTA AAAATGGTCC ATAATGCNCA        60

AATCAGNAAG GTTGANAAAG CTCTAAGTTT TTNACCTCCA NCTGATGCNC NNTCCTCNTA       120

AAGTTCANAT CCAAGCTTGC CCTCCAACTC TANCNCCTTC AATGGCACCT CCTTCTCTTC       180

AAAAGCACAC AAGAACACTT TCAAGCTCAA CCACACTCAC ACAAGCTCTA GAACNAGGGT       240

TAGGGCACAT TTAGGGTTTT GCTCTCTGGA AATGGTGTCT AAAAGTGAGG CCATAATGTT       300

CCTTATATAA GGCTCACTCC CACAATTAGG CTTTCAATCT GAACGTANTA CGCCCAGTGT       360

ACACTATGGT ACGCCCAACG TACTCGGTAG TCTCCGCGTC AANAATACAC TCATGAGTAC       420

GCGCAACGTA CTTTCCCTTA CGCCCAGCGT ACTCAAAAGC CAAACATTCT TTTCAAGGAC       480

TAATTTTGAC AACTTGAGGA AGAAAAGGA TCAAAGANAT ATACTTGAAT TCCGGGATGT       540

TACAATGAAG TTGANACCTT GGCTAAAAAA TTAAATTGGT TGTGGAAGCC GTTGGCTGAG       600

CAAGCAACAA GGGTAAAATT CGTAATCTAC AAATGGTGTT ATTTTCTATT TCTTCTTATT       660

ATTTTACTTG ATTTACGGGT AGTTTTTTTT TCTTACAAAA AATATTAAAG TTGATAAAGT       720

ATAGCCACTA AAATTGACTT TTTCCAAAAC ATAATGTCAA ATGGTGCGTA TATGTATCAT       780

GTTGTATTAN ATAATGAATA TGATGATNCT GTTCTATTTA ANCCGAAAAA ATTATCTAAT       840

GATTTTATAT TGGAAAACAA AGTTGTGATT TTTNGCATAA TATAATCAAA TCCNCTTTTG       900

TNTGGGAGGT GGATAAATGT GGTAAATTTA NAACAAGTGT TTTNACNTTG AAGGGTNTGG       960
```

```
                                                      -continued

AAAGGTTGAA AAAAGTTAAA ATGATAAAAT GTTTACACAA ATGTTGTATC CGACTGAATA      1020

TNATGTTTAA GGATNATTGT ATTAAATTGT TGATATATAG TAAGCATAAA TATTTAGAAT      1080

TGTGACTTAA ATTTATAAGT TATNCNAACT GGATTGAAAC ATTTTTGATA TANATTAGGA      1140

ATGAAAATGA GCAACCCTAA CATACTTATC TTTGGTAGTT TGGTTATTAT ATTTTTATTA      1200

NAATATAGAA NCATCCCTTT ATTTTAAACC CATATTGTGG ACGGACTTGA ATAAATGGGA      1260

AAAATGTACC TTGCTATTTA GCACAAAAAA ATTATAAAAA TGTACATTGC TATTTAGCAC      1320

AAACAAAAAA AAAAAACTTA TCCTTTTTGC ATTAGGTCAC AAAGAAATAT AAAATGGGAA      1380

ATGTGTTGCT ATTTAATGCA CTAAAAGAAA CTATTTTGCC TTTATTAAAC CGGGTAAACC      1440

AATAGAAAAA TGGAAGTACA TTGTCATTTA GCATGAAAAA AAATAACTTT CCATTTTTTG      1500

CATCCGGTCA CAATAATAGA AAAATGAAAG TACGTTGCTA TTTAGCGAAA CTAACTTCCT      1560

TTTTTCTTTT TGGCATCGTA TCATAAAATA TAGACTAAAA TACGTTAGTT TTACATTTTT      1620

AATACATTGA AATGTCTAAT CCACATGTTA TTCTATAAAA AGGGAAATGT AATTTACTTA      1680

TTCTTTGATT CTTTGGCTTC TTTTTAGTAC CCAAAACATC CCTCTATCCA TCTATTCCAA      1740

CTAAAATAAT GAAAACTATA TTCCTTCCAT TGTAGGGATG TTATAAATTT TGTAATTGTT      1800

TTTATGCAAA AAAGTGTTTT TTGTTAACTA GATTAACGAG ATTCATTTTT CAGCATTTTA      1860

GGAGAAGTTC ATCCATCTTT TGGATATGAA GTGCAAGCCA AGTTCTTTAA CATGGAATAT      1920

GAGGTCCCTA TATGCTCAAA AAATAGCAAA TGAGAAATTT TTTAAATTGG ATCCCCATAA      1980

AAGAAAATTT GTTAATGGTT GTTTTAATAT TGGTCAATGT GTCCACCGGA TGAGCATAAT      2040

ACTAGTTTAT AAGGGGTAAA GGTGGGTTTG GTGGGCCCAT TTATCTTTAT TATTTCTAAA      2100

AGTCAGAATT AAGTAAAAAA AATTATAAGA TAAATACCAT AAGGATAAAA AATCATTTTA      2160

TTTGGACCAA AGACCAAAGT TGTTAAGGGG CTGTTTGTTT TTTTTGTGAA GAGCTGTGCA      2220

ACCACTTTTG TCTGCGCCGC ACAGACAACG TGCAGACATA TGCCCTCGCA GAGTGTTTGT      2280

TTTTTGAAAG TGCGCAGACC AAAAAAACGT CTGCGCGAGG TCATCCTGGC GCATATATGT      2340

GTCACTGTCT TCAAAGGTCT TCAGACCTCA TTTTAACCAA AAAAAAAAAA GACCACCGGT      2400

TTTTTTTTTT TTTTTNTTCT TTCTCTTGTA GCTGAAAATG CATTTTTAAT CTTTATGACA      2460

TGAAATTAAG TTTGAAAAAT TAATTTATTT CAACAGCTGT AGACGTTAAA AACAAACAGT      2520

CTTCTTGTTG CAGACTGTGG ACATTTGGTC CACCTCTTCT ACCGCAGAGA CTTGCAGATG      2580

TGGTCCGCAG ACTGCAGACA TTTTGGCTTC AAATAAACAA ACATCACCTA ATTTGACTAC      2640

ACCACACGGA CCTCCAATGT AACAAAAAAA AGGTTGAAAC AAAGTTGCCT ATTTCTCCAT      2700

ATCCAGGGGC CATTTATGTA AGAGTTATCT AAATTTTAGT TCGGTAGATC AGTTCTCACA      2760

TTTTAACCGG GTAAAGTGTA TGTGTGTACG CGCGCACCTG AAAGGTTTGA ANGTAACTTC      2820

CAAACTGAAN CAANAATCGA TATGAAGTAT CAAGTTAGAG GTTCAATTGG TGAAGGAATC      2880

AGCTGGAGGT TGGGGAATCG AGCTTCCACT ATTAAGGTAA AATCCATAAC CCTAAATGTT      2940

GGTACGCTCA TATATCAAAT TGCGTGTTTT GTTGAATGAA AAAAGCATGC TCAAAAAACC      3000

AGTGTAAGGC ACGGTATATG ACATATTTAT AGTTACTGAT AACAAATTAT GATAATTTTG      3060

GGTTTACGTA AGTTAGGATT CGTACTTCAA CCAAATGTAA TAGTTTTTGT GAGTCTATCT      3120

ATGTATTTGG GGAATCACAT TAGCAACGGG ATTGTACTAG TAATTCGAAA AAGTCTTTTA      3180

AATAATTTTT CTGTTTATAA TTTATGAATA GTTTAGCGA CATCTAATAT TAAATAGAAT       3240

GTATCTGATA TTGAATTAAT GTCCTTAATG TGAACATAGA CCTTTTCCAT TTACTAATGC      3300

CTAATTATTA GTTTCTAATC AATAAATTTT AATTTCTGTT TTATGCTTCT AAGACAATAA      3360
```

-continued

```
AAATCCATGA TTTACCTTTA AATATTAACA AAAATGACCA TAAATAAATA AAAAATTAGG    3420

ATACCAAACC CCCCCGCCAT GCCCAATGTC TAAATATTCT TGATGCTTTT GCTTTTCCCT    3480

CTTTTCCTTG TTAGTCTATT ATTCTGGAGA GTTTGAGAGA GTTTCATACA AGAAAATTTC    3540

AAGAAGAAAG CAAAGGTCCA GGTATTCTCT TTTCTTAATT ATGTATTAAC TTACAAGCAT    3600

TTTTTACACG ATCCATGGTT TTTTGTGTAT GTTTTTCAAA TTGAAACTAG ATTGGGACTT    3660

TTGCCCTTGA TGATTCATAA GATATTGCAT GGAGTTGAGA TTGTGTAAGA AAAGTGGTGA    3720

ATAGAAAGAG CAAGTGAATC CAGATATAGT ATTGGTAATA TATGATGATG AGATAGAGAT    3780

ATGTTAAAAC TGGCTAGAAA ATTGTTTTAA TTTGAAATTT AGGTTGTTGA ATTTGAAAGA    3840

TACCAAGCTA ATAACTAATT AGTTATGCTA AATAGTTATA AGAACAACA AACTCGTAGT     3900

TTTTTTTTCA TGATTTTCAA CCTCTTCGTA CCAAACTAAA TTATAACAAA ATTGAATATC    3960

ATTCTCTGCA ATCAATTTTA ACTTTTGTTA TTATCATCAT GTCTAAAATT GCCACAAGTT    4020

TATTTTCATA GTCATATTGG ATTATGAAAG GACTATTTTT ACCAATTACA TCTTTACTTT    4080

ATGGCCAAAG CTAATACAAT CCGACTAAAC TAAAGGATTC TAGGATGCAT ATAGTTTGCT    4140

CCCCGATTAT AGATTTCTAT CTAATTTGTC TATTGTACTA ATTTAGGTGC CACCACAAGT    4200

AAATTCCTGA AATGGATGTC GTTAATGCCA TTCTTAAACC AGTTGTCGAG ACTCTCATGG    4260

TACCCGTTAA GAAACACATA GGGTACCTCA TTTCCTGCAG GCAATATATG AGGGAAATGG    4320

GTATCAAAAT GAGGGGATTG AATGCTACAA GACTTGGTGT CGAAGAGCAC GTGAACCGGA    4380

ACATAAGCAA CCAGCTTGAG GTTCCAGCCC AAGTCAGGGG TTGGTTTGAA GAAGTAGGAA    4440

AGATCAATGC AAAAGTGGAA AATTTCCCTA GCGATGTTGG CAGTTGTTTC AATCTTAAGG    4500

TTAGACACGG GGTCGGAAAG AGAGCCTCCA AGATAATTGA GGACATCGAC AGTGTCATGA    4560

GAGAACACTC TATCATCATT TGGAATGATC ATTCCATTCC TTTAGGAAGA ATTGATTCCA    4620

CGAAAGCATC CACCTCAATA CCATCAACCG ATCATCATGA TGAGTTCCAG TCAAGAGAGC    4680

AAACTTTCAC AGAAGCACTA AACGCACTCG ATCCTAACCA CAAATCCCAC ATGATAGCCT    4740

TATGGGGAAT GGGCGGAGTG GGGAAGACGA CAATGATGCA TCGGCTCAAA AAGGTTGTGA    4800

AAGAAAAGAA AATGTTTAAT TTTATAATTG AGGCGGTTGT AGGGGAAAAA ACAGACCCCA    4860

TTGCTATTCA ATCAGCTGTA GCAGATTACC TAGGTATAGA GCTCAATGAA AAAACTAAAC    4920

CAGCAAGAAC TGAGAAGCTT CGGAAATGGT TTGTGGACAA TTCTGGTGGT AAGAAGATCC    4980

TAGTCATACT CGACGATGTA TGGCAGTTTG TGGATCTGAA TGATATTGGT TTAAGTCCTT    5040

TACCAAATCA AGGTGTCGAC TTCAAGGTGT TGTTGACATC ACGAGACAAA GATGTTTGCA    5100

CTGAGATGGG AGCTGAAGTT AATTCAACTT TTAATGTGAA AATGTTAATA GAAACAGAAG    5160

CACAAAGTTT ATTCCACCAA TTTATAGAAA TTTCGGATGA TGTTGATCCT GAGCTCCATA    5220

ATATAGGAGT GAATATTGTA AGGAAGTGTG GGGGTCTACC CATTGCCATA AAAACCATGG    5280

CGTGTACTCT TAGAGGAAAA AGCAAGGATG CATGGAAGAA TGCACTTCTT CGTTTAGAGC    5340

ACTATGACAT TGAAAATATT GTTAATGGAG TTTTTAAAAT GAGTTACGAC AATCTCCAAG    5400

ATGAGGAGAC TAAATCCACC TTTTTGCTTT GTGGAATGTA TCCCGAARAC TTTGATATTC    5460

TTACCGAGGA GTTGGTGAGG TATGGATGGG GGTTGAAATT ATTTAAAAAA NTGTATACTA    5520

TAGGAGAAGC AAGAACCAGG CTCAACACAT GCATTGAGCG GCTCATTCAT ACAAATTTGT    5580

TGATGGAAGT TGATGATGTT AGGTGCATCA AGATGCATGA TCTTGTTCGT GCTTTTGTTT    5640

TGGATATGTA TTCTAAAGTC GAGCATGCTT CCATTGTCAA CCATAGTAAT ACACTAGAGT    5700
```

-continued

```
GGCATGCAGA TAATATGCAC GACTCTTGTA AAAGACTTTC ATTAACATGC AAGGGTATGT    5760

CTAAGTTTCC TACAGACCTG AAGTTTCCAA ACCTCTCCAT TTTGAAACTT ATGCATGAAG    5820

ATATATCATT GAGGTTTCCC AAAAACTTTT ATGAAGAAAT GGAGAAGCTT GAGGTTATAT    5880

CCTATGATAA AATGAAATAT CCATTGCTTC CCTCATCACC TCAATGTTCC GTCAACCTTC    5940

GCGTGTTTCA TCTACATAAA TGCTCGTTAG TGATGTTTGA CTGCTCTTGT ATTGGAAATC    6000

TGTCGAATCT AGAAGTGCTT AGCTTTGCTG ATTCTGCCAT TGACCGGTTG CCTTCCACAA    6060

TCGGAAAGTT GAAGAAGCTA AGGCTACTGG ATTTGACGAA TTGTTATGGT GTTCGTATAG    6120

ATAATGGTGT CTTAAAAAAA TTGGTCAAAC TGGAGGAGCT CTATATGACA GTGGTTGATC    6180

GAGGTCGAAA GGCGATTAGC CTCACAGATG ATAACTGCAA GGAGATGGCA GAGCGTTCAA    6240

AAGATATTTA TGCATTAGAA CTTGAGTTCT TTGAAAACGA TGCTCAACCA AAGAATATGT    6300

CATTTGAGAA GCTACAACGA TTCCAGATCT CAGTGGGGCG CTATTTATAT GGAGATTCCA    6360

TAAAGAGTAG GCACTCGTAT GAAAACACAT TGAAGTTGGT TCTTGAAAAA GGTGAATTAT    6420

TGGAAGCTCG AATGAACGAG TTGTTTAAGA AAACAGAGGT GTTATGTTTA AGTGTGGGAG    6480

ATATGAATGA TCTTGAAGAT ATTGAGGTTA AGTCATCCTC ACAACTTCTT CAATCTTCTT    6540

CGTTCAACAA TTTAAGAGTC CTTGTCGTTT CAAAGTGTGC AGAGTTGAAA CACTTCTTCA    6600

CACCTGGTGT TGCAAACACT TTAAAAAAGC TTGAGCATCT TGAAGTTTAC AAATGTGATA    6660

ATATGGAAGA ACTCATACGT AGCAGGGGTA GTGAAGAAGA GACGATTACA TTCCCCAAGC    6720

TGAAGTTTTT ATCTTTGTGT GGGCTACCAA AGCTATCGGG TTTGTGCGAT AATGTCAAAA    6780

TAATTGAGCT ACCACAACTC ATGGAGTTGG AACTTGACGA CATTCCAGGT TTCACAAGCA    6840

TATATCCCAT GAAAAAGTTT GAAACATTTA GTTTGTTGAA GGAAGAGGTA AATATAAATT    6900

TTTAATGCTA ATACATTACA AAGGATCTTT TCAGTTAAAT CTTTCAAAAT ATATTGTAAT    6960

TTGATTGTAT GGGGTATTAT TGTTGGATGG GACTATTAAT AAATGATTAT CTTGCAGGTT    7020

CTGATTCCTA AGTTAGAGAA ACTGCATGTT AGTAGTATGT GGAATCTGAA GGAGATATGG    7080

CCTTGCGAAT TTAATATGAG TGAGGAAGTT AAGTTCAGAG AGATTAAAGT GAGTAACTGT    7140

GATAAGCTTG TGAATTTGTT TCCGCACAAG CCCATATCTC TGCTGCATCA TCTTGAAGAG    7200

CTTAAAGTCA AGAATTGTGG TTCCATTGAA TCGTTATTCA ACATCCATTT GGATTGTGTT    7260

GGTGCAACTG GAGATGAATA CAACAACAGT GGTGTAAGAA TTATTAAAGT GATCAGTTGT    7320

GATAAGCTTG TGAATCTCTT TCCACACAAT CCCATGTCTA TACTGCATCA TCTTGAAGAG    7380

CTTGAAGTCG AGAATTGTGG TTCCATTGAA TCGTTATTCA ACATTGACTT GGATTGTGCT    7440

GGTGCAATTG GCAAGAAGA CAACAGCATC AGCTTAAGAA ACATCAAAGT GGAGAATTTA    7500

GGGAAGCTAA GANAGGTGTG GAGGATAAAA GGTGGAGATA ACTCTCGTCC CCTTGTTCAT    7560

GGCTTTCAAT CTGTTGAAAG CATAAGGGTT ACNAAATGTN AGAAGTTTAG AAATGTATTC    7620

ACACCTACCA CCACAAATTT TAATCTGGGG GCACTTTTGG AGATTTCAAT AGATGACTGC    7680

GGAGAAAACA GGGAAATGA CGAATCGGAA GAGAGTAGCC ATGAGCAAGA GCAGGTAAGG    7740

ATTTCAATTT CACTGTCTTA ATTAATGATT AAGCTCCTGC TTTTTGAATA AAAAAGGGAC    7800

AAACCATTTC ATGACTTAAT GTAGCAATAC AAGTCATGTA TAAGAGTGAC CAACTCTTTT    7860

TTATTTATAA AATGACTACA AAATATTTTT TTTCATTAGA GATCATGTAT AAATGTGACT    7920

AATTTTTCAT CACCTAACTT TAGTTGATAA ATCTTTATAA ATGTCACTAG TTACTTTTCA    7980

GTAAAATAAC AAATTTAATA AATTATCAAC AAAAAGCATC AACTAAAAAA ATCCCACAAC    8040

CCGTAATAAT TTAAAATAAA AGGATTTAAC ATCTAATACG AACAATTTTT TTTCTAAACA    8100
```

```
TGATTTGGAC CAAATATCAC CAGCAACTCA AGTTTGGAAT CGATTCAGCT TAAAACTTGA      8160

CCAGCATAAT TAGATAGATG AGAGTTGAAG CTAAAGTGCC TATATAAGTT CGTTTCATCT      8220

TTTTTCTTGA TCTTGATAGC AAGTTGAATG ATTTTCTTCT TCAAAATTGA TAAAAATCTA      8280

CATTATAAAG AGACTAGCTT GAAAAAAAAT GGTCTAGGTG GGTCTTGGGT TCTGGTAGAT      8340

GAAGATGGAA GGGGAGAGTA TGATTTCAAA GACACAACAC ATCCTTCATT TTATTTATTT      8400

ATTATTATTA TTATTTTTTG ATATCTTGCT CATATTTGTT ACAGATATGT GAGGTCTATT      8460

AATCTTTTTA AATATATAAA AAAATAAATA ACATAAATGA GAAAATTAAA TAAAGAATAA      8520

ATTAATAAGG GCACAATAGT CTTTTTAGGT AAGACAAGGA CCAAACACGC AACAAAAATA      8580

AACAGTAGGG ACCATCCGAT TTAAAAAAAA TAATTAGGGA CCAAAAACAT AAATTCCCCC      8640

AAACCATAGG GACCATTCAT GTAATTTACT CTTACTTTTC GTTTTGTTCA TATTTGGGTA      8700

ACTATTTTTT TTGTACACAT CTAGGTAACG AACTTGTTGA AGTGTTCCCA TTTAGGATGT      8760

GACCTACTAC AACCGATCAT AATAGTCATA TGTGAACACT TCCAACAACT TTATTACTTA      8820

GGTGTGTACA AAAAAACAAT AGTTACCATG ATGTGAACAT ACTGAAAAAT TAATTACCTT      8880

AGCAAGTTAT TTTCCCATTT AGGTTGTATG GAAACAGTTC CGTGAGACCG TGACTTGGAT      8940

GGTAGATAAA TTTAGTAAAC TTAACCCTTC AATTAACCTA CCTTTTTCTT ATTAACTCAA      9000

TTTCAACCTA AATTCTGATT CTTGTTTGAA AGTAAGTTGC ATCTTTATTT TTGTATTATC      9060

TTGTTGCATA GGATCCTTAG CATCTTTTAA TAATTTATTT GAAGGTGAAA GATCCAACTA      9120

TTTTTAATCT GTTGGCATTT TCCATCATTT GCAACTGTTT CTTGAAAAAA AAATACCTAA      9180

AATCAAAATA ACCATTTTCA AATCCAAAAT TATAAGAGAG AATTGTAAAT GGACATGGAA      9240

TCATAAATCA TTAACACAGT TCAGTAAACA AGTTGCTAAT TACATTTCTT GCTGTGCAGA      9300

TTGAAATTCT ATCAGAGAAA GAGACATTAC AAGAAGCCAC TGACAGTATT TCTAATGTTG      9360

TATTCCCATC CTGTCTCATG CACTCTTTTC ATAACCTCCA GAAACTTATA TTGAACAGAG      9420

TTAAAGGAGT GGAGGTGGTG TTTGAGATAG AGAGTGAGAG TCCAACAAGT AGAGAATTGG      9480

TAACAACTCA CCATAACCAA CAACAACCTA TTATACTTCC CAACCTCCAG GAATTGATTC      9540

TATGGAATAT GGACAACATG AGTCATGTGT GGAAGTGCAG CAACTGGAAT AAAATTCTTCA     9600

CTCTTCCAAA ACAACAATCA GAATCCCCAT TCCACAACCT CACAACCATA AAAATTATGT      9660

ATTGCAAAAG CATTAAGTAC TTGTTTTCGC CTCTCATGGC AGAACTTCTT TCCAACCTAA      9720

AGCATATCAA GATAAGAGAG TGTGATGGTA TTGGAGAAGT TGTTTCAAAC AGAGATGATG      9780

AGGATGAAGA AATGACTACA TTTACATCTA CCCACACAAC CACCACTTTG TTCCCTAGTC      9840

TTGATTCTCT CACTCTAAGT TTCCTGGAGA ATCTGAAGTG TATTGGTGGA GGTGGTGCCA      9900

AGGATGAAGG GAGCAATGAA ATATCTTTCA ATAATACCAC TGCAACTACT GCTGTTCTTG      9960

ATCAATTTGA GGTATGCTTT GTACATATTC AATTATTTAT TTAATTTCCT TTTTTATTTG     10020

CAATATTCTA TAAATAATAC ATTTTATACC CACTATACTA AGATAATAAT TACCTAGAGG     10080

GATGGATGCT ATGACACAGC TGCTACACTT CAGAAACTCT AGTAAGGGCA GTTATGGAAG     10140

TTCAATAAAA TGATAATGGC ATCTTTTGAT GGGTAATATA GGCAATTTAA GTTTTATTTC     10200

TGTTAAAGCA GTATTTAGCA AGTACTGGCC AGTAGGAGAG GAGAATATCA CCTTTTGTGA     10260

AAATCTGGTC ATTGTACCCA GAATTTAGTT AAATGTAACA TTTTAGATAT CAGGGGTCAT     10320

CAGGTGACAG ATATTGTAGA ATAGAACAAT ATATAATATC ACCCAAAACT ATTTTTTCTA     10380

AGGTTATTCT GTTAAATATG TGCTTTCTTG TTTTCATNGA ATTNGCATTC GTATATTTTA     10440
```

```
GGTGTTAAAG TGATTTTNTC TTCAATAAAT CCCGAAATTA ATTAAAAAAA AAAAAACAAA    10500

AGTACATTTT TGATGTGGAG AGCACTGGTA TCACTTAGTA TATAAAAAGC TTGATTTTGA    10560

ATTAACTTTC TTATACAAAA GTTGTGTATA TAGTTTAATT AGTTTACAT CATTTTTCCA     10620

TGTGGTGTTG CAGTTGTCTG AAGCAGGTGG TGTTTCTTGG AGCTTATGCC AATACGCTAG    10680

AGAGATGAGA ATAGAATTCT GCAATGCATT GTCAAGTGTA ATTCCATGTT ATGCAGCAGG    10740

ACAAATGCAA AAGCTGAAGG AGAGGACAGC GATTCTCGTA CGAACGGTTA CGATTCGACT    10800

GGCCGTCGTT TTACA                                                    10815
```

(2) INFORMATION FOR SEQ ID NO:22:

(i) SEQUENCE CHARACTERISTICS:
        (A) LENGTH: 1366 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1366
        (D) OTHER INFORMATION: /note= "RLG2A amino acids"

(xi) SEQUENCE DESCRIPTION: SEQ ID NO:22:

```
Met Asp Val Val Asn Ala Ile Leu Lys Pro Val Val Glu Thr Leu Met
1               5                   10                  15

Val Pro Val Lys Lys His Ile Gly Tyr Leu Ile Ser Cys Arg Gln Tyr
            20                  25                  30

Met Arg Glu Met Gly Ile Lys Met Arg Gly Leu Asn Ala Thr Arg Leu
        35                  40                  45

Gly Val Glu Glu His Val Asn Arg Asn Ile Ser Asn Gln Leu Glu Val
    50                  55                  60

Pro Ala Gln Val Arg Gly Trp Phe Glu Val Gly Lys Ile Asn Ala
65                  70                  75                  80

Lys Val Glu Asn Phe Pro Ser Asp Val Gly Ser Cys Phe Asn Leu Lys
                85                  90                  95

Val Arg His Gly Val Gly Lys Arg Ala Ser Lys Ile Ile Glu Asp Ile
            100                 105                 110

Asp Ser Val Met Arg Glu His Ser Ile Ile Ile Trp Asn Asp His Ser
        115                 120                 125

Ile Pro Leu Gly Arg Ile Asp Ser Thr Lys Ala Ser Thr Ser Ile Pro
    130                 135                 140

Ser Thr Asp His His Asp Glu Phe Gln Ser Arg Glu Gln Thr Phe Thr
145                 150                 155                 160

Glu Ala Leu Asn Ala Leu Asp Pro Asn His Lys Ser His Met Ile Ala
                165                 170                 175

Leu Trp Gly Met Gly Gly Val Gly Lys Thr Thr Met Met His Arg Leu
            180                 185                 190

Lys Lys Val Val Lys Glu Lys Lys Met Phe Asn Phe Ile Ile Glu Ala
        195                 200                 205

Val Val Gly Glu Lys Thr Asp Pro Ile Ala Ile Gln Ser Ala Val Ala
    210                 215                 220

Asp Tyr Leu Gly Ile Glu Leu Asn Glu Lys Thr Lys Pro Ala Arg Thr
225                 230                 235                 240

Glu Lys Leu Arg Lys Trp Phe Val Asp Asn Ser Gly Gly Lys Lys Ile
                245                 250                 255
```

```
Leu Val Ile Leu Asp Asp Val Trp Gln Phe Val Asp Leu Asn Asp Ile
            260                 265                 270

Gly Leu Ser Pro Leu Pro Asn Gln Gly Val Asp Phe Lys Val Leu Leu
            275                 280                 285

Thr Ser Arg Asp Lys Asp Val Cys Thr Glu Met Gly Ala Glu Val Asn
            290                 295                 300

Ser Thr Phe Asn Val Lys Met Leu Ile Glu Thr Glu Ala Gln Ser Leu
305                 310                 315                 320

Phe His Gln Phe Ile Glu Ile Ser Asp Val Asp Pro Glu Leu His
                    325                 330                 335

Asn Ile Gly Val Asn Ile Val Arg Lys Cys Gly Gly Leu Pro Ile Ala
            340                 345                 350

Ile Lys Thr Met Ala Cys Thr Leu Arg Gly Lys Ser Lys Asp Ala Trp
            355                 360                 365

Lys Asn Ala Leu Leu Arg Leu Glu His Tyr Asp Ile Glu Asn Ile Val
            370                 375                 380

Asn Gly Val Phe Lys Met Ser Tyr Asp Asn Leu Gln Asp Glu Glu Thr
385                 390                 395                 400

Lys Ser Thr Phe Leu Leu Cys Gly Met Tyr Pro Glu Xaa Phe Asp Ile
            405                 410                 415

Leu Thr Glu Glu Leu Val Arg Tyr Gly Trp Gly Leu Lys Leu Phe Lys
            420                 425                 430

Lys Xaa Tyr Thr Ile Gly Glu Ala Arg Thr Arg Leu Asn Thr Cys Ile
            435                 440                 445

Glu Arg Leu Ile His Thr Asn Leu Leu Met Glu Val Asp Asp Val Arg
            450                 455                 460

Cys Ile Lys Met His Asp Leu Val Arg Ala Phe Val Leu Asp Met Tyr
465                 470                 475                 480

Ser Lys Val Glu His Ala Ser Ile Val Asn His Ser Asn Thr Leu Glu
            485                 490                 495

Trp His Ala Asp Asn Met His Asp Ser Cys Lys Arg Leu Ser Leu Thr
            500                 505                 510

Cys Lys Gly Met Ser Lys Phe Pro Thr Asp Leu Lys Phe Pro Asn Leu
            515                 520                 525

Ser Ile Leu Lys Leu Met His Glu Asp Ile Ser Leu Arg Phe Pro Lys
530                 535                 540

Asn Phe Tyr Glu Glu Met Glu Lys Leu Glu Val Ile Ser Tyr Asp Lys
545                 550                 555                 560

Met Lys Tyr Pro Leu Leu Pro Ser Ser Pro Gln Cys Ser Val Asn Leu
            565                 570                 575

Arg Val Phe His Leu His Lys Cys Ser Leu Val Met Phe Asp Cys Ser
            580                 585                 590

Cys Ile Gly Asn Leu Ser Asn Leu Glu Val Leu Ser Phe Ala Asp Ser
            595                 600                 605

Ala Ile Asp Arg Leu Pro Ser Thr Ile Gly Lys Leu Lys Lys Leu Arg
            610                 615                 620

Leu Leu Asp Leu Thr Asn Cys Tyr Gly Val Arg Ile Asp Asn Gly Val
625                 630                 635                 640

Leu Lys Lys Leu Val Lys Leu Glu Glu Leu Tyr Met Thr Val Val Asp
            645                 650                 655

Arg Gly Arg Lys Ala Ile Ser Leu Thr Asp Asp Asn Cys Lys Glu Met
            660                 665                 670
```

```
Ala Glu Arg Ser Lys Asp Ile Tyr Ala Leu Glu Leu Glu Phe Phe Glu
            675                 680                 685

Asn Asp Ala Gln Pro Lys Asn Met Ser Phe Glu Lys Leu Gln Arg Phe
            690                 695                 700

Gln Ile Ser Val Gly Arg Tyr Leu Tyr Gly Asp Ser Ile Lys Ser Arg
705                 710                 715                 720

His Ser Tyr Glu Asn Thr Leu Lys Leu Val Leu Glu Lys Gly Glu Leu
            725                 730                 735

Leu Glu Ala Arg Met Asn Glu Leu Phe Lys Lys Thr Glu Val Leu Cys
            740                 745                 750

Leu Ser Val Gly Asp Met Asn Asp Leu Glu Asp Ile Glu Val Lys Ser
            755                 760                 765

Ser Ser Gln Leu Leu Gln Ser Ser Phe Asn Asn Leu Arg Val Leu
            770                 775                 780

Val Val Ser Lys Cys Ala Glu Leu Lys His Phe Phe Thr Pro Gly Val
785                 790                 795                 800

Ala Asn Thr Leu Lys Lys Leu Glu His Leu Glu Val Tyr Lys Cys Asp
            805                 810                 815

Asn Met Glu Glu Leu Ile Arg Ser Arg Gly Ser Glu Glu Thr Ile
            820                 825                 830

Thr Phe Pro Lys Leu Lys Phe Leu Ser Leu Cys Gly Leu Pro Lys Leu
            835                 840                 845

Ser Gly Leu Cys Asp Asn Val Lys Ile Ile Glu Leu Pro Gln Leu Met
850                 855                 860

Glu Leu Glu Leu Asp Asp Ile Pro Gly Phe Thr Ser Ile Tyr Pro Met
865                 870                 875                 880

Lys Lys Phe Glu Thr Phe Ser Leu Leu Lys Glu Val Leu Ile Pro
            885                 890                 895

Lys Leu Glu Lys Leu His Val Ser Ser Met Trp Asn Leu Lys Glu Ile
            900                 905                 910

Trp Pro Cys Glu Phe Asn Met Ser Glu Glu Val Lys Phe Arg Glu Ile
            915                 920                 925

Lys Val Ser Asn Cys Asp Lys Leu Val Asn Leu Phe Pro His Lys Pro
930                 935                 940

Ile Ser Leu Leu His His Leu Glu Glu Lys Val Lys Asn Cys Gly
945                 950                 955                 960

Ser Ile Glu Ser Leu Phe Asn Ile His Leu Asp Cys Val Gly Ala Thr
            965                 970                 975

Gly Asp Glu Tyr Asn Asn Ser Gly Val Arg Ile Ile Lys Val Ile Ser
            980                 985                 990

Cys Asp Lys Leu Val Asn Leu Phe Pro His Asn Pro Met Ser Ile Leu
            995                 1000                1005

His His Leu Glu Glu Leu Glu Val Glu Asn Cys Gly Ser Ile Glu Ser
            1010                1015                1020

Leu Phe Asn Ile Asp Leu Asp Cys Ala Gly Ala Ile Gly Gln Glu Asp
1025                1030                1035                1040

Asn Ser Ile Ser Leu Arg Asn Ile Lys Val Glu Asn Leu Gly Lys Leu
            1045                1050                1055

Arg Xaa Val Trp Arg Ile Lys Gly Gly Asp Asn Ser Arg Pro Leu Val
            1060                1065                1070

His Gly Phe Gln Ser Val Glu Ser Ile Arg Val Thr Lys Cys Xaa Lys
            1075                1080                1085

Phe Arg Asn Val Phe Thr Pro Thr Thr Thr Asn Phe Asn Leu Gly Ala
```

```
                1090                1095                1100
Leu Leu Glu Ile Ser Ile Asp Asp Cys Gly Glu Asn Arg Gly Asn Asp
1105                1110                1115                1120
Glu Ser Glu Glu Ser Ser His Glu Gln Glu Gln Ile Glu Ile Leu Ser
                1125                1130                1135
Glu Lys Glu Thr Leu Gln Glu Ala Thr Asp Ser Ile Ser Asn Val Val
            1140                1145                1150
Phe Pro Ser Cys Leu Met His Ser Phe His Asn Leu Gln Lys Leu Ile
            1155                1160                1165
Leu Asn Arg Val Lys Gly Val Glu Val Val Phe Glu Ile Glu Ser Glu
            1170                1175                1180
Ser Pro Thr Ser Arg Glu Leu Val Thr Thr His His Asn Gln Gln Gln
1185                1190                1195                1200
Pro Ile Ile Leu Pro Asn Leu Gln Glu Leu Ile Leu Trp Asn Met Asp
                1205                1210                1215
Asn Met Ser His Val Trp Lys Cys Ser Asn Trp Asn Lys Phe Phe Thr
                1220                1225                1230
Leu Pro Lys Gln Gln Ser Glu Ser Pro Phe His Asn Leu Thr Thr Ile
            1235                1240                1245
Lys Ile Met Tyr Cys Lys Ser Ile Lys Tyr Leu Phe Ser Pro Leu Met
1250                1255                1260
Ala Glu Leu Leu Ser Asn Leu Lys His Ile Lys Ile Arg Glu Cys Asp
1265                1270                1275                1280
Gly Ile Gly Glu Val Val Ser Asn Arg Asp Asp Glu Asp Glu Glu Met
                1285                1290                1295
Thr Thr Phe Thr Ser Thr His Thr Thr Thr Leu Phe Pro Ser Leu
                1300                1305                1310
Asp Ser Leu Thr Leu Ser Phe Leu Glu Asn Leu Lys Cys Ile Gly Gly
            1315                1320                1325
Gly Gly Ala Lys Asp Glu Gly Ser Asn Glu Ile Ser Phe Asn Asn Thr
1330                1335                1340
Thr Ala Thr Thr Ala Val Leu Asp Gln Phe Glu Val Cys Phe Val His
1345                1350                1355                1360
Ile Gln Leu Phe Ile Xaa
            1365

(2) INFORMATION FOR SEQ ID NO:23:

(i) SEQUENCE CHARACTERISTICS:
        (A) LENGTH: 11056 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..11056
        (D) OTHER INFORMATION: /note= "RLG2B"

(xi) SEQUENCE DESCRIPTION: SEQ ID NO:23:

AGTTTTTTTT TTTCCCAATA TCCATTTATA TGCGATTTAT TTCTGAAATA ATTTTATCAA     60

AACGCAGGAA ACAATGTAGA ATAATACTGG TATAATTAAT TATATAAAGT TATTAGGCTG    120

AAATCTTGAG GCTACTATAA TTTAATTATC ATAATTTGAA AATCATCAAA TTGTATTCCA    180

TGTATATTTA TGTTATCAGA TAATTAATAA TATGTGAGCC ACACAAATCC ACATCATCAG    240
```

```
ACACCCCACC TTATTGTCGG CTACCTCACC ACTTGCATGA TCCCGACATC TTCCCAACCC    300

CACCGACGAC TTGGGGTCTC CTTAATATAT CAATTATTTT CTGTAAGTAT TTATTTGTGT    360

AAATGTGTAA TGTCATTTTA CCTTTTTTCT AATATATACA GAAACATAAA TTTTAAATGA    420

AATTCAACTG CGTTTCATTC TTGCATTAAA AAAAAGACT GTACTGTTGT CAATATTTTA     480

CTTATAACCT GATTAATTAA TTAAAGCGTA ATTGCATAAT TTGCATTAGG TTGTAATTTT    540

GTGTTTTATA GGGAGGGTGA GGGTCACCGG GAATCAAAGC ACTTATGTAA AAGCAGGGGA    600

AATACAAAAA ATTTACTCGA AACAAATTTT ATTCAATTTA AGTGAGATAA TAATGTTCTG    660

ATTAGATTAT GAGAACTAGG AGATTTAAGT GATATATCCC ATTTAAAAGA AATTGCATTA    720

TTAATTTTGG ATCTCTTGAT GATGACAAAA TTAACTCGTG ACAGGTTATA TATCATATAC    780

AAAATGAGTG GCTATGCTTT CGCTTTCCAA AAAGCAATTA TAGTTATACT ACACCTACAA    840

ATTTTAAAAG GGGTTAAACA TATCAAAATA CTTGATAAGT AATTATATAA ATATGCATTT    900

AACCCTCTAA AGAAAATGCT ACTAAGCTTG GACCATCTCA GAATTACAAT CATACCCTTC    960

CCCTCAAAAA AGATTCGTAT ATATCATGTC ATTTGGCATT CATTTCTTTT TCACAATTCA   1020

TAGTTCTATT CTCAAAAAAT TCGAGTTCTC GTATTTGTAA GGAAGATCAG AAGAGACTGT   1080

TCACACAGGT ACTCTCTTTT ATTTATTGAT TCACATTCAT ATATGTTATT GTTTTCTTGC   1140

TTAATGGTTT CGTCAGTCTA ACTGCGCTTG CTGATTTAAA TTTCTTCACT TTCTTCCACG   1200

GATTTTTTAA ATATTAGTTT TGTGAATGAA CAATTGGTGA AGGAAAGAAA CATGGGAGTC   1260

TTTTCTAAAG TAAACCTAGA TACTTAGGTT ATAAGGGTAT ATGCTAAAAT GAACTATGCC   1320

CATTCACCTT TGCCTTTTCT TTTACTTTTT AGTTTTTAGA ATCCAAGTTT TCATATGTAT   1380

CTCGATGTGT GAGAAGAATA GGCATTAGAA AGGTAAAGGA CGTACATAAA ATTGATTAAT   1440

TAGTGAATGT TCTTTGATAT CATTATTTTT ACTCTCATAA AAAGCATATA GATCAAACAC   1500

AAATTGCTAC TTGTTAGTGT AACAACTTCG ACTTAATAAT GTTAATAATC AAGATTCTCT   1560

TGATTTCAAC TATTTTCTAA CCGAACAAGC TCACTAAAAA CTCATATTGC TTTGAGTCTG   1620

AGTGGTTTAT ATTTGGGGTT TTACATTTAA TTTTTTGTGC ATGAATGTGA AAATAGACTG   1680

CTTATTGATT CTTTGTGTTT CATTGAGTTG ATTTTCATTA TTACTACCTT ACAAATTGCT   1740

CAGTGATAGA TTTCCATTAA TTTGCTAATT CGGTTGCTTC TAAATATGTA GGAGCTACTA   1800

AAAGCAAAAA TATCGAGCAA TGTCGGACCC AACGGGATT GCTGGTGCCA TTATTAACCC    1860

AATTGCTCAG ACGGCCTTGG TTCCCGTTAC GGACCATGTA GGCTACATGA TTTCCTGCAG   1920

AAAATATGTG AGGGTCATGC AGATGAAAAT GACAGAGTTG AATACCTCAA GAATCAGTGT   1980

AGAGGAACAC ATTAGCCGGA ACACAAGAAA TCATCTTCAG TTCCATCTCA AACTAAGGAA   2040

TGGTTGGACC AAGTAGAAGG GATCAGAGCA AATGTGGAAA ACTTTCCGAT TGATGTCATC   2100

ACTTGTTGTA GTCTCAGGAT CAGGCACAAG CTTGGACAGA AAGCNTTCAA GATAACTGAG   2160

CAGATTGAAA GTCTAACGAG ACAACTCTCC CTGATCAGTT GGACTGATGA TCCAGTTCYT   2220

CTAGGAAGAG TTGGTTCCAT GAATGCATCC ACCTCTGCAT CATTAAGTGA TGATTTCCCA   2280

TCAAGAGAGA AAACTTTTAC ACAAGCACTA ATAGCACTCG AACCCAACCA AAAATTCCAC   2340

ATGGTAGCCT TGTGTGGGAT GGGTGGAGTG GGGAAGACTA GAATGATGCA AAGGCTGAAG   2400

AAGGCTGMTG AAGAAAAGAA ATTGTTTAAT TATATTGTTG GGGCAGTTAT AKGGGAAAAG   2460

ACGGACCCCT TTGCCATTCA AGAAGCTATA GCAGATTACC TCGGTATACA ACTCAATGAA   2520

AAAACTAAGC CAGCAAGAGC TGATAAGCTT CGTGAATGGT TCAAAAGAA TTCAGATGGA    2580

GGTAAGACTA AGTTCCTCAT AGTACTTGAC GATGTTTGGC AATTAGTTGA TCTTGAAGAT   2640
```

```
ATTGGGTTAA GTCCTTTTCC AAATCAAGGT GTCGACTTCA AGGTCTTGTT GACATCACGA    2700

GACTCACAAG TTTGCACTAT GATGGGGGTT GAAGCTAATT CAATTATTAA CGTGGGCCTT    2760

CTAACTGAAG CAGAAGCTCA AAGTCTGTTC CAACAATTTG TAGAAACTTC TGAGCCCGAG    2820

CTCCAGAAGA TAGGAGAGGA TATCGTAAGG AAGTGTTGCG GTCTACCTAT TGCCATAAAA    2880

ACCATGGCAT GTWCTCTTAG AAATAAAAGA AAGGATGCAT GGAAGGATGC ACTTTCGCGC    2940

ATAGAGCACT ATGACATTCA CAATGTTGCG CCCAAAGTCT TTGAAACGAG CTACCACAAT    3000

CTCCAAGAAG AGGAGACTAA ATCCACTTTT TTAATGTGTG GTTTGTTTCC CGAAGACTTC    3060

GATATTCCTA CTGAGGAGTT GATGAGGTAT GGATGGGGCT TGAAGCTATT TGATAGAGTT    3120

TATACGATTA GAGAAGCAAG AACCAGGCTC AACACCTGCA TTGAGCGACT GGTGCAGACA    3180

AATTTGTTAA TTGAAAGTGA TGATGTTGGG TGTGTCAAGA TGCATGATCT GGTCCGTGCT    3240

TTTGTTTTGG GTATGTTTTC TGAAGTCGAG CATGCTTCTA TTGTCAACCA TGGTAATATG    3300

CCTGGGTGGC CTGATGAAAA TGATATGATC GTGCACTCTT GCAAAAGAAT TCATTAACA    3360

TGCAAGGGTA TGATTGAGAT TCCAGTAGAC CTCAAGTTTC CTAAACTAAC GATTTTGAAA    3420

CTTATGCATG GAGATAAGTC GCTAAGGTTT CCTCAAGACT TTTATGAAGG AATGGAAAAG    3480

CTCCATGTTA TATCATACGA TAAAATGAAG TACCCATTGC TTCCTTTGGC ACCTCGATGC    3540

TCCACCAACA TTCGGGTGCT TCATCTCACT GAATGTTCAT TAAAGATGTT TGATTGCTCT    3600

TCTATCGGAA ATCTATCGAA TCTGGAAGTG CTGAGCTTTG CAAATTCTCA CATTGAATGG    3660

TTACCTTCCA CAGTCAGAAA TTTAAAGAAG CTAAGGTTAC TTGATCTGAG ATTTTGTGAT    3720

GGTCTCCGTA TAGAACAGGG TGTCTTGAAA AGTTTTGTCA AACTTGAAGA ATTTTATATT    3780

GGAGATGCAT CTGGGTTTAT AGATGATAAC TGCAATGAGA TGGCAGAGCG TTCTTACAAC    3840

CTTTCTGCAT TAGAATTCGC GTTCTTTAAT AACAAGGCTG AAGTGAAAAA TATGTCATTT    3900

GAGAATCTTG AACGATTCAA GATCTCAGTG GGATGCTCTT TTGATGAAAA TATCAATATG    3960

AGTAGCCACT CATACGAAAA CATGTTGCAA TTGGTGACCA ACAAAGGTGA TGTATTAGAC    4020

TCTAAACTTA ATGGGTTATT TTTGAAAACA GAGGTGCTTT TTTTAAGTGT GCATGGCATG    4080

AATGATCTTG AAGATGTTGA GGTGAAGTCG ACACATCCTA CTCAGTCCTC TTCATTCTGC    4140

AATTTAAAAG TTCTTATTAT TTCAAAGTGT GTAGAGTTGA GATACCTTTT CAAACTCAAT    4200

CTTGCAAACA CTTTGTCAAG ACTTGAGCAT CTAGAAGTTT GTGAATGTGA GAATATGGAA    4260

GAACTCATAC ATACTGGAAT TGGGGGTTGT GGAGAAGAGA CAATTACTTT CCCTAAGCTG    4320

AAGTTTTTAT CTTTGAGTCA ACTACCGAAG TTATCAAGTT TGTGCCATAA TGTCAACATA    4380

ATTGGGCTAC CACATCTCGT AGACTTGATA CTTAAGGGCA TTCCAGGTTT CACAGTCATT    4440

TATCCGCAGA ACAAGTTGCG AACATCTAGT TTGTTGAAGG AAGGGGTAGA TATATGTTCT    4500

TTATGTTAAT ACAATTTAAA TAATATTTTC AACCAAATTT TCATAATATA TCTGTAATTT    4560

GATTGTATGA TGTGTTATTG TTTATATGTG GCTATTAAGG GATGATTATT TTGCAGGTTG    4620

TGATTCCTAA GTTGGAGACA CTTCAAATTG ATGACATGGA GAACTTAGAA GAAATATGGC    4680

CTTGTGAACT TAGTGGAGGT GAGAAAGTTA AGTTGAGAGC GATTAAAGTG AGTAGCTGTG    4740

ATAAGCTTGT GAATCTATTT CCGCGCAATC CCATGTCTCT GTTGCATCAT CTTGAAGAGC    4800

TTACAGTCGA GAATTGCGGT TCCATTGAGT CGTTATTCAA CATTGACTTG GATTGTGTCG    4860

GTGCAATTGG AGAAGAAGAC AACAAGAGCC TCTTAAGAAG CATCAACGTG GAGAATTTAG    4920

GGAAGCTAAG AGAGGTGTGG AGGATAAAAG GTGCAGATAA CTCTGATCTC ATCAACGGTT    4980
```

```
TTCAAGCTGT TGAAAGCATA AAGATTGAAA AATGTAAGAG GTTTAGAAAT ATATTCACAC    5040

CTATCACCGC CAATTTTTAT CTGGAGGCAC TTTTGGAGAT TCAGATAGAA GGTTGCGGAG    5100

GAAATCACGA ATCAGAAGAG CAGGTAACGC TTTCAATTTC ACTTTCTTAA TTAATTAAGG    5160

ACTAAGCTCC TGTTTTTTGA ATAATAAAGA GGTGGGATGA CTAAACTTGG GCATCACAAT    5220

TGCAACAAAA TGTTACAAAC CATGAAACGT TCAAACCATT TCTTGAATTA AGGTTTCAAT    5280

ACAAGTCATT TAAAAATATG GCTTAAATTT TTTTTATATT TATGTATCAA CATGATTTTT    5340

CATTAGAGAT CATTATTATA ATAGTAAGTT TAAAGCAATT TAAATCAGAA CTAATTCTAA    5400

CTTTAGCTAA TAAATCGTTA TAAATGTAAA TAATTACTTT TTAGTGAAAT AAGCAACGGA    5460

TTTAATAAGT TAACAACTTA AATGTCATTT CCTAACAAAA AAAACTTTGG TTCAGAAAAA    5520

CCGCAATTCA AGATAACTAA AATAAAAATA TTTGACATTC ACTAAGAGCA TTTTTTTTTC    5580

TAAATATGAT TGCAAATGAA TAAAACTTAA ATTTATACAG AAAATTCTTT TATATATGTT    5640

ATACAAAATT TACAAATTGA AATTGGATAT GTTAATTAAC GGTTTATAAT TCTGGTATCA    5700

CAAAGGGATA TATAATAAAA TATTATTTTC TGTAGTCATT TGTAATTGTA CTAGTTTATA    5760

ACCCGTGGGA ACCATGAGTT CTAAAATTAG TTAAACTTTC ATAATAAAAA TTTATAATTA    5820

TTATTTATTT TAAATAAATT ATTAATTAAG AGATATATCA AAAATTTAAA GTTATTATAA    5880

CTTCAAATTT AACATATAAT TAGAAAATAT ATGATCATAA CTTCTGCACT CTCTTTGTAT    5940

AAATGCAGAG AAGCTATTAG TATATTTCTA ATCAAGTCCA AACCTAATGA AGCCTATATA    6000

ATTTTGTGAA AACTCAATTA GCATTAGGTT TTAAGAGTCA CCAAATTCAA AGAATAATCC    6060

AATGCTTTCA TTACCACTAT GGAGAAAATA TTTTCTTAGT TTAAATGAAA TGAAAACAAA    6120

CATTCAAACT AATTGTTGCT TATTAAACCA AAGACCCATT ACTTAGCCAA GAGTTTAACA    6180

AAAAAAAATT ACATTCATGT ATCATTATTC ATGACTAGAT ATATATGAAC ATGAAGGGAG    6240

TTTTTATAGA AAATATAATC ATAGATATTC AACATAACTT CAGGGAATTC CTCAAAATAA    6300

CCAAGTTATT CAAGAAATTA CATCCAAGTC AACCAAAGAG AAGTTTAGCC TAGCATGGCT    6360

AAACTCAAGA AACTAAAATA AGGATTAGAA GTACCAAACA TGTAGTAAGA ATCACAGTAA    6420

AAGATGATGT TGTTCTTGAT GTTCTTCTAA GTTCTTCAAG TCTCCAGTTG CTCCTAATAA    6480

TGCAAAGGAG AGCCATTAAA TTCGTATGTA TTGATCCCTT CAAAAGCTGC ACCAACCTCC    6540

CTTAAATAAC ACTCAAAGCA AAAATGACAA AATGCCCTGA AGGACCCTAT GTGGGTGCCT    6600

TGCGCGGGTG GAGCTGCATA CGAAAGGTCT TTGGTCTTTG TGAGGGTGAT GTTGTGCGGG    6660

ATAGCTTGTC GCATGCTTCC GCGCGGTTCA CGCACATGTG CACAGGTGAT GCATGGTGTG    6720

TGCGTTCTTG AGTTTTGAGC CTCCGATGCT TAGTCCACTT GGCCCAATTC GAGTCCAATC    6780

AGCTTATAAC CCATTTTTCT TCAAGTTATC TTCAAGTTAA GCCCAATTTG GCTTCTCCAA    6840

ATCATCCATA ACTTCACAGA ATCGCCCGTT CATCTTAATC CCGGATGCAC AATTATTCTC    6900

CCGTCTTCAT TTTAAGCAAG ATACCACCTT CTTCATGCTT CATCCATCAA TAGTACACTT    6960

CATGTATCAT CTCTACTAGT TATTTAGTCC ACAAATCCTT GTTGTCCTCC AAATTTAATT    7020

ATCTCATTTA GTTCCCCGTT CCGCTACTTT CCTTAAAATT TGGAATTAAG CTCAGAGAAA    7080

TATTAAGTAC CCGAAATGGT CATAAAATTA ACAAAAGGA AAATGCATGA AGATTAACTA    7140

AATGATGAAC GAAATATGCT AAAATAGACT ATAAAATGAA GTAAATAAAA TGAAATTATC    7200

GCACTCCGAC CACCCTTATG GCTTGTAGTC CACCCACCCT TCATTCCTTG TACCAATATG    7260

GGATGGAAAC ATCATTAATT AAGCCAAAAA GCTAACATAT AAGGGTTTAG TGACAAAGGT    7320

AAGTACTAAA GATGAAAATA ATCCATTTTT CTTGTTTTTA CACAACACAC ACATAGGGGC    7380
```

```
AGACGTAGGA TTTCAAAGTA CAGATTGTTG GTGGCACATA AGTGTTGCTG GTGACATTTT    7440

TTTTTTCTTT TTACGTGGTG GCACAACAGT AGGAAAAACG AAAAATTCGA AATTTTTTAC    7500

AATTTGTCTT AAAAAAAACA GGGGTTGTTG GTGCCACTAT GGACAACAAA GTTGAACTGC    7560

CCTACGCGCG CACACACACA CACACACATA GAGAGAGAGA GAGAGAGAGA GAGAGAGAGA    7620

AAGAAAGAAA GAGAGAGAGA GTTTGGGATG TGATACTTCT TTTAGGAAAA TGGAGTTATA    7680

TCTTTGATAT TGTATTTTTT TAATGTAATT TATNTATTTA ATCATTTTAG TTTATAAGTT    7740

NTATTTATTN GGNTATGAAA AAAAAAGTCT TTTATACATT GGATTTAACA TAAAAATCCA    7800

ACAATATTAA TCAAAAAGAC CAAACATGTG GACAATTATG TATATAATTA ATTCACAATA    7860

GTCTTTAGGA ATAGTATTAT ATATATAATT AATTCTCAAT GGTCTTAGGA ATAGTAAGTT    7920

CTTATATTTC AAACTTTTGC CACAATTCTT TGCTTACTTT GACACTTTTC CTTCCTAACT    7980

TTACATATAT ATATATATTA AAGCGCAAAG GTCATAGGAA TATAATATTT TCTATTATTC    8040

TACGTTTTGC CACAAAAGTT TGAACACTTT GCCACTTTTT GTCCCTCCTT AACCTTTTCA    8100

ATGTTTTGCG ACAAAAGTTC CAAAACTTTG CCACTTTGAT CATTCCTCAA CTTTTCACCG    8160

CATTAGTTTG TGGAGTTGGC AGTTTTGGTC CCTCTAACTT CGATATTCTC TACTGCTAGC    8220

CAAAAAGGGT TCCAGAGTTT CACACTTTTG GTCCCTGACA GTAACCAAAT GTGAGATGTC    8280

AAATTTTTGC CACATTAGTT TGTGGAGTTG TCCCTTTTGG TCCCCCCACA TTCGATATTC    8340

TACTATACGA TCTTATTTTT CTCAAATAAC AACACGTATA TTTCATCNCT AATTGGAAAA    8400

AGAGTTTTAA AANAAATAAC GACTAGGNNN GNGCNGAGTT TTTTTTNACA AGTTTGTATC    8460

AAATCATATC AAAATTTAAG GTGGAACGGT GACCACATTA ACCAGAAATG TAATTTATTC    8520

TTTGATTTTG ATAATTTTTA ATATTTTGTT GTGATCTATG TATTTAAAAG TAAACAACAA    8580

AGAACATAAT CCAAAACCCT AAATTGCAAG TCTCGCCCAA TTTCTCTATC ACTAGTCCTC    8640

ACTTACGATG GCGTTACGTC GCTCTCTCAC TGCTTACAAC CCTTTGTTGC TACTCATTAC    8700

AATAACGAAA AGTTGAATAT CCATATATTT ATTTGGATGT GGAATTGAAC GAATCTCGTC    8760

AAAATTTTGA TTTTGTTGAT GGATTTGAGT AGAAGTTTGG GCAGAACGGG AATGATGGTC    8820

TGCAAGTGGT TATAAACTTG ATTCTGAGTT ATTACTATAT ATGTAGCCTC TTTACAACGA    8880

CCAAGGTTTC TTCCAGGTAC CATTTGATCT TTTTAGAACT TAGTTTTCTG AAACACCCTG    8940

ATTTGGATCA AATATCACCA ACAACTCTTA AAAACTTGAT TAATCAATTG TTTTCTTCAT    9000

CTTGATAACA AGTGGAATGA TTTTCTACTT AGATTAACTT GAAAAAAAAG GTCCATGTGC    9060

GTCTGGTGGA TCTGGTAAAT GAAGATGGAA GGGAGAGCTG ACTTTAAAGA CACAAACACG    9120

TCACCATATC TCTTATTTTA TTTTAAATTT GCTTTTGGTG TATTTTCTTT TTTCCTATTT    9180

CTTTCTTTCT TGATCTCCAG ATGGTATGTG GTGTGGATAA TTTACACCTA GAGATTGGGA    9240

ACGATGGGAA GGGGTCTGTG ATTTATGGCT GGCCGAGTTT TACTTATTAA CTCAATTTCA    9300

ACCTAAATTC TGATTCTTGT TTGAAAATAA GTTGCATCTT TATTTTTGTA TTATCTTGTT    9360

GCATAGGATC CTTAGCATCT TTTAATAATT TATTTGAAGG TGAAAGATCC AACTATTTTT    9420

TAGCTGTTGG CATTTTCCAT CATTTGCAAC TGTTTCTTGA AAAAAAAATA CCTAAAATAA    9480

AAATAACCAT TTTCAAATCC AAAATTATAA GAGAGAATTG TAAATGGACA TGGAATCATA    9540

AATCATTAAC ACAGTTCAGT AAACAAGTTG CTAATTACAT TTCTTGCTGT GCAGATTGAA    9600

ATTCTATCAG AGAAAGAGAC ATTACAAGAA GCCACTGGCA GTATTTCAAA TCTTGTATTC    9660

CCATCCTGTC TCATGCACTC TTTTCATAAC CTCCGTGTGC TTACATTGGA TAATTATGAA    9720
```

-continued

| | |
|---|---|
| GGAGTGGAGG TGGTATTTGA GATAGAGAGT GAGAGTCCAA CATGTAGAGA ATTGGTAACA | 9780 |
| ACTCGCAATA ACCAACAACA GCCTATTATA CTTCCCTACC TCCAGGATTT GTATCTAAGG | 9840 |
| AATATGGACA ACACGAGTCA TGTGTGGAAG TGCAGCAACT GGAATAAATT CTTCACTCTT | 9900 |
| CCAAAACAAC AATCAGAATC CCCATTCCAC AACCTCACAA CCATAAATAT TCTTAAATGC | 9960 |
| AAAAGCATTA AGTACTTGTT TTCGCCTCTC ATGGCAGAAC TTCTTTCCAA CCTAAAGGAT | 10020 |
| ATCCGGATAA GTGAGTGTGA TGGTATTAAA GAAGTTGTTT CAAACAGAGA TGATGAGGAT | 10080 |
| GAAGAAATGA CTACATTTAC ATCTACCCAC ACAACCACCA CTTTGTTCCC TAGTCTTGAT | 10140 |
| TCTCTCACTC TAAGTTTCCT GGAGAATCTG AAGTGTATTG GTGGAAGTGG TGCCAAGGAT | 10200 |
| GAGGGGAGCA ATGAAATATC TTTCAATAAT ACCACTGCAA CTACTGCTGT TCTTGATCAA | 10260 |
| TTTGAAGTAT GCTTTGTACA TATTCCATTA TTTATTTAAT TTCCTTTTTT ATTTGCAATA | 10320 |
| TTCTATAAAT AATACATTTT ATACCCACTA TACTAAGATA ATAATTACCT AGAGGGATGG | 10380 |
| ATGCTATGAC ACAGCTGCTA CACTTCAGAA ACTCTARTAA GGGCAGTTAT GGAAGTTCAA | 10440 |
| TAAAATGATA ATGGCATCTT TTGATGGGTA ATATAGGCAA TTTAAGTTTT ATTTCTGTTA | 10500 |
| AAGCAGTATT TAGCAAGTAC TGGCCAGTAG GAGAGGAGAA TATCACCTTT TGTGAAAATC | 10560 |
| TGGTCATTGT ACCCAGAATT TAGTTAAATG TAACATTTTA GATATTAGGG GTTATCAGGT | 10620 |
| GACAGATATT GTAGAATAGA ACAATATGTA ATATTACCCA AAACTATTTT TTCTAAGGTT | 10680 |
| GCTCTGTTAA ATATGTGCTT TCTTGATTTC ATTGAATTTG CATTCCTATA TTTTAGGTGG | 10740 |
| TAAAGTGATT GTCTCTTCAA TAAATCCCGA AATTTTTTAA TTAAAAAAAA AAAAAACAAA | 10800 |
| AGTAAATTTT TGATATGGAG AGCACTGGTA TCATTTAGTA TATAAAAAAC AGATTTTGAA | 10860 |
| TTAAGTTTCT TATATAAAAG CTGTGTATAT AGTTTAATTA GTTTTACATC ATTTTTCCAT | 10920 |
| GTGGTGTTGC AGTTGTCTGA AGCAGGTGGT GTTTCTTGGA GCTTATGCCA ATACGCTAGA | 10980 |
| GAGATAAAAA TAGGCAACTG CCATGCATTG TCAAGTGTGA TTCCATGTTA TGCAGCAGTA | 11040 |
| CAAATGCAGA AAGCTT | 11056 |

(2) INFORMATION FOR SEQ ID NO:24:

(i) SEQUENCE CHARACTERISTICS:
        (A) LENGTH: 1066 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1066
        (D) OTHER INFORMATION: /note= "RLG2B amino acids"

(xi) SEQUENCE DESCRIPTION: SEQ ID NO:24:

```
Met Ser Asp Pro Thr Gly Ile Ala Gly Ala Ile Ile Asn Pro Ile Ala
  1               5                  10                  15

Gln Thr Ala Leu Val Pro Val Thr Asp His Val Gly Tyr Met Ile Ser
             20                  25                  30

Cys Arg Lys Tyr Val Arg Val Met Gln Met Lys Met Thr Glu Leu Asn
         35                  40                  45

Thr Ser Arg Ile Ser Val Glu Glu His Ile Ser Arg Asn Thr Arg Asn
     50                  55                  60

His Leu Gln Ile Pro Ser Gln Thr Lys Glu Trp Leu Asp Gln Val Glu
 65                  70                  75                  80
```

-continued

```
Gly Ile Arg Ala Asn Val Glu Asn Phe Pro Ile Asp Val Ile Thr Cys
                 85                  90                  95
Cys Ser Leu Arg Ile Arg His Lys Leu Gly Gln Lys Ala Phe Lys Ile
            100                 105                 110
Thr Glu Gln Ile Glu Ser Leu Thr Arg Gln Leu Ser Leu Ile Ser Trp
        115                 120                 125
Thr Asp Asp Pro Val Xaa Leu Gly Arg Val Gly Ser Met Asn Ala Ser
    130                 135                 140
Thr Ser Ala Ser Leu Ser Asp Asp Phe Pro Ser Arg Glu Lys Thr Phe
145                 150                 155                 160
Thr Gln Ala Leu Ile Ala Leu Glu Pro Asn Gln Lys Phe His Met Val
                165                 170                 175
Ala Leu Cys Gly Met Gly Gly Val Gly Lys Thr Arg Met Met Gln Arg
            180                 185                 190
Leu Lys Lys Ala Xaa Glu Glu Lys Lys Leu Phe Asn Tyr Ile Val Gly
        195                 200                 205
Ala Val Ile Xaa Glu Lys Thr Asp Pro Phe Ala Ile Gln Glu Ala Ile
    210                 215                 220
Ala Asp Tyr Leu Gly Ile Gln Leu Asn Glu Lys Thr Lys Pro Ala Arg
225                 230                 235                 240
Ala Asp Lys Leu Arg Glu Trp Phe Lys Lys Asn Ser Asp Gly Gly Lys
                245                 250                 255
Thr Lys Phe Leu Ile Val Leu Asp Asp Val Trp Gln Leu Val Asp Leu
            260                 265                 270
Glu Asp Ile Gly Leu Ser Pro Phe Pro Asn Gln Gly Val Asp Phe Lys
        275                 280                 285
Val Leu Leu Thr Ser Arg Asp Ser Gln Val Cys Thr Met Met Gly Val
    290                 295                 300
Glu Ala Asn Ser Ile Ile Asn Val Gly Leu Leu Thr Glu Ala Glu Ala
305                 310                 315                 320
Gln Ser Leu Phe Gln Gln Phe Val Glu Thr Ser Glu Pro Glu Leu Gln
                325                 330                 335
Lys Ile Gly Glu Asp Ile Val Arg Lys Cys Cys Gly Leu Pro Ile Ala
            340                 345                 350
Ile Lys Thr Met Ala Cys Xaa Leu Arg Asn Lys Arg Lys Asp Ala Trp
        355                 360                 365
Lys Asp Ala Leu Ser Arg Ile Glu His Tyr Asp Ile His Asn Val Ala
    370                 375                 380
Pro Lys Val Phe Glu Thr Ser Tyr His Asn Leu Gln Glu Glu Thr
385                 390                 395                 400
Lys Ser Thr Phe Leu Met Cys Gly Leu Phe Pro Glu Asp Phe Asp Ile
                405                 410                 415
Pro Thr Glu Glu Leu Met Arg Tyr Gly Trp Gly Leu Lys Leu Phe Asp
            420                 425                 430
Arg Val Tyr Thr Ile Arg Glu Ala Arg Thr Arg Leu Asn Thr Cys Ile
        435                 440                 445
Glu Arg Leu Val Gln Thr Asn Leu Leu Ile Glu Ser Asp Asp Val Gly
    450                 455                 460
Cys Val Lys Met His Asp Leu Val Arg Ala Phe Val Leu Gly Met Phe
465                 470                 475                 480
Ser Glu Val Glu His Ala Ser Ile Val Asn His Gly Asn Met Pro Gly
                485                 490                 495
Trp Pro Asp Glu Asn Asp Met Ile Val His Ser Cys Lys Arg Ile Ser
```

-continued

```
                500             505             510
Leu Thr Cys Lys Gly Met Ile Glu Ile Pro Val Asp Leu Lys Phe Pro
            515             520             525

Lys Leu Thr Ile Leu Lys Leu Met His Gly Asp Lys Ser Leu Arg Phe
530             535             540

Pro Gln Asp Phe Tyr Glu Gly Met Glu Lys Leu His Val Ile Ser Tyr
545             550             555             560

Asp Lys Met Lys Tyr Pro Leu Leu Pro Leu Ala Pro Arg Cys Ser Thr
                565             570             575

Asn Ile Arg Val Leu His Leu Thr Glu Cys Ser Leu Lys Met Phe Asp
            580             585             590

Cys Ser Ser Ile Gly Asn Leu Ser Asn Leu Glu Val Leu Ser Phe Ala
            595             600             605

Asn Ser His Ile Glu Trp Leu Pro Ser Thr Val Arg Asn Leu Lys Lys
            610             615             620

Leu Arg Leu Leu Asp Leu Arg Phe Cys Asp Gly Leu Arg Ile Glu Gln
625             630             635             640

Gly Val Leu Lys Ser Phe Val Lys Leu Glu Gly Phe Tyr Ile Gly Asp
                645             650             655

Ala Ser Gly Phe Ile Asp Asp Asn Cys Asn Glu Met Ala Glu Arg Ser
            660             665             670

Tyr Asn Leu Ser Ala Leu Glu Phe Ala Phe Phe Asn Asn Lys Ala Glu
            675             680             685

Val Lys Asn Met Ser Phe Glu Asn Leu Glu Arg Phe Lys Ile Ser Val
            690             695             700

Gly Cys Ser Phe Asp Glu Asn Ile Asn Met Ser Ser His Ser Tyr Glu
705             710             715             720

Asn Met Leu Gln Leu Val Thr Asn Lys Gly Asp Val Leu Asp Ser Lys
                725             730             735

Leu Asn Gly Leu Phe Leu Lys Thr Glu Val Leu Phe Leu Ser Val His
            740             745             750

Gly Met Asn Asp Leu Glu Asp Val Glu Val Lys Ser Thr His Pro Thr
            755             760             765

Gln Ser Ser Ser Phe Cys Asn Leu Lys Val Leu Ile Ile Ser Lys Cys
            770             775             780

Val Glu Leu Arg Tyr Leu Phe Lys Leu Asn Leu Ala Asn Thr Leu Ser
785             790             795             800

Arg Leu Glu His Leu Glu Val Cys Glu Cys Glu Asn Met Glu Glu Leu
                805             810             815

Ile His Thr Gly Ile Gly Gly Cys Gly Glu Thr Ile Thr Phe Pro
            820             825             830

Lys Leu Lys Phe Leu Ser Leu Ser Gln Leu Pro Lys Leu Ser Ser Leu
            835             840             845

Cys His Asn Val Asn Ile Ile Gly Leu Pro His Leu Val Asp Leu Ile
850             855             860

Leu Lys Gly Ile Pro Gly Phe Thr Val Ile Tyr Pro Gln Asn Lys Leu
865             870             875             880

Arg Thr Ser Ser Leu Leu Lys Glu Gly Val Val Ile Pro Lys Leu Glu
            885             890             895

Thr Leu Gln Ile Asp Asp Met Glu Asn Leu Glu Glu Ile Trp Pro Cys
            900             905             910

Glu Leu Ser Gly Gly Glu Lys Val Lys Leu Arg Ala Ile Lys Val Ser
            915             920             925
```

Ser Cys Asp Lys Leu Val Asn Leu Phe Pro Arg Asn Pro Met Ser Leu
    930                 935                 940

Leu His His Leu Glu Glu Leu Thr Val Glu Asn Cys Gly Ser Ile Glu
945                 950                 955                 960

Ser Leu Phe Asn Ile Asp Leu Asp Cys Val Gly Ala Ile Gly Glu Glu
                965                 970                 975

Asp Asn Lys Ser Leu Leu Arg Ser Ile Asn Val Glu Asn Leu Gly Lys
            980                 985                 990

Leu Arg Glu Val Trp Arg Ile Lys Gly Ala Asp Asn Ser Asp Leu Ile
        995                 1000                1005

Asn Gly Phe Gln Ala Val Glu Ser Ile Lys Ile Glu Lys Cys Lys Arg
    1010                1015                1020

Phe Arg Asn Ile Phe Thr Pro Ile Thr Ala Asn Phe Tyr Leu Glu Ala
1025                1030                1035                1040

Leu Leu Glu Ile Gln Ile Glu Gly Cys Gly Gly Asn His Glu Ser Glu
                1045                1050                1055

Glu Gln Val Thr Leu Ser Ile Ser Leu Ser
            1060                1065

(2) INFORMATION FOR SEQ ID NO:25:

(i) SEQUENCE CHARACTERISTICS:
        (A) LENGTH: 1369 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1369
        (D) OTHER INFORMATION: /note= "RLG2 consensus positions
            1-1400"

(xi) SEQUENCE DESCRIPTION: SEQ ID NO:25:

GGAAGACACA ATGATGCAAG GCTGAAGAAG GTTGTGGAAG AAAAGAAAAT GTTTAATTAT      60

ATTGTTGAGG CGGTTATAGG GGAAAAGACA GACCCCATTG CTATTCAGCA AGCTGTAGCA     120

GATTACCTCT GTATAGAGCT GAAAGAAAAC ACTAAACAAG CAAGAGCTGA TAAGCTTCGT     180

GAATGGTTCA AGGCCAAATC AGATGGAGGT AAGAATAAGT TCCTCGTAAT ACTTGACGAT     240

GTTTGGCAGT TTGTTGATCT TGAAGATATT GGTTTAAGTC CTTTTCCAAA TCAAGGTGTC     300

GACTTCAAGG TCTTGTTGAC TTCACGAGAC TCACATGTTT GCACTGTGAT GGGGGTTGAA     360

GCTAATTCAA TTCTTAATGT GGGACTTCTA ATAGAAGCAG AAGCACAAAG TTTGTTCCAC     420

CAATTTGTAG AAACTTCTGA GCCCGAGCTC CATAAGATAG GAGAAGATAT TGTAAGGAAG     480

TGTTGCGGTC TACCCATTGC CATCAAAACC ATGGCCTGTA CTCTTAGAAA TAAAAGAAAG     540

GATGCATGGA AGGATGCACT TTCTCGTTTA GAGCACCATG ACATTGGTAG TGTTGCGCCT     600

GAAGTTTTTA AAACGAGCTA CGACAATCTC CAAGACGAGG AGACTAAATC TATTTTTTTG     660

ATGTGTGGTT TGTTTCCTGA AGACTTTGAT ATTCCTACTG AGGAGTTGAT GAGGTATGGA     720

TGGGGCTTGA AATTATTTGA TAGAGTTTAT ACTATTAGAG AAGCAAGAAA CAGGCTCAAC     780

ACCTGCATTG AGCGACTGGT GCAGACAAAT TTGTTAATTG AAAGTGATGA TGTTGGGTGC     840

GTCAAGATGC ATGATCTGGT GCGTGCTTTT GTTTTGGGTA TGTTTTCTGA AGTCGAGCAT     900

GCTTCAATTG TCAACCATGG TAATATGCCT GGGTGGCCTG AGAAAATGAT ATGATCGTGT     960

```
ACTCTTGCAA AAGAATTTCA TTAACATGCA AGGGTATGTC TGAGTTTCCA GTAGACCTCA   1020

AGTTTCCAAA CCTAACGATT TTGAAACTTA TGCATGGAGA TAAGTCGCTA AGGTTTCCTC   1080

AAGACTTTTA TGAAGGAATG GAAAAGCTTC AGGTTATATC ATACGATAAA ATGAAGTATC   1140

CATTGCTTCC CTCGTCACCT CAATGCTCCA CCAACCTTCG AGTGCTTCAT CTCCATGAAT   1200

GTTCATTAAG GATGTTTGAT TGCTCTTCTA TTGGAAATCT TTTGAATCTG GAAGTGCTCA   1260

GCTTTGCTAA TTCTGGCATT GAATGGTTAC CTTCCACAAT CGGAAATTTG AAGAAGCTAA   1320

GGCTACTTGA TTTGACAAAT TGTTATGGTC TTCGTATAGA AAATGGTGT             1369
```

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "RLG2 consensus
            positions 1501-1525"

(xi) SEQUENCE DESCRIPTION: SEQ ID NO:26:

```
NNNNNNNNNN NNNNNNNNNN NNNNN                                        25
```

(2) INFORMATION FOR SEQ ID NO:27:

(i) SEQUENCE CHARACTERISTICS:
        (A) LENGTH: 1439 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1439
        (D) OTHER INFORMATION: /note= "RLG2A"

(xi) SEQUENCE DESCRIPTION: SEQ ID NO:27:

```
GGGGAAGACG ACAATGATGC ATCGGCTCAA AAAGGTTGTG AAAGAAAAGA AAATGTTTAA    60

TTTTATAATT GAGGCGGTTG TAGGGGAAAA AACAGACCCC ATTGCTATTC AATCAGCTGT   120

AGCAGATTAC CTAGGTATAG AGCTCAATGA AAAAACTAAA CCAGCAAGAA CTGAGAAGCT   180

TCGGAAATGG TTTGTGGACA ATTCTGGTGG TAAGAAGATC CTAGTCATAC TCGACGATGT   240

ATGGCAGTTT GTGGATCTGA ATGATATTGG TTTAAGTCCT TTACCAAATC AAGGTGTCGA   300

CTTCAAGGTG TTGTTGACAT CACGAGACAA AGATGTTTGC ACTGAGATGG GAGCTGAAGT   360

TAATTCAACT TTTAATGTGA AAATGTTAAT AGAAACAGAA GCACAAAGTT TATTCCACCA   420

ATTTATAGAA ATTTCGGATG ATGTTGATCC TGAGCTCCAT AATATAGGAG TGAATATTGT   480

AAGGAAGTGT GGGGGTCTAC CCATTGCCAT AAAAACCATG GCGTGTACTC TTAGAGGAAA   540

AAGCAAGGAT GCATGGAAGA ATGCACTTCT TCGTTTAGAG CACTATGACA TTGAAAATAT   600

TGTTAATGGA GTTTTTAAAA TGAGTTACGA CAATCTCCAA GATGAGGAGA CTAAATCCAC   660

CTTTTTGCTT TGTGGAATGT ATCCCGAAGA CTTTGATATT CTTACCGAGG AGTTGGTGAG   720

GTATGGATGG GGGTTGAAAT TATTTAAAAA AGTGTATACT ATAGGAGAAG CAAGAACCAG   780
```

```
GCTCAACACA TGCATTGAGC GGCTCATTCA TACAAATTTG TTGATGGAAG TTGATGATGT        840

TAGGTGCATC AAGATGCATG ATCTTGTTCG TGCTTTTGTT TTGGATATGT ATTCTAAAGT        900

CGAGCATGCT TCCATTGTCA ACCATAGTAA TACACTAGAG TGGCATGCAG ATAATATGCA        960

CGACTCTTGT AAAAGACTTT CATTAACATG CAAGGGTATG TCTAAGTTTC CTACAGACCT       1020

GAAGTTTCCA AACCTCTCCA TTTTGAAACT TATGCATGAA GATATATCAT TGAGGTTTCC       1080

CAAAAACTTT TATGAAGAAA TGGAGAAGCT TGAGGTTATA TCCTATGATA AAATGAAATA       1140

TCCATTGCTT CCCTCATCAC CTCAATGTTC CGTCAACCTT CGCGTGTTTC ATCTACATAA       1200

ATGCTCGTTA GTGATGTTTG ACTGCTCTTG TATTGGAAAT CTGTCGAATC TAGAAGTGCT       1260

TAGCTTTGCT GATTCTGCCA TTGACCGGTT GCCTTCCACA ATCGGAAAGT TGAAGAAGCT       1320

AAGGCTACTG GATTTGACGA ATTGTTATGG TGTTCGTATA GATAATGGTG TCTTAAAAAA       1380

ATTGGTCAAA CTGGAGGAGC TCTATATGAC AGTGGTTGAT CGAGGTCGAA AGGCGATTA       1439
```

(2) INFORMATION FOR SEQ ID NO:28:

(i) SEQUENCE CHARACTERISTICS:
        (A) LENGTH: 1500 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1500
        (D) OTHER INFORMATION: /note= "RLG2B"

(xi) SEQUENCE DESCRIPTION: SEQ ID NO:28:

```
TGGGGAAGAC TAGAATGATG CAAAGGCTGA AGAAGGCTGM TGAAGAAAAG AAATTGTTTA         60

ATTATATTGT TGGGGCAGTT ATAKGGGAAA AGACGGACCC CTTTGCCATT CAAGAAGCTA        120

TAGCAGATTA CCTCGGTATA CAACTCAATG AAAAAACTAA GCCAGCAAGA GCTGATAAGC        180

TTCGTGAATG GTTCAAAAAG AATTCAGATG GAGGTAAGAC TAAGTTCCTC ATAGTACTTG        240

ACGATGTTTG GCAATTAGTT GATCTTGAAG ATATTGGGTT AAGTCCTTTT CCAAATCAAG        300

GTGTCGACTT CAAGGTCTTG TTGACATCAC GAGACTCACA AGTTTGCACT ATGATGGGGG        360

TTGAAGCTAA TTCAATTATT AACGTGGGCC TTCTAACTGA AGCAGAAGCT CAAAGTCTGT        420

TCCAACAATT TGTAGAAACT TCTGAGCCCG AGCTCCAGAA GATAGGAGAG GATATCGTAA        480

GGAAGTGTTG CGGTCTACCT ATTGCCATAA AAACCATGGC ATGTWCTCTT AGAAATAAAA        540

GAAAGGATGC ATGGAAGGAT GCACTTTCGC GCATAGAGCA CTATGACATT CACAATGTTG        600

CGCCCAAAGT CTTTGAAACG AGCTACCACA ATCTCCAAGA AGAGGAGACT AAATCCACTT        660

TTTTAATGTG TGGTTTGTTT CCCGAAGACT TCGATATTCC TACTGAGGAG TTGATGAGGT        720

ATGGATGGGG CTTGAAGCTA TTTGATAGAG TTTATACGAT TAGAGAAGCA AGAACCAGGC        780

TCAACACCTG CATTGAGCGA CTGGTGCAGA CAAATTTGTT AATTGAAAGT GATGATGTTG        840

GGTGTGTCAA GATGCATGAT CTGGTCCGTG CTTTTGTTTT GGGTATGTTT TCTGAAGTCG        900

AGCATGCTTC TATTGTCAAC CATGGTAATA TGCCTGGGTG GCCTGATGAA AATGATATGA        960

TCGTGCACTC TTGCAAAAGA ATTTCATTAA CATGCAAGGG TATGATTGAG ATTCCAGTAG       1020

ACCTCAAGTT TCCTAAACTA ACGATTTTGA AACTTATGCA TGGAGATAAG TCGCTAAGGT       1080

TTCCTCAAGA CTTTTATGAA GGAATGGAAA AGCTCCATGT TATATCATAC GATAAAATGA       1140

AGTACCCATT GCTTCCTTTG GCACCTCGAT GCTCCACCAA CATTCGGGTG CTTCATCTCA       1200
```

```
CTGAATGTTC ATTAAAGATG TTTGATTGCT CTTCTATCGG AAATCTATCG AATCTGGAAG      1260

TGCTGAGCTT TGCAAATTCT CACATTGAAT GGTTACCTTC CACAGTCAGA AATTTAAAGA      1320

AGCTAAGGTT ACTTGATCTG AGATTTTGTG ATGGTCTCCG TATAGAACAG GGTGTCTTGA      1380

AAAGTTTTGT CAAACTTGAA GAATTTTATA TTGGAGATGC ATCTGGGTTT ATAGATGATA      1440

ACTGCAATGA GATGGCAGAG CGTTCTTACA ACCTTTCTGC ATTAGAATTC GCGTTCTTTA      1500
```

(2) INFORMATION FOR SEQ ID NO:29:

(i) SEQUENCE CHARACTERISTICS:
        (A) LENGTH: 1417 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1417
        (D) OTHER INFORMATION: /note= "RLG2C"

(xi) SEQUENCE DESCRIPTION: SEQ ID NO:29:

```
AACACACGTN CNGCAAAGGC TGAAGAAGTT GCCAAAGNAA AAGAGGAATT TGGTTATATC        60

ATCGAGGCGG TTATAGGGGA AATATCGGAC CCCATTGCTA TTCAGCAAGT TGTAGCAGAT       120

TACCTATGCA TAGAACTGAA AGAAAGCGAT AAGAAAACAA GAGCTGAGAA GCTTCGTCAA       180

GGGTTCAAGG CCAAATCAGA TGGAGGTAAC ACTAAGTTCC TCATAATATT GGATGATGTC       240

TGGCAGTCCG TTGATCTANA AGATATTGGT TTAAGCCCTT CTCCCAATCA ANGTGTCGAC       300

TTCAAGGTCT TGTTGACTTC ACGAGACGAA CATGTTTGCT CAGTGATGGG GGTTGAAGCT       360

AATTCAATTA TTAACGTGGG ACTTCTAATT GAAGCAGAAG CACAAAGATT GTTCCAGCAA       420

TTTGTAGAAA CTTCTGAGCC CGAGCTCCAC AAGATAGGAG AAGATATTGT TAGGAGGTGT       480

TGCGGTCTAC CCATTGCCAT CAAAACCATG GCGTGTACTC TAAGAAATAA AGAAAGGAT        540

GCATGGAAGG ATGCACTTTC TCGTTTACAA CACCATGACA TTGGTAATGT TGCTACTGCA       600

GTTTTTAGAA CCAGCTATGA GAATCTCCCG GACAAGGAGA CAAAATCTGT TTTTTTGATG       660

TGTGGTTTGT TTCCCGAAGA CTTCAATATT CCTACCGAGG AGTTGATGAG GTATGGATGG       720

GGCTAAAAGT TATTTGATAG AGTTTATACA ATTATAGAAG CAAGAAACAG GCTCAACACC       780

TGCATTGACC GACTGGTGCA GACAAATTTA CTAATTGGAA GTGATAATGG TGTACATGTC       840

AAGATGCATG ATCTGGTCCG TGCTTTTGTT TTGGGTATGT ATTCTGAAGT CGAGCAAGCT       900

TCAATTGTCA ACCATGGTAA TATGCCTGGG TGGCCTGATG AAAATGATAT GATCGTGCAC       960

TCTTGCAAAA GAATTTCATT AACATGCAAG GGTATGATTG AGTTTCCAGT AGACCTCAAG      1020

TTTCCTAAAC TAACGATTTT GAAACTTATG CATGGAGATA AATCGCTAAA GTTTCCTCAA      1080

GAATTTTATG AAGGAATGGA AAAGCTCCGG GTTATATCAT ACCATAAAAT GAAGTACCCA      1140

TTGCTTCCTT TGGCACCTCA ATGCTCCACC AACATTCGGG TGCTTCATCT CACGGAATGT      1200

TCATTAAAGA TGTTTGATTG CTCGTGTATT GGAAATCTAT CGAATCTGGA AGTGCTGAGC      1260

TTTGCTAATT CTTGCATTGA GTGGTTACCT TCCACGGTCA GAAATTTAAA AAAGCTAAGG      1320

TTACTTGATT TGAGATTGTG TTATGGTCTC CGTATAGAAC AGGGTGTCTT GAAAAGTTTG      1380

GTCAAACTTG AAGAATTTTA TATTGGAAAT GCATATG                              1417
```

(2) INFORMATION FOR SEQ ID NO:30:

(i) SEQUENCE CHARACTERISTICS:
        (A) LENGTH: 1412 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1412
        (D) OTHER INFORMATION: /note= "RLG2D"

(xi) SEQUENCE DESCRIPTION: SEQ ID NO:30:

```
AAGAAGTTGC CAAAGANAAG AGGAAGTTTG GTTATATCAT CGAGGCAGTT ATANGGGAAA      60

TATCGGACCC CATTGCTATT CAGCAAGTTG TAGCAGATTA CCTATGCATA GAGCTGAAAG     120

AAAGCGATAN GAAAACAAGA GCTGAGAAGC TTCGTCAAGG GTTCAAGGCC AAATCANATG     180

GAGGTAACAC TAAGTTCCTC ATAATATTGG ATGATGTCTG GCAGTCCGTT GATCTAGAAN     240

ATATTGGTTT AAGCCCTTCT CCCAATCAAG GTGTCNACTT CAAGGTCTTG TTGACTTCAC     300

GAGACGAACA TGTTTGCTCA GTGATGGGGG TTGAAGCTAA TTCAATTATT AACGTGGGAC     360

TTCTAATTGA ANCANAANCA CNAAGATTGT TCCAGCAATT TGTANAAACT TCTGAGCCCG     420

AGCTCCACAA GATANGAGAA NATATTGTTA GGAGGTGTTG CGGTCTACCC ATTGCCATCA     480

AAACCATGGC GTGTACTCTA AGAAATAAAA GAAAGGATGC ATGGAAGGAT GCACTTTCTC     540

GTTTACAACA CCATGACATT GGTAATGTTG CTACTGCAGT TTTTANAACC AGCTATGAGA     600

ATCTCCCGGA CAAGGAGACA AAATCTGTTT TTTTGATGTG TGGTTTGTTT CCCGAAGACT     660

TCAATATTCC TACCGAGGAG TTGATGANGT ATGGATGGGG CTTAAAGTTA TTTGATAGAG     720

TTTATACAAT TATAGAAGCA AGAAACAGGC TCAACACCTG CATTGAGCGA CTGGTGCAGG     780

CAAATTTACT AATTGGAAGT GATAATGGTG TACACGTCAA GATGCATGAT CTGGTCCGTG     840

CTTTTGTTTT GGGTATGTAT TCTGAAGTCG AGCAAGCTTC AATTGTCAAC CATGGTAATA     900

TGCCTGGGTG GCCTGATGAA AATGATATGA TCGTGCACTC TTGCAAAAGA ATTTCATTAA     960

CATGCAAGGG TATGATTGAG ATTCCAGTAG ACCTCAAGTT TCCTAAACTA ACGATTTTGA    1020

AACTTATGCA TGGAGATAAG TCTCTAAAGT TTCCTCAAGA ATTTTATGAA GGAATGGAAA    1080

AGCTCCAGGT TATATCATAC GATAAAATGA AGTACCCATT GCTTCCTTTG GCACCTCAAT    1140

GCTCCACCAA CATTCGGGTG CTTCATCTCA CTGAATGTTC ATTAAAGATG TTTGATTGCT    1200

CTTCTATCGG AAATCTATCG AATCTGGAAG TGCTGAGCTT TGCTAATTCT CGCATTGAAT    1260

GGTTACCTTC CACAGTCAGA AATTTAAAGA AGCTAAGGTT ACTTGATCTG AGATTTTGTG    1320

ATGGTCTCCG TATAGAACAG GGTGTCTTGA AAAGTTTGGT CAAACTTGAA GAATTTTATA    1380

TTGGAAATGC ATATGGGTTT ATAGATGTAA TG                                   1412
```

(2) INFORMATION FOR SEQ ID NO:31:

(i) SEQUENCE CHARACTERISTICS:
        (A) LENGTH: 1432 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1432
        (D) OTHER INFORMATION: /note= "RLG2E"

(xi) SEQUENCE DESCRIPTION: SEQ ID NO:31:

```
GGAAGACACA ATGATGCAAA GGTTGAAGAA GTTGCTAAAG AAAATAGAAT GTTCAATTAT      60
ATGGTTGAGG CAGTTATAGG GGAAAAGACA GACCCACTTG CTATTCAACA AGCTGTAGCG     120
GATTACCTTT GTATAGAGTT AAAAGAAAGC ACTAAACCAG CAAGAGCTGA TAAGCTTCGT     180
GAATGGTTTA AGGCCAACTC TGGAGAAGGT AAGAATAAGT TCCTTGTAAT ATTTGATGAT     240
GTTTGGCAGT CCGTTGATCT GGAAGACATT GGTTTAAGTC ATTTTCCAAA TCAAGGTGTC     300
GACTTCAAGG TCTTGTTGAC TTCACGAGAC TAACATGTKT GCMCAGTAAT GGGGGTTGAA     360
GCTAATTCAA TTCTTAATGT GGGACTTCTA GTAGAAGCAG AAGCACAAAG TTTGTTCCAG     420
CAATTTGTAG AAACTTTTGA GCCCGAGCTC CATAAGATAG GAGAAGATAT CGTAAGGAAG     480
TGTTGTGGTT TACCTATTGC CATTAAAACC ATGGCATGTA CTCTAAGAAA TAAAAGAAAG     540
GATGCATGGA AGGATGCACT TTTGCATTTA GAGTACCATG ACATTAGCAG TGTTGCGCCC     600
AAAGTCTTTG AAACGAGCTA CCATAATCTC CACAACAAGG AGACTAAATC TGTGTTTTTG     660
ATGTGTGGTT TTTTTCCTGA AGACTTCAAT ATTCCAATCG AGGAGTTGAT GAGGTATGGA     720
TGGGGCTTAA AGATATTTGA TAGAGTTTAT ACTATTAGAC AAGCAAGAAT CAGGCTCAAC     780
ACCTGCATTG AGCGACTGGT GCAGACAAAT TTGTTAATAG AAAGTGATGA TGGTGTGCAC     840
GTCAAGATGC ATGATCTGGT CCGTGCTTTC GTTTTGGTTA TGTTTTCTGA AGTTGAACAT     900
GCTTCAATTA TCAACCATGG TAATATGCTT GGATGGCCTG AAAATTATAT GACCAACTCT     960
TGCAAAACAA TTTCATTAAC ATGCAAGAGT ATGTCTGAAT TTCCGGGAGA TCTCAAGTTT    1020
CCAAACCTAA CGATTTTGAA ACTCATGCAT GGAGATAAGT TGCTAAGATA TCCTCAAGAC    1080
TTTTATGAAG GAATGGAAAA GCTCTGGGTT ATATCATATG ATGAAATGAA GTATCCATTG    1140
CTTCCCTCGT TACCTCAATG CTCCATCAAC CTTCGAGTGC TTCACCTCCA TCGATGCTCA    1200
TTAATGATGT TTGATTGCTC TTGTATTGGA AATATGTTGA ATCTGGAAGT GCTTAGCTTT    1260
GTTAAATCTG GCATTGAATG GTTACCTTCC ACAATAGGAA ATTTAAAGAA GCTAAGGTTA    1320
CTTGATCTGA GAGATTGTTA TGGTCTTCGT ATAGAAAAAG GTGTCTTGAA AAATTTGGTG    1380
AAAATTGAAG AACTTTATAT TGGTAGAGCA GATATTTTAT AGATAGAAGT AA            1432
```

(2) INFORMATION FOR SEQ ID NO:32:

(i) SEQUENCE CHARACTERISTICS:
        (A) LENGTH: 1438 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1438
        (D) OTHER INFORMATION: /note= "RLG2F"

(xi) SEQUENCE DESCRIPTION: SEQ ID NO:32:

```
CTTTGGAAGA CACAATGATG CAAAGGCTGA AAAGGTTGT GCATGAAAAG AAAATGTTTA      60
ACTTTATTGT TGAAGCAGTT ATAGGGGAAA AGACAGACCC CGTTGCCATT CAGGATGCTA     120
TAGCAGATTA CCTAGGTGTA GAGCTCAATG AAAAATCTAA GCAAGCAAGA GCTGATAAGC     180
TCCGTCAAGG ATTCAAGGAC AAATCAGATG GAGGCAAAAA TAAGTTCTTT GTAATACTTG     240
ACGATGTTTG GCAGTCTGTT GATCTGGAAG ATATTGGTTT AAGTCCTTTT CCAAATCAAG     300
```

```
GCGTCGACTT CAAGGTCTTG TTGACATCAC GAGACAGACA TGTTTGCACA GTGATGGGGG      360

TTGAAGCCAA ATTAATTCTA AACGTGGGAC TTCTAATTGA AGCTGAAGCA CAAAGTTTGT      420

TCCACCAATT TGTTGTCACT TCTGAGCCCG AGCTCCATAA GATAGGAGAA GATATTGTAA      480

AGAAGTGTTT CGGTCTGCCA ATTGCCATCA AAACCATGGC ATGTACTCTA CGACATAAAA      540

GAAAGGATGC ATGGAAGGAT GCACTTTCAC GTTTAGAGCA CCATGACATT CAAAGTGTTG      600

TGCCTAAAGT ATTTGAAACG AGCTACAACA ATCTCAAAGA CAAGGAGACT AAATCCGTAT      660

TTTTGATGTG TGGTTTGTTT CCTGAAGACT TGGATATACC TATCGAGGAG TTGATGAGGT      720

ATGGATGGGG CTTAAGATTA TTTGATAGAG TTAATACTAT TACACAAGCA AGAAACAGGC      780

TCAACACCTG CATTGAGCGA CTGGTGCACA CAAATTTGTT AATTGAAAGT GTTGATGGTG      840

TGCATGTCAA GATGCATGAT CTGGTTCGTG CTTTTGTTTT GGGAATGTTT TCTGAAGTGG      900

AGCATGCTTC AATTGTCAAC CATGGTAATA TGCCCGAGTG GACTGAAAAT GATATGACTG      960

ACTCTTGCAA ACAAATTTCA TTAACATGCA AGAGTATGTT GGAGTTTCCT GGAGACCTCA     1020

AGTTTCCAAA CCTAAAGATT TTGAAACTTA TGCATGGAGG TAAGTCACTA AGGTATCCTC     1080

AAGACTTTTA TCAAGGAATG GAAAAGCTGG AGGTTATATC ATACGATGAA ATGAAGTATC     1140

CATTGCTTCC CTCGTTGCCT CAATGTTCCA CCATCCTTCG AGTGCTTCAT CTCCATGAAT     1200

GTTCATTAAG GATGTTTGAT TGCTCTTCAA TCGGTAATCT TTTCAACATG GAAGTGCTCA     1260

GCTTTGCTAA TTCTAGCATT GAATTGTTAC CTTCCGTAAT TGGAAATTTG AAGAAGTTGC     1320

GGCTGCTAGA TTTGACAAAC TGTTATGGTG TTCGTATAGA AAAGGATGTC TTGAAAAATT     1380

TGGTGAAACT TGAAGAGCTT TATATTAGGA ATGGTCTACC AGTTTACAGA GGATAATA      1438

(2) INFORMATION FOR SEQ ID NO:33:

(i) SEQUENCE CHARACTERISTICS:
         (A) LENGTH: 1466 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..1466
         (D) OTHER INFORMATION: /note= "RLG2G"

(xi) SEQUENCE DESCRIPTION: SEQ ID NO:33:

GGAAGACACG ATGATGAAGA ACTGAAGGAG GTCGTGGGAC AAAAGAAATC ATTCAATATT       60

ATTATTCAAG TGGTCATAGG AGAGAAGACA AACCCTATTG CAATTCAGCA AGCTGTAGCA      120

GATTACCTCT CTATAGAGCT GAAAGAAAAC ACTAAAGAAG CAAGAGCTGA TAAGCTTCGT      180

AAACGGTTTG AAGCCGATGG AGGAAAGAAT AAGTTCCTTG TAATACTTGA CGATGTATGG      240

CAGTTTGTCG ATCTTGAAGA TATTGGTTTA AGTCCTCTGC CAAATAAAGG TGTCAACTTC      300

AAGGTCTTGT TGACGTCAAG AGATTCACAT GTTTGCACTC TGATGGGAGC TGAAGCAAAT      360

TCAATTCTTA ATATAAAAGT TTTAAAGAT GTAGAAGGAC AAAGTTTGTT CCGCCAGTTT      420

GCTAAAAATG CGGGTGATGA TGACCTGGAT CCTGCTTTCA ATGGGATAGC AGATAGTATT      480

GCAAGTAGAT GTCAAGGTTT GCCCATTGCC ATCAAAACCA TTGCCTTAAG TCTTAAAGGT      540

AGAAGCAAGT CTGCATGGGA CGTTGCACTT TCTCGTCTGG AGAATCATAA GATTGGTAGT      600

GAAGAAGTTG TGCGTGAAGT TTTTAAAATT AGCTACGACA ATCTCCAAGA TGAGGTTACT      660

AAATCTATTT TTTTACTTTG TGCTTTATTT CCTGAAGATT TTGATATTCC TACTGAGGAG      720
```

```
TTGGTGAGGT ATGGGTGGGG CTTGAAATTA TTTATAGAAG CAAAAACTAT AAGAGAAGCA      780

AGAAACAGGC TCAACACCTG CACTGAGCGG CTTAGGGAGA CAAATTTGTT ATTTGGAAGT      840

GATGACATTG GATGTGTCAA GATGCACGAT GTGGTGCGTG ATTTTGTTTT GCATATATTC      900

TCAGAAGTCC AACACGCTTC AATTGTCAAC CATGGTAACG TGTCAGAGTG GCTAGAGGAA      960

AATCATAGCA TCTACTCTTG TAAAAGAATT TCATTAACAT GCAAGGGTAT GTCTCAGTTT     1020

CCCAAAGACC TCAAATTTCC AAACCTTTCA ATTTTGAAAC TTATGCATGG AGATAAGTCA     1080

CTGAGCTTTC CTGAAAACTT TTATGGAAAG ATGGAAAAGG TTCAGGTAAT ATCATATGAT     1140

AAATTGATGT ATCCATTGCT TCCCTCATCA CTTGAATGCT CCACCAACGT TCGAGTGCTT     1200

CATCTTCATT ACTGTTCATT AAGGATGTTT GATTGCTCTT CAATTGGTAA TCTTCTCAAC     1260

ATGGAAGTGC TCAGCTTTGC TAATTCTAAC ATTGAATGGT TACCATCTAC AATTGGAAAT     1320

TTGAAGAAGC TAAGGCTACT AGATTTGACA AATTGTAAAG GTCTTCGTAT AGATAATGGT     1380

GTCTTAAAAA ATTTGGTCAA ACTTGAAGAG CTTTATATGG GTGTTAATCG TCCGTATGGA     1440

CAGGCCGTTA GCTTGACAGA TGAAAA                                          1466

(2) INFORMATION FOR SEQ ID NO:34:

(i) SEQUENCE CHARACTERISTICS:
        (A) LENGTH: 1420 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1420
        (D) OTHER INFORMATION: /note= "RLG2H"

(xi) SEQUENCE DESCRIPTION: SEQ ID NO:34:

TGAAGGAGGT TGTGGAACGA AAGAAAATGT TCAGTATTAT TGTTCAAGTG GTCATAGGAG       60

AGAAGACAAA CCCTATTGCT ATTCAGCAAG CTGTAGCAGA TTACCTCTCT ATAGAGCTGA      120

AAGAAAACAC TAAAGAAGCA AGAGCTGATA AGCTTCGTAA ATGGTTCGAG GCCGATGGAG      180

GAAAGAATAA GTTCCTTGTA ATACTTGACG ATGTATGGCA GTTTGTCGAT CTTGAAGATA      240

TTGGTTTAAG TCCTCTGCCA AATAAAGGTG TCAACTTCAA GGTCTTGTTG ACGTCAAGAG      300

ATTCACATGT TTGCACTCTG ATGGGAGCCG AAGCCAATTC AATTCTCAAT ATAAAAGTTT      360

TAACAGCTGT AGAAGGACAA AGTTTGTTCC GCCAGTTTGC TAAAAATGCG GGTGATGATG      420

ACCTGGATCC TGCTTTCAAT AGGATAGCAG ATAGTATTGC AAGTAGATGT CAAGGTTTGC      480

CCATTGCCAT CAAAACCATT GCCTTAAGTC TTAAAGGTAG AAGCAAGCCT GCGTGGGACC      540

ATGCGCTTTC TCGTTTGGAG AACCATAAGA TTGGTAGTGA AGAAGTTGTG CGTGAAGTTT      600

TTAAAATTAG CTATGACAAT CTCCAAGATG AGATTACTAA ATCTATTTTT TTACTTTGTG      660

CTTTATTTCC TGAAGATTTT GATATTCCTA CTGAGGAGTT GATGAGGTAT GGATGGGGCT      720

TGAAATTATT TATAGAAGCA AAAACTATAA GAGAAGCAAG AAACAGGCTC AACACCTGCA      780

CTGAGCGGCT TAGGGAGACA AATTTGTTAT TTGGAAGCGA TGACATTGGA TGCGTCAAGA      840

TGCACGATGT GGTGCGTGAT TTTGTTTTGC ATATATTCTC AGAAGTCCAG CACGCTTCAA      900

TTGTCAACCA TGGTAACGTG TCAGAGTGGC TAGAGGAAAA TCATAGCATC TACTCTTGTA      960

AAAGAATTTC ATTAACATGC AAGGGTATGT CTGAGTTTCC CAAAGACCTC AAATTTCCAA     1020
```

```
ACCTTTCAAT TTTGAAACTT ATGCATGGAG ATAAGTCGCT GAGCTTTCCT GAAAACTTTT        1080

ATGGAAAGAT GGAAAAGGTT CAGGTAATAT CATATGATAA ATTGATGTAT CCATTGCTTC        1140

CCTCATCACT TGAATGCTCC ACTAACGTTC GAGTGCTTCA TCTCCATTAT TGTTCATTAA        1200

GGATGTTTGA TTGCTCTTCA ATTGGTAATC TTCTCAACAT GGAAGTGCTC AGCTTTGCTA        1260

ATTCTAACAT TGAATGGTTA CCATCTACAA TTGGAAATTT GAAGAAGCTA AGGCTACTAG        1320

ATTTGACAAA TTGTAAAGGT CTTCGTATAG ATAATGGTGT CTTAAAAAAT TTGGTCAAAC        1380

TTGAAGAGCT TTATATGGGT GTTAATCATC CGTATGGACT                              1420

(2) INFORMATION FOR SEQ ID NO:35:

(i) SEQUENCE CHARACTERISTICS:
        (A) LENGTH: 1442 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1442
        (D) OTHER INFORMATION: /note= "RLG2I"

(xi) SEQUENCE DESCRIPTION: SEQ ID NO:35:

ATGCAAGAAG AGCTGGAAGG AGGTTGTGGA ACAAAAGAAA ACGTTCAATA TTATTGTTCA          60

AGTGGTCATA GGAGAGAAGA CAAACCCTAT TGCTATTCAG CAAGCTGTAG CAGATTCCCT         120

CTCTATAGAG CTGAAAGAAA ACACTAAAGA AGCAAGAGCT GATAAGCTTC GTAAATGGTT         180

CGAGGCTGAT GGAGGAAANA ATAAGTTCCT CGTNATACTT GACGATGTAT GGCNGTTTGT         240

TGATCTTGAA NATATTGGTT TAAGTCCTCA TCCAAATNAA GGTGTCANCT TCAAGGTCTT         300

GTTGACGTCA AGAGATTCAC ATGTTTGCAC TCTGATGGGA GCTGAAGCCA ATTCAATTCT         360

CAATATAAAA GTTTTAAAAG ATGTAGAAGG AAAAAGTTTG TTCCGCCAGT TTGCTAAAAA         420

TGCGGGTGAT GATGACCTGG ATCCTGCTTT CATTGGGATA GCAGATAGTA TTGCAAGTAG         480

ATGTCAAGGT TTGCCCATTG CCATCAAAAC CATTGCCTTA AGTCTTAAAG GTAGAAGCAA         540

GTCTGCATGG GACGTTGCAC TTTCTCGTCT GGAGAATCAT AAGATTGGTA GTGAAGAAGT         600

TGTGCGTGAA GTTTTTAAAA TTAGCTATGA CAATCTCCAA GATGAGGTTA CTAAATCTAT         660

TTTTTTACTT TGTGCTTTAT TTCCTGAAGA TTTTGATATT CCTACTGAGG AGTTGGTGAG         720

GTATGGGTGG GGCTTGAAAT TATTTATAGA AGCAAAAACT ATAAGAGAAG CAAGAAACAG         780

GCTCAACACC TGCACTGAGC GGCTTAGGGA GACAAATTTG TTATTTGGAA GTGATGACAT         840

TGGATGCGTC AAGATGCACG ATGTGGTGCG TGATTTTGTT TTGCATATAT TCTCAGAAGT         900

CCAGCACGCT TCAATTGTCA ACCATGGTAA TGTGTCAGAG TGGCTAGAGG AAAATCATAG         960

CATCTACTCT TGTAAAAGAA TTTCATTAAC ATGCAAGGGT ATGTCTGAGT TCCCAAAGA         1020

CCTCAAATTT CCAAACCTTT CAATTTTGAA ACTTATGCAT GGAGATAAGT CGCTGAGCTT        1080

TCCTGAAAAC TTTTATGGAA AGATGGAAAA GGTTCAGGTA ATATCATATG ATAAATTGAT        1140

GTATCCATTG CTTCCCTCAT CACTTGAATG CTCCACCAAC CTTCGAGTGC TTCATCTCCA        1200

TGAATGTTCA TTAAGGATGT TGATTGCTC TTCAATTGGT AATCTTCTCA ACATGGAAGT         1260

GCTCAGCTTT GCTAATTCTG GCATTGAATG GTTACCATCT ACAATTGGAA ATTTGAAGAA        1320

GCTAAGGCTA CTGGATCTGA CAGATTGTGG AGGTCTTCAT ATAGATAATG GCGTCTTAAA        1380

AAATTTGGTC AAACTTGAAG AGCTTTATAT GGGTGCTAAT CGTCTGTTTG GAAAGTGCCA        1440
```

(2) INFORMATION FOR SEQ ID NO:36:

(i) SEQUENCE CHARACTERISTICS:
        (A) LENGTH: 1474 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1474
        (D) OTHER INFORMATION: /note= "RLG2J"

(xi) SEQUENCE DESCRIPTION: SEQ ID NO:36:

```
TT                                                                           1442

GAAAGAGGTC GTGGACANAA GAAAACGTTC AATATTATTG TTCAAGTGGT CATAGGAGAG             60

AAGACAAACC CTATTGCTAT CCAGCAAGCT GTAGCAGATT ACCTCTCTAT AGAGCTGAAA            120

GAAAACACTA AAGAAGCAAG AGCTGATAAG CTTCGTAAAC GGTTCGAAGC CGATGGAGGA            180

AAGAATAAGT TCCTTGTNAT ACTTGACGAT GTTTGGCAGT TTTTCGATCT TGAANATATT            240

GGTTTAAGTC CTCTGCCAAA TAAAGGTGTC NACTTCAAGG TCTTGTTGAC GTCNAGANAT            300

TCNCATGTTT GCACTCTGAT GGGAGCTGAA GCCAATTCNA TTCTCAATNT AAAAGTTTTA            360

NAAGATGTTC AAGGAAAAAG TTTGTCCGCC ANTTTGCTAA AAATGCGGGT GATNATGACC            420

TGGATCCNGC TTTCATTGGG ATANCANATA GTNTTGCCAG TNGATGTCNA GGGTTTGNCC            480

ATTGCCNTCA AAACCATTGN CTTNAGTCTT AAAGGTAGAA GCAAGTCTGC ATGGGACGTC            540

GCACTTTCTC GTCTGGAGAA TCATAAGATT GGTAGTGAAG AAGTTGTGCG NGAAGTTTTT            600

AAAATNAGCT ATGACAATCT CCAAGATGAG GTTACTAAAT CTATTTTTTT ACTCTGTGCT            660

TTATTTCCTG AAGATTTTGA TATTCCTATT GAGGAGTTGG TGAGGTATGG GTGGGGCTTG            720

AAATTATTTA TAGAAGCAAA AACTATAAGA GAAGCAAGAA ACAGGCTCAA CAACTGCACT            780

GAGCGGCTTA GGGAGACAAA TTTGTTATTT GGAAGTCATG ACTTTGGGTG CGTCAAGATG            840

CACGATGTGG TGCGTGATTT TGTTTTGCAT ATGTTTTCAG AAGTCAAGCA TGCTTCAATT            900

GTCAACCATG GTAACATGTC AGAGTGGCCA GAGAAAAATG ATACCAGCAA CTCTTGTAAA            960

AGAATTTCAT TAACATGCAA GGGTATGTCT AAGTTTCCTA AAGACATCAA CTATCCAAAC           1020

CTTTTGATTT TGAAACTTAT GCATGGAGAT AAGTCGCTGT GCTTTCCTGA AAACTTTTAT           1080

GGAAAGATGG AAAAGGTTCA GGTAATATCA TATGATAAAT TGATGTATCC ATTGCTTCCC           1140

TCATCACTTG AATGCTCCAC TAACGTTCGA GTGCTTCATC TCCATTATTG TTCATTAAGG           1200

ATGTTTGATT GCTCTTCAAT TGGTAATCTT CTCAACATGG AAGTGCTCAG CTTTGCTAAT           1260

TCTAACATTG AATGGTTACC ATCTACAATT GGAAATTTGA AGAAGCTAAG GCTACTAGAT           1320

TTGACAAATT GTAAAGGTCT TCGTATAGAT AATGGTGTCT TAAAAAATTT GGTCAAACTT           1380

GAAGAGCTTT ATATGGGTGT TAATCGTCCG TATGACAGG CCGTTAGCTT GACAGATGAA            1440

AACTGGCNAT GGAAATGGCA GANCCTTTTT CACA                                      1474
```

(2) INFORMATION FOR SEQ ID NO:37:

(i) SEQUENCE CHARACTERISTICS:
        (A) LENGTH: 1437 base pairs
        (B) TYPE: nucleic acid
        (C) STRANDEDNESS: single
        (D) TOPOLOGY: linear (ii) MOLECULE TYPE: DNA (ix) FEATURE:
    (A) NAME/KEY: -
    (B) LOCATION: 1..1437
    (D) OTHER INFORMATION: /note= "RLG2K"

(xi) SEQUENCE DESCRIPTION: SEQ ID NO:37:

```
TTTGGAAGAC ACGATGATGA ANAGGCTGAA AAATATTATT AAAGAAAAGA GGACGTTTCA      60
TTATATTGTT TTGGTGGTTA TAAAGGAAAA TATGGATCTC ATTTCCATCC AGGATGCTGT     120
AGCAGATTAT CTGGATATGA AGCTAACAGA AAGCAATGAA TCAGAAAGAG CCGATAAACT     180
TCGTGAAGGG TTTCAGGCCA AATCAGATGG AGGTAAGAAT AGGTTCCTCA TAATACTGGA     240
TGATGTATGG CAATCTGTTA ATATGGAAGA TATTGGTTTA AGTCCTTTTC CGAATCAAGG     300
TGTCGACTTC AAGGTCTTGT TGACCTCGGA AAACAAAGAT GTTTGTGCAA AAATGGGAGT     360
TGAAGCTAAT TTAATTTTCG ACGTGAAATT CTTAACAGAA GAAGAAGCAC AAAGTTTGTT     420
TTATCAATTT GTAAAAGTTT CTGATACCCA CCTTGATAAG ATTGGAAAAG CTATTGTAAG     480
AAACTGTGGT GGTCTACCCA TTGCCATCAA AACCATAGCC AATACTCTTA AAAATANAAA     540
CAAGGATGTT TGGAAGGATG CACTTTCTCG TATAGAGCAT CATGACATTG AGACAATTGC     600
ACATGTTGTT TTTCAAATGA GCTACGACAA TCTCCAAAAC GAAGAAGCTC AATCCATTTT     660
TTTGCTTTGT GGATTGTTTC CTGAAGACTT TGATATTCCT ACTGAGGAAT TGGTGANGTA     720
TGGATGGGGA TTGAGAGTAT TTAATGGAGT GTATACTATA GGAGAAGCAA GACACAGGTT     780
GAACGCCTAC ATCGAGCTGC TCAAGGATTC TAATTTATTG ATTGAAAGTG ATGATGTTCA     840
CTGCATCAAG ATGCATGATT TAGTTCGTGC TTTTGTTTTG GATACGTTTA ATAGATTCAA     900
GCATTCTTTG ATTGTTAACC ATGGTAATGG TGGTATGTTA GGGTGGCCTG AAAATGATAT     960
GAGTGCCTCA TCTTGCAAAA GAATTTCATT AATATGCAAG GGCATGTCCG ATTTTCCTAG    1020
AGACGTAAAG TTTCCAAATC TCTTGATTTT GAAACTTATG CATGCAGATA AGTCTTTGAA    1080
GTTTCCTCAA GACTTTTATG GAGAAATGAA GAAGCTTCAG GTTATATCAT ACGATCACAT    1140
GAAGTATCCC TTGCTTCCAA CATCACCTCA ATGCTCCACC AACCTTCGTG TGCTTCATCT    1200
TCATCAATGC TCATTGATGT TTGATTGCTC TTCTATTGGA AATCTGTTGA ATCTGGAAGT    1260
GCTCAGCTTT GCTAATTCTG GTATTGAGTG GTTGCCTTCC ACAATCGGAA ATTTGAAGGA    1320
GCTAAGGGTA CTAGATTTGA CAAATTGTGA TGGTCTTCGT ATAGATAATG GTGTCCTAAA    1380
GAAATTGGTG AAACTTGAAG AGCTTTATAT GAGAGTTGGT GGTCGATATC AAAAGGC      1437
```

(2) INFORMATION FOR SEQ ID NO:38:

(i) SEQUENCE CHARACTERISTICS:
        (A) LENGTH: 1398 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1398
        (D) OTHER INFORMATION: /note= "RLG2L"

(xi) SEQUENCE DESCRIPTION: SEQ ID NO:38:

```
GTTCAGTTAC ATGGTCGAGG CAGTTATAGG GGAAAAGACA GACCCCATTG CTATTCAACA      60
AGCTGTANCC GATTACCTNC GTATACAGTT CAAAGAAAGC ACTAAACCAG CAAGAGCTGA     120
```

```
TAAGCTTCGT GAATGGTTCA AGGCCNACTC TGNAGANGGT AAGAATAAGT TCCTNGTAAT    180

ATTTGATGAC GTCTGGCAGT CCGTTGATCT GGAAGATATT GGNTTAAGTC CTTTTCCAAA    240

TCAANGTGTC GACTTCAAGG TCTTGTTGAC TTCACGAGAC NAACACGTTT GCACAATGAT    300

GGGGGTTNAA GCTAATTCAN TTATTNATGT GGGACTTCTA ACTGAAGTAG AAGCACNAAG    360

TCTGTTCCAN CAATTTGTAG AAACTTNTGA GCCCGAGCTC TGTAAGATAN GANAAGTTAT    420

CGTAAGAAAG TGTTGCGGTC TACCTATTGC CATCAAAACC ATGGCGTGTT CTCTTAGAAA    480

TAAAAGAAAG GATGCATGGA AGGATGCACT TTCNCGTATA GAGCACTATG ACATTCNTNG    540

TGTTGCGCCC AAAGTCTTTG AAACAAAAAA CCATAATCTC CACAACAAGG AGACTAAATC    600

CGCGTTTTTG ATGTGTGGTT TGTTTCCTGA AGACTTCAAT ATTCCTACCG AGGAGTTGAT    660

GAGGTATGGA TGGGGCTTAA AGCTATTTGA CAGAGTTTAT ACAATTAGAG AAGCAAGAAC    720

CAGGCTCAAC ACCTGCATTG AGCGACTTGT GCAGACAAAT TTGTTAATTG AAAGTGATGA    780

TGTTGGGTGT GTCAAGATGC ATGATCTGGT GCGTGCTTTT GTTTTGGGTA TGTATTCTGA    840

AGTCGAGCAT GCTTCAATTG TCAACCATGG TAATATGCAT GGGTGGACTA AAAATGATAT    900

GAACGACTCT TGCAAAACAG TTTCTTTAAC ATGCGAGAGT GTGTCTGAGT TTCCAGGAGA    960

CCTCAAGTTT CCAAACCTAA AGCTTTTGAA ACTTATGCAT GGAGATAAGA TGCTAAGGTT   1020

TTCTCAAGAC TTTTATGAAG GAATGGAAAA GCTCCAGGTA ATATCATACC ATAAAATGAA   1080

GTATCCATTG CTTCCCTCGT CACCTCAATG CTCCACCAAC CTTCGAGTGC TTCATCTTCA   1140

TCGGTGTTCA TTACGGATGC TTGATTGCTC TTGTATCGGA AATTTGACGA ATCTGGAAGT   1200

GTTGAGCTTC GCTAATTCTG GCATTGAACG GATACCTTCA GCAATCGGAA ATTTGAAGAA   1260

GCTTAGGCAA CTTGATCTGA GAGGTCGTTA TGGTCTTTGT ATAGAACAGG GTGTCTTGAA   1320

AAATTTGGTC GAACTTGAAG AACTTTATAT TGGAAATGCA TCTGCGTTTA GAGATTATAA   1380

CTGCAATGAG ATGGCAGA                                                 1398

(2) INFORMATION FOR SEQ ID NO:39:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1441
        (D) OTHER INFORMATION: /note= "RLG2M"

(xi) SEQUENCE DESCRIPTION: SEQ ID NO:39:

GCTGAAGAAG CTGCTGAAGA AAAGAAATTG TTTAATTATA TTGTTGGGGC AGTTATAGGG     60

GAAAAGACGG ACCCCTTTGC CATTCAAGAA GCTATAGCAG ATTACCTCGG TATACAACTC    120

AATGAAAAAA CTAAGCCAGC AAGAGCTGAT AAGCTTCGTG AATGGTTCAA AAAGAATTCA    180

GATGGAGGTA AGACTAAGTT CCTCATANTA CTTGACGATG TTTGGCAATT AGTTGATCTT    240

GAAGATATTG GGTTAAGTCC TTTTCCAAAT CAAGGTGTCG ACTTCAAGGT CTTGTTGACA    300

TCACGAGACT CACAAGTTTG CACTATGATG GGGGTTGAAG CTAATTCAAT TATTAACGTG    360

GGCCTTCTAN CTGAAGCAGA AGCTCAAAGT CTGTTCCAAC AATTTGTAGA AACTTCTGAG    420

CCCGAGCTCC AGAAGATAGG AGAGGATATC GTAAGGAAGT GTTGCGGTCT ACCTATTGCC    480
```

```
ATAAAAACCA TGGCATGTAC TCTTAGAAAT AAAAGAAAGG ATGCATGGAA GGATGCACTT    540

TCGCGCATAG AGCACTATGA CATTCACAAT GTTGCGCCCA AAGTCTTTGA AACGAGCTAC    600

CACAATCTCC AAGAAGAGGA GACTAAATCC ACTTTTTTAA TGTGTGGTTT GTTTCCCGAA    660

GACTTCGATA TTCCTACTGA GGAGTTGATG AGGTATGGAT GGGGCTTGAA GCTATTTGAT    720

AGAGTTTATA CGATTAGAGA AGCAAGAACC AGGCTCAACA CCTGCATTGA GCGACTGGTG    780

CAGACAAATT TGTTAATTGA AAGTGATGAT GTTGGGTGTG TCAAGATGCA TGATCTGGTC    840

CGTGCTTTTG TTTTGGGTAT GTTTTCTGAA GTCGAGCATG CTTCTATTGT CAACCATGGT    900

AATATGCCTG GGTGGCCTGA TGAAAATGAT ATGATCGTGC ACTCTTGCAA AAGAATTTCA    960

TTAACATGCA AGGGTATGAT TGAGATTCCA GTAGACCTCA AGTTTCCTAA ACTAACGATT   1020

TTGAAACTTA TGCATGGAGA TAAGTCGCTA AGGTNTCCNC NAGACTTTTA TGAAGGAATG   1080

GAAAAGCTCC NTGTTATATC ATACGATAAA ATGAAGTNCC CATTGCTTCC TTTGGCACCT   1140

CGATGCTCCA CCAACATTCG GGTGCTTCAT CTCACTGAAT GTTCATTAAA GATGTTTGAT   1200

TGCTCNTCNA TCGGAAATCT ATCNAATCTG GAAGTGCTGA NCTTTGCAAA TTCTCNCATT   1260

GAATGGTNGC CTTCCCCNGT CGGAAATTTA AAAAAGCTAA GGTTGCTTGA TCTGAAATTT   1320

TGTGATNGTC TCCCTNTAGA ACAAGGTGTC TTGAAAACTT TTGTCCACNT GAANAATTTA   1380

TNTTGGAGAC CCTCTGGGTT TATNNATGAA AACTGCCATG ANATGGCAGA CCTTTCAACC   1440

A                                                                   1441
```

(2) INFORMATION FOR SEQ ID NO:40:

(i) SEQUENCE CHARACTERISTICS:
        (A) LENGTH: 472 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..472
        (D) OTHER INFORMATION: /note= "RLG2 consensus protein"

(xi) SEQUENCE DESCRIPTION: SEQ ID NO:40:

```
Gly Glu Thr Thr Leu Lys Glu Val Val Glu Lys Lys Met Phe Asn
1               5                   10                  15

Tyr Ile Val Glu Ala Val Ile Gly Glu Lys Thr Asp Pro Ile Ala Ile
            20                  25                  30

Gln Gln Ala Val Ala Asp Tyr Leu Gly Ile Glu Leu Lys Glu Ser Thr
        35                  40                  45

Lys Pro Ala Arg Ala Asp Lys Leu Arg Glu Trp Phe Lys Ala Glu Ser
    50                  55                  60

Asp Gly Gly Lys Asn Lys Phe Leu Val Ile Leu Asp Asp Val Trp Gln
65                  70                  75                  80

Ser Val Asp Leu Glu Asp Ile Gly Leu Ser Pro Phe Pro Asn Gln Gly
                85                  90                  95

Val Asp Phe Lys Val Leu Leu Thr Ser Arg Asp Ser His Val Cys Thr
            100                 105                 110

Val Met Gly Val Glu Ala Asn Ser Ile Leu Asn Val Gly Leu Leu Ile
        115                 120                 125

Glu Ala Glu Ala Gln Ser Leu Phe Gln Gln Phe Val Glu Thr Ser Glu
    130                 135                 140
```

```
Pro Glu Leu His Lys Ile Gly Glu Asp Ile Val Arg Lys Cys Cys Gly
145                 150                 155                 160

Leu Pro Ile Ala Ile Lys Thr Met Ala Cys Thr Leu Arg Asn Lys Arg
            165                 170                 175

Lys Asp Ala Trp Lys Asp Ala Leu Ser Arg Leu Glu His His Asp Ile
            180                 185                 190

Gly Ser Val Ala Pro Lys Val Phe Glu Thr Ser Tyr Asp Asn Leu Gln
            195                 200                 205

Asp Glu Glu Thr Lys Ser Ile Phe Leu Met Cys Gly Leu Phe Pro Glu
210                 215                 220

Asp Phe Asp Ile Pro Thr Glu Glu Leu Met Arg Tyr Gly Trp Gly Leu
225                 230                 235                 240

Lys Leu Phe Asp Arg Val Tyr Thr Ile Arg Glu Ala Arg Asn Arg Leu
            245                 250                 255

Asn Thr Cys Ile Glu Arg Leu Val Gln Thr Asn Leu Leu Ile Glu Ser
            260                 265                 270

Asp Asp Val Gly Cys Val Lys Met His Asp Leu Val Arg Ala Phe Val
            275                 280                 285

Leu Gly Met Phe Ser Glu Val Glu His Ala Ser Ile Val Asn His Gly
290                 295                 300

Asn Met Pro Gly Trp Pro Glu Glu Asn Asp Ile Val His Ser Cys Lys
305                 310                 315                 320

Arg Ile Ser Leu Thr Cys Lys Gly Met Ser Glu Phe Pro Val Asp Leu
            325                 330                 335

Lys Phe Pro Asn Leu Thr Ile Leu Lys Leu Met His Gly Asp Lys Ser
            340                 345                 350

Leu Arg Phe Pro Gln Asp Phe Tyr Glu Gly Met Glu Lys Leu Gln Val
            355                 360                 365

Ile Ser Tyr Asp Lys Met Lys Tyr Pro Leu Leu Pro Ser Ser Pro Gln
370                 375                 380

Cys Ser Thr Asn Leu Arg Val Leu His Leu His Glu Cys Ser Leu Arg
385                 390                 395                 400

Met Phe Asp Cys Ser Ser Ile Gly Asn Leu Leu Asn Leu Glu Val Leu
            405                 410                 415

Ser Phe Ala Asn Ser Gly Ile Glu Trp Leu Pro Ser Thr Ile Gly Asn
            420                 425                 430

Leu Lys Lys Leu Arg Leu Leu Asp Leu Thr Asn Cys Tyr Gly Leu Arg
            435                 440                 445

Ile Glu Asn Gly Val Leu Lys Asn Leu Val Lys Leu Glu Glu Leu Tyr
450                 455                 460

Ile Gly Asn Ala Asn Gly Phe Gly
465                 470

(2) INFORMATION FOR SEQ ID NO:41:

(i) SEQUENCE CHARACTERISTICS:
        (A) LENGTH: 479 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..479
        (D) OTHER INFORMATION: /note= "RLG2A protein"
```

-continued (xi) SEQUENCE DESCRIPTION: SEQ ID NO:41:

```
Gly Lys Thr Thr Met Met His Arg Leu Lys Lys Val Val Lys Glu Lys
1               5                   10                  15

Lys Met Phe Asn Phe Ile Ile Glu Ala Val Val Gly Glu Lys Thr Asp
                20                  25                  30

Pro Ile Ala Ile Gln Ser Ala Val Ala Asp Tyr Leu Gly Ile Glu Leu
            35                  40                  45

Asn Glu Lys Thr Lys Pro Ala Arg Thr Glu Lys Leu Arg Lys Trp Phe
        50                  55                  60

Val Asp Asn Ser Gly Gly Lys Lys Ile Leu Val Ile Leu Asp Asp Val
65                  70                  75                  80

Trp Gln Phe Val Asp Leu Asn Asp Ile Gly Leu Ser Pro Leu Pro Asn
                85                  90                  95

Gln Gly Val Asp Phe Lys Val Leu Leu Thr Ser Arg Asp Lys Asp Val
            100                 105                 110

Cys Thr Glu Met Gly Ala Glu Val Asn Ser Thr Phe Asn Val Lys Met
        115                 120                 125

Leu Ile Glu Thr Glu Ala Gln Ser Leu Phe His Gln Phe Ile Glu Ile
    130                 135                 140

Ser Asp Asp Val Asp Pro Glu Leu His Asn Ile Gly Val Asn Ile Val
145                 150                 155                 160

Arg Lys Cys Gly Gly Leu Pro Ile Ala Ile Lys Thr Met Ala Cys Thr
                165                 170                 175

Leu Arg Gly Lys Ser Lys Asp Ala Trp Lys Asn Ala Leu Leu Arg Leu
            180                 185                 190

Glu His Tyr Asp Ile Glu Asn Ile Val Asn Gly Val Phe Lys Met Ser
        195                 200                 205

Tyr Asp Asn Leu Gln Asp Glu Glu Thr Lys Ser Thr Phe Leu Leu Cys
    210                 215                 220

Gly Met Tyr Pro Glu Xaa Phe Asp Ile Leu Thr Glu Glu Leu Val Arg
225                 230                 235                 240

Tyr Gly Trp Gly Leu Lys Leu Phe Lys Lys Xaa Tyr Thr Ile Gly Glu
                245                 250                 255

Ala Arg Thr Arg Leu Asn Thr Cys Ile Glu Arg Leu Ile His Thr Asn
            260                 265                 270

Leu Leu Met Glu Val Asp Asp Val Arg Cys Ile Lys Met His Asp Leu
        275                 280                 285

Val Arg Ala Phe Val Leu Asp Met Tyr Ser Lys Val Glu His Ala Ser
    290                 295                 300

Ile Val Asn His Ser Asn Thr Leu Glu Trp His Ala Asp Asn Met His
305                 310                 315                 320

Asp Ser Cys Lys Arg Leu Ser Leu Thr Cys Lys Gly Met Ser Lys Phe
                325                 330                 335

Pro Thr Asp Leu Lys Phe Pro Asn Leu Ser Ile Leu Lys Leu Met His
            340                 345                 350

Glu Asp Ile Ser Leu Arg Phe Pro Lys Asn Phe Tyr Glu Glu Met Glu
        355                 360                 365

Lys Leu Glu Val Ile Ser Tyr Asp Lys Met Lys Tyr Pro Leu Leu Pro
    370                 375                 380

Ser Ser Pro Gln Cys Ser Val Asn Leu Arg Val Phe His Leu His Lys
385                 390                 395                 400

Cys Ser Leu Val Met Phe Asp Cys Ser Cys Ile Gly Asn Leu Ser Asn
                405                 410                 415
```

-continued

```
Leu Glu Val Leu Ser Phe Ala Asp Ser Ala Ile Asp Arg Leu Pro Ser
            420                 425                 430

Thr Ile Gly Lys Leu Lys Lys Leu Arg Leu Leu Asp Leu Thr Asn Cys
            435                 440                 445

Tyr Gly Val Arg Ile Asp Asn Gly Val Leu Lys Lys Leu Val Lys Leu
            450                 455                 460

Glu Glu Leu Tyr Met Thr Val Val Asp Arg Gly Arg Lys Ala Ile
465                 470                 475
```

(2) INFORMATION FOR SEQ ID NO:42:

(i) SEQUENCE CHARACTERISTICS:
        (A) LENGTH: 481 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..481
        (D) OTHER INFORMATION: /note= "RLG2B protein"

(xi) SEQUENCE DESCRIPTION: SEQ ID NO:42:

```
Gly Lys Thr Arg Met Met Gln Arg Leu Lys Lys Ala Xaa Glu Glu Lys
1               5                   10                  15

Lys Leu Phe Asn Tyr Ile Val Gly Ala Val Ile Xaa Glu Lys Thr Asp
            20                  25                  30

Pro Phe Ala Ile Gln Glu Ala Ile Ala Asp Tyr Leu Gly Ile Gln Leu
            35                  40                  45

Asn Glu Lys Thr Lys Pro Ala Arg Ala Asp Lys Leu Arg Glu Trp Phe
50                  55                  60

Lys Lys Asn Ser Asp Gly Lys Thr Lys Phe Leu Ile Val Leu Asp
65                  70                  75                  80

Asp Val Trp Gln Leu Val Asp Leu Glu Asp Ile Gly Leu Ser Pro Phe
            85                  90                  95

Pro Asn Gln Gly Val Asp Phe Lys Val Leu Leu Thr Ser Arg Asp Ser
            100                 105                 110

Gln Val Cys Thr Met Met Gly Val Glu Ala Asn Ser Ile Ile Asn Val
            115                 120                 125

Gly Leu Leu Thr Glu Ala Glu Ala Gln Ser Leu Phe Gln Gln Phe Val
            130                 135                 140

Glu Thr Ser Glu Pro Glu Leu Gln Lys Ile Gly Glu Asp Ile Val Arg
145                 150                 155                 160

Lys Cys Cys Gly Leu Pro Ile Ala Ile Lys Thr Met Ala Cys Xaa Leu
            165                 170                 175

Arg Asn Lys Arg Lys Asp Ala Trp Lys Asp Ala Leu Ser Arg Ile Glu
            180                 185                 190

His Tyr Asp Ile His Asn Val Ala Pro Lys Val Phe Glu Thr Ser Tyr
            195                 200                 205

His Asn Leu Gln Glu Glu Glu Thr Lys Ser Thr Phe Leu Met Cys Gly
            210                 215                 220

Leu Phe Pro Glu Asp Phe Asp Ile Pro Thr Glu Glu Leu Met Arg Tyr
225                 230                 235                 240

Gly Trp Gly Leu Lys Leu Phe Asp Arg Val Tyr Thr Ile Arg Glu Ala
            245                 250                 255
```

```
Arg Thr Arg Leu Asn Thr Cys Ile Glu Arg Leu Val Gln Thr Asn Leu
            260                 265                 270

Leu Ile Glu Ser Asp Asp Val Gly Cys Val Lys Met His Asp Leu Val
            275                 280                 285

Arg Ala Phe Val Leu Gly Met Phe Ser Glu Val Glu His Ala Ser Ile
            290                 295                 300

Val Asn His Gly Asn Met Pro Gly Trp Pro Asp Glu Asn Asp Met Ile
305                 310                 315                 320

Val His Ser Cys Lys Arg Ile Ser Leu Thr Cys Lys Gly Met Ile Glu
                    325                 330                 335

Ile Pro Val Asp Leu Lys Phe Pro Lys Leu Thr Ile Leu Lys Leu Met
                340                 345                 350

His Gly Asp Lys Ser Leu Arg Phe Pro Gln Asp Phe Tyr Glu Gly Met
                355                 360                 365

Glu Lys Leu His Val Ile Ser Tyr Asp Lys Met Lys Tyr Pro Leu Leu
370                 375                 380

Pro Leu Ala Pro Arg Cys Ser Thr Asn Ile Arg Val Leu His Leu Thr
385                 390                 395                 400

Glu Cys Ser Leu Lys Met Phe Asp Cys Ser Ser Ile Gly Asn Leu Ser
                    405                 410                 415

Asn Leu Glu Val Leu Ser Phe Ala Asn Ser His Ile Glu Trp Leu Pro
                420                 425                 430

Ser Thr Val Arg Asn Leu Lys Lys Leu Arg Leu Leu Asp Leu Arg Phe
                435                 440                 445

Cys Asp Gly Leu Arg Ile Glu Gln Gly Val Leu Lys Ser Phe Val Lys
450                 455                 460

Leu Glu Glu Phe Tyr Ile Gly Asp Ala Ser Gly Phe Ile Asp Asp Asn
465                 470                 475                 480

Cys (2) INFORMATION FOR SEQ ID NO:43:

(i) SEQUENCE CHARACTERISTICS:
        (A) LENGTH: 472 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..472
        (D) OTHER INFORMATION: /note= "RLG2C protein"

(xi) SEQUENCE DESCRIPTION: SEQ ID NO:43:

Asn Thr Arg Xaa Ala Lys Ala Glu Glu Val Ala Lys Xaa Lys Glu Glu
1               5                   10                  15

Phe Gly Tyr Ile Ile Glu Ala Val Ile Gly Glu Ile Ser Asp Pro Ile
                20                  25                  30

Ala Ile Gln Gln Val Val Ala Asp Tyr Leu Cys Ile Glu Leu Lys Glu
            35                  40                  45

Ser Asp Lys Lys Thr Arg Ala Glu Lys Leu Arg Gln Gly Phe Lys Ala
            50                  55                  60

Lys Ser Asp Gly Gly Asn Thr Lys Phe Leu Ile Ile Leu Asp Asp Val
65                  70                  75                  80

Trp Gln Ser Val Asp Leu Xaa Asp Ile Gly Leu Ser Pro Ser Pro Asn
                85                  90                  95
```

-continued

```
Gln Xaa Val Asp Phe Lys Val Leu Leu Thr Ser Arg Asp Glu His Val
    100                 105                 110

Cys Ser Val Met Gly Val Glu Ala Asn Ser Ile Ile Asn Val Gly Leu
    115                 120                 125

Leu Ile Glu Ala Glu Ala Gln Arg Leu Phe Gln Gln Phe Val Glu Thr
    130                 135                 140

Ser Glu Pro Glu Leu His Lys Ile Gly Glu Asp Ile Val Arg Arg Cys
145                 150                 155                 160

Cys Gly Leu Pro Ile Ala Ile Lys Thr Met Ala Cys Thr Leu Arg Asn
                165                 170                 175

Lys Arg Lys Asp Ala Trp Lys Asp Ala Leu Ser Arg Leu Gln His His
                180                 185                 190

Asp Ile Gly Asn Val Ala Thr Ala Val Phe Arg Thr Ser Tyr Glu Asn
                195                 200                 205

Leu Pro Asp Lys Glu Thr Lys Ser Val Phe Leu Met Cys Gly Leu Phe
                210                 215                 220

Pro Glu Asp Phe Asn Ile Pro Thr Glu Glu Leu Met Arg Tyr Gly Trp
225                 230                 235                 240

Gly Leu Lys Leu Phe Asp Arg Val Tyr Thr Ile Ile Glu Ala Arg Asn
                245                 250                 255

Arg Leu Asn Thr Cys Ile Asp Arg Leu Val Gln Thr Asn Leu Leu Ile
                260                 265                 270

Gly Ser Asp Asn Gly Val His Val Lys Met His Asp Leu Val Arg Ala
                275                 280                 285

Phe Val Leu Gly Met Tyr Ser Glu Val Glu Gln Ala Ser Ile Val Asn
                290                 295                 300

His Gly Asn Met Pro Gly Trp Pro Asp Glu Asn Asp Met Ile Val His
305                 310                 315                 320

Ser Cys Lys Arg Ile Ser Leu Thr Cys Lys Gly Met Ile Glu Phe Pro
                325                 330                 335

Val Asp Leu Lys Phe Pro Lys Leu Thr Ile Leu Lys Leu Met His Gly
                340                 345                 350

Asp Lys Ser Leu Lys Phe Pro Gln Glu Phe Tyr Glu Gly Met Glu Lys
                355                 360                 365

Leu Arg Val Ile Ser Tyr His Lys Met Lys Tyr Pro Leu Leu Pro Leu
                370                 375                 380

Ala Pro Gln Cys Ser Thr Asn Ile Arg Val Leu His Leu Thr Glu Cys
385                 390                 395                 400

Ser Leu Lys Met Phe Asp Cys Ser Cys Ile Gly Asn Leu Ser Asn Leu
                405                 410                 415

Glu Val Leu Ser Phe Ala Asn Ser Cys Ile Glu Trp Leu Pro Ser Thr
                420                 425                 430

Val Arg Asn Leu Lys Lys Leu Arg Leu Leu Asp Leu Arg Leu Cys Tyr
                435                 440                 445

Gly Leu Arg Ile Glu Gln Gly Val Leu Lys Ser Leu Val Lys Leu Glu
                450                 455                 460

Glu Phe Tyr Ile Gly Asn Ala Tyr
465                 470
```

(2) INFORMATION FOR SEQ ID NO:44:

(i) SEQUENCE CHARACTERISTICS:
        (A) LENGTH: 470 amino acids
        (B) TYPE: amino acid

```
        (C) STRANDEDNESS:
        (D) TOPOLOGY: linear (ii) MOLECULE TYPE: protein (ix) FEATURE:
        (A) NAME/KEY: -
        (B) LOCATION: 1..470
        (D) OTHER INFORMATION: /note= "RLG2D protein"

(xi) SEQUENCE DESCRIPTION: SEQ ID NO:44:
```

```
Glu Val Ala Lys Xaa Lys Arg Lys Phe Gly Tyr Ile Ile Glu Ala Val
1               5                   10                  15

Ile Xaa Glu Ile Ser Asp Pro Ile Ala Ile Gln Gln Val Val Ala Asp
            20                  25                  30

Tyr Leu Cys Ile Glu Leu Lys Glu Ser Asp Xaa Lys Thr Arg Ala Glu
            35                  40                  45

Lys Leu Arg Gln Gly Phe Lys Ala Lys Ser Xaa Gly Gly Asn Thr Lys
50                  55                  60

Phe Leu Ile Ile Leu Asp Asp Val Trp Gln Ser Val Asp Leu Glu Xaa
65                  70                  75                  80

Ile Gly Leu Ser Pro Ser Pro Asn Gln Gly Val Xaa Phe Lys Val Leu
            85                  90                  95

Leu Thr Ser Arg Asp Glu His Val Cys Ser Val Met Gly Val Glu Ala
            100                 105                 110

Asn Ser Ile Ile Asn Val Gly Leu Leu Ile Glu Xaa Xaa Xaa Xaa Arg
            115                 120                 125

Leu Phe Gln Gln Phe Val Xaa Thr Ser Glu Pro Glu Leu His Lys Ile
130                 135                 140

Xaa Glu Xaa Ile Val Arg Arg Cys Cys Gly Leu Pro Ile Ala Ile Lys
145                 150                 155                 160

Thr Met Ala Cys Thr Leu Arg Asn Lys Arg Lys Asp Ala Trp Lys Asp
            165                 170                 175

Ala Leu Ser Arg Leu Gln His His Asp Ile Gly Asn Val Ala Thr Ala
            180                 185                 190

Val Phe Xaa Thr Ser Tyr Glu Asn Leu Pro Asp Lys Glu Thr Lys Ser
            195                 200                 205

Val Phe Leu Met Cys Gly Leu Phe Pro Glu Asp Phe Asn Ile Pro Thr
210                 215                 220

Glu Glu Leu Met Xaa Tyr Gly Trp Gly Leu Lys Leu Phe Asp Arg Val
225                 230                 235                 240

Tyr Thr Ile Ile Glu Ala Arg Asn Arg Leu Asn Thr Cys Ile Glu Arg
            245                 250                 255

Leu Val Gln Ala Asn Leu Leu Ile Gly Ser Asp Asn Gly Val His Val
            260                 265                 270

Lys Met His Asp Leu Val Arg Ala Phe Val Leu Gly Met Tyr Ser Glu
            275                 280                 285

Val Glu Gln Ala Ser Ile Val Asn His Gly Asn Met Pro Gly Trp Pro
            290                 295                 300

Asp Glu Asn Asp Met Ile Val His Ser Cys Lys Arg Ile Ser Leu Thr
305                 310                 315                 320

Cys Lys Gly Met Ile Glu Ile Pro Val Asp Leu Lys Phe Pro Lys Leu
            325                 330                 335

Thr Ile Leu Lys Leu Met His Gly Asp Lys Ser Leu Lys Phe Pro Gln
            340                 345                 350

Glu Phe Tyr Glu Gly Met Glu Lys Leu Gln Val Ile Ser Tyr Asp Lys
```

```
                    355                 360                 365
Met Lys Tyr Pro Leu Leu Pro Leu Ala Pro Gln Cys Ser Thr Asn Ile
            370                 375                 380

Arg Val Leu His Leu Thr Glu Cys Ser Leu Lys Met Phe Asp Cys Ser
385                 390                 395                 400

Ser Ile Gly Asn Leu Ser Asn Leu Glu Val Leu Ser Phe Ala Asn Ser
                405                 410                 415

Arg Ile Glu Trp Leu Pro Ser Thr Val Arg Asn Leu Lys Lys Leu Arg
            420                 425                 430

Leu Leu Asp Leu Arg Phe Cys Asp Gly Leu Arg Ile Glu Gln Gly Val
        435                 440                 445

Leu Lys Ser Leu Val Lys Leu Glu Glu Phe Tyr Ile Gly Asn Ala Tyr
    450                 455                 460

Gly Phe Ile Asp Val Met
465             470

(2) INFORMATION FOR SEQ ID NO:45:

(i) SEQUENCE CHARACTERISTICS:
        (A) LENGTH: 471 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..471
        (D) OTHER INFORMATION: /note= "RLG2E protein"

(xi) SEQUENCE DESCRIPTION: SEQ ID NO:45:

Gly Arg His Asn Asp Ala Lys Val Glu Glu Val Ala Lys Glu Asn Arg
1               5                   10                  15

Met Phe Asn Tyr Met Val Glu Ala Val Ile Gly Glu Lys Thr Asp Pro
            20                  25                  30

Leu Ala Ile Gln Gln Ala Val Ala Asp Tyr Leu Cys Ile Glu Leu Lys
        35                  40                  45

Glu Ser Thr Lys Pro Ala Arg Ala Asp Lys Leu Arg Glu Trp Phe Lys
    50                  55                  60

Ala Asn Ser Gly Glu Gly Lys Asn Lys Phe Leu Val Ile Phe Asp Asp
65              70                  75                  80

Val Trp Gln Ser Val Asp Leu Glu Asp Ile Gly Leu Ser His Phe Pro
            85                  90                  95

Asn Gln Gly Val Asp Phe Lys Val Leu Leu Thr Ser Arg Asp His Val
                100                 105                 110

Cys Xaa Val Met Gly Val Glu Ala Asn Ser Ile Leu Asn Val Gly Leu
        115                 120                 125

Leu Val Glu Ala Glu Ala Gln Ser Leu Phe Gln Gln Phe Val Glu Thr
    130                 135                 140

Phe Glu Pro Glu Leu His Lys Ile Gly Glu Asp Ile Val Arg Lys Cys
145                 150                 155                 160

Cys Gly Leu Pro Ile Ala Ile Lys Thr Met Ala Cys Thr Leu Arg Asn
                165                 170                 175

Lys Arg Lys Asp Ala Trp Lys Asp Ala Leu Leu His Leu Glu Tyr His
            180                 185                 190

Asp Ile Ser Ser Val Ala Pro Lys Val Phe Glu Thr Ser Tyr His Asn
        195                 200                 205
```

```
Leu His Asn Lys Glu Thr Lys Ser Val Phe Leu Met Cys Gly Phe Phe
    210                 215                 220
Pro Glu Asp Phe Asn Ile Pro Ile Glu Leu Met Arg Tyr Gly Trp
225                 230                 235                 240
Gly Leu Lys Ile Phe Asp Arg Val Tyr Thr Ile Arg Gln Ala Arg Ile
                245                 250                 255
Arg Leu Asn Thr Cys Ile Glu Arg Leu Val Gln Thr Asn Leu Leu Ile
                260                 265                 270
Glu Ser Asp Asp Gly Val His Val Lys Met His Asp Leu Val Arg Ala
            275                 280                 285
Phe Val Leu Val Met Phe Ser Glu Val Glu His Ala Ser Ile Ile Asn
        290                 295                 300
His Gly Asn Met Leu Gly Trp Pro Glu Asn Tyr Met Thr Asn Ser Cys
305                 310                 315                 320
Lys Thr Ile Ser Leu Thr Cys Lys Ser Met Ser Glu Phe Pro Gly Asp
                325                 330                 335
Leu Lys Phe Pro Asn Leu Thr Ile Leu Lys Leu Met His Gly Asp Lys
                340                 345                 350
Leu Leu Arg Tyr Pro Gln Asp Phe Tyr Glu Gly Met Glu Lys Leu Trp
            355                 360                 365
Val Ile Ser Tyr Asp Glu Met Lys Tyr Pro Leu Leu Pro Ser Leu Pro
        370                 375                 380
Gln Cys Ser Ile Asn Leu Arg Val Leu His Leu His Arg Cys Ser Leu
385                 390                 395                 400
Met Met Phe Asp Cys Ser Cys Ile Gly Asn Met Leu Asn Leu Glu Val
                405                 410                 415
Leu Ser Phe Val Lys Ser Gly Ile Glu Trp Leu Pro Ser Thr Ile Gly
                420                 425                 430
Asn Leu Lys Lys Leu Arg Leu Leu Asp Leu Arg Asp Cys Tyr Gly Leu
            435                 440                 445
Arg Ile Glu Lys Gly Val Leu Lys Asn Leu Val Lys Ile Glu Glu Leu
        450                 455                 460
Tyr Ile Gly Arg Ala Asp Ile
465                 470

(2) INFORMATION FOR SEQ ID NO:46:

(i) SEQUENCE CHARACTERISTICS:
        (A) LENGTH: 477 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..477
        (D) OTHER INFORMATION: /note= "RLG2F protein"

(xi) SEQUENCE DESCRIPTION: SEQ ID NO:46:

Leu Glu Asp Thr Met Met Gln Arg Leu Lys Lys Val Val His Glu Lys
1               5                   10                  15
Lys Met Phe Asn Phe Ile Val Glu Ala Val Ile Gly Glu Lys Thr Asp
                20                  25                  30
Pro Val Ala Ile Gln Asp Ala Ile Ala Asp Tyr Leu Gly Val Glu Leu
            35                  40                  45
```

-continued

```
Asn Glu Lys Ser Lys Gln Ala Arg Ala Asp Lys Leu Arg Gln Gly Phe
         50                  55                  60

Lys Asp Lys Ser Asp Gly Gly Lys Asn Lys Phe Phe Val Ile Leu Asp
 65                  70                  75                  80

Asp Val Trp Gln Ser Val Asp Leu Glu Asp Ile Gly Leu Ser Pro Phe
                     85                  90                  95

Pro Asn Gln Gly Val Asp Phe Lys Val Leu Leu Thr Ser Arg Asp Arg
                100                 105                 110

His Val Cys Thr Val Met Gly Val Glu Ala Lys Leu Ile Leu Asn Val
            115                 120                 125

Gly Leu Leu Ile Glu Ala Glu Ala Gln Ser Leu Phe His Gln Phe Val
        130                 135                 140

Val Thr Ser Glu Pro Glu Leu His Lys Ile Gly Glu Asp Ile Val Lys
145                 150                 155                 160

Lys Cys Phe Gly Leu Pro Ile Ala Ile Lys Thr Met Ala Cys Thr Leu
                165                 170                 175

Arg His Lys Arg Lys Asp Ala Trp Lys Asp Ala Leu Ser Arg Leu Glu
                180                 185                 190

His His Asp Ile Gln Ser Val Val Pro Lys Val Phe Glu Thr Ser Tyr
            195                 200                 205

Asn Asn Leu Lys Asp Lys Glu Thr Lys Ser Val Phe Leu Met Cys Gly
        210                 215                 220

Leu Phe Pro Glu Asp Leu Asp Ile Pro Ile Glu Glu Leu Met Arg Tyr
225                 230                 235                 240

Gly Trp Gly Leu Arg Leu Phe Asp Arg Val Asn Thr Ile Thr Gln Ala
                245                 250                 255

Arg Asn Arg Leu Asn Thr Cys Ile Glu Arg Leu Val His Thr Asn Leu
                260                 265                 270

Leu Ile Glu Ser Val Asp Gly Val His Val Lys Met His Asp Leu Val
            275                 280                 285

Arg Ala Phe Val Leu Gly Met Phe Ser Glu Val Glu His Ala Ser Ile
        290                 295                 300

Val Asn His Gly Asn Met Pro Glu Trp Thr Glu Asn Asp Met Thr Asp
305                 310                 315                 320

Ser Cys Lys Gln Ile Ser Leu Thr Cys Lys Ser Met Leu Glu Phe Pro
                325                 330                 335

Gly Asp Leu Lys Phe Pro Asn Leu Lys Ile Leu Lys Leu Met His Gly
                340                 345                 350

Gly Lys Ser Leu Arg Tyr Pro Gln Asp Phe Tyr Gln Gly Met Glu Lys
            355                 360                 365

Leu Glu Val Ile Ser Tyr Asp Glu Met Lys Tyr Pro Leu Leu Pro Ser
        370                 375                 380

Leu Pro Gln Cys Ser Thr Ile Leu Arg Val Leu His Leu His Glu Cys
385                 390                 395                 400

Ser Leu Arg Met Phe Asp Cys Ser Ser Ile Gly Asn Leu Phe Asn Met
                405                 410                 415

Glu Val Leu Ser Phe Ala Asn Ser Ser Ile Glu Leu Leu Pro Ser Val
                420                 425                 430

Ile Gly Asn Leu Lys Lys Leu Arg Leu Leu Asp Leu Thr Asn Cys Tyr
            435                 440                 445

Gly Val Arg Ile Glu Lys Asp Val Leu Lys Asn Leu Val Lys Leu Glu
450                 455                 460

Glu Leu Tyr Ile Arg Asn Gly Leu Pro Val Tyr Arg Gly
```

-continued 465 470 475

(2) INFORMATION FOR SEQ ID NO:47:

(i) SEQUENCE CHARACTERISTICS:
 (A) LENGTH: 488 amino acids
 (B) TYPE: amino acid
 (C) STRANDEDNESS:
 (D) TOPOLOGY: linear (ii) MOLECULE TYPE: protein (ix) FEATURE:
 (A) NAME/KEY: -
 (B) LOCATION: 1..488
 (D) OTHER INFORMATION: /note= "RLG2G protein"

(xi) SEQUENCE DESCRIPTION: SEQ ID NO:47:

```
Gly Arg His Asp Asp Glu Glu Leu Lys Glu Val Val Gly Gln Lys Lys
1               5                   10                  15

Ser Phe Asn Ile Ile Ile Gln Val Val Ile Gly Glu Lys Thr Asn Pro
            20                  25                  30

Ile Ala Ile Gln Gln Ala Val Ala Asp Tyr Leu Ser Ile Glu Leu Lys
        35                  40                  45

Glu Asn Thr Lys Glu Ala Arg Ala Asp Lys Leu Arg Lys Arg Phe Glu
    50                  55                  60

Ala Asp Gly Gly Lys Asn Lys Phe Leu Val Ile Leu Asp Asp Val Trp
65                  70                  75                  80

Gln Phe Val Asp Leu Glu Asp Ile Gly Leu Ser Pro Leu Pro Asn Lys
                85                  90                  95

Gly Val Asn Phe Lys Val Leu Leu Thr Ser Arg Asp Ser His Val Cys
            100                 105                 110

Thr Leu Met Gly Ala Glu Ala Asn Ser Ile Leu Asn Ile Lys Val Leu
        115                 120                 125

Lys Asp Val Glu Gly Gln Ser Leu Phe Arg Gln Phe Ala Lys Asn Ala
    130                 135                 140

Gly Asp Asp Leu Asp Pro Ala Phe Asn Gly Ile Ala Asp Ser Ile
145                 150                 155                 160

Ala Ser Arg Cys Gln Gly Leu Pro Ile Ala Ile Lys Thr Ile Ala Leu
                165                 170                 175

Ser Leu Lys Gly Arg Ser Lys Ser Ala Trp Asp Val Ala Leu Ser Arg
            180                 185                 190

Leu Glu Asn His Lys Ile Gly Ser Glu Val Val Arg Glu Val Phe
        195                 200                 205

Lys Ile Ser Tyr Asp Asn Leu Gln Asp Glu Val Thr Lys Ser Ile Phe
    210                 215                 220

Leu Leu Cys Ala Leu Phe Pro Glu Asp Phe Asp Ile Pro Thr Glu Glu
225                 230                 235                 240

Leu Val Arg Tyr Gly Trp Gly Leu Lys Leu Phe Ile Glu Ala Lys Thr
                245                 250                 255

Ile Arg Glu Ala Arg Asn Arg Leu Asn Thr Cys Thr Glu Arg Leu Arg
            260                 265                 270

Glu Thr Asn Leu Leu Phe Gly Ser Asp Asp Ile Gly Cys Val Lys Met
        275                 280                 285

His Asp Val Val Arg Asp Phe Val Leu His Ile Phe Ser Glu Val Gln
    290                 295                 300

His Ala Ser Ile Val Asn His Gly Asn Val Ser Glu Trp Leu Glu Glu
305                 310                 315                 320
```

```
Asn His Ser Ile Tyr Ser Cys Lys Arg Ile Ser Leu Thr Cys Lys Gly
                325                 330                 335

Met Ser Gln Phe Pro Lys Asp Leu Lys Phe Pro Asn Leu Ser Ile Leu
            340                 345                 350

Lys Leu Met His Gly Asp Lys Ser Leu Ser Phe Pro Glu Asn Phe Tyr
            355                 360                 365

Gly Lys Met Glu Lys Val Gln Val Ile Ser Tyr Asp Lys Leu Met Tyr
            370                 375                 380

Pro Leu Leu Pro Ser Ser Leu Glu Cys Ser Thr Asn Val Arg Val Leu
385                 390                 395                 400

His Leu His Tyr Cys Ser Leu Arg Met Phe Asp Cys Ser Ser Ile Gly
                405                 410                 415

Asn Leu Leu Asn Met Glu Val Leu Ser Phe Ala Asn Ser Asn Ile Glu
                420                 425                 430

Trp Leu Pro Ser Thr Ile Gly Asn Leu Lys Lys Leu Arg Leu Leu Asp
            435                 440                 445

Leu Thr Asn Cys Lys Gly Leu Arg Ile Asp Asn Gly Val Leu Lys Asn
    450                 455                 460

Leu Val Lys Leu Glu Glu Leu Tyr Met Gly Val Asn Arg Pro Tyr Gly
465                 470                 475                 480

Gln Ala Val Ser Leu Thr Asp Glu
                485

(2) INFORMATION FOR SEQ ID NO:48:

(i) SEQUENCE CHARACTERISTICS:
        (A) LENGTH: 472 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..472
        (D) OTHER INFORMATION: /note= "RLG2H protein"

(xi) SEQUENCE DESCRIPTION: SEQ ID NO:48:

Lys Glu Val Val Glu Arg Lys Lys Met Phe Ser Ile Ile Val Gln Val
1               5                  10                  15

Val Ile Gly Glu Lys Thr Asn Pro Ile Ala Ile Gln Gln Ala Val Ala
            20                  25                  30

Asp Tyr Leu Ser Ile Glu Leu Lys Glu Asn Thr Lys Glu Ala Arg Ala
            35                  40                  45

Asp Lys Leu Arg Lys Trp Phe Glu Ala Asp Gly Gly Lys Asn Lys Phe
        50                  55                  60

Leu Val Ile Leu Asp Asp Val Trp Gln Phe Val Asp Leu Glu Asp Ile
65                  70                  75                  80

Gly Leu Ser Pro Leu Pro Asn Lys Gly Val Asn Phe Lys Val Leu Leu
                85                  90                  95

Thr Ser Arg Asp Ser His Val Cys Thr Leu Met Gly Ala Glu Ala Asn
            100                 105                 110

Ser Ile Leu Asn Ile Lys Val Leu Thr Ala Val Glu Gly Gln Ser Leu
            115                 120                 125

Phe Arg Gln Phe Ala Lys Asn Ala Gly Asp Asp Leu Asp Pro Ala
        130                 135                 140
```

```
Phe Asn Arg Ile Ala Asp Ser Ile Ala Ser Arg Cys Gln Gly Leu Pro
145                 150                 155                 160

Ile Ala Ile Lys Thr Ile Ala Leu Ser Leu Lys Gly Arg Ser Lys Pro
            165                 170                 175

Ala Trp Asp His Ala Leu Ser Arg Leu Glu Asn His Lys Ile Gly Ser
            180                 185                 190

Glu Glu Val Val Arg Glu Val Phe Lys Ile Ser Tyr Asp Asn Leu Gln
            195                 200                 205

Asp Glu Ile Thr Lys Ser Ile Phe Leu Leu Cys Ala Leu Phe Pro Glu
            210                 215                 220

Asp Phe Asp Ile Pro Thr Glu Glu Leu Met Arg Tyr Gly Trp Gly Leu
225                 230                 235                 240

Lys Leu Phe Ile Glu Ala Lys Thr Ile Arg Glu Ala Arg Asn Arg Leu
            245                 250                 255

Asn Thr Cys Thr Glu Arg Leu Arg Glu Thr Asn Leu Leu Phe Gly Ser
            260                 265                 270

Asp Asp Ile Gly Cys Val Lys Met His Asp Val Val Arg Asp Phe Val
            275                 280                 285

Leu His Ile Phe Ser Glu Val Gln His Ala Ser Ile Val Asn His Gly
290                 295                 300

Asn Val Ser Glu Trp Leu Glu Glu Asn His Ser Ile Tyr Ser Cys Lys
305                 310                 315                 320

Arg Ile Ser Leu Thr Cys Lys Gly Met Ser Glu Phe Pro Lys Asp Leu
            325                 330                 335

Lys Phe Pro Asn Leu Ser Ile Leu Lys Leu Met His Gly Asp Lys Ser
            340                 345                 350

Leu Ser Phe Pro Glu Asn Phe Tyr Gly Lys Met Glu Lys Val Gln Val
            355                 360                 365

Ile Ser Tyr Asp Lys Leu Met Tyr Pro Leu Leu Pro Ser Ser Leu Glu
            370                 375                 380

Cys Ser Thr Asn Val Arg Val Leu His Leu His Tyr Cys Ser Leu Arg
385                 390                 395                 400

Met Phe Asp Cys Ser Ser Ile Gly Asn Leu Leu Asn Met Glu Val Leu
            405                 410                 415

Ser Phe Ala Asn Ser Asn Ile Glu Trp Leu Pro Ser Thr Ile Gly Asn
            420                 425                 430

Leu Lys Lys Leu Arg Leu Leu Asp Leu Thr Asn Cys Lys Gly Leu Arg
            435                 440                 445

Ile Asp Asn Gly Val Leu Lys Asn Leu Val Lys Leu Glu Glu Leu Tyr
450                 455                 460

Met Gly Val Asn His Pro Tyr Gly
465                 470
```

(2) INFORMATION FOR SEQ ID NO:49:

(i) SEQUENCE CHARACTERISTICS:
        (A) LENGTH: 480 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..480
        (D) OTHER INFORMATION: /note= "RLG2I protein"

(xi) SEQUENCE DESCRIPTION: SEQ ID NO:49:

```
Cys Lys Lys Ser Trp Lys Glu Val Val Glu Gln Lys Lys Thr Phe Asn
1               5                   10                  15

Ile Ile Val Gln Val Val Ile Gly Glu Lys Thr Asn Pro Ile Ala Ile
            20                  25                  30

Gln Gln Ala Val Ala Asp Ser Leu Ser Ile Glu Leu Lys Glu Asn Thr
        35                  40                  45

Lys Glu Ala Arg Ala Asp Lys Leu Arg Lys Trp Phe Glu Ala Asp Gly
50                  55                  60

Gly Xaa Asn Lys Phe Leu Val Ile Leu Asp Val Trp Xaa Phe Val
65                  70                  75                  80

Asp Leu Glu Xaa Ile Gly Leu Ser Pro His Pro Asn Xaa Gly Val Xaa
            85                  90                  95

Phe Lys Val Leu Leu Thr Ser Arg Asp Ser His Val Cys Thr Leu Met
            100                 105                 110

Gly Ala Glu Ala Asn Ser Ile Leu Asn Ile Lys Val Leu Lys Asp Val
        115                 120                 125

Glu Gly Lys Ser Leu Phe Arg Gln Phe Ala Lys Asn Ala Gly Asp Asp
    130                 135                 140

Asp Leu Asp Pro Ala Phe Ile Gly Ile Ala Asp Ser Ile Ala Ser Arg
145                 150                 155                 160

Cys Gln Gly Leu Pro Ile Ala Ile Lys Thr Ile Ala Leu Ser Leu Lys
                165                 170                 175

Gly Arg Ser Lys Ser Ala Trp Asp Val Ala Leu Ser Arg Leu Glu Asn
            180                 185                 190

His Lys Ile Gly Ser Glu Glu Val Val Arg Glu Val Phe Lys Ile Ser
        195                 200                 205

Tyr Asp Asn Leu Gln Asp Glu Val Thr Lys Ser Ile Phe Leu Leu Cys
    210                 215                 220

Ala Leu Phe Pro Glu Asp Phe Asp Ile Pro Thr Glu Glu Leu Val Arg
225                 230                 235                 240

Tyr Gly Trp Gly Leu Lys Leu Phe Ile Glu Ala Lys Thr Ile Arg Glu
                245                 250                 255

Ala Arg Asn Arg Leu Asn Thr Cys Thr Glu Arg Leu Arg Glu Thr Asn
            260                 265                 270

Leu Leu Phe Gly Ser Asp Asp Ile Gly Cys Val Lys Met His Asp Val
        275                 280                 285

Val Arg Asp Phe Val Leu His Ile Phe Ser Glu Val Gln His Ala Ser
    290                 295                 300

Ile Val Asn His Gly Asn Val Ser Glu Trp Leu Glu Glu Asn His Ser
305                 310                 315                 320

Ile Tyr Ser Cys Lys Arg Ile Ser Leu Thr Cys Lys Gly Met Ser Glu
                325                 330                 335

Phe Pro Lys Asp Leu Lys Phe Pro Asn Leu Ser Ile Leu Lys Leu Met
            340                 345                 350

His Gly Asp Lys Ser Leu Ser Phe Pro Glu Asn Phe Tyr Gly Lys Met
        355                 360                 365

Glu Lys Val Gln Val Ile Ser Tyr Asp Lys Leu Met Tyr Pro Leu Leu
    370                 375                 380

Pro Ser Ser Leu Glu Cys Ser Thr Asn Leu Arg Val Leu His Leu His
385                 390                 395                 400

Glu Cys Ser Leu Arg Met Phe Asp Cys Ser Ser Ile Gly Asn Leu Leu
                405                 410                 415
```

```
Asn Met Glu Val Leu Ser Phe Ala Asn Ser Gly Ile Glu Trp Leu Pro
            420                 425                 430

Ser Thr Ile Gly Asn Leu Lys Lys Leu Arg Leu Leu Asp Leu Thr Asp
            435                 440                 445

Cys Gly Gly Leu His Ile Asp Asn Gly Val Leu Lys Asn Leu Val Lys
            450                 455                 460

Leu Glu Glu Leu Tyr Met Gly Ala Asn Arg Leu Phe Gly Lys Cys His
465                 470                 475                 480

(2) INFORMATION FOR SEQ ID NO:50:

(i) SEQUENCE CHARACTERISTICS:
        (A) LENGTH: 479 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..479
        (D) OTHER INFORMATION: /note= "RLG2J protein"

(xi) SEQUENCE DESCRIPTION: SEQ ID NO:50:

Glu Arg Gly Arg Gly Xaa Lys Lys Thr Phe Asn Ile Ile Val Gln Val
1               5                   10                  15

Val Ile Gly Glu Lys Thr Asn Pro Ile Ala Ile Gln Gln Ala Val Ala
            20                  25                  30

Asp Tyr Leu Ser Ile Glu Leu Lys Glu Asn Thr Lys Glu Ala Arg Ala
            35                  40                  45

Asp Lys Leu Arg Lys Arg Phe Glu Ala Asp Gly Gly Lys Asn Lys Phe
50                  55                  60

Leu Val Ile Leu Asp Asp Val Trp Gln Phe Phe Asp Leu Glu Xaa Ile
65                  70                  75                  80

Gly Leu Ser Pro Leu Pro Asn Lys Gly Val Xaa Phe Lys Val Leu Leu
            85                  90                  95

Thr Ser Arg Xaa Ser His Val Cys Thr Leu Met Gly Ala Glu Ala Asn
            100                 105                 110

Ser Ile Leu Asn Xaa Lys Val Leu Xaa Asp Val Gln Gly Lys Ser Leu
            115                 120                 125

Ser Ala Xaa Leu Leu Lys Met Arg Val Xaa Met Thr Trp Ile Xaa Leu
            130                 135                 140

Ser Leu Gly Xaa Xaa Ile Val Leu Pro Val Asp Val Xaa Gly Leu Xaa
145                 150                 155                 160

Ile Ala Xaa Lys Thr Ile Xaa Xaa Ser Leu Lys Gly Arg Ser Lys Ser
            165                 170                 175

Ala Trp Asp Val Ala Leu Ser Arg Leu Glu Asn His Lys Ile Gly Ser
            180                 185                 190

Glu Glu Val Val Arg Glu Val Phe Lys Xaa Ser Tyr Asp Asn Leu Gln
            195                 200                 205

Asp Glu Val Thr Lys Ser Ile Phe Leu Leu Cys Ala Leu Phe Pro Glu
            210                 215                 220

Asp Phe Asp Ile Pro Ile Glu Glu Leu Val Arg Tyr Gly Trp Gly Leu
225                 230                 235                 240

Lys Leu Phe Ile Glu Ala Lys Thr Ile Arg Glu Ala Arg Asn Arg Leu
            245                 250                 255
```

-continued

```
Asn Asn Cys Thr Glu Arg Leu Arg Glu Thr Asn Leu Leu Phe Gly Ser
            260                 265                 270

His Asp Phe Gly Cys Val Lys Met His Asp Val Val Arg Asp Phe Val
            275                 280                 285

Leu His Met Phe Ser Glu Val Lys His Ala Ser Ile Val Asn His Gly
            290                 295                 300

Asn Met Ser Glu Trp Pro Glu Lys Asn Asp Thr Ser Asn Ser Cys Lys
305                 310                 315                 320

Arg Ile Ser Leu Thr Cys Lys Gly Met Ser Lys Phe Pro Lys Asp Ile
                325                 330                 335

Asn Tyr Pro Asn Leu Leu Ile Leu Lys Leu Met His Gly Asp Lys Ser
            340                 345                 350

Leu Cys Phe Pro Glu Asn Phe Tyr Gly Lys Met Glu Lys Val Gln Val
            355                 360                 365

Ile Ser Tyr Asp Lys Leu Met Tyr Pro Leu Leu Pro Ser Ser Leu Glu
370                 375                 380

Cys Ser Thr Asn Val Arg Val Leu His Leu His Tyr Cys Ser Leu Arg
385                 390                 395                 400

Met Phe Asp Cys Ser Ser Ile Gly Asn Leu Leu Asn Met Glu Val Leu
                405                 410                 415

Ser Phe Ala Asn Ser Asn Ile Glu Trp Leu Pro Ser Thr Ile Gly Asn
            420                 425                 430

Leu Lys Lys Leu Arg Leu Leu Asp Leu Thr Asn Cys Lys Gly Leu Arg
            435                 440                 445

Ile Asp Asn Gly Val Leu Lys Asn Leu Val Lys Leu Glu Glu Leu Tyr
450                 455                 460

Met Gly Val Asn Arg Pro Tyr Gly Gln Ala Val Ser Leu Thr Asp
465                 470                 475
```

(2) INFORMATION FOR SEQ ID NO:51:

(i) SEQUENCE CHARACTERISTICS:
        (A) LENGTH: 478 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..478
        (D) OTHER INFORMATION: /note= "RLG2K protein"

(xi) SEQUENCE DESCRIPTION: SEQ ID NO:51:

```
Leu Glu Asp Thr Met Met Xaa Arg Leu Lys Asn Ile Ile Lys Glu Lys
1               5                   10                  15

Arg Thr Phe His Tyr Ile Val Leu Val Val Ile Lys Glu Asn Met Asp
            20                  25                  30

Leu Ile Ser Ile Gln Asp Ala Val Ala Asp Tyr Leu Asp Met Lys Leu
                35                  40                  45

Thr Glu Ser Asn Glu Ser Glu Arg Ala Asp Lys Leu Arg Glu Gly Phe
50                  55                  60

Gln Ala Lys Ser Asp Gly Gly Lys Asn Arg Phe Leu Ile Ile Leu Asp
65                  70                  75                  80

Asp Val Trp Gln Ser Val Asn Met Glu Asp Ile Gly Leu Ser Pro Phe
                85                  90                  95

Pro Asn Gln Gly Val Asp Phe Lys Val Leu Leu Thr Ser Glu Asn Lys
```

```
            100                 105                 110
Asp Val Cys Ala Lys Met Gly Val Glu Ala Asn Leu Ile Phe Asp Val
            115                 120                 125
Lys Phe Leu Thr Glu Glu Ala Gln Ser Leu Phe Tyr Gln Phe Val
            130                 135                 140
Lys Val Ser Asp Thr His Leu Asp Lys Ile Gly Lys Ala Ile Val Arg
145                 150                 155                 160
Asn Cys Gly Gly Leu Pro Ile Ala Ile Lys Thr Ile Ala Asn Thr Leu
                165                 170                 175
Lys Asn Xaa Asn Lys Asp Val Trp Lys Asp Ala Leu Ser Arg Ile Glu
                180                 185                 190
His His Asp Ile Glu Thr Ile Ala His Val Val Phe Gln Met Ser Tyr
            195                 200                 205
Asp Asn Leu Gln Asn Glu Glu Ala Gln Ser Ile Phe Leu Leu Cys Gly
            210                 215                 220
Leu Phe Pro Glu Asp Phe Asp Ile Pro Thr Glu Glu Leu Val Xaa Tyr
225                 230                 235                 240
Gly Trp Gly Leu Arg Val Phe Asn Gly Val Tyr Thr Ile Gly Glu Ala
                245                 250                 255
Arg His Arg Leu Asn Ala Tyr Ile Glu Leu Leu Lys Asp Ser Asn Leu
            260                 265                 270
Leu Ile Glu Ser Asp Asp Val His Cys Ile Lys Met His Asp Leu Val
            275                 280                 285
Arg Ala Phe Val Leu Asp Thr Phe Asn Arg Phe Lys His Ser Leu Ile
            290                 295                 300
Val Asn His Gly Asn Gly Gly Met Leu Gly Trp Pro Glu Asn Asp Met
305                 310                 315                 320
Ser Ala Ser Ser Cys Lys Arg Ile Ser Leu Ile Cys Lys Gly Met Ser
                325                 330                 335
Asp Phe Pro Arg Asp Val Lys Phe Pro Asn Leu Leu Ile Leu Lys Leu
            340                 345                 350
Met His Ala Asp Lys Ser Leu Lys Phe Pro Gln Asp Phe Tyr Gly Glu
            355                 360                 365
Met Lys Lys Leu Gln Val Ile Ser Tyr Asp His Met Lys Tyr Pro Leu
            370                 375                 380
Leu Pro Thr Ser Pro Gln Cys Ser Thr Asn Leu Arg Val Leu His Leu
385                 390                 395                 400
His Gln Cys Ser Leu Met Phe Asp Cys Ser Ile Gly Asn Leu Leu
                405                 410                 415
Asn Leu Glu Val Leu Ser Phe Ala Asn Ser Gly Ile Glu Trp Leu Pro
            420                 425                 430
Ser Thr Ile Gly Asn Leu Lys Glu Leu Arg Val Leu Asp Leu Thr Asn
            435                 440                 445
Cys Asp Gly Leu Arg Ile Asp Asn Gly Val Leu Lys Lys Leu Val Lys
            450                 455                 460
Leu Glu Glu Leu Tyr Met Arg Val Gly Gly Arg Tyr Gln Lys
465                 470                 475

(2) INFORMATION FOR SEQ ID NO:52:

(i) SEQUENCE CHARACTERISTICS:
        (A) LENGTH: 465 amino acids
        (B) TYPE: amino acid
        (C) STRANDEDNESS:
        (D) TOPOLOGY: linear
```

(ii) MOLECULE TYPE: protein (ix) FEATURE:
    (A) NAME/KEY: -
    (B) LOCATION: 1..465
    (D) OTHER INFORMATION: /note= "RLG2L protein"

(xi) SEQUENCE DESCRIPTION: SEQ ID NO:52:

```
Phe Ser Tyr Met Val Glu Ala Val Ile Gly Glu Lys Thr Asp Pro Ile
  1               5                  10                  15

Ala Ile Gln Gln Ala Val Xaa Asp Tyr Leu Arg Ile Gln Phe Lys Glu
                 20                  25                  30

Ser Thr Lys Pro Ala Arg Ala Asp Lys Leu Arg Glu Trp Phe Lys Ala
             35                  40                  45

Xaa Ser Xaa Xaa Gly Lys Asn Lys Phe Leu Val Ile Phe Asp Asp Val
         50                  55                  60

Trp Gln Ser Val Asp Leu Glu Asp Ile Gly Leu Ser Pro Phe Pro Asn
 65                  70                  75                  80

Gln Xaa Val Asp Phe Lys Val Leu Leu Thr Ser Arg Asp Xaa His Val
                 85                  90                  95

Cys Thr Met Met Gly Val Xaa Ala Asn Ser Xaa Ile Xaa Val Gly Leu
                100                 105                 110

Leu Thr Glu Val Glu Ala Xaa Ser Leu Phe Xaa Gln Phe Val Glu Thr
                115                 120                 125

Xaa Glu Pro Glu Leu Cys Lys Ile Xaa Xaa Val Ile Val Arg Lys Cys
    130                 135                 140

Cys Gly Leu Pro Ile Ala Ile Lys Thr Met Ala Cys Ser Leu Arg Asn
145                 150                 155                 160

Lys Arg Lys Asp Ala Trp Lys Asp Ala Leu Ser Arg Ile Glu His Tyr
                165                 170                 175

Asp Ile Xaa Xaa Val Ala Pro Lys Val Phe Glu Thr Lys Asn His Asn
                180                 185                 190

Leu His Asn Lys Glu Thr Lys Ser Ala Phe Leu Met Cys Gly Leu Phe
    195                 200                 205

Pro Glu Asp Phe Asn Ile Pro Thr Glu Glu Leu Met Arg Tyr Gly Trp
    210                 215                 220

Gly Leu Lys Leu Phe Asp Arg Val Tyr Thr Ile Arg Glu Ala Arg Thr
225                 230                 235                 240

Arg Leu Asn Thr Cys Ile Glu Arg Leu Val Gln Thr Asn Leu Leu Ile
                245                 250                 255

Glu Ser Asp Asp Val Gly Cys Val Lys Met His Asp Leu Val Arg Ala
                260                 265                 270

Phe Val Leu Gly Met Tyr Ser Glu Val Glu His Ala Ser Ile Val Asn
                275                 280                 285

His Gly Asn Met His Gly Trp Thr Lys Asn Asp Met Asn Asp Ser Cys
                290                 295                 300

Lys Thr Val Ser Leu Thr Cys Gly Ser Val Ser Glu Phe Pro Gly Asp
305                 310                 315                 320

Leu Lys Phe Pro Asn Leu Lys Leu Leu Lys Leu Met His Gly Asp Lys
                325                 330                 335

Met Leu Arg Phe Ser Gln Asp Phe Tyr Glu Gly Met Glu Lys Leu Gln
                340                 345                 350

Val Ile Ser Tyr His Lys Met Lys Tyr Pro Leu Leu Pro Ser Ser Pro
                355                 360                 365
```

```
Gln Cys Ser Thr Asn Leu Arg Val Leu His Leu His Arg Cys Ser Leu
    370                 375                 380

Arg Met Leu Asp Cys Ser Cys Ile Gly Asn Leu Thr Asn Leu Glu Val
385                 390                 395                 400

Leu Ser Phe Ala Asn Ser Gly Ile Glu Arg Ile Pro Ser Ala Ile Gly
                405                 410                 415

Asn Leu Lys Lys Leu Arg Gln Leu Asp Leu Arg Gly Arg Tyr Gly Leu
            420                 425                 430

Cys Ile Glu Gln Gly Val Leu Lys Asn Leu Val Glu Leu Glu Glu Leu
        435                 440                 445

Tyr Ile Gly Asn Ala Ser Ala Phe Arg Asp Tyr Asn Cys Asn Glu Met
    450                 455                 460

Ala
465

(2) INFORMATION FOR SEQ ID NO:53:

(i) SEQUENCE CHARACTERISTICS:
        (A) LENGTH: 480 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..480
        (D) OTHER INFORMATION: /note= "RLG2M protein"

(xi) SEQUENCE DESCRIPTION: SEQ ID NO:53:

Ala Glu Glu Ala Ala Glu Glu Lys Lys Leu Phe Asn Tyr Ile Val Gly
1               5                   10                  15

Ala Val Ile Gly Glu Lys Thr Asp Pro Phe Ala Ile Gln Glu Ala Ile
            20                  25                  30

Ala Asp Tyr Leu Gly Ile Gln Leu Asn Glu Lys Thr Lys Pro Ala Arg
        35                  40                  45

Ala Asp Lys Leu Arg Glu Trp Phe Lys Lys Asn Ser Asp Gly Gly Lys
50                  55                  60

Thr Lys Phe Leu Ile Xaa Leu Asp Asp Val Trp Gln Leu Val Asp Leu
65                  70                  75                  80

Glu Asp Ile Gly Leu Ser Pro Phe Pro Asn Gln Gly Val Asp Phe Lys
                85                  90                  95

Val Leu Leu Thr Ser Arg Asp Ser Gln Val Cys Thr Met Met Gly Val
            100                 105                 110

Glu Ala Asn Ser Ile Ile Asn Val Gly Leu Leu Xaa Glu Ala Glu Ala
        115                 120                 125

Gln Ser Leu Phe Gln Gln Phe Val Glu Thr Ser Glu Pro Glu Leu Gln
    130                 135                 140

Lys Ile Gly Glu Asp Ile Val Arg Lys Cys Cys Gly Leu Pro Ile Ala
145                 150                 155                 160

Ile Lys Thr Met Ala Cys Thr Leu Arg Asn Lys Arg Lys Asp Ala Trp
                165                 170                 175

Lys Asp Ala Leu Ser Arg Ile Glu His Tyr Asp Ile His Asn Val Ala
            180                 185                 190

Pro Lys Val Phe Glu Thr Ser Tyr His Asn Leu Gln Glu Glu Glu Thr
        195                 200                 205

Lys Ser Thr Phe Leu Met Cys Gly Leu Phe Pro Glu Asp Phe Asp Ile
```

```
            210                 215                 220
Pro Thr Glu Glu Leu Met Arg Tyr Gly Trp Gly Leu Lys Leu Phe Asp
225                 230                 235                 240

Arg Val Tyr Thr Ile Arg Glu Ala Arg Thr Arg Leu Asn Thr Cys Ile
                245                 250                 255

Glu Arg Leu Val Gln Thr Asn Leu Leu Ile Glu Ser Asp Asp Val Gly
                260                 265                 270

Cys Val Lys Met His Asp Leu Val Arg Ala Phe Val Leu Gly Met Phe
                275                 280                 285

Ser Glu Val Glu His Ala Ser Ile Val Asn His Gly Asn Met Pro Gly
290                 295                 300

Trp Pro Asp Glu Asn Asp Met Ile Val His Ser Cys Lys Arg Ile Ser
305                 310                 315                 320

Leu Thr Cys Lys Gly Met Ile Glu Ile Pro Val Asp Leu Lys Phe Pro
                325                 330                 335

Lys Leu Thr Ile Leu Lys Leu Met His Gly Asp Lys Ser Leu Arg Xaa
                340                 345                 350

Pro Xaa Asp Phe Tyr Glu Gly Met Glu Lys Leu Xaa Val Ile Ser Tyr
                355                 360                 365

Asp Lys Met Lys Xaa Pro Leu Leu Pro Leu Ala Pro Arg Cys Ser Thr
                370                 375                 380

Asn Ile Arg Val Leu His Leu Thr Glu Cys Ser Leu Lys Met Phe Asp
385                 390                 395                 400

Cys Ser Ser Ile Gly Asn Leu Ser Asn Leu Glu Val Leu Xaa Phe Ala
                405                 410                 415

Asn Ser Xaa Ile Glu Trp Xaa Pro Ser Pro Val Gly Asn Leu Lys Lys
                420                 425                 430

Leu Arg Leu Leu Asp Leu Lys Phe Cys Asp Xaa Leu Pro Xaa Glu Gln
                435                 440                 445

Gly Val Leu Lys Thr Phe Val His Xaa Xaa Asn Leu Xaa Trp Arg Pro
                450                 455                 460

Ser Gly Phe Xaa Xaa Glu Asn Cys His Xaa Met Ala Asp Leu Ser Thr
465                 470                 475                 480
```

(2) INFORMATION FOR SEQ ID NO:54:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..187
        (D) OTHER INFORMATION: /note= "AC15-2 consensus
           positions 1-200"

(xi) SEQUENCE DESCRIPTION: SEQ ID NO:54:

```
TGTGAGACCG TGACTTGGAT GGTAGATAAA TTTAGTAAAC TTAACCCTTC AATTAACCTA     60

CCTTTTTCTT ATTAACTCAA TTTCAAGCTA AATTCTGATT CTTGTTTGAA ATAAGTTGC    120

ATCTTTATTT TTGTATTATC TTGTTGCATA GGATCCTTAG CATCTTTTAA TAATTTATTT   180

GAAGGTG                                                             187
```

(2) INFORMATION FOR SEQ ID NO:55:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..100
        (D) OTHER INFORMATION: /note= "AC15-2 consensus positions
            701-800"

(xi) SEQUENCE DESCRIPTION: SEQ ID NO:55:

AGTGCAGCAA CTGGAATAAA TTCTTCACTC TTCCAAAACA ACAATCAGAA TCCCCATTCC    60

ACAACCTCAC AACCATAAAT ATTTATTAAT GCAAAAGCAT                          100

(2) INFORMATION FOR SEQ ID NO:56:

(i) SEQUENCE CHARACTERISTICS:
        (A) LENGTH: 779 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..779
        (D) OTHER INFORMATION: /note= "AC15-2A"

(xi) SEQUENCE DESCRIPTION: SEQ ID NO:56:

TGTGAGACCG TGACTTGGAT GGTAGATAAA TTTAGTAAAC TTAACCCTTC AATTAACCTA    60

CCTTTTTCTT ATTAACTCAA TTTCAACCTA AATTCTGATT CTTGTTTGAA AGTAAGTTGC    120

ATCTTTATTT TTGTATTATC TTGTTGCATA GGATCCTTAG CATCTTTTAA TAATTTATTT    180

GAAGGTGAAA GATCCAACTA TTTTTAATCT GTTGGCATTT TCCATCATTT GCAACTGTTT    240

CTTGAAAAAA AAATACCTAA AATCAAAATA ACCATTTTCA AATCCAAAAT TATAAGAGAG    300

AATTGTAAAT GGACATGGAA TCATAAATCA TTAACACAGT TCAGTAAACA AGTTGCTAAT    360

TACATTTCTT GCTGTGCAGA TTGAAATTCT ATCAGAGAAA GAGACATTAC AAGAAGCCAC    420

TGACAGTATT TCTAATGTTG TATTCCCATC CTGTCTCATG CACTCTTTTC ATAACCTCCA    480

GAAACTTATA TTGAACAGAG TTAAAGGAGT GGAGGTGGTG TTTGAGATAG AGAGTGAGAG    540

TCCAACAAGT AGAGAATTGG TAACAACTCA CCATAACCAA CAACAACCTA TTATACTTCC    600

CAACCTCCAG GAATTGATTC TATGGAATAT GGACAACATG AGTCATGTGT GGAAGTGCAG    660

CAACTGGAAT AAATTCTTCA CTCTTCCAAA ACAACAATCA GAATCCCCAT TCCACAACCT    720

CACAACCATA AAAATTATGT ATTGCAAAAG CATTAAGTAC TTGTTTTCAC CTCTCACGG    779

(2) INFORMATION FOR SEQ ID NO:57:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..777

(D) OTHER INFORMATION: /note= "AC15-2B"

(xi) SEQUENCE DESCRIPTION: SEQ ID NO:57:

| | | | | | |
|---|---|---|---|---|---|
| TGKGAGACCG | TGACTTGGAT | GGTAGATAAA | TTTAGTAAAC | TTAACCCTTC | AATTAACCTA | 60 |
| CCTTTTTCTT | ATTAACTCAA | TTTCAAGCTA | AATTCTGATT | CTTGTTKGAA | AGTAAGTTGC | 120 |
| ATCTTTATGT | TTGTATTATC | TTGTTGCATA | GGATCCTTAG | CATCTTTTAA | TAATTTATTT | 180 |
| GAAGGTGAAA | GATCCAACTA | TTTTTAATCT | GTTGGCATTT | TCCATCATTT | GCAACTGTTT | 240 |
| CTTGAAAAAA | ATACCTAAAA | TCAAAATAAC | CATTTTCATA | TCCAAAATTA | TAAGAGAAA | 300 |
| TTGTTAACGG | ACATGGAATC | ATAAATCATT | AACACAGTTC | AGTACACAGG | TTGCTAATTA | 360 |
| CATTTCTTGC | TGTGCAGATT | GAAATTCTAT | CAGAGAAAGA | GACATTACAA | GAAGCCACTG | 420 |
| GCAGTATTTC | AAATATTGTA | TTCCCATCCT | GTCTCATGCA | CTCTTTTCAT | AACCTCCATA | 480 |
| AACTTAACTT | GAACAGAGTT | GAAGGAGTGG | AGGTGGTGTT | TGAGATAGAG | AGTGAGAGTC | 540 |
| CAACAAGTAG | AGAATTGGTA | ACAACTCGCA | ATAACCAACA | ACAGCCTATT | ATACTTCCCT | 600 |
| ACCTCCAGGA | TTTGTATCTA | AGGAATATGG | ACAACACGAG | TCATGTGTGG | AAGTGCAGCA | 660 |
| ACTGGAATAA | ATTCTTCACT | CTTCCAAAAC | AACAATCAGA | ATCCCCATTC | CACAACCTCA | 720 |
| CAACCATAAA | TATTCTTAAA | TGCAAAAGCA | TTAAGTACTT | GTTTTCACCT | CTCACGG | 777 |

(2) INFORMATION FOR SEQ ID NO:58:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..777
        (D) OTHER INFORMATION: /note= "AC15-2C"

(xi) SEQUENCE DESCRIPTION: SEQ ID NO:58:

| | | | | | |
|---|---|---|---|---|---|
| GTGAGACCGT | GACTTGGATG | GTAGATAAAT | TTAGTAAACT | TAACCCTTCA | ATTAACCTAC | 60 |
| CTTTTTCTTA | TTAACTCAAT | TTCAACCTAA | ATTCTGATTC | TTGTTTGAAA | ATAAGTTGCA | 120 |
| TCTTTATTTT | TGTATTATCT | TGTTGCATAG | GATCCTTAGC | ATCTTTTAAT | AATTTATTTG | 180 |
| AAGGTGAAAG | ATCCAACTAT | TTTTAATCTG | TTGACGTTTT | CCATCATTTG | CAACTGTTTC | 240 |
| TTGAAAAAAA | AATACCTAAA | ATCAAAATAA | CCATTTTCAA | ATCCAAAATT | ATAAGAGAGA | 300 |
| ATTGTAAATG | GACATGGAAT | CATAAATCAT | TAACACAGTT | CAGTAAACAA | GTTGCTAATT | 360 |
| ACATTTCTTG | CTGTGCAGAT | TGAAATTCTA | TCAGAGAAAG | AGACATTACA | AGAAGCCACT | 420 |
| GGCAGTATTT | CAAATCTTGT | ATTCCCATCC | TGTCTCATGC | ACTCTTTTCA | TAACCTCCGT | 480 |
| GTGCTTACAT | TGGATAATTA | TGAAGGAGTG | GAGGTGGTGT | TTGAGATAGA | GAGTGAGAGT | 540 |
| CCAACAAGTA | GAGAATTGGT | AACAACTCAC | AATAACCAAC | AACAGCCTAT | TATACTTCCC | 600 |
| TACCTCCAGG | AATTGTATCT | AAGGAATATG | GACAACACGA | GTCATGTGTG | GAAGTGCAGC | 660 |
| AACTGGAATA | AATTCTTCAC | TCTTCCAAAA | CAACAATCAG | AATCACCATT | CCACAACCTC | 720 |
| ACAACCATAG | AAATGAGATG | GTGTCATGGC | TTTAGGTACT | TGTTTCACCT | CTCACGG | 777 |

(2) INFORMATION FOR SEQ ID NO:59:

(i) SEQUENCE CHARACTERISTICS:
        (A) LENGTH: 788 base pairs (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..788
        (D) OTHER INFORMATION: /note= "AC15-2D"

(xi) SEQUENCE DESCRIPTION: SEQ ID NO:59:

```
GTGAGACCGT GACTTGGATG GCAGATAAAT TTAGTAAACT TAACCCTTCA ATTAACCTAC      60

CTTTTTCTTA TTAACTCAAT TTCAAGCTAA ATTCTGATTC TTGTTTGAAA ATAAGTTGCA     120

TCTTTATTTT TGCATATTAT CTTGTTGCAT AGGATCCTTA GCATCTTTTA ATAGTTTATT     180

TGAAGCTGAA AGATCCAACT AGTTTTGATC TGTTGGCATT TTCCATCATT TGCAACTGTT     240

TCTTGAAAAA AAATACCTAA AATCAAAATA ACCATTTTCA AATCCAAAAT TATAAGAGAG     300

AATTGTTAAT GGACGTGGAA TCATAAATCA TTAACACAGT TCAGTACACA AGTTGCTAAT     360

TACATTTCTT GCTGTGCAGA TTGAAATTCT ATCAGAGAAA GAGACATTAC AAGAAGTCAC     420

TGATACTAAT ATTTCTAATG ATGTTGTATT ATTCCCATCC TGTCTCATGC ACTCTTTTCA     480

TAACCTCCAT AAACTTAAAT TGGAAAATTA TGAAGGAGTG GAGGTGGTGT TTGAGATAGA     540

GAGTGAGAGT CCAACATGTA GAGAATTGGT AACAACTCAC AATAACCAAC AACAGCCTAT     600

TATACTTCCC AACCTCCAGG AATTGTATCT AAGGAATATG GACAACACGA GTCATGTGTG     660

GAAGTGCAGC AACTGGAATA AATTCTTCAC TCTTCCAAAA CAACAATCAG AATCACCATT     720

CCACAACCTC ACAACCATAG AAATGAGATG GTGTCATGGC TTTAGGTACT TGTTTTCACC     780

TCTCACGG                                                             788
```

(2) INFORMATION FOR SEQ ID NO:60:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..721
        (D) OTHER INFORMATION: /note= "AC15-2E"

(xi) SEQUENCE DESCRIPTION: SEQ ID NO:60:

```
TGTGAGACCG TGACTTGGAT GTGAAGATAA ATTTAGTAAA CTCCATCTCT TGTTTGAAAA      60

TAATCCACAT CTTACTTAAA ATATATTTAT TGTTGCATAG AAGCCTATAA CATCTTCTAA     120

TAATCCCTCT GAAGGTGAGA GATCAAACTA TTTGTAATCT GTTGACAATT TCAATCATTT     180

GCAATTGTTC CTTGAAAAAT TACTTAGAAT CAAAGAAATA TTTTTCTAAT CCAAAATTAT     240

AAGAGAGAAT TGGGAATGGA CAGTGTAATT ATAAATCATT AACACAATTC AATATTCAAG     300

TTACTAATTA CATTTATTGT TGGGATATAT GTGTGCAGAC TGATACTCTG TCAGAGGAAG     360

AGATATTACA AGAAGTCACT GGTAGTATTT CTAATGTTGC AGTCCCATCC AGTCTCATAC     420

ACTCTTTTCC TAACCTCCGT AGACTTGAAT GGAGAAATA TAAGGGAGTG GAGGTTGTGT     480

TTGAAATAGA GAGTCCCACA AGTAGAGAAT TGGTAACAAC TCAACATAGT CAACAACCAC     540

TACTTCTCAA CCTTGAGGAA TTGCATCTAA GTTTTATGGG AAGCATGAGT CATGTGTGGA     600
```

-continued

```
AGTGCAACTG GAATAAATTC TTCACTCTTT CAAAACAATC TGAATCCCCA TTCCAGAACC        660

TCACAGCCAT ATACCTGATG GACTGCAGAA GCATTAAGTA CTTGTTTTCA CCTCTCACGG        720

A                                                                       721
```

(2) INFORMATION FOR SEQ ID NO:61:

(i) SEQUENCE CHARACTERISTICS:
        (A) LENGTH: 781 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..781
        (D) OTHER INFORMATION: /note= "AC15-2G"

(xi) SEQUENCE DESCRIPTION: SEQ ID NO:61:

```
TGTGAGACCG TGACTTGGAT GGCAGATAAA TTTAGTAAAC TTAACCCTTC AATTAACCTA         60

CCTTTTTCTT ATTAACTCAA TTTCAACCTA AATTCGGACT CTTGTTTGAA ATAAGTTGC         120

ATCTTTATTT TTGTATTATC TTGTTGCATA GGATCCTTAG CATCTTTTAA TAATTTATTT        180

GAAGGTGAAA GATCAAACTA TTTTTTAGCT GTTGGCATTT TCCATCATTT GCAACTGTTT        240

CTTGAAAAAA AAAATACCTA AAATCAAAAT AACCATTTTC AAATCCAAAA TTATAAGATA        300

GAATTGTTAA TGGACATGGA ATCATAGATC ATTAACACAG TTCAGTAAAC AAGTTGCTAA        360

TTACATTTCT TGCTGTGCAG ATTGAAATTC TATCAGAGAA AGAGACATTA CAAGAAGCCA        420

CTGACAGTAT TTCTAATGTT GTATTCCCAT CCTGTCTCAT GCACTCTTTT CATAACCTCC        480

ATAAACTTAA ATTGAAGAGA GTTAAAGGAG TGGAGGTGGT GTTTGAGATA GAGGGTGAGA        540

GTCCAACAAG TAGAGAATTG GTAACAACTC ACAATAACCA ACAACAGCCT ATTATACTTC        600

CCTACCTCCA GGAATTAGTT CTAAGGAATA TGGACAACAC GAGTCATGTG TGGAAGTGCA        660

GCAACTGGAA TAAATTCTTC ACTCTTCCAA AACAACAATC AGAATCCCCA TTCCACAACC        720

TCACAACCAT AAATATTTAC AGATGCAAAA CCATTAAGTA CTTGTTTTCA CCTCTCACGG        780

A                                                                       781
```

(2) INFORMATION FOR SEQ ID NO:62:

(i) SEQUENCE CHARACTERISTICS:
        (A) LENGTH: 738 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..738
        (D) OTHER INFORMATION: /note= "AC15-2H"

(xi) SEQUENCE DESCRIPTION: SEQ ID NO:62:

```
GTGAGACCGT GACTTGGATG GTAGATAAAT TTAGTAAACT TAACCCTTCA ATTAACCTAC         60

CTTTTTCTTA TTAACTCGAT TTCAAGCTAA ATTCTGATTC TTGTTTGAAA ATAAGTTAGC        120

ATATTTATTT TTGTATTAT CTTGTTGCAT AGGATCCTTA GCATCTTTTA ATAATCTGTT        180

GGCATTTTCC ATCATTTGCA ACTGTTTCTT GAAAAAAAAA TACCTAAAAT CAAAATAACC        240

ATTTTCAAAT CCAAAATTAT AAGAGAGAAT TGTTAATGGA CATGGAATCA TAAATCATTA        300
```

```
ACACAGTTCA GTACACAAGT TGCTAATTAC ATTTCTTGCT GTGCAGATTG AAATTCTATC    360

AGAGAAAGAG ACATTACAAG AAGCCACTGG CAGTATTTCT AATGTTGTAT TCCCACCCTG    420

TCTCATGCAC TCTTTTCATA ACCTCCATAA ACTAAAAATG AAGAAGTATA AAGGAGTGGA    480

GGTGGTGTTT GAGATAGAGA GTCCAACAAG TAGAGAATTG GTAACAACTC ACCATAACGA    540

ACAACATCCT ATTATACTTC CTAACCTCCA GCATTTGGAT CTAAGGAATA TGGACAACAT    600

GATTCATGTG TGGAAGTGCA GCAACTGGAA TAAATTCTTC ACTCTTCCAA AACAACAATC    660

AGAATCCCCA TTCCACAACC TCAGTAACAT ACATATTTAT GAATGCAAAA ACATTAAGTA    720

CTTGTTTTCA CCTCTCMC                                                  738
```

(2) INFORMATION FOR SEQ ID NO:63:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..722
        (D) OTHER INFORMATION: /note= "AC15-2I"

(xi) SEQUENCE DESCRIPTION: SEQ ID NO:63:

```
AGATAAATTT AGTAAACTTA ACCCTTCAAT TAACCTACCT TTTTCTTATT AACTCAATTT     60

CAAGCTAAAT TCTGATTCTT GTTTGAAAAT AAGTTAGCAT TTTTATGTTT GTATTATCCT    120

GTTGCATAGG ATCCTTAGCA TCTTTTAATA ATTTATTTGA AGGTGAAAGA TCCAACTATT    180

TTTTAGCTGT TGGCATTTTC CATCATTTGC AACTGTTTCT TGAAAAAAAA ATACCTAAAA    240

TCAAATAAC CATTTTCAAA TCCAAAATTA TAAGAGAGAA TTGTAAATGG ACATGGAATC     300

ATAAATCATT AACACAGTTC AGTAAACAAG TTGCTAATTA CATTTCTTGC TGTGCAGATT    360

GAAATTCTAT CAGAGAAAGA GACATTACAA GAAGCCACTG GCAGTATTTC AAATCTTGTA    420

TTCCCATCCT GTCTCATGCA CTCTTTTCAT AACCTCCATA AACTTAACTT GAAAGAGTTG    480

AAGGAGTGGA GGTGGTGTTT GAGATAGAGA GTGAGAGTCC AACAAGTAGA GAATTGGTAA    540

CAACTCACCA TAACCAACAA CAGCCTGTTA TATTTCCCAA CCTCCAGCAT TTGGATCTAA    600

GGGGTATGGA CAACATGATT CACGTGTGGA AGTGCAGCAA CTGGAATAAA TTCTTCACTC    660

TTCCAAAACA ACAATCAGAA TCCCCATTCC ACAACCTCAC AACCATAAAT ATTGAGTTTT    720

GC                                                                  722
```

(2) INFORMATION FOR SEQ ID NO:64:

(i) SEQUENCE CHARACTERISTICS:
        (A) LENGTH: 784 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..784
        (D) OTHER INFORMATION: /note= "AC15-2J"

(xi) SEQUENCE DESCRIPTION: SEQ ID NO:64:

```
CCAAAACACA AATTGAAAAC CNGGATCATC CAAATAACAT CATCCACTTC CAAATGAGCC    60

CAAATTCAAT TATTCAAGGN TTCTAAGCCT GTTAATGCCC ATTCTTGGAT TACCACCCCG   120

CAATGGGAAA CGATTCAAAA CAGGGCGTTA CATAATTTGT TGTGGTTTTG TATTTTTTAT   180

TTCCGGTGAA GGTGAAAGAT CCAACTATTT TTAATCTGTT GGCATTTTCC ATCATTTGCA   240

ACTGTTTTTT GAAAAAAAAA TACCTAAAAT CAAAATAACC ATTTTCAAAT CCAAAATTAT   300

AAGAGAGAAT TGTAAATGGA CATGGAATCT TAAATCATTA ACACAGTTCA GTACACAAGT   360

TGCTAATTAC ATTTCTTGCT GTGCAGATTG AAATTCTATC AGAGAAAGAG ACATTACAAG   420

AAGCCACTGA CAGTATTTCT AATGTTGTAT TCCCATCCTG TCTCATGCAC TCTTTTCATA   480

ACCTCCAGAA ACTTATATTG AACAGAGTTA AAGGAGTGGA GGTGGTGTTT GAGATAGAGA   540

GTGAGAGTCC AACAAGTAGA GAATTGGTAA CAACTCACCA TAACCAACAA CAGCCTGTTA   600

TATTTCCCAA CCTCCAGCAT TTGGATCTAA GGGGTATGGA CAACATGATT CGCGTGTGGA   660

AGTGCAGCAA CTGGAATAAA TTCTTCACTC TTCCAAAACA ACAATCAGAA TCCCCATTCC   720

ACAACCTCAC AACCATAAAT ATTGATTTTT GCAGAAGCAT TAAGTACTTG TTTTCACCTC   780

TCAC                                                                784

(2) INFORMATION FOR SEQ ID NO:65:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..699
        (D) OTHER INFORMATION: /note= "AC15-2L"

(xi) SEQUENCE DESCRIPTION: SEQ ID NO:65:

GATAATTTAG TAAACTCAAT TTCAAGCCAA CTCTGTCTCT TGTTTGAAAA TAGTTCACAT    60

CTTAATTAAA ATATGTTTTC ATGTTTCATA GGAGCATATA ACAGCTTTCA ATTATTTATC   120

TCCAACACTT TTTAATTTGT TGAGAATTTT CATCATATGC AAATGTTTCT TGAAAAATTG   180

CCTAAAATCA AAATATTTTT CAAATCCAAA ATTCTAAGAG ATAATTGTGA ATGGACTTGA   240

AGTTATAAAT CATTTACTAC ACACTTCATT AGTGAAGTTA CTAATTACAT ATCTTGTTGG   300

GATATATATG CACAGACTGA TATTCTGTCA GAGGAAGAGA CATTGCGAGA AATCACTGGC   360

AATATTTCTA ATGTTGCATT CCCATCCTGT CTCATACCCT CTTTTCATAA CCTCCATAAA   420

CTTTACTTGA AGAAGTATGA AGGAGTGAAG GTGGTGTTTG AGATGGAGAA TCCAACAAGT   480

AGAGAATTGG TAACAACTCA CCATAACCAA CAACAGCCTA TACTTCTCAA CCTCCAGGAA   540

TTATATCTAT ATAATATGGA CAACATGAGC CATGTATGGA AGTGCAACCG GTATAGGTTC   600

TTCAATCTTC CAAAACAACA ATCTGAATCA ACATTCCACA ACCTCACAAC CATACATGTG   660

TTCCAATGCA AAAGCATTAA GTACTTGTTT TCACCCCTC                          699

(2) INFORMATION FOR SEQ ID NO:66:

(i) SEQUENCE CHARACTERISTICS:
        (A) LENGTH: 778 base pairs
        (B) TYPE: nucleic acid
        (C) STRANDEDNESS: single
        (D) TOPOLOGY: linear
```

(ii) MOLECULE TYPE: DNA (ix) FEATURE:
    (A) NAME/KEY: -
    (B) LOCATION: 1..778
    (D) OTHER INFORMATION: /note= "AC15-2N"

(xi) SEQUENCE DESCRIPTION: SEQ ID NO:66:

```
TGTGAGACCG TGACTTGGAT GGTAGATAAA TTTAGTAAAC TTAACCCTTC AATTAACCTA      60
CCTTTTTCTT ATTAACTCAA TTTCAAGCTA AATTCTGATT CTTGTTTGAA AGTAAGTTGC     120
ATCTTTATGT TTGTATTATC TTGTTGCATA GGATCCTTAG CATCTTTTAA TAATTTATTT     180
GAAGGTGAAA GATCCAACTA TTTTTAATCT GTTGGCATTT TCCATCATTT GCAACTGTTT     240
CTTGAAAAAA ATACCTAAAA TCAAAATAAC CATTTTCATA TCCAAAATTA TAAGAGAGAA     300
TTGTTAACGG ACATGGAATC ATAAATCATT AACACAGTTC AGTACACAGG TTGCTAATTA     360
CATTTCTTGC TGTGCAGATT GAAATTCTAT CAGAGAAAGA GACATTACAA GAAGCCACTG     420
GCAGTATTTC AAATATTGTA TTCCCATCCT GTCTCATGCA CTCTTTTCAT AACCTCCATA     480
AACTTAACTT GAACAGAGTT GAAGGAGTGG AGGTGGTGTT TGAGATAGAG AGTGAGAGTC     540
CAACAAGTAG AGAATTGGTA ACAACTCACC ATAACCAACA ACAACCTATT ATACTTCCCA     600
ACCTCCAGGA ATTGATTCTA TGGAATATGG ACAACATGAG TCATGTGTGG AAGTGCGGCA     660
ACTGGAATAA ATTCTTCACT CTTCCAAAAG AACAATCAGA ATCCCCATTC CACAACCTCA     720
GTAACATACA TATTTATGAA TGCAAAAGCA TTAAGTACTT GTTTTCACCT CTCACGGA      778
```

(2) INFORMATION FOR SEQ ID NO:67:

(i) SEQUENCE CHARACTERISTICS:
        (A) LENGTH: 763 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..763
        (D) OTHER INFORMATION: /note= "AC15-2O"

(xi) SEQUENCE DESCRIPTION: SEQ ID NO:67:

```
AGAGCAGAGC AGTATGGATT TCATTTCACT TTCTACTTAC TTAAGGATTA GCTTCTGTTT      60
TTTTGAATAA AAAAGGGGAC ATCTTCTAAT AATGCACATC TTAAATTAAA AAGTATTTAA     120
TTGTTGCATA GCAGCGTATA ACATCTTCTA ATAATTTATC TGAAGGTGAA AGATCCAACT     180
ACTTCTAATT TGTTAACAAT TTCAATCATT TGCAAATGTT CCTTAAAAAA TTAATTACCT     240
GAAATCAAAA CAATCTTCTT CAAATCCAAA ATTATGAGAC AGAATTGAGA AGGGATGTGA     300
AATTATAAAC CATTAACACA ATTCCATGCT CACGTTACTA ATTACATTTC TTGTTGGGAT     360
ATATATGTAC AGACTGATAT TTTGTCAGAG GAAGTGAAAT TACAAGAAGT CACTGATACT     420
ATTTCTAATG TTGTATTCAC ATCGTGTCTC ATACACTCTT TTTATAACAA CCTCCGTAAA     480
CTCAACTTGG AGAAGTATGG AGGAGTTGAG GTTGTGTTTG AGATAGAGAG TTCAACAAGT     540
AGAGAATTGG TAACAACATA CCATAAACAA CAACAACAAC AACAACCTAT ATTTCCCAAC     600
CTTGAGGAAT TATATCTATA TTATATGGAC AACATGAGTC ATGTATGGAA GTGCAACAAC     660
TGGAATAAAT TTTTACAACA ATCAGAATCC CCATTCCACA ACCTCACAAC CATACACATG     720
TCCGATTGCA AAAGCATTAA GTACTTGTTT TCACCTCTCA CGG                       763
```

(2) INFORMATION FOR SEQ ID NO:68:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..461
        (D) OTHER INFORMATION: /note= "RLG3"

(xi) SEQUENCE DESCRIPTION: SEQ ID NO:68:

```
AATGGCAAAA GAAGTCGGAG CAAGAGCTAA GTTAGAGCAT CTATTTGACG TCATTATCAT        60

GGTAGATGTC ACTCAAGCAC CCAACAAGAA CACAATTCAA AGTAGTATTT CAGAACAGTT       120

GGGATTAAAA CTGCAAGAAG AGAGCTTGTT GGTAAGAGCA GCTAGGGTAA GTGCGAGGTT       180

AAAAATGCTT ACAAGGGTGC TGGTGATATT AGACGATATA TGGTCAAGGC TTGACATGGA       240

GGAACTTGGG ATTCCCTTTG GATCAGATAG ACAACACCAC GGCTGCAAAA TCTTGTTGAC       300

TTCAAGAAGT ATTAGTGCTT GTAACCAGAT GAGAGCTGAT AGAATCTTTA AAATACGAGA       360

AATGCCACTG AATGAAGCAT GGCTTCTTTT CGAAAGAACA GCTAAAAAAG CTCCGAATCT       420

GCATCAAGTA GCAAGAGATA TCGTGGAGGA GTGTGGTGGG C                          461
```

(2) INFORMATION FOR SEQ ID NO:69:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..524
        (D) OTHER INFORMATION: /note= "RLG4"

(xi) SEQUENCE DESCRIPTION: SEQ ID NO:69:

```
GAATTCGGTG TTGGTAAGAC AACTCTTGCC TCTTCTGTTT ATGATGAAAT CTCTAGCAAG        60

TTTGATGGTT GCTGCTTTCT AAAAATATCT GGGAGGAATC AAGTAATAAA GACGGTATAG       120

AAAGATTGCA AGAAAAAATC ATTTGTGATG TTTTGAAACA AGAGCAAGTG GGCGTAGGGA       180

GAGTTGAAGA AGGAAAGCGC ATGATAAAGG ATAGGTTACA ACATAGAAAG GTATTGATTG       240

TGCTTGATGA TGTCGACAAC GTTGAGCAGC TAGCTAGAAC AGTTGGCTGG ATCACATGAT       300

TGGTTTGGTG AAGGTAGCCG CATAATAATC ACAACTAGAG ATGAACATGT ATTAATTGCA       360

CACAAAGTAG ATGTGATACA CAATATAAGC TTGTTAAACA ACGATGAAGC TATGCATCTC       420

TTCTGCAAGC AAGCACCACG GGGTCACAAA CGTATACAAG ATTATGAGCA ACTTTTAAAA       480

CATGTGGTTT CTTATGCTGG TGGGCTTCCA CTAGCACTGT CGAC                       524
```

(2) INFORMATION FOR SEQ ID NO:70:

(i) SEQUENCE CHARACTERISTICS:
        (A) LENGTH: 4163 base pairs
        (B) TYPE: nucleic acid
        (C) STRANDEDNESS: single
        (D) TOPOLOGY: linear -continued (ii) MOLECULE TYPE: DNA (ix) FEATURE:
    (A) NAME/KEY: -
    (B) LOCATION: 1..4163
    (D) OTHER INFORMATION: /note= "RLG1-E169"

(xi) SEQUENCE DESCRIPTION: SEQ ID NO:70:

```
ATCGTAACCG TTCGTACGAG ANCGCTGTCC CTCCTTCATC TTTTGTCATA TGTCATATTC      60

TCATNNATTN TGCCACATNT AATTTTGTGG TTATTTTAAA TTAATTTTTA TTCCACATGT     120

CATTTTATGA GTTTTTCTAT TTTATTGAGT TTCACATAAT ATTTAAATGT AATAACAATA     180

AATGCATATT TATTTTTCTT TAAATAAACG CATATAATAT ATAGATTAAA ATCATATAAT     240

ACATAGGTTA AACTCATATA ATACATATGT TCATCCCCAG TTTATTTATA TGTCTCATCC     300

TTAATTTATT TATTATTTAT TTATTAGAGT AGATGATCTT TGTGATATTA AAAATTTAAT     360

TTGTTCAAAA TTTAAAATTA TTAATAATCC CACAATTTGA ATAAAATTAA AAAAAATGGN     420

CCCACCATTA GTCCATCACT TTTTCAGCTC ATCAATATCG TGAGTATTCT CCTTCGTTTC     480

CACCCTAATC AATATTTCCA GCGAATGACA GACTCCTACG GCGTTTCTGA ATTTGCGTTC     540

CGACACTGTT CATTGAAGGA GATAATAAAT CAAATGGAGC TGCTCCAATG TTCATTGCTG     600

ATGAAAGGTG AATTGTATGT GAAGANAATG TCAGCGATCN ATCTCCATCC GGAACCCACC     660

ACATTATCAG TGTACCACCA AACCACTCAA AACGGYGGAA GTAGRRAKAC WRKAAAGTCA     720

TGAAGAATAG ATTATTTTTG TCCTCATGGG CTGACTGAGG AGCGGGTTTA GTTCATCATT     780

TTTCTTTGAN CAAAGAATTA TCGGTCCATC GAATTTTTAC ATCGACAAAG AAGTTTCACT     840

TCGCAATGTT TTGTTAAACA ATTTTTAATC TTTTTATCTT TTCGTTGAAA CTCCTCAATT     900

GCAACTTGCA ACTTGCAACT TTTGGGCCCA CAAATTTGTG GTGGGCGTTA ATTTAATCCA     960

CATATTCACT GTAAACAATA ATTCAAATCG ATCTCTGTTC ATCCAATTCA TCAACATCTC    1020

TTGATAATTG AAATCATTCA CGCTTCATCC ATTTCATCCA CATCTATACT ATATTCTCTG    1080

CTCTTATCAT ATTAAACGAT GGCTGAAATC GTTCTTTCTG CCTTCTTGAC AGTGGTGTTT    1140

GAAAAGCTGG CATYTGAAGC CTTGAAGAAG ATTGTTCGCT CCAAAAGAAT TGAATCTGAG    1200

CTTAAGAAAT TGAAGGAGAC ATTAGACCAA ATCCAAGATC TGCTTAACGA TGCTTCCCAG    1260

AAGGAAGTAA CTAATGAAGC CGTTAAAAGA TGGCTGAATG ATCTCCAACA TTTGGCTTAT    1320

GACATAGACG ACCTACTTGA TGATYTTGCA ACTGAAGCTG TTCAWCGTGA GTTGACCGAG    1380

GAGGGTGGAG CCTCCTCCAG TATGGTAAGA AAACTAATCC CAAGTTGTTG CACAAGTTTC    1440

TCACAAAGTA ATAGGATGCA TGCCAAGTTA GATGATATTG CCACCAGGTT ACAAGAACTG    1500

GTAGAGGCAA AAAATAATCT TGGTTTAAGT GTGATAACAT ATGAAAAGCC AAAAATTGAA    1560

AGGTATGAGG CGTCTTTGGT AGATGAAAGC GGTACTGTCG GACGTGAAGA TGATAAGAAA    1620

AAATTGCTGG AGAAGCTGTT GGGGGATAAA GATGAATCAG GGAGTCAAAA CTTCAGCATC    1680

GTGCCCATAG TTGGTATGGG TGGAGTTGGT AAAACAACTC TAGCTAGACT TTTGTATGAT    1740

GAAAAGAAAG TGAAGGATCA CTTCGAACTC AGGGCTTGGG TTTGTGTTTC TGATGAGTTC    1800

AGTGTTCCCA ATATAAGCAG AGTTATTTAT CAATCTGTGA CTGGGGAAAA GAAGGAGTTT    1860

GAAGACTTAA ATCTGCTTCA AGAAGCTCTT AAAGAGAAAC TTAGGAACCA GCTATTTCTA    1920

ATAGTTTTGG ATGATGTGTG GTCTGAAAGC TATGGTGATT GGGAGAAATT AGTGGGCCCA    1980

TTCCTTGCGG GGTCTCCTGG AAGTAGAATA ATCATGACAA CTCGGAAGGA GCAATTGCTC    2040

AGAAAGCTGG GCTTTTCTCA TCAAGACCCT CTGGAGGGTC TATCACAAGA TGATGCTTTG    2100
```

-continued

```
TCTTTGTTTG CTCAACACGC ATTTGGTGTA CCAAACTTTG ATTCACATCC AACACTAAGG    2160

CCACATGGAG AACTGTTTGT GAAGAAATGT GATGGCTTAC CTCTAGCYTT AAGAACACTT    2220

GGAAGGTTAT TAAGGACAAA AACAGACGAG GAACAATGGA AGGAGCTGTT GGATAGTGAG    2280

ATATGGAGGT TAGGAAAGAG CGATGAGATT GTTCCGGCTC TTAGACTAAG CTACAATGAT    2340

CTTTCTGCCW CTTTGAAGCT RTTRTTTGCA TAYTGCTCCT TGTTTCCCAA GGACTATGAG    2400

TTTGACAAGG AGGAGTTGAT TCTATTGTGG ATGGCAGAAG GGTTTTTGCA CCAACCAACT    2460

AYAAACAAGT CAAAGCAACG KTTGGGTCTT GAATATTTTR AAGAGTTRTT GTCAAGRTCR    2520

TTTTTTCAAC ATGCTCCTAA TRRCAAATCS TTGTTTGTGA TGCATGACCT ATTGAATGAT    2580

TTGGCTACAT TTGTTGCTGG AGAATTTTTT TCAAGGTTAG ACATAGAGAT GAAGAAGGAA    2640

TTTAGGATGS AATCTTTGGA RAAGCACCGM CATATGTCAT TTGTATGTGA GRATTACATA    2700

GGTTACAAAA RGTTCGAGCC ATTTAGAGGA GCTAAAAATT TGAGAACATT TTTAGCATTG    2760

TCTGTTGGGG TGGTAGAAGA TTGGAAGATG TTTTACTTAT CAAACAAGGT CTTGAATGAC    2820

WTACTTCARG ATTTACCATT GTTAAGGGTC CTRAKTTTGA TTRRTCTTAY AATAASYRAG    2880

GTACCARAAK TCGTSGGTAG TATGAASCAC TTGCGGTATC TTAATCTATC WGRAACTTWA    2940

ATCACMCATT TACCGGAAWA TKTCTGCAAT CTTTATAATT TACARACCCT GATTGTKTCT    3000

GGCTGTGAMT ATTTAGTTAA KTTGCCCAAR ACCTTCTCAA ASCTTAAAAA TTTGCASCAT    3060

TTTGACATGA GGGRTACTCC KAAKTTRAAR AACATGCCCT TARGGATTGG TGARTTGAAA    3120

ARTCTACAAA CTCTCTTYMG TAACATTGGC ATAGCAATAA CCGAGCTTAA GAACTTGCAM    3180

AAYCTCCATG GGAAARTTTG TATTGGCGGG CTGGGAAAAA TGGAAAATGC MGTKGGATGC    3240

ACGTTAAGCG AACTTGTCTC ANAAAAAGGT TWAATGARTT ANAAACTGGR WTKGGGGGTG    3300

ATRAATTTAA TGTTTTCCGA AATGGGAACA CTTGAAAAAA NAAGGTCCTC AATGAATTGA    3360

ATGCCTCATA ATGGTAYTCY AAMWAARRRY YYWTARWWAT TWMGKAWRRK GKGTTYATRR    3420

TKTTMYRAAW WAGRGTKTKK KARGTAGGTT TCATCCAATC ACCCAAGTGG GAAAATAGAT    3480

GATATTTTCA GGGCYTACTG ATGAGATGTG GAGAGGTATG ATAGGGTNTC TTGGGGCGGT    3540

AGAAGAAATA AGCATCCATT CTTGTAATGA AATAAGATAT YTGTGGGAAT CAGAAGCAGA    3600

GGCAAGTAAG GTTCTTATGA ATTTAAAGAA GTTGGATTTA GGTGAATGTG AAAATTTGGT    3660

GAGTTTAGGG GAGAAAAAGG AGGATAATCA TAATATTAAT AGTGGGAGCA GCCTAACATC    3720

TTTTAGGAGG TTGAATGTAT GGAGATGTAA CAGCTTGGAG CATTGCAGGT GTCCAGATAG    3780

CATGGAGAAT TTGTATATGC ACATGTGTGA TTCAATNACA TCCGTCTCCT TCCCAACAGG    3840

AGGAGGACAG AAGATCAAGT CACTTACCAT CACTGATTGC AAGAAGCTTT CGGAAGAGGA    3900

GTTGGGAGGA CGAGAGAGGA CAAGAGTGCT TATAAACTCA AAAATGCAGA TGCTTGAATC    3960

AGTAGATATA CGTAATTGGC CAAATCTGAA ATCTATCAGT GAATTGAGTT GCTTCATTCA    4020

CCTGAACAGA TTATATATAT CAAACTGTCC GAGTRTGGAG TCATTTCCTG ACCATGAGTT    4080

GCCAAATCTC ACCTCCTTAA CAGATCGAAG GAGAGGACAG CGATTTTCGT ACGAACGGTT    4140

ACGATTCGAC TGGCCGTCGT TTT                                           4163
```

(2) INFORMATION FOR SEQ ID NO:71:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

Gly Val Gly Lys Thr Thr
1               5

(2) INFORMATION FOR SEQ ID NO:72:

(i) SEQUENCE CHARACTERISTICS:
           (A) LENGTH: 6 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:72:

Gly Leu Pro Leu Ala Leu
1               5

(2) INFORMATION FOR SEQ ID NO:73:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1..17
           (D) OTHER INFORMATION: /note= "sense primer PLOOPAG"

(xi) SEQUENCE DESCRIPTION: SEQ ID NO:73:

GGNGTNGGNA AAACGAC                                                      17

(2) INFORMATION FOR SEQ ID NO:74:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1..17
           (D) OTHER INFORMATION: /note= "sense primer PLOOPAA"

(xi) SEQUENCE DESCRIPTION: SEQ ID NO:74:

GGNGTNGGNA AAACAAC                                                      17

(2) INFORMATION FOR SEQ ID NO:75:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1..17
           (D) OTHER INFORMATION: /note= "sense primer PLOOPAT"

(xi) SEQUENCE DESCRIPTION: SEQ ID NO:75:

GGNGTNGGNA AAACTAC                                                17

(2) INFORMATION FOR SEQ ID NO:76:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "sense primer PLOOPAC"

(xi) SEQUENCE DESCRIPTION: SEQ ID NO:76:

GGNGTNGGNA AAACCAC                                                17

(2) INFORMATION FOR SEQ ID NO:77:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "sense primer PLOOPGG"

(xi) SEQUENCE DESCRIPTION: SEQ ID NO:77:

GGNGTNGGNA AGACGAC                                                17

(2) INFORMATION FOR SEQ ID NO:78:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "sense primer PLOOPGA"

(xi) SEQUENCE DESCRIPTION: SEQ ID NO:78:

GGNGTNGGNA AGACAAC                                                17

(2) INFORMATION FOR SEQ ID NO:79:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "sense primer PLOOPGT"

(xi) SEQUENCE DESCRIPTION: SEQ ID NO:79:

GGNGTNGGNA AGACTAC                                                    17

(2) INFORMATION FOR SEQ ID NO:80:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "sense primer PLOOPGC"

(xi) SEQUENCE DESCRIPTION: SEQ ID NO:80:

GGNGTNGGNA AGACCAC                                                    17

(2) INFORMATION FOR SEQ ID NO:81:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "antisense primer GLPL1"

(xi) SEQUENCE DESCRIPTION: SEQ ID NO:81:

AGNGCNAGNG GNAGGCC                                                    17

(2) INFORMATION FOR SEQ ID NO:82:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "antisense primer GLPL2"

(xi) SEQUENCE DESCRIPTION: SEQ ID NO:82:

AGNGCNAGNG GNAGACC                                                    17

(2) INFORMATION FOR SEQ ID NO:83:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17

(D) OTHER INFORMATION: /note= "antisense primer GLPL3"

(xi) SEQUENCE DESCRIPTION: SEQ ID NO:83:

AGNGCNAGNG GNAGTCC                                                      17

(2) INFORMATION FOR SEQ ID NO:84:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "antisense primer GLPL4"

(xi) SEQUENCE DESCRIPTION: SEQ ID NO:84:

AGNGCNAGNG GNAGCCC                                                      17

(2) INFORMATION FOR SEQ ID NO:85:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "antisense primer GLPL5"

(xi) SEQUENCE DESCRIPTION: SEQ ID NO:85:

AANGCCAANG GCAAACC                                                      17

(2) INFORMATION FOR SEQ ID NO:86:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "antisense primer GLPL6"

(xi) SEQUENCE DESCRIPTION: SEQ ID NO:86:

AANGCCAANG GCAATCC                                                      17

(2) INFORMATION FOR SEQ ID NO:87:

(i) SEQUENCE CHARACTERISTICS:
        (A) LENGTH: 13149 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -

(B) LOCATION: 1..13149
(D) OTHER INFORMATION: /note= "RG2A"

(xi) SEQUENCE DESCRIPTION: SEQ ID NO:87:

```
AAAGTTCATA TCCAAGCTTG CCCTCCAACT CTAGCTCCTT CAATGGCACC TCCTTCTCTT      60

CAAAAGCACA CAAGAACACT TTCAAGCTCA ACCACACTCA CACAAGCTCT AGAACGAGGG     120

TTAGGGCACA TTTAGGGTTT TGCTCTCTGG AAATGGTGTC TAAAAGTGAG GCCATAATGT     180

TCCTTATATA AGGCTCACTC CCACAATTAG GCTTTCAATC TGAACGTANT ACGCCCAGTG     240

TACACTATGG TACGCCCAAC GTACTCGGTA GTCTCCGCGT CAANAATACA CTCATGAGTA     300

CGCGCAACGT ACTTTCCCTT ACGCCCAGCG TACTCAAAAG CCAAACATTC TTTTCAAGGA     360

CTAATTTTGA CAACTTGAGG AAAGAAAAGG ATCAAAGANA TATACTTGAA TTCCGGGATG     420

TTACAATGAA GTTGANACCT TGGCTAAAAA ATTAAATTGG TTGTGGAAGC CGTTGGCTGA     480

GCAAGCAACA AGGGTAAAAT TCGTAATCTA CAAATGGTGT TATTTTCTAT TTCTTCTTAT     540

TATTTTACTT GATTTACGGG TAGTTTTTTT TTCTTACAAA AAATATTAAA GTTGATAAAG     600

TATAGCCACT AAAATTGACT TTTTCCAAAA CATAATGTCA AATGGTGCGT ATATGTATCA     660

TGTTGTATTA NATAATGAAT ATGATGATNC TGTTCTATTT AANCCGAAAA AATTATCTAA     720

TGATTTTATA TTGAAAACA AAGTTGTGAT TTTTNGCATA ATATAATCAA ATCCNCTTTT     780

GTNTGGGAGG TGGATAAATG TGGTAAATTT ANAACAAGTG TTTTNACNTT GAAGGGTNTG     840

GAAAGGTTGA AAAAAGTTAA AATGATAAAA TGTTTACACA AATGTTGTAT CCGACTGAAT     900

ATNATGTTTA AGGATNATTG TATTAAATTG TTGATATATA GTAAGCATAA ATATTTAGAA     960

TTGTGACTTA AATTTATAAG TTATNCNAAC TGGATTGAAA CATTTTTGAT ATANATTAGG    1020

AATGAAAATG AGCAACCCTA ACATACTTAT CTTTGGTAGT TTGGTTATTA TATTTTATT     1080

ANAATATAGA ANCATCCCTT TATTTTAAAC CCATATTGTG GACGGACTTG AATAAATGGG    1140

AAAAATGTAC CTTGCTATTT AGCACAAAAA AATTATAAAA ATGTACATTG CTATTTAGCA    1200

CAAACAAAAA AAAAAAACTT ATCCTTTTTG CATTAGGTCA CAAAGAAATA TAAAATGGGA    1260

AATGTGTTGC TATTTAATGC ACTAAAAGAA ACTATTTTGC CTTTATTAAA CCGGGTAAAC    1320

CAATAGAAAA ATGGAAGTAC ATTGTCATTT AGCATGAAAA AAAATAACTT TCCATTTTTT    1380

GCATCCGGTC ACAATAATAG AAAAATGAAA GTACGTTGCT ATTTAGCGAA ACTAACTTCC    1440

TTTTTTCTTT TTGGCATCGT ATCATAAAAT ATAGACTAAA ATACGTTAGT TTTACATTTT    1500

TAATACATTG AAATGTCTAA TCCACATGTT ATTCTATAAA AAGGGAAATG TAATTTACTT    1560

ATTCTTTGAT TCTTTGGCTT CTTTTTAGTA CCCAAAACAT CCCTCTATCC ATCTATTCCA    1620

ACTAAAATAA TGAAAACTAT ATTCCTTCCA TTGTAGGGAT GTTATAAATT TTGTAATTGT    1680

TTTTATGCAA AAAAGTGTTT TTTGTTAACT AGATTAACGA GATTCATTTT TCAGCATTTT    1740

AGGAGAAGTT CATCCATCTT TTGGATATGA AGTGCAAGCC AAGTTCTTTA ACATGGAATA    1800

TGAGGTCCCT ATATGCTCAA AAAATAGCAA ATGAGAAATT TTTTAAATTG GATCCCCATA    1860

AAAGAAAATT TGTTAATGGT TGTTTTAATA TTGGTCAATG TGTCCACCGG ATGAGCATAA    1920

TACTAGTTTA TAAGGGGTAA AGGTGGGTTT GGTGGGCCCA TTTATCTTTA TTATTTCTAA    1980

AAGTCAGAAT TAAGTAAAAA AAATTATAAG ATAAATACCA TAAGGATAAA AAATCATTTT    2040

ATTTGGACCA AAGACCAAAG TTGTTAAGGG GCTGTTTGTT TTTTTTGTGA AGAGCTGTGC    2100

AACCACTTTT GTCTGCGCCG CACAGACAAC GTGCAGACAT ATGCCCTCGC AGAGTGTTTG    2160

TTTTTTGAAA GTGCGCAGAC CAAAAAAACG TCTGCGCGAG GTCATCCTGG CGCATATATG    2220
```

```
TGTCACTGTC TTCAAAGGTC TTCAGACCTC ATTTTAACCA AAAAAAAAAA AGACCACCGG    2280

TTTTTTTTTT TTTTTTNTTC TTTCTCTTGT AGCTGAAAAT GCATTTTTAA TCTTTATGAC    2340

ATGAAATTAA GTTTGAAAAA TTAATTTATT TCAACAGCTG TAGACGTTAA AAACAAACAG    2400

TCTTCTTGTT GCAGACTGTG GACATTTGGT CCACCTCTTC TACCGCAGAG ACTTGCAGAT    2460

GTGGTCCGCA GACTGCAGAC ATTTTGGCTT CAAATAAACA AACATCACCT AATTTGACTA    2520

CACCACACGG ACCTCCAATG TAACAAAAAA AAGGTTGAAA CAAAGTTGCC TATTTCTCCA    2580

TATCCAGGGG CCATTTATGT AAGAGTTATC TAAATTTTAG TTCGGTAGAT CAGTTCTCAC    2640

ATTTTAACCG GGTAAAGTGT ATGTGTGTAC GCGCGCACCT GAAAGGTTTG AANGTAACTT    2700

CCAAACTGAA NCAANAATCG ATATGAAGTA TCAAGTTAGA GGTTCAATTG GTGAAGGAAT    2760

CAGCTGGAGG TTGGGGAATC GAGCTTCCAC TATTAAGGTA AAATCCATAA CCCTAAATGT    2820

TGGTACGCTC ATATATCAAA TTGCGTGTTT TGTTGAATGA AAAAAGCATG CTCAAAAAAC    2880

CAGTGTAAGG CACGGTATAT GACATATTTA TAGTTACTGA TAACAAATTA TGATAATTTT    2940

GGGTTTACGT AAGTTAGGAT TCGTACTTCA ACCAAATGTA ATAGTTTTTG TGAGTCTATC    3000

TATGTATTTG GGGAATCACA TTAGCAACGG GATTGTACTA GTAATTCGAA AAAGTCTTTT    3060

AAATAATTTT TCTGTTTATA ATTTATGAAT AGTTTTAGCG ACATCTAATA TTAAATAGAA    3120

TGTATCTGAT ATTGAATTAA TGTCCTTAAT GTGAACATAG ACCTTTTCCA TTTACTAATG    3180

CCTAATTATT AGTTTCTAAT CAATAAATTT TAATTTCTGT TTTATGCTTC TAAGACAATA    3240

AAAATCCATG ATTTACCTTT AAATATTAAC AAAAATGACC ATAAATAAAT AAAAAATTAG    3300

GATACCAAAC CCCCCCGCCA TGCCCAATGT CTAAATATTC TTGATGCTTT TGCTTTTCCC    3360

TCTTTTCCTT GTTAGTCTAT TATTCTGGAG AGTTTGAGAG AGTTTCATAC AAGAAAATTT    3420

CAAGAAGAAA GCAAAGGTCC AGGTATTCTC TTTTCTTAAT TATGTATTAA CTTACAAGCA    3480

TTTTTTACAC GATCCATGGT TTTTTGTGTA TGTTTTTCAA ATTGAAACTA GATTGGGACT    3540

TTTGCCCTTG ATGATTCATA AGATATTGCA TGGAGTTGAG ATTGTGTAAG AAAAGTGGTG    3600

AATAGAAAGA GCAAGTGAAT CCAGATATAG TATTGGTAAT ATATGATGAT GAGATAGAGA    3660

TATGTTAAAA CTGGCTAGAA AATTGTTTTA ATTTGAAATT TAGGTTGTTG AATTTGAAAG    3720

ATACCAAGCT AATAACTAAT TAGTTATGCT AAATAGTTAT AAAGAACAAC AAACTCGTAG    3780

TTTTTTTTTC ATGATTTTCA ACCTCTTCGT ACCAAACTAA ATTATAACAA AATTGAATAT    3840

CATTCTCTGC AATCAATTTT AACTTTTGTT ATTATCATCA TGTCTAAAAT TGCCACAAGT    3900

TTATTTTCAT AGTCATATTG GATTATGAAA GGACTATTTT TACCAATTAC ATCTTTACTT    3960

TATGGCCAAA GCTAATACAA TCCGACTAAA CTAAAGGATT CTAGGATGCA TATAGTTTGC    4020

TCCCCGATTA TAGATTTCTA TCTAATTTGT CTATTGTACT AATTTAGGTG CCACCACAAG    4080

TAAATTCCTG AAATGGATGT CGTTAATGCC ATTCTTAAAC CAGTTGTCGA GACTCTCATG    4140

GTACCCGTTA AGAAACACAT AGGGTACCTC ATTTCCTGCA GGCAATATAT GAGGGAAATG    4200

GGTATCAAAA TGAGGGGATT GAATGCTACA AGACTTGGTG TCGAAGAGCA CGTGAACCGG    4260

AACATAAGCA ACCAGCTTGA GGTTCCAGCC CAAGTCAGGG GTTGGTTTGA AGAAGTAGGA    4320

AAGATCAATG CAAAGTGGA AAATTTCCCT AGCGATGTTG GCAGTTGTTT CAATCTTAAG    4380

GTTAGACACG GGTCGGAAA GAGAGCCTCC AAGATAATTG AGGACATCGA CAGTGTCATG    4440

AGAGAACACT CTATCATCAT TTGGAATGAT CATTCCATTC CTTTAGGAAG AATTGATTCC    4500

ACGAAAGCAT CCACCTCAAT ACCATCAACC GATCATCATG ATGAGTTCCA GTCAAGAGAG    4560

CAAACTTTCA CAGAAGCACT AAACGCACTC GATCCTAACC ACAAATCCCA CATGATAGCC    4620
```

```
TTATGGGAA TGGGCGGAGT GGGGAAGACG ACAATGATGC ATCGGCTCAA AAAGGTTGTG   4680

AAAGAAAAGA AAATGTTTAA TTTTATAATT GAGGCGGTTG TAGGGGAAAA AACAGACCCC   4740

ATTGCTATTC AATCAGCTGT AGCAGATTAC CTAGGTATAG AGCTCAATGA AAAAACTAAA   4800

CCAGCAAGAA CTGAGAAGCT TCGGAAATGG TTTGTGGACA ATTCTGGTGG TAAGAAGATC   4860

CTAGTCATAC TCGACGATGT ATGGCAGTTT GTGGATCTGA ATGATATTGG TTTAAGTCCT   4920

TTACCAAATC AAGGTGTCGA CTTCAAGGTG TTGTTGACAT CACGAGACAA AGATGTTTGC   4980

ACTGAGATGG GAGCTGAAGT TAATTCAACT TTTAATGTGA AAATGTTAAT AGAAACAGAA   5040

GCACAAAGTT TATTCCACCA ATTTATAGAA ATTTCGGATG ATGTTGATCC TGAGCTCCAT   5100

AATATAGGAG TGAATATTGT AAGGAAGTGT GGGGGTCTAC CCATTGCCAT AAAAACCATG   5160

GCGTGTACTC TTAGAGGAAA AAGCAAGGAT GCATGGAAGA ATGCACTTCT TCGTTTAGAG   5220

CACTATGACA TTGAAAATAT TGTTAATGGA GTTTTTAAAA TGAGTTACGA CAATCTCCAA   5280

GATGAGGAGA CTAAATCCAC CTTTTTGCTT TGTGGAATGT ATCCCGAAGA CTTTGATATT   5340

CTTACCGAGG AGTTGGTGAG GTATGGATGG GGGTTGAAAT TATTTAAAAA AGTGTATACT   5400

ATAGGAGAAG CAAGAACCAG GCTCAACACA TGCATTGAGC GGCTCATTCA TACAAATTTG   5460

TTGATGGAAG TTGATGATGT TAGGTGCATC AAGATGCATG ATCTTGTTCG TGCTTTTGTT   5520

TTGGATATGT ATTCTAAAGT CGAGCATGCT TCCATTGTCA ACCATAGTAA TACACTAGAG   5580

TGGCATGCAG ATAATATGCA CGACTCTTGT AAAAGACTTT CATTAACATG CAAGGGTATG   5640

TCTAAGTTTC CTACAGACCT GAAGTTTCCA AACCTCTCCA TTTTGAAACT TATGCATGAA   5700

GATATATCAT TGAGGTTTCC CAAAAACTTT TATGAAGAAA TGGAGAAGCT TGAGGTTATA   5760

TCCTATGATA AAATGAAATA TCCATTGCTT CCCTCATCAC CTCAATGTTC CGTCAACCTT   5820

CGCGTGTTTC ATCTACATAA ATGCTCGTTA GTGATGTTTG ACTGCTCTTG TATTGGAAAT   5880

CTGTCGAATC TAGAAGTGCT TAGCTTTGCT GATTCTGCCA TTGACCGGTT GCCTTCCACA   5940

ATCGGAAAGT TGAAGAAGCT AAGGCTACTG GATTTGACGA ATTGTTATGG TGTTCGTATA   6000

GATAATGGTG TCTTAAAAAA ATTGGTCAAA CTGGAGGAGC TCTATATGAC AGTGGTTGAT   6060

CGAGGTCGAA AGGCGATTAG CCTCACAGAT GATAACTGCA AGGAGATGGC AGAGCGTTCA   6120

AAAGATATTT ATGCATTAGA ACTTGAGTTC TTTGAAAACG ATGCTCAACC AAAGAATATG   6180

TCATTTGAGA AGCTACAACG ATTCCAGATC TCAGTGGGGC GCTATTTATA TGGAGATTCC   6240

ATAAAGAGTA GGCACTCGTA TGAAAACACA TTGAAGTTGG TTCTTGAAAA AGGTGAATTA   6300

TTGGAAGCTC GAATAACGA GTTGTTTAAG AAAACAGAGG TGTTATGTTT AAGTGTGGGA   6360

GATATGAATG ATCTTGAAGA TATTGAGGTT AAGTCATCCT CACAACTTCT TCAATCTTCT   6420

TCGTTCAACA ATTTAAGAGT CCTTGTCGTT TCAAAGTGTG CAGAGTTGAA ACACTTCTTC   6480

ACACCTGGTG TTGCAAACAC TTTAAAAAAG CTTGAGCATC TTGAAGTTTA CAAATGTGAT   6540

AATATGGAAG AACTCATACG TAGCAGGGGT AGTGAAGAAG AGACGATTAC ATTCCCCAAG   6600

CTGAAGTTTT TATCTTTGTG TGGGCTACCA AAGCTATCGG GTTTGTGCGA TAATGTCAAA   6660

ATAATTGAGC TACCACAACT CATGGAGTTG GAACTTGACG ACATTCCAGG TTTCACAAGC   6720

ATATATCCCA TGAAAAGTT TGAAACATTT AGTTTGTTGA AGGAAGAGGT AAATATAAAT   6780

TTTTAATGCT AATACATTAC AAAGGATCTT TTCAGTTAAA TCTTTCAAAA TATATTGTAA   6840

TTTGATTGTA TGGGGTATTA TTGTTGGATG GGACTATTAA TAAATGATTA TCTTGCAGGT   6900

TCTGATTCCT AAGTTAGAGA AACTGCATGT TAGTAGTATG TGGAATCTGA AGGAGATATG   6960
```

-continued

```
GCCTTGCGAA TTTAATATGA GTGAGGAAGT TAAGTTCAGA GAGATTAAAG TGAGTAACTG   7020

TGATAAGCTT GTGAATTTGT TTCCGCACAA GCCCATATCT CTGCTGCATC ATCTTGAAGA   7080

GCTTAAAGTC AAGAATTGTG GTTCCATTGA ATCGTTATTC AACATCCATT TGGATTGTGT   7140

TGGTGCAACT GGAGATGAAT ACAACAACAG TGGTGTAAGA ATTATTAAAG TGATCAGTTG   7200

TGATAAGCTT GTGAATCTCT TTCCACACAA TCCCATGTCT ATACTGCATC ATCTTGAAGA   7260

GCTTGAAGTC GAGAATTGTG GTTCCATTGA ATCGTTATTC AACATTGACT TGGATTGTGC   7320

TGGTGCAATT GGGCAAGAAG ACAACAGCAT CAGCTTAAGA AACATCAAAG TGGAGAATTT   7380

AGGGAAGCTA AGAGAGGTGT GGAGGATAAA AGGTGGAGAT AACTCTCGTC CCCTTGTTCA   7440

TGGCTTTCAA TCTGTTGAAA GCATAAGGGT TACAAAATGT AAGAAGTTTA GAAATGTATT   7500

CACACCTACC ACCACAAATT TTAATCTGGG GGCACTTTTG GAGATTTCAA TAGATGACTG   7560

CGGAGAAAAC AGGGGAAATG ACGAATCGGA AGAGAGTAGC CATGAGCAAG AGCAGGTAAG   7620

GATTTCAATT TCACTGTCTT AATTAATGAT TAAGCTCCTG CTTTTTGAAT AAAAAAGGGA   7680

CAAACCATTT CATGACTTAA TGTAGCAATA CAAGTCATGT ATAAGAGTGA CCAACTCTTT   7740

TTTATTTATA AAATGACTAC AAAATATTTT TTTTCATTAG AGATCATGTA TAAATGTGAC   7800

TAATTTTTCA TCACCTAACT TTAGTTGATA AATCTTTATA AATGTCACTA GTTACTTTTC   7860

AGTAAAATAA CAAATTTAAT AAATTATCAA CAAAAAGCAT CAACTAAAAA AATCCCACAA   7920

CCCGTAATAA TTTAAAATAA AAGGATTTAA CATCTAATAC GAACAATTTT TTTTCTAAAC   7980

ATGATTTGGA CCAAATATCA CCAGCAACTC AAGTTTGGAA TCGATTCAGC TTAAAACTTG   8040

ACCAGCATAA TTAGATAGAT GAGAGTTGAA GCTAAAGTGC CTATATAAGT TCGTTTCATC   8100

TTTTTTCTTG ATCTTGATAG CAAGTTGAAT GATTTTCTTC TTCAAAATTG ATAAAAATCT   8160

ACATTATAAA GAGACTAGCT TGAAAAAAAA TGGTCTAGGT GGGTCTTGGG TTCTGGTAGA   8220

TGAAGATGGA AGGGGAGAGT AGATTTCAAA GACACAACAC ATCCTTCATT TTATTTATTT   8280

ATTATTATTA TTATTTTTTG ATATCTTGCT CATATTTGTT ACAGATATGT GAGGTCTATT   8340

AATCTTTTTA AATATATAAA AAAATAAATA ACATAAATGA GAAAATTAAA TAAGAATAA    8400

ATTAATAAGG GCACAATAGT CTTTTTAGGT AAGACAAGGA CCAAACACGC AACAAAAATA   8460

AACAGTAGGG ACCATCCGAT TTAAAAAAAA TAATTAGGGA CCAAAAACAT AAATTCCCCC   8520

AAACCATAGG GACCATTCAT GTAATTTACT CTTACTTTTC GTTTTGTTCA TATTTGGGTA   8580

ACTATTTTTT TTGTACACAT CTAGGTAACG AACTTGTTGA AGTGTTCCCA TTAGGATGT    8640

GACCTACTAC AACCGATCAT AATAGTCATA TGTGAACACT TCCAACAACT TTATTACTTA   8700

GGTGTGTACA AAAAAACAAT AGTTACCATG ATGTGAACAT ACTGAAAAAT TAATTACCTT   8760

AGCAAGTTAT TTTCCCATTT AGGTTGTATG GAAACAGTTC CGTGAGACCG TGACTTGGAT   8820

GGTAGATAAA TTTAGTAAAC TTAACCCTTC AATTAACCTA CCTTTTTCTT ATTAACTCAA   8880

TTTCAACCTA AATTCTGATT CTTGTTTGAA AGTAAGTTGC ATCTTTATTT TTGTATTATC   8940

TTGTTGCATA GGATCCTTAG CATCTTTTAA TAATTTATTT GAAGGTGAAA GATCCAACTA   9000

TTTTTAATCT GTTGGCATTT TCCATCATTT GCAACTGTTT CTTGAAAAAA AAATACCTAA   9060

AATCAAAATA ACCATTTTCA AATCCAAAAT TATAAGAGAG AATTGTAAAT GGACATGGAA   9120

TCATAAATCA TTAACACAGT TCAGTAAACA AGTTGCTAAT TACATTTCTT GCTGTGCAGA   9180

TTGAAATTCT ATCAGAGAAA GAGACATTAC AAGAAGCCAC TGACAGTATT TCTAATGTTG   9240

TATTCCCATC CTGTCTCATG CACTCTTTTC ATAACCTCCA GAAACTTATA TTGAACAGAG   9300

TTAAAGGAGT GGAGGTGGTG TTTGAGATAG AGAGTGAGAG TCCAACAAGT AGAGAATTGG   9360
```

```
TAACAACTCA CCATAACCAA CAACAACCTA TTATACTTCC CAACCTCCAG GAATTGATTC    9420

TATGGAATAT GGACAACATG AGTCATGTGT GGAAGTGCAG CAACTGGAAT AAATTCTTCA    9480

CTCTTCCAAA ACAACAATCA GAATCCCCAT TCCACAACCT CACAACCATA AAAATTATGT    9540

ATTGCAAAAG CATTAAGTAC TTGTTTTCGC CTCTCATGGC AGAACTTCTT TCCAACCTAA    9600

AGCATATCAA GATAAGAGAG TGTGATGGTA TTGGAGAAGT TGTTTCAAAC AGAGATGATG    9660

AGGATGAAGA AATGACTACA TTTACATCTA CCCACACAAC CACCACTTTG TTCCCTAGTC    9720

TTGATTCTCT CACTCTAAGT TTCCTGGAGA ATCTGAAGTG TATTGGTGGA GGTGGTGCCA    9780

AGGATGAGGG GAGCAATGAA ATATCTTTCA ATAATACCAC TGCAACTACT GCTGTTCTTG    9840

ATCAATTTGA GGTATGCTTT GTACATATTC AATTATTTAT TTAATTTCCT TTTTTATTTG    9900

CAATATTCTA TAAATAATAC ATTTTATACC CACTATACTA AGATAATAAT TACCTAGAGG    9960

GATGGATGCT ATGACACAGC TGCTACACTT CAGAAACTCT AGTAAGGGCA GTTATGGAAG   10020

TTCAATAAAA TGATAATGGC ATCTTTTGAT GGGTAATATA GGCAATTTAA GTTTTATTTC   10080

TGTTAAAGCA GTATTTAGCA AGTACTGGCC AGTAGGAGAG GAGAATATCA CCTTTTGTGA   10140

AAATCTGGTC ATTGTACCCA GAATTTAGTT AAATGTAACA TTTTAGATAT CAGGGGTCAT   10200

CAGGTGACAG ATATTGTAGA ATAGAACAAT ATATAATATC ACCCAAAACT ATTTTTTCTA   10260

AGGTTATTCT GTTAAATATG TGCTTTCTTG TTTTCATNGA ATTNGCATTC GTATATTTTA   10320

GGTGTTAAAG TGATTTTNTC TTCAATAAAT CCCGAAATTA ATTAAAAAAA AAAAAACAAA   10380

AGTACATTTT TGATGTGGAG AGCACTGGTA TCACTTAGTA TATAAAAAGC TTGATTTTGA   10440

ATTAACTTTC TTATACAAAA GTTGTGTATA TAGTTTAATT AGTTTTACAT CATTTTTCCA   10500

TGTGGTGTTG CAGTTGTCTG AAGCAGGTGG TGTTTCTTGG AGCTTATGCC AATACGCTAG   10560

AGAGATGAGA ATAGAATTCT GCAATGCATT GTCAAGTGTA ATTCCATGTT ATGCAGCAGG   10620

ACAAATGCAA AAGCTTCAAG TGCTGACAGT AAGTGATTGC AAAGGGATGA AGGAGGTATT   10680

TGAAACTCAA TTAAGGAGGA GCAGCAACAA AAACAACAAG AGTGGTGCAG GTGAGGAAGG   10740

AATTCCAAGA GTAAATAACA ATGTTATTAT GCTTTCTGGT CTGAAGATAT GGAAATCAG    10800

CTTTTGTGGG GGTTTGGAAC ATATATTCAC ATTCTCTGCA CTTGAAAGCC TGAGACAGCT   10860

CCAAGAGTTA AAGATAACAT TTTGCTACGG AATGAAAGTG ATTGTGAAGA AGGAAGAAGA   10920

TGAATATGGA GAGCAGTAAA CAACAACAAC AACAACAATA ACGAAGGGGG CATCATCATC   10980

ATCATCTTCT TCATCTTCTA AGGAGGTTGT GGTCTTTCCT CGTCTCAAAT CCATTGAACT   11040

AAATGATGTA CCAGAGCTGG TAGGATTCTT CTTGGGGAAG AATGAGTTCC GGTTGCCTTC   11100

ATTGGAAGAA GTTACCATCA AGTATTGCTC AAAAATGATG GTGTTTGCAG CTGGTGGGTC   11160

CACAGCTCCC CAACTCAAGT ATATACACAC AGAATTAGGC AGACATGCTC TTGATCAAGA   11220

ATCTGGCCTT AACTTTCATC AGGTATATAT ATTTCTTTAA TTGGCATCAT CTAATTAAGA   11280

AAGATATCAT TCCTGCCAAG TAAATTTACT TCAAACACAT TCACACTGGT TTCAGTCTAA   11340

GTTTATGTTG TTCTAGGAAG GCCAAAATGG GAAAGCAAGA TAGGGAAAAA TAGTGTATTT   11400

CAGTGGAAAG GGTATTTTAG GTATTTTCTG TCAAAAGTTG TTATTGCAGG CTTTTTAGTA   11460

CCTGGAATCG TGTGTGGGAG GAGCATTATT ATTCTGATTT GCTTGTTTCT TTATCATTTT   11520

TTCTTAGCCT CTGGAACAGC TAGAAACCCT TTTAATCTTT TGATTTTCAA TGACAAAATT   11580

TTTCCTGTTA CTACATTTGA TTGTTGTTCT TCATGGTTCT AAGTGAGTTA TTGGCTCATC   11640

TGTTACTTCT TTTGATTGTT ATTTTCATAT CATGTTAGTC ACTTGAATCA AGCTTTTCTA   11700
```

```
TTTTCAACCA GGGCAAAAGG TCAAAAGTAA CCTACTTTAT GAGATCAAAA ACAGCAACCC    11760

ATCGGATAAC TTTTAGTTGG AGTTAATAGT TACAATTACC ATTGTGATTA ATAATTATAA    11820

TATCTTGTAT TAATTCATAA AAATTGGTAC AGCACATATA TGACATTTCA AAGGTTTTTG    11880

TTTGACATAT ATATGCCTCT GGCGTTTTCT TTATTGGACA TGCAGACCTC ATTCCAAAGT    11940

TTATACGGTG ACACCTTGGG CCCTGTAACT TCAGAAGGGA CAACTTGTTC TTTTCATAAC    12000

TTGATCGAAT TATATATGGA ATTTAATGAT GCTGTTAAAA AGATTATTCC ATCCAGTGAG    12060

TTGCTGCAAC TGCAAAAGCT GGAAAAGATT CATGTGACTT ATTGTAATTG GGTAGAGGAG    12120

GTATTTGAAA CTGCATTGGA AGCAGCAGGG AGAAATGGAA ATAGTGGAAT TGGTTTTGAT    12180

GAATCGTCAC AAACAACTAC CACTACTCTT GTCAATCTTC CAAACCTCAG AGAAATGAAG    12240

TTATGGTATC TAAATTGTCT GAGGTATATA TGGAAGAGCA ATCAGTGGAC AGCATTTGAG    12300

TTTCAAACC TAACAAGAGT CGATATATGG GGATGTGATA GGTTAGAACA TGTATTTACT     12360

AGTTCCATGG TTGGTAGTCT ATTGCAACTC CAAGAGCTAC GCATATGGAA CTGCAGTCAG    12420

ATAGAGGTCG TGATTGTTCA GGATGCAGAT GTTTGTGTAG AAGAAGACAA AGAGAAAGAA    12480

TCTGATGGCA AGACGAATAA GGAGATACTT GTGTTACCTC GTCTAAAGTC CTTGATATTA    12540

AAACACCTTC CAWGTCTTAA GGGGTTTAGC TTGGGGAAGG AGGATTTTTC ATTCCCATTA    12600

TTGGATACYT TGGAAATCTA CRAATGCCCA GCAATAACCA CCTTCACCAA GGGAAATTCC    12660

RCTACTCCAC AGCTAAAAGA AATTGAAACA MATTTTGGCT TCTTTTATGC TGCAGGGGAA    12720

AAAGACATCA ACTCCTCTAT TATAAAGATC AAACAACAGG TAAACCAGAT CTTTGTTGCT    12780

TNNATAATTC TTAAACNACA TNTGAAAAGC TTCATGCAAG TTTTTTTNGT TATATNGTCA    12840

AAAACCGCAA CCTACATTTT CAGCTTTANA TTTATGTACT TTATGCAGGA TTTCAAACAA    12900

GACTCTGATT AATGTGAAGT GAATATTAAA GGTAAATTAT ATTTTCATGT TCCTAGTNGC    12960

CTATTAATTA AAGGCCTTTT AGTTCGNGAT TTTTGGATGT ATTCTTCATG ATGATGTCAA    13020

TCTTCTAATA CCCCATTCAT TGTTTGGTTG AATGTTGACT CTATGTCAGG ATGAATATTC    13080

AAGGGAAGAA TTGTTCATCA TATGAAGGAC ATTAAAGAAC ATGGATGCTC TGAAGATGTT    13140

GGGAACACA                                                           13149
```

(2) INFORMATION FOR SEQ ID NO:88:

(i) SEQUENCE CHARACTERISTICS:
  (A) LENGTH: 1890 amino acids
  (B) TYPE: amino acid
  (C) STRANDEDNESS:
  (D) TOPOLOGY: linear (ii) MOLECULE TYPE: protein (ix) FEATURE:
  (A) NAME/KEY: -
  (B) LOCATION: 1..1890
  (D) OTHER INFORMATION: /note= "RG2A deduced sequence"

(xi) SEQUENCE DESCRIPTION: SEQ ID NO:88:

```
Met Asp Val Val Asn Ala Ile Leu Lys Pro Val Glu Thr Leu Met
1               5                   10                  15

Val Pro Val Lys Lys His Ile Gly Tyr Leu Ile Ser Cys Arg Gln Tyr
                20                  25                  30

Met Arg Glu Met Gly Ile Lys Met Arg Gly Leu Asn Ala Thr Arg Leu
            35                  40                  45

Gly Val Glu Glu His Val Asn Arg Asn Ile Ser Asn Gln Leu Glu Val
        50                  55                  60
```

```
Pro Ala Gln Val Arg Gly Trp Phe Glu Val Gly Lys Ile Asn Ala
65                  70                  75                  80

Lys Val Glu Asn Phe Pro Ser Asp Val Gly Ser Cys Phe Asn Leu Lys
            85                  90                  95

Val Arg His Gly Val Gly Lys Arg Ala Ser Lys Ile Ile Glu Asp Ile
                100                 105                 110

Asp Ser Val Met Arg Glu His Ser Ile Ile Ile Trp Asn Asp His Ser
            115                 120                 125

Ile Pro Leu Gly Arg Ile Asp Ser Thr Lys Ala Ser Thr Ser Ile Pro
    130                 135                 140

Ser Thr Asp His His Asp Glu Phe Gln Ser Arg Glu Gln Thr Phe Thr
145                 150                 155                 160

Glu Ala Leu Asn Ala Leu Asp Pro Asn His Lys Ser His Met Ile Ala
                165                 170                 175

Leu Trp Gly Met Gly Gly Val Gly Lys Thr Thr Met Met His Arg Leu
                180                 185                 190

Lys Lys Val Val Lys Glu Lys Lys Met Phe Asn Phe Ile Ile Glu Ala
            195                 200                 205

Val Val Gly Glu Lys Thr Asp Pro Ile Ala Ile Gln Ser Ala Val Ala
    210                 215                 220

Asp Tyr Leu Gly Ile Glu Leu Asn Glu Lys Thr Lys Pro Ala Arg Thr
225                 230                 235                 240

Glu Lys Leu Arg Lys Trp Phe Val Asp Asn Ser Gly Lys Lys Ile
                245                 250                 255

Leu Val Ile Leu Asp Asp Val Trp Gln Phe Val Asp Leu Asn Asp Ile
                260                 265                 270

Gly Leu Ser Pro Leu Pro Asn Gln Gly Val Asp Phe Lys Val Leu Leu
            275                 280                 285

Thr Ser Arg Asp Lys Asp Val Cys Thr Glu Met Gly Ala Glu Val Asn
    290                 295                 300

Ser Thr Phe Asn Val Lys Met Leu Ile Glu Thr Glu Ala Gln Ser Leu
305                 310                 315                 320

Phe His Gln Phe Ile Glu Ile Ser Asp Asp Val Asp Pro Glu Leu His
                325                 330                 335

Asn Ile Gly Val Asn Ile Val Arg Lys Cys Gly Gly Leu Pro Ile Ala
            340                 345                 350

Ile Lys Thr Met Ala Cys Thr Leu Arg Gly Lys Ser Lys Asp Ala Trp
    355                 360                 365

Lys Asn Ala Leu Leu Arg Leu Glu His Tyr Asp Ile Glu Asn Ile Val
370                 375                 380

Asn Gly Val Phe Lys Met Ser Tyr Asp Asn Leu Gln Asp Glu Glu Thr
385                 390                 395                 400

Lys Ser Thr Phe Leu Leu Cys Gly Met Tyr Pro Glu Asp Phe Asp Ile
                405                 410                 415

Leu Thr Glu Glu Leu Val Arg Tyr Gly Trp Gly Leu Lys Leu Phe Lys
            420                 425                 430

Lys Val Tyr Thr Ile Gly Glu Ala Arg Thr Arg Leu Asn Thr Cys Ile
    435                 440                 445

Glu Arg Leu Ile His Thr Asn Leu Leu Met Glu Val Asp Asp Val Arg
            450                 455                 460

Cys Ile Lys Met His Asp Leu Val Arg Ala Phe Val Leu Asp Met Tyr
465                 470                 475                 480
```

-continued

```
Ser Lys Val Glu His Ala Ser Ile Val Asn His Ser Asn Thr Leu Glu
            485                 490                 495

Trp His Ala Asp Asn Met His Asp Ser Cys Lys Arg Leu Ser Leu Thr
            500                 505                 510

Cys Lys Gly Met Ser Lys Phe Pro Thr Asp Leu Lys Phe Pro Asn Leu
            515                 520                 525

Ser Ile Leu Lys Leu Met His Glu Asp Ile Ser Leu Arg Phe Pro Lys
530                 535                 540

Asn Phe Tyr Glu Glu Met Glu Lys Leu Glu Val Ile Ser Tyr Asp Lys
545                 550                 555                 560

Met Lys Tyr Pro Leu Leu Pro Ser Ser Pro Gln Cys Ser Val Asn Leu
            565                 570                 575

Arg Val Phe His Leu His Lys Cys Ser Leu Val Met Phe Asp Cys Ser
            580                 585                 590

Cys Ile Gly Asn Leu Ser Asn Leu Glu Val Leu Ser Phe Ala Asp Ser
            595                 600                 605

Ala Ile Asp Arg Leu Pro Ser Thr Ile Gly Lys Leu Lys Lys Leu Arg
            610                 615                 620

Leu Leu Asp Leu Thr Asn Cys Tyr Gly Val Arg Ile Asp Asn Gly Val
625                 630                 635                 640

Leu Lys Lys Leu Val Lys Leu Glu Glu Leu Tyr Met Thr Val Val Asp
            645                 650                 655

Arg Gly Arg Lys Ala Ile Ser Leu Thr Asp Asp Asn Cys Lys Glu Met
            660                 665                 670

Ala Glu Arg Ser Lys Asp Ile Tyr Ala Leu Glu Leu Glu Phe Phe Glu
            675                 680                 685

Asn Asp Ala Gln Pro Lys Asn Met Ser Phe Glu Lys Leu Gln Arg Phe
            690                 695                 700

Gln Ile Ser Val Gly Arg Tyr Leu Tyr Gly Asp Ser Ile Lys Ser Arg
705                 710                 715                 720

His Ser Tyr Glu Asn Thr Leu Lys Leu Val Leu Glu Lys Gly Glu Leu
            725                 730                 735

Leu Glu Ala Arg Met Asn Glu Leu Phe Lys Lys Thr Glu Val Leu Cys
            740                 745                 750

Leu Ser Val Gly Asp Met Asn Asp Leu Glu Asp Ile Glu Val Lys Ser
            755                 760                 765

Ser Ser Gln Leu Leu Gln Ser Ser Phe Asn Asn Leu Arg Val Leu
            770                 775                 780

Val Val Ser Lys Cys Ala Glu Leu Lys His Phe Phe Thr Pro Gly Val
785                 790                 795                 800

Ala Asn Thr Leu Lys Lys Leu Glu His Leu Glu Val Tyr Lys Cys Asp
            805                 810                 815

Asn Met Glu Glu Leu Ile Arg Ser Arg Gly Ser Glu Glu Thr Ile
            820                 825                 830

Thr Phe Pro Lys Leu Lys Phe Leu Ser Leu Cys Gly Leu Pro Lys Leu
            835                 840                 845

Ser Gly Leu Cys Asp Asn Val Lys Ile Ile Glu Leu Pro Gln Leu Met
850                 855                 860

Glu Leu Glu Leu Asp Asp Ile Pro Gly Phe Thr Ser Ile Tyr Pro Met
865                 870                 875                 880

Lys Lys Phe Glu Thr Phe Ser Leu Leu Lys Glu Glu Val Leu Ile Pro
            885                 890                 895

Lys Leu Glu Lys Leu His Val Ser Ser Met Trp Asn Leu Lys Glu Ile
```

-continued

```
                  900                 905                 910
Trp Pro Cys Glu Phe Asn Met Ser Glu Glu Val Lys Phe Arg Glu Ile
            915                 920                 925

Lys Val Ser Asn Cys Asp Lys Leu Val Asn Leu Phe Pro His Lys Pro
930                 935                 940

Ile Ser Leu Leu His His Leu Glu Glu Leu Lys Val Lys Asn Cys Gly
945                 950                 955                 960

Ser Ile Glu Ser Leu Phe Asn Ile His Leu Asp Cys Val Gly Ala Thr
            965                 970                 975

Gly Asp Glu Tyr Asn Asn Ser Gly Val Arg Ile Ile Lys Val Ile Ser
            980                 985                 990

Cys Asp Lys Leu Val Asn Leu Phe Pro His Asn Pro Met Ser Ile Leu
            995                 1000                1005

His His Leu Glu Glu Leu Glu Val Glu Asn Cys Gly Ser Ile Glu Ser
            1010                1015                1020

Leu Phe Asn Ile Asp Leu Asp Cys Ala Gly Ala Ile Gly Gln Glu Asp
1025                1030                1035                1040

Asn Ser Ile Ser Leu Arg Asn Ile Lys Val Glu Asn Leu Gly Lys Leu
            1045                1050                1055

Arg Glu Val Trp Arg Ile Lys Gly Gly Asp Asn Ser Arg Pro Leu Val
            1060                1065                1070

His Gly Phe Gln Ser Val Glu Ser Ile Arg Val Thr Lys Cys Lys Lys
            1075                1080                1085

Phe Arg Asn Val Phe Thr Pro Thr Thr Asn Phe Asn Leu Gly Ala
            1090                1095                1100

Leu Leu Glu Ile Ser Ile Asp Asp Cys Gly Glu Asn Arg Gly Asn Asp
1105                1110                1115                1120

Glu Ser Glu Glu Ser Ser His Glu Gln Glu Gln Ile Glu Ile Leu Ser
            1125                1130                1135

Glu Lys Glu Thr Leu Gln Glu Ala Thr Asp Ser Ile Ser Asn Val Val
            1140                1145                1150

Phe Pro Ser Cys Leu Met His Ser Phe His Asn Leu Gln Lys Leu Ile
            1155                1160                1165

Leu Asn Arg Val Lys Gly Val Glu Val Val Phe Glu Ile Glu Ser Glu
            1170                1175                1180

Ser Pro Thr Ser Arg Glu Leu Val Thr Thr His His Asn Gln Gln Gln
1185                1190                1195                1200

Pro Ile Ile Leu Pro Asn Leu Gln Glu Leu Ile Leu Trp Asn Met Asp
            1205                1210                1215

Asn Met Ser His Val Trp Lys Cys Ser Asn Trp Asn Lys Phe Phe Thr
            1220                1225                1230

Leu Pro Lys Gln Gln Ser Glu Ser Pro Phe His Asn Leu Thr Thr Ile
            1235                1240                1245

Lys Ile Met Tyr Cys Lys Ser Ile Lys Tyr Leu Phe Ser Pro Leu Met
            1250                1255                1260

Ala Glu Leu Leu Ser Asn Leu Lys His Ile Lys Ile Arg Glu Cys Asp
1265                1270                1275                1280

Gly Ile Gly Glu Val Val Ser Asn Arg Asp Asp Glu Asp Glu Glu Met
            1285                1290                1295

Thr Thr Phe Thr Ser Thr His Thr Thr Thr Thr Leu Phe Pro Ser Leu
            1300                1305                1310

Asp Ser Leu Thr Leu Ser Phe Leu Glu Asn Leu Lys Cys Ile Gly Gly
            1315                1320                1325
```

-continued

```
Gly Gly Ala Lys Asp Glu Gly Ser Asn Glu Ile Ser Phe Asn Asn Thr
    1330                1335                1340

Thr Ala Thr Thr Ala Val Leu Asp Gln Phe Glu Leu Ser Glu Ala Gly
1345                1350                1355                1360

Gly Val Ser Trp Ser Leu Cys Gln Tyr Ala Arg Glu Met Arg Ile Glu
        1365                1370                1375

Phe Cys Asn Ala Leu Ser Ser Val Ile Pro Cys Tyr Ala Ala Gly Gln
            1380                1385                1390

Met Gln Lys Leu Gln Val Leu Thr Val Ser Asp Cys Lys Gly Met Lys
        1395                1400                1405

Glu Val Phe Glu Thr Gln Leu Arg Arg Ser Ser Asn Lys Asn Lys
    1410                1415                1420

Ser Gly Ala Gly Glu Glu Gly Ile Pro Arg Val Asn Asn Val Ile
1425                1430                1435                1440

Met Leu Ser Gly Leu Lys Ile Leu Glu Ile Ser Phe Cys Gly Gly Leu
            1445                1450                1455

Glu His Ile Phe Thr Phe Ser Ala Leu Glu Ser Leu Arg Gln Leu Gln
        1460                1465                1470

Glu Leu Lys Ile Thr Phe Cys Tyr Gly Met Lys Val Ile Val Lys Lys
        1475                1480                1485

Glu Glu Asp Glu Tyr Gly Glu Gln Xaa Thr Thr Thr Thr Thr Ile
    1490                1495                1500

Thr Lys Gly Ala Ser Ser Ser Ser Ser Ser Ser Ser Lys Glu Val
1505                1510                1515                1520

Val Val Phe Pro Arg Leu Lys Ser Ile Glu Leu Asn Asp Val Pro Glu
        1525                1530                1535

Leu Val Gly Phe Phe Leu Gly Lys Asn Glu Phe Arg Leu Pro Ser Leu
        1540                1545                1550

Glu Glu Val Thr Ile Lys Tyr Cys Ser Lys Met Met Val Phe Ala Ala
        1555                1560                1565

Gly Gly Ser Thr Ala Pro Gln Leu Lys Tyr Ile His Thr Glu Leu Gly
    1570                1575                1580

Arg His Ala Leu Asp Gln Glu Ser Gly Leu Asn Phe His Gln Thr Ser
1585                1590                1595                1600

Phe Gln Ser Leu Tyr Gly Asp Thr Leu Gly Pro Val Thr Ser Glu Gly
        1605                1610                1615

Thr Thr Cys Ser Phe His Asn Leu Ile Glu Leu Tyr Met Glu Phe Asn
        1620                1625                1630

Asp Ala Val Lys Lys Ile Ile Pro Ser Ser Glu Leu Leu Gln Leu Gln
        1635                1640                1645

Lys Leu Glu Lys Ile His Val Thr Tyr Cys Asn Trp Val Glu Glu Val
    1650                1655                1660

Phe Glu Thr Ala Leu Glu Ala Ala Gly Arg Asn Gly Asn Ser Gly Ile
1665                1670                1675                1680

Gly Phe Asp Glu Ser Ser Gln Thr Thr Thr Thr Thr Leu Val Asn Leu
            1685                1690                1695

Pro Asn Leu Arg Glu Met Lys Leu Trp Tyr Leu Asn Cys Leu Arg Tyr
        1700                1705                1710

Ile Trp Lys Ser Asn Gln Trp Thr Ala Phe Glu Phe Pro Asn Leu Thr
        1715                1720                1725

Arg Val Asp Ile Trp Gly Cys Asp Arg Leu Glu His Val Phe Thr Ser
    1730                1735                1740
```

```
Ser Met Val Gly Ser Leu Leu Gln Leu Gln Glu Leu Arg Ile Trp Asn
1745                1750                1755                1760

Cys Ser Gln Ile Glu Val Val Ile Val Gln Asp Ala Asp Val Cys Val
            1765                1770                1775

Glu Glu Asp Lys Glu Lys Glu Ser Asp Gly Lys Thr Asn Lys Glu Ile
            1780                1785                1790

Leu Val Leu Pro Arg Leu Lys Ser Leu Ile Leu Lys His Leu Pro Cys
        1795                1800                1805

Leu Lys Gly Phe Ser Leu Gly Lys Glu Asp Phe Ser Phe Pro Leu Leu
    1810                1815                1820

Asp Thr Leu Glu Ile Tyr Lys Cys Pro Ala Ile Thr Thr Phe Thr Lys
1825                1830                1835                1840

Gly Asn Ser Thr Thr Pro Gln Leu Lys Glu Ile Glu Thr His Phe Gly
            1845                1850                1855

Phe Phe Tyr Ala Ala Gly Glu Lys Asp Ile Asn Ser Ser Ile Ile Lys
            1860                1865                1870

Ile Lys Gln Gln Asp Phe Lys Gln Asp Ser Asp Xaa Cys Glu Val Asn
        1875                1880                1885

Ile Lys
    1890

(2) INFORMATION FOR SEQ ID NO:89:

(i) SEQUENCE CHARACTERISTICS:
        (A) LENGTH: 15062 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..15062
        (D) OTHER INFORMATION: /note= "RG2B"

(xi) SEQUENCE DESCRIPTION: SEQ ID NO:89:

TTTTTTAAGA TCAGGGATTC AAATTCAGCC CTAGTGATTA CAATTGTGTC TAAACTTTCC    60

CATACCTTCA CATTATTGTA AGTATACTTT CTCAGTTTCT CTCTTGGAAG CTTCCTTGGT   120

ATTTTAACTC GTGTTCTAAT ATTTAACTCT GATAGTTATT TTGGCCAATC TACTATCTGC   180

ATGTCCGGTT ATTGAATCCG AAGGCACTGG AATCTTGGAT TCCATTCCGT TGTGTGTTTG   240

GTTGCCAAAT GAACGGAATT GAATTATGTA AGATTCCTTC AAAATCCATG TTTAGGTATA   300

TCGTTGTTTC TTGGGATGGA TGGTAAAGAA CGGAATTTCT CCTGTTCATT TTTTAATGAA   360

AGACCAAATT GACCTTATAA ACCTGTTAAA AAAATTACAT TCCAGTTTTC TTAACAAACT   420

GAAAATGGTA AAGGAGTGTG ATTGAATTCC AATCTGTTTC CTGTCCAAAA CACGTGACGG   480

AATATTACAA TTCCTTCAAA TTTCATTTTC TTAAATTGTT ATTCCCTTTC TTACAAAAAC   540

AAGGTAAACG AAACACCCGC TTACTTAATC ATACTCCTAC ATGATGTAAA TGAAAAGGGT   600

ATAAATGGTA TTTTATTCAC AGGGATGAGT CACCATGGTC ATGAAAGAAT CATTAACCGC   660

CCTTACCCAA TTCATGTTTG CCCCTAAAAT ATGATTTAAA GTAATATTGG CTTATGGGAT   720

TCAAGTTGAC TTTTTTGTGG CGAAGAAATA ATGAAAATCT TCATTTCTAA AGTGTCTTCT   780

ACCACTGACA TTTTCTAAGA AAGAACTTGC TAGAAGAAGG TGGGTTGTTT AGTCTTTTTA   840

CTCTTTAAAT GTGAAGACTG TTGAGTTATT ATTATTATTT TGCCAACTAT GGACAACTTG   900

TTTAGTTTTT TTTTTTCCCC AATATCCATT TATATGCGAT TTATTTCTGA ATAATTTTA    960
```

```
TCAAAACGCA GGAAACAATG TAGAATAATA CTGGTATAAT TAATTATATA AAGTTATTAG    1020

GCTGAAATCT TGAGGCTACT ATAATTTAAT TATCATAATT TGAAAATCAT CAAATTGTAT    1080

TCCATGTATA TTTATGTTAT CAGATAATTA ATAATATGTG AGCCACACAA ATCCACATCA    1140

TCAGACACCC CACCTTATTG TCGGCTACCT CACCACTTGC ATGATCCCGA CATCTTCCCA    1200

ACCCCACCGA CGACTTGGGG TCTCCTTAAT ATATCAATTA TTTTCTGTAA GTATTTATTT    1260

GTGTAAATGT GTAATGTCAT TTTACCTTTT TTCTAATATA TACAGAAACA TAAATTTTAA    1320

ATGAAATTCA ACTGCGTTTC ATTCTTGCAT TAAAAAAAAA GACTGTACTG TTGTCAATAT    1380

TTTACTTATA ACCTGATTAA TTAATTAAAG CGTAATTGCA TAATTTGCAT TAGGTTGTAA    1440

TTTTGTGTTT TATAGGGAGG GTGAGGGTCA CCGGGAATCA AAGCACTTAT GTAAAAGCAG    1500

GGAAATACAA AAAATTTACT CGAAACAAAT TTTATTCAAT TTAAGTGAGA TAATAATGTT    1560

CTGATTAGAT TATGAGAACT AGGAGATTTA AGTGATATAT CCCATTTAAA AGAAATTGCA    1620

TTATTAATTT TGGATCTCTT GATGATGACA AAATTAACTC GTGACAGGTT ATATATCATA    1680

TACAAAATGA GTGGCTATGC TTTCGCTTTC CAAAAAGCAA TTATAGTTAT ACTACACCTA    1740

CAAATTTTAA AAGGGGTTAA ACATATCAAA ATACTTGATA AGTAATTATA TAAATATGCA    1800

TTTAACCCTC TAAAGAAAAT GCTACTAAGC TTGGACCATC TCAGAATTAC AATCATACCC    1860

TTCCCCTCAA AAAAGATTCG TATATATCAT GTCATTTGGC ATTCATTTCT TTTTCACAAT    1920

TCATAGTTCT ATTCTCAAAA AATTCGAGTT CTCGTATTTG TAAGGAAGAT CAGAAGAGAC    1980

TGTTCACACA GGTACTCTCT TTTATTTATT GATTCACATT CATATATGTT ATTGTTTTCT    2040

TGCTTAATGG TTTCGTCAGT CTAACTGCGC TTGCTGATTT AAATTTCTTC ACTTTCTTCC    2100

ACGGATTTTT TAAATATTAG TTTTGTGAAT GAACAATTGG TGAAGGAAAG AAACATGGGA    2160

GTCTTTTCTA AAGTAAACCT AGATACTTAG GTTATAAGGG TATATGCTAA AATGAACTAT    2220

GCCCATTCAC CTTTGCCTTT TCTTTTACTT TTTAGTTTTT AGAATCCAAG TTTTCATATG    2280

TATCTCGATG TGTGAGAAGA ATAGGCATTA GAAAGGTAAA GGACGTACAT AAAATTGATT    2340

AATTAGTGAA TGTTCTTTGA TATCATTATT TTTACTCTCA TAAAAAGCAT ATAGATCAAA    2400

CACAAATTGC TACTTGTTAG TGTAACAACT TCGACTTAAT AATGTTAATA ATCAAGATTC    2460

TCTTGATTTC AACTATTTTC TAACCGAACA AGCTCACTAA AAACTCATAT TGCTTTGAGT    2520

CTGAGTGGTT TATATTTGGG GTTTTACATT TAATTTTTTG TGCATGAATG TGAAAATAGA    2580

CTGCTTATTG ATTCTTTGTG TTTCATTGAG TTGATTTTCA TTATTACTAC CTTACAAATT    2640

GCTCAGTGAT AGATTTCCAT TAATTTGCTA ATTCGGTTGC TTCTAAATAT GTAGGAGCTA    2700

CTAAAAGCAA AAATATCGAG CAATGTCGGA CCCAACGGGG ATTGCTGGTG CCATTATTAA    2760

CCCAATTGCT CAGACGGCCT TGGTTCCCGT TACGGACCAT GTAGGCTACA TGATTTCCTG    2820

CAGAAAATAT GTGAGGGTCA TGCAGATGAA AATGACAGAG TTGAATACCT CAAGAATCAG    2880

TGTAGAGGAA CACATTAGCC GGAACACAAG AAATCATCTT CAGATTCCAT CTCAAACTAA    2940

GGAATGGTTG GACCAAGTAG AAGGGATCAG AGCAAATGTG GAAACTTTC CGATTGATGT    3000

CATCACTTGT TGTAGTCTCA GGATCAGGCA CAAGCTTGGA CAGAAAGCCT TCAAGATAAC    3060

TGAGCAGATT GAAAGTCTAA CGAGACAACT CTCCCTGATC AGTTGGACTG ATGATCCAGT    3120

TCCTCTAGGA AGAGTTGGTT CCATGAATGC ATCCACCTCT GCATCATTAA GTGATGATTT    3180

CCCATCAAGA GAGAAAACTT TTACACAAGC ACTAAAAGCA CTCGAACCCA ACCAAAAATT    3240

CCACATGGTA GCCTTGTGTG GGATGGGTGG AGTGGGGAAG ACTAGAATGA TGCAAAGGCT    3300
```

```
GAAGAAGGCT GCTGAAGAAA AGAAATTGTT TAATTATATT GTTGGGGCAG TTATAGGGGA    3360

AAAGACGGAC CCCTTTGCCA TTCAAGAAGC TATAGCAGAT TACCTCGGTA TACAACTCAA    3420

TGAAAAAACT AAGCCAGCAA GAGCTGATAA GCTTCGTGAA TGGTTCAAAA AGAATTCAGA    3480

TGGAGGTAAG ACTAAGTTCC TCATAGTACT TGACGATGTT TGGCAATTAG TTGATCTTGA    3540

AGATATTGGG TTAAGTCCTT TTCCAAATCA AGGTGTCGAC TTCAAGGTCT TGTTGACATC    3600

ACGAGACTCA CAAGTTTGCA CTATGATGGG GGTTGAAGCT AATTCAATTA TTAACGTGGG    3660

CCTTCTAACT GAAGCAGAAG CTCAAAGTCT GTTCCAACAA TTTGTAGAAA CTTCTGAGCC    3720

CGAGCTCCAG AAGATAGGAG AGGATATCGT AAGGAAGTGT TGCGGTCTAC CTATTGCCAT    3780

AAAAACCATG GCATGTACTC TTAGAAATAA AGAAAGGAT GCATGGAAGG ATGCACTTTC     3840

GCGCATAGAG CACTATGACA TTCACAATGT TGCGCCCAAA GTCTTTGAAA CGAGCTACCA    3900

CAATCTCCAA GAAGAGGAGA CTAAATCCAC TTTTTTAATG TGTGGTTTGT TTCCCGAAGA    3960

CTTCGATATT CCTACTGAGG AGTTGATGAG GTATGGATGG GGCTTGAAGC TATTTGATAG    4020

AGTTTATACG ATTAGAGAAG CAAGAACCAG GCTCAACACC TGCATTGAGC GACTGGTGCA    4080

GACAAATTTG TTAATTGAAA GTGATGATGT TGGGTGTGTC AAGATGCATG ATCTGGTCCG    4140

TGCTTTTGTT TTGGGTATGT TTTCTGAAGT CGAGCATGCT TCTATTGTCA ACCATGGTAA    4200

TATGCCTGGG TGGCCTGATG AAAATGATAT GATCGTGCAC TCTTGCAAAA GAATTTCATT    4260

AACATGCAAG GGTATGATTG AGATTCCAGT AGACCTCAAG TTTCCTAAAC TAACGATTTT    4320

GAAACTTATG CATGGAGATA AGTCGCTAAG GTTTCCTCAA GACTTTTATG AAGGAATGGA    4380

AAAGCTCCAT GTTATATCAT ACGATAAAAT GAAGTACCCA TTGCTTCCTT TGGCACCTCG    4440

ATGCTCCACC AACATTCGGG TGCTTCATCT CACTGAATGT TCATTAAAGA TGTTTGATTG    4500

CTCTTCTATC GGAAATCTAT CGAATCTGGA AGTGCTGAGC TTTGCAAATT CTCACATTGA    4560

ATGGTTACCT TCCACAGTCA GAAATTTAAA GAAGCTAAGG TTACTTGATC TGAGATTTTG    4620

TGATGGTCTC CGTATAGAAC AGGGTGTCTT GAAAAGTTTT GTCAAACTTG AAGAATTTTA    4680

TATTGGAGAT GCATCTGGGT TTATAGATGA TAACTGCAAT GAGATGGCAG AGCGTTCTTA    4740

CAACCTTTCT GCATTAGAAT TCGCGTTCTT TAATAACAAG GCTGAAGTGA AAAATATGTC    4800

ATTTGAGAAT CTTGAACGAT TCAAGATCTC AGTGGGATGC TCTTTTGATG AAAATATCAA    4860

TATGAGTAGC CACTCATACG AAAACATGTT GCAATTGGTG ACCAACAAAG GTGATGTATT    4920

AGACTCTAAA CTTAATGGGT TATTTTTGAA AACAGAGGTG CTTTTTTTAA GTGTGCATGG    4980

CATGAATGAT CTTGAAGATG TTGAGGTGAA GTCGACACAT CCTACTCAGT CCTCTTCATT    5040

CTGCAATTTA AAAGTTCTTA TTATTTCAAA GTGTGTAGAG TTGAGATACC TTTTCAAACT    5100

CAATCTTGCA AACACTTTGT CAAGACTTGA GCATCTAGAA GTTTGTGAAT GTGAGAATAT    5160

GGAAGAACTC ATACATACTG GAATTGGGGG TTGTGGAGAA GAGACAATTA CTTTCCCTAA    5220

GCTGAAGTTT TTATCTTTGA GTCAACTACC GAAGTTATCA AGTTTGTGCC ATAATGTCAA    5280

CATAATTGGG CTACCACATC TCGTAGACTT GATACTTAAG GGCATTCCAG GTTTCACAGT    5340

CATTTATCCG CAGAACAAGT TGCGAACATC TAGTTTGTTG AAGGAAGGGG TAGATATATG    5400

TTCTTTATGT TAATACAATT TAAATAATAT TTTCAACCAA ATTTTCATAA TATATCTGTA    5460

ATTTGATTGT ATGATGTGTT ATTGTTTATA TGTGGCTATT AAGGGATGAT TATTTTGCAG    5520

GTTGTGATTC CTAAGTTGGA GACACTTCAA ATTGATGACA TGGAGAACTT AGAAGAAATA    5580

TGGCCTTGTG AACTTAGTGG AGGTGAGAAA GTTAAGTTGA GAGCGATTAA AGTGAGTAGC    5640

TGTGATAAGC TTGTGAATCT ATTTCCGCGC AATCCCATGT CTCTGTTGCA TCATCTTGAA    5700
```

```
GAGCTTACAG TCGAGAATTG CGGTTCCATT GAGTCGTTAT TCAACATTGA CTTGGATTGT    5760

GTCGGTGCAA TTGGAGAAGA AGACAACAAG AGCCTCTTAA GAAGCATCAA CGTGGAGAAT    5820

TTAGGGAAGC TAAGAGAGGT GTGGAGGATA AAAGGTGCAG ATAACTCTCA TCTCATCAAC    5880

GGTTTTCAAG CTGTTGAAAG CATAAAGATT GAAAAATGTA AGAGGTTTAG AAATATATTC    5940

ACACCTATCA CCGCCAATTT TTATCTGGTG GCACTTTTGG AGATTCAGAT AGAAGGTTGC    6000

GGAGGAAATC ACGAATCAGA AGAGCAGGTA ACGCTTTCAA TTTCACTTTC TTAATTAATT    6060

AAGGACTAAG CTCCTGTTTT TTGAATAATA AAGAGGTGGG ATGACTAAAC TTGGGCATCA    6120

CAATTGCAAC AAAATGTTAC AAACCATGAA ACGTTCAAAC CATTTCTTGA ATTAAGGTTT    6180

CAATACAAGT CATTTAAAAA TATGGCTTAA ATTTTTTTTA TATTTATGTA TCAACATGAT    6240

TTTTCATTAG AGATCATTAT TATAATAGTA AGTTTAAAGC AATTTAAATC AGAACTAATT    6300

CTAACTTTAG CTAATAAATC GTTATAAATG TAAATAATTA CTTTTTAGTG AAATAAGCAA    6360

CGGATTTAAT AAGTTAACAA CTTAAATGTC ATTTCCTAAC AAAAAAAACT ATTTGGTTCA    6420

GAAAAACCGT AATTCAAGAT AACTAAAATA AAAATATTTG ACATTCACTA AGAGCATTTT    6480

TTTTTCTAAA TATGATTGCA AATGAATAAA ACTTAAATTT ATACAGAAAA TTCTTTTATA    6540

TATGTTATAC AAAATTTACA AATTGAAATT GGATATGTTA ATAACGGTT TATAATTCTG     6600

GTATCACAAA GGGATATATA ATAAAATATT ATTTTCTGTA GTCATTTGTA ATTGTACTAG    6660

TTTATAACCC GTGGGAACCA TGAGTTCTAA AATTAGTTAA ACTTTCATAA TAAAAATTTA    6720

TAATTATTAT TTATTTTAAA TAAATTATTA ATTAAGAGAT ATATCAAAAA TTTAAAGTTA    6780

TTATAACTTC AAATTTAACA TATAATTAGA AAATATATGA TCATAACTTT CTGCAACTCT    6840

TCTTTTGTAT TAAAATGACC AGAGAAGCTC TTAGTATATT TCTAATCAAA GTCTCAAAMC    6900

TAATGAAGCA TATAATTTGT GAAAATCAAT TAGCATTAGG TTTTAAGAGT CACCAAATTC    6960

AAAGAATAAT CCAATGCTTT CATTACCACT ATGGAGAAAA TATTTTCTTA GTTTAAATGA    7020

AATGAAAACA AACATTCAAA CTAATTGTTG CTTATTAAAC CAAAGACCCA TTACTTAGCC    7080

AAGAGTTTAA CAAAAAAAAA TTACATTCAT GTATCATTAT TCATGACTAG ATATATATGA    7140

ACATGAAGGG AGTTTTTATA GAAAATATAA TCATAGATAT TCAACATAAC TTCAGGGAAT    7200

TCCTCAAAAT AACCAAGTTA TTCAAGAAAT TACATCCAAG TCAACCAAAG AGAAGTTTAG    7260

CCTAGCATGG CTAAACTCAA GAAACTAAAA TAAGGATTAG AAGTACCAAA CATGTAGTAA    7320

GAATCACAGT AAAAGATGAT GTTGTTCTTG ATGTTCTTCT AAGTTCTTCA AGTCTCCAGT    7380

TGCTCCTAAT AATGCAAAGG AGAGCCATTA AATTCGTATG TATTGATCCC TTCAAAAGCT    7440

GCACCAACCT CCCTTAAATA ACACTCAAAG CAAAAATGAC AAAATTGCCC CTGAAGGACC    7500

CTATGTGGGT GCCTTGCGCG GGTGGAGCTG CATACGAAAG GTCTTTGGTC TTTGTGAGGG    7560

TGATGTTGTG CGGGATAGCT TGTCGCATGC TTCCGCGCGG TTCACGCACA TGTGCACAGG    7620

TGATGCATGG TGTGTGCGTT CTTGAGTTTT GAGCCTCCGA TGCTTAGTCC ACTTGGCCCA    7680

ATTCGAGTCC AATCAGCTTA TAACCCATTT TTCTTCAAGT TATCTTCAAG TTAAGCCCAA    7740

TTTGCCTTCT CCAAATCATC CATAACTTCA CAGAATCGCC CGTTCATCTT AATCCCGGAT    7800

GCACAATTAT TCTCCCGTCT TCATTTTAAG CAAGATACCA CCTTCTTCAT GCTTCATCCA    7860

TCAATAGTAC ACTTCATGTA TCATCTCTAC TAGTTATTTA GTCCACAATC CTTGTTGTCC    7920

TCCAAATTTA ATTATCTCAT TTAGTTCCCG TTCCGCTAGT TTCCTTAAAA TTTGCAATTA    7980

AGCTCAGAGA AATATTAAGT ACCCGAAATG GTCATAAAAT AACAAAAGG AAAATATGCA     8040
```

-continued

```
TGAAGATTAA CTAAATGATG AACGAAATAT GCTAAAATAG ACTATAAAAT GAAGTAAATA      8100

AAATGAAATT ATCGCACTCC GACCACCCTT ATAGGCTTGT AGTCCACCCA CCCTTCATTC      8160

CTTGTACCAA TATGGGATGG AAACATCATT AATTAAGCCA AAAAGCTAAC ATATAAGGGT      8220

TTAGTGACAA AGGTAAGTAC TAAAGATGAA AATAATCCAT TTTTCTTGTA TATACACAAC      8280

ACACACATAG GGGCAGACGT AGGATTTCAA AGTACAGATT GTTGGTGGCA CATAAGTGTT      8340

GCTGGTGACA TTTTTTTTTT TTTTTTACGT AGTGGCACAA CAGTAGGAAA ACGAAAAAT      8400

TCGAAATTTT TTACAATTTG TCTAAAAAAA ACAGTGGTTG TTGGTGCCAC TATGGACACC      8460

AAAGTTGAAC TGCCCCCACG CGCGCACACA CACACACACA CATAGAGAGA GAGAGAGAGA      8520

GAGAGAGAGA GAGAAAGAAA GAAAGAGAGA GAGAGTTTGG GATGTGATAC TTCTTTTAGG      8580

AAAATGGAGT TATATCTTTG ATATTGTATT TTTTTAATGT AATTTATATA TTTAATCATT      8640

TTAGTTTATA AGTTTTATTT ATTTTGATAT GAAAAAAAAA GTCTTTTATA CATTGGATTT      8700

AACATAAAAA TCCAACAATA TTAATCAAAA AGACCAMACA TGTGGACAMW TATGTATATA      8760

AWTAATTCAC AATAGTCTTT AGGAATAGNA TTATATATAT AATTAATTCT CAATGGTCTT      8820

AGGAATAGTA AGTTCTTATA TTTCAAACTT TNGCCACAAT TCTTTGKTTA CTTWGACACT      8880

TYCCTCTCTC TAATTATATA TATATATATA TATATATATA TATATATACA CACACACACA      8940

CACACACTAG ATGTGTGCCC GCGCAAAGCA GTGACGTNNN GGAGAANACT TTCTTAAGCA      9000

TAAATAATTA TTATATTTTT TATTGGGTAT TATATAATAA AAAATTACAA CTTTTAAATA      9060

AAATATTTAT GTTATACTT TATATTTATA TTGCTTGTAT ACTATTAATA TAATAAATTA      9120

ATATTTATGT CTAATTTATG AAATGTAAAT TAATTTAAAT ACATGAATTT AATATTTTTA      9180

AAATTTTCAG TTTGCTTCAA ATTGAGTTTC TTAATTATTT TTTTTAATTC ANGTATTCAA      9240

ACTTTTGGTA AGTATTAAAG AATTATTTAT GCATAATTGA TTTATACAAA AAACTTTGTA      9300

ACTTATACAT CTTAAAATTC AAGATATAAC TAACATGTTT TACAATATAT ATATATATAT      9360

ATATATATAT ATATATATAT ATATATATAT ATATATATAT TAAAGCGCAA AGGTCATAGG      9420

AATAGAATAT TTTCTATTAT TCTACGTTTT GCCACAAAAG TTTGAACACT TTGCCACTTT      9480

TTGTCCCTCC TTAACCTTTT CAATGTTTTG CGACAAAAGT TCCAAAACTT TGCCACTTTG      9540

ATCATTCCTC AACTTTTCAC CGCAATTAGT TTGTGGAGTT GGCAGTTTTG ATCCCCCTAA      9600

CTTCGATATT CTCTACTGCT AGCCAAAAAG GGTTCCAGAG TTTCACACTT TTGGTCCCTG      9660

ACAGTAACCA AATGTGAGAT GTCAAATTTT TGCCACATTA GTTTGTGGAG TTGTCCCTTT      9720

TGGTCCCCCC ACATTCGATA TTCTANTATA CGACCTTATT TTTNTCAAAT AACAACACGT      9780

ATATTTAATT ACCAATTATA GAAATAGATA TCAAATAAAG TATTTGTAAC ACTGTGTAAG      9840

AACGGTGCTA CTATAGGTAA AAATAAACAT TTCAAAGTAC GATATCCTAA TTGGAAAAAG      9900

AGTTTTAAAA AAATAACGAC TAGGGGCGAG TTTTTTTTAC AAGTTTGTAT CAAATCATAT      9960

CAAAATTTAA GGTGGAACGG TGACCACATT AACCAGAAAT GTAATTTATT CTTTGATTTT     10020

GATAATTTTT AATATTTTGT TGTGATCTAT GTATTTAAAA GTAAACAACA AAGAACATAA     10080

TCCAAAACCC TAAATTGCAA GTCTCGCCCA ATTTCTCTAT CACTAGTCCT CACTTACGAT     10140

GGCGTTACGT CGCTCTCTCA CTGCTTACAA CCCTTTGTTG CTACTCATTA CAATAACGAA     10200

AAGTTGAATA TCCATATATT TATTTGGATG TGGAATTGAA CGAATCTCGT CAAAATTTTG     10260

ATTTTGTTGA TGGATTTGAG TAGAAGTTTG GGCAGAACGG GAATGATGGT CTGCAAGTGG     10320

TTATAAACTT GATTCTGAGT TATTACTATA TATGTAGCCT CTTTACAACG ACCAAGGTTT     10380

CTTCCAGGTA CCATTTGATC TTTTTAGAAC TTAGTTTTCT GAAACACCCT GATTTGGATC     10440
```

```
AAATATCACC AACAACTCTT AAAAACTTGA TTAATCAATT GTTTTCTTCA TCTTGATAAC    10500

AAGTGGAATG ATTTTCTACT TAGATTAACT TGAAAAAAAA GGTCCATGTG CGTCTGGTGG    10560

ATCTGGTAAA TGAAGATGGA AGGGAGAGCT GACTTTAAAG ACACAAACAC GTCACCATAT    10620

CTCTTATTTT ATTTTAAATT TGCTTTTGGT GTATTTTCTT TTTTCCTATT TCTTTCTTTC    10680

TTGATCTCCA GATGGTATGT GGTGTGGATA ATTTACACCT AGAGATTGGG AACGATGGGA    10740

AGGGGTCTGT GATTTATGGC TGGCCGAGTT TTACTTATTA ACTCAATTTC AACCTAAATT    10800

CTGATTCTTG TTTGAAAATA AGTTGCATCT TTATTTTTGT ATTATCTTGT TGCATAGGAT    10860

CCTTAGCATC TTTTAATAAT TTATTTGAAG GTGAAAGATC CAACTATTTT TTAGCTGTTG    10920

GCATTTTCCA TCATTTGCAA CTGTTTCTTG AAAAAAAAAT ACCTAAAATA AAAATAACCA    10980

TTTTCAAATC CAAAATTATA AGAGAGAATT GTAAATGGAC ATGGAATCAT AAATCATTAA    11040

CACAGTTCAG TAAACAAGTT GCTAATTACA TTTCTTGCTG TGCAGATTGA AATTCTATCA    11100

GAGAAAGAGA CATTACAAGA AGCCACTGGC AGTATTTCAA ATCTTGTATT CCCATCCTGT    11160

CTCATGCACT CTTTTCATAA CCTCCGTGTG CTTACATTGG ATAATTATGA AGGAGTGGAG    11220

GTGGTATTTG AGATAGAGAG TGAGAGTCCA ACATGTAGAG AATTGGTAAC AACTCGCAAT    11280

AACCAACAAC AGCCTATTAT ACTTCCCTAC CTCCAGGATT TGTATCTAAG GAATATGGAC    11340

AACACGAGTC ATGTGTGGAA GTGCAGCAAC TGGAATAAAT TCTTCACTCT TCCAAAACAA    11400

CAATCAGAAT CCCCATTCCA CAACCTCACA ACCATAAATA TTCTTAAATG CAAAAGCATT    11460

AAGTACTTGT TTTCGCCTCT CATGGCAGAA CTTCTTTCCA ACCTAAAGGA TATCCGGATA    11520

AGTGAGTGTG ATGGTATTAA AGAAGTTGTT TCAAACAGAG ATGATGAGGA TGAAGAAATG    11580

ACTACATTTA CATCTACCCA CACAACCACC ACTTTGTTCC CTAGTCTTGA TTCTCTCACT    11640

CTAAGTTTCC TGGAGAATCT GAAGTGTATT GGTGGAGGTG GTGCCAAGGA TGAGGGGAGC    11700

AATGAAATAT CTTTCAATAA TACCACTGCA ACTACTGCTG TTCTTGATCA ATTTGAGGTA    11760

TGCTTTGTAC ATATTCAATT ATTTATTTAA TTTCCTTTTT TATTTGCAAT ATTCTATAAA    11820

TAATACATTT TATACCCACT ATACTAAGAT AATAATTACC TAGAGGGATG GATGCTATGA    11880

CACAGCTGCT ACACTTCAGA AACTCTAGTA AGGGCAGTTA TGGAAGTTCA ATAAAATGAT    11940

AATGGCATCT TTTGATGGGT AATATAGGCA ATTTAAGTTT TATTTCTGTT AAAGCAGTAT    12000

TTAGCAAGTA CTGGCCAGTA GGAGAGGAGA ATATCACCTT TTGTGAAAAT CTGGTCATTG    12060

TACCCAGAAT TTAGTTAAAT GTAACATTTT AGATATTAGG GGACATCAGG TGACAGATAT    12120

TGTAGAATAG AACAATATAT AATATTACCC AAAACTATTT TTTCTAAGGT TATTCTGTTA    12180

AATATGTGCT TTCTTGATTT CATTGAATTT GCATTCCTAT ATTTTAGGTG GTAAAGTGAT    12240

TGTCTCTTCA ATAAATCCCG AAATTAATTA AAAAAGAAAA AAACAAAAGT AAATTTTTGA    12300

TATGGAGAGC ACTGGTATCA TTTAGTATAT AAAAAAACTA GATTTGAAT TAAGTTTCTT    12360

ATATAAAAGC TGTGTATATA GTTTAATTAG TTTTACATCA TTTTTCCATG TGGTGTTGCA    12420

GTTGTCTGAA GCAGGTGGTG TTTCTTGGAG TTTATGCCAA TACGCTAGAG AGATARAAAT    12480

AGKTGGATGC TATGCATTGT CAAGTGTGAT TCCATGTTAT GCAGCAGGAC AAATGCAAAA    12540

GCTTCAAGTG CTGAGAATAG AGTCTTGTGA TGGCATGAAG GAGGTATTTG AAACTCAATT    12600

AGGGACGAGC AGCAACAAAA ACAACGAGAA GAGTGGTTGC GAGGAAGGAA TTCCAAGAGT    12660

AAATAACAAT GTTATTATGC TTCCCAATCT AAAGATATTA AGTATTGGAA ATTGTGGGGG    12720

TTTGGAACAT ATATTCACAT TCTCTGCACT TGAAAGCCTG AGACAGCTCC AAGAGTTAAA    12780
```

```
GATAAAATTT TGCTACGGAA TGAAAGTGAT TGTGAAGAAG GAAGAAGATG AATATGGAGA    12840

GCAGCAAACA ACAACAACAA CAACGAAGGG GGCATCTTCT TCTTCTTCTT CTTCTTCTTC    12900

TTCTTCTTCT AAGAAGGTTG TGGTCTTTCC TTGTCTAAAG TCCATTGTAT TGGTCAATCT    12960

ACCAGAGCTG GTAGGATTCT TCTTGGGGAT GAATGAGTTC CGGTTGCCTT CATTAGATAA    13020

ACTTAAGATC AAGAAATGCC CAAAAATGAT GGTGTTTACA GCTGGTGGGT CCACAGCTCC    13080

CCAACTCAAG TATATACACA AAGATTAGG CAAACATACT CTTGATCAAG AATCTGGCCT     13140

TAACTTTCAT CAGGTATATA TATATTTCTT TAATTGGCAT CATCTAATTA AGAAAGATAT    13200

CATTCCTGCC AAGTAAATTT ACTTCAAACA CATTCACACT GGTTTCAGTC TAAGTTTATG    13260

TTGTTCTAAG AAGGCCAAAA TGGGAAAGCA AGATAGGGAA AAATAGTGTA TTTCAGTGGA    13320

AAGGGTATTT TAGGCATTTT CTGTCAAAAG TTGTTATTGC AGGCTTTTTA GTACCTGGAA    13380

TCGTGTGTGG GAGGAGCATT ATTATTCTGA TTTGCTTGTT TCTTTATCAT TTTTTCTTAG    13440

CCTCTCGAAC AGCTAGAAAC CCTTTTAATC TTTTGATTTT CAATGACGAA ATTTTTCCCT    13500

GTTACTCCAT TTGATTGTTG TTCTTCATGG TTCTAAGTGA GTTATTGGCT CATCTGTTAC    13560

TTCTTTTGAT TGTTATTTTC ATATCATGTT GTCCTTTGAA TCAAGCTTTT CCATTTTCAA    13620

CCAGGGCAAA AGGTCAAAAG TAACCTACTT TATGAGATCA AAAACAGCAA CCCATCGGAT    13680

AACTTTTAGT TGGAGTTAAT AGTTACAATT ACCATTGTGA TTAATAATTA TAATATCTTG    13740

TATTAATTCA TAAAAATTGG TACAGCACAT ATATGCATT TCAAAGGTTT TTGTTTGACA     13800

TATATATGCC TCTGGCGTTT TCTTTATTGG ACTTGCAGAC CTCATTCCAA AGTTTATACG    13860

GTGACACCTT GGGCCCTGCT ACTTCAGAAG GGACAACTTG GTCTTTTCAT AACTTTATCG    13920

AATTAGATGT GGAAGGTAAT CATGATGTTA AAAAGATTAT TCCATCCAGT GAGTTGCTGC    13980

AACTGCAAAA GCTGGAAAAG ATTAATGTAA GGTGGTGTAA AAGGGTAGAG GAGGTATTTG    14040

AAACTGCATT GGAAGCAGCA GGGAGAAATG GAAATAGTGG AATTGGTTTT GATGAATCGT    14100

CACAAACAAC TACCACTACT CTTGTCAATC TTCCAAACCT TAGAGAAATG AACTTATGGG    14160

GTCTAGATTG TCTGAGGTAT ATATGGAAGA GCAATCAGTG GACAGCATTT GAGTTTCCAA    14220

ACCTAACAAG AGTTGATATC TATAAATGTA AAAGGTTAGA ACATGTATTT ACTAGTTCCA    14280

TGGTTGGTAG TCTATCGCAA CTCCAAGAGC TACATATATC CAACTGCAGT GAGATGGAGG    14340

AGGTGATTGT TAAGGATGCA GATGATTCTG TAGAAGAAGA CAAAGAGAAA GAATCTGATG    14400

GGGAGACGAA TAAGGAGATA CTTGTGTTAC CTCGTCTAAA CTCCTTGATA TTAAGAGAAC    14460

TTCCATGTCT TAAGGGGTTT AGCTTGGGGA AGGAGGATTT TTCATTCCCA TTATTGGATA    14520

CTTTAAGAAT TGAGGAATGC CCAGCAATAA CCACCTTCAC CAAGGGAAAT TCCGCTACTC    14580

CACAGCTAAA AGAAATTGAA ACACATTTTG GCTCGTTTTG TGCTGCAGGG GAAAAAGACA    14640

TCAACTCTCT TATAAAGATC AAACAACAGG TAAATCAGAT CTTTGTTGCT TTAATAATTC    14700

TTAAACTACA TTTGAAAAGC TTCATGCAAG TTTTTTTTGT TATATTGTCA AAAACCGCAA    14760

CCTACATTTT CAGCTTTATA TTTATGTACT TTATGCAGGA GTTCAAACAA GACTCTGATT    14820

AATGTGAAGT AAATACTAAA GGTAAATTAT ATTTTCATGT TCCTAGTTGC CTATTAATTA    14880

ATTGCCTTTT AGTTCATGAT TTTTGGATGC ATTCTTCATG ATGATGTCAA TCTTCTAATA    14940

CCCCATTCAT TGTTTGGTTG AATGTTGACT CTATGTCTTG ATGAATATTC AAGGGAAGAA    15000

TTGTTCATCA TATGAAGGAC ATTAAAGAAG AACATGGATG CTATGAAGAT GTGGGAAAAC    15060
AA                                                                  15062
```

(2) INFORMATION FOR SEQ ID NO:90:

(i) SEQUENCE CHARACTERISTICS:
        (A) LENGTH: 1323 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1323
        (D) OTHER INFORMATION: /note= "RG2B deduced sequence"

(xi) SEQUENCE DESCRIPTION: SEQ ID NO:90:

```
Met Ser Asp Pro Thr Gly Ile Ala Gly Ala Ile Ile Asn Pro Ile Ala
1               5                   10                  15

Gln Thr Ala Leu Val Pro Val Thr Asp His Val Gly Tyr Met Ile Ser
            20                  25                  30

Cys Arg Lys Tyr Val Arg Val Met Gln Met Lys Met Thr Glu Leu Asn
        35                  40                  45

Thr Ser Arg Ile Ser Val Glu Glu His Ile Ser Arg Asn Thr Arg Asn
50                  55                  60

His Leu Gln Ile Pro Ser Gln Thr Lys Glu Trp Leu Asp Gln Val Glu
65                  70                  75                  80

Gly Ile Arg Ala Asn Val Glu Asn Phe Pro Ile Asp Val Ile Thr Cys
                85                  90                  95

Cys Ser Leu Arg Ile Arg His Lys Leu Gly Gln Lys Ala Phe Lys Ile
            100                 105                 110

Thr Glu Gln Ile Glu Ser Leu Thr Arg Gln Leu Ser Leu Ile Ser Trp
        115                 120                 125

Thr Asp Asp Pro Val Pro Leu Gly Arg Val Gly Ser Met Asn Ala Ser
130                 135                 140

Thr Ser Ala Ser Leu Ser Asp Asp Phe Pro Ser Arg Glu Lys Thr Phe
145                 150                 155                 160

Thr Gln Ala Leu Lys Ala Leu Glu Pro Asn Gln Lys Phe His Met Val
                165                 170                 175

Ala Leu Cys Gly Met Gly Gly Val Gly Lys Thr Arg Met Met Gln Arg
            180                 185                 190

Leu Lys Lys Ala Ala Glu Glu Lys Lys Leu Phe Asn Tyr Ile Val Gly
        195                 200                 205

Ala Val Ile Gly Glu Lys Thr Asp Pro Phe Ala Ile Gln Glu Ala Ile
210                 215                 220

Ala Asp Tyr Leu Gly Ile Gln Leu Asn Glu Lys Thr Lys Pro Ala Arg
225                 230                 235                 240

Ala Asp Lys Leu Arg Glu Trp Phe Lys Lys Asn Ser Asp Gly Gly Lys
                245                 250                 255

Thr Lys Phe Leu Ile Val Leu Asp Asp Val Trp Gln Leu Val Asp Leu
            260                 265                 270

Glu Asp Ile Gly Leu Ser Pro Phe Pro Asn Gln Gly Val Asp Phe Lys
        275                 280                 285

Val Leu Leu Thr Ser Arg Asp Ser Gln Val Cys Thr Met Met Gly Val
290                 295                 300

Glu Ala Asn Ser Ile Ile Asn Val Gly Leu Leu Thr Glu Ala Glu Ala
305                 310                 315                 320

Gln Ser Leu Phe Gln Gln Phe Val Glu Thr Ser Glu Pro Glu Leu Gln
                325                 330                 335
```

-continued

```
Lys Ile Gly Glu Asp Ile Val Arg Lys Cys Cys Gly Leu Pro Ile Ala
            340                 345                 350
Ile Lys Thr Met Ala Cys Thr Leu Arg Asn Lys Arg Lys Asp Ala Trp
        355                 360                 365
Lys Asp Ala Leu Ser Arg Ile Glu His Tyr Asp Ile His Asn Val Ala
    370                 375                 380
Pro Lys Val Phe Glu Thr Ser Tyr His Asn Leu Gln Glu Glu Glu Thr
385                 390                 395                 400
Lys Ser Thr Phe Leu Met Cys Gly Leu Phe Pro Glu Asp Phe Asp Ile
            405                 410                 415
Pro Thr Glu Glu Leu Met Arg Tyr Gly Trp Gly Leu Lys Leu Phe Asp
        420                 425                 430
Arg Val Tyr Thr Ile Arg Glu Ala Arg Thr Arg Leu Asn Thr Cys Ile
    435                 440                 445
Glu Arg Leu Val Gln Thr Asn Leu Leu Ile Glu Ser Asp Asp Val Gly
    450                 455                 460
Cys Val Lys Met His Asp Leu Val Arg Ala Phe Val Leu Gly Met Phe
465                 470                 475                 480
Ser Glu Val Glu His Ala Ser Ile Val Asn His Gly Asn Met Pro Gly
            485                 490                 495
Trp Pro Asp Glu Asn Asp Met Ile Val His Ser Cys Lys Arg Ile Ser
            500                 505                 510
Leu Thr Cys Lys Gly Met Ile Glu Ile Pro Val Asp Leu Lys Phe Pro
        515                 520                 525
Lys Leu Thr Ile Leu Lys Leu Met His Gly Asp Lys Ser Leu Arg Phe
    530                 535                 540
Pro Gln Asp Phe Tyr Glu Gly Met Glu Lys Leu His Val Ile Ser Tyr
545                 550                 555                 560
Asp Lys Met Lys Tyr Pro Leu Leu Pro Leu Ala Pro Arg Cys Ser Thr
            565                 570                 575
Asn Ile Arg Val Leu His Leu Thr Glu Cys Ser Leu Lys Met Phe Asp
            580                 585                 590
Cys Ser Ser Ile Gly Asn Leu Ser Asn Leu Glu Val Leu Ser Phe Ala
        595                 600                 605
Asn Ser His Ile Glu Trp Leu Pro Ser Thr Val Arg Asn Leu Lys Lys
    610                 615                 620
Leu Arg Leu Leu Asp Leu Arg Phe Cys Asp Gly Leu Arg Ile Glu Gln
625                 630                 635                 640
Gly Val Leu Lys Ser Phe Val Lys Leu Glu Glu Phe Tyr Ile Gly Asp
            645                 650                 655
Ala Ser Gly Phe Ile Asp Asp Asn Cys Asn Glu Met Ala Glu Arg Ser
            660                 665                 670
Tyr Asn Leu Ser Ala Leu Glu Phe Ala Phe Asn Asn Lys Ala Glu
    675                 680                 685
Val Lys Asn Met Ser Phe Glu Asn Leu Glu Arg Phe Lys Ile Ser Val
    690                 695                 700
Gly Cys Ser Phe Asp Glu Asn Ile Asn Met Ser Ser His Ser Tyr Glu
705                 710                 715                 720
Asn Met Leu Gln Leu Val Thr Asn Lys Gly Asp Val Leu Asp Ser Lys
            725                 730                 735
Leu Asn Gly Leu Phe Leu Lys Thr Glu Val Leu Phe Leu Ser Val His
        740                 745                 750
```

-continued

```
Gly Met Asn Asp Leu Glu Asp Val Glu Val Lys Ser Thr His Pro Thr
        755                 760                 765

Gln Ser Ser Ser Phe Cys Asn Leu Lys Val Leu Ile Ile Ser Lys Cys
    770                 775                 780

Val Glu Leu Arg Tyr Leu Phe Lys Leu Asn Leu Ala Asn Thr Leu Ser
785                 790                 795                 800

Arg Leu Glu His Leu Glu Val Cys Glu Cys Glu Asn Met Glu Glu Leu
                805                 810                 815

Ile His Thr Gly Ile Gly Gly Cys Gly Glu Thr Ile Thr Phe Pro
            820                 825                 830

Lys Leu Lys Phe Leu Ser Leu Ser Gln Leu Pro Lys Leu Ser Ser Leu
                835                 840                 845

Cys His Asn Val Asn Ile Ile Gly Leu Pro His Leu Val Asp Leu Ile
    850                 855                 860

Leu Lys Gly Ile Pro Gly Phe Thr Val Ile Tyr Pro Gln Asn Lys Leu
865                 870                 875                 880

Arg Thr Ser Ser Leu Leu Lys Glu Gly Val Val Ile Pro Lys Leu Glu
                885                 890                 895

Thr Leu Gln Ile Asp Asp Met Glu Asn Leu Glu Glu Ile Trp Pro Cys
                900                 905                 910

Glu Leu Ser Gly Gly Glu Lys Val Lys Leu Arg Ala Ile Lys Val Ser
            915                 920                 925

Ser Cys Asp Lys Leu Val Asn Leu Phe Pro Arg Asn Pro Met Ser Leu
    930                 935                 940

Leu His His Leu Glu Glu Leu Thr Val Glu Asn Cys Gly Ser Ile Glu
945                 950                 955                 960

Ser Leu Phe Asn Ile Asp Leu Asp Cys Val Gly Ala Ile Gly Glu Glu
                965                 970                 975

Asp Asn Lys Ser Leu Leu Arg Ser Ile Asn Val Glu Asn Leu Gly Lys
            980                 985                 990

Leu Arg Glu Val Trp Arg Ile Lys Gly Ala Asp Asn Ser His Leu Ile
        995                 1000                1005

Asn Gly Phe Gln Ala Val Glu Ser Ile Lys Ile Glu Lys Cys Lys Arg
    1010                1015                1020

Phe Arg Asn Ile Phe Thr Pro Ile Thr Ala Asn Phe Tyr Leu Val Ala
1025                1030                1035                1040

Leu Leu Glu Ile Gln Ile Glu Gly Cys Gly Gly Asn His Glu Ser Glu
                1045                1050                1055

Glu Gln Ile Glu Ile Leu Ser Glu Lys Glu Thr Leu Gln Glu Ala Thr
            1060                1065                1070

Gly Ser Ile Ser Asn Leu Val Phe Pro Ser Cys Leu Met His Ser Phe
        1075                1080                1085

His Asn Leu Arg Val Leu Thr Leu Asp Asn Tyr Glu Gly Val Glu Val
    1090                1095                1100

Val Phe Glu Ile Glu Ser Glu Ser Pro Thr Cys Arg Glu Leu Val Thr
1105                1110                1115                1120

Thr Arg Asn Asn Gln Gln Gln Pro Ile Ile Leu Pro Tyr Leu Gln Asp
                1125                1130                1135

Leu Tyr Leu Arg Asn Met Asp Asn Thr Ser His Val Trp Lys Cys Ser
            1140                1145                1150

Asn Trp Asn Lys Phe Phe Thr Leu Pro Lys Gln Gln Ser Glu Ser Pro
        1155                1160                1165

Phe His Asn Leu Thr Thr Ile Asn Ile Leu Lys Cys Lys Ser Ile Lys
```

-continued

```
              1170              1175              1180
Tyr Leu Phe Ser Pro Leu Met Ala Glu Leu Leu Ser Asn Leu Lys Asp
1185              1190              1195              1200

Ile Arg Ile Ser Glu Cys Asp Gly Ile Lys Glu Val Val Ser Asn Arg
              1205              1210              1215

Asp Asp Glu Asp Glu Glu Met Thr Thr Phe Thr Ser Thr His Thr Thr
          1220              1225              1230

Thr Thr Leu Phe Pro Ser Leu Asp Ser Leu Thr Leu Ser Phe Leu Glu
      1235              1240              1245

Asn Leu Lys Cys Ile Gly Gly Gly Ala Lys Asp Glu Gly Ser Asn
  1250              1255              1260

Glu Ile Ser Phe Asn Asn Thr Thr Ala Thr Thr Ala Val Leu Asp Gln
1265              1270              1275              1280

Phe Glu Leu Ser Glu Ala Gly Gly Val Ser Trp Ser Leu Cys Gln Tyr
              1285              1290              1295

Ala Arg Glu Ile Glu Ile Val Gly Cys Tyr Ala Leu Ser Ser Val Ile
          1300              1305              1310

Pro Cys Tyr Ala Ala Gly Gln Met Gln Lys Leu
      1315              1320
```

(2) INFORMATION FOR SEQ ID NO:91:

(i) SEQUENCE CHARACTERISTICS:
        (A) LENGTH: 12730 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..12730
        (D) OTHER INFORMATION: /note= "RG2C"

(xi) SEQUENCE DESCRIPTION: SEQ ID NO:91:

```
ATAATATTAC ACAAAGGTAA CGTCATTAAT TAATTACGAT ACGAGACAGA CTTTTTCACT    60

CGGACATNAA CGGTCTATTC CTAACTTNAN NTAATTNAAT GAATTTAGGA TGTGCTAATA   120

TGCATGTAAN ATTCGCTACC GTCATCTTTC AAATGACCAT ATTTTTATGT ATTTATAATG   180

AATCAATGAA AAACCGGATT TCTATTTAAA ATTCTTAAAA CTTCATCTTT TAAGCCAGGG   240

TGAATACAAT TGCTAGATCC ACTGTTAATT TCCATCGAAT TATGCCTGAT CAATTGTTGG   300

CTGCCTACGA TGCAGGTGCT ACCACAAGAA TATGGCCATG GAAACTGCTA ATGAAATTAT   360

AAAACAAGTT GTTCCAGTTC TCATGGTTCC TATTAACGAT TACCTACGCT ACCTCGTTTC   420

CTGCAGAAAG TACATCAGTG ACATGGATTT GAAAATGAAG GAATTAAAAG AAGCAAAAGA   480

CAATGTTGAA GAGCACAAGA ATCATAACAT TAGTAATCGT CTTGAGGTTC CAGCAGCTCA   540

AGTCCAGAGC TGGTTGGAAG ATGTAGAAAA GATCAATGCA AAAGTGGAAA CTGTTCCTAA   600

AGATGTCGGC TGTTGCTTCA ATCTAAAGAT TAGGTACAGG GCCGGAAGGG ATGCCTTCAA   660

TATAATTGAG GAGATCGACA GTGTCATGAG ACGACACTCT CTGATCACTT GGACCGATCA   720

TCCCATTCCT TTGGGAAGAG TTGATTCCGT GATGGCATCC ACCTCTACGC TTTCAACTGA   780

ACACAATGAC TTCCAGTCAA GAGAGGTAAG GTTTAGTGAA GCACTCAAAG CACTTGAGGC   840

CAACCACATG ATAGCCTTAT GTGGAATGGG GGGAGTGGGG AAGACCCACA TGATGCAAAG   900

GCTGAAGAAG GTTGCCAAAG AAAAGAGGAA GTTTGGTTAT ATCATCGAGG CGGTTATAGG   960
```

```
GGAAATATCG GACCCCATTG CTATTCAGCA AGTTGTAGCA GATTACCTAT GCATAGAACT    1020

GAAAGAAAGC GATAAGAAAA CAAGAGCTGA GAAGCTTCGT CAAGGGTTCA AGGCCAAATC    1080

AGATGGAGGT AACACTAAGT TCCTCATAAT ATTGGATGAT GTCTGGCAGT CCGTTGATCT    1140

AGAAGATATT GGTTTAAGCC CTTCTCCCAA TCAAGGTGTC GACTTCAAGG TCTTGTTGAC    1200

TTCACGAGAC GAACATGTTT GCTCAGTGAT GGGGGTTGAA GCTAATTCAA TTATTAACGT    1260

GGGACTTCTA ATTGAAGCAG AAGCACAAAG ATTGTTCCAG CAATTTGTAG AAACTTCTGA    1320

GCCCGAGCTC CACAAGATAG GAGAAGATAT TGTTAGGAGG GTTGCGGTC TACCCATTGC     1380

CATCAAAACC ATGGCGTGTA CTCTAAGAAA TAAAAGAAAG GATGCATGGA AGGATGCACT    1440

TTCTCGTTTA CAACACCATG ACATTGGTAA TGTTGCTACT GCAGTTTTTA GAACCAGCTA    1500

TGAGAATCTC CCGGACAAGG AGACAAAATC TGTTTTTTTG ATGTGTGGTT TGTTTCCCGA    1560

AGACTTCAAT ATTCCTACCG AGGAGTTGAT GAGGTATGGA TGGGGCTTAA AGTTATTTGA    1620

TAGAGTTTAT ACAATTATAG AAGCAAGAAA CAGGCTCAAC ACCTGCATTG ACCGACTGGT    1680

GCAGACAAAT TTACTAATTG GAAGTGATAA TGGTGTACAT GTCAAGATGC ATGATCTGGT    1740

CCGTGCTTTT GTTTTGGGTA TGTATTCTGA AGTCGAGCAA GCTTCAATTG TCAACCATGG    1800

TAATATGCCT GGGTGGCCTG ATGAAAATGA TATGATCGTG CACTCTTGCA AAAGAATTTC    1860

ATTAACATGC AAGGGTATGA TTGAGTTTCC AGTAGACCTC AAGTTCCTA AACTAACGAT     1920

TTTGAAACTT ATGCATGGAG ATAAATCGCT AAAGTTTCCT CAAGAATTTT ATGAAGGAAT    1980

GGAAAAGCTC CGGGTTATAT CATACCATAA AATGAAGTAC CCATTGCTTC CTTTGGCACC    2040

TCAATGCTCC ACCAACATTC GGGTGCTTCA TCTCACGGAA TGTTCATTAA AGATGTTTGA    2100

TTGCTCGTGT ATTGGAAATC TATCGAATCT GGAAGTGCTG AGCTTTGCTA ATTCTTGCAT    2160

TGAGTGGTTA CCTTCCACGG TCAGAAATTT AAAAAAGCTA AGGTTACTTG ATTTGAGATT    2220

GTGTTATGGT CTCCGTATAG AACAGGGTGT CTTGAAAAGT TTGGTCAAAC TTGAAGAATT    2280

TTATATTGGA AATGCATATG GGTTTATAGA TGATAACTGC AAGGAGATGG CAGAGCGTTC    2340

TTACAACCTT TCTGCATTAG AATTCGCGTT CTTTAATAAC AAGGCTGAAG TGAAAAATAT    2400

GTCATTTGAG AATCTTGAAC GATTTAAGAT CTCAGTGGGA TGCTCTTTTG ATGGAAATAT    2460

CAATATGAGT AGCCACTCAT ACGAAAACAT GTTGCGATTG GTGACCAACA AAGGTGATGT    2520

ATTAGACTCT AAACTTAATG GGTTATTTTT GAAAACAGAG GTGCTTTTTT TAAGTGTGCA    2580

TGGCATGAAT GATCTTGAAG ATGTTGAGGT GAAGTCGACA CATCCTACTC AGTCCTCTTC    2640

ATTCTGCAAT TTAAAAGTCC TTATTATTTC AAAGTGTGTA GAGTTGAGAT ACCTTTTCAA    2700

ACTCAATGTT GCAAACACTT TGTCAAGACT TGAGCATCTA GAAGTTTGTA AATGCAAGAA    2760

TATGGAAGAA CTCATACATA CTGGGATTGG GGGTTGTGGA GAAGAGACAA TTACTTTCCC    2820

CAAGCTGAAG TTTTTATCTT TGAGTCAACT ACCGAAGTTA TCAGGTTTGT GCCATAATGT    2880

CAACATAATT GGGCTACCAC ATCTCGTAGA CTTGAAACTT AAGGGCATTC AGGTTTCAC     2940

AGTCATTTAT CCGCAGAACA AGTTGCGAAC ATCTAGTTTG TTGAAGGAAG AGGTAGATAT    3000

ATGTTCTTTA TGTTAATACA ATTTAAACAA TATTTTCAAC CAAATTTTCA TAATATATCT    3060

GTAATTTGAT TGTATGATGT GTTATTGTTT ATATGTGGCT ATTAAGGGAT GATAATTTTG    3120

CAGGTTGTGA TTCCTAAGTT GGAGACACTT CAAATTGATG ACATGGAGAA CTTAGAAGAA    3180

ATATGGCCTT GTGAACTTAG TGGAGGTGAG AAAGTTAAGT TGAGAGAGAT TAAAGTGAGT    3240

AGCTGTGATA AGCTTGTGAA TCTATTTCCG CGCAATCCCA TGTCTCTGTT GCATCATCTT    3300

GAAGAGCTTA CAGTCGAGAA TTGCGGTTCC ATTGAGTCGT TATTCAACAT TGACTTGGAT    3360
```

```
TGTGTCGGTG CAATTGGAGA AGAAGACAAC AAGAGCCTCT TAAGAAGCAT CAACGTGGAG    3420

AATTTAGGGA AGCTAAGAGA GGTGTGGAGG ATAAAAGGTG CAGATAACTC TCATCTCATC    3480

AATGGTTTTC AAGCTGTTGA AAGCATAAAG ATTGAAAAAT GTAAGAGGTT TAGAAATATA    3540

TTCACACCTA TCACCGCCAA TTTTTATCTG GTGGCACTTT TGGAGATTCA GATAGAAGGT    3600

TGCGGAGGAA ATCACGAATC AGAAGAGCAG GTAACGCTTT CAATTTCACT TTCTTAATTA    3660

ATTANGGACT AAGCTCCTGT TTTTTGAATA ATAAAGAGGT GGGATGACTA AACTTGGGCA    3720

TCACAATTGC AACAAAATGT TACAAACCAT GAAACGCTCA AACCATTTCT TGAATTAAGG    3780

TTTCAATACA AGTCATTTAA AAATATGGCT TAAATTTTTT TATATTTATG TATCAACATG    3840

ATTTTTCATT AGAGATCATT ATTATAATAG TAAGTTTAAA GCAATTTAAA TTAGAACTAA    3900

TTCTAACTTT AGCTAATAAA TCGTTATAAA TGTAAATAAT TACTTTTTAG TGAAATAAGC    3960

AACGGATTTA ATAAGTTAAC AACTTAAATG TCATTTCCTA ACAAAAAAAA CTATTTGGTT    4020

CAGAAAAACT GTAATTCAAG ATAACTAAAA TAAAAATATT TGACATTCAC TAAGAGCATT    4080

TTTTTCTAAA TATGATTGCA AATGAATAAA ACTTAAATTT ATACAGAAAA GATTTTTATA    4140

TATGTTATAC AAAATTTACA AATTGAAATT GGATATGTTA ATTAACGGTT TATAATTCTG    4200

GTATCACAAA GGGATATATA ATAAAATATT ATTTTTCTGT AGTCATTTAT AATTGTACTA    4260

GTTTATAACC CGTGGGAACC ATGAGTTCTA AAATTAGTTA AACTTTCATA ATAAAAATTT    4320

ATAATTATTA TTTATTTTAA ATAAATTATT AATTAAGAGA TATATCAAAA ATTTAAAGTT    4380

ATTATAACTT CAAATTTAAC ATATAATTAA AAAATATATG ATCATAACTT TCCGCAACTC    4440

TTCTTTTGTA TTAAAATGAC CAGAGAAGCT CTTAGTATAT TTTCTAAATC AAAGTCACAA    4500

AACTAATGAA GCATATAATT TTGTGAAAAT CAATTAGCAT TAGGTTTTAA GAGTCACCAA    4560

ATTCAAAGAG TAATCCAATG CTTTCATTAC CACTATGGAG AAAATATTTT CTTAGTTTAA    4620

ATGAAATGAA AACAAACATT CAAACTAATT GTTGCTTATT AAACCAAAGA CCCATTACTT    4680

AGCCAAGAGT TTAACCAAAA AAAATTACAT TCATGTATCA TTATTAATGA CTAGATATAT    4740

ATGAATATGA AGGGAGTTTT TATAGAAAAT ATAATCATAG ATATTCAACA TAACTTCATG    4800

GAATTCCTCA AAATAACCAA GTTATTCAAG AAATTACATC CAAGTCAACC AAAGAGAAGT    4860

TTAGCCTAGC ATGGCTAAAC TCAAGAAAAT AAAATAAGGA TTAGAAGTAC CAAACATGTA    4920

GTAAGAATCA CAGTAAAAGA TGATGTTGTT CTTGATGTTC TTCTAAGTTC TTCAAGTCTC    4980

CAGTTGCTCC TAATAATGCA AAGGAGAGCC ATTAAATTCG TATGTATTGA TCCCTTCAAA    5040

AGCTGCACCA ACCTCCCTTA AATAACACTC AAAGCAAAAA TGACAAAATT GCCCCTGAAG    5100

GACCCTATGC GGGTGCCTTG CGCGGGTGGA GCTGAATATG AAAGGTCTTT GGTCTTTGTG    5160

AGGGTGATGT TGTGCGGGTT AGCTTGTCGC ATGCTTCCGC GCGGTTCGCG CACATGTGCA    5220

CAGGTGATGC ATGGTGTGTA CGTTCTTGAC TTTTGAGCCT CCGATGCTTA GTCCACTTGG    5280

CCCAATTCGA GTCCAATCAA CTTATGACCC ATTTTTCTTC AAGTTATCTT CAAGTTAAGC    5340

CCAATTTGCC TTCTCCAAAT CATCCATAAC TTCACAGAAT CGCCCGTTCA TCTTAATCCC    5400

GAATGAACAA TTATTCTCCC GTCTTCATTT TAAGCAAGAT ACCACCTTCT TCATGCTTCA    5460

TCCATCAATA GTACACTTCA TGTATCATCT CTACTAGTTA TTTAGTCCAC AGTCCTTGTT    5520

GTCCTCCAAA TTTAATTATC TCATTTAGTT CCCGTTCCGC TAGTTTCCTT AAAATTTGCA    5580

ATTAAGCTCA CAGAAATATT AAGTACCCGA AATGGTCATA AATAACAGA AAGGAAAATA    5640

TGCATGAAGA TTAACTAAAT GATGAACGAA ATATGCTAAA ATAGACTATA AAATGAAGTA    5700
```

```
AATAAAATGA AATTATCGCA CTCCGACCAC CCTTATAGGC TTGTAGTCCA CCCACCCTTC    5760

ATTCCTTGTA CCAATATGGG ATGGAAACAT CATTAATTAA GCCAAAAAAC TAACATATAA    5820

GGGGTGAGTG ACAAAGGTAA GTACTAAAGA TGAAAAAAAT CCATTTTTCT TGTATATACA    5880

CAACACACAC ATAGGGGCAG ACGTAGGATT TCATAGTACA GATTGTTGGT GGCACATAAG    5940

TGTTGCTAGT GACATTTTTT TTTTCTTTTA CGTAGTGGCA CAACAGTARA AAAACRAAA     6000

AATTCGAAAT TTTTTACAAT GTGCCTAAAA AAACAGTGG TTGTTGGTGC CACTATGGAC     6060

ACCAAAGTTG AACTGCCCCT GCGCGCGCAC ACACACACAC ACATAAAGAG AGAGAGAGAG    6120

AGAGAGAGAG AGAGAGAGAG AGAGAGTTTG GGATGTGATA CTTCTTTTGG GAAAATGGAG    6180

TTATATCTTT GATATTGTAT TTTTTTAATG TAATTTATAT ATTTAATCAT TTAGTTTAT     6240

AAGTTTTATT TATTTKGATA TGAAAAAAAA AGTCTTTTAT ACATTGGATT TAACATAAAA    6300

ATCCAACAAT ATTAATCAAA AAGACCAAAC ATGTGGACAA TTATGTATAT AATTAATTCA    6360

CAATAGTCTT TAGGAATAGN ATTATATATA TAATTAATTC TCAATGGTCT TAGGAATAGT    6420

AAGTTCTTAT ATTTCAAACN TTTGCCACAN TTCTTTGNTT ACTTNGACAC TTTYCTCTMW    6480

NNANWMWWTW ATATATATAT ATATATATAT ATAHAHAHAH AVACACACAC ACTAGATGTG    6540

TGCCMGCGCA AAGCAGTGAC GTNNNGGAGA ANACTTTCTT AAGCATAAAT AATTATTATA    6600

TTTTTTATTG GGTATTATAT AATAAAAAAT TACAACTTTT AAATAAAATA TTTATGTTTA    6660

TACTTTATAT TTATATTGCT TGTATACTAT TAATATAATA AATTAATATT TATGTCTAAT    6720

TTATGAAATG TAAATTAATT TAAATACATG AATTTAATAT TTTTAAAATT TTCAGTTTGC    6780

TTCAAATTGA GTTTCTTAAT TATTGACCAA ACATGTGGAC AATTATGTAT ATAATTAATT    6840

CACAATAGTC TTTAGGAATA GTATTATATA TATAATTAAT TCTCAATGGT CTTAGGAATA    6900

GTAAGTTCTT ATATTTCAAA CTTTTGCCAC AATTCTTTGC TTACTTTGAC ACTTTTCCTT    6960

CCTAACTTTA CATATATATA TATATTAAAG CGCAAAGGTC ATAGGAATAT AATATTTTCT    7020

ATTATTCTAC GTTTTGCCAC AAAAGTTTGA ACACTTTGCC ACTTTTTGTC CCTCCTTAAC    7080

CTTTTCAATG TTTTGCGACA AAAGTTCCAA AACTTTGCCA CTTTGATCAT TCCTCAACTT    7140

TTCACCGCAT TAGTTTGTGG AGTTGGCAGT TTTGGTCCCT CTAACTTCGA TATTCTCTAC    7200

TGCTAGCCAA AAAGGGTTCC AGAGTTTCAC ACTTTTGGTC CCTGACAGTA ACCAAATGTG    7260

AGATGTCAAA TTTTTGCCAC ATTAGTTTGT GGAGTTGTCC CTTTTGGTCC CCCCACATTC    7320

GATATTCTAC TATACGATCT TATTTTTCTC AAATAACAAC ACGTATATTT AATTACTAAT    7380

GATAGAAATA GATATCAAAT AAAGTATTTG TAACACTGTG TAGAGTTTTT TTTTACAAGT    7440

TTGTATCAAA TCATATCAAA ATTTAAGGTG GAACGGTGAC CACATTAACC AGAAATGTAA    7500

TTTATTCTTT GATTTGATA ATTTTTAATA TTTTGTTGTG ATCTATGTAT TTAAAAGTAA     7560

ACAACAAAGA ACATAATCCA AAACCCTAAA TTGCAAGTCT CGCCCAATTT CTCTATCACT    7620

AGTCCTCACT TACGATGGCG TTACGTCGCT CTCTCACTGC TTACAACCCT TGTTGCTAC     7680

TCATTACAAT AACGAAAAGT TGAATATCCA TATATTTATT TGGATGTGGA ATTGAACGAA    7740

TCTCGTCAAA TTTTTGATTT AGTTGATGGA TTTGAGTAGA AGTTTGGGCA GAACGGGAAT    7800

GATGGTCTGC AAGTGGTTAT AAACTTGATT CTGAGTTATT ACTATATATG TAGCCTCTTT    7860

ACAACGACCA AGGTTTCTTC CAGGTACCAT TTGATCTTTT TAGAACTTAG TTTTCTGAAA    7920

CACCCTGATT TGGATCAAAT ATCACCAACA ACTCTTAAAA ACTTGATTAA TCAATTGTTT    7980

ACTTCATCTT GATAACAAGT GGAATGATTT TCTACTTGAA AAAAAGGTC CATGTGCGTC     8040

TGGTGGATCT GGTAAATGAA GATGGAAGGG AGAGCTGACT TTAAAGACAC AAACACGTCA    8100
```

```
CCATATCTTT TATTTTATTT TAAATTTTCT TTTTTCCTAT TTCTTTCTTT CTTGATCTCC    8160

AGATGGTATG TGGTGTGGAT AATTTACACA TAGAGATTGG GAACGACTGT GATTTAGAGA    8220

GGACGTGGCT TGGGGTTGAG GATGGTTTAT GGCTGGCCGA GTTTCATTTA TATAAACAAA    8280

CAAATATATA AAACAAGGGG TAAAATGGCC ATCTTATATG TATTTAACCG TCCTCTTTTT    8340

TTTTTTTTTT TTTTTTTTTT TTTTTTTTTG TAATTTAAGA AGGGGTATAC CAGTGTCAGC    8400

CTCTTATTCC CAACCAGTCA AATAGGGACT TAGGTTGTTT GGAAACAGTT CCGTGAGACC    8460

GTGACTTGGA TGGTAGATAA ATTTAGTAAA CTTAACCCTT CAATTAACCT ACCTTTTTCT    8520

TATTAACTCA ATTTCAACCT AAATTCTGAT TCTTGTTTGA AAATAAGTTG CATCTTTATT    8580

TTTGTATTAT CTTGTTGCAT AGGATCCTTA GCATCTTTTA ATAATTTATT TGAAGGTGAA    8640

AGATCCAACT ATTTTTAATC TGTTGACGTT TTCCATCATT TGCAACTGTT TCTTGAAAAA    8700

AAAATACCTA AAATCAAAAT AACCATTTTC AAATCCAAAA TTATAAGAGA GAATTGTAAA    8760

TGGACATGGA ATCATAAATC ATTAACACAG TTCAGTAAAC AAGTTGCTAA TTACATTTCT    8820

TGCTGTGCAG ATTGAAATTC TATCAGAGAA AGAGACATTA CAAGAAGCCA CTGGCAGTAT    8880

TTCAAATCTT GTATTCCCAT CCTGTCTCAT GCACTCTTTT CATAACCTCC GTGTGCTTAC    8940

ATTGGATAAT TATGAAGGAG TGGAGGTGGT GTTTGAGATA GAGAGTGAGA GTCCAACAAG    9000

TAGAGAATTG GTAACAACTC ACAATAACCA ACAACAGCCT ATTATACTTC CCTACCTCCA    9060

GGAATTGTAT CTAAGGAATA TGGACAACAC GAGTCATGTG TGGAAGTGCA GCAACTGGAA    9120

TAAATTCTTC ACTCTTCCAA AACAACAATC AGAATCACCA TTCCACAACC TCACAACCAT    9180

AGAAATGAGA TGGTGTCATG GCTTTAGGTA CTTGTTTTCG CCTCTCATGG CAGAACTTCT    9240

TTCCAACCTA AGAAAGTCA AGATACTTGG GTGTGATGGT ATTAAGAAG TTGTTTCAAA    9300

CAGAGATGAT GAGGATGAAG AAATGACTAC ATTTACATCT ACCCACAAAA CCACCAACTT    9360

GTTCCCTCAT CTTGATTCTC TCACTCTAAA CCAACTGAAG AATCTGAAGT GTATTGGTGG    9420

AGGTGGTGCC AAGGATGAGG GGAGCAATGA AATATCTTTC AATAATACCA CTGCAACGAC    9480

TGCTGTTCTT GATCAATTTG AGGTATGCTT TGTACATATT CAATTATTTA TTTAATTTCC    9540

TTTTTTATTT GCAATATTCT ATAAATAATA CATTTTATAC CCACTATACT AAGATAATAA    9600

TTACCTAGAG GGATGGATGC TATGACACAG CTGCTACACT TCAGAAACTC TAGTAAGGGC    9660

AGTTATGGAA GTTCAATAAA ATGATAATGG CATCTTTTGA TGGGTAATAT AGGCAATTTA    9720

AGTTTTATTT CTGTTAAAGC AGTATTTAGC AAGTACTGGC CAGTAGGAGA GGAGAATATC    9780

ACCTTTTGTG AAAATCTGGT CATTGTACCC AGAATTTAGT TAAATGTAAC ATTTTAGATA    9840

TTAGGGGTTA TCAGGTGACA GATATTGTAG AATAGAACAA TATGTAATAT TACCCAAAAC    9900

TATTTTTTCT AAGGTTGCTC TGTTAAATAT GTGCTTTCTT GATTTCATTG AATTTGCATT    9960

CCTATATTTT AGGTGGTAAA GTGATTGTCT CTTCAATAAA TCCCGAAATT AATTAAAAAA    10020

AAAAAAACAA AAGTAAATTT TTGATATGGA GAGCACTGGT ATCATTTAGT ATATAAAAAA    10080

ACTAGATTTT GAATTAAGTT TCTTATATAA AAGCTGTGTA TATAGTTTAA TTAGTTTTAC    10140

ATCATTTTTC CATGTGGTGT TGCAGTTGTC TGAAGCAGGT GGTGTTTCTT GGAGCTTATG    10200

CCAATACGCT AGAGAGATAA AAATAGGCAA CTGCCATGCA TTGTCAAGTG TGATTCCATG    10260

TTATGCAGCA GGACAAATGC AAAAGCTTCA AGTGCTGAGA GTAATGGCTT GCAATGGGAT    10320

GAAGGAGGTA TTTGAAACTC AATTAGGGAC GAGCAGCAAC AAAAACAACG AGAAGAGTGG    10380

TTGTGAGGAA GGAATTCCAA GAGTAAATAA CAATGTTATT ATGCTTCCCA ATCTAAAGAT    10440
```

-continued

```
ATTAAGTATT GGAAATTGTG GGGGTTTGGA ACATATATTC ACATTCTCTG CACTTGAAAG    10500

CCTGAGACAG CTCCAAGAGT TAACGATTAA GGGTTGCTAC AGAATGAAAG TGATTGTGAA    10560

GAAGGAAGAA GATGAATATG GAGAGCAGCA AACAACAACA ACAACAACGA AGGGGGCATC    10620

TTCTTCTTCT TCTTCTTCTA AGAAGGTGGT GGTCTTTCCT TGTCTAAAGT CCATTGTATT    10680

GGTCAATCTA CCAGAGCTGG TAGGATTCTT CTTGGGGATG AATGAGTTCC GGTTGCCTTC    10740

ATTAGATAAA CTTATCATCG AGAAATGCCC AAAAATGATG GTGTTTACAG CTGGTGGGTC    10800

CACAGCTCCC CAACTCAAGT ATATACACAC AAGATTAGGC AAACATACTC TTGATCAAGA    10860

ATCTGGCCTT AACTTTCATC AGGTACATAT ATATTCCTTT AATTGGCATC ATCTAATTAA    10920

GAAAGATATC ATTCCTGCCA AGTAAATTTA CTTCAAACAC ATTCACACTA GTTTCAGTCC    10980

AAGTTTATGT TGTTCTAGGA AGGCCAAAAT GGGAAAGCAA GATAGGGAAA AATAGAGTAT    11040

TTCAGTGGAA AGGGTATTTT AGGTATTTTC TGTCAAAAAT TGTTATTGCA GGCTTTTTAG    11100

TACCTGGAAG AGCATGATTA TTCTCGATTT GCTTGTTTCT TTATCATTTT TCTTAGCCTA    11160

GCATGATTTT CAATGAAATC TTTCCCTGTT ACTCCATTTG ATTGTTGTTC TTCATGGTTC    11220

TAAGTGAGTT AGTGGCTCAT CTGTTACTTC TTTTGATTGT TATTTTCATA GCATGTTGTC    11280

ACTTGAATCA AGCTTTTCCA TTTTCAACAA GGACAAAAGG TCAAAACTAA CCTACTTTAT    11340

GAGATCAAAA ATAGCAACCC ATCGGATAAC TTTTAGTTGG AGTAATACT TACAATTACC      11400

ATTGTGATTA ATAATTATAA TATCTTGTAT TAATTCATAA AAATTGGTAC AGCACATATA    11460

TGACATTTCA AAGGTTTTTG TTTGACATAT ATATGCCTCT GGCGTTTTCT TTATTGGACA    11520

TGCAGACTTC ATTCCAAAGT TTATACGGTG ACACCTTGGG CCCTGCTACT TCAGAAGGGA    11580

CAACTTGGTC TTTTCATAAC TTTATCGAAT TAGATGTGAA ATCTAATCAT GATGTTAAAA    11640

AGATTATTCC ATCCAGTGAG TTGCTGCAAC TGCAAAAGCT GGTAAAGATT AATGTAATGT    11700

GGTGTAAAAG GGTAGAGGAG GTATTTGAAA CTGCATTGGA AGCAGCAGGG AGAAATGGAA    11760

ATAGTGGAAT TGGTTTTGAT GAATCGTCAC AAACAACTAC CACTACTCTT GTCAATCTTC    11820

CAAACCTTGG AGAAATGAAG TTACGGGTC TCGATTGTCT GAGGTATATA TGGAAGAGCA      11880

ATCAGTGGAC AGCATTTGAG TTTCCAAACC TAACAAGAGT TGAAATTTAT GAATGTAATT    11940

CATTAGAACA TGTATTTACT AGTTCCATGG TTGGTAGTCA ATTGCAACTC CAAGAGCTAG    12000

AGATTGGTTT GTGCAACCAT ATGGAGGTCG TGCATGTTCA GGATGCAGAT GTTTCTGTAG    12060

AAGAAGACAA AGAGAAAGAA TCTGATGGCA AGATGAATAA GGAGATACTT GTGTTACCTC    12120

ATCTAAAGTC ATTGAAATTA CTACTTCTTC AAAGTCTTAA GGGGTTTAGC TTGGGGAAGG    12180

AGGATTTTTC ATTCCCATTA TTGGATACTT TGGAAATCTA CGAATGCCCA GCAATAACCA    12240

CCTTCACCAA GGGAAATTCC GCTACTCCAC AGCTAAAAGA AATGGAAACA AATTTTGGCT    12300

TCTTTTATGC TGCAGGGGAA AAAGACATCA ACTCCTCTAT TATAAAGATC AAACAACAGG    12360

TAAACCAGAT CTTTGTTGCT TTAATAATTC TTAAACTACA TTTGAAAAGC TTCATGCAAG    12420

TTTTTTTGT TATATTGTCA AAAACCGCAA CCTACATTTT CAGCTTTATA TTTATGTACT      12480

TTATGCAGGA TTTCAAACAA GACTCTGATT AATGTGAAGT GAATATTAAA GGTAAATTAT    12540

ATTTTCATGT TCCTAGTTGC CTATTAATTA AAGGCCTTTT AGTTCGTGAT TTTTGGATGT    12600

ATTCTTCATG ATGATGTCAA TCTTCTAATA CCCCATTCAT TGTTTGGTTG AATGTTGACT    12660

CTATGTCAGG ATGAATATTC AAGGGAAGAA TTGTTCATCA TATGAAGGAC ATTAAAGAAC    12720

ATGGTGCTAT                                                          12730
```

```
(2) INFORMATION FOR SEQ ID NO:92:

(i) SEQUENCE CHARACTERISTICS:
        (A) LENGTH: 1805 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1805
        (D) OTHER INFORMATION: /note= "RG2C deduced sequence"

(xi) SEQUENCE DESCRIPTION: SEQ ID NO:92:

Met Ala Met Glu Thr Ala Asn Glu Ile Ile Lys Gln Val Val Pro Val
1               5                  10                  15

Leu Met Val Pro Ile Asn Asp Tyr Leu Arg Tyr Leu Val Ser Cys Arg
                20                  25                  30

Lys Tyr Ile Ser Asp Met Asp Leu Lys Met Lys Glu Leu Lys Glu Ala
            35                  40                  45

Lys Asp Asn Val Glu Glu His Lys Asn His Asn Ile Ser Asn Arg Leu
50                  55                  60

Glu Val Pro Ala Ala Gln Val Gln Ser Trp Leu Glu Asp Val Glu Lys
65                  70                  75                  80

Ile Asn Ala Lys Val Glu Thr Val Pro Lys Asp Val Gly Cys Cys Phe
                85                  90                  95

Asn Leu Lys Ile Arg Tyr Arg Ala Gly Arg Asp Ala Phe Asn Ile Ile
                100                 105                 110

Glu Glu Ile Asp Ser Val Met Arg Arg His Ser Leu Ile Thr Trp Thr
            115                 120                 125

Asp His Pro Ile Pro Leu Gly Arg Val Asp Ser Val Met Ala Ser Thr
130                 135                 140

Ser Thr Leu Ser Thr Glu His Asn Asp Phe Gln Ser Arg Glu Val Arg
145                 150                 155                 160

Phe Ser Glu Ala Leu Lys Ala Leu Glu Ala Asn His Met Ile Ala Leu
                165                 170                 175

Cys Gly Met Gly Gly Val Gly Lys Thr His Met Met Gln Arg Leu Lys
                180                 185                 190

Lys Val Ala Lys Glu Lys Arg Lys Phe Gly Tyr Ile Ile Glu Ala Val
            195                 200                 205

Ile Gly Glu Ile Ser Asp Pro Ile Ala Ile Gln Gln Val Val Ala Asp
210                 215                 220

Tyr Leu Cys Ile Glu Leu Lys Glu Ser Asp Lys Lys Thr Arg Ala Glu
225                 230                 235                 240

Lys Leu Arg Gln Gly Phe Lys Ala Lys Ser Asp Gly Gly Asn Thr Lys
                245                 250                 255

Phe Leu Ile Ile Leu Asp Asp Val Trp Gln Ser Val Asp Leu Glu Asp
                260                 265                 270

Ile Gly Leu Ser Pro Ser Pro Asn Gln Gly Val Asp Phe Lys Val Leu
            275                 280                 285

Leu Thr Ser Arg Asp Glu His Val Cys Ser Val Met Gly Val Glu Ala
            290                 295                 300

Asn Ser Ile Ile Asn Val Gly Leu Leu Ile Glu Ala Glu Ala Gln Arg
305                 310                 315                 320

Leu Phe Gln Gln Phe Val Glu Thr Ser Glu Pro Glu Leu His Lys Ile
                325                 330                 335
```

-continued

```
Gly Glu Asp Ile Val Arg Arg Cys Cys Gly Leu Pro Ile Ala Ile Lys
            340                 345                 350

Thr Met Ala Cys Thr Leu Arg Asn Lys Arg Lys Asp Ala Trp Lys Asp
            355                 360                 365

Ala Leu Ser Arg Leu Gln His His Asp Ile Gly Asn Val Ala Thr Ala
            370                 375                 380

Val Phe Arg Thr Ser Tyr Glu Asn Leu Pro Asp Lys Glu Thr Lys Ser
385                 390                 395                 400

Val Phe Leu Met Cys Gly Leu Phe Pro Glu Asp Phe Asn Ile Pro Thr
                405                 410                 415

Glu Glu Leu Met Arg Tyr Gly Trp Gly Leu Lys Leu Phe Asp Arg Val
            420                 425                 430

Tyr Thr Ile Ile Glu Ala Arg Asn Arg Leu Asn Thr Cys Ile Asp Arg
            435                 440                 445

Leu Val Gln Thr Asn Leu Leu Ile Gly Ser Asp Asn Gly Val His Val
450                 455                 460

Lys Met His Asp Leu Val Arg Ala Phe Val Leu Gly Met Tyr Ser Glu
465                 470                 475                 480

Val Glu Gln Ala Ser Ile Val Asn His Gly Asn Met Pro Gly Trp Pro
                485                 490                 495

Asp Glu Asn Asp Met Ile Val His Ser Cys Lys Arg Ile Ser Leu Thr
            500                 505                 510

Cys Lys Gly Met Ile Glu Phe Pro Val Asp Leu Lys Phe Pro Lys Leu
            515                 520                 525

Thr Ile Leu Lys Leu Met His Gly Asp Lys Ser Leu Lys Phe Pro Gln
            530                 535                 540

Glu Phe Tyr Glu Gly Met Glu Lys Leu Arg Val Ile Ser Tyr His Lys
545                 550                 555                 560

Met Lys Tyr Pro Leu Leu Pro Leu Ala Pro Gln Cys Ser Thr Asn Ile
                565                 570                 575

Arg Val Leu His Leu Thr Glu Cys Ser Leu Lys Met Phe Asp Cys Ser
            580                 585                 590

Cys Ile Gly Asn Leu Ser Asn Leu Glu Val Leu Ser Phe Ala Asn Ser
            595                 600                 605

Cys Ile Glu Trp Leu Pro Ser Thr Val Arg Asn Leu Lys Lys Leu Arg
            610                 615                 620

Leu Leu Asp Leu Arg Leu Cys Tyr Gly Leu Arg Ile Glu Gln Gly Val
625                 630                 635                 640

Leu Lys Ser Leu Val Lys Leu Glu Glu Phe Tyr Ile Gly Asn Ala Tyr
                645                 650                 655

Gly Phe Ile Asp Asp Asn Cys Lys Glu Met Ala Glu Arg Ser Tyr Asn
            660                 665                 670

Leu Ser Ala Leu Glu Phe Ala Phe Asn Asn Lys Ala Glu Val Lys
            675                 680                 685

Asn Met Ser Phe Glu Asn Leu Glu Arg Phe Lys Ile Ser Val Gly Cys
            690                 695                 700

Ser Phe Asp Gly Asn Ile Asn Met Ser Ser His Ser Tyr Glu Asn Met
705                 710                 715                 720

Leu Arg Leu Val Thr Asn Lys Gly Asp Val Leu Asp Ser Lys Leu Asn
                725                 730                 735

Gly Leu Phe Leu Lys Thr Glu Val Leu Phe Leu Ser Val His Gly Met
            740                 745                 750
```

```
Asn Asp Leu Glu Asp Val Glu Val Lys Ser Thr His Pro Thr Gln Ser
            755                 760                 765
Ser Ser Phe Cys Asn Leu Lys Val Leu Ile Ile Ser Lys Cys Val Glu
        770                 775                 780
Leu Arg Tyr Leu Phe Lys Leu Asn Val Ala Asn Thr Leu Ser Arg Leu
785                 790                 795                 800
Glu His Leu Glu Val Cys Lys Cys Lys Asn Met Glu Glu Leu Ile His
                805                 810                 815
Thr Gly Ile Gly Gly Cys Gly Glu Thr Ile Thr Phe Pro Lys Leu
            820                 825                 830
Lys Phe Leu Ser Leu Ser Gln Leu Pro Lys Leu Ser Gly Leu Cys His
            835                 840                 845
Asn Val Asn Ile Ile Gly Leu Pro His Leu Val Asp Leu Lys Leu Lys
850                 855                 860
Gly Ile Pro Gly Phe Thr Val Ile Tyr Pro Gln Asn Lys Leu Arg Thr
865                 870                 875                 880
Ser Ser Leu Leu Lys Glu Val Val Ile Pro Lys Leu Glu Thr Leu
                885                 890                 895
Gln Ile Asp Asp Met Glu Asn Leu Glu Ile Trp Pro Cys Glu Leu
            900                 905                 910
Ser Gly Gly Glu Lys Val Lys Leu Arg Glu Ile Lys Val Ser Ser Cys
        915                 920                 925
Asp Lys Leu Val Asn Leu Phe Pro Arg Asn Pro Met Ser Leu Leu His
930                 935                 940
His Leu Glu Glu Leu Thr Val Glu Asn Cys Gly Ser Ile Glu Ser Leu
945                 950                 955                 960
Phe Asn Ile Asp Leu Asp Cys Val Gly Ala Ile Gly Glu Glu Asp Asn
                965                 970                 975
Lys Ser Leu Leu Arg Ser Ile Asn Val Glu Asn Leu Gly Lys Leu Arg
            980                 985                 990
Glu Val Trp Arg Ile Lys Gly Ala Asp Asn Ser His Leu Ile Asn Gly
        995                 1000                1005
Phe Gln Ala Val Glu Ser Ile Lys Ile Glu Lys Cys Lys Arg Phe Arg
    1010                1015                1020
Asn Ile Phe Thr Pro Ile Thr Ala Asn Phe Tyr Leu Val Ala Leu Leu
1025                1030                1035                1040
Glu Ile Gln Ile Glu Gly Cys Gly Gly Asn His Glu Ser Glu Glu Gln
                1045                1050                1055
Ile Glu Ile Leu Ser Glu Lys Glu Thr Leu Gln Glu Ala Thr Gly Ser
            1060                1065                1070
Ile Ser Asn Leu Val Phe Pro Ser Cys Leu Met His Ser Phe His Asn
        1075                1080                1085
Leu Arg Val Leu Thr Leu Asp Asn Tyr Glu Gly Val Glu Val Val Phe
    1090                1095                1100
Glu Ile Glu Ser Glu Ser Pro Thr Ser Arg Glu Leu Val Thr Thr His
1105                1110                1115                1120
Asn Asn Gln Gln Gln Pro Ile Ile Leu Pro Tyr Leu Gln Glu Leu Tyr
                1125                1130                1135
Leu Arg Asn Met Asp Asn Thr Ser His Val Trp Lys Cys Ser Asn Trp
            1140                1145                1150
Asn Lys Phe Phe Thr Leu Pro Lys Gln Gln Ser Glu Ser Pro Phe His
        1155                1160                1165
Asn Leu Thr Thr Ile Glu Met Arg Trp Cys His Gly Phe Arg Tyr Leu
```

-continued

```
        1170                1175                1180
Phe Ser Pro Leu Met Ala Glu Leu Leu Ser Asn Leu Lys Lys Val Lys
1185                1190                1195                1200

Ile Leu Gly Cys Asp Gly Ile Lys Glu Val Val Ser Asn Arg Asp Asp
                1205                1210                1215

Glu Asp Glu Glu Met Thr Thr Phe Thr Ser Thr His Lys Thr Thr Asn
            1220                1225                1230

Leu Phe Pro His Leu Asp Ser Leu Thr Leu Asn Gln Leu Lys Asn Leu
        1235                1240                1245

Lys Cys Ile Gly Gly Gly Ala Lys Asp Glu Gly Ser Asn Glu Ile
    1250                1255                1260

Ser Phe Asn Asn Thr Thr Ala Thr Thr Ala Val Leu Asp Gln Phe Glu
1265                1270                1275                1280

Leu Ser Glu Ala Gly Gly Val Ser Trp Ser Leu Cys Gln Tyr Ala Arg
                1285                1290                1295

Glu Ile Lys Ile Gly Asn Cys His Ala Leu Ser Ser Val Ile Pro Cys
            1300                1305                1310

Tyr Ala Ala Gly Gln Met Gln Lys Leu Gln Val Leu Arg Val Met Ala
        1315                1320                1325

Cys Asn Gly Met Lys Glu Val Phe Glu Thr Gln Leu Gly Thr Ser Ser
1330                1335                1340

Asn Lys Asn Asn Glu Lys Ser Gly Cys Glu Glu Gly Ile Pro Arg Val
1345                1350                1355                1360

Asn Asn Asn Val Ile Met Leu Pro Asn Leu Lys Ile Leu Ser Ile Gly
                1365                1370                1375

Asn Cys Gly Gly Leu Glu His Ile Phe Thr Phe Ser Ala Leu Glu Ser
            1380                1385                1390

Leu Arg Gln Leu Gln Glu Leu Thr Ile Lys Gly Cys Tyr Arg Met Lys
        1395                1400                1405

Val Ile Val Lys Lys Glu Glu Asp Glu Tyr Gly Glu Gln Gln Thr Thr
    1410                1415                1420

Thr Thr Thr Thr Lys Gly Ala Ser Ser Ser Ser Ser Ser Lys Lys
1425                1430                1435                1440

Val Val Val Phe Pro Cys Leu Lys Ser Ile Val Leu Val Asn Leu Pro
                1445                1450                1455

Glu Leu Val Gly Phe Phe Leu Gly Met Asn Glu Phe Arg Leu Pro Ser
            1460                1465                1470

Leu Asp Lys Leu Ile Ile Glu Lys Cys Pro Lys Met Met Val Phe Thr
        1475                1480                1485

Ala Gly Gly Ser Thr Ala Pro Gln Leu Lys Tyr Ile His Thr Arg Leu
    1490                1495                1500

Gly Lys His Thr Leu Asp Gln Glu Ser Gly Leu Asn Phe His Gln Thr
1505                1510                1515                1520

Ser Phe Gln Ser Leu Tyr Gly Asp Thr Leu Gly Pro Ala Thr Ser Glu
                1525                1530                1535

Gly Thr Thr Trp Ser Phe His Asn Phe Ile Glu Leu Asp Val Lys Ser
            1540                1545                1550

Asn His Asp Val Lys Lys Ile Ile Pro Ser Ser Glu Leu Leu Gln Leu
        1555                1560                1565

Gln Lys Leu Val Lys Ile Asn Val Met Trp Cys Lys Arg Val Glu Glu
    1570                1575                1580

Val Phe Glu Thr Ala Leu Glu Ala Ala Gly Arg Asn Gly Asn Ser Gly
1585                1590                1595                1600
```

```
Ile Gly Phe Asp Glu Ser Ser Gln Thr Thr Thr Thr Leu Val Asn
            1605                1610                1615

Leu Pro Asn Leu Gly Glu Met Lys Leu Arg Gly Leu Asp Cys Leu Arg
        1620                1625                1630

Tyr Ile Trp Lys Ser Asn Gln Trp Thr Ala Phe Glu Phe Pro Asn Leu
            1635                1640                1645

Thr Arg Val Glu Ile Tyr Glu Cys Asn Ser Leu Glu His Val Phe Thr
        1650                1655                1660

Ser Ser Met Val Gly Ser Leu Leu Gln Leu Gln Glu Leu Glu Ile Gly
1665                1670                1675                1680

Leu Cys Asn His Met Glu Val Val His Val Gln Asp Ala Asp Val Ser
            1685                1690                1695

Val Glu Glu Asp Lys Glu Lys Glu Ser Asp Gly Lys Met Asn Lys Glu
        1700                1705                1710

Ile Leu Val Leu Pro His Leu Lys Ser Leu Lys Leu Leu Leu Leu Gln
            1715                1720                1725

Ser Leu Lys Gly Phe Ser Leu Gly Lys Glu Asp Phe Ser Phe Pro Leu
        1730                1735                1740

Leu Asp Thr Leu Glu Ile Tyr Glu Cys Pro Ala Ile Thr Thr Phe Thr
1745                1750                1755                1760

Lys Gly Asn Ser Ala Thr Pro Gln Leu Lys Glu Met Glu Thr Asn Phe
            1765                1770                1775

Gly Phe Phe Tyr Ala Ala Gly Leu Lys Asp Ile Asn Ser Ser Ile Ile
        1780                1785                1790

Lys Ile Lys Gln Gln Asp Phe Lys Gln Asp Ser Asp Xaa
        1795                1800                1805

(2) INFORMATION FOR SEQ ID NO:93:

(i) SEQUENCE CHARACTERISTICS:
        (A) LENGTH: 5506 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..5506
        (D) OTHER INFORMATION: /note= "RG2D"

(xi) SEQUENCE DESCRIPTION: SEQ ID NO:93:

ACGACCACTA TAGGGCGAAT TGGGCCCGAC GTCGCATGCT CCCGGCCGCC ATGGCCGCGG      60

GATGTAAAAC GACGGCCAGT CGAATCGTAA CCGTTCGTAC GAGAATCGCT GTCCTCTCCT     120

TCAACCATTT AATGTATATG AGCTAAATTG AAACATCTAC TATCATGTTT AAATTTATAA     180

ACTTTTTCCT TTAGATTCAC TTGTCTGGAT GTGTTTAATA AAACCCAATT TCCCACATGC     240

GTAGAGATCA TAGATGTAAC TATTGTTAAT CAATTTTGCC TGCCAAGTTT TAATAATTAT     300

ACTTGGATAT TAACAAAACT TTATCTAACG ACCAAGGTAA TATTAAAAAT AGGTTATTAT     360

TCTTCATGCT AATTAAAAGA TGGGTTGCAA AAGTGAGACC ATGAAAACAT TAACACGTTG     420

ATATTTTCAA CTTTTATTCT TTCATATTCA CCATATTTTT TACTTTCGTA TTGATTAATC     480

ATCTTTCAAT CACAGGCTCC TTGGCAAAAA GTCAGATCTA TTAACAAATA CTTCCATGTG     540

GTTGCAAATT ACAAGGATTT CAACATAATT ACCAAAACAT AGCATTATCA TAAGATCGAA     600

TAATAATCAA ATTCTTCTAT AATATTACAC AAAGGTAACG TCATTAATTA ATTACGATAC     660
```

```
GAGACAGACT TTTTCACTCG TGACATCAAC GGTCTATTCT AACTTTACTT AATTAAATGA    720

ATCTAGGATG TGCTCATATG CATGTAATAT TTGCTACCGT CATCTTTCAA ATGACCATAT    780

TTTTATGTAT TTATAATGAA TCAATGAAAA ACCGGATTTC TATTTAAAAT TCTTAAAACT    840

TCATCTTTTA AGCCAGGGTG AATACAATTG TAGATCCACT GTTAATTTCC ATCGATTATG    900

CGTGATCAAT TGTTGGCTGC ATACGATGCA GGTGCTACCA AAGAATATG GCCATGGAAA    960

CTGCTAATGA AATTATAAAA CAAGTTGTTC CAGTTCTCAT GGTTCCTATT AACGATTACC   1020

TACGCTACGT CGTTTCCTGC AGAAAGTACA TCAGTGACAT GGATTTGAAA ATGAAGGAAT   1080

TAAAAGAAGC AAAAGACAAT GTTGAAGAGC ACAAGAATCA TAACATTAGT AATCGTCTTG   1140

AGGTTCCAGC AGCTCAAGTC CAGAGCTGGT TGGAAGATGA AGAAAAGATC AATGCAAAAG   1200

TGGAAACTGT TCCTAAAGAT GTCGGCTGTT GCTTCAATCT AAAGATTAGG TACAGGGCCG   1260

GAAGGGATGC CTTCAATATA ATTGAGGAGA TCGACAGTGT CATGAGACGA CACTCTCTGA   1320

TCACTTGGAC CGATCATCCC ATTCCTTTGG GAAGAGTTGA TTCCGTGATG GCATCCACCT   1380

CTACGCTTTC AACTGAACAC AATGACTTCC AGTCAAGAGA GGTAAGGTTT AGTGAAGCAC   1440

TCAAAGCACT TGAGGCCAAC CACATGATAG CATTATGTGG AATGGGGAGA GTGGGGAAGA   1500

CCCACATGAT GCAAAGGCTG AAGAAGGTTG CCAAAGAAAA GAGGAAGTTT GGTTATATCA   1560

TCGAGGCAGT TATAGGGGAA ATATCGGACC CCATTGCTAT TCAGCAAGTT GTAGCAGATT   1620

ACCTATGCAT AGAGCTGAAA GAAAGCGATA AGAAAACAAG AGCTGAGAAG CTTCGTCAAG   1680

GGTTCAAGGC CAAATCAGAT GGAGGTAACA CTAAGTTCCT CATAATATTG GATGATGTCT   1740

GGCAGTCCGT TGATCTAGAA GATATTGGTT TAAGCCCTTC TCCCAATCAA GGTGTCGACT   1800

TCAAGGTCTT GTTGACTTCA CGAGACGAAC ATGTTTGCTC AGTGATGGGG GTTGAAGCTA   1860

ATTCAATTAT TAACGTGGGA CTTCTAATTG AAGCAGAAGC ACAAAGATTG TTCCAGCAAT   1920

TTGTAGAAAC TTCTGAGCCC GAGCTCCACA AGATAGGAGA AGATATTGTT AGGAGGTGTT   1980

GCGGTCTACC CATTGCCATC AAAACCATGG CGTGTACTCT AAGAAATAAA AGAAAGGATG   2040

CATGGAAGGA TGCACTTTCT CGTTTACAAC ACCATGACAT TGGTAATGTT GCTACTGCAG   2100

TTTTTAGAAC CAGCTATGAG AATCTCCCGG ACAAGGAGAC AAAATCTGTT TTTTTGATGT   2160

GTGGTTTGTT TCCCGAAGAC TTCAATATTC CTACCGAGGA GTTGATGAGG TATGGATGGG   2220

GCTTAAAGTT ATTTGATAGA GTTTATACAA TTATAGAAGC AAGAAACAGG CTCAACACCT   2280

GCATTGAGCG ACTGGTGCAG GCAAATTTAC TAATTGGAAG TGATAATGGT GTACACGTCA   2340

AGATGCATGA TCTGGTCCGT GCTTTTGTTT TGGGTATGTA TTCTGAAGTC GAGCAAGCTT   2400

CAATTGTCAA CCATGGTAAT ATGCCTGGGT GGCCTGATGA AAATGATATG ATCGTGCACT   2460

CTTGCAAAAG AATTTCATTA ACATGCAAGG GTATGATTGA GATTCCAGTA GACCTCAAGT   2520

TTCCTAAACT AACGATTTTG AAACTTATGC ATGGAGATAA GTCTCTAAAG TTTCCTCAAG   2580

AATTTTATGA AGGAATGGAA AAGCTCCAGG TTATATCATA CGATAAAATG AAGTACCCAT   2640

TGCTTCCTTT GGCACCTCAA TGCTCCACCA ACATTCGGGT GCTTCATCTC ACTGAATGTT   2700

CATTAAAGAT GTTTGATTGC TCTTCTATCG GAAATCTATC GAATCTGGAA GTGCTGAGCT   2760

TTGCTAATTC TCGCATTGAA TGGTTACCTT CCACAGTCAG AAATTTAAAG AAGCTAAGGT   2820

TACTTGATCT GAGATTTGT GATGGTCTCC GTATAGAACA GGGTGTCTTG AAAAGTTTGG   2880

TCAAACTTGA AGAATTTTAT ATTGGAAATG CATATGGGTT TATAGATGAT AACTGCAAGG   2940

ACATGGCAGA GCGTTCTTAC AACCTTTCTG CATTAGAATT CGCGTTCTTT AATAACAAGG   3000
```

-continued

```
CTGAAGTGAA AAATATGTCA TTTGAGAATC TTGAACGATT CAAGATCTCA GTGGGGTGCT    3060
CTTTTGATGG AAATATCAGT ATGAGTAGCC ACTCATACGA AAACATGTTG CAATTGGTGA    3120
CCAACAAAGG TGATGTATTA GACTCTAAAC TTAATGGGTT ATTTTTGAAA ACAGAGGTGC    3180
TTTTTTTAAG TGTGCATGGC ATGAATGATC TTGAAGATGT TGAGGTGAAG TCGACACATC    3240
CTACTCAGTC CTCTTCATTC TGCAATTTAA AAGTCCGTAT TATTTCAAAG TGTGTAGAGT    3300
TGAGATACCT TTTCAAACTC CATGTTGCAA ACACTTTGTC AAGCCTTGAG CATCTAGAAG    3360
TTTGTGGATG CGAAAATATG GAAGAACTCA TACATACTGG GATTGGGGGT TGTGGAGAAG    3420
AGACAATTAC TTTCCCCAAG CTGAAGTCTT TATCTTTGAG TCAACTACCG AAGTTATCAG    3480
GTTTGTGCCA TAATGTCAAC ATAATTGGGC TACCACATCT CGTAGACTTG AAACTTAAGG    3540
GCATTCCAGG TTTCACAGTC ATTTATCCGC AGAACAAGTT GCGAACATCT AGTTTGTTGA    3600
AGGAAGAGGT AGATATATGT TCTTTATGTT AATACAATTT AAATAATATT TTCAACCAAA    3660
ATTTCATAAT ATATCTGTAA TTTGATTGTA TGATGTGTTA TTGTTTATAT GTGGCTATTA    3720
AGGGATGATT ATTTTGCAGG TTGTGATTCC TAAGTTGGAG ACACTTCAAA TTGATGGCAT    3780
GGAGAACTTA GAAGAAATAT GGCCTTGTGA GCTTAGTGGA GGTGAGAAAG TTAAGTTGAG    3840
AGAGATTAAA GTGAGTAGCT GTGATAAGCT TGTGAATCTA TTTCCGCACA ATCCCATGTC    3900
TCTGTTGCAT CATCTTGAAG AGCTTAAAGT CAAAAATTGT CGTTCCATTG AGTCGTTATT    3960
CAACATCGAC TTGGATTGTG TCAGTGCAAT TGGAGAAGAA GACAACAAGA GCATCTTAAG    4020
AAGAATCAAA GTGAAGAATT TAGGGAAGCT AAGAGAGGTG TGGAGGATAA AAGGTGCAGA    4080
TAACTCTCGT CCCCTCATCC ATGGCTTTCC AGCTGTTGAA AGCATAAGTA TCTGGGGATG    4140
TAAGCGGTTT AGAAATATAT TCACACCTAT CACCGCCAAT TTTGATCTGG TGGCACTTTT    4200
GGAGATTCAC ATAGGAAATT ACAGAGAAAA TCATGAATCG GAAGAGCAGG TAACGCTTTC    4260
AATTTCACTT TCTTACTTAA TTAAGGACTA AGCTCTTGTT TTTTGAATAA TAAAGAGGTG    4320
GGATGACTAA ACTTGGGCAT CACAATTGTA ACAAAATGTT ACAAACCATG AACGTACAAA    4380
CCATTTCTTG AATTAAGGTT TCAATACAAG TCATTTACAA ATATGGCTTA AGTTTTTTA    4440
TATTTATGTA TCAACATTAT TTTTCATTAG AGGTCATTAT TATAATAGTA AGTTTAAAGC    4500
AATTTAAATT AGCACTAATT TTTCATCATC TAACTTTAGC TAATAAATCG TTATAAATGT    4560
CAATAGCTAA AATAAAAATA TTTGACATTC ACTGAGAGCA ATTTTTTCTA AACATGATTG    4620
CAAATGATTA AAACTTAAAT TTAAACTAAA AAGATTTTTA TATATGTTAT ACAAAATTTA    4680
CAAATTGAAA TTGGATATGT TAATTAACAG TTTATAATTA TTGTATTACA AAGCGATATA    4740
TAATAAAATA TTATTTTTCT GTAGTCATGT ATAATTGTAT ATGTAAATGA TTTTTTAAGA    4800
TGGTAGAAGT GGAAACTAGT CAATCTCACT TAACTCATTG TCACACCAGT TTTATATCCG    4860
TTTCTCTCTC TCTCTCTTCT TGCCTCCATC TTTTTTCAAC TCATAACACA TAAAAATAAC    4920
ATATTTTCCA ACACATTTAA GTCACTACCA CATCATTATT TTTAATTTAA TTAAATTAGA    4980
AAATATAAAA TTAAATAAAA CATAACATTT TTTTATTAAA AGGCACTAAT ACAAATAAAA    5040
AGATACACGG TAAATAAAAA AACGATAATT AGAAAAAAAA CATAATAAAA AAAGACAACA    5100
TTAAAAATAW AAAGCGACAA CTAAAATTAA CTAATGATCA AGAAAATTCT AAAACTCCCA    5160
CCATATTTTT CTGCAATTTG TCATTTATGT TCAAACACCA TTCGCAGAAT CCCTCCTATC    5220
AAGTGATCAT GTTGATTGAG AAAAAACTGT ATGTCTCTCT CATGTATCTC CAAGTCCAAC    5280
AAGTTAGCTT TCATTTCTTC ATTTTCTCAT GTAAGACGCA AATTTTCATC CCGATATTGT    5340
TTTCTATCTT CCACCTCTAC TTTATTCACA GTGTGGATGA AGGAGAGGAC AGCGATTCTC    5400
```

-continued

```
GTACGAACGG TTACGATTCG ACTGGCCGTC GTTTTACAAT CCCGCGGCCA TGGCGGCCGG    5460

GAGCATGCGA CGTCGGGCCC ATTCGCCCTA TAGTGGTCGT AATACA                  5506
```

(2) INFORMATION FOR SEQ ID NO:94:

(i) SEQUENCE CHARACTERISTICS:
        (A) LENGTH: 7832 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..7832
        (D) OTHER INFORMATION: /note= "RG2D continuation"

(xi) SEQUENCE DESCRIPTION: SEQ ID NO:94:

```
TGAGCCTCCG ATGCTTAGTC CACTTGGCAC AGTTCAAGTC CAATCAACTT ATAACCCATT     60

TTTCTTCAAG TTGTCTTCAA GTTAAGCCCA ATTTGCCTTC TCCAAATCAT CCATAACTTC    120

ATGGAATCGC CCCTTCATCT TAATCCCGAA TGCACAATTA TTCTCCCATC TTCATTTTAA    180

GCAAGAGGCC ACCTTCTTCA TGCTTCATCC ATCAATAGTC TGTTGGAATA GTGTCTAAGG    240

CTGCAACTAT ATTAGACAAG TATTTGACCC GGTTGTGCAT GGTCCTTTTG GGTTGCCTTC    300

ACCATAGCAA CTTGATAGGA TGATTTATTA AGAGAGTA AATATTATTA ATATATTATG     360

AGAATAATAT AATGAATAAT ATATTTGTTA TTTGATTAAT ATAAGTCATA GAATTAATTA    420

GAATTAATTT GGTGACTTAA AGAGATTAAT TAAATAAAGG GGTATAAACT GTCAATTGTT    480

TGATAGTTAA GCTTTAGACT GTAAATCCAT TTGGATATGG TATGGACGAA TCCTAAGGGA    540

TTTAGGATAG CTAAAATCGT CCATATGAGT TATCTAAGAA GGATTTGGAT AGCCTTAAGA    600

GAAGATTATC TGATAGGGAC TTATCTGTAA TCCTTAAGGA GTCTACAAGT ATAAATAGAC    660

CCTATGGCTG ATGGAATTCG ACACATCTCC TAAAGTAAGA GAGCCTTGGC CGAATTCCTC    720

CCCTCACCTC TCTCCTAAAT CATTCTTCTT GCTATTGGTG TTTGTAAGCC ATTAGAGGAG    780

TGACATTTGT GACTCTAGAA TCTCCAAGAC CTCAAGATCA ACAAGGAATT CAAAGGTATG    840

ATTCTAGATC TGTTTCAATG TTGTTATTTG TCCTAATTAG TCATTAGAAG ACTTGGATTC    900

AAAGCATGTT TATTAGAAAG CCTAGATCYG AGCAATAGGG TTTTGCATGC GCACATAGGA    960

AAGTTCTTAT GGCTAAAACC CATCATAGTC CACTTCATGT ATCATCTCTA CTAGTTATTT   1020

AGTCCATAAT CCTTGTTGTC CTCCAAGTTT AATTACCTCC CTTAGTTCCT GTTCTGCTAG   1080

TTTCCTTAAA ATTTGCTATT AAGATCACAG AACTAGAGAG TACCCAAAAT GGTTATAAAA   1140

TAACAAAAAG GAAATATGC ATGAAGATTA ACTAAATTAT AAATGTAATA TGCTAAAATA    1200

AACTATAAAA AAAAAGTAAA TAAAATGAAA CTATCACACT CCGACCACCC TTATAGGCTT   1260

GTACTGCACC CACCCTTCAT TCCTTGTACC AATATGGGAT GGAAACATTA TTCATTAAGC   1320

CAAAAAACTA ACATTTAAGG GGTGAGTGAC AAAGGTAAGT ACTAAAGACA ACAATAATCC   1380

ATTTTTCTTG TACATACACA ACACACACAT AGGGGCGGAC GTAGGATTTG TAGTATGTGT   1440

TGTGGGTGAC ACATTTTTTC TTTTACGTAG TGACACAATA GTAGAGAAAA CGAGAAATTC   1500

CAATTTTTTA CATTGTGTTC GAAAAAATAT ACAGGGGTTG CTGGTGCTAC TCTGGGCACC   1560

AAAGTGGAAC CGCCCCTGCA CACACACACA CATAGAGGGA GAGAGAGAGG AGAAAGAGAG   1620

AGAGAGAGAG AGAGAGAGAG AGAGAGATTT TGGGATGTGA TACTTCTTTT GGGAAAATGG   1680
```

```
AGCAATATCT TTAATATTGT ATTTTTTTAA TGTAATTTAT ATATTTAATC ATTTTAGTTT      1740

ATAACTTTTA GTTTTTTTTA TTTTAATCTG TATATTTAAT CATTTCAGTT TATAAGTTTT      1800

ATTTATTTTG GTATACCAGA AAAAAAAGTC TTTTATGTGT TGGATTTAAC ATAAAAATCT      1860

AACAATATTA ATCAAAAAGA CCAAACATGT GGACAATTAT GTATATAATT AATTCTCAAT      1920

GGTCTTAGTG TAACGATATA AATTTCAAAA CAATTTTTCA CATTAAAAAA AACACTTTCA      1980

GTCATAATTG TTATAAATTA TCATTGTATC ACAAAATCAG TTCATAACAT CACATCCCAA      2040

GATCAATAAA GTGTAAATAC TCCTCATGTG TGTACTAATC AAGCCGACGC CTTCCCGCGA      2100

TTCTCACTGG TACCTGAAAC ACGTAACATA ACAACTGTAA GCATAAATGC TTAGTGAGTT      2160

CCCCAAAATA CCACATACCA CATATATGCC TTTCCAGGCC ATAACTCTGT AGGATCTTCC      2220

GACCCAAGTG TCTCAGGGGA CTTCCGTCCC GAATCCCGGT AGACCTTCCG GTCCTACCCG      2280

TATTGACCTT CCGGTCCGTA TCATACAAA CATACATAAC ACATACATAT CACATAACAA      2340

CATATAGCAC ATACATCTCA TAACATAAAA GACCTTCCGG TCACATAAAG GTACCCTTCC      2400

AGGTACAGTA TAGTGAGAAN ACTCACCTCG TATGATGTCT AATACCTCAC GTGCTCGATA      2460

TCCCTGAATC TCGAAACAAT GACCTAGCCC CGCCTACTCA CATAAAGTAA TTATTTCAAA      2520

TCATTAACGG CTCTCAAGGC TAGACTACAT CCCTTTCTAT AAATCCACAG AAGGGTAAAA      2580

GACCATTTTA CCCCTCCTTG ACCCAAAAGT CCAAATGTTG ATCAAAACCC CAAAAGTCAA      2640

CGAAAGACAA TGGTCAACTT TGACCCTACT CGTGGAGTGC ACAAAGGTGA CTCGGCAAGT      2700

ACATGCGGGT CCTCTGAATC CTTTCAGTCT CTCTTGGCTC GTCGAGTCTT TCTTCCACCC      2760

GACGAGTTAC ACCTGTCATG AATCGCGGGG CAACCCCGAC TCGACTTGTC GAGTCCGCTC      2820

ATGGACTCAA CGAGTTCATT CCATGCTCAC ACTCAAATGA CCTCCTGAGG TCAGATCTGT      2880

TCCTCTAATC CATAGATCTG ACCTTCCCAA GCTCAATAAA CACGTAAAGG TTCGAACTTG      2940

ATACTCATGC AACGTCCAAA TGATTCTACT TGATGATTTA GCCCCAAATA CAACATCCTA      3000

AGTCCATACG ACCTTATTTT TCTCAAATAA CAACACATAT ATTTAATTAC CAATGACAGT      3060

AATAGATATC ATATAAAGTA TTTGTAACAC TTTGTAAGAA CCTTGCTACT ATAGGTAAAA      3120

AGAAACATTT CAAAGTACAT GCCCTAATTA GAAAAAAAGT TATAAAAAAA TAATGACTAG      3180

GGGCGTGTTT TTTTTACTAG TTTGTATCAA ATTATATCAA AATTTAAGGT GGAAAAGAAT      3240

GACGACCACA TTAACCAGAA ATGTAATTAT TTTTTTATTT GGTAATTTTT AATATTTGTT      3300

GTGATCTATG TATTTAAAAG TAAATATCAA ACAAGAACAT AATCCAAACC CTAAATTGCA      3360

AGTCTCGCCC AATTTCTCTA TCACTAGTCC TCACTTACGA TGGCGTTACG TCGCTCTCTC      3420

ACTTCCTACA ACCCATTGTT GCTACTAATT ACACTAACGA AAAGTTGAAT ATCCATATAT      3480

TTATTTGGAT GTGAAATTGA ACGAATCTCG TCAAATTTTT TATTTGTTG ATGGATTTGA      3540

GTGGAAGTTT AGGCAGAACG GGAATGATGG TCTGCAAGTG GTTATAAACA TGGGTGAAGA      3600

TAAAATGGAG TTGTCGCCGT TGTATTATAG ATCTCTTAGG GGTTTGATTC TGAGTTATTA      3660

CTGTATACGT AGCCTCTTTA CAACGACCAT TCTTCCAAGT ACCATTTGAT CTTTTTAGAA      3720

TCCAGTTGTC TGAAACACCC TGATTTGGAT CAAATATCAC CAACAACTCT TAAGAACTGG      3780

ACTAATTAAT TGTTTTCTTG ATCTTGATAA CAAGAGGAAA CACGTCACCA TATCTTTTAT      3840

TTTAAATTTG CTTTTGGTGT ATTTTCTTTC TTCCCATTTC TTTCTTGATC TGTTCCAGAT      3900

GGTATTTGGT GTGGATAATT TACACCTGGA GATTGTGAAC GATGGGAAGG GGTATGTGAT      3960

TTACAGAGGA TGTGGCTTGT GGTTGAGGAT GGTTTATGGC TGGCCGAGTC TAATTTATAT      4020

TTATATAAAC AAATAAATAT ATAAAACAAG GGTAAAATAT GTATTTAAGC GTCCTCTTTT      4080
```

```
AATGGTGACA ATTTTTACAG TTTACTCTCT TTGTTTTTTA ATTGTGATGC CCACGATCGA    4140

ACTCATTCAT CCCCCCCCCT TTTTTTTTTA AAATAAAAAA TTAAGAAGGG GTACCACCAT    4200

ATACCCGTGT CAGCTTCTTA TTCCCAAGCA GTCAAATAGG GACTTAGGTT GTATGGAAAC    4260

AGTTCCGTGA CTTGGATGGC AGATAAATTT AGTAAACTTA ACCCTTCAAT TAACCTACCT    4320

TTTTCTTATT AACTCAATTT CAAGCTAAAT TCTGATTCTT GTTGAAAAT AAGTTGCATC    4380

TTTATTTTTG CATATTATCT TGTTGCATAG GATCCTTAGC ATCTTTTAAT AGTTTATTTG    4440

AAGCTGAAAG ATCCAACTAG TTTTGATCTG TTGGCATTTT CCATCATTTG CAACTGTTTC    4500

TTGAAAAAAA ATACCTAAAA TCAAAATAAC CATTTTCAAA TCCAAAATTA TAAGAGAGAA    4560

TTGTTAATGG ACGTGGAATC ATAAATCATT AACACAGTTC AGTACACAAG TTGCTAATTA    4620

CATTTCTTGC TGTGCAGATT GAAATTCTAT CAGAGAAAGA GACATTACAA GAAGTCACTG    4680

ATACTAATAT TTCTAATGAT GTTGTATTAT TCCCATCCTG TCTCATGCAC TCTTTTCATA    4740

ACCTCCATAA ACTTAAATTG GAAAATTATG AAGGAGTGGA GGTGGTGTTT GAGATAGAGA    4800

GTGAGAGTCC AACATGTAGA GAATTGGTAA CAACTCACAA TAACCAACAA CAGCCTATTA    4860

TACTTCCCAA CCTCCAGGAA TTGTATCTAA GGAATATGGA CAACACGAGT CATGTGTGGA    4920

AGTGCAGCAA CTGGAATAAA TTCTTCACTC TTCCAAAACA ACAATCAGAA TCACCATTCC    4980

ACAACCTCAC AACCATAGAA ATGAGATGGT GTCATGGCTT TAGGTACTTG TTTTCGCCTC    5040

TCATGGCAGA ACTTCTTTCC AACCTAAAGA AAGTCAAGAT ACTTGGGTGT GATGGTATTG    5100

AAGAAGTTGT TCAAACAGA GATGATGAGG ATGAAGAAAT GACTACATTT ACATCTACCC    5160

ACACAACCAC CAACTTGTTC CCTCATCTTG ATTCTCTCAC TCTAAAATAC ATGCACTGTC    5220

TGAAGTGTAT TGGTGGAGGT GGTGCCAAGG ATGAGGGGAG CAATGAAATA TCTTTCAATA    5280

ATACCACTAC AACTACCGAT CAATTTAAGG TATGTTTGTA CATATTTAAT TATATATTTA    5340

ATTTCCTTGT TAATTTCCTT TTCTTTGCAA TATTCTATGC GAACTCAAGA ATGGGATTTG    5400

GAGGCATATA AAGTTACATT CATTTGAACA AGTATTACCT TTTATTTGTT ATTTATCATT    5460

TTCATATCAA GTACCTATAA CATTTCTTTT TTATTTTTCT AATTAGAAGA GGTCCACATG    5520

TCTAATTAGG TTTTCCATTC TATGTGTAAC CTCTATTCTC TCTGTAATCA AGCATCTTAG    5580

ATTATTTATC CATTTTCATA ATTGTGTTTA TTTTTACAGT TTTTTTTTTT ATTTAATTTT    5640

AATAATTTAA TTTTAATTTA TTTATTATTT TTTTTTTGGT AATTGCAACC TGTCATATAT    5700

TCAAGTCTTA ATGTAACATA ATAATACATT TTATACCCAC TATACTAAGA TAATAATTAC    5760

CTAAAGGGAT GGATGCCATG ACACTGCTAC ACTTCAGNAA CTCTAGTAAG GGCAGTTATG    5820

GAAGTTCAAT AAAATGATAA TGGCATCTTT TGATGGGTAA TATAGGCAAT TTAAGTTTTA    5880

TTTCTGTTAA AGCAGTATTT AGCTAGTAGT GGCCAGTAGG AGAGGAGAAT ATCACCTTTT    5940

GTCAAAATCT GGTCATTGTA CCCAGAATTT AGTTAAATGT AACATTTTAG ATATTAGGGG    6000

TCATCAGGTG ACAGATATTG TAGAATAGAA CAATATGTAA TATTACCCAA ACTATTTTT    6060

TCTAAGGTTG CTCTGTTAAA TATGTGCTTT CTTGATTTCA TTGAATTTGC ATTCGTATAT    6120

TTTAGGTGGT AAACTGATTG TCTCTTCAAT AAATCCTGAA ATTAATTAAA AAAAAAAAA    6180

CAAAAGTACA TTTTTGATTT GGAGAGCACT GGTATCATTT AGTATAGAAA AAACTAGAT     6240

TTTGAATTAY CTTTCTTATA TAAAAGTTGT GTATATAGTT TAATTAGTTT TACATCATTT    6300

TTCTATGTGT TGTTGCAGTT GTCTGAAGCA GGTGGTGTTT GTTGGAGCTT ATGCCAATAC    6360

TCTAGAGAGA TAGAGATATA TAGGTGTGAT GCACTGTCAA GTGTAATTCC ATGTTACGCA    6420
```

```
GCAGGACAAA TGCAAAAGCT GCAAGTGCTG ACAGTCAGTT CTTGTAATGG TCTGAAGGAG    6480

GTATTTGAAA CTCAATTAGG GACGAGCAGC AACAAAAACA ACGAGAAGAG TGGTTGTGAG    6540

GAAGGAATTC CAAGAGTAAA TAACAATGTT ATTATGCTTC CCAATCTAAA GATATTGGAA    6600

ATCTACGGTT GTGGGGGTTT GGAACATATA TTCACATTCT CTGCACTTGA AAGCCTGAGA    6660

CAGCTCCAAG AGTAACGAT TAAGGGTTAC TACTCTTGTC AATCTTCCAA ACCTCAAAGA    6720

AATGAGGTTG GAGTGGCTAA GTAATCTGAG GTATATATGG AAGAGCAATC AGTGGACAGC    6780

ATTTGAGTTT CCAAACCTAA CAAGAGTTGA AATTTGTGAA TGTAATTCAT TAGAACATGT    6840

ATTTACTAGT TCCATGGTTG GTAGTCTATT GCAACTCCAA GAGCTACATA TATTTAACTG    6900

CAGTCTGATG GAGGAGGTAA TTGTTAAGGA TGCAGATGTT TCTGTAGAAG AAGACAAAGA    6960

GAAAGAATCT GATGGCAAGA CGAATAAGGA GATACTTGTG TTACCTCATC TAAAGTCCTT    7020

GAAATTACAA CTTCTTCGAA GTCTTAAGGG GTTTAGCTTG GGGAAGGAGG ATTTTTCATT    7080

CCCATTATTG GATACTTTAG AAATCAAAAG ATGCCCAACA ATAACCACCT TCACCAAAGG    7140

AAATTCCGCT ACTCCACAAC TAAAAGAAAT ACAAACAAAT TTTGGCTTCT TTTATGCTGC    7200

AGGGGAAAAA GACATCAACT CTCTTATAAA GATCAAACAA CAGGTAAATC AGATCTTTGT    7260

TGCTTTAATA ATTCTTAAAC TACATTTGAA AAGCTTCATG CAAGTTTTTT TGTTATATTG    7320

TCAAAAACCG CAACCTACAT TCAGCTTTAT ATTTATGTAC TTTATGCAGG ATTTCAAACA    7380

AGACTCAGAT TAATGTGAAG TGAATATTAA AGGTAAATTA TATTTTCATG TTCCTAGTTG    7440

CCTATTAATT AATGGCCTTT TAGTTCATGA TTTTTGGATG TATTCTTCAT GATGATGTGA    7500

ATCTTCTAAT ACCCCATTCA TTGTTTGGTT GAATGTTGAC TCTATGTCAG GATGAATATT    7560

CAAGGGAAGA ATTGTTCATC AWATGAAGGA CATTAAAGAA CATGGATGCT ATGAAGATGT    7620

TGGGAAAACA TATGTATCAA GTGGCAARCT GCTTAATGAT CTAAGTTTGT TGGTTGANGA    7680

TGTTGATTTT AATATTTCAA ATTCATTGGT TATATGGGCT TATCAATAGT GTTAATGGGA    7740

TAATGAGTGA CTTAACCTAA ATTATGTTGT TGGTAAATGT TGGACAAGTA TGGAAAATTA    7800

GGAATGACTT GTGAAAAAAA AATAAAAAAA AA                                  7832
```

(2) INFORMATION FOR SEQ ID NO:95:

(i) SEQUENCE CHARACTERISTICS:
    (A) LENGTH: 1604 amino acids
    (B) TYPE: amino acid
    (C) STRANDEDNESS:
    (D) TOPOLOGY: linear (ii) MOLECULE TYPE: protein (ix) FEATURE:
    (A) NAME/KEY: -
    (B) LOCATION: 1..1604
    (D) OTHER INFORMATION: /note= "RG2D deduced sequence"

(xi) SEQUENCE DESCRIPTION: SEQ ID NO:95:

```
Met Ala Met Glu Thr Ala Asn Glu Ile Ile Lys Gln Val Val Pro Val
 1               5                  10                  15

Leu Met Val Pro Ile Asn Asp Tyr Leu Arg Tyr Val Val Ser Cys Arg
                20                  25                  30

Lys Tyr Ile Ser Asp Met Asp Leu Lys Met Lys Glu Leu Lys Glu Ala
            35                  40                  45

Lys Asp Asn Val Glu Glu His Lys Asn His Asn Ile Ser Asn Arg Leu
        50                  55                  60

Glu Val Pro Ala Ala Gln Val Gln Ser Trp Leu Glu Asp Val Glu Lys
```

-continued

```
                65                  70                  75                  80
Ile Asn Ala Lys Val Glu Thr Val Pro Lys Asp Val Gly Cys Cys Phe
                85                  90                  95
Asn Leu Lys Ile Arg Tyr Arg Ala Gly Arg Asp Ala Phe Asn Ile Ile
                100                 105                 110
Glu Glu Ile Asp Ser Val Met Arg Arg His Ser Leu Ile Thr Trp Thr
                115                 120                 125
Asp His Pro Ile Pro Leu Gly Arg Val Asp Ser Val Met Ala Ser Thr
                130                 135                 140
Ser Thr Leu Ser Thr Glu His Asn Asp Phe Gln Ser Arg Glu Val Arg
145                 150                 155                 160
Phe Ser Glu Ala Leu Lys Ala Leu Glu Ala Asn His Met Ile Ala Leu
                165                 170                 175
Cys Gly Met Gly Arg Val Gly Lys Thr His Met Met Gln Arg Leu Lys
                180                 185                 190
Lys Val Ala Lys Glu Lys Arg Lys Phe Gly Tyr Ile Ile Glu Ala Val
                195                 200                 205
Ile Gly Glu Ile Ser Asp Pro Ile Ala Ile Gln Gln Val Val Ala Asp
                210                 215                 220
Tyr Leu Cys Ile Glu Leu Lys Glu Ser Asp Lys Lys Thr Arg Ala Glu
225                 230                 235                 240
Lys Leu Arg Gln Gly Phe Lys Ala Lys Ser Asp Gly Gly Asn Thr Lys
                245                 250                 255
Phe Leu Ile Ile Leu Asp Asp Val Trp Gln Ser Val Asp Leu Glu Asp
                260                 265                 270
Ile Gly Leu Ser Pro Ser Pro Asn Gln Gly Val Asp Phe Lys Val Leu
                275                 280                 285
Leu Thr Ser Arg Asp Glu His Val Cys Ser Val Met Gly Val Glu Ala
                290                 295                 300
Asn Ser Ile Ile Asn Val Gly Leu Leu Ile Glu Ala Glu Ala Gln Arg
305                 310                 315                 320
Leu Phe Gln Gln Phe Val Glu Thr Ser Glu Pro Glu Leu His Lys Ile
                325                 330                 335
Gly Glu Asp Ile Val Arg Arg Cys Cys Gly Leu Pro Ile Ala Ile Lys
                340                 345                 350
Thr Met Ala Cys Thr Leu Arg Asn Lys Arg Lys Asp Ala Trp Lys Asp
                355                 360                 365
Ala Leu Ser Arg Leu Gln His His Asp Ile Gly Asn Val Ala Thr Ala
370                 375                 380
Val Phe Arg Thr Ser Tyr Glu Asn Leu Pro Asp Lys Glu Thr Lys Ser
385                 390                 395                 400
Val Phe Leu Met Cys Gly Leu Phe Pro Glu Asp Phe Asn Ile Pro Thr
                405                 410                 415
Glu Glu Leu Met Arg Tyr Gly Trp Gly Leu Lys Leu Phe Asp Arg Val
                420                 425                 430
Tyr Thr Ile Ile Glu Ala Arg Asn Arg Leu Asn Thr Cys Ile Glu Arg
                435                 440                 445
Leu Val Gln Ala Asn Leu Leu Ile Gly Ser Asp Asn Gly Val His Val
                450                 455                 460
Lys Met His Asp Leu Val Arg Ala Phe Val Leu Gly Met Tyr Ser Glu
465                 470                 475                 480
Val Glu Gln Ala Ser Ile Val Asn His Gly Asn Met Pro Gly Trp Pro
                485                 490                 495
```

```
Asp Glu Asn Asp Met Ile Val His Ser Cys Lys Arg Ile Ser Leu Thr
                500                 505                 510
Cys Lys Gly Met Ile Glu Ile Pro Val Asp Leu Lys Phe Pro Lys Leu
            515                 520                 525
Thr Ile Leu Lys Leu Met His Gly Asp Lys Ser Leu Lys Phe Pro Gln
        530                 535                 540
Glu Phe Tyr Glu Gly Met Glu Lys Leu Gln Val Ile Ser Tyr Asp Lys
545                 550                 555                 560
Met Lys Tyr Pro Leu Leu Pro Leu Ala Pro Gln Cys Ser Thr Asn Ile
                565                 570                 575
Arg Val Leu His Leu Thr Glu Cys Ser Leu Lys Met Phe Asp Cys Ser
            580                 585                 590
Ser Ile Gly Asn Leu Ser Asn Leu Glu Val Leu Ser Phe Ala Asn Ser
        595                 600                 605
Arg Ile Glu Trp Leu Pro Ser Thr Val Arg Asn Leu Lys Lys Leu Arg
    610                 615                 620
Leu Leu Asp Leu Arg Phe Cys Asp Gly Leu Arg Ile Glu Gln Gly Val
625                 630                 635                 640
Leu Lys Ser Leu Val Lys Leu Glu Glu Phe Tyr Ile Gly Asn Ala Tyr
                645                 650                 655
Gly Phe Ile Asp Asp Asn Cys Lys Asp Met Ala Glu Arg Ser Tyr Asn
            660                 665                 670
Leu Ser Ala Leu Glu Phe Ala Phe Phe Asn Asn Lys Ala Glu Val Lys
        675                 680                 685
Asn Met Ser Phe Glu Asn Leu Glu Arg Phe Lys Ile Ser Val Gly Cys
    690                 695                 700
Ser Phe Asp Gly Asn Ile Ser Met Ser Ser His Ser Tyr Glu Asn Met
705                 710                 715                 720
Leu Gln Leu Val Thr Asn Lys Gly Asp Val Leu Asp Ser Lys Leu Asn
                725                 730                 735
Gly Leu Phe Leu Lys Thr Glu Val Leu Phe Leu Ser Val His Gly Met
            740                 745                 750
Asn Asp Leu Glu Asp Val Glu Val Lys Ser Thr His Pro Thr Gln Ser
        755                 760                 765
Ser Ser Phe Cys Asn Leu Lys Val Arg Ile Ile Ser Lys Cys Val Glu
    770                 775                 780
Leu Arg Tyr Leu Phe Lys Leu His Val Ala Asn Thr Leu Ser Ser Leu
785                 790                 795                 800
Glu His Leu Glu Val Cys Gly Cys Glu Asn Met Glu Glu Leu Ile His
                805                 810                 815
Thr Gly Ile Gly Gly Cys Gly Glu Thr Ile Thr Phe Pro Lys Leu
            820                 825                 830
Lys Ser Leu Ser Leu Ser Gln Leu Pro Lys Leu Ser Gly Leu Cys His
        835                 840                 845
Asn Val Asn Ile Ile Gly Leu Pro His Leu Val Asp Leu Lys Leu Lys
    850                 855                 860
Gly Ile Pro Gly Phe Thr Val Ile Tyr Pro Gln Asn Lys Leu Arg Thr
865                 870                 875                 880
Ser Ser Leu Leu Lys Glu Val Val Ile Pro Lys Leu Glu Thr Leu
                885                 890                 895
Gln Ile Asp Gly Met Glu Asn Leu Glu Glu Ile Trp Pro Cys Glu Leu
            900                 905                 910
```

-continued

```
Ser Gly Gly Glu Lys Val Lys Leu Arg Glu Ile Lys Val Ser Ser Cys
        915                 920                 925

Asp Lys Leu Val Asn Leu Phe Pro His Asn Pro Met Ser Leu Leu His
930                 935                 940

His Leu Glu Glu Leu Lys Val Lys Asn Cys Arg Ser Ile Glu Ser Leu
945                 950                 955                 960

Phe Asn Ile Asp Leu Asp Cys Val Ser Ala Ile Gly Glu Glu Asp Asn
                965                 970                 975

Lys Ser Ile Leu Arg Arg Ile Lys Val Lys Asn Leu Gly Lys Leu Arg
                980                 985                 990

Glu Val Trp Arg Ile Lys Gly Ala Asp Asn Ser Arg Pro Leu Ile His
                995                1000                1005

Gly Phe Pro Ala Val Glu Ser Ile Ser Ile Trp Gly Cys Lys Arg Phe
       1010                1015                1020

Arg Asn Ile Phe Thr Pro Ile Thr Ala Asn Phe Asp Leu Val Ala Leu
1025                1030                1035                1040

Leu Glu Ile His Ile Gly Asn Tyr Arg Glu Asn His Glu Ser Glu Glu
                1045                1050                1055

Gln Ile Glu Ile Leu Ser Glu Lys Glu Thr Leu Gln Glu Val Thr Asp
                1060                1065                1070

Thr Asn Ile Ser Asn Asp Val Val Leu Phe Pro Ser Cys Leu Met His
       1075                1080                1085

Ser Phe His Asn Leu His Lys Leu Lys Leu Glu Asn Tyr Glu Gly Val
       1090                1095                1100

Glu Val Val Phe Glu Ile Glu Ser Gly Ser Pro Thr Cys Arg Glu Leu
1105                1110                1115                1120

Val Thr Thr His Asn Asn Gln Gln Gln Pro Ile Ile Leu Pro Asn Leu
                1125                1130                1135

Gln Glu Leu Tyr Leu Arg Asn Met Asp Asn Thr Ser His Val Trp Lys
                1140                1145                1150

Cys Ser Asn Trp Asn Lys Phe Phe Thr Leu Pro Lys Gln Gln Ser Glu
       1155                1160                1165

Ser Pro Phe His Asn Leu Thr Thr Ile Glu Met Arg Trp Cys His Gly
       1170                1175                1180

Phe Arg Tyr Leu Phe Ser Pro Leu Met Ala Glu Leu Leu Ser Asn Leu
1185                1190                1195                1200

Lys Lys Val Lys Ile Leu Gly Cys Asp Gly Ile Glu Glu Val Val Ser
                1205                1210                1215

Asn Arg Asp Asp Glu Asp Glu Glu Met Thr Thr Phe Thr Ser Thr His
                1220                1225                1230

Thr Thr Thr Asn Leu Phe Pro His Leu Asp Ser Leu Thr Leu Lys Tyr
       1235                1240                1245

Met His Cys Leu Lys Cys Ile Gly Gly Gly Ala Lys Asp Glu Gly
       1250                1255                1260

Ser Asn Glu Ile Ser Phe Asn Asn Thr Thr Thr Thr Asp Gln Phe
1265                1270                1275                1280

Lys Leu Ser Glu Ala Gly Gly Val Cys Trp Ser Leu Cys Gln Tyr Ser
                1285                1290                1295

Arg Glu Ile Glu Ile Tyr Arg Cys Asp Ala Leu Ser Ser Val Ile Pro
                1300                1305                1310

Cys Tyr Ala Ala Gly Gln Met Gln Lys Leu Gln Val Leu Thr Val Ser
       1315                1320                1325

Ser Cys Asn Gly Leu Lys Glu Val Phe Glu Thr Gln Leu Gly Thr Ser
```

```
                1330              1335              1340
Ser Asn Lys Asn Asn Glu Lys Ser Gly Cys Glu Glu Gly Ile Pro Arg
1345              1350              1355              1360

Val Asn Asn Asn Val Ile Met Leu Pro Asn Leu Lys Ile Leu Glu Ile
                1365              1370              1375

Tyr Gly Cys Gly Gly Leu Glu His Ile Phe Thr Phe Ser Ala Leu Glu
                1380              1385              1390

Ser Leu Arg Gln Leu Gln Glu Leu Thr Ile Lys Gly Tyr Tyr Thr Leu
                1395              1400              1405

Val Asn Leu Pro Asn Leu Lys Glu Met Arg Leu Glu Trp Leu Ser Asn
                1410              1415              1420

Leu Arg Tyr Ile Trp Lys Ser Asn Gln Trp Thr Ala Phe Glu Phe Pro
1425              1430              1435              1440

Asn Leu Thr Arg Val Glu Ile Cys Glu Cys Asn Ser Leu Glu His Val
                1445              1450              1455

Phe Thr Ser Ser Met Val Gly Ser Leu Leu Gln Leu Gln Glu Leu His
                1460              1465              1470

Ile Phe Asn Cys Ser Leu Met Glu Glu Val Ile Val Lys Asp Ala Asp
                1475              1480              1485

Val Ser Val Glu Glu Asp Lys Glu Lys Glu Ser Asp Gly Lys Thr Asn
                1490              1495              1500

Lys Glu Ile Leu Val Leu Pro His Leu Lys Ser Leu Lys Leu Gln Leu
1505              1510              1515              1520

Leu Arg Ser Leu Lys Gly Phe Ser Leu Gly Lys Glu Asp Phe Ser Phe
                1525              1530              1535

Pro Leu Leu Asp Thr Leu Glu Ile Lys Arg Cys Pro Thr Ile Thr Thr
                1540              1545              1550

Phe Thr Lys Gly Asn Ser Ala Thr Pro Gln Leu Lys Glu Ile Gln Thr
                1555              1560              1565

Asn Phe Gly Phe Phe Tyr Ala Ala Gly Glu Lys Asp Ile Asn Ser Leu
                1570              1575              1580

Ile Lys Ile Lys Gln Gln Asp Phe Lys Gly Asp Ser Asp Xaa Cys Glu
1585              1590              1595              1600

Val Asn Ile Lys
```

(2) INFORMATION FOR SEQ ID NO:96:

(i) SEQUENCE CHARACTERISTICS:
        (A) LENGTH: 1427 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1427
        (D) OTHER INFORMATION: /note= "RG2E"

(xi) SEQUENCE DESCRIPTION: SEQ ID NO:96:

```
TGGGAAGACA CAATGATGCA AAGGTTGAAG AAGGTTGCTA AAGAAAATAG AATGTTCAAT     60

TATATGGTTG AGGCAGTTAT AGGGGAAAAG ACAGACCCAC TTGCTATTCA ACAAGCTGTA    120

GCGGATTACC TTTGTATAGA GTTAAAAGAA AGCACTAAAC CAGCAAGAGC TGATAAGCTT    180

CGTGAATGGT TTAAGGCCAA CTCTGGAGAA GGTAAGAATA AGTTCCTTGT AATATTTGAT    240

GATGTTTGGC AGTCCGTTGA TCTGGAAGAC ATTGGTTTAA GTCATTTTCC AAATCAAGGT    300
```

-continued

```
GTCGACTTCA AGGTCTTGTT GACTTCACGA GACGAACATG TTTGCACAGT AATGGGGGTT      360

GAAGCTAATT CAATTCTTAA TGTGGGACTT CTAGTAGAAG CAGAAGCACA AAGTTTGTTC      420

CAGCAATTTG TAGAAACTTT TGAGCCCGAG CTCCATAAGA TAGGAGAAGA TATCGTAAGG      480

AAGTGTTGTG GTTTACCTAT TGCCATTAAA ACCATGGCAT GTACTCTAAG AAATAAAAGA      540

AAGGATGCAT GGAAGGATGC ACTTTTGCAT TTAGAGTACC ATGACATTAG CAGTGTTGCG      600

CCCAAAGTCT TTGAAACGAG CTACCATAAT CTCCACAACA AGGAGACTAA ATCTGTGTTT      660

TTGATGTGTG GTTTTTTTCC TGAAGACTTC AATATTCCAA TCGAGGAGTT GATGAGGTAT      720

GGATGGGGCT TAAAGATATT TGATAGAGTT TATACTATTA GACAAGCAAG AATCAGGCTC      780

AACACCTGCA TTGAGCGACT GGTGCAGACA AATTTGTTAA TAGAAAGTGA TGATGGTGTG      840

CACGTCAAGA TGCATGATCT GGTCCGTGCT TTCGTTTTGG TTATGTTTTC TGAAGTTGAA      900

CATGCTTCAA TTATCAACCA TGGTAATATG CTTGGATGGC CTGAAAATTA TATGACCAAC      960

TCTTGCAAAA CAATTTCATT AACATGCAAG AGTATGTCTG AATTTCCGGG AGATCTCAAG     1020

TTTCCAAACC TAACGATTTT GAAACTCATG CATGGAGATA AGTTGCTAAG ATATCCTCAA     1080

GACTTTTATG AAGGAATGGA AAAGCTCTGG GTTATATCAT ATGATGAAAT GAAGTATCCA     1140

TTGCTTCCCT CGTTACCTCA ATGCTCCATC AACCTTCGAG TGCTTCACCT CCATCGATGC     1200

TCATTAATGA TGTTTGATTG CTCTTGTATT GGAAATATGT TGAATCTGGA AGTGCTTAGC     1260

TTTGTTAAAT CTGGCATTGA ATGGTTACCT TCCACAATAG GAAATTTAAA GAAGCTAAGG     1320

TTACTTGATC TGAGAGATTG TTATGGTCTT CGTATAGAAA AAGGTGTCTT GAAAAATTTG     1380

GTGAAAATTG GAGGAATTTA TATTGGTAGA GCAGATATTT TATAGAT                   1427
```

(2) INFORMATION FOR SEQ ID NO:97:

(i) SEQUENCE CHARACTERISTICS:
        (A) LENGTH: 475 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..475
        (D) OTHER INFORMATION: /note= "RG2E deduced sequence"

(xi) SEQUENCE DESCRIPTION: SEQ ID NO:97:

```
Trp Glu Asp Thr Met Met Gln Arg Leu Lys Lys Val Ala Lys Glu Asn
1               5                   10                  15

Arg Met Phe Asn Tyr Met Val Glu Ala Val Ile Gly Glu Lys Thr Asp
            20                  25                  30

Pro Leu Ala Ile Gln Gln Ala Val Ala Asp Tyr Leu Cys Ile Glu Leu
        35                  40                  45

Lys Glu Ser Thr Lys Pro Ala Arg Ala Asp Lys Leu Arg Glu Trp Phe
    50                  55                  60

Lys Ala Asn Ser Gly Glu Gly Lys Asn Lys Phe Leu Val Ile Phe Asp
65                  70                  75                  80

Asp Val Trp Gln Ser Val Asp Leu Glu Asp Ile Gly Leu Ser His Phe
                85                  90                  95

Pro Asn Gln Gly Val Asp Phe Lys Val Leu Leu Thr Ser Arg Asp Glu
            100                 105                 110

His Val Cys Thr Val Met Gly Val Glu Ala Asn Ser Ile Leu Asn Val
```

```
                115                 120                 125
Gly Leu Leu Val Glu Ala Glu Ala Gln Ser Leu Phe Gln Gln Phe Val
            130                 135             140
Glu Thr Phe Glu Pro Glu Leu His Lys Ile Gly Glu Asp Ile Val Arg
145                 150                 155                 160
Lys Cys Cys Gly Leu Pro Ile Ala Ile Lys Thr Met Ala Cys Thr Leu
                165                 170                 175
Arg Asn Lys Arg Lys Asp Ala Trp Lys Asp Ala Leu Leu His Leu Glu
            180                 185             190
Tyr His Asp Ile Ser Ser Val Ala Pro Lys Val Phe Glu Thr Ser Tyr
            195                 200                 205
His Asn Leu His Asn Lys Glu Thr Lys Ser Val Phe Leu Met Cys Gly
            210                 215             220
Phe Phe Pro Glu Asp Phe Asn Ile Pro Ile Glu Glu Leu Met Arg Tyr
225                 230                 235                 240
Gly Trp Gly Leu Lys Ile Phe Asp Arg Val Tyr Thr Ile Arg Gln Ala
                245                 250                 255
Arg Ile Arg Leu Asn Thr Cys Ile Glu Arg Leu Val Gln Thr Asn Leu
            260                 265                 270
Leu Ile Glu Ser Asp Asp Gly Val His Val Lys Met His Asp Leu Val
        275                 280                 285
Arg Ala Phe Val Leu Val Met Phe Ser Glu Val Glu His Ala Ser Ile
290                 295                 300
Ile Asn His Gly Asn Met Leu Gly Trp Pro Glu Asn Tyr Met Thr Asn
305                 310                 315                 320
Ser Cys Lys Thr Ile Ser Leu Thr Cys Lys Ser Met Ser Glu Phe Pro
                325                 330                 335
Gly Asp Leu Lys Phe Pro Asn Leu Thr Ile Leu Lys Leu Met His Gly
            340                 345             350
Asp Lys Leu Leu Arg Tyr Pro Gln Asp Phe Tyr Glu Gly Met Glu Lys
            355                 360             365
Leu Trp Val Ile Ser Tyr Asp Glu Met Lys Tyr Pro Leu Leu Pro Ser
        370                 375             380
Leu Pro Gln Cys Ser Ile Asn Leu Arg Val Leu His Leu His Arg Cys
385                 390                 395                 400
Ser Leu Met Met Phe Asp Cys Ser Cys Ile Gly Asn Met Leu Asn Leu
                405                 410                 415
Glu Val Leu Ser Phe Val Lys Ser Gly Ile Glu Trp Leu Pro Ser Thr
            420                 425             430
Ile Gly Asn Leu Lys Lys Leu Arg Leu Leu Asp Leu Arg Asp Cys Tyr
        435                 440             445
Gly Leu Arg Ile Glu Lys Gly Val Leu Lys Asn Leu Val Lys Ile Gly
        450                 455             460
Gly Ile Tyr Ile Gly Arg Ala Asp Ile Leu Xaa
465                 470             475
```

(2) INFORMATION FOR SEQ ID NO:98:

(i) SEQUENCE CHARACTERISTICS:
        (A) LENGTH: 1434 base pairs
        (B) TYPE: nucleic acid
        (C) STRANDEDNESS: single
        (D) TOPOLOGY: linear (ii) MOLECULE TYPE: DNA (ix) FEATURE:
    (A) NAME/KEY: -
    (B) LOCATION: 1..1434
    (D) OTHER INFORMATION: /note= "RG2F"

(xi) SEQUENCE DESCRIPTION: SEQ ID NO:98:

| | |
|---|---|
| CTGTGGAAGA CACAATGATG CAAAGGCTGA AAAAGGTTGT GCATGAAAAG AAAATGTTTA | 60 |
| ACTTTATTGT TGAAGCAGTT ATAGGGGAAA AGACAGACCC CGTTGCCATT CAGGATGCTA | 120 |
| TAGCAGATTA CCTAGGTGTA GAGCTCAATG AAAAATCTAA GCAAGCAAGA GCTGATAAGC | 180 |
| TCCGTCAAGG ATTCAAGGAC AAATCAGATG GAGGCAAAAA TAAGTTCTTT GTAATACTTG | 240 |
| ACGATGTTTG GCAGTCTGTT GATCTGGAAG ATATTGGTTT AAGTCCTTTT CCAAATCAAG | 300 |
| GCGTCGACTT CAAGGTCTTG TTGACATCAC GAGACAGACA TGTTTGCACA GTGATGGGGG | 360 |
| TTGAAGCCAA ATTAATTCTA AACGTGGAC TTCTAATTGA AGCTGAAGCA CAAAGTTTGT | 420 |
| TCCACCAATT TGTTGTCACT TCTGAGCCCG AGCTCCATAA GATAGGAGAA GATATTGTAA | 480 |
| AGAAGTGTTT CGGTCTGCCA ATTGCCATCA AAACCATGGC ATGTACTCTA CGACATAAAA | 540 |
| GAAAGGATGC ATGGAAGGAT GCACTTTCAC GTTAGAGCA CCATGACATT CAAAGTGTTG | 600 |
| TGCCTAAAGT ATTTGAAACG AGCTACAACA ATCTCAAAGA CAAGGAGACT AAATCCGTAT | 660 |
| TTTTGATGTG TGGTTTGTTT CCTGAAGACT TGGATATACC TATCGAGGAG TTGATGAGGT | 720 |
| ATGGATGGGG CTTAAGATTA TTTGATAGAG TTAATACTAT TACACAAGCA AGAAACAGGC | 780 |
| TCAACACCTG CATTGAGCGA CTGGTGCACA CAAATTTGTT AATTGAAAGT GTTGATGGTG | 840 |
| TGCATGTCAA GATGCATGAT CTGGTTCGTG CTTTTGTTTT GGGAATGTTT TCTGAAGTGG | 900 |
| AGCATGCTTC AATTGTCAAC CATGGTAATA TGCCCGAGTG GACTGAAAAT GATATGACTG | 960 |
| ACTCTTGCAA ACAAATTTCA TTAACATGCA AGAGTATGTT GGAGTTTCCT GGAGACCTCA | 1020 |
| AGTTTCCAAA CCTAAAGATT TTGAAACTTA TGCATGGAGG TAAGTCACTA AGGTATCCTC | 1080 |
| AAGACTTTTA TCAAGGAATG GAAAAGCTGG AGGTTATATC ATACGATGAA ATGAAGTATC | 1140 |
| CATTGCTTCC CTCGTTGCCT CAATGTTCCA CCATCCTTCG AGTGCTTCAT CTCCATGAAT | 1200 |
| GTTCATTAAG GATGTTTGAT TGCTCTTCAA TCGGTAATCT TTTCAACATG GAAGTGCTCA | 1260 |
| GCTTTGCTAA TTCTAGCATT GAATTGTTAC CTTCCGTAAT TGGAAATTTG AAGAAGTTGC | 1320 |
| GGCTGCTAGA TTTGACAAAC TGTTATGGTG TTCGTATAGA AAAGGATGTC TTGAAAAATT | 1380 |
| TGGTGAAACT TGAAGAGCTT TATATTAGGA ATGGTCTACC AGTTTACAGA GGAT | 1434 |

(2) INFORMATION FOR SEQ ID NO:99:

(i) SEQUENCE CHARACTERISTICS:
        (A) LENGTH: 477 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..477
        (D) OTHER INFORMATION: /note= "RG2F deduced sequence"

(xi) SEQUENCE DESCRIPTION: SEQ ID NO:99:

Val Glu Asp Thr Met Met Gln Arg Leu Lys Lys Val Val His Glu Lys
1               5                   10                  15

Lys Met Phe Asn Phe Ile Val Glu Ala Val Ile Gly Glu Lys Thr Asp
            20                  25                  30

-continued

```
Pro Val Ala Ile Gln Asp Ala Ile Ala Asp Tyr Leu Gly Val Glu Leu
     35                  40                  45

Asn Glu Lys Ser Lys Gln Ala Arg Ala Asp Lys Leu Arg Gln Gly Phe
 50                  55                  60

Lys Asp Lys Ser Asp Gly Gly Lys Asn Lys Phe Phe Val Ile Leu Asp
 65                  70                  75                  80

Asp Val Trp Gln Ser Val Asp Leu Glu Asp Ile Gly Leu Ser Pro Phe
             85                  90                  95

Pro Asn Gln Gly Val Asp Phe Lys Val Leu Thr Ser Arg Asp Arg
            100                 105                 110

His Val Cys Thr Val Met Gly Val Glu Ala Lys Leu Ile Leu Asn Val
            115                 120                 125

Gly Leu Leu Ile Glu Ala Glu Ala Gln Ser Leu Phe His Gln Phe Val
        130                 135                 140

Val Thr Ser Glu Pro Glu Leu His Lys Ile Gly Glu Asp Ile Val Lys
145                 150                 155                 160

Lys Cys Phe Gly Leu Pro Ile Ala Ile Lys Thr Met Ala Cys Thr Leu
                165                 170                 175

Arg His Lys Arg Lys Asp Ala Trp Lys Asp Ala Leu Ser Arg Leu Glu
            180                 185                 190

His His Asp Ile Gln Ser Val Val Pro Lys Val Phe Glu Thr Ser Tyr
        195                 200                 205

Asn Asn Leu Lys Asp Lys Glu Thr Lys Ser Val Phe Leu Met Cys Gly
    210                 215                 220

Leu Phe Pro Glu Asp Leu Asp Ile Pro Ile Glu Glu Leu Met Arg Tyr
225                 230                 235                 240

Gly Trp Gly Leu Arg Leu Phe Asp Arg Val Asn Thr Ile Thr Gln Ala
                245                 250                 255

Arg Asn Arg Leu Asn Thr Cys Ile Glu Arg Leu Val His Thr Asn Leu
            260                 265                 270

Leu Ile Glu Ser Val Asp Gly Val His Val Lys Met His Asp Leu Val
        275                 280                 285

Arg Ala Phe Val Leu Gly Met Phe Ser Glu Val Glu His Ala Ser Ile
290                 295                 300

Val Asn His Gly Asn Met Pro Glu Trp Thr Glu Asn Asp Met Thr Asp
305                 310                 315                 320

Ser Cys Lys Gln Ile Ser Leu Thr Cys Lys Ser Met Leu Glu Phe Pro
                325                 330                 335

Gly Asp Leu Lys Phe Pro Asn Leu Lys Ile Leu Lys Leu Met His Gly
            340                 345                 350

Gly Lys Ser Leu Arg Tyr Pro Gln Asp Phe Tyr Gln Gly Met Glu Lys
        355                 360                 365

Leu Glu Val Ile Ser Tyr Asp Glu Met Lys Tyr Pro Leu Leu Pro Ser
    370                 375                 380

Leu Pro Gln Cys Ser Thr Ile Leu Arg Val Leu His Leu His Glu Cys
385                 390                 395                 400

Ser Leu Arg Met Phe Asp Cys Ser Ser Ile Gly Asn Leu Phe Asn Met
                405                 410                 415

Glu Val Leu Ser Phe Ala Asn Ser Ser Ile Glu Leu Leu Pro Ser Val
            420                 425                 430

Ile Gly Asn Leu Lys Lys Leu Arg Leu Leu Asp Leu Thr Asn Cys Tyr
        435                 440                 445

Gly Val Arg Ile Glu Lys Asp Val Leu Lys Asn Leu Val Lys Leu Glu
```

|     | 450 |     |     |     | 455 |     |     |     | 460 |
| --- | --- | --- | --- | --- | --- | --- | --- | --- | --- |
Glu Leu Tyr Ile Arg Asn Gly Leu Pro Val Tyr Arg Gly
465                 470                 475

(2) INFORMATION FOR SEQ ID NO:100:

(i) SEQUENCE CHARACTERISTICS:
        (A) LENGTH: 1465 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1465
        (D) OTHER INFORMATION: /note= "RG2G"

(xi) SEQUENCE DESCRIPTION: SEQ ID NO:100:

```
GAAGACACGA TGATGAAGAA CTGAAGGAGG TCGTGGGACA AAAGAAATCA TTCAATATTA      60

TTATTCAAGT GGTCATAGGA GAGAAGACAA ACCCTATTGC AATTCAGCAA GCTGTAGCAG     120

ATTACCTCTC TATAGAGCTG AAAGAAAACA CTAAAGAAGC AAGAGCTGAT AAGCTTCGTA     180

AACGGTTTGA AGCCGATGGA GGAAAGAATA AGTTCCTTGT AATACTTGAC GATGTATGGC     240

AGTTTGTCGA TCTTGAAGAT ATTGGTTTAA GTCCTCTGCC AAATAAAGGT GTCAACTTCA     300

AGGTCTTGTT GACGTCAAGA GATTCACATG TTTGCACTCT GATGGGAGCT GAAGCAAATT     360

CAATTCTTAA TATAAAAGTT TTAAAAGATG TAGAAGGACA AAGTTTGTTC CGCCAGTTTG     420

CTAAAAATGC GGGTGATGAT GACCTGGATC CTGCTTTCAA TGGGATAGCA GATAGTATTG     480

CAAGTAGATG TCAAGGTTTG CCCATTGCCA TCAAAACCAT TGCCTTAAGT CTTAAAGGTA     540

GAAGCAAGTC TGCATGGGAC GTTGCACTTT CTCGTCTGGA GAATCATAAG ATTGGTAGTG     600

AAGAAGTTGT GCGTGAAGTT TTTAAAATTA GCTACGACAA TCTCCAAGAT GAGGTTACTA     660

AATCTATTTT TTTACTTTGT GCTTTATTTC CTGAAGATTT TGATATTCCT ACTGAGGAGT     720

TGGTGAGGTA TGGGTGGGGC TTGAAATTAT TTATAGAAGC AAAAACTATA AGAGAAGCAA     780

GAAACAGGCT CAACACCTGC ACTGAGCGGC TTAGGGAGAC AAATTTGTTA TTTGAAGTG     840

ATGACATTGG ATGTGTCAAG ATGCACGATG TGGTGCGTGA TTTTGTTTTG CATATATTCT     900

CAGAAGTCCA ACACGCTTCA ATTGTCAACC ATGGTAACGT GTCAGAGTGG CTAGAGGAAA     960

ATCATAGCAT CTACTCTTGT AAAAGAATTT CATTAACATG CAAGGGTATG TCTCAGTTTC    1020

CCAAAGACCT CAAATTTCCA AACCTTTCAA TTTTGAAACT TATGCATGGA GATAAGTCAC    1080

TGAGCTTTCC TGAAAACTTT TATGGAAAGA TGGAAAAGGT TCAGGTAATA TCATATGATA    1140

AATTGATGTA TCCATTGCTT CCCTCATCAC TTGAATGCTC CACCAACGTT CGAGTGCTTC    1200

ATCTTCATTA CTGTTCATTA AGGATGTTTG ATTGCTCTTC AATTGGTAAT CTTCTCAACA    1260

TGGAAGTGCT CAGCTTTGCT AATTCTAACA TTGAATGGTT ACCATCTACA ATTGGAAATT    1320

TGAAGAAGCT AAGGCTACTA GATTTGACAA ATTGTAAAGG TCTTCGTATA GATAATGGTG    1380

TCTTAAAAAA TTTGGTCAAA CTTGAAGAGC TTTATATGGG TGTTAATCGT CCGTATGGAC    1440

AGGCCGTTAG CTTGACAGAT GAAAA                                        1465
```

(2) INFORMATION FOR SEQ ID NO:101:

(i) SEQUENCE CHARACTERISTICS:
        (A) LENGTH: 487 amino acids
        (B) TYPE: amino acid

```
        (C) STRANDEDNESS:
        (D) TOPOLOGY: linear (ii) MOLECULE TYPE: protein (ix) FEATURE:
        (A) NAME/KEY: -
        (B) LOCATION: 1..487
        (D) OTHER INFORMATION: /note= "RG2G deduced sequence"

(xi) SEQUENCE DESCRIPTION: SEQ ID NO:101:

Arg His Asp Asp Glu Glu Leu Lys Glu Val Val Gly Gln Lys Lys Ser
1               5                   10                  15

Phe Asn Ile Ile Ile Gln Val Val Ile Gly Glu Lys Thr Asn Pro Ile
            20                  25                  30

Ala Ile Gln Gln Ala Val Ala Asp Tyr Leu Ser Ile Glu Leu Lys Glu
        35                  40                  45

Asn Thr Lys Glu Ala Arg Ala Asp Lys Leu Arg Lys Arg Phe Glu Ala
    50                  55                  60

Asp Gly Gly Lys Asn Lys Phe Leu Val Ile Leu Asp Asp Val Trp Gln
65                  70                  75                  80

Phe Val Asp Leu Glu Asp Ile Gly Leu Ser Pro Leu Pro Asn Lys Gly
                85                  90                  95

Val Asn Phe Lys Val Leu Leu Thr Ser Arg Asp Ser His Val Cys Thr
            100                 105                 110

Leu Met Gly Ala Glu Ala Asn Ser Ile Leu Asn Ile Lys Val Leu Lys
        115                 120                 125

Asp Val Glu Gly Gln Ser Leu Phe Arg Gln Phe Ala Lys Asn Ala Gly
    130                 135                 140

Asp Asp Asp Leu Asp Pro Ala Phe Asn Gly Ile Ala Asp Ser Ile Ala
145                 150                 155                 160

Ser Arg Cys Gln Gly Leu Pro Ile Ala Ile Lys Thr Ile Ala Leu Ser
                165                 170                 175

Leu Lys Gly Arg Ser Lys Ser Ala Trp Asp Val Ala Leu Ser Arg Leu
            180                 185                 190

Glu Asn His Lys Ile Gly Ser Glu Glu Val Val Arg Glu Val Phe Lys
        195                 200                 205

Ile Ser Tyr Asp Asn Leu Gln Asp Glu Val Thr Lys Ser Ile Phe Leu
    210                 215                 220

Leu Cys Ala Leu Phe Pro Glu Asp Phe Asp Ile Pro Thr Glu Glu Leu
225                 230                 235                 240

Val Arg Tyr Gly Trp Gly Leu Lys Leu Phe Ile Glu Ala Lys Thr Ile
                245                 250                 255

Arg Glu Ala Arg Asn Arg Leu Asn Thr Cys Thr Glu Arg Leu Arg Glu
            260                 265                 270

Thr Asn Leu Leu Phe Gly Ser Asp Asp Ile Gly Cys Val Lys Met His
        275                 280                 285

Asp Val Val Arg Asp Phe Val Leu His Ile Phe Ser Glu Val Gln His
    290                 295                 300

Ala Ser Ile Val Asn His Gly Asn Val Ser Glu Trp Leu Glu Glu Asn
305                 310                 315                 320

His Ser Ile Tyr Ser Cys Lys Arg Ile Ser Leu Thr Cys Lys Gly Met
                325                 330                 335

Ser Gln Phe Pro Lys Asp Leu Lys Phe Pro Asn Leu Ser Ile Leu Lys
            340                 345                 350

Leu Met His Gly Asp Lys Ser Leu Ser Phe Pro Glu Asn Phe Tyr Gly
```

```
                    355                 360                 365
Lys Met Glu Lys Val Gln Val Ile Ser Tyr Asp Lys Leu Met Tyr Pro
            370                 375                 380

Leu Leu Pro Ser Ser Leu Glu Cys Ser Thr Asn Val Arg Val Leu His
385                 390                 395                 400

Leu His Tyr Cys Ser Leu Arg Met Phe Asp Cys Ser Ser Ile Gly Asn
                405                 410                 415

Leu Leu Asn Met Glu Val Leu Ser Phe Ala Asn Ser Asn Ile Glu Trp
            420                 425                 430

Leu Pro Ser Thr Ile Gly Asn Leu Lys Lys Leu Arg Leu Leu Asp Leu
                435                 440                 445

Thr Asn Cys Lys Gly Leu Arg Ile Asp Asn Gly Val Leu Lys Asn Leu
            450                 455                 460

Val Lys Leu Glu Glu Leu Tyr Met Gly Val Asn Arg Pro Tyr Gly Gln
465                 470                 475                 480

Ala Val Ser Leu Thr Asp Glu
                485

(2) INFORMATION FOR SEQ ID NO:102:

(i) SEQUENCE CHARACTERISTICS:
        (A) LENGTH: 1419 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1419
        (D) OTHER INFORMATION: /note= "RG2H"

(xi) SEQUENCE DESCRIPTION: SEQ ID NO:102:

TGAAGGAGGT TGTGGAACGA AGAAAAATGT TCAGTATTAT TGTTCAAGTG GTCATAGGAG     60

AGAAGACAAA CCCTATTGCT ATTCAGCAAG CTGTAGCAGA TTACCTCTCT ATAGAGCTGA    120

AAGAAAACAC TAAAGAAGCA AGAGCTGATA AGCTTCGTAA ATGGTTCGAG GCCGATGGAG    180

GAAGAATAA GTTCCTTGTA ATACTTGACG ATGTATGGCA GTTTGTCGAT CTTGAAGATA     240

TTGGTTTAAG TCCTCTGCCA AATAAAGGTG TCAACTTCAA GGTCTTGTTG ACGTCAAGAG    300

ATTCACATGT TTGCACTCTG ATGGGAGCCG AAGCCAATTC AATTCTCAAT ATAAAAGTTT    360

TAACAGCTGT AGAAGGACAA AGTTTGTTCC GCCAGTTTGC TAAAAATGCG GGTGATGATG    420

ACCTGGATCC TGCTTTCAAT AGGATAGCAG ATAGTATTGC AAGTAGATGT CAAGGTTTGC    480

CCATTGCCAT CAAAACCATT GCCTTAAGTC TTAAAGGTAG AAGCAAGCCT GCGTGGGACC    540

ATGCGCTTTC TCGTTTGGAG AACCATAAGA TTGGTAGTGA AGAAGTTGTG CGTGAAGTTT    600

TTAAAATTAG CTATGACAAT CTCCAAGATG AGATTACTAA ATCTATTTTT TTACTTTGTG    660

CTTTATTTCC TGAAGATTTT GATATTCCTA CTGAGGAGTT GATGAGGTAT GGATGGGGCT    720

TGAAATTATT TATAGAAGCA AAAACTATAA GAGAAGCAAG AAACAGGCTC AACACCTGCA    780

CTGAGCGGCT TAGGGAGACA AATTTGTTAT TGGAAGCGA TGACATTGGA TGCGTCAAGA    840

TGCACGATGT GGTGCGTGAT TTTGTTTTGC ATATATTCTC AGAAGTCCAG CACGCTTCAA    900

TTGTCAACCA TGGTAACGTG TCAGAGTGGC TAGAGGAAAA TCATAGCATC TACTCTTGTA    960

AAAGAATTTC ATTAACATGC AAGGGTATGT CTGAGTTTCC CAAAGACCTC AAATTTCCAA   1020

ACCTTTCAAT TTTGAAACTT ATGCATGGAG ATAAGTCGCT GAGCTTTCCT GAAAACTTTT   1080
```

```
ATGGAAAGAT GGAAAAGGTT CAGGTAATAT CATATGATAA ATTGATGTAT CCATTGCTTC      1140

CCTCATCACT TGAATGCTCC ACTAACGTTC GAGTGCTTCA TCTCCATTAT TGTTCATTAA      1200

GGATGTTTGA TTGCTCTTCA ATTGGTAATC TTCTCAACAT GGAAGTGCTC AGCTTTGCTA      1260

ATTCTAACAT TGAATGGTTA CCATCTACAA TTGGAAATTT GAAGAAGCTA AGGCTACTAG      1320

ATTTGACAAA TTGTAAAGGT CTTCGTATAG ATAATGGTGT CTTAAAAAAT TTGGTCAAAC      1380

TTGAAGAGCT TTATATGGGT GTTAATCATC CGTATGGAC                             1419
```

(2) INFORMATION FOR SEQ ID NO:103:

(i) SEQUENCE CHARACTERISTICS:
        (A) LENGTH: 472 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..472
        (D) OTHER INFORMATION: /note= "RG2H deduced sequence"

(xi) SEQUENCE DESCRIPTION: SEQ ID NO:103:

```
Lys Glu Val Val Glu Arg Lys Lys Met Phe Ser Ile Ile Val Gln Val
1               5                   10                  15

Val Ile Gly Glu Lys Thr Asn Pro Ile Ala Ile Gln Gln Ala Val Ala
            20                  25                  30

Asp Tyr Leu Ser Ile Glu Leu Lys Glu Asn Thr Lys Glu Ala Arg Ala
        35                  40                  45

Asp Lys Leu Arg Lys Trp Phe Glu Ala Asp Gly Gly Lys Asn Lys Phe
    50                  55                  60

Leu Val Ile Leu Asp Asp Val Trp Gln Phe Val Asp Leu Glu Asp Ile
65                  70                  75                  80

Gly Leu Ser Pro Leu Pro Asn Lys Gly Val Asn Phe Lys Val Leu Leu
                85                  90                  95

Thr Ser Arg Asp Ser His Val Cys Thr Leu Met Gly Ala Glu Ala Asn
            100                 105                 110

Ser Ile Leu Asn Ile Lys Val Leu Thr Ala Val Glu Gly Gln Ser Leu
        115                 120                 125

Phe Arg Gln Phe Ala Lys Asn Ala Gly Asp Asp Leu Asp Pro Ala
    130                 135                 140

Phe Asn Arg Ile Ala Asp Ser Ile Ala Ser Arg Cys Gln Gly Leu Pro
145                 150                 155                 160

Ile Ala Ile Lys Thr Ile Ala Leu Ser Leu Lys Gly Arg Ser Lys Pro
                165                 170                 175

Ala Trp Asp His Ala Leu Ser Arg Leu Glu Asn His Lys Ile Gly Ser
            180                 185                 190

Glu Glu Val Val Arg Glu Val Phe Lys Ile Ser Tyr Asp Asn Leu Gln
        195                 200                 205

Asp Glu Ile Thr Lys Ser Ile Phe Leu Leu Cys Ala Leu Phe Pro Glu
    210                 215                 220

Asp Phe Asp Ile Pro Thr Glu Glu Leu Met Arg Tyr Gly Trp Gly Leu
225                 230                 235                 240

Lys Leu Phe Ile Glu Ala Lys Thr Ile Arg Glu Ala Arg Asn Arg Leu
                245                 250                 255
```

```
Asn Thr Cys Thr Glu Arg Leu Arg Glu Thr Asn Leu Leu Phe Gly Ser
            260                 265                 270

Asp Asp Ile Gly Cys Val Lys Met His Asp Val Val Arg Asp Phe Val
            275                 280                 285

Leu His Ile Phe Ser Glu Val Gln His Ala Ser Ile Val Asn His Gly
            290                 295                 300

Asn Val Ser Glu Trp Leu Glu Gly Asn His Ser Ile Tyr Ser Cys Lys
305                 310                 315                 320

Arg Ile Ser Leu Thr Cys Lys Gly Met Ser Glu Phe Pro Lys Asp Leu
                325                 330                 335

Lys Phe Pro Asn Leu Ser Ile Leu Lys Leu Met His Gly Asp Lys Ser
            340                 345                 350

Leu Ser Phe Pro Glu Asn Phe Tyr Gly Lys Met Glu Lys Val Gln Val
            355                 360                 365

Ile Ser Tyr Asp Lys Leu Met Tyr Pro Leu Leu Pro Ser Ser Leu Glu
            370                 375                 380

Cys Ser Thr Asn Val Arg Val Leu His Leu His Tyr Cys Ser Leu Arg
385                 390                 395                 400

Met Phe Asp Cys Ser Ser Ile Gly Asn Leu Leu Asn Met Glu Val Leu
                405                 410                 415

Ser Phe Ala Asn Ser Asn Ile Glu Trp Leu Pro Ser Thr Ile Gly Asn
            420                 425                 430

Leu Lys Lys Leu Arg Leu Leu Asp Leu Thr Asn Cys Lys Gly Leu Arg
            435                 440                 445

Ile Asp Asn Gly Val Leu Lys Asn Leu Val Lys Leu Glu Glu Leu Tyr
            450                 455                 460

Met Gly Val Asn His Pro Tyr Gly
465                 470

(2) INFORMATION FOR SEQ ID NO:104:

(i) SEQUENCE CHARACTERISTICS:
        (A) LENGTH: 1436 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1436
        (D) OTHER INFORMATION: /note= "RG2I"

(xi) SEQUENCE DESCRIPTION: SEQ ID NO:104:

AAGAAGAGCT GAAGGAGGTT GTGGAACAAA AGAAAACGTT CAATATTATT GTTCAAGTGG      60

TCATAGGAGA GAAGACAAAC CCTATTGCTA TTCAGCAAGC TGTAGCAGAT TCCCTCTCTA     120

TAGAGCTGAA AGAAACACT  AAAGAAGCAA GAGCTGATAA GCTTCGTAAA TGGTTCGAGG     180

CTGATGGAGG AAAGAATAAG TTCCTCGTNA TACTTGACGA TGTATGGCNG TTTGTTGATC     240

TTGAAGATAT TGGTTTAAGT CCTCATCCAA ATAAAGGTGT CANCTTCAAG GTCTTGTTGA     300

CGTCAAGAGA TTCACATGTT TGCACTCTGA TGGGAGCTGA AGCCAATTCA ATTCTCAATA     360

TAAAAGTTTT AAAAGATGTA GAAGGAAAAA GTTTGTTCCG CCAGTTTGCT AAAAATGCGG     420

GTGATGATGA CCTGGATCCT GCTTTCATTG GGATAGCAGA TAGTATTGCA AGTAGATGTC     480

AAGGTTTGCC CATTGCCATC AAAACCATTG CCTTAAGTCT TAAAGGTAGA AGCAAGTCTG     540

CATGGGACGT TGCACTTTCT CGTCTGGAGA ATCATAAGAT TGGTAGTGAA GAAGTTGTGC     600
```

```
GTGAAGTTTT TAAAATTAGC TATGACAATC TCCAAGATGA GGTTACTAAA TCTATTTTTT    660

TACTTTGTGC TTTATTTCCT GAAGATTTTG ATATTCCTAC TGAGGAGTTG GTGAGGTATG    720

GGTGGGGCTT GAAATTATTT ATAGAAGCAA AAACTATAAG AGAAGCAAGA AACAGGCTCA    780

ACACCTGCAC TGAGCGGCTT AGGGAGACAA ATTTGTTATT TGGAAGTGAT GACATTGGAT    840

GCGTCAAGAT GCACGATGTG GTGCGTGATT TTGTTTTGCA TATATTCTCA GAAGTCCAGC    900

ACGCTTCAAT TGTCAACCAT GGTAATGTGT CAGAGTGGCT AGAGGAAAAT CATAGCATCT    960

ACTCTTGTAA AAGAATTTCA TTAACATGCA AGGGTATGTC TGAGTTTCCC AAAGACCTCA    1020

AATTTCCAAA CCTTTCAATT TTGAAACTTA TGCATGGAGA TAAGTCGCTG AGCTTTCCTG    1080

AAAACTTTTA TGGAAAGATG GAAAAGGTTC AGGTAATATC ATATGATAAA TTGATGTATC    1140

CATTGCTTCC CTCATCACTT GAATGCTCCA CCAACCTTCG AGTGCTTCAT CTCCATGAAT    1200

GTTCATTAAG GATGTTTGAT TGCTCTTCAA TTGGTAATCT TCTCAACATG GAAGTGCTCA    1260

GCTTTGCTAA TTCTGGCATT GAATGGTTAC CATCTACAAT TGGAAATTTG AAGAAGCTAA    1320

GGCTACTGGA TCTGACAGAT TGTGGAGGTC TTCATATAGA TAATGGCGTC TTAAAAAATT    1380

TGGTCAAACT TGAAGAGCTT TATATGGGTG CTAATCGTCT GTTTGGAAAG TGCCAT       1436

(2) INFORMATION FOR SEQ ID NO:105:

(i) SEQUENCE CHARACTERISTICS:
        (A) LENGTH: 478 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..478
        (D) OTHER INFORMATION: /note= "RG2I deduced sequence"

(xi) SEQUENCE DESCRIPTION: SEQ ID NO:105:

Glu Glu Leu Lys Glu Val Val Glu Gln Lys Lys Thr Phe Asn Ile Ile
1               5                   10                  15

Val Gln Val Val Ile Gly Glu Lys Thr Asn Pro Ile Ala Ile Gln Gln
            20                  25                  30

Ala Val Ala Asp Ser Leu Ser Ile Glu Leu Lys Glu Asn Thr Lys Glu
        35                  40                  45

Ala Arg Ala Asp Lys Leu Arg Lys Trp Phe Glu Ala Asp Gly Gly Lys
    50                  55                  60

Asn Lys Phe Leu Val Ile Leu Asp Asp Val Trp Xaa Phe Val Asp Leu
65                  70                  75                  80

Glu Asp Ile Gly Leu Ser Pro His Pro Asn Lys Gly Val Xaa Phe Lys
                85                  90                  95

Val Leu Leu Thr Ser Arg Asp Ser His Val Cys Thr Leu Met Gly Ala
            100                 105                 110

Glu Ala Asn Ser Ile Leu Asn Ile Lys Val Leu Lys Asp Val Glu Gly
        115                 120                 125

Lys Ser Leu Phe Arg Gln Phe Ala Lys Asn Ala Gly Asp Asp Asp Leu
    130                 135                 140

Asp Pro Ala Phe Ile Gly Ile Ala Asp Ser Ile Ala Ser Arg Cys Gln
145                 150                 155                 160

Gly Leu Pro Ile Ala Ile Lys Thr Ile Ala Leu Ser Leu Lys Gly Arg
                165                 170                 175
```

```
Ser Lys Ser Ala Trp Asp Val Ala Leu Ser Arg Leu Glu Asn His Lys
            180                 185                 190

Ile Gly Ser Glu Glu Val Val Arg Glu Val Phe Lys Ile Ser Tyr Asp
        195                 200                 205

Asn Leu Gln Asp Glu Val Thr Lys Ser Ile Phe Leu Leu Cys Ala Leu
    210                 215                 220

Phe Pro Glu Asp Phe Asp Ile Pro Thr Glu Leu Val Arg Tyr Gly
225                 230                 235                 240

Trp Gly Leu Lys Leu Phe Ile Glu Ala Lys Thr Ile Arg Glu Ala Arg
                245                 250                 255

Asn Arg Leu Asn Thr Cys Thr Glu Arg Leu Arg Glu Thr Asn Leu Leu
            260                 265                 270

Phe Gly Ser Asp Asp Ile Gly Cys Val Lys Met His Asp Val Val Arg
        275                 280                 285

Asp Phe Val Leu His Ile Phe Ser Glu Val Gln His Ala Ser Ile Val
    290                 295                 300

Asn His Gly Asn Val Ser Glu Trp Leu Glu Glu Asn His Ser Ile Tyr
305                 310                 315                 320

Ser Cys Lys Arg Ile Ser Leu Thr Cys Lys Gly Met Ser Glu Phe Pro
                325                 330                 335

Lys Asp Leu Lys Phe Pro Asn Leu Ser Ile Leu Lys Leu Met His Gly
            340                 345                 350

Asp Lys Ser Leu Ser Phe Pro Glu Asn Phe Tyr Gly Lys Met Glu Lys
        355                 360                 365

Val Gln Val Ile Ser Tyr Asp Lys Leu Met Tyr Pro Leu Leu Pro Ser
    370                 375                 380

Ser Leu Glu Cys Ser Thr Asn Leu Arg Val Leu His Leu His Glu Cys
385                 390                 395                 400

Ser Leu Arg Met Phe Asp Cys Ser Ser Ile Gly Asn Leu Leu Asn Met
                405                 410                 415

Glu Val Leu Ser Phe Ala Asn Ser Gly Ile Glu Trp Leu Pro Ser Thr
            420                 425                 430

Ile Gly Asn Leu Lys Lys Leu Arg Leu Leu Asp Leu Thr Asp Cys Gly
        435                 440                 445

Gly Leu His Ile Asp Asn Gly Val Leu Lys Asn Leu Val Lys Leu Glu
    450                 455                 460

Glu Leu Tyr Met Gly Ala Asn Arg Leu Phe Gly Lys Cys His
465                 470                 475
```

(2) INFORMATION FOR SEQ ID NO:106:

(i) SEQUENCE CHARACTERISTICS:
        (A) LENGTH: 4211 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..4211
        (D) OTHER INFORMATION: /note= "RG2J"

(xi) SEQUENCE DESCRIPTION: SEQ ID NO:106:

```
ATGTCCGACC CAACAGGGAT TGTTGGTGCC ATTATTAACC CAATTGCTCA AACGGCCTTG      60

GTTCCCCTTA CAGACCATGT AGGCTACATG ATTTCCTGCA GAAAATATGT GAGGGACATG     120
```

-continued

```
CAAATGAAAA TGACAGAGTT AAATACCTCA AGAATCAGTG CAGAGGAACA CATTAGCCGG      180
AACACAAGAA ATCATCTTCA GATTCCATCT CAAATTAAGG ATTGGTTGGA CCAAGTAGAA      240
GGGATCAGAG CGAATGTTGC AAACTTTCCA ATTGATGTCA TCAGTTGTTG TAGTCTCAGG      300
ATCAGGCACA AGCTTGGACA GAAAGCCTTC AAGATAACTG AGCAGATCGA AAGTCTAACG      360
AGACAAAATT CGCTGATTAT CTGGACTGAT GAACCTGTTC CCCTGGGAAG AGTTGGTTCC      420
ATGATTGCAT CCACCTCTGC AGCATCAAGT GATCATCATG ATGTCTTCCC TTCAAGAGAG      480
CAAATTTTTA GGAAAGCACT AGAAGCACTT GAACCCGTCC AAAAATCCCA CATAATAGCC      540
TTATGGGGGA TGGGCGGAGT GGGGAAGACC ACGATGATGA AGAAGCTGAA AGAGGTCGTG      600
GAACAAAAGA AAACGTGCAA TATTATTGTT CAAGTGGTCA TAGGAGAGAA GACAAACCCT      660
ATTGCTATCC AGCAAGCTGT AGCAGATTAC CTCTCTATAG AGCTGAAAGA AAACACTAAA      720
GAAGCAAGAG CTGATAAGCT TCGTAAACGG TTCGAAGCCG ATGGAGGAAA GAATAAGTTC      780
CTTGTAATAC TTGACGATGT ATGGCAGTTT TTCGATCTTG AAGATATTGG TTTAAGTCCT      840
CTGCCAAATA AAGGTGTCAA CTTCAAGGTC TTGTTGACGT CAAGAGATTC ACATGTTTGC      900
ACTCTGATGG GAGCTGAAGC CAATTCTATT CTCAATATAA AGTTTTAAA AGATGTAGAA       960
GGAAAAAGTT TGTTCCGCCA GTTTGCTAAA AATGCGGGTG ATGATGACCT GGATCCTGCT     1020
TTCATTGGGA TAGCAGATAG TATTGCAAGT AGATGTCAAG GTTTGCCCAT TGCCATCAAA     1080
ACCATTGCCT TAAGTCTTAA AGGTAGAAGC AAGTCTGCAT GGGACGTCGC ACTTTCTCGT     1140
CTGGAGAATC ATAAGATTGG TAGTGAAGAA GTTGTGCGTG AAGTTTTTAA AATTAGCTAT     1200
GACAATCTCC AAGATGAGGT TACTAAATCT ATTTTTTTAC TCTGTGCTTT ATTTCCTGAA     1260
GATTTTGATA TTCCTATTGA GGAGTTGGTG AGGTATGGGT GGGGCTTGAA ATTATTTATA     1320
GAAGCAAAAA CTATAAGAGA AGCAAGAAAC AGGCTCAACA ACTGCACTGA GCGGCTTAGG     1380
GAGACAAATT TGTTATTTGG AAGTCATGAC TTTGGGTGCG TCAAGATGCA CGATGTGGTG     1440
CGTGATTTTG TTTTGCATAT GTTTTCAGAA GTCAAGCATG CTTCAATTGT CAACCATGGT     1500
AACATGTCAG AGTGGCCAGA GAAAAATGAT ACCAGCAACT CTTGTAAAAG AATTTCATTA     1560
ACATGCAAGG GTATGTCTAA GTTTCCTAAA GACATCAACT ATCCAAACCT TTTGATTTTG     1620
AAACTTATGC ATGGAGATAA GTCGCTGTGC TTTCCTGAAA ACTTTTATGG AAAGATGGAA     1680
AAGGTTCAGG TAATATCATA TGATAAATTG ATGTATCCAT TGCTTCCCTC ATCACTTGAA     1740
TGCTCCACTA ACGTTCGAGT GCTTCATCTC CATTATTGTT CATTAAGGAT GTTTGATTGC     1800
TCTTCAATTG GTAATCTTCT CAACATGGAA GTGCTCAGCT TTGCTAATTC TAACATTGAA     1860
TGGTTACCAT CTACAATTGG AAATTTGAAG AAGCTAAGGC TACTAGATTT GACAAATTGT     1920
AAAGGTCTTC GTATAGATAA TGGTGTCTTA AAAAATTTGG TCAAACTTGA AGAGCTTTAT     1980
ATGGGTGTTA ATCGTCCGTA TGGACAGGCC GTTAGCTTGA CAGATGAAAA CTGCAATGAA     2040
ATGGTAGAAG GTTCCAAAAA ACTTCTTGCA CTAGAATATG AGTTGTTTAA ATACAATGCT     2100
CAAGTGAAGA ATATATCCTT CGAGAATCTT AAACGATTCA AGATCTCAGT GGGATGTTCT     2160
TTACATGGAT CTTTCAGTAA AAGCAGGCAC TCATACGAAA ACACGTTGAA GTTGGCCATT     2220
GACAAAGGCG AACTATTGGA ATCCCGAATG AACGGGTTGT TTGAGAAAAC GGAGGTTCTT     2280
TGTTTAAGTG TGGGGGATAT GTATCATCTT TCAGATGTTA AGGTGAAGTC CTCTTCGTTC     2340
TACAATTTAA GAGTCCTTGT CGTTTCAGAG TGTGCAGAGT TGAAACACCT CTTCACACTT     2400
GGTGTTGCAA ATACTTTGTC AAAGCTTGAG CATCTTAAAG TCTACAAATG CGATAATATG     2460
```

-continued

```
GAAGAACTCA TACATACCGG GGGTAGTGAA GGAGATACAA TTACATTCCC CAAGCTGAAG    2520

CTTTTATATT TGCATGGGCT GCCAAACCTA TTGGGTTTGT GTCTTAATGT CAACGCAATT    2580

GAGCTACCAA AACTTGTGCA AATGAAGCTT TACAGCATTC CGGGTTTCAC AAGCATTTAT    2640

CCGCGGAACA AGTTGGAAGC ATCTAGTTTG TTGAAAGAAG AGGTACATAT ACATATAGTT    2700

TATGTTAATA CATTTTAAAC AATCTTTTCA ACTAAAAGTT TCAGAATATA TCTGTATTTT    2760

GATTGTATGA TGTGTTAGTG TTTGGATGTG GCTATTAAAG GATAATTATT TGGCAGGTTG    2820

TGATTCCTAA GTTGGATATA CTTGAAATTC ATGACATGGA GAATTTAAAG GAAATATGGC    2880

CTAGTGAGCT TAGTAGAGGT GAGAAAGTTA AGTTGAGAAA GATTAAAGTG AGAAATTGTG    2940

ATAAACTTGT GAATCTATTT CCACACAATC CCATGTCTCT GCTGCATCAT CTTGAAGAGC    3000

TTATAGTCGA GAAATGTGGT TCCATTGAAG AGTTGTTCAA CATCGACTTG GATTGTGCCA    3060

GTGTAATTGG AGAAGAAGAC AACAACAGCA GCTTAAGAAA CATCAATGTG GAGAATTCAA    3120

TGAAGCTAAG AGAGGTGTGG AGGATAAAAG GTGCAGATAA CTCTCGTCCC CTCTTTCGTG    3180

GCTTTCAAGT TGTTGAAAAG ATAATCATTA CGAGATGTAA GAGGTTTACA AATGTATTCA    3240

CACCTATCAC CACAAATTTT GATCTGGGGG CACTTTTGGA GATTTCAGTT GATTGTAGAG    3300

GAAATGATGA ATCAGACCAA AGTAACCAAG AGCAAGAGCA GGTATGGATT TCAATTTTAC    3360

TCTTTTACTT AATTAATGAT TAAGCCCCTG CTTTTTAATA AAAGGGGAC AAACCATTTC     3420

TTGACTTAAT GTTGCAATAC AAGTCATGTA TAAGAGTGAT TAACTTTTTT TTATTTATAA    3480

AATAACTACA AAACATGTTT TTTCATTATA GATCATGTAT AAATGTGACT AATTTTTTTC    3540

ATCGCCTAAC TTTTGTTGAT AAATCATTAG AAATGTCACT AATTACTTTT TAGTATTTAT    3600

AAAATAACTA CAAAACATGT TTTTTCATTA TAGATCATGT ATATATCAAC TAAAAATATT    3660

ATTCCCTTAC ACAAAAAAAA AAGGTTCAAG AAAGCCTGTA TTTCGAAATA ACTAAAAAGA    3720

AAATATTTGA TATTCACTAA GAGAAATTTT TTTCTAAACA TGATCGCAAA TGATTAAAAC    3780

TTAAATTAAA ACTAAAAAGA TTTTTATATA TGTTATNCAA AATTAAAATT TGAAATTAAG    3840

TTTATAATTC TNGTNTCACA AAGGGATATA TATAGTAAAA TATTATTTTT TTGCAGTCAT    3900

GCATAGTTGT ATTTTTAAAT GATTATTAA CGTGGTAGGA GTGGAAACCA CTCAATCTAG     3960

TAGACCCACT ATCACATGTC ACATCAGCTT TACATCTATT TTTCTTTCTC CTTTTTTCAT    4020

CTTTTTAAAC TCATAACACN TAAAANTANC ATATTTTCCA ACACACTNAA CTCATTGTCA    4080

CATTATTATT TTTAATTTAA TTAAATTNGA AAATTAAAAT TAANTAAANC NTAACATTTT    4140

TTAATTAAAA AATATTAATC CAAATAAAAA NTNCACGATA AATTAAAAAN GTTTANTTTG    4200

GAAAAAAANC C                                                        4211
```

(2) INFORMATION FOR SEQ ID NO:107:

(i) SEQUENCE CHARACTERISTICS:
        (A) LENGTH: 6701 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..6701
        (D) OTHER INFORMATION: /note= "RG2J continuation"

(xi) SEQUENCE DESCRIPTION: SEQ ID NO:107:

```
ATAACCCTTT CAAGGGTCAA CTCAAGTCCA AGTTAAAGTC AAGGTCAAAA CCTTGGTTAA       60
```

-continued

```
AGTCAACTTT GGTCAAAGTC AACATCTACT TGACTCACCT CACCGAGTTG GTCCACCAAC    120

TTGTCGAGTC CCTTAATCCA CAAACTTCAA GAACTTCGAT CCTACTCGTC GAGTCTTTCA    180

AGAACTCTTC GAGTTTCCAT TACACAGAAT CGGGACCTTT TGCTCATGAC TCGCCGAGTT    240

CATCCTTGAA CTTGTCGAGT CTAGCTTCAT ACGAGTTCGA GTGTTTAGTC CTTGACTCGT    300

CGAGTTCTTC CTTGAACTCG TCGAGTCCAT CTTCGTATAG TTGGGACATT GCCTTGAACT    360

CACCGAGTTC ATCATTGAAC TCATCGAGTC CTTCGATCTT CAAGTCCATA ATCCTGTCCA    420

TCTTGTTGAG TCCTCTTCTA GACTCAACCA GATTCCTCAG AAACAGAAAA GGTTAGGGAA    480

CCATTACCTG ACTCGCCGAG TCCCAAGAAC GAATCCCCGA GTCCCCCAAT GTCCATGACC    540

ATACAATCGA TTTTCGTTGG GCTCATTGCA TCCAAAGCAT AGATCTAACC TCCTAGGGTC    600

CATATTACAC GTAAAGCTAC GAACTTGACG TCCATGCATG GGGGATTTGG CTCAAATGGC    660

ATTAAAATGG GGTTTATCTG ATGCATGGGA CTCCCATGGC CATAAAGTTA ACACCTTTAT    720

GCCATGGGAA TCCTCAATGG TTCCATATCT GAAGTTAACA CTCTACAATA TGTTCTAAAC    780

CCGAAGGTGG CTTAGAAATG CCCCAAAATG GCAAGATTCA AGCCTAAAAG GAGATCTAAC    840

AAATGATAAG TCAAGGTTCA AGCTTTTTAC CTTGAATAAG CTGGAAATGA AGCAAAATCT    900

CTGGATCCAC TTGCTTCTTC AAGAACCCCC AAGCTTCCAC TTCTTCCTTC AAGTTTCAAA    960

CAACTTTAAA CACTCAAAAA TGGCTCAAGA ACACTCAAAA AGCTTTAGGG TTTCGAGTTA   1020

GGGCTTTTTG GAAGCGAGAG GGACGATGGG GGCTGAAATG AGGCTAGAAA AAGTGTTTAA   1080

ATAGGGGCA AACCCTAAAT ATTAGGGTTT CATCCAGGCA GCCCTACTCG TCGAGTCGGG    1140

CTCCCGACTG GTCGAGTAGG TCACTTAAAA CCCGCGTCCA TAATCCAGTC TACTCGACGA   1200

GTTGGGCCTC CAACTCGTCG ATTCCGAGTG CAAAACGTTC AATTACTTAA ATTTAAATAT   1260

GTACCAGGAA CCGGGTGTTA CAGTTGAGAC TTTATACCTC CATAAGATAG ATCTAGGTGC   1320

ACATAGCCTG GATCCACAAG CTCCATGTCA ACAAGCGACT CTTCAAGAAG TTCATTCTTC   1380

CTCCTTAAGC ACCAAAAAAC ACACAAAATC ACCATGAAGC TCAAGAAATA CTCAAATAGA   1440

GGATAGGGTT TCGTTCGTAG GGTTAGAGAG GATGGAGGCT AGAGGAAATG AGGGATAGAG   1500

GCGAGTTAAG GTCTTTAAAT AGGGTCCAAG ACCCTAAATT AGGGTTTTAA TCTGGCCAGA   1560

CGAACGCAGG GTGTTCCCAA ATGCATATGT GTCCAAATTC TCGTGTGCGC CATGCGTACC   1620

TCCCTTGTAC GCCATGTGTA CCGGGTTTGG TCCAAACCCT TCTAACTTCA AATGATCATA   1680

ACTTGCACCC CTTATCTGTT TTCGATGTTC TTTATATCCA CGGAAAGGTA ACAAGAAGCC   1740

CTATACTTCT ATAAACTTTA TTTAATCTGA AAACCAACCG AAATTAAATC CAAAATTCAT   1800

AAAAGTCCCG AACCAACACA TTTACCGATA CCCTTGGGCT CCAAAACACA AATTGAAAAC   1860

CCGGATCATC CAAACTACAT CATCCACCTC CAAATGAGCC CAAACTCAAT TATTCAAGGG   1920

TTCTAAGCCT GTTAATGCCC ACTCCTCGAT TACCACCCCG CAATGGGAAA CGATTCAAAA   1980

CAGGGCGTTA CATAATTTGT TGTGGTTTTG TATTTTTTAT TTCCGGTGAA GGTGAAAGAT   2040

CCAACTATTT TTAATCTGTT GGCATTTTCC ATCATTTGCA ACTGTTTCTT GAAAAAAAAA   2100

TACCTAAAAT CAAAATAACC ATTTTCAAAT CCAAAATTAT AAGAGAGAAT TGTAAATGGA   2160

CATGGAATCT TAAATCATTA ACACAGTTCA GTACACAAGT TGCTAATTAC ATTTCTTGCT   2220

GTGCAGATTG AAATTCTATC AGAGAAAGAG ACATTACAAG AAGCCACTGA CAGTATTTCT   2280

AATGTTGTAT TCCATCCTG TCTCATGCAC TCTTTTCATA ACCTCCAGAA ACTTATATTG    2340

AACAGAGTTA AAGGAGTGGA GGTGGTGTTT GAGATAGAGA GTGAGAGTCC AACAAGTAGA   2400
```

```
GAATTGGTAA CAACTCACCA TAACCAACAA CAGCCTGTTA TATTTCCCAA CCTCCAGCAT      2460

TTGGATCTAA GGGGTATGGA CAACATGATT CGCGTGTGGA AGTGCAGCAA CTGGAATAAA      2520

TTCTTCACTC TTCCAAAACA ACAATCAGAA TCCCCATTCC ACAACCTCAC AACCATAAAT      2580

ATTGATTTTT GCAGAAGCAT TAAGTACTTG TTTTCACCTC TCATGGCAGA ACTTCTTTCC      2640

AACCTAAAGA AAGTCAATAT AAAATGGTGT TATGGTATTG AAGAAGTTGT TTCAAACAGA      2700

GATGATGAGG ATGAAGAAAT GACTACATTT ACATCTACCC ACACAACCAC CATCTTGTTC      2760

CCTCATCTTG ATTCTCTCAC TCTAAGTTTC CTGGAGAATC TGAAGTGTAT TGGTGGAGGT      2820

GGTGCCAAGG ATGAGGGGAG CAATGAAATA TCTTTCAATA ATACCACTGC AACTACTGCT      2880

GTTCTTGATC AATTTGAGGT ATGCTTTGTT CATATTCAAT TATTTATTTA ATTTCCTTTT      2940

TTATTTGCAA TATTCTATAA ATAATACATT TTATACCCAC TATACTAAGA TAATAATTAC      3000

CTAGAGGGAT GGATGCTATG ACACAGCTGC TACACTTCAG AAACTCTAGT AAGGGCAGTT      3060

ATGGAAGTTC AATAAAATGA TAATGGCATC TTTTGATGGG TAATATAGGC AATTTAAGTT      3120

TTATTTCTGT TAAAGCAGTA TTTAGCAAGT ACTGGCCAGT AGGAGAGGAG AATATCACCT      3180

TTTGTGAAAA TCTGGTCATT GTACCCAGAA TTTAGTTAAA TGTAACATTT TAGATATCAG      3240

GGGACATCAG GTGACAGATA TTGTAGAATA GAACAATATA TAATATTACC CAAAACTATT      3300

TTTTCTAAGG TTTTTCTGTT AAATATGTGC TTTCTTGATT TCATTGAATT TGCATTCCTA      3360

TATTTTAGGT GGTAAAGTGA TTGTCTCTTC AATAAATCCC GAAATTAATT AAAAAAAAAA      3420

AAAAACAAAA GTAAATTTTT GATATGGAGA GCACTGGTAT CATTTAGTAT ATAAAAAAAC      3480

TAGATTTTGA ATTAAGTTTC TTATATAAAA GCTGTGTATA TAGTTTAATT AGTTTTACAT      3540

CATTTTTCCA TGTGGTGTTG CAGTTGTCTG AAGCAGGTGG TGTTTCTTGG AGCTTATGCC      3600

AATACGCTAG AGAGATAAGT ATAGAATTCT GCAATGCATT GTCAAGTGTG ATTCCATGTT      3660

ATGCAGCAGG ACAAATGCAA AAGCTTCAAG TGCTGACAGT CAGTTCTTGT AATGGTCTGA      3720

AGGAGGTATT TGAAACTCAA TTAAGGAGGA GCAGCAACAA AAACAACGAG AAGAGTGGTT      3780

GTGATGAAGG AAATGGTGGA ATTCCAAGAG TAAATAACAA TGTTATTATG CTTTCTGGTC      3840

TGAAGATATT GGAAATCAGC TTTTGTGGGG GTTTGGAACA TATATTCACA TTCTCTGCAC      3900

TTGAAAGCCT GAGACAGCTC GAAGAGTTAA CGATAATGAA TTGCTGGTCA ATGAAAGTGA      3960

TTGTGAAGAA GGAAGAAGAT GAATATGGAG AGCAGCAAAC AACAACAACA ACGAAGGGGA      4020

CTTCTTCTTC TTCTTCTTCT TCTTCTTCTT CTTCTTCTTC TTCTTCTTCT CCTCCTTCTT      4080

CTTCTAAGAA GGTTGTGGTC TTTCCTTGTC TAAAGTCCAT TGTATTGGTC AATCTACCAG      4140

AGCTGGTAGG ATTCTTCTTG GGGATGAATG AGTTCCGGTT GCCTTCATTA GATGAACTTA      4200

TCATCGAGAA ATGCCCAAAA ATGATGGTGT TTACAGCTGG TGGGTCCACA GCTCCCAAC       4260

TCAAGTATAT ACACACAAGA TTAGGCAAAC ATACTATTGA TCAAGAATCT GGCCTTAACT      4320

TTCATCAGGT ATATATGTTT CTTTAATTGG CATCATCTAA TTAAGAAAGA TATCATTCCT      4380

GCCAAGTAAA TTTACTTCAA ACACATTCAC ACTGGTTTCA GTCTAAGTTT ATGTTGTTCT      4440

AGGAAGGCCA AAATGGGAAA GCAAGATAGG GAAAAATAGT GTATTTCAGT GGAAAGGGTA      4500

TTTTAGGTAT TTTCTGTCAA AAGTTGTTAT TGCAGGCTTT TTAGTACCTG GAATCGTGTG      4560

TGGGAGGAGC ATTATTATTC TGATTTGCTT GTTTCTTTAT CATTTTTTCT TAGCCTCTCG      4620

AACAGCTAGA AACCCTTTTA ATCTTTTGAT TTTAAATGAC AAAATTTTTC CCTGTTACTC      4680

TATTTGATTG TTGTTCTTCA TGGTTCTAAG TGAGTTATTG GCTCATCTGT TACTTCTTTT      4740

GATTGTTATT TTCATAGCAT GTTAGTCACT TGAATCAAGC TTTTTCATTT TCAACCAGGG      4800
```

```
CAAAAGGTCA AAAGTAACCT ACTTTATGAG ATCAAAAACA GCAACCCATC GGATAACTTT    4860

TAGTTGGAGT TAATAGTTAC AATTACCATT GTGATTAATA ATTATAATAT CCTGTATTAA    4920

TTCATAAAAA TTGGTACAGC ACATATATGA CATTTCAAAG GTTTTTGTTT GACATATATA    4980

TGCCTCTGGC GTTTTCTTTA TTGGACTTGC AGACCTCATT CCAAAGTTTA TACGGTGACA    5040

CCTTGGGCCC TGCTACTTCA GAAGGGACAA CTTGGTCTTT TCATAACTTG ATTGAATTAG    5100

ATGTGAAATT TAATAAGGAT GTTAAAAAGA TTATTCCATC CAGTGAGTTG CTGCAACTGC    5160

AAAAGCTGGA AAAGATAAAT ATAAACAGTT GTGTTGGGGT AGAGGAGGTA TTTGAAACTG    5220

CATTGGAAGC AGCAGGGAGA AATGGAAATA GTGGAATTGG TTTTGATGAA TCGTCACAAA    5280

CAACTACCAC TACTCTTGTC AATCTTCCAA ACCTTAGAGA AATGAACTTA TGGGGTCTAG    5340

ATTGTCTGAG GTATATATGG AAGAGCAATC AGTGGACAGC ATTTGAGTTT CCAAAACTAA    5400

CAAGAGTTGA AATTAGTAAT TGCAACAGTT TAGAACATGT ATTTACTAGT TCCATGGTTG    5460

GTAGTCTATC GCAACTCCAA GAGCTACATA TAAGTCAGTG CAAACTTATG GAGGAGGTGA    5520

TTGTTAAGGA TGCAGATGTT TCTGTAGAAG AAGACAAAGA GAAAGAATCT GATGGCAAGA    5580

TGAATAAGGA GATACTTGCG TTACCTAGTC TAAAGTCCCT GAAATTAGAA AGCTTACCAT    5640

CTCTTGAGGG GTTTAGCTTG GGGAAGGAGG ATTTTTCATT CCCATTATTG GATACTTTAA    5700

GAATTGAGGA ATGCCCAGCA ATAACCACCT TCACCAAGGG AAATTCCGCT ACTCCACAAC    5760

TAAGAGAAAT AGAAACAAGA TTTGGCTCGG TTTATGCAGG GGAAGACATC AAATCCTCTA    5820

TTATAAAGAT CAAACAACAG GTAAATCAGA TCATTGTTGG TTTAATAATT CTTAAACTAC    5880

ATTTGAAAAG TTTCATGTAA GTTTTTTATT ATTGTCAAAA GCCGCAACCT ATATTTTCAA    5940

CTTTATATTT ATGTACTTTA TGCAGGATTT CAAAAAAGCC CAGGACTCTA TTTAATGTGA    6000

AGTAAATACT AGAAGAGGTA AATTCTATTT ACATGTCTCC TGATTGCCTA TTAATTAATG    6060

GCCTTTCAGT TCATGGTTTT TGGATGTATT CTTCATGATG ACGTGAATGT TTAAATACCC    6120

CACTAGTTAA TTGTTAGGTT GAATGTTGAT GACCAAAGGA CTATATGTCG GGAAGAATAT    6180

TCAAGGAAAG AATTGTTCAT CATATGAAGG GCATTAAATT AAGAAGAACA TGGATGCTAT    6240

GAAGATGTTG GGAAAATATA TGAATCAAAT AACAAGCTAC TCACTTATCT AAGTTTGTTG    6300

GTTGAGGATG TTGATTTTAA TATTTCAAAT TCATTGGTAT CATTATATGG GTTTATCAGT    6360

AGTGTTAATG GGATAATGAG CAACTTAACC TTAAATTATG CTGTTGGTAA ATGTTGGACT    6420

CAAGTATGGA AAATTAGGAA TAACTTGTGA AAAATATATG CAAAAGTAGG ATTGAGATTT    6480

TCAATGAAAA AAATTATGAA ACTATACTAC TATAGTATAT AAATAAATTC AACTTACTGT    6540

TGGGTATATT GGAAGCACAT ATCATGAAAG TAACTAGAAG CAGAATTTGT TCCCATCTTC    6600

ATCTACTTAT AGTTTCCATT TCTTACTTGT AAAAATCTGA TTAAACTTTA GAGTTATTTC    6660

TATTTTTTAC CAACCAAAAT TTTCATATAA AGGCCACAAG T                       6701
```

(2) INFORMATION FOR SEQ ID NO:108:

(i) SEQUENCE CHARACTERISTICS:
        (A) LENGTH: 1854 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1854

(D) OTHER INFORMATION: /note= "RG2J deduced sequence"

(xi) SEQUENCE DESCRIPTION: SEQ ID NO:108:

```
Met Ser Asp Pro Thr Gly Ile Val Gly Ala Ile Ile Asn Pro Ile Ala
1               5                   10                  15

Gln Thr Ala Leu Val Pro Leu Thr Asp His Val Gly Tyr Met Ile Ser
            20                  25                  30

Cys Arg Lys Tyr Val Arg Asp Met Gln Met Lys Met Thr Glu Leu Asn
            35                  40                  45

Thr Ser Arg Ile Ser Ala Glu Glu His Ile Ser Arg Asn Thr Arg Asn
    50                  55                  60

His Leu Gln Ile Pro Ser Gln Ile Lys Asp Trp Leu Asp Gln Val Glu
65                  70                  75                  80

Gly Ile Arg Ala Asn Val Ala Asn Phe Pro Ile Asp Val Ile Ser Cys
                85                  90                  95

Cys Ser Leu Arg Ile Arg His Lys Leu Gly Gln Lys Ala Phe Lys Ile
            100                 105                 110

Thr Glu Gln Ile Glu Ser Leu Thr Arg Gln Asn Ser Leu Ile Ile Trp
            115                 120                 125

Thr Asp Glu Pro Val Pro Leu Gly Arg Val Gly Ser Met Ile Ala Ser
130                 135                 140

Thr Ser Ala Ala Ser Ser Asp His His Asp Val Phe Pro Ser Arg Glu
145                 150                 155                 160

Gln Ile Phe Arg Lys Ala Leu Glu Ala Leu Glu Pro Val Gln Lys Ser
                165                 170                 175

His Ile Ile Ala Leu Trp Gly Met Gly Gly Val Gly Lys Thr Thr Met
            180                 185                 190

Met Lys Lys Leu Lys Glu Val Val Glu Gln Lys Lys Thr Cys Asn Ile
            195                 200                 205

Ile Val Gln Val Val Ile Gly Glu Lys Thr Asn Pro Ile Ala Ile Gln
            210                 215                 220

Gln Ala Val Ala Asp Tyr Leu Ser Ile Glu Leu Lys Glu Asn Thr Lys
225                 230                 235                 240

Glu Ala Arg Ala Asp Lys Leu Arg Lys Arg Phe Glu Ala Asp Gly Gly
                245                 250                 255

Lys Asn Lys Phe Leu Val Ile Leu Asp Asp Val Trp Gln Phe Phe Asp
                260                 265                 270

Leu Glu Asp Ile Gly Leu Ser Pro Leu Pro Asn Lys Val Asn Phe
            275                 280                 285

Lys Val Leu Leu Thr Ser Arg Asp Ser His Val Cys Thr Leu Met Gly
            290                 295                 300

Ala Glu Ala Asn Ser Ile Leu Asn Ile Lys Val Leu Lys Asp Val Glu
305                 310                 315                 320

Gly Lys Ser Leu Phe Arg Gln Phe Ala Lys Asn Ala Gly Asp Asp Asp
                325                 330                 335

Leu Asp Pro Ala Phe Ile Gly Ile Ala Asp Ser Ile Ala Ser Arg Cys
            340                 345                 350

Gln Gly Leu Pro Ile Ala Ile Lys Thr Ile Ala Leu Ser Leu Lys Gly
            355                 360                 365

Arg Ser Lys Ser Ala Trp Asp Val Ala Leu Ser Arg Leu Glu Asn His
    370                 375                 380

Lys Ile Gly Ser Glu Glu Val Val Arg Glu Val Phe Lys Ile Ser Tyr
385                 390                 395                 400
```

-continued

```
Asp Asn Leu Gln Asp Glu Val Thr Lys Ser Ile Phe Leu Leu Cys Ala
                405                 410                 415
Leu Phe Pro Glu Asp Phe Asp Ile Pro Ile Glu Glu Leu Val Arg Tyr
            420                 425                 430
Gly Trp Gly Leu Lys Leu Phe Ile Glu Ala Lys Thr Ile Arg Glu Ala
            435                 440                 445
Arg Asn Arg Leu Asn Asn Cys Thr Glu Arg Leu Arg Glu Thr Asn Leu
    450                 455                 460
Leu Phe Gly Ser His Asp Phe Gly Cys Val Lys Met His Asp Val Val
465                 470                 475                 480
Arg Asp Phe Val Leu His Met Phe Ser Glu Val Lys His Ala Ser Ile
                485                 490                 495
Val Asn His Gly Asn Met Ser Glu Trp Pro Glu Lys Asn Asp Thr Ser
                500                 505                 510
Asn Ser Cys Lys Arg Ile Ser Leu Thr Cys Lys Gly Met Ser Lys Phe
            515                 520                 525
Pro Lys Asp Ile Asn Tyr Pro Asn Leu Leu Ile Leu Lys Leu Met His
    530                 535                 540
Gly Asp Lys Ser Leu Cys Phe Pro Glu Asn Phe Tyr Gly Lys Met Glu
545                 550                 555                 560
Lys Val Gln Val Ile Ser Tyr Asp Lys Leu Met Tyr Pro Leu Leu Pro
                565                 570                 575
Ser Ser Leu Glu Cys Ser Thr Asn Val Arg Val Leu His Leu His Tyr
            580                 585                 590
Cys Ser Leu Arg Met Phe Asp Cys Ser Ser Ile Gly Asn Leu Leu Asn
            595                 600                 605
Met Glu Val Leu Ser Phe Ala Asn Ser Asn Ile Glu Trp Leu Pro Ser
    610                 615                 620
Thr Ile Gly Asn Leu Lys Lys Leu Arg Leu Leu Asp Leu Thr Asn Cys
625                 630                 635                 640
Lys Gly Leu Arg Ile Asp Asn Gly Val Leu Lys Asn Leu Val Lys Leu
                645                 650                 655
Glu Glu Leu Tyr Met Gly Val Asn Arg Pro Tyr Gly Gln Ala Val Ser
            660                 665                 670
Leu Thr Asp Glu Asn Cys Asn Glu Met Val Glu Gly Ser Lys Lys Leu
    675                 680                 685
Leu Ala Leu Glu Tyr Glu Leu Phe Lys Tyr Asn Ala Gln Val Lys Asn
690                 695                 700
Ile Ser Phe Glu Asn Leu Lys Arg Phe Lys Ile Ser Val Gly Cys Ser
705                 710                 715                 720
Leu His Gly Ser Phe Ser Lys Ser Arg His Ser Tyr Glu Asn Thr Leu
                725                 730                 735
Lys Leu Ala Ile Asp Lys Gly Glu Leu Leu Glu Ser Arg Met Asn Gly
            740                 745                 750
Leu Phe Glu Lys Thr Glu Val Leu Cys Leu Ser Val Gly Asp Met Tyr
            755                 760                 765
His Leu Ser Asp Val Lys Val Lys Ser Ser Ser Phe Tyr Asn Leu Arg
    770                 775                 780
Val Leu Val Val Ser Glu Cys Ala Glu Leu Lys His Leu Phe Thr Leu
785                 790                 795                 800
Gly Val Ala Asn Thr Leu Ser Lys Leu Glu His Leu Lys Val Tyr Lys
                805                 810                 815
Cys Asp Asn Met Glu Glu Leu Ile His Thr Gly Gly Ser Glu Gly Asp
```

-continued

```
                  820                 825                 830
Thr Ile Thr Phe Pro Lys Leu Lys Leu Leu Tyr Leu His Gly Leu Pro
            835                 840                 845

Asn Leu Leu Gly Leu Cys Leu Asn Val Asn Ala Ile Glu Leu Pro Lys
    850                 855                 860

Leu Val Gln Met Lys Leu Tyr Ser Ile Pro Gly Phe Thr Ser Ile Tyr
865                 870                 875                 880

Pro Arg Asn Lys Leu Glu Ala Ser Ser Leu Leu Lys Glu Val Val
            885                 890                 895

Ile Pro Lys Leu Asp Ile Leu Glu Ile His Asp Met Glu Asn Leu Lys
            900                 905                 910

Glu Ile Trp Pro Ser Glu Leu Ser Arg Gly Glu Lys Val Lys Leu Arg
            915                 920                 925

Lys Ile Lys Val Arg Asn Cys Asp Lys Leu Val Asn Leu Phe Pro His
            930                 935                 940

Asn Pro Met Ser Leu Leu His His Leu Glu Glu Leu Ile Val Glu Lys
945                 950                 955                 960

Cys Gly Ser Ile Glu Glu Leu Phe Asn Ile Asp Leu Asp Cys Ala Ser
            965                 970                 975

Val Ile Gly Glu Glu Asp Asn Asn Ser Ser Leu Arg Asn Ile Asn Val
            980                 985                 990

Glu Asn Ser Met Lys Leu Arg Glu Val Trp Arg Ile Lys Gly Ala Asp
            995                 1000                1005

Asn Ser Arg Pro Leu Phe Arg Gly Phe Gln Val Val Glu Lys Ile Ile
            1010                1015                1020

Ile Thr Arg Cys Lys Arg Phe Thr Asn Val Phe Thr Pro Ile Thr Thr
1025                1030                1035                1040

Asn Phe Asp Leu Gly Ala Leu Leu Glu Ile Ser Val Asp Cys Arg Gly
            1045                1050                1055

Asn Asp Glu Ser Asp Gln Ser Asn Gln Glu Gln Gln Ile Glu Ile
            1060                1065                1070

Leu Ser Glu Lys Glu Thr Leu Gln Glu Ala Thr Asp Ser Ile Ser Asn
            1075                1080                1085

Val Val Phe Pro Ser Cys Leu Met His Ser Phe His Asn Leu Gln Lys
            1090                1095                1100

Leu Ile Leu Asn Arg Val Lys Gly Val Glu Val Phe Glu Ile Glu
1105                1110                1115                1120

Ser Glu Ser Pro Thr Ser Arg Glu Leu Val Thr Thr His Asn Gln
            1125                1130                1135

Gln Gln Pro Val Ile Phe Pro Asn Leu Gln His Leu Asp Leu Arg Gly
            1140                1145                1150

Met Asp Asn Met Ile Arg Val Trp Lys Cys Ser Asn Trp Asn Lys Phe
            1155                1160                1165

Phe Thr Leu Pro Lys Gln Gln Ser Glu Ser Pro Phe His Asn Leu Thr
            1170                1175                1180

Thr Ile Asn Ile Asp Phe Cys Arg Ser Ile Lys Tyr Leu Phe Ser Pro
1185                1190                1195                1200

Leu Met Ala Glu Leu Leu Ser Asn Leu Lys Lys Val Asn Ile Lys Trp
            1205                1210                1215

Cys Tyr Gly Ile Glu Glu Val Val Ser Asn Arg Asp Asp Glu Asp Glu
            1220                1225                1230

Glu Met Thr Thr Phe Thr Ser Thr His Thr Thr Ile Leu Phe Pro
            1235                1240                1245
```

```
His Leu Asp Ser Leu Thr Leu Ser Phe Leu Glu Asn Leu Lys Cys Ile
    1250                1255                1260
Gly Gly Gly Gly Ala Lys Asp Glu Gly Ser Asn Glu Ile Ser Phe Asn
1265                1270                1275                1280
Asn Thr Thr Ala Thr Thr Ala Val Leu Asp Gln Phe Glu Leu Ser Glu
                1285                1290                1295
Ala Gly Gly Val Ser Trp Ser Leu Cys Gln Tyr Ala Arg Glu Ile Ser
                1300                1305                1310
Ile Glu Phe Cys Asn Ala Leu Ser Ser Val Ile Pro Cys Tyr Ala Ala
            1315                1320                1325
Gly Gln Met Gln Lys Leu Gln Val Leu Thr Val Ser Ser Cys Asn Gly
            1330                1335                1340
Leu Lys Glu Val Phe Glu Thr Gln Leu Arg Arg Ser Ser Asn Lys Asn
1345                1350                1355                1360
Asn Glu Lys Ser Gly Cys Asp Glu Gly Asn Gly Gly Ile Pro Arg Val
                1365                1370                1375
Asn Asn Asn Val Ile Met Leu Ser Gly Leu Lys Ile Leu Glu Ile Ser
                1380                1385                1390
Phe Cys Gly Gly Leu Glu His Ile Phe Thr Phe Ser Ala Leu Glu Ser
            1395                1400                1405
Leu Arg Gln Leu Glu Glu Leu Thr Ile Met Asn Cys Trp Ser Met Lys
            1410                1415                1420
Val Ile Val Lys Lys Glu Glu Asp Glu Tyr Gly Glu Gln Gln Thr Thr
1425                1430                1435                1440
Thr Thr Thr Lys Gly Thr Ser Ser Ser Ser Ser Ser Ser Ser Ser Ser
                1445                1450                1455
Ser Ser Ser Ser Ser Ser Pro Pro Ser Ser Lys Lys Val Val Val
                1460                1465                1470
Phe Pro Cys Leu Lys Ser Ile Val Leu Val Asn Leu Pro Glu Leu Val
            1475                1480                1485
Gly Phe Phe Leu Gly Met Asn Glu Phe Arg Leu Pro Ser Leu Asp Glu
            1490                1495                1500
Leu Ile Ile Glu Lys Cys Pro Lys Met Met Val Phe Thr Ala Gly Gly
1505                1510                1515                1520
Ser Thr Ala Pro Gln Leu Lys Tyr Ile His Thr Arg Leu Gly Lys His
                1525                1530                1535
Thr Ile Asp Gln Glu Ser Gly Leu Asn Phe His Gln Asp Ile Tyr Met
                1540                1545                1550
Pro Leu Ala Phe Ser Leu Leu Asp Leu Gln Thr Ser Phe Gln Ser Leu
            1555                1560                1565
Tyr Gly Asp Thr Leu Gly Pro Ala Thr Ser Glu Gly Thr Thr Trp Ser
    1570                1575                1580
Phe His Asn Leu Ile Glu Leu Asp Val Lys Phe Asn Lys Asp Val Lys
1585                1590                1595                1600
Lys Ile Ile Pro Ser Ser Glu Leu Leu Gln Leu Gln Lys Leu Glu Lys
                1605                1610                1615
Ile Asn Ile Asn Ser Cys Val Gly Val Glu Glu Val Phe Glu Thr Ala
                1620                1625                1630
Leu Glu Ala Ala Gly Arg Asn Gly Asn Ser Gly Ile Gly Phe Asp Glu
            1635                1640                1645
Ser Ser Gln Thr Thr Thr Thr Ser Leu Val Asn Leu Pro Asn Leu Arg
            1650                1655                1660
```

```
Glu Met Asn Leu Trp Gly Leu Asp Cys Leu Arg Tyr Ile Trp Lys Ser
1665                1670                1675                1680

Asn Gln Trp Thr Ala Phe Glu Phe Pro Lys Leu Thr Arg Val Glu Ile
            1685                1690                1695

Ser Asn Cys Asn Ser Leu Glu His Val Phe Thr Ser Ser Met Val Gly
            1700                1705                1710

Ser Leu Ser Gln Leu Gln Glu Leu His Ile Ser Gln Cys Lys Leu Met
        1715                1720                1725

Glu Glu Val Ile Val Lys Asp Ala Asp Val Ser Val Glu Glu Asp Lys
        1730                1735                1740

Glu Lys Glu Ser Asp Gly Lys Met Asn Lys Glu Ile Leu Ala Leu Pro
1745                1750                1755                1760

Ser Leu Lys Ser Leu Lys Leu Glu Ser Leu Pro Ser Leu Glu Gly Phe
            1765                1770                1775

Ser Leu Gly Lys Glu Asp Phe Ser Phe Pro Leu Leu Asp Thr Leu Arg
            1780                1785                1790

Ile Glu Glu Cys Pro Ala Ile Thr Thr Phe Thr Lys Gly Asn Ser Ala
            1795                1800                1805

Thr Pro Gln Leu Arg Glu Ile Glu Thr Arg Phe Gly Ser Val Tyr Ala
    1810                1815                1820

Gly Glu Asp Ile Lys Ser Ser Ile Ile Lys Ile Lys Gln Gln Asp Phe
1825                1830                1835                1840

Lys Lys Ala Gln Asp Ser Ile Xaa Cys Glu Val Asn Thr Arg
            1845                1850
```

(2) INFORMATION FOR SEQ ID NO:109:

(i) SEQUENCE CHARACTERISTICS:
        (A) LENGTH: 5829 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..5829
        (D) OTHER INFORMATION: /note= "RG2K"

(xi) SEQUENCE DESCRIPTION: SEQ ID NO:109:

```
TGGGATTCCA TATATAAAAA CATATATTTT TATAAAGTGG GATTCCATTG TTTATATAGA      60

TTTTTATTCA CCAATAGACA ATAGATTAAA AAAAGATATA AAAACATGTC GGCTTTTGAC     120

TAAAAATATA GATTTTTATG AATAGAATAT TCAATTTGCT TAACTCGTTT AAAAAAAATG     180

AAAAAGATGT CGATATAAAA TCTCATATGG GCCTTCTTTA CCATTCAAAT AGTAAAATAG     240

TAAAAGATAC TTGTTTGGGG CATGAACTGA CCATAGTCAA ACCCATACAA AATCAAACGA     300

ATCCCACATG GATGATGACG ATGGGGTCGC AGTAAATGTG TTTTGGTCCT TTTTTTTCGA     360

GAGAACAGAA GCTTCTGCTC TTCATCTTCT TTAGATTTTG GGGATTTTCT GGTTTCAGGG     420

GTTTGTGAGT GGAAACTAAA TTGAAGCAAA AAAGTATGGT ATAATTGGTT GCTAGTGAAA     480

TTGATGCTTT CTATTACTAT CATCTTTAAA ATTGTCAAAA CATTATGTAT TAAATTATGA     540

GATCGAAAGT GGTCTATGGG CCAAAGGTAA TACAAGCTTA CTCAATGAAA TGAATCTAGG     600

ATGCATCATG CATGTATTGG TTAGATTAAA GATTTTCATC AAATTTCCTT TATCAAATTG     660

TTGTATACCA TGTTATGTAG GTGCTACCAC AAGCCATAAC ATCGAGCAAT GGAGTGTATT     720

ACTGGCATCT TTAGCAACCC GTTTGCTCAG TGTCTCATCG CTCCTGTGAA AGAACACCTT     780
```

```
TGCCTTCTGA TTTTCTATAC ACAATATGTA GGGGATATGC TTACTGCAAT GACGGAGTTG    840

AATGCTGCAA AAGACATTGT TGAAGAGCGG AAGAATCAAA ACGTAGAAAA ATGTTTTGAG    900

GTTCCAAACC ATGTCAACCG TTGGTTGGAA GATGTTCAAA CAATCAACAG AAAAGTGGAA    960

CGTGTTCTTA ACGATAATTG CAATTGGTTC AATCTATGTA ATAGGTACAT GCTCGCAGTG   1020

AAAGCCTTGG AGATAACTCA GGAGATCGAT CATGCCATGA AACAACTCTC TCGGATAGAA   1080

TGGACTGATG ATTCAGTTCC TTTGGGAAGA AATGATTCCA CAAAGGCATC CACCTCTACA   1140

CCATCAAGTG ATTACAATGA CTTCGAGTCA AGAGAACACA CTTTTAGGAA AGCACTTGAA   1200

GCACTTGGAT CCAACCACAC ATCCCACATG GTAGCCTTAT GGGGGATGGG TGGAGTTGGG   1260

AAGACCACGA TGATGAAGAG GCTGAAAAAT ATTATTAAAG AAAAGAGGAC GTTTCATTAT   1320

ATTGTTTTGG TGGTTATAAA GGAAAATATG GATCTCATTT CCATCCAGGA TGCTGTAGCA   1380

GATTATCTGG ATATGAAGCT AACAGAAAGC AATGAATCAG AAAGAGCCGA TAAACTTCGT   1440

GAAGGGTTTC AGGCCAAATC AGATGGAGGT AAGAATAGGT TCCTCATAAT ACTGGATGAT   1500

GTATGGCAAT CTGTTAATAT GGAAGATATT GGTTTAAGTC CTTTTCCGAA TCAAGGTGTC   1560

GACTTCAAGG TCTTGTTGAC CTCGGAAAAC AAAGATGTTT GTGCAAAAAT GGGAGTTGAA   1620

GCTAATTTAA TTTTCGACGT GAAATTCTTA ACAGAAGAAG AAGCACAAAG TTTGTTTTAT   1680

CAATTTGTAA AAGTTTCTGA TACCCACCTT GATAAGATTG AAAAGCTAT TGTAAGAAAC    1740

TGTGGTGGTC TACCCATTGC CATCAAAACC ATAGCCAATA CTCTTAAAAA TAGAAACAAG   1800

GATGTATGGA AGGATGCACT TTCTCGTATA GAGCATCATG ACATTGAGAC AATTGCACAT   1860

GTTGTTTTTC AAATGAGCTA CGACAATCTC CAAAACGAAG AAGCTCAATC CATTTTTTTG   1920

CTTTGTGGAT TGTTTCCTGA AGACTTTGAT ATTCCTACTG AGGAATTGGT GAGGTATGGA   1980

TGGGGATTGA GAGTATTTAA TGGAGTGTAT ACTATAGGAG AAGCAAGACA CAGGTTGAAC   2040

GCCTACATCG AGCTGCTCAA GGATTCTAAT TTATTGATTG AAAGTGATGA TGTTCACTGC   2100

ATCAAGATGC ATGATTTAGT TCGTGCTTTT GTTTTGGATA CGTTTAATAG ATTCAAGCAT   2160

TCTTTGATTG TTAACCATGG TAATGGTGGT ATGTTAGGGT GGCCTGAAAA TGATATGAGT   2220

GCCTCATCTT GCAAAAGAAT TTCATTAATA TGCAAGGGCA TGTCCGATTT TCCTAGAGAC   2280

GTAAAGTTTC CAAATCTCTT GATTTTGAAA CTTATGCATG CAGATAAGTC TTTGAAGTTT   2340

CCTCAAGACT TTTATGGAGA AATGAAGAAG CTTCAGGTTA TATCATACGA TCACATGAAG   2400

TATCCCTTGC TTCCAACATC ACCTCAATGC TCCACCAACC TTCGTGTGCT TCATCTTCAT   2460

CAATGCTCAT TGATGTTTGA TTGCTCTTCT ATTGGAAATC TGTTGAATCT GGAAGTGCTC   2520

AGCTTTGCTA ATTCTGGTAT TGAGTGGTTG CCTTCCACAA TCGGAAATTT GAAGGAGCTA   2580

AGGGTACTAG ATTTGACAAA TTGTGATGGT CTTCGTATAG ATAATGGTGT CCTAAAGAAA   2640

TTGGTGAAAC TTGAAGAGCT TTATATGAGA GTTGGTGGTC GATATCAAAA GGCCATTAGC   2700

TTCACTGATG AAAACTGCAA TGAAATGGCA GAGCGTTCAA AAAATCTTTC TGCATTAGAA   2760

TTTGAGTTCT TCAAAAACAA TGCTCAACCA AAGAATATGT CATTTGAGAA TCTTGAACGA   2820

TTCAAGATCT CAGTGGGATG TTATTTTAAG GGAGATTTCG GTAAGATCTT TCACTCTTTT   2880

GAAAACACGT TGCGGTTGGT CACCAACAGA ACTGAAGTTC TTGAATCTAG GCTTAATGAG   2940

TTGTTTGAGA AAACAGATGT TCTTTATTTA AGTGTGGGAG ATATGAATGA TCTTGAAGAT   3000

GTTGAGGTAA AGTTGGCACA TCTTCCTAAA TCCTCTTCCT TCCACAATTT AAGAGTCCTT   3060

ATCATTTCTG AGTGTATAGA GTTGAGATAC CTTTTCACAC TTGATGTTGC AAACACTTTG   3120
```

```
TCAAAGCTTG AGCATCTTCA AGTTTACGAA TGCGATAATA TGGAAGAAAT CATACATACA    3180

GAGGGTAGAG GAGAAGTGAC AATTACATTC CCAAAGCTGA AGTTTTTATC ATTGTGTGGG    3240

CTACCAAATC TGTTGGGTTT GTGTGGTAAT GTGCACATAA TTAATCTACC ACAACTCACA    3300

GAGTTGAAAC TTAATGGCAT TCCAGGTTTC ACAAGCATAT ATCCTGAAAA AGATGTTGAA    3360

ACATCTAGTT TGTTGAATAA AGAGGTAAAT GTGTTTTATG TTAATACAAT ACAATCTTTT    3420

CAATTAACCG TTTCAAAATA TATTGTATGA TTTATTTTTG TTTGGATGGG GTTATTAATG    3480

GGTGATTATT TCTCAGGTTG TAATTCCTAA TTTGGAGAAA CTTGATATTA GTTATATGAA    3540

GGATTTGAAA GAGATATGGC CTTGTGAATT AGGGATGAGT CAGGAAGTTG ATGTTTCTAC    3600

GTTGAGAGTG ATTAAAGTAA GCAGTTGTGA TAATCTTGTG AATCTATTCC CGTGCAATCC    3660

TATGCCATTG ATACATCACC TTGAAGAGCT TCAAGTGATA TTTTGTGGTT CCATTGAAGT    3720

GTTATTCAAC ATTGAGTTGG ATTCTATTGG TCAAATTGGA GAAGGCATCA ACAATAGCAG    3780

CTTGAGAATC ATCCAATTGC AGAACTTAGG GAAGCTAAGT GAGGTGTGGA GGATAAAAGG    3840

TGCGGATAAC TCTAGTCTTC TCATCAGTGG CTTTCAAGGT GTTGAAAGCA TTATCGTTAA    3900

CAAATGCAAG ATGTTTAGAA ATGTATTCAC ACCTACCACC ACCAATTTTG ATCTGGGGC     3960

ACTTATGGAG ATTCGGATAC AAGATTGTGG AGAAAAGAGG AGAAACAACG AATTGGTAGA    4020

GAGTAGCCAA GAGCAAGAGC AGGTATGGCT TTCAATTTCA CTTTCTTACT TAATGAAGGA    4080

TTAAGCTCCT GCTTTTTGAA TAAAAAGTGG ATGAATGACT AAATTCGGGA ATGCCACCCG    4140

GAAAGTTATC AACCATTTAG CTACACCATT TTTTGAACTA ATGTTGCAAT AAATGCATAA    4200

TATAATTAAA AAATGGTCAT TGATAAATGT AAACCAACCT TTTTTATTTA TTAAAATGTC    4260

TACAATAAAT GATTTCTTT ATTATATATC ATTTTATAAC AATAAGCTTA AAGATGTTTA     4320

AATAGCCAAT GTCAGTTATA GATCGTAACT AATTTTTTAT TAACTAGTTT TAGTTAAGAT    4380

ATCACTCATT ATTATTTTTA TAGAAAAAAG ACAAGATTGG CTAATCCTCA TAAGAATTTG    4440

GAAGATTTAA GCAAAATATA GAGCTTTTCC AAACATAGCC AATAGTTTCT TTTGCAGGTC    4500

CCATCTACGA AATTATCAAT AGATTTGCGA TTTTTTTTTG GCACCCGGGA AATTTCCATT    4560

AATTAAAAAA AAGTTCAAGC CATTTTGTAG TTGGCACCTG CAAAATGGTA GTTTGCACCT    4620

GCGGAAATCA CCTTTCACCA TTTCGCATCT ATGACTTGTG AAAATGTTAA TTTGTGAAAT    4680

GGTCATGTGC ACCTCATGAG AAATACGAAA TGGTCAGTAA TATGACTTTT TTATATAAAT    4740

ATGATGGTGG CATATATTTA TAGGAAAATA TAGCTGCACG ATATTAATTA ATAGTGAAAT    4800

TAGTTAACTG TATACGATAA GTATACAAAA TTTATATGTA TGAAGTATAC TCAATTTAGG    4860

ACGACTCGGG CAATGAAATC ATCATTTAAT AGGAGCAATG AAATCATTTT CGAAAAATGT    4920

TTACAAATGA ATAAAATATT AAATTAAACT TAAAACATTT TGTTAGTAGT TTGAAATTTA    4980

CAAACTGAAA TTTGTTGTAT TTATTAACAT TTATAAATGT TGTACTATGA TTTTTTCCTT    5040

GTTTGCAAAT ATTCCTTAAA AATCCACCTA AAATCAAAAT AATTAATCTT TTTCAAGTTG    5100

AAAAATGAAA ATCGTATGAT ATAACCGTGT ATGGATGTGG AATTATATAT CAGTTACTAA    5160

TTACATTTTT TGTTGGGATA TATGTGCGCA GATTGATATT GCAATCCCAT TCACTCTCAC    5220

ACACTCTTTC CAAAACCTCC GTAAACTTGC TTTGGAAAAG TATGAAGGAG TGGAGGTGGT    5280

GTTTGAGATA GAGAGTCCAA CAAGTAGAGA ATTGATAACA ATTCACCATA ATCAACAACC    5340

ACTACTTCCC AACCTTGAGT TATTGGATAT AAGTTTTATG GACAGCATGA GTCATGTATG    5400

GAAGTGCAAC TGGAATAAAT TCTTCATTCT TCAAAAACAA CAGTCAGAAT CCCCATTCTG    5460

TAATCTCACA ACCATACATA TTCAATATTG CCAAAGCATT AAGTACTTGT TTTCAACTCT    5520
```

| | |
|---|---|
| CATGGCAAAA CTTCTTTCCA ACCTAAAGAA GGTCGAGGTA AGAGAGTGTC ATGGTATTGA | 5580 |
| AGAAGTTGTT TCGAACAGAG ATGATGAAGA TGAGGAAAAG ACTACATTTA CATCTACATC | 5640 |
| TTCTGAAAAA AGCACTAATT TGTTCCCTCG TCTTGAATCT CTCGCTCTTT ATCAACTTCC | 5700 |
| AAATCTCAAG TGTATTGGTG GTGGTGGTTC TGCCAACAGT GGGAACAATG AAATATCTCT | 5760 |
| TGATAATTCC ACTACTACTA CTTCTTTTGT TGATCAATCT AAGGTATGTT TTTTTTTTN | 5820 |
| GTTNCCCTT | 5829 |

(2) INFORMATION FOR SEQ ID NO:110:

(i) SEQUENCE CHARACTERISTICS:
        (A) LENGTH: 2150 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..2150
        (D) OTHER INFORMATION: /note= "RG2K continuation"

(xi) SEQUENCE DESCRIPTION: SEQ ID NO:110:

| | |
|---|---|
| CCTCCCTAAT AATACATGTT ATGCACACTA TACTAACATA TTAGACACGT AAAGGATAAA | 60 |
| TGCTATGCCT CATATAATAC GTTATATTTA TAATCTTTAA ACAATCAAAT TTATTAAACA | 120 |
| AATAACTAAG TGTGAGCAAA GGCAGGTACC CGACTAAATT GCCCAAAACC AGTCTGGTGG | 180 |
| TTCGTGGAAT GTTGGGCCAG GTCGTTAAAA CGTCTACACA CCGGTTCTTT AAATCACAGA | 240 |
| TCCGCTTCTC ATACTGTGAA CCCGGTTTTA ATTTTAAAAG AAAATTTCAT TATAAAGTAA | 300 |
| ATGACTTAAA CCATTACAAA CAACAAAAAT TTACCATTAC AATGTTGGAC TATCATTATT | 360 |
| TGCAACATAA AACTGAAAAT ACACATATTT CCTTCTGATA TCAGCATGAG TGGCTGGTTG | 420 |
| GCTAACCCAA AAATCCATGC ATTGTAGATG TGTGTTACAA CACATAGTAT CAATGAAAGG | 480 |
| CATATTTTTA GGCTAGAATT TAACAATCTG TAATAATATT CCCTAAAACT AATATCATCA | 540 |
| TCAACCAACT AATATAAAAC CATTGGGTTC GTCATTTTAG GTACAAAACA TAGATTTTTC | 600 |
| TAAGCTTGTT GTATTTAAAC ATATGCTTTC TAAACTTAAT TGATTTTGCA TTCCAAAATT | 660 |
| TTAGGTTGTA AAGTGGTATG TCATTTGTTG TCTTTTCAAC ATTAATTGTA CAAAAACCAA | 720 |
| AACTACATAA TTGATGTAGA TATCATAACA ATTGTGTTAT TTAGTATATA AAAACTAAAT | 780 |
| TTTGAATTGA ATTTCTTATA CAAAAGTTGT GTCTATGTAT ACATGTTTAT GTAGGTAATA | 840 |
| GACAATTAGT CTCTGTTAAG TATATGGAGT TTAATTTTTA GACTAATTTT TCATGTGTTG | 900 |
| CAGTTTTATC AGGCAGGTGG CGTTTTTTGG ACGTTATGCC AATACTCCAG AGAGATAAAT | 960 |
| ATAAGGGAGT GTTATGCATT GTCAAGTGTA ATTCCATGTT ATGCAGCAGG ACAGATGCAA | 1020 |
| AATGTTCAAG TGCTGAATAT ATACAGGTGC AACTCAATGA AGGAGTTATT TGAAACTCAA | 1080 |
| GGGATGAACA ACAACAATGG TGACAGTGGT TGTGATGAAG GAAATGGTTG TATACCAGCA | 1140 |
| ATTCCAAGAC TAAATAACGT TATTATGCTA CCCAATCTAA AGATATTGAA GATTGAAGAT | 1200 |
| TGTGGTCATC TGGAACATGT ATTCACATTC TCTGCACTTG GAAGCCTGAG ACAGCTCGAA | 1260 |
| GAGTTAACGA TAGAGAAATG CAAGGCAATG AAAGTGATAG TGAAGGAAGA AGATGAATAT | 1320 |
| GGAGAGCAAA CAACAAAGGC ATCTTCGAAG GAGGTTGTGG TCTTTCCTCG TCTCAAGTCC | 1380 |
| ATTGAACTGG AAAATCTACA AGAGCTCATG GGTTTCTACT TAGGGAAGAA TGAGATTCAG | 1440 |

```
TGGCCTTCAT TGGATAAGGT TATGATCAAG AATTGCCCAG AAATGATGGT GTTTGCACCT    1500

GGTGAGTCCA CAGTTCCCAA GCGCAAGTAT ATAAATACAA GCTTTGGCAT ATATGGGATG    1560

GAGGAGGTAC TTGAAACTCA AGGGATGAAC AACAATAATG ATGACAATTG TTGTGATGAT    1620

GGAAATGGTG GAATTCCAAG ACTAAATAAC GTTATTATGT TTCCAAATAT AAAGATATTG    1680

CAAATCAGCA ATTGTGGCAG TTTGAACAT ATATTCACAT TCTCTGCACT TGAAAGCCTG     1740

ATGCAGCTCA AGAGTTAAC AATAGCGGAT TGCAAGGCAA TGAAAGTGAT TGTGAAGGAG     1800

GAATATGATG TAGAGCAAAC AAGGGTATTG AAGGCTGTGG TATTTTCTTG TCTAAAGTCC    1860

ATTACACTAT GCCATCTACC AGAGTTGGTG GGTTTCTTCT TGGGGAAGAA TGAGTTCTGG    1920

TGGCCTTCAT TGGATAAGGT TACCATCATT GATTGCCCAC AAATGATGGG GTTCACACCT    1980

GGTGGGTCAA CAACTTCCCA CCTCAAGTAC ATACACTCAA GCTTAGGCAA ACATACTCTT    2040

GAATGTGGCC TTAATTTCAA GTCACAACTA CTGCATATCA TCAGGTATAA TTATTATTCT    2100

TTNACACCAT CTAATTATGG AATCATGACG CTAATTACAG TATTAAACAC              2150
```

(2) INFORMATION FOR SEQ ID NO:111:

(i) SEQUENCE CHARACTERISTICS:
        (A) LENGTH: 1074 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1074
        (D) OTHER INFORMATION: /note= "RG2K deduced sequence"

(xi) SEQUENCE DESCRIPTION: SEQ ID NO:111:

```
Met Glu Cys Ile Thr Gly Ile Phe Ser Asn Pro Phe Ala Gln Cys Leu
1               5                   10                  15

Ile Ala Pro Val Lys Glu His Leu Cys Leu Leu Ile Phe Tyr Thr Gln
                20                  25                  30

Tyr Val Gly Asp Met Leu Thr Ala Met Thr Glu Leu Asn Ala Ala Lys
            35                  40                  45

Asp Ile Val Glu Glu Arg Lys Asn Gln Asn Val Glu Lys Cys Phe Glu
        50                  55                  60

Val Pro Asn His Val Asn Arg Trp Leu Glu Asp Val Gln Thr Ile Asn
65                  70                  75                  80

Arg Lys Val Glu Arg Val Leu Asn Asp Asn Cys Asn Trp Phe Asn Leu
                85                  90                  95

Cys Asn Arg Tyr Met Leu Ala Val Lys Ala Leu Glu Ile Thr Gln Glu
                100                 105                 110

Ile Asp His Ala Met Lys Gln Leu Ser Arg Ile Glu Trp Thr Asp Asp
            115                 120                 125

Ser Val Pro Leu Gly Arg Asn Asp Ser Thr Lys Ala Ser Thr Ser Thr
        130                 135                 140

Pro Ser Ser Asp Tyr Asn Asp Phe Glu Ser Arg Glu His Thr Phe Arg
145                 150                 155                 160

Lys Ala Leu Glu Ala Leu Gly Ser Asn His Thr Ser His Met Val Ala
                165                 170                 175

Leu Trp Gly Met Gly Val Gly Lys Thr Thr Met Met Lys Arg Leu
            180                 185                 190

Lys Asn Ile Ile Lys Glu Lys Arg Thr Phe His Tyr Ile Val Leu Val
```

-continued

```
              195                 200                     205
Val Ile Lys Glu Asn Met Asp Leu Ile Ser Ile Gln Asp Ala Val Ala
210                 215                 220

Asp Tyr Leu Asp Met Lys Leu Thr Glu Ser Asn Glu Ser Glu Arg Ala
225                 230                 235                 240

Asp Lys Leu Arg Glu Gly Phe Gln Ala Lys Ser Asp Gly Gly Lys Asn
                245                 250                 255

Arg Phe Leu Ile Ile Leu Asp Asp Val Trp Gln Ser Val Asn Met Glu
                260                 265                 270

Asp Ile Gly Leu Ser Pro Phe Pro Asn Gln Gly Val Asp Phe Lys Val
                275                 280                 285

Leu Leu Thr Ser Glu Asn Lys Asp Val Cys Ala Lys Met Gly Val Glu
290                 295                 300

Ala Asn Leu Ile Phe Asp Val Lys Phe Leu Thr Glu Glu Ala Gln
305                 310                 315                 320

Ser Leu Phe Tyr Gln Phe Val Lys Val Ser Asp Thr His Leu Asp Lys
                325                 330                 335

Ile Gly Lys Ala Ile Val Arg Asn Cys Gly Gly Leu Pro Ile Ala Ile
                340                 345                 350

Lys Thr Ile Ala Asn Thr Leu Lys Asn Arg Asn Lys Asp Val Trp Lys
                355                 360                 365

Asp Ala Leu Ser Arg Ile Glu His His Asp Ile Glu Thr Ile Ala His
370                 375                 380

Val Val Phe Gln Met Ser Tyr Asp Asn Leu Gln Asn Glu Glu Ala Gln
385                 390                 395                 400

Ser Ile Phe Leu Leu Cys Gly Leu Phe Pro Glu Asp Phe Asp Ile Pro
                405                 410                 415

Thr Glu Glu Leu Val Arg Tyr Gly Trp Gly Leu Arg Val Phe Asn Gly
                420                 425                 430

Val Tyr Thr Ile Gly Glu Ala Arg His Arg Leu Asn Ala Tyr Ile Glu
                435                 440                 445

Leu Leu Lys Asp Ser Asn Leu Ile Glu Ser Asp Val His Cys
450                 455                 460

Ile Lys Met His Asp Leu Val Arg Ala Phe Val Leu Asp Thr Phe Asn
465                 470                 475                 480

Arg Phe Lys His Ser Leu Ile Val Asn His Gly Asn Gly Met Leu
                485                 490                 495

Gly Trp Pro Glu Asn Asp Met Ser Ala Ser Cys Lys Arg Ile Ser
                500                 505                 510

Leu Ile Cys Lys Gly Met Ser Asp Phe Pro Arg Asp Val Lys Phe Pro
                515                 520                 525

Asn Leu Leu Ile Leu Lys Leu Met His Ala Asp Lys Ser Leu Lys Phe
530                 535                 540

Pro Gln Asp Phe Tyr Gly Glu Met Lys Lys Leu Gln Val Ile Ser Tyr
545                 550                 555                 560

Asp His Met Lys Tyr Pro Leu Leu Pro Thr Ser Pro Gln Cys Ser Thr
                565                 570                 575

Asn Leu Arg Val Leu His Leu His Gln Cys Ser Leu Met Phe Asp Cys
                580                 585                 590

Ser Ser Ile Gly Asn Leu Leu Asn Leu Glu Val Leu Ser Phe Ala Asn
                595                 600                 605

Ser Gly Ile Glu Trp Leu Pro Ser Thr Ile Gly Asn Leu Lys Glu Leu
610                 615                 620
```

-continued

```
Arg Val Leu Asp Leu Thr Asn Cys Asp Gly Leu Arg Ile Asp Asn Gly
625                 630                 635                 640

Val Leu Lys Lys Leu Val Lys Leu Glu Glu Leu Tyr Met Arg Val Gly
                645                 650                 655

Gly Arg Tyr Gln Lys Ala Ile Ser Phe Thr Asp Glu Asn Cys Asn Glu
                660                 665                 670

Met Ala Glu Arg Ser Lys Asn Leu Ser Ala Leu Glu Phe Glu Phe Phe
                675                 680                 685

Lys Asn Asn Ala Gln Pro Lys Asn Met Ser Phe Glu Asn Leu Glu Arg
                690                 695                 700

Phe Lys Ile Ser Val Gly Cys Tyr Phe Lys Gly Asp Phe Gly Lys Ile
705                 710                 715                 720

Phe His Ser Phe Glu Asn Thr Leu Arg Leu Val Thr Asn Arg Thr Glu
                725                 730                 735

Val Leu Glu Ser Arg Leu Asn Glu Leu Phe Glu Lys Thr Asp Val Leu
                740                 745                 750

Tyr Leu Ser Val Gly Asp Met Asn Asp Leu Glu Asp Val Glu Val Lys
                755                 760                 765

Leu Ala His Leu Pro Lys Ser Ser Phe His Asn Leu Arg Val Leu
770                 775                 780

Ile Ile Ser Glu Cys Ile Glu Leu Arg Tyr Leu Phe Thr Leu Asp Val
785                 790                 795                 800

Ala Asn Thr Leu Ser Lys Leu Glu His Leu Gln Val Tyr Glu Cys Asp
                805                 810                 815

Asn Met Glu Glu Ile Ile His Thr Glu Gly Arg Gly Glu Val Thr Ile
                820                 825                 830

Thr Phe Pro Lys Leu Lys Phe Leu Ser Leu Cys Gly Leu Pro Asn Leu
                835                 840                 845

Leu Gly Leu Cys Gly Asn Val His Ile Ile Asn Leu Pro Gln Leu Thr
                850                 855                 860

Glu Leu Lys Leu Asn Gly Ile Pro Gly Phe Thr Ser Ile Tyr Pro Glu
865                 870                 875                 880

Lys Asp Val Glu Thr Ser Ser Leu Leu Asn Lys Glu Val Val Ile Pro
                885                 890                 895

Asn Leu Glu Lys Leu Asp Ile Ser Tyr Met Lys Asp Leu Lys Glu Ile
                900                 905                 910

Trp Pro Cys Glu Leu Gly Met Ser Gln Glu Val Asp Val Ser Thr Leu
                915                 920                 925

Arg Val Ile Lys Val Ser Ser Cys Asp Asn Leu Val Asn Leu Phe Pro
930                 935                 940

Cys Asn Pro Met Pro Leu Ile His His Leu Glu Glu Leu Gln Val Ile
945                 950                 955                 960

Phe Cys Gly Ser Ile Glu Val Leu Phe Asn Ile Glu Leu Asp Ser Ile
                965                 970                 975

Gly Gln Ile Gly Glu Gly Ile Asn Asn Ser Ser Leu Arg Ile Ile Gln
                980                 985                 990

Leu Gln Asn Leu Gly Lys Leu Ser Glu Val Trp Arg Ile Lys Gly Ala
                995                 1000                1005

Asp Asn Ser Ser Leu Leu Ile Ser Gly Phe Gln Gly Val Glu Ser Ile
                1010                1015                1020

Ile Val Asn Lys Cys Lys Met Phe Arg Asn Val Phe Thr Pro Thr Thr
1025                1030                1035                1040
```

```
Thr Asn Phe Asp Leu Gly Ala Leu Met Glu Ile Arg Ile Gln Asp Cys
            1045                1050                1055

Gly Glu Lys Arg Arg Asn Asn Glu Leu Val Glu Ser Ser Gln Glu Gln
        1060                1065                1070

Glu Gln
```

(2) INFORMATION FOR SEQ ID NO:112:

(i) SEQUENCE CHARACTERISTICS:
        (A) LENGTH: 1448 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1448
        (D) OTHER INFORMATION: /note= "RG2L"

(xi) SEQUENCE DESCRIPTION: SEQ ID NO:112:

```
GGAAGACACA ATGATGCAAA GACTGAAGAA GGTTGCCAAA GAAAATAGAA TGTTCAGTTA      60

CATGGTCGAG GCAGTTATAG GGAAAAAGAC AGACCCAATT GCTATTCAAC AAGCTGTAGC     120

CGATTACCTT CGTATACAGT TCAAAGAAAG CACTAAACCA GCAAGAGCTG ATAAGCTTCG     180

TGAATGGTTC AAGGCCCACT CTGNAGACGG TAAGAATAAG TTCCTCGTAA TATTTGATGA     240

CGTCTGGCAG TCCGTTGATC TGGAAGATAT TGGNTTAAGT CCTTTTCCAA ATCAAGGTGT     300

CGACTTCAAG GTCTTGTTGA CTTCACGAGA CGAACACGTT TGCACAATGA TGGGGGTTGA     360

AGCTAATTCA GTTATTAATG TGGGACTTCT AACTGAAGTA GAAGCACAAA GTCTGTTCCA     420

GCAATTTGTA GAAACTTTTG AGCCCGAGCT CTGTAAGATA GGAGAAGTTA TCGTAAGAAA     480

GTGTTGCGGT CTACCTATTG CCATCAAAAC CATGGCGTGT ACTCTAAGAA ATAAAAGAAA     540

GGATGCATGG AAGGATGCAC TTTCACGTAT AGAGCACTAT GACATTCGTA GTGTTGCGCC     600

TAAAGTCTTT GAAACAAGCT ATCACAATCT CCAAGACAGG GAGACTAAAT CCGTGTTTTT     660

GATGTGTGGT TTGTTTCCTG AAGACTTCAA TATTCCTACC GAGGAGTTGA TGAGGTATGG     720

ATGGGGCTTA AAGCTATTTG ACAGAGTTTA TACAATTAGA GAAGCAAGAA CCAGGCTCAA     780

CACCTGCATT GAGCGACTTG TGCAGACAAA TTTGTTAATT GAAAGTGATG ATGTTGGGTG     840

TGTCAAGATG CATGATCTGG TGCGTGCTTT TGTTTTGGGT ATGTATTCTG AAGTCGAGCA     900

TGCTTCAATT GTCAACCATG GTAATATGCA TGGGTGGACT AAAAATGATA TGAACGACTC     960

TTGCAAAACA GTTTCTTTAA CATGCGAGAG TGTGTCTGAG TTTCCAGGAG ACCTCAAGTT    1020

TCCAAACCTA AAGCTTTTGA AACTTATGCA TGGAGATAAG ATGCTAAGGT TTTCTCAAGA    1080

CTTTTATGAA GGAATGGAAA AGCTCCAGGT AATATCATAC CATAAAATGA AGTATCCATT    1140

GCTTCCCTCG TCACCTCAAT GCTCCACCAA CCTTCGAGTG CTTCATCTTC ATCGGTGTTC    1200

ATTACGGATG CTTGATTGCT CTTGTATCGG AAATTTGACG AATCTGGAAG TGTTGAGCTT    1260

CGCTAATTCT GGCATTGAAC GGATACCTTC AGCAATCGGA AATTTGAAGA AGCTTAGGCA    1320

ACTTGATCTG AGAGGTCGTT ATGGTCTTTG TATAGAACAG GGTGTCTTGA AAAATTTGGT    1380

CGAACTTGAA GAACTTTATA TTGGAAATGC ATCTGCGTTT AGAGATTATA ACTGCAATGA    1440

GATGGCAG                                                            1448
```

(2) INFORMATION FOR SEQ ID NO:113:

-continued

```
    (i) SEQUENCE CHARACTERISTICS:
        (A) LENGTH: 482 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..482
        (D) OTHER INFORMATION: /note= "RG2L deduced sequence"

(xi) SEQUENCE DESCRIPTION: SEQ ID NO:113:

Glu Asp Thr Met Met Gln Arg Leu Lys Lys Val Ala Lys Glu Asn Arg
1               5                   10                  15

Met Phe Ser Tyr Met Val Glu Ala Val Ile Gly Glu Lys Thr Asp Pro
            20                  25                  30

Ile Ala Ile Gln Gln Ala Val Ala Asp Tyr Leu Arg Ile Gln Phe Lys
        35                  40                  45

Glu Ser Thr Lys Pro Ala Arg Ala Asp Lys Leu Arg Glu Trp Phe Lys
50                  55                  60

Ala His Ser Xaa Asp Gly Lys Asn Lys Phe Leu Val Ile Phe Asp Asp
65                  70                  75                  80

Val Trp Gln Ser Val Asp Leu Glu Asp Ile Gly Leu Ser Pro Phe Pro
            85                  90                  95

Asn Gln Gly Val Asp Phe Lys Val Leu Leu Thr Ser Arg Asp Glu His
            100                 105                 110

Val Cys Thr Met Met Gly Val Glu Ala Asn Ser Val Ile Asn Val Gly
            115                 120                 125

Leu Leu Thr Glu Val Glu Ala Gln Ser Leu Phe Gln Gln Phe Val Glu
        130                 135                 140

Thr Phe Glu Pro Glu Leu Cys Lys Ile Gly Glu Val Ile Val Arg Lys
145                 150                 155                 160

Cys Cys Gly Leu Pro Ile Ala Ile Lys Thr Met Ala Cys Thr Leu Arg
                165                 170                 175

Asn Lys Arg Lys Asp Ala Trp Lys Asp Ala Leu Ser Arg Ile Glu His
            180                 185                 190

Tyr Asp Ile Arg Ser Val Ala Pro Lys Val Phe Glu Thr Ser Tyr His
        195                 200                 205

Asn Leu Gln Asp Arg Glu Thr Lys Ser Val Phe Leu Met Cys Gly Leu
210                 215                 220

Phe Pro Glu Asp Phe Asn Ile Pro Thr Glu Glu Leu Met Arg Tyr Gly
225                 230                 235                 240

Trp Gly Leu Lys Leu Phe Asp Arg Val Tyr Thr Ile Arg Glu Ala Arg
                245                 250                 255

Thr Arg Leu Asn Thr Cys Ile Glu Arg Leu Val Gln Thr Asn Leu Leu
            260                 265                 270

Ile Glu Ser Asp Asp Val Gly Cys Val Lys Met His Asp Leu Val Arg
        275                 280                 285

Ala Phe Val Leu Gly Met Tyr Ser Glu Val Glu His Ala Ser Ile Val
290                 295                 300

Asn His Gly Asn Met His Gly Trp Thr Lys Asn Asp Met Asn Asp Ser
305                 310                 315                 320

Cys Lys Thr Val Ser Leu Thr Cys Glu Ser Val Ser Glu Phe Pro Gly
                325                 330                 335

Asp Leu Lys Phe Pro Asn Leu Lys Leu Leu Lys Leu Met His Gly Asp
```

```
              340             345             350
Lys Met Leu Arg Phe Ser Gln Asp Phe Tyr Glu Gly Met Glu Lys Leu
            355                 360             365

Gln Val Ile Ser Tyr His Lys Met Lys Tyr Pro Leu Leu Pro Ser Ser
    370                 375             380

Pro Gln Cys Ser Thr Asn Leu Arg Val Leu His Leu His Arg Cys Ser
385                 390             395                 400

Leu Arg Met Leu Asp Cys Ser Cys Ile Gly Asn Leu Thr Asn Leu Glu
                405             410                 415

Val Leu Ser Phe Ala Asn Ser Gly Ile Glu Arg Ile Pro Ser Ala Ile
            420             425             430

Gly Asn Leu Lys Lys Leu Arg Gln Leu Asp Leu Arg Gly Arg Tyr Gly
            435             440             445

Leu Cys Ile Glu Gln Gly Val Leu Lys Asn Leu Val Glu Leu Glu Glu
            450             455             460

Leu Tyr Ile Gly Asn Ala Ser Ala Phe Arg Asp Tyr Asn Cys Asn Glu
465                 470             475                 480

Met Ala
```

(2) INFORMATION FOR SEQ ID NO:114:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1074
        (D) OTHER INFORMATION: /note= "RG2M"

(xi) SEQUENCE DESCRIPTION: SEQ ID NO:114:

```
GGGGAAGACA CAATAGATGC AAAGGCTGAA GAAGTTGCCA AGAAAAGAG  AATGTTCAGT     60

TATATCATTG AGGCGGTTAT AGGGGAAAAG ACAGACCCCA TTTCCATTCA GGAAGCTATA    120

TCATATTACC TTGGTGTAGA GCTCAATGCA AATACTAAGT CAGTAAGAGC TGATATGCTT    180

CGTCAAGGGT TCAAGGCCAA ATCTGATGTA GGTAAGGATA AATTCTTAAT AATACTCGAC    240

GATGTATGGC AGTCTGTTGA TTTGAAGAT  ATTGGATTAA GTCCATTTCC AAATCAAGGT    300

GTTAACTTCA AGGTCCTGTT AACATCACGA GACCGACATA TTTGCACTGT GATGGGGGTT    360

GAAGGTCATT CGATTTTTAA TGTGGGACTT CTCACAGAAG CAGAATCAAA AAGATTGTTC    420

TGGCAGTTTG TAGAAGGTTC TGATCCTGAG CTCCATAAGA TAGGAGAAGA TATTGTAAGT    480

AAGTGTTGTG GTCTACCCAT TGCCATTAAA ACCATGGCAT GTACACTTAG AGATAAAAGT    540

ACGGATGCAT GGAAGGATGC ACTGTCTCGT TTAGAGCATC ATGACATTGA AAATGTTGCC    600

TCTAAAGTTT TTAGAGCGAG CTATGACCAT CTCCAAGACG AGGAGACTAA ATCCACTTTT    660

TTTCTATGTG GATTGTTTCC AGAAGATTCC AATATTCCTA TGGAGGAGTT GGTGAGGTAT    720

GGGTGGGGAT TGAAATTATT TAAAAAAGTG TATACCATAA GAGAAGCAAG AACTAGGCTC    780

AACACTTGCA TTGAGCGGCT CATCTATACC AATTTGTTGA TAAAAGTTGA TGATGTTCAG    840

TGCATCAAGA TGCATGATCT CATCCGTTCT TTTGTTTTGG ATATGTTTTC TAAAGTTGAG    900

CATGCTTCGA TTGTCAACCA TGGTAATACG CTAGAGTGGC CTGCAGATNA TNTGCACGAC    960

TCTTGTAAAG GGCTTTCATT AACATGCAAG GGTANATGTG AGTTTTGTGG AGACCTNAAN   1020
```

TTTCCAACCC TAATGATTTT AAAACTTATG CATGGAGATA AATCGCTAAG GTTT        1074

(2) INFORMATION FOR SEQ ID NO:115:

(i) SEQUENCE CHARACTERISTICS:
        (A) LENGTH: 358 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..358
        (D) OTHER INFORMATION: /note= "RG2M deduced sequence"

(xi) SEQUENCE DESCRIPTION: SEQ ID NO:115:

```
Gly Glu Asp Thr Ile Asp Ala Lys Ala Glu Glu Val Ala Lys Glu Lys
  1               5                  10                  15

Arg Met Phe Ser Tyr Ile Ile Glu Ala Val Ile Gly Glu Lys Thr Asp
                 20                  25                  30

Pro Ile Ser Ile Gln Glu Ala Ile Ser Tyr Tyr Leu Gly Val Glu Leu
             35                  40                  45

Asn Ala Asn Thr Lys Ser Val Arg Ala Asp Met Leu Arg Gln Gly Phe
 50                  55                  60

Lys Ala Lys Ser Asp Val Gly Lys Asp Lys Phe Leu Ile Ile Leu Asp
 65                  70                  75                  80

Asp Val Trp Gln Ser Val Asp Leu Glu Asp Ile Gly Leu Ser Pro Phe
                 85                  90                  95

Pro Asn Gln Gly Val Asn Phe Lys Val Leu Leu Thr Ser Arg Asp Arg
                100                 105                 110

His Ile Cys Thr Val Met Gly Val Glu Gly His Ser Ile Phe Asn Val
            115                 120                 125

Gly Leu Leu Thr Glu Ala Glu Ser Lys Arg Leu Phe Trp Gln Phe Val
130                 135                 140

Glu Gly Ser Asp Pro Glu Leu His Lys Ile Gly Glu Asp Ile Val Ser
145                 150                 155                 160

Lys Cys Cys Gly Leu Pro Ile Ala Ile Lys Thr Met Ala Cys Thr Leu
                165                 170                 175

Arg Asp Lys Ser Thr Asp Ala Trp Lys Asp Ala Leu Ser Arg Leu Glu
            180                 185                 190

His His Asp Ile Glu Asn Val Ala Ser Lys Val Phe Arg Ala Ser Tyr
        195                 200                 205

Asp His Leu Gln Asp Glu Glu Thr Lys Ser Thr Phe Phe Leu Cys Gly
210                 215                 220

Leu Phe Pro Glu Asp Ser Asn Ile Pro Met Glu Glu Leu Val Arg Tyr
225                 230                 235                 240

Gly Trp Gly Leu Lys Leu Phe Lys Lys Val Tyr Thr Ile Arg Glu Ala
                245                 250                 255

Arg Thr Arg Leu Asn Thr Cys Ile Glu Arg Leu Ile Tyr Thr Asn Leu
            260                 265                 270

Leu Ile Lys Val Asp Asp Val Gln Cys Ile Lys Met His Asp Leu Ile
        275                 280                 285

Arg Ser Phe Val Leu Asp Met Phe Ser Lys Val Glu His Ala Ser Ile
290                 295                 300

Val Asn His Gly Asn Thr Leu Glu Trp Pro Ala Asp Xaa Xaa His Asp
```

```
305                 310                 315                 320
Ser Cys Lys Gly Leu Ser Leu Thr Cys Lys Gly Xaa Cys Glu Phe Cys
                325                 330                 335

Gly Asp Leu Xaa Phe Pro Thr Leu Met Ile Leu Lys Leu Met His Gly
                340                 345                 350

Asp Lys Ser Leu Arg Phe
        355
```

(2) INFORMATION FOR SEQ ID NO:116:

(i) SEQUENCE CHARACTERISTICS:
        (A) LENGTH: 7521 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..7521
        (D) OTHER INFORMATION: /note= "RG2N"

(xi) SEQUENCE DESCRIPTION: SEQ ID NO:116:

```
AGGTAAAATC CATAACCCTA AATGTTGGTA CGCTCATATA TCAAATTGCG TGTTTTGTTG      60

AATGAAAAAA GCATGCTCAA AAACCAGTG TAAGGCACGG TATATGACAT ATTTATAGTT     120

ACTGATAACA AATTATGATA ATTTTGGGTT TACRTAAGTT AGGATTCGTA CTTCAACCAA    180

ATGTAATAGT TTTTGTGAGT CTATCTATGT ATTTGGGGAA TCACATTAGC AACGGGATTG    240

TACTAGTAAT TCGAAAAAGT CTTTTAAATA ATTTTTCTGT TTATAATTTA TGAATAGTTT    300

TAGCGACATC TAATATTAAA TAGAATGTAT CTGATATTGA ATTAATGTCC TTAATGTGAA    360

CATAGACCTT TTCCATTTAC TAATGCCTAA TTATTAGTTT CTAATCAATA AATTTTAATT    420

TCTGTTTTAT GCTTCTAAGA CAATAAAAAT CCATGATTTA CCTTTAAATA TTAACAAAAA    480

TGACCATAAA TAAATAAAAA ATTAGGATAC CAAACCCCCC CGCCATGCCC AATGTCTAAA    540

TATTCTTGAT GCTTTTGCTT TTCCCTCTTT TCCTTGTTAG TCTATTATTC TGGAGAGTTT    600

GAGAGAGTTT CATACAAGAA AATTTCAAGA AGAAAGCAAA GGTCCAGGTA TTCTCTTTTC    660

TTAATTATGT ATTAACTTAC AAGCATTTTT TACACGATCC ATGGTTTTTT GTGTATGTTT    720

TTCAAATTGA AACTAGATTG GGACTTTTGC CCTTGATGAT TCATAAGATA TTGCATGGAG    780

TTGAGATTGT GTAAGAAAAG TGGTGAATAG AAAGAGCAAG TGAATCCAGA TATAGTATTG    840

GTAATATATG ATGATGAGAT AGAGATATGT TAAAACTGGC TAGAAAATTG TTTTAATTTG    900

AAATTTAGGT KGTTGAATTT GAAAGATACC AAGCTAATAA CTAATTAGTT ATGCTAAWTA    960

GTTATAAAGA ACAACAAACT CTTAGTTTTT TTTTTCATGA TTTTCAACCT CTTTGTACCA   1020

AACTAAATTA TAGCAAAATT GAATATCATT CTCTGCAATC AATCTTAACT TTTGTTATTA   1080

TCATCATGTC TAAAATTGCC ACAAGTTTAT TTTCAAAGTC ATATTGGATT ATGAAAGGAC   1140

TATTTTTACC AATTACATCT TTACTTTATG GGCCAAAGCT AATACAATCC GACTAAACTA   1200

AAGGAATATG GGATGCATAT AGTTTGCTTC CCGATTATAG ATTTCTATCT AATTTGTCTA   1260

TTGTACTAAT TTAGGTGCCA CCACAAGTAA ATTTGTTAAA TGGATATCGT TAATGCCATT   1320

CTTAAACCAG TTGTCGAGAC TCTCATGGTA CCCGTTAAGA AACACATAGG GTACCTCATT   1380

TCCTGCAGGC AATATATGAG GGAAATGGGT ATCAAAATGA GGGGATTGAA TGCTACTAGA   1440

CTTGGTGTCG AAGAGCATGT GAACCGGAAC ATAAGCAACC AGCTTGAGGT TCCAGCCCAA   1500
```

```
GGCAGGGGTT GGTATGAAGA AGTAGGAAAG ATCAATGCAA AAGTGGAAAA TTTTCCTAGC    1560

GATGTTGGCA GTTGTTTCAA TCTTAAGGTT AGACACGGGG TCGGAAAGAG AGCCTCCAAG    1620

ATAATTGAGG ACATCGACAG TGTCATGAGA GAACACTCTA TCATCATCTG GAATGATCAT    1680

TCCATTCTTC TAGGAAGAAT TGATTCCACG AAAGCATCCA CCTCAATACC ATCAACCGAT    1740

CATCATGATG AGTTCCAGTC AAGAGAGCAA ACTTTCACAG AAGCACTAAA CGCACTCGAT    1800

CCTAACCACA AATCCCACAT GATAGCCTTA TGGGAATGG GCGGAGTGGG GAAGACGACA     1860

ATGATGCATC GGCTGAAAAA GGTTGTGAAA GAAAAGAAAA TGTTTAATTT TATTGTTGAG    1920

GCGGTTGTAG GGGAAAAAAC AGACCCCATT GCTATTCAAT CAGCTGTGGC AGATTACCTA    1980

GGTATAGAGC TCAATGAAAA AACTAAACCA GCAAGAACTG AGAAGCTTCG TAAATGGTTT    2040

GTGGACAATT CTGCTGGTAA GAAGATCCTA GTCATACTCG ACGATGTATG GCAGTTTGTA    2100

GATCTGAATG ATATTGGTTT AAGTCCTTTA CCAAATCAAG GTGTCGACTT CAAGGTGTTG    2160

TTGACATCAC GAGACAAAGA TGTTTGCACT GAGATGGGAG CTGAAGTTAA TTCAACTTTT    2220

AATGTGAAAA TGTTAATAGA AACAGAAGCA CAAAGTTTAT TCCACCAATT TGTAGAAATT    2280

TCGGATGATG TTGATCGTGA GCTCCATAAT ATAGGAGTGA ATATTGTAAG GAAGTGTGGC    2340

GGTCTACCCA TTGTCATCAA AACCATGGCG TGTACTCTTA GAGGAAAAAG CAAGGATGCA    2400

TGGAAGAATG CACTTCTTCG TTTAGTGAAC TACAACATTG AAAATATAGT GAATGGAGTT    2460

TTTAAAATGA GTTACGACAA TCTCCAAGAT GAGGAGACTA AATCCACCTT TTTGCTTTGT    2520

GGAATGTTTC CCGAAGACTT TAATATTCCT ACCGAGGAGT TGGTGAGGTA TGGATGGGGG    2580

TTGAAATTAT TTAAAAAAGT GTATACTATA GGAGAAGCAA GAATCAGGCT CAACACATGC    2640

ATTGAGCGGC TCATTCATAC AAATTTGTTG ATTGAAGTTG ATGATGTTAG GTGCATCAAG    2700

ATGCATGATC TTGTCCGTGC TTTTGTTTTG GATATGTATT CTAAAGTCGA GCATGCTTCC    2760

ATTGTCAACC ATGGTAATAC ACTAGAGTGG CATGTGGATA ATATGCACAA CTCTTGTAAA    2820

AGACTTTCAT TAACATGCAA GGGTATGTCT AAGTTTCCTA CAGACCTCAA GTTTCCAAAC    2880

CTCTCGATTT TGAAACTTAT GCATGAAGAT ATATCATTGA GGTTTCCCAA AAACTTTTAT    2940

GAAGAAATGG AGAAGCTTGA GGTTATATCC TATGATAAAA TGAAATATCC ATTGCTTCCC    3000

TCATCACCGC AATGCTCCGT CAACCTTTGC GTGTTTCATC TCCATAAATG CTCGTTAGTG    3060

ATGTTTGACT GCTCTTGTAT TGGAAATCTG TCGAATCTAG AAGTGCTTAG CTTTGCTGAT    3120

TCTGCCATTG ACCTGTTGCC TTCCACAATC GGAATTTTGA AGAAGCTAAG GCTACTGGAT    3180

TTGACAAATT GTTATGGTCT TTGTATAGCT AATGGTGTCT TTAAAAAATT GGTCAAACTT    3240

GAAGAGCTCT ATATGACAGT GGTTAATGGA GGAGTTCGAA AGGCGATCAG CCTCACTGAG    3300

GATAACTGCA ATGAGATGGC AGAACGTTCA AAAGACCTTT CTGCATTAGA ACTTGAGTTC    3360

TTTGAAAACA ATGCTCAGCC AAAGAATATG TCATTTGAGA AGCTACAACG ATTCCAGATC    3420

TCAGTGGGGT GCTATTTATA TGGAGCTTCC ATAAAGAGCA GGCACTCGTA TGAAAACACA    3480

TTGAAGTTGG TTATTGACAA AGGTGAATTA TTTGAATCTT GAATGAACGG CCTGTTTAAG    3540

AAAACAGAGG TGTTATGTTT AAGTGTGGGA GATATGAATG ATCTTGAAGA TRTTGAGGTT    3600

AAGTCATCCT CACAACYTCT TCAATCTTCT TCGTTCAACA ATTTAAGAGT CCTTGTCGTT    3660

TCAAAGTGTG CAGAGTTGAA ACACTTCTTC ACACCTGGTG TTGCAAACAC TTTAAAAAAG    3720

CTTGAGCATC TTGAAGTTTA CAAATGTGAT AAATATGGAAG AACTCATACG TAGCAGGGGT    3780

AGTGAAGAAG AGACGATTAC ATTCCCCAAG CTGAAGTTTT TATCTTTGTG TGGGCTACCA    3840

AAGCTATCGG GTTTGTGCGA TAATGTCAAA ATAATTGAGC TACCACAACT CATGGAGTTG    3900
```

```
GAACTTGACG ACATTCCAGG TTTCACAAGC ATATATCCCA TGAAAAAGTT TGAAACATTT    3960

AGTTTGTTGA AGGAAGAGGT AAATATAAAT TTTTAATGCT AATACATTAC AAAGGATCTT    4020

TTCAGTTAAA TCTTTCAAAA TATATTGTAA TTTGATTGTA TGGGGTATTA TTGTTGGATG    4080

GGACTATTAA TAAATGATTA TCTTGCAGGT TCTGATTCCT AAGTTAGAGA AACTGCATGT    4140

TAGTAGTATG TGGAATCTGA AGGAGATATG GCCTTGCGAA TTTAATATGA GTGAGGAAGT    4200

TAAGTTCAGA GAGATTAAAG TGAGTAACTG TGATAAGCTT GTGAATTTGT TTCCGCACAA    4260

GCCCATATCT CTGCTGCGTC ATCTTGAAGA GCTTAAAGTC AAGAATTGTG GTTCCATTGA    4320

ATCGTTATTC AACATCCATT TGGATTGTGC TGGTGCAACT GGAGATGAAT ACAACAACAG    4380

TGGTGTAAGA ATTATTAAAG TGATCAGTTG TGATAAGCTT GTGAATCTCT TTCCACACAA    4440

TCCCATGTCT ATACTGCATC ATCTTGAAGA GCTTGAAGTC GAGAATTGTG GTTCCATTGA    4500

ATCGTTATTC AACATTGACT TGGATTGTGC TGGTGCAATT GGGCAAGAAG ACAACAGAAG    4560

CAGCTTAAGA AACATCAAAG TGGAGAATTT AGGGAAGCTA AGAGAGGTGT GGAGGATAAA    4620

AGGTGGAGAT AACTCTCGTC CCCTTGTTCA TGGCTTTCAA TCTGTTGAAA GCATAAGGGT    4680

TACAAAATGT AAGAGGTTTA GAAATGTATT CACACCTACC ACCACAAATT TAATCTGGG    4740

GGCACTTTTG GAGATTTCAA TAGATGACTG CGGAGAAAAC AGGGAAAATG ACGAATCGGA    4800

AGAGAGTAGC CATGAGCAAG AGCAGGTAAG GATTTCAATT TCACTTTCKT ACTTAATTAA    4860

TGATTAAGCT CCTGCTTTTT RAATAAAAAA GGGACAAACC ATTTCATGAC TTAATGTAGC    4920

AATACAAGTC ATGTATAAGA GTGACCAACT CTTTTTTATT TATAAAATGA CTACAAAATA    4980

TTTTTTTTCA TTAGAGATCA TGTATAAATG TGACTAATTT TTCATCACCT AACTTTAGTT    5040

GATAAATCTT TATAAATGTC ACTAGTTACT TTTCAGTAAA ATAACAAATT TAATAAATTA    5100

TCAACAAAAA GCATCAACTA AAAAAATCCC ACAACCCGTA ATAATTTAAA ATAAAAGGAT    5160

TTAACATCTA ATACGAACAA TTTTTTTTCT AAACATGATT TGGACCAAAT ATCACCAGCA    5220

ACTCAAGTTT GGAATCGATT CAGCTTAAAA CTTGACCARC ATAATTAGAT AGATGAGAGT    5280

TGAAGCTAAA GTGCCTATAT AAGTTCGTTT CATCTTTTTT CTTGATCTTG ATAGCAAGTT    5340

GAATSATTTT CTTCTTCAAA ATTGATAAAA ATCTACATTA TAAAGAGACT AGCTTGAAAA    5400

AAAATGGTCT AGGTGGGTCT TGGGTCTGGT AGATGAAGAT GGAAGGGAGA GTAGATTTCA    5460

AAGACACAAA CACATCTTCA TTTTATTTAT TTATTTATTA TTATTATTTT TTGATATCTT    5520

GCTCATATTT GTTACAGATA TGTGAGGTCT ATTAATCTTT TTAAATATAT AAAAAATAAA    5580

TACATAAATG AGAAAATTAA ATAAAGAATA AATTAATAAG GGCACAATAG TCTTTTTTGG    5640

TAAGACAAGG ACCAAAAGCG CAACAAAAGT AAACAGTAGG GACCATCCGA TTTAAAAAAT    5700

TAATTAGGGA CCAAAAACAT AAATTCCCCC AAACCATAGG GACCATTCGT GTAATTTACT    5760

CTTGCTTTTC GTTTTGTTCA TATTTGGGTA ACTATTTTTT TTGTACATAT CTAGGTAACG    5820

AACTTGTTGA AAGTGTTCAC ATCTACGATG TGACCTACTA CAACCGATCA TAATGGTCAT    5880

ATATGAACAC TTCCAACAAG TTTGTTATCT AGGTGTGTAC AAAAAAACGA TAGTTACCAT    5940

GATGTGAACA TACCAAAAAA TTAATTACCT TAGCAAGTTA TTTTCCCATT TAGGTTGTAT    6000

GGAAACAGTT CCGTGAGACC GTGACTTGGA TGGTAGATAA ATTTAGTAAA CTTAACCCTT    6060

CAATTAACCT ACCTTTTTCT TATTAACTCA ATTTCAAGCT AAATTCTGAT TCTTGTTTGA    6120

AAGTAAGTTG CATCTTTATG TTTGTATTAT CTTGTTGCAT AGGATCCTTA GCATCTTTTA    6180

ATAATTTATT TGAAGGTGAA AGATCCAACT ATTTTTAATC TGTTGGCATT TTCCATCATT    6240
```

```
TGCAACTGTT TCTTGAAAAA AANNTACCTA AAATCAAAAT AACCATTTTC ATATCCAAAA    6300

TTATAAGAGA GAATTGTTAA CGGACATGGA ATCATAAATC ATTAACACAG TTCAGTACAC    6360

AGGTTGCTAA TTACATTTCT TGCTGTGCAG ATTGAAATTC TATCAGAGAA AGAGACATTA    6420

CAAGAAGCCA CTGGCAGTAT TTCAAATATT GTATTCCCAT CCTGTCTCAT GCACTCTTTT    6480

CATAACCTCC ATAAACTTAA CTTGAACAGA GTTGAAGGAG TGGAGGTGGT GTTTGAGATA    6540

GAGAGTGAGA GTCCAACAAG TAGAGAATTG GTAACAACTC ACCATAACCA ACAACAACCT    6600

ATTATACTTC CCAACCTCCA GGAATTGATT CTATGGAATA TGGACAACAT GAGTCATGTG    6660

TGGAAGTGCG GCAACTGGAA TAAATTCTTC ACTCTTCCAA AAGAACAATC AGAATCCCCA    6720

TTCCACAACC TCAGTAACAT ACATATTTAT GAATGCAAAA GCATTAAGTA CTTGTTTTCA    6780

CCTCTCATGG CAGAACTTCT TTCCAACCTA AAGCATATCG AGATAAGAGA GTGTGATGGT    6840

ATTGAAGAAG TTGTTTCAAA AAGAGATGGT GAGGATGAAG ACATGACTAC ATCTACNNNN    6900

NNNGCACACA ACCACCACTT TTTCCCTCAT CTTGATTCTC TCACTCTAAA GCAACTGAAG    6960

AATCTGAAGT GTATTGGTGG AGGTGGTGCC AAGGATGAGG GGAGCAATGA AATATCTTTC    7020

AATAATACCA CTGCAACTAC TGCTGTTCTT GATCAATTTG AGGTATGCTT TGTACATATT    7080

CAATTATTTA TTTAATTTCC TTGTTAATTT CCTTTTTTCT TTGCAATATT CTATGAAAAA    7140

AATCACCAAA TCACAAATAA GAGATTTAAA CTTTTATTTC ACACCCATGC GGACTCAAGA    7200

ATGGGATTTG GAGGCATATA AAGTTACATT CATTTGAACA AGTATTACCA TTTATTTGTT    7260

ATTTATCATT TTCATATCAT TTACTGATAA CATTTCTTTT TTACTTTTCT AATTAGAAAA    7320

GGTCCACATG TCTAATTAGG TTTTCCATTC TATGTGAATC CTCTATTCTG TCTGTAATCA    7380

AGCATCTTAG ATTATTTATC CATTTTCATA ATTGTGTTTA TATTGACAGT TTTTTTCTTT    7440

TTATAGTTGT AATTGCAACC TGTCATATWT TMWWKKCWWW ATKYWMWWAR TAATACATTT    7500

TATACCCWCT ATACTAAGAT A                                             7521
```

(2) INFORMATION FOR SEQ ID NO:117:

(i) SEQUENCE CHARACTERISTICS:
        (A) LENGTH: 483 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..483
        (D) OTHER INFORMATION: /note= "RG2N deduced sequence"

(xi) SEQUENCE DESCRIPTION: SEQ ID NO:117:

```
Leu Gly Lys Thr Thr Met Met His Arg Leu Lys Lys Val Val Lys Glu
1               5                   10                  15

Lys Lys Met Phe Asn Phe Ile Val Glu Ala Val Val Gly Glu Lys Thr
            20                  25                  30

Asp Pro Ile Ala Ile Gln Ser Ala Val Ala Asp Tyr Leu Gly Ile Glu
        35                  40                  45

Leu Asn Glu Lys Thr Lys Pro Ala Arg Thr Glu Lys Leu Arg Lys Trp
    50                  55                  60

Phe Val Asp Asn Ser Ala Gly Lys Lys Ile Leu Val Ile Leu Asp Asp
65                  70                  75                  80

Val Trp Gln Phe Val Asp Leu Asn Asp Ile Gly Leu Ser Pro Leu Pro
                85                  90                  95
```

```
Asn Gln Gly Val Asp Phe Lys Val Leu Leu Thr Ser Arg Asp Lys Asp
            100                 105                 110
Val Cys Thr Glu Met Gly Ala Glu Val Asn Ser Thr Phe Asn Val Lys
            115                 120                 125
Met Leu Ile Glu Thr Glu Ala Gln Ser Leu Phe His Gln Phe Val Glu
        130                 135                 140
Ile Ser Asp Asp Val Asp Arg Glu Leu His Asn Ile Gly Val Asn Ile
145                 150                 155                 160
Val Arg Lys Cys Gly Gly Leu Pro Ile Val Ile Lys Thr Met Ala Cys
                165                 170                 175
Thr Leu Arg Gly Lys Ser Lys Asp Ala Trp Lys Asn Ala Leu Leu Arg
            180                 185                 190
Leu Val Asn Tyr Asn Ile Glu Asn Ile Val Asn Gly Val Phe Lys Met
        195                 200                 205
Ser Tyr Asp Asn Leu Gln Asp Glu Glu Thr Lys Ser Thr Phe Leu Leu
        210                 215                 220
Cys Gly Met Phe Pro Glu Asp Phe Asn Ile Pro Thr Glu Glu Leu Val
225                 230                 235                 240
Arg Tyr Gly Trp Gly Leu Lys Leu Phe Lys Lys Val Tyr Thr Ile Gly
                245                 250                 255
Glu Ala Arg Ile Arg Leu Asn Thr Cys Ile Glu Arg Leu Ile His Thr
                260                 265                 270
Asn Leu Leu Ile Glu Val Asp Asp Val Arg Cys Ile Lys Met His Asp
        275                 280                 285
Leu Val Arg Ala Phe Val Leu Asp Met Tyr Ser Lys Val Glu His Ala
        290                 295                 300
Ser Ile Val Asn His Gly Asn Thr Leu Glu Trp His Val Asp Asn Met
305                 310                 315                 320
His Asn Ser Cys Lys Arg Leu Ser Leu Thr Cys Lys Gly Met Ser Lys
                325                 330                 335
Phe Pro Thr Asp Leu Lys Phe Pro Asn Leu Ser Ile Leu Lys Leu Met
            340                 345                 350
His Glu Asp Ile Ser Leu Arg Phe Pro Lys Asn Phe Tyr Glu Glu Met
            355                 360                 365
Glu Lys Leu Glu Val Ile Ser Tyr Asp Lys Met Lys Tyr Pro Leu Leu
        370                 375                 380
Pro Ser Ser Pro Gln Cys Ser Val Asn Leu Cys Val Phe His Leu His
385                 390                 395                 400
Lys Cys Ser Leu Val Met Phe Asp Cys Ser Cys Ile Gly Asn Leu Ser
                405                 410                 415
Asn Leu Glu Val Leu Ser Phe Ala Asp Ser Ala Ile Asp Leu Leu Pro
            420                 425                 430
Ser Thr Ile Gly Ile Leu Lys Lys Leu Arg Leu Leu Asp Leu Thr Asn
        435                 440                 445
Cys Tyr Gly Leu Cys Ile Ala Asn Gly Val Phe Lys Lys Leu Val Lys
        450                 455                 460
Leu Glu Glu Leu Tyr Met Thr Val Val Asn Gly Gly Val Arg Lys Ala
465                 470                 475                 480
Ile Ser Leu
```

(2) INFORMATION FOR SEQ ID NO:118:

(i) SEQUENCE CHARACTERISTICS:

(A) LENGTH: 5111 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..5111
(D) OTHER INFORMATION: /note= "RG2O"

(xi) SEQUENCE DESCRIPTION: SEQ ID NO:118:

```
TTGTAAAACG ACGGCCAGTC GAATCGTAAC CGTTCGTACG AGAATCGCTG TCCTCTCCTT      60

CATTTGAATC ATGATATTTG AATATCGATA CTTTTGACTG TAGCTTTTGG GTCGATTTTT     120

TAGCAAGATA CATAACTGGC CAAACCCATT GGCTATTTTA GCCCAAAATA TGAAATGGAC     180

TGGATTGTTT TTTTCCTTTC TAACACGCAC ACATCTGGCG ATCAGTATCA CTCCATTATG     240

AAGACCTAGT CAAATTCATT AACGTTCAGT CGTTCCTTCA AAGTTTCAAA GTTCCAACTT     300

CCAACTTCCC TCTTTTTTTT TTCTTTCCTC GATTCTGATT TGAATCCGAT TCTGCGACGA     360

AGGAGAGCTT GGTCAGAGGG CTGTGATTCT TGAGTCTTGA CCTCCGAATC TAGCTGGATT     420

ATTTTCGACA CACCAGACCA CGTATCAGGT TGCTCATCCC GAAATACTGC TTTGCAAACT     480

GTTGTATCAT CGCCTAGGAA ATTAAGTTTC TTTTTTGGCT CTGTTACTGA ATCAGTAGCT     540

TTGCAACTTG CTCATTATAA GCTGATCCAT ATTTTACATA TCTTTTGAAG AATAATAGGT     600

ACTGACTTTA CCTTTCTGAT GAGAGCGATT TAAGAGATAC CTCTGTAAAA TCCATTTTTG     660

TGAAGGGATC TGGGTTAGTT TTTAAAGGAT TTGCTACAAC AGTATCCCAC AAACGATCTA     720

TTTCCCATTT NACTCATCCG CTCAAGATCT ATCCACCTTT ATATATGTTA ATTGGGAGTC     780

TTCCATGGTG CAATGAATCT AGGATGCATT TAGAAGCCCA ATCCATTACA AGTTTTCATC     840

CAATTTCATG TGACAAGTTG TTGGTTACTA TGTAGGTACT TCCACAATTA AGAATTTCCA     900

GCAATGGATG TTGTTAATGC CATTCTTAAA CCAGTTGCCG AGACACTTAT GGAACCTGTT     960

AAGAAACATC TAGGCTACAT CATTTCCAGC ACAAAACATG TGAGGGATAT GAGTAACAAA    1020

ATGAGGGAGT TGAACGCTGC AAGACATGCT GAAGAAGACC ACTTGGACAG AACATAAGA     1080

ACTCGTCTTG AGATTTCAAA TCAAGTTAGG AGTTGGTTAG AAGAAGTAGA AAAGATCGAT    1140

GCAAAAGTAA AAGCCCTTCC TAGTGATGTC ACCGCTTGTT GCAGTCTCAA GATCAAACAT    1200

GAAGTCGGAA GGGAAGCCTT GAAGCTAATT GTGGAGATTG AAAGTGCCAC AAGACAACAC    1260

TCTTTGATCA CCTGGACTGA TCATCCCATT CCTCTGGGAA AAGTTGATTC CATGAAGGCA    1320

TCGATGTCCA CAGCATCAAC CGATTACAAT GACTTTCAGT CAAGAGAAAA AACTTTTACT    1380

CAAGCATTGA AAGCACTTGA ACCAAACAAC GCTTCCCACA TGATAGCGTT ATGTGGGATG    1440

GGTGGAGTGG GGAAGACCAC AATGATGCAA AGACTAAAAA AAGTTGCTAA ACAAAATAGA    1500

ATGTTCAGTT ATATGGTTGA GGCAGTTATA GGGGAAAAGA CGGACCCAAT TGCTATTCAA    1560

CAAGCTGTAG CGGATTACCT TCGTATAGAG TTAAAAGAAA GCACTAAACC AGCAAGAGCT    1620

GATAAGCTTC GTGAATGGTT CAAGGCCAAC TCTGGAGAAG GTAAGAATAA ATTCCTTGTA    1680

ATACTTGATG ACGTCTGGCA GTCTGTTGAT CTAGAAGATA TTGGTTTAAG TCCTTTTCCA    1740

AATCAAGGTG TCGACTTCAA GGTCTTATTG ACTTCACGAG ACGAACATGT TGCACAGTA     1800

ATGGAGTTG GATCTAATTC AATTCTTAAT GTGGGACTTC TAATAGAAGC AGAAGCACAA     1860

AGTTTGTTCC AACAATTTGT AGAAACTTCT GAGCCCGAGC TCCATAAGAT AGGAGAAGAT    1920

ATTGTAAGGA AGTGTTGCGG TCTACCTATT GCCATCAAAA CCATGGCATG TACTCTTAGA    1980
```

```
AATAAAAGAA AGGATGCTTG GAAGGATGCA CTTTCGCGTA TAGAGCACTA TGACCTTCGC    2040

AATGTTGCGC CTAAAGTCTT TGAAACGAGC TACCACAATC TCCATGACAA AGAGACTAAA    2100

TCAGTGTTTT TGATGTGTGG TTTGTTTCCG GAAGACTTCA ATATTCCTAC TGAGGAGTTG    2160

ATGAGGTATG GATGGGGATT AAAGATATTT GATAGAGTCT ATACATTTAT AGAAGCAAGA    2220

AACAGGATCA ACACCTGCAT TGAGCGACTG GTGCAGACAA ATTTGTTAAT TGAAAGTGAT    2280

GATGTTGGGT GTGTCAAGAT GCATGATCTG GTCCGTGCTT TTGTTTTAGG TATGTATTCT    2340

GAAGTAGAGC ATGCTTCAGT TGTCAACCAT GGTAATATAC CTGGATGGAC TGAAAATGAT    2400

CCGACTGACT CTTGTAAAGC AATTTCATTA ACATGCGAGA GTATGTCTGG AAACATTCCA    2460

GGAGACTTCA AGTTTCCAAA CCTAACGATT TTGAAACTTA TGCATGGAGA TAAGTCGCTA    2520

AGATTTCCAC AAGACTTTTA TGAAGGAATG GAAAAGCTCC AGGTTATATC ATACGATAAA    2580

ATGAAGTATC CAATGCTTCC CTTGTCTCCT CAATGCTCCA CCAACCTTCG AGTGCTTCAT    2640

CTCCATGAAT GTTCATTAAA GATGTTTGAT TGCTCTTGTA TTGGAAATAT GGCGAATGTG    2700

GAAGTGTTGA GCTTTGCTAA TTCTGGCATT GAAATGTTAC CTTCCACTAT CGGAAATTTA    2760

AAGAAGCTAA GGTTACTTGA TTTAACAGAT TGTCATGGTC TTCATATAAC ACACGGTGTC    2820

TTTAACAATT TGGTCAAACT TGAAGAGTTG TATATGGGAT TTTCTGATCG ACCTGATCAA    2880

ACTCGTGGTA ATATTAGCAT GACAGATGTC AGCTACAATG AATTAGCAGA ACGTTCAAAA    2940

GGCCTTTCTG CATTAGAGTT CCAGTTCTTT GAAAACAATG CCCAACCAAA TAATATGTCG    3000

TTTGGGAAAC TTAAACGATT CAAGATCTCA ATGGGATGCA CTTTATATGG AGGATCAGAT    3060

TACTTTAAGA AAACGTATGC TGTCCAAAAC ACATTGAAGT TGGTTACTAA CAAAGGTGAA    3120

CTATTGGACT CTAGAATGAA CGAGTTGTTT GTTGAAACAG AAATGCTTTG TTTAAGTGTT    3180

GATGATATGA ATGATCTTGG TGATGTTTGT GTGAAGTCCT CACGTTCTCC TCAACCTTCT    3240

GTGTTCAAAA TTCTAAGAGT CTTTGTCGTT TCCAAGTGTG TTGAGTTGAG ATACCTTTTC    3300

ACAATTGGTG TAGCCAAGGA TTTGTCAAAT CTTGAGCATC TTGAAGTTGA TTCATGTAAT    3360

AATATGGAAC AACTCATATG TATTGAGAAT GCTGGAAAAG AGACAATTAC ATTCCTAAAG    3420

CTGAAGATTT TATCTTTGAG TGGGCTACCA AAGCTTTCGG GTTTGTGCCA AAATGTCAAC    3480

AAACTTGAGC TACCACAACT CATAGAGTTG AAACTTAAGG GCATTCCAGG GTTCACATGC    3540

ATTTATCCGC AAAACAAGTT GGAAACATCT AGTTTGTTGA AGGAAGAGGT AGATATATGT    3600

TTTATGTTAA TACAAGTTAA AAAATCTTTT TAACTAAAAG TTTCAGTATA TATATCTATA    3660

TGTCTATAAT TTGATTATAT GATGTATTAG TGTTTGGATG TGGCTATTAA GGGATGATTA    3720

TTTTGCAGGT TGTGATTCCT AAGTTGGAGA CACTTCAAAT TGATGAGATG GAGAATTTAA    3780

AGGAAATATG GCATTATAAA GTTAGTAATG GTGAGAGAGT TAAGTTGAGA AAGATTGAAG    3840

TGAGTAACTG TGATAAGCTT GTGAATCTAT TTCCACACAA CCCCATGTCT CTGCTGCATC    3900

ATCTTGAAGA GCTTGAAGTC AAGAAATGTG GTTCCATTGA ATCGTTATTC AACATCGACT    3960

TGGATTGTGT TGATGCCATA GGAGAAGAAG ACAACATGAG GAGCTTAAGA AACATTAAAG    4020

TGAAGAATTC ATGGAAGTTA AGAGAAGTGT GGTGTATAAA AGGTGAAAAT AACTCTTGCC    4080

CCCTTGTTTC TGGCTTTCAA GCTGTTGAAA GCATAAGCAT TGAAAGTTGT AAGAGGTTTA    4140

GAAATGTATT CACACCTACC ACCACCAATT TTAATATGGG GGCACTTTTG GAGATATCAA    4200

TAGATGACTG TGGAGAATAC ATGGAAAATG AAAAATCGGA AAAGAGTAGC CAAGAGCAAG    4260

AGCAGGTATG GATTTCAATT TCACTTTCTT ACTTACTTAA GGATTAAGCT TCTGTTTTTT    4320
```

```
TGAATAAAAA AGGGACATCT TCTAATAATG CACATCTTAA ATTAAAAAGT ATTTAATTGT    4380

TGCATAGCAG CGTATAACAT CTTCTAATAA TTTATCTGAA GGTGAAAGAT CCAACTACTT    4440

CTAATTTGTT AACAATTTCA ATCATTTGCA AATGTTCCTT AAAAAATTAA TTACCTGAAA    4500

TCAAAACAAT CTTCTTCAAA TCCAAAATTA TGAGACAGAA TTGAGAAGGG ATGTGAAATT    4560

ATAAACCATT AACACAATTC CATGCTCACG TTACTAATTA CATTTCTTGT TGGGATATAT    4620

ATGTACAGAC TGATATTTTG TCAGAGGAAG TGAAATTACA AGAAGTCACT GATACTATTT    4680

CTAATGTTGT ATTCACATCG TGTCTCATAC ACTCTTTTTA TAACAACCTC CGTAAACTCA    4740

ACTTGGAGAA GTATGGAGGA GTTGAGGTTG TGTTTGAGAT AGAGAGTTCA ACAAGTAGAG    4800

AATTGGTAAC AACATACCAT AAACAACAAC AACAACAACA ACCTATATTT CCCAACCTTG    4860

AGGAATTATA TCTATATTAT ATGGACAACA TGAGTCATGT ATGGAAGTGC AACAACTGGA    4920

ATAAATTTTT ACAACAATCA GAATCCCCAT TCCACAACCT CACAACCATA CACATGTCCG    4980

ATTGCAAAAG CATTAAGTAC TTGTTTTCAC CTCTCATGGC AGAACTTCTT TCCAACCTAA    5040

AGAGAATCAA TATTGACGAG TGTGATGGTA TTGAAGAAAT TGTTTCAAAA AGAGATGATG    5100

TGGATGAAGA A                                                        5111
```

(2) INFORMATION FOR SEQ ID NO:119:

(i) SEQUENCE CHARACTERISTICS:
        (A) LENGTH: 1222 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1222
        (D) OTHER INFORMATION: /note= "RG20 deduced sequence"

(xi) SEQUENCE DESCRIPTION: SEQ ID NO:119:

```
Met Asp Val Val Asn Ala Ile Leu Lys Pro Val Ala Glu Thr Leu Met
 1               5                  10                  15

Glu Pro Val Lys Lys His Leu Gly Tyr Ile Ile Ser Ser Thr Lys His
                20                  25                  30

Val Arg Asp Met Ser Asn Lys Met Arg Glu Leu Asn Ala Ala Arg His
            35                  40                  45

Ala Glu Glu Asp His Leu Asp Arg Asn Ile Arg Thr Arg Leu Glu Ile
        50                  55                  60

Ser Asn Gln Val Arg Ser Trp Leu Glu Glu Val Glu Lys Ile Asp Ala
65                  70                  75                  80

Lys Val Lys Ala Leu Pro Ser Asp Val Thr Ala Cys Cys Ser Leu Lys
                85                  90                  95

Ile Lys His Glu Val Gly Arg Glu Ala Leu Lys Leu Ile Val Glu Ile
            100                 105                 110

Glu Ser Ala Thr Arg Gln His Ser Leu Ile Thr Trp Thr Asp His Pro
        115                 120                 125

Ile Pro Leu Gly Lys Val Asp Ser Met Lys Ala Ser Met Ser Thr Ala
    130                 135                 140

Ser Thr Asp Tyr Asn Asp Phe Gln Ser Arg Glu Lys Thr Phe Thr Gln
145                 150                 155                 160

Ala Leu Lys Ala Leu Glu Pro Asn Asn Ala Ser His Met Ile Ala Leu
                165                 170                 175
```

-continued

```
Cys Gly Met Gly Gly Val Gly Lys Thr Thr Met Met Gln Arg Leu Lys
            180                 185                 190
Lys Val Ala Lys Gln Asn Arg Met Phe Ser Tyr Met Val Glu Ala Val
            195                 200                 205
Ile Gly Glu Lys Thr Asp Pro Ile Ala Ile Gln Gln Ala Val Ala Asp
            210                 215                 220
Tyr Leu Arg Ile Glu Leu Lys Glu Ser Thr Lys Pro Ala Arg Ala Asp
225                 230                 235                 240
Lys Leu Arg Glu Trp Phe Lys Ala Asn Ser Gly Glu Gly Lys Asn Lys
                245                 250                 255
Phe Leu Val Ile Leu Asp Asp Val Trp Gln Ser Val Asp Leu Glu Asp
                260                 265                 270
Ile Gly Leu Ser Pro Phe Pro Asn Gln Gly Val Asp Phe Lys Val Leu
            275                 280                 285
Leu Thr Ser Arg Asp Glu His Val Cys Thr Val Met Gly Val Gly Ser
            290                 295                 300
Asn Ser Ile Leu Asn Val Gly Leu Leu Ile Glu Ala Glu Ala Gln Ser
305                 310                 315                 320
Leu Phe Gln Gln Phe Val Glu Thr Ser Glu Pro Glu Leu His Lys Ile
                325                 330                 335
Gly Glu Asp Ile Val Arg Lys Cys Cys Gly Leu Pro Ile Ala Ile Lys
                340                 345                 350
Thr Met Ala Cys Thr Leu Arg Asn Lys Arg Lys Asp Ala Trp Lys Asp
            355                 360                 365
Ala Leu Ser Arg Ile Glu His Tyr Asp Leu Arg Asn Val Ala Pro Lys
            370                 375                 380
Val Phe Glu Thr Ser Tyr His Asn Leu His Asp Lys Glu Thr Lys Ser
385                 390                 395                 400
Val Phe Leu Met Cys Gly Leu Phe Pro Glu Asp Phe Asn Ile Pro Thr
                405                 410                 415
Glu Glu Leu Met Arg Tyr Gly Trp Gly Leu Lys Ile Phe Asp Arg Val
                420                 425                 430
Tyr Thr Phe Ile Glu Ala Arg Asn Arg Ile Asn Thr Cys Ile Glu Arg
            435                 440                 445
Leu Val Gln Thr Asn Leu Leu Ile Glu Ser Asp Val Gly Cys Val
            450                 455                 460
Lys Met His Asp Leu Val Arg Ala Phe Val Leu Gly Met Tyr Ser Glu
465                 470                 475                 480
Val Glu His Ala Ser Val Val Asn His Gly Asn Ile Pro Gly Trp Thr
                485                 490                 495
Glu Asn Asp Pro Thr Asp Ser Cys Lys Ala Ile Ser Leu Thr Cys Glu
            500                 505                 510
Ser Met Ser Gly Asn Ile Pro Gly Asp Phe Lys Phe Pro Asn Leu Thr
            515                 520                 525
Ile Leu Lys Leu Met His Gly Asp Lys Ser Leu Arg Phe Pro Gln Asp
            530                 535                 540
Phe Tyr Glu Gly Met Glu Lys Leu Gln Val Ile Ser Tyr Asp Lys Met
545                 550                 555                 560
Lys Tyr Pro Met Leu Pro Leu Ser Pro Gln Cys Ser Thr Asn Leu Arg
                565                 570                 575
Val Leu His Leu His Glu Cys Ser Leu Lys Met Phe Asp Cys Ser Cys
                580                 585                 590
Ile Gly Asn Met Ala Asn Val Glu Val Leu Ser Phe Ala Asn Ser Gly
```

-continued

```
              595                 600                 605
Ile Glu Met Leu Pro Ser Thr Ile Gly Asn Leu Lys Lys Leu Arg Leu
            610                 615                 620

Leu Asp Leu Thr Asp Cys His Gly Leu His Ile Thr His Gly Val Phe
625                 630                 635                 640

Asn Asn Leu Val Lys Leu Glu Glu Leu Tyr Met Gly Phe Ser Asp Arg
                    645                 650                 655

Pro Asp Gln Thr Arg Gly Asn Ile Ser Met Thr Asp Val Ser Tyr Asn
                660                 665                 670

Glu Leu Ala Glu Arg Ser Lys Gly Leu Ser Ala Leu Glu Phe Gln Phe
            675                 680                 685

Phe Glu Asn Asn Ala Gln Pro Asn Asn Met Ser Phe Gly Lys Leu Lys
690                 695                 700

Arg Phe Lys Ile Ser Met Gly Cys Thr Leu Tyr Gly Gly Ser Asp Tyr
705                 710                 715                 720

Phe Lys Lys Thr Tyr Ala Val Gln Asn Thr Leu Lys Leu Val Thr Asn
                    725                 730                 735

Lys Gly Glu Leu Leu Asp Ser Arg Met Asn Glu Leu Phe Val Glu Thr
                740                 745                 750

Glu Met Leu Cys Leu Ser Val Asp Asp Met Asn Asp Leu Gly Asp Val
            755                 760                 765

Cys Val Lys Ser Ser Arg Ser Pro Gln Pro Ser Val Phe Lys Ile Leu
770                 775                 780

Arg Val Phe Val Val Ser Lys Cys Val Glu Leu Arg Tyr Leu Phe Thr
785                 790                 795                 800

Ile Gly Val Ala Lys Asp Leu Ser Asn Leu Glu His Leu Glu Val Asp
                    805                 810                 815

Ser Cys Asn Asn Met Glu Gln Leu Ile Cys Ile Glu Asn Ala Gly Lys
                820                 825                 830

Glu Thr Ile Thr Phe Leu Lys Leu Lys Ile Leu Ser Leu Ser Gly Leu
            835                 840                 845

Pro Lys Leu Ser Gly Leu Cys Gln Asn Val Asn Lys Leu Glu Leu Pro
850                 855                 860

Gln Leu Ile Glu Leu Lys Leu Lys Gly Ile Pro Gly Phe Thr Cys Ile
865                 870                 875                 880

Tyr Pro Gln Asn Lys Leu Glu Thr Ser Ser Leu Leu Lys Glu Glu Val
                    885                 890                 895

Val Ile Pro Lys Leu Glu Thr Leu Gln Ile Asp Glu Met Glu Asn Leu
                900                 905                 910

Lys Glu Ile Trp His Tyr Lys Val Ser Asn Gly Glu Arg Val Lys Leu
            915                 920                 925

Arg Lys Ile Glu Val Ser Asn Cys Asp Lys Leu Val Asn Leu Phe Pro
930                 935                 940

His Asn Pro Met Ser Leu Leu His His Leu Glu Glu Leu Glu Val Lys
945                 950                 955                 960

Lys Cys Gly Ser Ile Glu Ser Leu Phe Asn Ile Asp Leu Asp Cys Val
                    965                 970                 975

Asp Ala Ile Gly Glu Glu Asp Asn Met Arg Ser Leu Arg Asn Ile Lys
                980                 985                 990

Val Lys Asn Ser Trp Lys Leu Arg Glu Val Trp Cys Ile Lys Gly Glu
            995                 1000                1005

Asn Asn Ser Cys Pro Leu Val Ser Gly Phe Gln Ala Val Glu Ser Ile
        1010                1015                1020
```

```
Ser Ile Glu Ser Cys Lys Arg Phe Arg Asn Val Phe Thr Pro Thr Thr
1025                1030                1035                1040

Thr Asn Phe Asn Met Gly Ala Leu Leu Glu Ile Ser Ile Asp Asp Cys
                1045                1050                1055

Gly Glu Tyr Met Glu Asn Glu Lys Ser Glu Lys Ser Ser Gln Glu Gln
            1060                1065                1070

Glu Gln Thr Asp Ile Leu Ser Glu Glu Val Lys Leu Gln Glu Val Thr
        1075                1080                1085

Asp Thr Ile Ser Asn Val Val Phe Thr Ser Cys Leu Ile His Ser Phe
            1090                1095                1100

Tyr Asn Leu Arg Lys Leu Asn Leu Glu Lys Tyr Gly Gly Val Glu
1105                1110                1115                1120

Val Val Phe Glu Ile Glu Ser Ser Thr Ser Arg Glu Leu Val Thr Thr
                1125                1130                1135

Tyr His Lys Gln Gln Gln Gln Gln Pro Ile Phe Pro Asn Leu Glu
            1140                1145                1150

Glu Leu Tyr Leu Tyr Tyr Met Asp Asn Met Ser His Val Trp Lys Cys
            1155                1160                1165

Asn Asn Trp Asn Lys Phe Leu Gln Gln Ser Glu Ser Pro Phe His Asn
1170                1175                1180

Leu Thr Thr Ile His Met Ser Asp Cys Lys Ser Ile Lys Tyr Leu Phe
1185                1190                1195                1200

Ser Pro Leu Met Ala Glu Leu Leu Ser Asn Leu Lys Arg Ile Asn Ile
                1205                1210                1215

Asp Glu Cys Asp Gly Ile
            1220

(2) INFORMATION FOR SEQ ID NO:120:

(i) SEQUENCE CHARACTERISTICS:
        (A) LENGTH: 1403 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1403
        (D) OTHER INFORMATION: /note= "RG2P"

(xi) SEQUENCE DESCRIPTION: SEQ ID NO:120:

CCCATTGCTA TTCAGGAAGC AGTAGCAGAT TACCTCNGTA TAGAGCTCAA AGAAAAAACT      60

AAATCNGCAA GAGCTGATAT GCTTCGTAAA ATGTTAGTTG CCAAGTCCGA TGGTGGTAAA     120

AATAAGTTCC TAGTAATACT TGACGATGTA TGGCAGTTTG TTGATTTAGA AGATATCGGT     180

TTAAGTCCTT TGCCAAATCA AGGTGTTAAC TTCAAGGTCT TGCTAACATC ACGGGATGTA     240

GATGTTTGCA CTATGATGGG AGTCGAAGCC AATTCAATTC TCAACATGAA AATCTTACTA     300

GATGAAGAAG CACAAAGTTT GTTCATGGAG TTTGTACAAA TTTCGAGTGA TGTTGATCCC     360

AAGCTTCATA AGATAGGAGA AGATATTGTA AGAAAGTGTT GTGGTTTGCC TATTGCCATC     420

AAAACCATGG CCCTTACTCT TAGAAATAAA AGCAAGGATG CATGGAGTGA TGCACTTTCT     480

CGTTTAGAGC ATCATGACCT TCACAATTTT GTGAATGAAG TTTTTGGAAT TAGCTACGAC     540

TATCTTCAAG ACCAGGAGAC TAAATATATC TTTTTGCTTT GTGGATTGTT TCCCGAAGAC     600

TACAATATTC CTCCTGAGGA GTTAATGAGG TATGGATGGG GCTTAAATTT ATTTAAAAAA     660
```

```
GTGTATACTA TAAGAGAAGC AAGAGCCAGA CTCAACACCT GCATTGAGCG GCTTATCCAT    720

ACCAATTTGT TGATGGAAGG AGATGTTGTT GGGTGTGTAA AGATGCATGA TCTAGCACTT    780

GCTTTTGTTA TGGATATGTT TTCTAAAGTG CAGGATGCTT CAATTGTCAA CCATGGTAGC    840

ATGTCAGGGT GGCCTGAAAA TGATGTGAGT GGCTCTTGCC AAAGAATTTC ATTAACATGC    900

AAGGGTATGT CTGGGTTTCC TATAGACCTC AACTTTCCAA ACCTCACAAT TTTAAAACTT    960

ATGCATGGAG ATAAGTTTCT CAAGTTTCCT CCAGACTTTT ATGAACAAAT GGAAAAGCTT   1020

CAAGTTGTAT CGTTTCATGA AATGAAATAT CCGTTTCTTC CCTCGTCTCC TCAATATTGC   1080

TCCACCAACC TTCGAGTTCT TCATCTCCAT CAATGCTCAT TGATGTTTGA TTGCTCTTGT   1140

ATTGGAAATC TGTTTAATCT GGAAGTGTTG AGCTTTGCTA ATTCTGGCAT TGAATGGTTA   1200

CCTTCCAGAA TTGGAAATTT GAAGAAGCTA AGGCTACTAG ATTTGACAGA TTGTTTTGGT   1260

CTTCGTATAG ATAAGGGTGT CTTAAAAAAT TTGGTCAAAC TTGAAGAGGT TTATATGAGA   1320

GTTGCTGTTC GAAGCAAAAA AGCCGGAAAT AGAAAAGCCA TTAGCTTCAC AGATGATAAC   1380

TGCAATGAGA TGGCAGAGCG TTC                                           1403
```

(2) INFORMATION FOR SEQ ID NO:121:

(i) SEQUENCE CHARACTERISTICS:
        (A) LENGTH: 468 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..468
        (D) OTHER INFORMATION: /note= "RG2P deduced sequence"

(xi) SEQUENCE DESCRIPTION: SEQ ID NO:121:

```
Pro Ile Ala Ile Gln Glu Ala Val Ala Asp Tyr Leu Xaa Ile Glu Leu
1               5                   10                  15

Lys Glu Lys Thr Lys Ser Ala Arg Ala Asp Met Leu Arg Lys Met Leu
                20                  25                  30

Val Ala Lys Ser Asp Gly Gly Lys Asn Lys Phe Leu Val Ile Leu Asp
            35                  40                  45

Asp Val Trp Gln Phe Val Asp Leu Glu Asp Ile Gly Leu Ser Pro Leu
        50                  55                  60

Pro Asn Gln Gly Val Asn Phe Lys Val Leu Leu Thr Ser Arg Asp Val
65                  70                  75                  80

Asp Val Cys Thr Met Met Gly Val Glu Ala Asn Ser Ile Leu Asn Met
                85                  90                  95

Lys Ile Leu Leu Asp Glu Glu Ala Gln Ser Leu Phe Met Glu Phe Val
                100                 105                 110

Gln Ile Ser Ser Asp Val Asp Pro Lys Leu His Lys Ile Gly Glu Asp
            115                 120                 125

Ile Val Arg Lys Cys Cys Gly Leu Pro Ile Ala Ile Lys Thr Met Ala
        130                 135                 140

Leu Thr Leu Arg Asn Lys Ser Lys Asp Ala Trp Ser Asp Ala Leu Ser
145                 150                 155                 160

Arg Leu Glu His His Asp Leu His Asn Phe Val Asn Glu Val Phe Gly
                165                 170                 175

Ile Ser Tyr Asp Tyr Leu Gln Asp Gln Glu Thr Lys Tyr Ile Phe Leu
```

```
                    180                 185                 190
Leu Cys Gly Leu Phe Pro Glu Asp Tyr Asn Ile Pro Pro Glu Glu Leu
            195                 200                 205

Met Arg Tyr Gly Trp Gly Leu Asn Leu Phe Lys Lys Val Tyr Thr Ile
    210                 215                 220

Arg Glu Ala Arg Ala Arg Leu Asn Thr Cys Ile Glu Arg Leu Ile His
225                 230                 235                 240

Thr Asn Leu Leu Met Glu Gly Asp Val Val Gly Cys Val Lys Met His
                245                 250                 255

Asp Leu Ala Leu Ala Phe Val Met Asp Met Phe Ser Lys Val Gln Asp
                260                 265                 270

Ala Ser Ile Val Asn His Gly Ser Met Ser Gly Trp Pro Glu Asn Asp
            275                 280                 285

Val Ser Gly Ser Cys Gln Arg Ile Ser Leu Thr Cys Lys Gly Met Ser
290                 295                 300

Gly Phe Pro Ile Asp Leu Asn Phe Pro Asn Leu Thr Ile Leu Lys Leu
305                 310                 315                 320

Met His Gly Asp Lys Phe Leu Lys Phe Pro Pro Asp Phe Tyr Glu Gln
                325                 330                 335

Met Glu Lys Leu Gln Val Val Ser Phe His Glu Met Lys Tyr Pro Phe
                340                 345                 350

Leu Pro Ser Ser Pro Gln Tyr Cys Ser Thr Asn Leu Arg Val Leu His
                355                 360                 365

Leu His Gln Cys Ser Leu Met Phe Asp Cys Ser Cys Ile Gly Asn Leu
            370                 375                 380

Phe Asn Leu Glu Val Leu Ser Phe Ala Asn Ser Gly Ile Glu Trp Leu
385                 390                 395                 400

Pro Ser Arg Ile Gly Asn Leu Lys Lys Leu Arg Leu Leu Asp Leu Thr
                405                 410                 415

Asp Cys Phe Gly Leu Arg Ile Asp Lys Gly Val Leu Lys Asn Leu Val
                420                 425                 430

Lys Leu Glu Glu Val Tyr Met Arg Val Ala Val Arg Ser Lys Lys Ala
            435                 440                 445

Gly Asn Arg Lys Ala Ile Ser Phe Thr Asp Asp Asn Cys Asn Glu Met
450                 455                 460

Ala Glu Arg Ser
465

(2) INFORMATION FOR SEQ ID NO:122:

(i) SEQUENCE CHARACTERISTICS:
        (A) LENGTH: 1437 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1437
        (D) OTHER INFORMATION: /note= "RG2Q"

(xi) SEQUENCE DESCRIPTION: SEQ ID NO:122:

TGGGAAGAC ACAGTGATAG AAAARAAAAA GAATGTTGTG GAAAAGAGGA AAATGTTTGA      60

TTATGCTGTT GTGGCGGTTA TAGGGGAAAA GACGGACCCT ATTGCTCTTC AGAAAACTGT    120

TGCGGATTAC TTGCATATTG AGCTAAATGA AAGCACTAAA CTAGCAAGAG CAGATAAACT    180
```

```
TTGCAAATGG TTCAAGGACA ACTCGGATGG AGGTAAGAAA AAGTTCCTCG TAATACTCGA      240

CGATGTTTGG CAATCTGTTG ATTTGGAAGA TATTGGTTTA AGTACTCCTT TTCCAAATCA      300

AGGTGTCAAC TTCAAGGTTT TGTTGACATC ACGAAAGAGA GAAATTTGCA CAATGATGGG      360

AGTTGAAGCT GATTTAATTC TCAATGTCAA AGTCTTAGAA GAAGAAGAAG CACAAAAGTT      420

GTTCCTCCAG TTTGTAGAAA TTGGTGACCA ATACCACGAG CTTCATCAGA TAGGGGTACA      480

TATAGTAAAG AAGTGTTATG GTTTACCCAT TGCCATTAAA ACCATGGCTC TTACTTTAAG      540

AAATAAAAGA AAGGATTCAT GGAAGGACGC ACTCTCTCGT TTAGAGGACC ATGACACTGA      600

AAATGTTGCA AATGCAGTTT TCGAGATGAA CTACCGCAAT CTACAAGATG AGGAGACCAA      660

AGCCATTTTT TTGCTTTGCG GTTTGTTCCC CGAAGACTTT GATATTCCTA CTGAGGAGTT      720

GGTGAGGTAT GGATGGGGCT TAAATCTATT TAAAAAAGTG TATACCATAA GAAAGGCAAG      780

AACGAGATCG CATACATGTA TTGAGCGACT CTTGGATTCA AATTTGTTGA TTGAAAGTAA      840

CGATATTCGG TGCGTCAAGA TACACGATCT GGTGCGCGCT TTTGTTTTGG ATATGTATTG      900

TAAAGTTGAG CATGCTTCAA TTGTCAACCA TGGTAATATG CGGACCGAAT ATAATATGGC      960

TGACTCTTGC AAAACAATTT CATTAACATA CAAGAGTATG TCTGGGTTTG AGTTTCCAGG     1020

AGACCTCAAG TTTCCAAACC TAACAGTTTT GAAACTTATG CAGGAGATA AGTCTCTAAG     1080

GTTTCCTCAA GACTTTTATC AATCAATGGA AAAACTTCGG GTTATATCAT ATGATAAAAT     1140

GAAGTATCCA TTGCTTCCCT CATCACCTCA ATGCTCCACT AACATCCGAG TGCTTCGTCT     1200

CCATGAATGT TCATTAAGGA TGTTTGATTG CTCTTGTATT GGAAAGCTAT TGAATTTGGA     1260

AGTCCTCAGC TTTTTTAATT CTAACATTGA ATGGTTACCT TCCACAATCA GAAATTTAAA     1320

AAAGCTAAGG CTACTAGATT TGAGATATTG TGATCGTCTT CGTATAGAAC AAGGTGTCTT     1380

GAAAAATTTG GTCAAACTTG AAGAACTTTA TACTGGATAT ACATCAGCGT TTACAGA       1437
```

(2) INFORMATION FOR SEQ ID NO:123:

(i) SEQUENCE CHARACTERISTICS:
        (A) LENGTH: 479 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..479
        (D) OTHER INFORMATION: /note= "RG2Q deduced sequence"

(xi) SEQUENCE DESCRIPTION: SEQ ID NO:123:

```
Gly Glu Asp Thr Val Ile Glu Lys Lys Asn Val Val Glu Lys Arg
 1               5                  10                  15

Lys Met Phe Asp Tyr Ala Val Val Ala Val Ile Gly Glu Lys Thr Asp
                20                  25                  30

Pro Ile Ala Leu Gln Lys Thr Val Ala Asp Tyr Leu His Ile Glu Leu
            35                  40                  45

Asn Glu Ser Thr Lys Leu Ala Arg Ala Asp Lys Leu Cys Lys Trp Phe
        50                  55                  60

Lys Asp Asn Ser Asp Gly Gly Lys Lys Lys Phe Leu Val Ile Leu Asp
65                  70                  75                  80

Asp Val Trp Gln Ser Val Asp Leu Glu Asp Ile Gly Leu Ser Thr Pro
                85                  90                  95
```

```
Phe Pro Asn Gln Gly Val Asn Phe Lys Val Leu Leu Thr Ser Arg Lys
            100                 105                 110

Arg Glu Ile Cys Thr Met Met Gly Val Glu Ala Asp Leu Ile Leu Asn
        115                 120                 125

Val Lys Val Leu Glu Glu Glu Ala Gln Lys Leu Phe Leu Gln Phe
    130                 135                 140

Val Glu Ile Gly Asp Gln Tyr His Glu Leu His Gln Ile Gly Val His
145                 150                 155                 160

Ile Val Lys Lys Cys Tyr Gly Leu Pro Ile Ala Ile Lys Thr Met Ala
                165                 170                 175

Leu Thr Leu Arg Asn Lys Arg Lys Asp Ser Trp Lys Asp Ala Leu Ser
            180                 185                 190

Arg Leu Glu Asp His Asp Thr Glu Asn Val Ala Asn Ala Val Phe Glu
        195                 200                 205

Met Asn Tyr Arg Asn Leu Gln Asp Glu Glu Thr Lys Ala Ile Phe Leu
    210                 215                 220

Leu Cys Gly Leu Phe Pro Glu Asp Phe Asp Ile Pro Thr Glu Glu Leu
225                 230                 235                 240

Val Arg Tyr Gly Trp Gly Leu Asn Leu Phe Lys Lys Val Tyr Thr Ile
                245                 250                 255

Arg Lys Ala Arg Thr Arg Ser His Thr Cys Ile Glu Arg Leu Leu Asp
            260                 265                 270

Ser Asn Leu Leu Ile Glu Ser Asn Asp Ile Arg Cys Val Lys Ile His
        275                 280                 285

Asp Leu Val Arg Ala Phe Val Leu Asp Met Tyr Cys Lys Val Glu His
    290                 295                 300

Ala Ser Ile Val Asn His Gly Asn Met Arg Thr Glu Tyr Asn Met Ala
305                 310                 315                 320

Asp Ser Cys Lys Thr Ile Ser Leu Thr Tyr Lys Ser Met Ser Gly Phe
                325                 330                 335

Glu Phe Pro Gly Asp Leu Lys Phe Pro Asn Leu Thr Val Leu Lys Leu
            340                 345                 350

Met Xaa Gly Asp Lys Ser Leu Arg Phe Pro Gln Asp Phe Tyr Gln Ser
        355                 360                 365

Met Glu Lys Leu Arg Val Ile Ser Tyr Asp Lys Met Lys Tyr Pro Leu
    370                 375                 380

Leu Pro Ser Ser Pro Gln Cys Ser Thr Asn Ile Arg Val Leu Arg Leu
385                 390                 395                 400

His Glu Cys Ser Leu Arg Met Phe Asp Cys Ser Cys Ile Gly Lys Leu
                405                 410                 415

Leu Asn Leu Glu Val Leu Ser Phe Phe Asn Ser Asn Ile Glu Trp Leu
            420                 425                 430

Pro Ser Thr Ile Arg Asn Leu Lys Lys Leu Arg Leu Leu Asp Leu Arg
        435                 440                 445

Tyr Cys Asp Arg Leu Arg Ile Glu Gln Gly Val Leu Lys Asn Leu Val
    450                 455                 460

Lys Leu Glu Glu Leu Tyr Thr Gly Tyr Thr Ser Ala Phe Thr Glu
465                 470                 475

(2) INFORMATION FOR SEQ ID NO:124:

(i) SEQUENCE CHARACTERISTICS:
        (A) LENGTH: 12793 base pairs
        (B) TYPE: nucleic acid
        (C) STRANDEDNESS: single
```

(D) TOPOLOGY: linear (ii) MOLECULE TYPE: DNA (ix) FEATURE:
    (A) NAME/KEY: -
    (B) LOCATION: 1..12793
    (D) OTHER INFORMATION: /note= "RG2S"

(xi) SEQUENCE DESCRIPTION: SEQ ID NO:124:

```
ATTTGGGGTT TTACATTTAA TTTTTTGTGC ATGAATGTGA AAATAGACTG CTTATTGATT      60
CTTTGTGTTT CATTGAGTTG ATTTTCATTA TTACTACCTT ACAAATTGCT CAGTGATAGA     120
TTTCCATTAA TTTGCTAATT CGGTTGCTTC TAAATATGTA GGAGCTACTA AAAGCAAAAA     180
TATCGAGCAA TGTCGGACCC AACGGGGATT GCTGGTGCCA TTATTAACCC AATTGCTCAG     240
AGGGCCTTGG TTCCCGTTAC AGACCATGTA GGCTACATGA TTTCCTGCAG AAAATATGTG     300
AGGGTCATGC AGACGAAAAT GACAGAGTTG AATACCTCAA GAATCAGTGT AGAGGAACAC     360
ATTAGCCGGA ACACAAGAAA TCATCTTCAG ATTCCATCTC AAATTAAGGA TTGGTTGGAC     420
CAAGTAGAAG GGATCAGAGC AAATGTGGAA AACTTTCCGA TTGATGTCAT CACTTGTTGT     480
AGTCTCAGGA TCAGGCACAA GCTTGGACAG AAAGCCTTCA AGATAACTGA GCAGATTGAA     540
AGTCTAACAA GACAGCTCTC CCTGATCAGT TGGACTGATG ATCCAGTTCC TCTAGGAAGA     600
GTTGGTTCCA TGAATGCATC CACCTCTGCA TCATCAAGTG ATGATTTCCC ATCAAGAGAG     660
AAAACTTTTA CACAAGCACT AAAAGCACTC GAACCCAACC AACAATTCCA CATGGTAGCC     720
TTGTGTGGGA TGGGTGGAGT AGGGAAGACT AGAATGATGC AAAGGCTGAA GAAGGCCGCT     780
GAAGAAAAGA AATTGTTTAA TTATATTGTT AGGGCAGTTA TAGGGAAAAA GACGGACCCC     840
TTTGCCATTC AAGAAGCTAT AGCAGATTAC CTCGGTATAC AACTCAATGA AAAAACTAAG     900
CCAGCAAGAG CTGATAAGCT TCGTGAATGG TTCAAAAAGA ATTCAGATGG AGGTAAGACT     960
AAGTTCCTCA TAGTACTTGA CGATGTTTGG CAATTAGTTG ATCTTGAAGA TATTGGGTTA    1020
AGTCCTTTTC CAAATCAAGG TGTCGACTTC AAGGTCTTGT TGACATCACG AGACTCACAA    1080
GTTTGCACTA TGATGGGGGT TGAAGCTAAT TCAATTATTA ACGTGGGCCT TCTAACTGAA    1140
GCAGAAGCTC AAAGTCTGTT CCAGCAATTT GTAGAAACTT CTGAGCCCGA GCTCAGAAG    1200
ATAGGAGAGG ATATCGTAAG GAAGTGTTGC GGTCTACCTA TTGCCATAAA AACCATGGCA    1260
TGTACTCTTA GAAATAAAAG AAAGGATGCA TGGAAGGATG CACTTTCGCG CATAGAGCAC    1320
TATGACATTC ACAATGTTGC GCCCAAAGTC TTTGAAACGA GCTACCACAA TCTCCAAGAA    1380
GAGGAGACTA AATCCACTTT TTTAATGTGT GGTTTGTTTC CCGAAGACTT CGATATTCCT    1440
ACTGAGGAGT TGATGAGGTA TGGATGGGGC TTGAAGCTAT TTGATAGAGT TTATACGATT    1500
AGAGAAGCAA GAACCAGGCT CAACACCTGC ATTGAGCGAC TGGTGCAGAC AAATTTGTTA    1560
ATTGAAAGTG ATGATGTTGG GTGTGTCAAG ATGCATGATC TGGTCCGTGC TTTTGTTTTG    1620
GGTATGTTTT CTGAAGTCGA GCATGCTTCT ATTGTCAACC ATGGTAATAT GCCCGAGTGG    1680
ACTGAAAATG ATATAACTGA CTCTTGCAAA AGAATTTCAT TAACATGCAA GAGTATGTCT    1740
AAGTTTCCAG GAGATTTCAA GTTTCCAAAC CTAATGATTT TGAAACTTAT GCATGGAGAT    1800
AAGTCGCTAA GGTTTCCTCA AGACTTTTAT GAAGGAATGG AAAAGCTCCA TGTTATATCA    1860
TACGATAAAA TGAAGTACCC ATTGCTTCCT TTGGCACCTC GATGCTCCAC CAACATTCGG    1920
GTGCTTCATC TCACTAAATG TTCATTAAAG ATGTTTGATT GCTCTTGTAT TGGAAATCTA    1980
TCGAATCTGG AAGTGCTGAG CTTTGCTAAT TCTCGCATTG AATGGTTACC TTCCACAGTC    2040
```

```
AGAAATTTAA AGAAGCTAAG GTTACTTGAT CTGAGATTTT GTGATGGTCT CCGTATAGAA    2100

CAGGGTGTCT TGAAAAGTTT AGTCAAACTT GAAGAATTTT ATATTGGAAA TGCATCTGGG    2160

TTTATAGATG ATAACTGCAA TGAGATGGCA GAGCGTTCTG ACAACCTTTC TGCATTAGAA    2220

TTCGCGTTCT TTAATAACAA GGCTGAAGTG AAAAATATGT CATTTGAGAA TCTTGAACGA    2280

TTCAAGATCT CAGTGGGACG CTCTTTTGAT GGAAATATCA ATATGAGTAG CCACTCATAC    2340

GAAAACATGT TGCAATTGGT GACCAACAAA GGTGATGTAT TAGACTCTAA ACTTAATGGG    2400

TTATTTTTGA AAACAAAGGT GCTTTTTTTA AGTGTGCATG GCATGAATGA TCTTGAAGAT    2460

GTTGAGGTGA AGTCGACACA TCCTACTCAG TCCTCTTCAT TCTGCAATTT AAAAGTTCTT    2520

ATTATTTCAA AGTGTGTAGA GTTGAGATAC CTTTTCAAAC TCAATCTTGC AAACACTTTG    2580

TCAAGACTTG AGCATCTAGA AGTTTGTGAA TGCGAGAATA TGGAAGAACT CATACATACT    2640

GGAATTTGTG GAGAAGAGAC AATTACTTTC CCTAAGCTGA AGTTTTTATC TTTGAGTCAA    2700

CTACCGAAGT TATCAAGTTT GTGCCATAAT GTCAACATAA TTGGGCTACC ACATCTCGTA    2760

GACTTGATAC TTAAGGGCAT TCCAGGTTTC ACAGTCATTT ATCCGCAGAA CAAGTTGCGA    2820

ACATCTAGTT TGTTGAAGGA AGAGGTAGAT ATATGTTCTT TATGTTAATA CAATTTAAAT    2880

AATATTTTCA ACCAAATTTT CATAATATAT CTGTAATTTG ATTGTATGAT GTGTTATTGT    2940

TTATATGTGG CTATTAAGGG ATGATTATTT TGCAGGTTGT GATTCCTAAG TTGGAGACAC    3000

TTCAAATTGA TGCATGGAG AACTTAGAAG AAATATGGCC TTGTGAACTT AGTGGAGGTG    3060

AGAAAGTTAA GTTGAGAGAG ATTAAAGTGA GTAGCTGTGA TAAGCTTGTG AATCTATTTC    3120

CGCGCAATCC CATGTCTCTG TTGCATCATC TTGAAGAGCT TAAAGTCAAG AATTGCGGTT    3180

CCATTGAATC GTTATTCAAC ATTGACTTGG ATTGTGTCGG TGCAATTGGA GAAGAAGACA    3240

ACAAGAGCCT CTTAAGAAGC ATCAACATGG AGAATTTAGG GAAGCTAAGA GAGGTGTGGA    3300

GGATAAAAGG TGCAGATAAC TCTCATCTCA TCAACGGTTT TCAAGCTGTT GAAAGCATAA    3360

AGATTGAAAA ATGTAAGAGG TTTAGCAATA TATTCACACC TATCACCGCC AATTTTTATC    3420

TGGTGGCACT TTTGGAGATT CAGATAGAAG GTTGCGGAGG AAATCACGAA TCAGAAGAGC    3480

AGGTAACGCT TTCAATTTAA CTTTCTTAAG TAATTAAGGA CTAACCTCCT GTTTTTTGAA    3540

TAATAAAGAG GTGGGATGAC TAAACTTGGG CATCACAATT GCAACAAAAT GTTACAAACC    3600

ATGAAACGTT CAAACCATTT CTTGAATTAA GGTTTCAATA CAAGTCATTT AAAAATATGG    3660

CTTAAATTTT TTTATATTTA TGTATCAACA TGATTTTTCA TTAGAGATCA TTATTATAAT    3720

AGTAAGTTTA AAGCAATTTA AATTAGAACT AATTCTAACT TTAGCTAATA AATCGTTATA    3780

AATGTAAATA ATTACTTTTT AGTGAAATAA GCAACGGATT TAATAAGTTA ACAACTTAAA    3840

TGTCATTTCC TAACAAAAAA AACTATTTGG TTCAGAAGAA CCGTAATTCA AGATAACTAA    3900

AATAAAAATA TTTGACATTC ACTAAGAGCA TTTTTTTTTC TAAATATGAT TGCAAATGAA    3960

TAAAACTTAA ATTTATACAG AAAAGATTTT TATATATGTT ATACAAAATT TACAAATTGA    4020

AACTGGATAT GTTAATTAAC GGTTTATAAT TCTGGTATCA CAAAGGGATA TATAATAAAA    4080

TATTATTTTC TGTAGTCATT TATAATTGTA CTAGTTTATA ACCCGTGGGA ACCATGAGTT    4140

CTAAAATTAG TTAAACTTTC ATAATAAAAA TTTATAATTA TTATTTATTT TAAATAAATT    4200

ATTAATTAAG AGATGTATCA AAAATTTAAA GTTATTATAA CTTCAAATTT AACATATAAT    4260

TAGAAAATAT ATGATCATAA CTTTCCGCAA CTCTTCTTTT GTATTAAAAT GCCCAGAGAA    4320

GCTCTTAGTA YATTTTCTAA ATCAAAGTCA CAAAACTAAT GAAGCATATA ATTTTGTGAA    4380

AATCAATTAG CATTAGGTTT TAAGAGTCAC CAAATTCAAA GAGTAATCCA ATGCTTTCAT    4440
```

```
TACCACTATG GAGAAAATAT TTTCTTAGTT TAAATGAAAT GAAACAAAC ATTCAAACTA      4500

ATTGTTGCTT ACTAAACCAA AGACCCATTA CTTAGCCAAG AGTTTAACCA AAAAAAATTA     4560

CATTCATGTA TCATTATTCA TGACTAGATA TATATGAACA TGAAGGGAGT TTTTATAGAA     4620

AATATAATCA TAGATATTCA ACATAACTTC ATGGAATTCC TCAAAATAAC CAAGTTATTC     4680

AAGAAATTAC ATCCAAGTCA ACCAAAGAGA AGTTTAGCCT AGCATGGCTA AACTCAAGAA     4740

AATAAAATAA GGATTAGAAG TACCAAACAT GTAGTAAGAA TCACAGTAAA AGATGATGTT     4800

GTTCTTGATG TTCTTCTAAG TTCTTCAAGT CTCCAGTTGC TCCTAATAAT GCAAAGGAGA     4860

GCCATTAAAT TCGTATGTAT TGATCCCTTC AAAAGCTGCA CCAACCTCCC TTAAATAACA     4920

CTCAAAGCAA AAATGACAAA ATTGCCCCTG AAGGACCCTA TGCGGGTGCC TTGCGCGGGT     4980

GGAGCTGAAT ACGAAAGGTC TTTGGTCTTT GTGAGGGTGA TGCTGTGCGG GTTAGCTTGT     5040

CGCATGCTTC CGCGCGGTTC GCGCACATGT GCACAAGTGA TGCATGGTGT GTACGTTCTT     5100

GAGTTTTGAG CCTCCGATGC TTAGTCCATT TGGCCCAATT CGAGTCCAAT CAGCTTATGA     5160

CCCATTTTTC TTCAAGTTAT CTTCAAGTTA TCTTCAAGTT AAGCCCAAAT TGCCTTCTCC     5220

AAATCATCCA TAACTTCACA AAATCGCCCG TTCATCTTAA TCCCGAATGC ACAATTATTC     5280

TCCTGTCTTC CTTTTAAGCA AGATACCACC TTCTTCATGC TTCATCCATC AATAGTACAC     5340

TTCATGTATC ATCTCTACTA GTTATTTAGT CCACAATCCT TATTGTCCTC CAAATTTAAT     5400

TATCTCATTT AGTTCCCGTT CCACTAGTTT CCTTAAAATT TGCAATTAAG CTCACACAAA     5460

TATTAAGTAC CTGAAATGGT CATAAAATAA CAAAAAGGAA AATATGCATG AAGATTAACT     5520

AAATGATGAA CGAAATATGC TAAAATAGAC TATAAAATGA AGTAAATAAA ATGAAATTAT     5580

CGCACTCCGA CCACCCTTAT AGGCTTGTAG TCCATCCACC CTTCATTCCT TGTACCAATA     5640

TGGGATGGAA ACATCATTAA TTAAGCCAAA AAACTAACAT ATAAGGGGTG AGTGACAAAG     5700

GTAAGTACTA AAGATGAAAA TAATCCATTT TTYTTGTATA TACACAACAC ACACATAGGG     5760

GCAGACGTAG GATTTCATAG TACAGATTGT TGGTGGCACA TAAGTGTTGC TGGTGACACT     5820

TTTTTTTTCT TTTACGTAGT GGCACAACAG TAGAAAAAAC GARAAATTCG AAATTTTTTA     5880

CAATGTGTST AAAAAAAAYA GTGGTTGTTG GTGCCACTAT GGACACCAAA GTTGAACTGC     5940

CCCTGCGCGC RCACACACAC ACACATAGAG AGAGAGAGAG AGAGAGAGAG AGAGAGAGAG     6000

ARAGWAWGRR RGAKAKARMC SMSYTTGGGA TGTGATACTT CTTTTAGGAA AATGGAGTTA     6060

TATCTTGAT ATTGTATTTT TTTAATGTAA TTTATATATT TAATCATTTT AGTTTATAAG      6120

TTTTATTTAT TTTGATATGA AAAAAAAAGT CTTTTATACA TTGGATTTAA CATAAAAATC     6180

CAACAATATT AATCAAAAAG ACCAMACATG TGGACAMWTA TGTATATAAW TAATTCACAA     6240

TAGTCTTTAG GAATAGNATT ATATATATAA TTAATTCTCA ATGGTCTTAG GAATAGTAAG    6300

TTCTTATATT TCAAACTTTN GCCACAATTC TTTGKTTACT TWGACACTTY CCTCTCTCTA     6360

ATTATATATA TATATATATA TATATATATA TATATACACA CACACACACA CACACTAGAT    6420

GTGTGCCCGC GCAAAGCAGT GACGTNNNGG AGAANACTTT CTTAAGCATA AATAATTATT     6480

ATATTTTTA TTGGGTATTA TATAATAAAA AATTACAACT TTTAAATAAA ATATTTATGT      6540

TTATACTTTA TATTTATATT GCTTGTATAC TATTAATATA ATAAATTAAT ATTTATGTCT    6600

AATTTATGAA ATGTAAATTA ATTTAAATAC ATGAATTTAA TATTTTTAAA ATTTTCAGTT    6660

TGCTTCAAAT TGAGTTTCTT AATTATTTTT TTTAATTCAN GTATTCAAAC TTTTGGTAAG    6720

TATTAAAGAA TTATTTATGC ACAATTGATT TATACAAAAA ACTTTGTAAC TTATACATCT     6780
```

```
TAAAATTCAA GATATAACTA ACATGTTTTA CAATATATAT ATATATANAT ATATATATAT    6840

ATATATATAT ATATATATAT ATATATAGTA AAGCGCANAG GTCATAGGNA NAGANTATTT    6900

TCTATTATTC TACGTTTTGC CACAAAAGTT TGAACACTTT GCCACTTTTT GTCCCTCCTT    6960

AACCTTTTCA ATGTTTTGCG ACAAAAGTTC CAAAACTTTG CCACTTTGAT CATTCCTCAA    7020

CTTTTCACCG CATTAGTTTG TGGAGTTGGC AGTTTTGGTC CCCCTAACTT CGATATTTTC    7080

TCCTGCTAGC CAAAAAGGGT TCCAGAGTTT CACANTTTTG GTCCCTGACA ATAACCAAAT    7140

GTGAGATGTC AAATTTTTGC CACATTAGTT TGTGGAGTTG TCCCTTTTGG TCCCCCCACA    7200

TTCGATATTC TACTATACGA CCTTATTTTT CTCAAATAAC AACACGTATA TTTAATTACC    7260

AATGATAGAA ATAGATATCA AATAAAGTAT TTGTAACACC GTGTAAGAAC GGTGCTACTA    7320

TAGGTAAAAA TAAACATTTC AAAGTACGAT GTCCTAATTG GAAAAGAGT TTTAAAAAAA     7380

TAACAACTAG GGGCGAGTTT TTTTTACAAG TTTGTATCAA ATCATATCAA AATTTAAGGT    7440

GGAACGGTGA CCACATTAAC CAGAAATGTA ATTTATTCTT TGATTTTGAT AATTTTTAAT    7500

ATTTTGTTGT GATCTATGTA TTTAAAAGTA ACAACAAAG AACATAATCC AAAACCCTAA     7560

ATTGCAAGTC TCGCCCAATT TCTCTATCAC TAGTCGTCAC TTACGATGGC GTTACGTCGC    7620

TCTCTCACTT CTTACAACCC TTTGTTGCTA CTCATTACAA TAACGAAAAG TTGAATATCC    7680

ATATATTTAT TTGGATGTGG AATTGAACAA ATCTCGTCAA ATTTTTGATT TTGTTGATGG    7740

ATTTGAGTAG AAGTTTGGGC AGAACGGGAA TGATGGTCTG CAAGTGGTTA TAAACTTGAT    7800

TCTGAGTTAT TACTATATAT GTAGCCTCTT TACAACGACC AAGGTTTCTT CCAGGTACCA    7860

TTTGATCTTT TTAGAACCCA GTTGTCTGAA ACACCCTGAT TTGGATCAAA TATCACCAAC    7920

AACTCTTAAA AACTTGATTA ATCAATTGTT TTCTTCATCT TGATAACAAG TGGAATGATT    7980

TTCTACTTAG ATTAACTTGA AAAAAAAGGT CCATGTGCGT CTGGTGGATC TGGTAAATGA    8040

AGATGGAAGG GAGAGCTGAC TTTAAAGACA CAAACACGTC ACCATATCTT TTATTTTATT    8100

TTAAATTTGC TTTTTTCCTA TTTCTTTCTT TCTTGATCTC CAGATGGTAT GTGGTGTGGA    8160

TAATTTACAC ATAGAGATTG GAACGACTG TGTTTTAGAG AGGACGTGGC TTGGGGTTGA     8220

GGATGGTTTA TGGCTGGCCG AGTTTCATTT ATATAAACAA ACAAATATAT AAAACAAGGG    8280

GTAAAATGGC CATCTTATAT GTATTTAACC GTCCTTTTTT ATTTTTTTTT TATTTTTAAA    8340

TTTAAGAAGG GGTATACCAG TGTCAGCCTC TTATTCCCAA CCAGGCAACC AGTCAAATAG    8400

GGACTTAGGT TGTTTGGAAA CAGTTCCGTG AGACCGTGAC TTGGATGGTA GATAAATTTA    8460

GTAAACTTAA CCCTTCAATT AACCTACCTT TTTCTTATTA ACTCAATTTC AACCTAAATT    8520

CTGATTCTTG TTTGAAAATA AGTTGCATCT TTATGTTTGT ATTATCCTGT TGCATAGGAT    8580

CCTTAGCATC TTTTAATAAT TTATTTGAAG GTGAAAGATC CAACTATTTT TTAGCTGTTG    8640

GCATTTTCCA TCATTTGCAA CTGTTTCTTG AAAAAAAAAT ACCTAAAATC AAAATAACCA    8700

TTTTCAAATC CAAAATTATA AGAGAGAATT GTTAATGGAC GTGGAATCGT AAATCATTAA    8760

CACAGTTCAG TACACAAGTT GCTAATTACA TTTCTTGCTG TGCAGATTGA AATTCTATCA    8820

GAGAAAGAGA CATTACAAGA AGTCACTGAT ACTAATATTT CTAATGATGT TGTATTATTC    8880

CCATCCTGTC TCATGCACTC TTTTCATAAC CTCCATAAAC TTAAATTGGA GAGAGTTAAA    8940

GGAGTGGAGG TGGTGTTTGA GATAGAGAGT GAGAGTCCAA CAAGTAGAGA ATTGGTAACA    9000

ACTCACCATA ACCAACAACA TCCTATTATA CTTCCCAACC TCCAGGAATT GGATCTAAGT    9060

TTTATGGACA ACATGAGTCA TGTGTGGAAG TGCAGCAACT GGAATAAATT CTTCACTCTT    9120

CCAAAACAAC AATCAGAATC CCCATTCCAC AACCTCACAA CCATACACAT GTTCAGCTGC    9180
```

-continued

```
AGAAGCATTA AGTACTTGTT TTCGCCTCTC ATGGCAGAAC TTCTTTCCAA CCTAAAGGAT    9240

ATCTGGATAA GTGGGTGTAA TGGTATTAAA GAAGTTGTTT CAAAGAGAGA TGATGAGGAT    9300

GAAGAAATGA CTACATTTAC ATCTACCCAC ACAACCACCA TCTTGTTCCC TCATCTTGAT    9360

TCTCTCACTC TAAGACTACT GGAGAATCTG AAGTGTATTG GTGGAGGTGG TGCCAAGGAT    9420

GAGGGGAGCA ATGAAATATC TTTCAATAAT ACCACTGCAA CTACTGCTGT TCTTGATCAA    9480

TTTGAGGTAT GCTTTGTACA TATTCAATTA TTTATTTAAT TTCCTTTTTT CTTTGCAATA    9540

TTCTATAAAT AATACATTTT ATACCCACTA TACTAAGATA ATAATTACCT AGAGGGATGG    9600

ATGCTATGAC ACAGCTGCTA CACTTCAGAA ACTCTAGTAA GGGCAGTTAT GGAAGTTCAA    9660

TAAAATGATA ATGGCATCTT TTGATGGGTA ATATAGGCAA TTTAAGTTTT ATTTCTGTTA    9720

AAGCAGTATT TAGCAAGTAC TGGCCAGTAG GAGAGGAGAA TATCACCTTT TGTGAAAATC    9780

TGGTCATTGT ACCCAAGAAT TTAGTTAAAT GTAACATTTT AGATATCAGG GGACATCAGG    9840

TGACAGATAT TGTAGAATAG AACAATATAT AATATTACCC AAAACTATTT TTTCTAAGGT    9900

TATTCTGTTA AATATGTGCT TTCTTGATTT CATTGAATTT GCATTCCTAT ATTTTAGGTG    9960

GTAAAGTGAT TGTCTCTTCA ATAAATCCCG AAATTAATTA AAAAAAAAAA AAACAAAAGT   10020

AAATTTTTGA TATGGAGAGC ACTGGTATCA TTTAGTATAT AAAAAAACTA GATTTTGAAT   10080

TAAGTTTCTT ATATAAAAGC TGTGTATATA GTTAATTAG TTTTACATCA TTTTTCCATG    10140

TGGTGTTGCA GTTGTCTGAA GCAGGTGGTG TTTCTTGGAG TTTATGCCAA TACGCTAGAG   10200

AGATAGAGAT ATCAAGTGT AATGTATTGT CAAGTGTGAT TCCATGTTAT GCAGCAGGAC    10260

AAATGCAAAA GCTTCAAGTG CTGAGAGTAA CGGGTTGTGA TGGCATGAAG GAGGTATTTG   10320

AAACTCAATT AGGGACGAGC AGCAACAAAA ACAGAAAGGG TGGTGGTGAT GAAGGAAATG   10380

GTGGAATTCC AAGAGTAAAT AACAATGTTA TTATGCTTCC CAATCTAAAG ACATTGAAAA   10440

TCTACATGTG CGGGGGTTTG GAACATATAT TCACATTCTC TGCACTTGAA AGCCTGACAC   10500

AGCTCCAAGA GTTAAAGATA GTGGGTTGCT ACGGAATGAA AGTGATTGTG AAGAAGGAAG   10560

AAGATGAATA TGGAGAGCAG CAAACAACAA CAACAACAAC AACGAAGGGG GCATCTTCTT   10620

CTTCTTCTTC TTCTTCTTCT AAGAAGGTTG TGGTCTTTCC CCGTCTAAAG TCCATTGAAC   10680

TATTCAATCT ACCAGAGCTG GTAGGATTCT TCTTGGGGAT GAATGAGTTC CGGTTGCCTT   10740

CATTGGAAGA AGTTACCATC AAGTATTGCT CAAAAATGAT GGTGTTTGCA GCTGGTGGGT   10800

CCACAGCTCC CCAACTCAAG TATATACACA CAAGATTAGG CAAACATACT CTTGATCAAG   10860

AATCTGGCCT TAACTTTCAT CAGGTATATA TATATTCCTT TAATTGGCAT GATCTAATTA   10920

AGAAAGATAT CATTCCTGCC AAGTAAATTT ACTTCAAACA CATTCACACT GGTTTCAGTC   10980

TAAGTTTATG TTGTTCTAGG AAGGCCAAAA TGGGAAAGCA AGATAGGGAA AAATAGTGTA   11040

TTTCAGTGGA AAGGGTATTT TAGGTATTTT CTGTCAAAAG TTGTTATTGC AGGCTTTTA    11100

GTACCTGGAA TCGTGTGTGG GAGGAGCGTT ATTATTCTGA TTTGCTTGTT TCTTTATCAT   11160

TTTTTCTTAG CCTCTCGAAC AGCTAGAAAC CCTTTTAATC TTTTGATTTT AAATGACAAA   11220

ATTTTTCCCT GTTACTCTAT TTGATTGTTG TTCTTCATGG TTCTAAGTGA GTTATTGGCT   11280

CATCTGTTAC TTCTTTTGAT TGTTATTTTC ATATCATGTT GTCCTTTGAA TCAAGCTTTT   11340

CCATTTTCAA CCAGGGCAAA AGGTCAAAAG TAACCTACTT TATGAGATCA AAACAGCAA    11400

CCCATCGGAT AACTTTTAGT TGGAGTTAAT AGTTACAATT ACCATTGTGA TTAATAATTA   11460

TAATATCTTG TATTAATTCA TTAAAATTGG TACAGCACAT ATATGACATT TTAAAGGTTT   11520
```

```
GTTTTTGTTW GACATATATA TGCCTCTGGC GTTTTCTTTA TTGGACATGC AGACCTCATT    11580

CCAAAGTTTA TACGGTGACA CCTCGGGCCC TGCTACTTCA GAAGGGACAA CTTGGTCTTT    11640

TCATAACTTG ATCGAATTAG ATATGGAATT AAATTATGAT GTTAAAAGA TTATTCCATC     11700

CAGTGAGTTG CTGCAACTGC AAAAGCTGGA AAAGATTCAT GTGAGTAGTT GTTATTGGGT    11760

AGAGGAGGTA TTTGAAACTG CATTGGAAGC AGCAGGGAGA AATGGAAATA GTGGAATTGG    11820

TTTTGATGAA TCGTCACAAA CTACTACTAC TACTACTCTT TTCAATCTTC GAAACCTCAG    11880

AGAAATGAAG TTGCATTTTC TACGTGGTCT GAGGTATATA TGGAAGAGCA ATCAGTGGAC    11940

AGCATTTGAG TTTCCAAACC TAACAAGAGT TCATATAAGT AGGTGTAGAA GGTTAGAACA    12000

TGTATTTACT AGTTCCATGG TTGGTAGTCT ATTGCAACTC CAAGAGCTAG ATATTAGTTG    12060

GTGCAACCAT ATGGAGGAGG TGATTGTTAA GGATGCAGAT GTTTCTGTTG AAGAAGACAA    12120

AGAGAGAGAA TCTGATGGCA AGACGAATAA GGAGATACTT GTGTTACCTC GTCTAAAATC    12180

CTTGAAATTA AAATGCCTTC CATGTCTTAA GGGGTTTAGC TTGGGGAAGG AGGATTTTTC    12240

ATTCCCATTA TTGGATACTT TAGAAATCTA CAAATGCCCA GCAATAACGA CCTTCACCAA    12300

GGGAAATTCT GCTACTCCAC AGCTAAAAGA AATAGAAACA AGATTTGGCT CGTTTTATGC    12360

AGGGGAAGAC ATCAACTCCT CTATTATAAA AGATCAAAC AACAGGTAAA TCAGATCTTT      12420

GTTGCTTTAA TAATTCTTAA ACTACATTTG AAAAGCTTCA TGCAAGTTTT TTTTGTTATA    12480

TTGTCAAAAA CCGCAACCTA CATTTTCAGC TTTATATTTA TGTACTTTAT GCAGGAGTTC    12540

AAACAAAACT CTGATTAATG TGAAGTGAAT ATTAAAGGTA AATTATATTT TCATGTTCCT    12600

AGTTGCCTAT TAATTAATGG CCTTTTAGTT CRTGATTTTT GGATGTAGTY WTCATGATGA    12660

TGTGAATCTT CTAATACCCC ATTCATTGTT TGGTTGAATG TTGACTCTAT GTCAGGATGA    12720

ATATTCAAGG GAAGAATTGT TCATCATATG AAGGACATTA AAGAACATGG ATGCTATGAA    12780

GATGTTGGAA RAC                                                      12793

(2) INFORMATION FOR SEQ ID NO:125:

(i) SEQUENCE CHARACTERISTICS:
        (A) LENGTH: 1817 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..1817
        (D) OTHER INFORMATION: /note= "RG2S deduced sequence"

(xi) SEQUENCE DESCRIPTION: SEQ ID NO:125:

Met Ser Asp Pro Thr Gly Ile Ala Gly Ala Ile Ile Asn Pro Ile Ala
1               5                   10                  15

Gln Arg Ala Leu Val Pro Val Thr Asp His Val Gly Tyr Met Ile Ser
                20                  25                  30

Cys Arg Lys Tyr Val Arg Val Met Gln Thr Lys Met Thr Glu Leu Asn
            35                  40                  45

Thr Ser Arg Ile Ser Val Glu Glu His Ile Ser Arg Asn Thr Arg Asn
        50                  55                  60

His Leu Gln Ile Pro Ser Gln Ile Lys Asp Trp Leu Asp Gln Val Glu
65                  70                  75                  80

Gly Ile Arg Ala Asn Val Glu Asn Phe Pro Ile Asp Val Ile Thr Cys
                85                  90                  95
```

```
Cys Ser Leu Arg Ile Arg His Lys Leu Gly Gln Lys Ala Phe Lys Ile
            100                 105                 110

Thr Glu Gln Ile Glu Ser Leu Thr Arg Gln Leu Ser Leu Ile Ser Trp
        115                 120                 125

Thr Asp Asp Pro Val Pro Leu Gly Arg Val Gly Ser Met Asn Ala Ser
    130                 135                 140

Thr Ser Ala Ser Ser Ser Asp Asp Phe Pro Ser Arg Glu Lys Thr Phe
145                 150                 155                 160

Thr Gln Ala Leu Lys Ala Leu Glu Pro Asn Gln Gln Phe His Met Val
                165                 170                 175

Ala Leu Cys Gly Met Gly Gly Val Gly Lys Thr Arg Met Met Gln Arg
            180                 185                 190

Leu Lys Lys Ala Ala Glu Glu Lys Lys Leu Phe Asn Tyr Ile Val Arg
        195                 200                 205

Ala Val Ile Gly Glu Lys Thr Asp Pro Phe Ala Ile Gln Glu Ala Ile
    210                 215                 220

Ala Asp Tyr Leu Gly Ile Gln Leu Asn Glu Lys Thr Lys Pro Ala Arg
225                 230                 235                 240

Ala Asp Lys Leu Arg Glu Trp Phe Lys Lys Asn Ser Asp Gly Gly Lys
                245                 250                 255

Thr Lys Phe Leu Ile Val Leu Asp Asp Val Trp Gln Leu Val Asp Leu
            260                 265                 270

Glu Asp Ile Gly Leu Ser Pro Phe Pro Asn Gln Gly Val Asp Phe Lys
        275                 280                 285

Val Leu Leu Thr Ser Arg Asp Ser Gln Val Cys Thr Met Met Gly Val
    290                 295                 300

Glu Ala Asn Ser Ile Ile Asn Val Gly Leu Leu Thr Glu Ala Glu Ala
305                 310                 315                 320

Gln Ser Leu Phe Gln Gln Phe Val Glu Thr Ser Glu Pro Glu Leu Gln
                325                 330                 335

Lys Ile Gly Glu Asp Ile Val Arg Lys Cys Cys Gly Leu Pro Ile Ala
            340                 345                 350

Ile Lys Thr Met Ala Cys Thr Leu Arg Asn Lys Arg Lys Asp Ala Trp
        355                 360                 365

Lys Asp Ala Leu Ser Arg Ile Glu His Tyr Asp Ile His Asn Val Ala
    370                 375                 380

Pro Lys Val Phe Glu Thr Ser Tyr His Asn Leu Gln Glu Glu Thr
385                 390                 395                 400

Lys Ser Thr Phe Leu Met Cys Gly Leu Phe Pro Glu Asp Phe Asp Ile
                405                 410                 415

Pro Thr Glu Glu Leu Met Arg Tyr Gly Trp Gly Leu Lys Leu Phe Asp
            420                 425                 430

Arg Val Tyr Thr Ile Arg Glu Ala Arg Thr Arg Leu Asn Thr Cys Ile
        435                 440                 445

Glu Arg Leu Val Gln Thr Asn Leu Leu Ile Glu Ser Asp Asp Val Gly
    450                 455                 460

Cys Val Lys Met His Asp Leu Val Arg Ala Phe Val Leu Gly Met Phe
465                 470                 475                 480

Ser Glu Val Glu His Ala Ser Ile Val Asn His Gly Asn Met Pro Glu
                485                 490                 495

Trp Thr Glu Asn Asp Ile Thr Asp Ser Cys Lys Arg Ile Ser Leu Thr
            500                 505                 510
```

-continued

```
Cys Lys Ser Met Ser Lys Phe Pro Gly Asp Phe Lys Phe Pro Asn Leu
        515                 520                 525

Met Ile Leu Lys Leu Met His Gly Asp Lys Ser Leu Arg Phe Pro Gln
    530                 535                 540

Asp Phe Tyr Glu Gly Met Glu Lys Leu His Val Ile Ser Tyr Asp Lys
545                 550                 555                 560

Met Lys Tyr Pro Leu Leu Pro Leu Ala Pro Arg Cys Ser Thr Asn Ile
            565                 570                 575

Arg Val Leu His Leu Thr Lys Cys Ser Leu Lys Met Phe Asp Cys Ser
            580                 585                 590

Cys Ile Gly Asn Leu Ser Asn Leu Glu Val Leu Ser Phe Ala Asn Ser
        595                 600                 605

Arg Ile Glu Trp Leu Pro Ser Thr Val Arg Asn Leu Lys Lys Leu Arg
    610                 615                 620

Leu Leu Asp Leu Arg Phe Cys Asp Gly Leu Arg Ile Glu Gln Gly Val
625                 630                 635                 640

Leu Lys Ser Leu Val Lys Leu Glu Glu Phe Tyr Ile Gly Asn Ala Ser
            645                 650                 655

Gly Phe Ile Asp Asp Asn Cys Asn Glu Met Ala Glu Arg Ser Asp Asn
            660                 665                 670

Leu Ser Ala Leu Glu Phe Ala Phe Phe Asn Asn Lys Ala Glu Val Lys
        675                 680                 685

Asn Met Ser Phe Glu Asn Leu Glu Arg Phe Lys Ile Ser Val Gly Arg
    690                 695                 700

Ser Phe Asp Gly Asn Ile Asn Met Ser Ser His Ser Tyr Glu Asn Met
705                 710                 715                 720

Leu Gln Leu Val Thr Asn Lys Gly Asp Val Leu Asp Ser Lys Leu Asn
            725                 730                 735

Gly Leu Phe Leu Lys Thr Lys Val Leu Phe Leu Ser Val His Gly Met
            740                 745                 750

Asn Asp Leu Glu Asp Val Glu Val Lys Ser Thr His Pro Thr Gln Ser
        755                 760                 765

Ser Ser Phe Cys Asn Leu Lys Val Leu Ile Ile Ser Lys Cys Val Glu
    770                 775                 780

Leu Arg Tyr Leu Phe Lys Leu Asn Leu Ala Asn Thr Leu Ser Arg Leu
785                 790                 795                 800

Glu His Leu Glu Val Cys Glu Cys Glu Asn Met Glu Glu Leu Ile His
            805                 810                 815

Thr Gly Ile Cys Gly Glu Glu Thr Ile Thr Phe Pro Lys Leu Lys Phe
            820                 825                 830

Leu Ser Leu Ser Gln Leu Pro Lys Leu Ser Ser Leu Cys His Asn Val
        835                 840                 845

Asn Ile Ile Gly Leu Pro His Leu Val Asp Leu Ile Leu Lys Gly Ile
    850                 855                 860

Pro Gly Phe Thr Val Ile Tyr Pro Gln Asn Lys Leu Arg Thr Ser Ser
865                 870                 875                 880

Leu Leu Lys Glu Val Val Ile Pro Lys Leu Glu Thr Leu Gln Ile
            885                 890                 895

Asp Asp Met Glu Asn Leu Glu Glu Ile Trp Pro Cys Glu Leu Ser Gly
            900                 905                 910

Gly Glu Lys Val Lys Leu Arg Glu Ile Lys Val Ser Ser Cys Asp Lys
        915                 920                 925

Leu Val Asn Leu Phe Pro Arg Asn Pro Met Ser Leu Leu His His Leu
```

-continued

```
        930              935              940
Glu Glu Leu Lys Val Lys Asn Cys Gly Ser Ile Glu Ser Leu Phe Asn
945              950              955              960

Ile Asp Leu Asp Cys Val Gly Ala Ile Gly Glu Glu Asp Asn Lys Ser
            965              970              975

Leu Leu Arg Ser Ile Asn Met Glu Asn Leu Gly Lys Leu Arg Glu Val
            980              985              990

Trp Arg Ile Lys Gly Ala Asp Asn Ser His Leu Ile Asn Gly Phe Gln
            995              1000             1005

Ala Val Glu Ser Ile Lys Ile Glu Lys Cys Lys Arg Phe Ser Asn Ile
        1010             1015             1020

Phe Thr Pro Ile Thr Ala Asn Phe Tyr Leu Val Ala Leu Leu Glu Ile
1025             1030             1035             1040

Gln Ile Glu Gly Cys Gly Gly Asn His Glu Ser Glu Glu Gln Ile Glu
                1045             1050             1055

Ile Leu Ser Glu Lys Glu Thr Leu Gln Glu Val Thr Asp Thr Asn Ile
            1060             1065             1070

Ser Asn Asp Val Val Leu Phe Pro Ser Cys Leu Met His Ser Phe His
        1075             1080             1085

Asn Leu His Lys Leu Lys Leu Glu Arg Val Lys Gly Val Glu Val Val
    1090             1095             1100

Phe Glu Ile Glu Ser Glu Ser Pro Thr Ser Arg Glu Leu Val Thr Thr
1105             1110             1115             1120

His His Asn Gln Gln His Pro Ile Ile Leu Pro Asn Leu Gln Glu Leu
                1125             1130             1135

Asp Leu Ser Phe Met Asp Asn Met Ser His Val Trp Lys Cys Ser Asn
            1140             1145             1150

Trp Asn Lys Phe Phe Thr Leu Pro Lys Gln Gln Ser Glu Ser Pro Phe
        1155             1160             1165

His Asn Leu Thr Thr Ile His Met Phe Ser Cys Arg Ser Ile Lys Tyr
    1170             1175             1180

Leu Phe Ser Pro Leu Met Ala Glu Leu Leu Ser Asn Leu Lys Asp Ile
1185             1190             1195             1200

Trp Ile Ser Gly Cys Asn Gly Ile Lys Glu Val Val Ser Lys Arg Asp
            1205             1210             1215

Asp Glu Asp Glu Glu Met Thr Thr Phe Thr Ser Thr His Thr Thr Thr
            1220             1225             1230

Ile Leu Phe Pro His Leu Asp Ser Leu Thr Leu Arg Leu Leu Glu Asn
            1235             1240             1245

Leu Lys Cys Ile Gly Gly Gly Ala Lys Asp Glu Gly Ser Asn Glu
    1250             1255             1260

Ile Ser Phe Asn Asn Thr Thr Ala Thr Ala Val Leu Asp Gln Phe
1265             1270             1275             1280

Glu Leu Ser Glu Ala Gly Gly Val Ser Trp Ser Leu Cys Gln Tyr Ala
            1285             1290             1295

Arg Glu Ile Glu Ile Ser Lys Cys Asn Val Leu Ser Ser Val Ile Pro
            1300             1305             1310

Cys Tyr Ala Ala Gly Gln Met Gln Lys Leu Gln Val Leu Arg Val Thr
        1315             1320             1325

Gly Cys Asp Gly Met Lys Glu Val Phe Glu Thr Gln Leu Gly Thr Ser
        1330             1335             1340

Ser Asn Lys Asn Arg Lys Gly Gly Gly Asp Glu Gly Asn Gly Gly Ile
1345             1350             1355             1360
```

-continued

```
Pro Arg Val Asn Asn Val Ile Met Leu Pro Asn Leu Lys Thr Leu
            1365                1370                1375
Lys Ile Tyr Met Cys Gly Gly Leu Glu His Ile Phe Thr Phe Ser Ala
            1380                1385                1390
Leu Glu Ser Leu Thr Gln Leu Gln Glu Leu Lys Ile Val Gly Cys Tyr
            1395                1400                1405
Gly Met Lys Val Ile Val Lys Lys Glu Glu Asp Glu Tyr Gly Glu Gln
    1410                1415                1420
Gln Thr Thr Thr Thr Thr Thr Thr Lys Gly Ala Ser Ser Ser Ser
1425                1430                1435                1440
Ser Ser Ser Ser Lys Lys Val Val Val Phe Pro Arg Leu Lys Ser Ile
            1445                1450                1455
Glu Leu Phe Asn Leu Pro Glu Leu Val Gly Phe Phe Leu Gly Met Asn
            1460                1465                1470
Glu Phe Arg Leu Pro Ser Leu Glu Glu Val Thr Ile Lys Tyr Cys Ser
            1475                1480                1485
Lys Met Met Val Phe Ala Ala Gly Gly Ser Thr Ala Pro Gln Leu Lys
            1490                1495                1500
Tyr Ile His Thr Arg Leu Gly Lys His Thr Leu Asp Gln Glu Ser Gly
1505                1510                1515                1520
Leu Asn Phe His Gln Thr Ser Phe Gln Ser Leu Tyr Gly Asp Thr Ser
            1525                1530                1535
Gly Pro Ala Thr Ser Glu Gly Thr Thr Trp Ser Phe His Asn Leu Ile
            1540                1545                1550
Glu Leu Asp Met Glu Leu Asn Tyr Asp Val Lys Lys Ile Ile Pro Ser
            1555                1560                1565
Ser Glu Leu Leu Gln Leu Gln Lys Leu Glu Lys Ile His Val Ser Ser
    1570                1575                1580
Cys Tyr Trp Val Glu Glu Val Phe Glu Thr Ala Leu Glu Ala Ala Gly
1585                1590                1595                1600
Arg Asn Gly Asn Ser Gly Ile Gly Phe Asp Glu Ser Ser Gln Thr Thr
            1605                1610                1615
Thr Thr Thr Thr Leu Phe Asn Leu Arg Asn Leu Arg Glu Met Lys Leu
            1620                1625                1630
His Phe Leu Arg Gly Leu Arg Tyr Ile Trp Lys Ser Asn Gln Trp Thr
            1635                1640                1645
Ala Phe Glu Phe Pro Asn Leu Thr Arg Val His Ile Ser Arg Cys Arg
            1650                1655                1660
Arg Leu Glu His Val Phe Thr Ser Ser Met Val Gly Ser Leu Leu Gln
1665                1670                1675                1680
Leu Gln Glu Leu Asp Ile Ser Trp Cys Asn His Met Glu Glu Val Ile
            1685                1690                1695
Val Lys Asp Ala Asp Val Ser Val Glu Glu Asp Lys Glu Arg Glu Ser
            1700                1705                1710
Asp Gly Lys Thr Asn Lys Glu Ile Leu Val Leu Pro Arg Leu Lys Ser
            1715                1720                1725
Leu Lys Leu Lys Cys Leu Pro Cys Leu Lys Gly Phe Ser Leu Gly Lys
            1730                1735                1740
Glu Asp Phe Ser Phe Pro Leu Leu Asp Thr Leu Glu Ile Tyr Lys Cys
1745                1750                1755                1760
Pro Ala Ile Thr Thr Phe Thr Lys Gly Asn Ser Ala Thr Pro Gln Leu
            1765                1770                1775
```

```
Lys Glu Ile Glu Thr Arg Phe Gly Ser Phe Tyr Ala Gly Glu Asp Ile
        1780                1785                1790

Asn Ser Ser Ile Ile Lys Arg Ser Asn Asn Arg Ser Ser Asn Lys Thr
    1795                1800                1805

Leu Ile Asn Val Lys Xaa Ile Leu Lys
    1810            1815
```

(2) INFORMATION FOR SEQ ID NO:126:

(i) SEQUENCE CHARACTERISTICS:
        (A) LENGTH: 1464 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1464
        (D) OTHER INFORMATION: /note= "RG2T"

(xi) SEQUENCE DESCRIPTION: SEQ ID NO:126:

```
GGAAGACGAC AATGGTGCAA CGGTTGAAGA AGGTTGTGAA AGATAAGAAG ATGTTCCATT      60

ATATTGTCGA GGTGGTTGTA GGGGCAAACA CTGACCCCAT TGCTATCCAG GATACTGTTG     120

CAGATTACCT CAGCATAGAA CTGAAAGGAA ATACGAGAGA TGCAAGGGCT TATAAGCTTC     180

GTGAATGCTT TAAGGCCCTC TCTGGTGGAG GTAAGATGAG GTTCCTAGTA ATTCTTGACG     240

ATGTATGGAG CCCTGTTGAT CTGGATGATA TCGGTTTAAG TTCTTTGCCA AATCAAGGTG     300

TTGACTTCAA GGTCTTGCTG ACATCACGCA ACAGTGATAT CTGCATGATG ATGGGAGCTA     360

GTTTAATTTT CAACCTCAAT ATGTTAACAG ACGAGGAAGC ACATAATTTT TTCCGTCGAT     420

ACGCAGAAAT TTCTTATGAT GCTGATCCCG AGCTTATTAA GATAGGAGAA GCTATTGTAG     480

AGAAATGTGG TGGTTTACCC ATTGCCATCA AAACTATGGC CGTTACTCTT AGAAATAAAC     540

GCAAAGATGC ATGGAAAGAT GCACTTTCTC GTTTAGAGCA CCGTGACACT CATAATGTTG     600

TGGCTGATGT TCTTAAATTG AGCTACAGCA ATATCCAAGA CGAGGAGACT CGGTCGATTT     660

TTTTGCTATG TGGTTTGTTT CCTGAAGACT TTGATATTCC TACCGAAGAC TTAGTGAGGT     720

ATGGATGGGG ATTGAAAATA TTTACCAGAG TGTATACTAT GAGACATGCA AGAAAAAGGT     780

TGGACACGTG CATTGAGCGG CTTATGCATG CCAACATGTT GATAAAAAGT GATAATGTTG     840

GATTTGTCAA GATGCATGAT CTGGTTCGTG CTTTTGTTTT GGGCATGTTA TCTGAAGTCG     900

AGCATGCATC AATTGTCAAC CATGGGGATA TGCCAGGGTG GTTTGAAACT GCAAATGATA     960

AGAACAGCTT GTGCAAAAGA ATTTCATTAA CATGCAAAGG TATGTCTGCG ATTCCTGAAG    1020

ACCTCACGTT TCCAAACCTC TCGATCCTGA AATTAATGGA TGGAGACGAG TCACTGAGGT    1080

TTCCTGAAGG CTTTTATGGA GAAATGGAAA ACCTTCAGGT TATATCATAT GATAACATGA    1140

AGCAGCCATT TCTTCCACAA TCACTTCAAT GCTCCAATGT TCGAGTGCTT CATCTCCATC    1200

ACTGCTCATT AATGTTTGAT TGCTCTTCTA TTGGAAATCT TTTGAATCTC GAGGTGCTCA    1260

GCATTGCTAA TTCTGCCATT AAATTGTTAC CCTCCACTAT TGGAGATCTG AAGAAGCTAA    1320

GGCTCCTGGA TTTGACAAAT TGTGTTGGTC TCTGTATAGC TAATGGCGTC TTTAGAAATT    1380

TGGTCAAACT TGAAGAGCTT TATATGAGAG TTGATGATCG AGATTCGTTT TTTGTGAAAG    1440

CTGATGACAG CAAGACCATT ACCT                                           1464
```

(2) INFORMATION FOR SEQ ID NO:127:

```
    (i) SEQUENCE CHARACTERISTICS:
        (A) LENGTH: 487 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..487
        (D) OTHER INFORMATION: /note= "RG2T deduced sequence"

(xi) SEQUENCE DESCRIPTION: SEQ ID NO:127:

Lys Thr Thr Met Val Gln Arg Leu Lys Lys Val Val Lys Asp Lys Lys
1               5                  10                  15

Met Phe His Tyr Ile Val Glu Val Val Gly Ala Asn Thr Asp Pro
            20                  25                  30

Ile Ala Ile Gln Asp Thr Val Ala Asp Tyr Leu Ser Ile Glu Leu Lys
        35                  40                  45

Gly Asn Thr Arg Asp Ala Arg Ala Tyr Lys Leu Arg Glu Cys Phe Lys
50                  55                  60

Ala Leu Ser Gly Gly Gly Lys Met Lys Phe Leu Val Ile Leu Asp Asp
65                  70                  75                  80

Val Trp Ser Pro Val Asp Leu Asp Asp Ile Gly Leu Ser Ser Leu Pro
                85                  90                  95

Asn Gln Gly Val Asp Phe Lys Val Leu Leu Thr Ser Arg Asn Ser Asp
            100                 105                 110

Ile Cys Met Met Met Gly Ala Ser Leu Ile Phe Asn Leu Asn Met Leu
        115                 120                 125

Thr Asp Glu Glu Ala His Asn Phe Phe Arg Arg Tyr Ala Glu Ile Ser
130                 135                 140

Tyr Asp Ala Asp Pro Glu Leu Ile Lys Ile Gly Glu Ala Ile Val Glu
145                 150                 155                 160

Lys Cys Gly Gly Leu Pro Ile Ala Ile Lys Thr Met Ala Val Thr Leu
                165                 170                 175

Arg Asn Lys Arg Lys Asp Ala Trp Lys Asp Ala Leu Ser Arg Leu Glu
            180                 185                 190

His Arg Asp Thr His Asn Val Val Ala Asp Val Leu Lys Leu Ser Tyr
        195                 200                 205

Ser Asn Ile Gln Asp Glu Glu Thr Arg Ser Ile Phe Leu Leu Cys Gly
210                 215                 220

Leu Phe Pro Glu Asp Phe Asp Ile Pro Thr Glu Asp Leu Val Arg Tyr
225                 230                 235                 240

Gly Trp Gly Leu Lys Ile Phe Thr Arg Val Tyr Thr Met Arg His Ala
                245                 250                 255

Arg Lys Arg Leu Asp Thr Cys Ile Glu Arg Leu Met His Ala Asn Met
            260                 265                 270

Leu Ile Lys Ser Asp Asn Val Gly Phe Val Lys Met His Asp Leu Val
        275                 280                 285

Arg Ala Phe Val Leu Gly Met Leu Ser Glu Val Glu His Ala Ser Ile
290                 295                 300

Val Asn His Gly Asp Met Pro Gly Trp Phe Glu Thr Ala Asn Asp Lys
305                 310                 315                 320

Asn Ser Leu Cys Lys Arg Ile Ser Leu Thr Cys Lys Gly Met Ser Ala
                325                 330                 335
```

```
Ile Pro Glu Asp Leu Thr Phe Pro Asn Leu Ser Ile Leu Lys Leu Met
            340                 345                 350

Asp Gly Asp Glu Ser Leu Arg Phe Pro Glu Gly Phe Tyr Gly Glu Met
            355                 360                 365

Glu Asn Leu Gln Val Ile Ser Tyr Asp Asn Met Lys Gln Pro Phe Leu
            370                 375                 380

Pro Gln Ser Leu Gln Cys Ser Asn Val Arg Val Leu His Leu His His
385                 390                 395                 400

Cys Ser Leu Met Phe Asp Cys Ser Ser Ile Gly Asn Leu Leu Asn Leu
                405                 410                 415

Glu Val Leu Ser Ile Ala Asn Ser Ala Ile Lys Leu Leu Pro Ser Thr
            420                 425                 430

Ile Gly Asp Leu Lys Lys Leu Arg Leu Leu Asp Leu Thr Asn Cys Val
            435                 440                 445

Gly Leu Cys Ile Ala Asn Gly Val Phe Arg Asn Leu Val Lys Leu Glu
            450                 455                 460

Glu Leu Tyr Met Arg Val Asp Asp Arg Asp Ser Phe Phe Val Lys Ala
465                 470                 475                 480

Asp Asp Ser Lys Thr Ile Thr
                485

(2) INFORMATION FOR SEQ ID NO:128:

(i) SEQUENCE CHARACTERISTICS:
        (A) LENGTH: 1038 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1038
        (D) OTHER INFORMATION: /note= "RG2U"

(xi) SEQUENCE DESCRIPTION: SEQ ID NO:128:

GCCTTGTGTG GGATGGGTGG AGTGGGAAAG ACCACTGTGA TGAAGAAGCT GAAGGAGGTT      60

GTGGTAGGAA AGAAACTGTT TAATCATTAT GTTGAGGCGG TTATAGGGGA AAAGACAGAC     120

CCCATTGCTA TTCAACAAGC TGTTGCCGAG TACCTTGGTA TAAGTCTAAC CGAAACCACT     180

AAACCAGCAA GAACTGATAA GCTCCGTACA TGGTTTGCAA ACAACTCAAA TGGAGGAAAG     240

AAGAAGTTCC TGGTAATACT AGACGATGTA TGGCAACCAG TTGATTTGGA AGATATTGGT     300

TTAAGTCGTT TTCCAAATCA AGATGTTGAC TTCAAGGTCT TGATTACATC ACGGGACCAA     360

TCAGTTTGCA CTGAGATGGG AGTTAAAGCT GATTTAGTTC TCAAGGTGAG TGTCCTGGAG     420

GAAGCGGAAG CACACAGTTT GTTCCTCCAA TTTTTAGAAC CTTCTGATGA TGTCGATCCT     480

GAGCTCAATA AAATCGGAGA AGAAATTGTA AAGAAGTGTT GCAGACTACC CATTGCTATC     540

AAAACCATGG CCTGAACTCT TAGAAGTAAA AGTAAGGATA CATGGAAGAA TGCCCTTTCT     600

CGTTTACAAC ACCATGACAT TAACACAATT GCGTCTACTG TTTTCCAAAC TAGCTATGAC     660

AATCTCGAAG ACGAGGTGAC TAAAGCTACT TTTTTGCTTT GTGGTTTATT TCCGGAGGAC     720

TTCAATATTC CTACCGAGGA CCTATTGAGG TATGGATGGG GATTGAAGTT ATTCAAGGAA     780

GTAGATACTA TACGAGAAGC AAGATCCAAG TTGAAAGCCT GCATTGAGCG GCTCATGCAT     840

ACCAATTTGT TGATCGAAGG TGATGATGTT AGGTACGTTA AGATGCATGA TCTGGTGCGT     900

GCTTTTGTTT TGGATATGTT TTCTAAAGCC GAGCATGCAT CTATTGTCAA CCATGGTAGT     960
```

AGTAAGCCAA GGTGGCCTGA AACTGAAAGT GATGTGAGCT CCTCTTGCAA AAGAATTTCA    1020

TTAACATGCA AGGGTNTG                                                 1038

(2) INFORMATION FOR SEQ ID NO:129:

(i) SEQUENCE CHARACTERISTICS:
        (A) LENGTH: 346 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..346
        (D) OTHER INFORMATION: /note= "RG2U deduced sequence"

(xi) SEQUENCE DESCRIPTION: SEQ ID NO:129:

```
Ala Leu Cys Gly Met Gly Gly Val Gly Lys Thr Thr Val Met Lys Lys
 1               5                  10                  15

Leu Lys Glu Val Val Gly Lys Lys Leu Phe Asn His Tyr Val Glu
             20                  25                  30

Ala Val Ile Gly Glu Lys Thr Asp Pro Ile Ala Ile Gln Gln Ala Val
             35                  40                  45

Ala Glu Tyr Leu Gly Ile Ser Leu Thr Glu Thr Thr Lys Pro Ala Arg
50                   55                  60

Thr Asp Lys Leu Arg Thr Trp Phe Ala Asn Asn Ser Asn Gly Gly Lys
65                   70                  75                  80

Lys Lys Phe Leu Val Ile Leu Asp Asp Val Trp Gln Pro Val Asp Leu
                 85                  90                  95

Glu Asp Ile Gly Leu Ser Arg Phe Pro Asn Gln Asp Val Asp Phe Lys
                100                 105                 110

Val Leu Ile Thr Ser Arg Asp Gln Ser Val Cys Thr Glu Met Gly Val
            115                 120                 125

Lys Ala Asp Leu Val Leu Lys Val Ser Val Leu Glu Glu Ala Glu Ala
130                 135                 140

His Ser Leu Phe Leu Gln Phe Leu Glu Pro Ser Asp Val Asp Pro
145                 150                 155                 160

Glu Leu Asn Lys Ile Gly Glu Ile Val Lys Lys Cys Cys Arg Leu
                165                 170                 175

Pro Ile Ala Ile Lys Thr Met Ala Xaa Thr Leu Arg Ser Lys Ser Lys
                180                 185                 190

Asp Thr Trp Lys Asn Ala Leu Ser Arg Leu Gln His His Asp Ile Asn
            195                 200                 205

Thr Ile Ala Ser Thr Val Phe Gln Thr Ser Tyr Asp Asn Leu Glu Asp
210                 215                 220

Glu Val Thr Lys Ala Thr Phe Leu Leu Cys Gly Leu Phe Pro Glu Asp
225                 230                 235                 240

Phe Asn Ile Pro Thr Glu Asp Leu Leu Arg Tyr Gly Trp Gly Leu Lys
                245                 250                 255

Leu Phe Lys Glu Val Asp Thr Ile Arg Glu Ala Arg Ser Lys Leu Lys
            260                 265                 270

Ala Cys Ile Glu Arg Leu Met His Thr Asn Leu Leu Ile Glu Gly Asp
            275                 280                 285

Asp Val Arg Tyr Val Lys Met His Asp Leu Val Arg Ala Phe Val Leu
            290                 295                 300
```

```
Asp Met Phe Ser Lys Ala Glu His Ala Ser Ile Val Asn His Gly Ser
305                 310                 315                 320

Ser Lys Pro Arg Trp Pro Glu Thr Glu Ser Asp Val Ser Ser Cys
                325                 330                 335

Lys Arg Ile Ser Leu Thr Cys Lys Gly Xaa
                340                 345
```

(2) INFORMATION FOR SEQ ID NO:130:

(i) SEQUENCE CHARACTERISTICS:
        (A) LENGTH: 1454 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1454
        (D) OTHER INFORMATION: /note= "RG2V"

(xi) SEQUENCE DESCRIPTION: SEQ ID NO:130:

```
CTGTGGAAGA CACGAATGAT SAAGAAGCTG AAGGAGGTCG TGGAACAAAA GAAAATGTTC        60

AATATTATTG TTCAAGTGGT CATAGGAGAG AAGACAAACC CTATTGCTAT TCAGCAAGCT       120

GTAGCAGATT ACCTCTCTAT TGAGCTGAAA GAAAACACTA AGAAGCAAG AGCTGATAAG        180

CTTCGTNAAT GGTTCGAGGA CGATGGAGGA AAGAATAAGT TCCTTGTAAT ACTTGATGAT       240

GTATGGCAGT TTGTCGATCT TGAAGATATT GGTTTAAGTC CTCTGCCAAA TAAAGGTGTC       300

AACTTCAAGG TCTTGTTGAC GTTAAGAGAT TCACATGTTT GCACTCTGAT GGGAGCTGAA       360

GCCAATTCAA TTCTCAATAT AAAAGTTTTA AAAGATGTTN AAGGACAAAG TTTGTTCCGC       420

CAGTTTGCTA AAAATGCAGG TGATGATGAC CTGGATCCTG CTTTCAATGG GATAGCAGAT       480

AGTATTGCAA GTAGATGTCA AGGTTTGCCC ATTGCCATCA AAACCATTGC CTTAAGTCTT       540

AAAGGTAGAA GCAAGCCTGC GTGGGACCAT GCGCTTTCTC GTTTGGAGAA CCATAAGATT       600

GGTAGTGAAG AAGTTGTGCG TGAAGTTTTT AAAATTAGCT ATGACAATCT CCAAGATGAG       660

GTTACTAAAT CTATTTTTWT ACTTTGTGCT TTATTTCCTG AAGATTTTGA TATTCCTATT       720

GAGGAGTTGG TGAGGTATGG GTGGGGCTTG AAATTATTTA TAGAAGCAAA AACTATAAGA       780

GAAGCAAGAA ACAGGCTCAA CACCTGCACT GAGCGGCTTA GGGAGACAAA TTTGTTATTT       840

GGAAGTGATG ACATTGGATG CGTCAAGATG CACGATGTGG TGCGTGATTT TGTTTGGTAT       900

ATATTCTCAG AAGTCCAGCA CGCTTCAATT GTCAACCATG GTAATGTGTC AGAGTGGCTA       960

GAGGAAAATC ATAGCATCTA CTCTTGTAAA AGAATTTCAT TAACATGCAA GGGTATGTCT      1020

GAGTTTCCCA AAGACCTCAA ATTTCCAAAC CTTTCAATTT TGAAACTTAT GCATGGAGAT      1080

AAGTCGNTGA GCTTTCCTGA AGACTTTTAT GGAAAGATGG AAAAGGTTCA GGTAATATCA      1140

TATGATAAAT TGATGTATCC ATTGCTTCCC TCATCACTTG AATGCTCCAC TAACGTTCGA      1200

GTGCTTCATC TCCATTATTG TTCATTAAGG ATGTTTGATT GCTCTTCAAT TGGTAATCTT      1260

CTCAACATGG AAGTGCTCAG CTTTGCTAAT TCTAACATTG AATGGTTACC ATCTACAATT      1320

GGAAATTTGA AGAAGCTAAG GCTACTAGAT TTGACAAATT GTAAAGGTCT TCGTATAGAT      1380

AATGGTGTCT TAAAAAATTT GGTCAAACTT GAAGAGCTTT ATATGGGTGT TAATGTCCGT      1440

ATGGACCAGG CCGT                                                       1454
```

(2) INFORMATION FOR SEQ ID NO:131:

(i) SEQUENCE CHARACTERISTICS:
      (A) LENGTH: 485 amino acids
      (B) TYPE: amino acid
      (C) STRANDEDNESS:
      (D) TOPOLOGY: linear (ii) MOLECULE TYPE: protein (ix) FEATURE:
      (A) NAME/KEY: -
      (B) LOCATION: 1..485
      (D) OTHER INFORMATION: /note= "RG2V deduced sequence"

(xi) SEQUENCE DESCRIPTION: SEQ ID NO:131:

```
Leu Trp Lys Thr Arg Met Xaa Lys Lys Leu Lys Glu Val Val Glu Gln
1               5                   10                  15

Lys Lys Met Phe Asn Ile Ile Val Gln Val Val Ile Gly Glu Lys Thr
            20                  25                  30

Asn Pro Ile Ala Ile Gln Gln Ala Val Ala Asp Tyr Leu Ser Ile Glu
        35                  40                  45

Leu Lys Glu Asn Thr Lys Glu Ala Arg Ala Asp Lys Leu Arg Xaa Trp
50                  55                  60

Phe Glu Asp Asp Gly Gly Lys Asn Lys Phe Leu Val Ile Leu Asp Asp
65                  70                  75                  80

Val Trp Gln Phe Val Asp Leu Glu Asp Ile Gly Leu Ser Pro Leu Pro
                85                  90                  95

Asn Lys Gly Val Asn Phe Lys Val Leu Leu Thr Leu Arg Asp Ser His
            100                 105                 110

Val Cys Thr Leu Met Gly Ala Glu Ala Asn Ser Ile Leu Asn Ile Lys
        115                 120                 125

Val Leu Lys Asp Val Xaa Gly Gln Ser Leu Phe Arg Gln Phe Ala Lys
130                 135                 140

Asn Ala Gly Asp Asp Asp Leu Asp Pro Ala Phe Asn Gly Ile Ala Asp
145                 150                 155                 160

Ser Ile Ala Ser Arg Cys Gln Gly Leu Pro Ile Ala Ile Lys Thr Ile
                165                 170                 175

Ala Leu Ser Leu Lys Gly Arg Ser Lys Pro Ala Trp Asp His Ala Leu
            180                 185                 190

Ser Arg Leu Glu Asn His Lys Ile Gly Ser Glu Glu Val Val Arg Glu
        195                 200                 205

Val Phe Lys Ile Ser Tyr Asp Asn Leu Gln Asp Glu Val Thr Lys Ser
210                 215                 220

Ile Phe Xaa Leu Cys Ala Leu Phe Pro Glu Asp Phe Asp Ile Pro Ile
225                 230                 235                 240

Glu Glu Leu Val Arg Tyr Gly Trp Gly Leu Lys Leu Phe Ile Glu Ala
                245                 250                 255

Lys Thr Ile Arg Glu Ala Arg Asn Arg Leu Asn Thr Cys Thr Glu Arg
            260                 265                 270

Leu Arg Glu Thr Asn Leu Leu Phe Gly Ser Asp Asp Ile Gly Cys Val
        275                 280                 285

Lys Met His Asp Val Val Arg Asp Phe Val Trp Tyr Ile Phe Ser Glu
290                 295                 300

Val Gln His Ala Ser Ile Val Asn His Gly Asn Val Ser Glu Trp Leu
305                 310                 315                 320

Glu Glu Asn His Ser Ile Tyr Ser Cys Lys Arg Ile Ser Leu Thr Cys
                325                 330                 335
```

```
Lys Gly Met Ser Glu Phe Pro Lys Asp Leu Lys Phe Pro Asn Leu Ser
            340                 345                 350

Ile Leu Lys Leu Met His Gly Asp Lys Ser Xaa Ser Phe Pro Glu Asp
        355                 360                 365

Phe Tyr Gly Lys Met Glu Lys Val Gln Val Ile Ser Tyr Asp Lys Leu
    370                 375                 380

Met Tyr Pro Leu Leu Pro Ser Ser Leu Glu Cys Ser Thr Asn Val Arg
385                 390                 395                 400

Val Leu His Leu His Tyr Cys Ser Leu Arg Met Phe Asp Cys Ser Ser
                405                 410                 415

Ile Gly Asn Leu Leu Asn Met Glu Val Leu Ser Phe Ala Asn Ser Asn
            420                 425                 430

Ile Glu Trp Leu Pro Ser Thr Ile Gly Asn Leu Lys Leu Arg Leu
        435                 440                 445

Leu Asp Leu Thr Asn Cys Lys Gly Leu Arg Ile Asp Asn Gly Val Leu
    450                 455                 460

Lys Asn Leu Val Lys Leu Glu Glu Leu Tyr Met Gly Val Asn Val Arg
465                 470                 475                 480

Met Asp Gln Ala Val
            485

(2) INFORMATION FOR SEQ ID NO:132:

(i) SEQUENCE CHARACTERISTICS:
        (A) LENGTH: 1096 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1096
        (D) OTHER INFORMATION: /note= "RG2W"

(xi) SEQUENCE DESCRIPTION: SEQ ID NO:132:

TTGGGAAAGA GACAATGATG AAGAATTGAA AGAGGTTGTG GTTGAAAAGA AAATGTTTAA     60

TCATTATGTG GAGGCGGTTA TAGGGGAGAA GACGGACCCC ATTGCTATTC AGCAAGCCGT    120

TGCAGAGTAC CTTGGTATAA TTCTAACAGA AACCACTAAG GCAGCAAGAA CCGATAAGCT    180

ACGTGCATGG CTTTCTGACA ATTCAGATGG AGGAAGAAAG AAGTTCCTAG TAATACTAGA    240

CGATGTATGG CATCCGGTTG ATATGGAAGA TATTGGTTTA AGTCGTTTCC CAAATCAAGG    300

TGTCGACTTC AAGGTCTTGA TTACATCACG GGACCAAGCT GTTTGCACTG AGATGGGAGT    360

TAAAGCTGAT TCAGTTATCA AGGTGAGTGT CCTAGAGGAA GCTGAAGCAC AAAGCTTATT    420

CTGCCAACTT TGGGAACCTT CTGATGATGT CGATCCTGAG CTCCATCAGA TTGGAGAAGA    480

AATTGTAAGG AAGTGTTGTG GTTTACCCAT TGCAATAAAA ACCATGGCCT GCACTCTTAG    540

AAGTAAAAGC AAGGATACAT GGAAGAATGC ACTTTCTCGT TTACAACACC ATGACATTAA    600

CACAGTCGCG CCTACTGTTT TTCAAACCAG CTATGACAAT CTCCAAGATG AGGTGACTGG    660

AGATACTTTT TTGCTATGTG GTTTGTTTCC GGAGGACTTC GATATTCCTA CTGAAGACTT    720

ATTGAAGTAT GGATGGGGCT TAAAATTATT CAAGGGAGTG GATTCTGTAA GAGAAGCAAG    780

ATACCAGTTG AACGCCTGCA TTGAGCGGCT CGTGCATACC AATTTGTTGA TTGAAAGTGA    840

TGTTGTTGGG TGCGTCAAGT TGCACGATCT GGTGCGTGCT TTTATTTTGG ATATGTTTTG    900
```

```
TAAAGCGGAG CATGCTTCGA TTGTCAACCA TGGTAGTAGT AAGCCTGGGT GGCCTGAAAC    960

TGAAAATGAT GTGATCAGGA CCTCCTGCAA AAGAATCTCA TTAACATGCA AGGGTATGAT   1020

TGAGTTTTCT AGTGACCTCA AGTTTCCAAA TGTCTTGATT TTAAAACTTA TGCATGGAGA   1080

TAAGTCGCTA AGGTTT                                                   1096
```

(2) INFORMATION FOR SEQ ID NO:133:

(i) SEQUENCE CHARACTERISTICS:
        (A) LENGTH: 365 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..365
        (D) OTHER INFORMATION: /note= "RG2W deduced sequence"

(xi) SEQUENCE DESCRIPTION: SEQ ID NO:133:

```
Trp Glu Arg Asp Asn Asp Glu Glu Leu Lys Glu Val Val Glu Lys
 1               5                  10                  15

Lys Met Phe Asn His Tyr Val Glu Ala Val Ile Gly Glu Lys Thr Asp
                20                  25                  30

Pro Ile Ala Ile Gln Gln Ala Val Ala Glu Tyr Leu Gly Ile Ile Leu
                35                  40                  45

Thr Glu Thr Thr Lys Ala Ala Arg Thr Asp Lys Leu Arg Ala Trp Leu
        50                  55                  60

Ser Asp Asn Ser Asp Gly Gly Arg Lys Lys Phe Leu Val Ile Leu Asp
65                  70                  75                  80

Asp Val Trp His Pro Val Asp Met Glu Asp Ile Gly Leu Ser Arg Phe
                85                  90                  95

Pro Asn Gln Gly Val Asp Phe Lys Val Leu Ile Thr Ser Arg Asp Gln
                100                 105                 110

Ala Val Cys Thr Glu Met Gly Val Lys Ala Asp Ser Val Ile Lys Val
                115                 120                 125

Ser Val Leu Glu Glu Ala Glu Ala Gln Ser Leu Phe Cys Gln Leu Trp
130                 135                 140

Glu Pro Ser Asp Asp Val Asp Pro Glu Leu His Gln Ile Gly Glu Glu
145                 150                 155                 160

Ile Val Arg Lys Cys Cys Gly Leu Pro Ile Ala Ile Lys Thr Met Ala
                165                 170                 175

Cys Thr Leu Arg Ser Lys Ser Lys Asp Thr Trp Lys Asn Ala Leu Ser
                180                 185                 190

Arg Leu Gln His His Asp Ile Asn Thr Val Ala Pro Thr Val Phe Gln
                195                 200                 205

Thr Ser Tyr Asp Asn Leu Gln Asp Glu Val Thr Gly Asp Thr Phe Leu
        210                 215                 220

Leu Cys Gly Leu Phe Pro Glu Asp Phe Asp Ile Pro Thr Glu Asp Leu
225                 230                 235                 240

Leu Lys Tyr Gly Trp Gly Leu Lys Leu Phe Lys Gly Val Asp Ser Val
                245                 250                 255

Arg Glu Ala Arg Tyr Gln Leu Asn Ala Cys Ile Glu Arg Leu Val His
                260                 265                 270

Thr Asn Leu Leu Ile Glu Ser Asp Val Val Gly Cys Val Lys Leu His
        275                 280                 285
```

```
Asp Leu Val Arg Ala Phe Ile Leu Asp Met Phe Cys Lys Ala Glu His
    290                 295                 300

Ala Ser Ile Val Asn His Gly Ser Ser Lys Pro Gly Trp Pro Glu Thr
305                 310                 315                 320

Glu Asn Asp Val Ile Arg Thr Ser Cys Lys Arg Ile Ser Leu Thr Cys
                325                 330                 335

Lys Gly Met Ile Glu Phe Ser Ser Asp Leu Lys Phe Pro Asn Val Leu
                340                 345                 350

Ile Leu Lys Leu Met His Gly Asp Lys Ser Leu Arg Phe
            355                 360                 365
```

(2) INFORMATION FOR SEQ ID NO:134:

(i) SEQUENCE CHARACTERISTICS:
        (A) LENGTH: 503 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..503
        (D) OTHER INFORMATION: /note= "RG5"

(xi) SEQUENCE DESCRIPTION: SEQ ID NO:134:

```
GGGGGGGTGG GGAAGNCGAC TCTAGCCCAG AAGNTCTATA ATGACCATAA AATAAAAGGA      60

AGCTTTAGTA ACAAGCATG GATCTGTGTT TCTCAACAAT ATTCTGATAT TTCAGTTTTG     120

AAAGAAGTCC TTCGGAACAT CGGTGTTGAT TATAAGCATG ATGAAACTGT TGGAGAACTT    180

AGCAGAAGGC TTGCAATAGC TGTCGAAAAT GCAAGTTTCT TCTTGTGTT GGATGATATT     240

TGGCAACATG AGGTGTGGAC TAATTTACTC AGAGCCCCAT TAAACACTGC AGCTACAGGA    300

ATAATTCTAG TAACAACTCG TAATGATACA GTTGCACGAG CAATTGGGGT GGAAGATATT    360

CATCGAGTAG AATTGATGTC AGATGAAGTA GGATGGAAAT TGCTTTTGAA GAGTATGAAC    420

ATTAGCAAAG AAAGTGAAGT AGAAAACCTA CGAGTTTTAG GGGTTGACAT TGTTCGTTTG    480

TGTGGTGGCC TCCCCCTAGC CTT                                            503
```

(2) INFORMATION FOR SEQ ID NO:135:

(i) SEQUENCE CHARACTERISTICS:
        (A) LENGTH: 168 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..168
        (D) OTHER INFORMATION: /note= "RG5 deduced sequence"

(xi) SEQUENCE DESCRIPTION: SEQ ID NO:135:

```
Gly Gly Val Gly Lys Thr Thr Leu Ala Gln Lys Xaa Tyr Asn Asp His
1               5                   10                  15

Lys Ile Lys Gly Ser Phe Ser Lys Gln Ala Trp Ile Cys Val Ser Gln
            20                  25                  30

Gln Tyr Ser Asp Ile Ser Val Leu Lys Glu Val Leu Arg Asn Ile Gly
        35                  40                  45
```

```
Val Asp Tyr Lys His Asp Glu Thr Val Gly Glu Leu Ser Arg Arg Leu
 50                  55                  60

Ala Ile Ala Val Glu Asn Ala Ser Phe Phe Leu Val Leu Asp Asp Ile
 65                  70                  75                  80

Trp Gln His Glu Val Trp Thr Asn Leu Leu Arg Ala Pro Leu Asn Thr
                 85                  90                  95

Ala Ala Thr Gly Ile Ile Leu Val Thr Thr Arg Asn Asp Thr Val Ala
                100                 105                 110

Arg Ala Ile Gly Val Glu Asp Ile His Arg Val Glu Leu Met Ser Asp
                115                 120                 125

Glu Val Gly Trp Lys Leu Leu Leu Lys Ser Met Asn Ile Ser Lys Glu
130                 135                 140

Ser Glu Val Glu Asn Leu Arg Val Leu Gly Val Asp Ile Val Arg Leu
145                 150                 155                 160

Cys Gly Gly Leu Pro Leu Ala Leu
                165
```

(2) INFORMATION FOR SEQ ID NO:136:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..485
        (D) OTHER INFORMATION: /note= "RG7"

(xi) SEQUENCE DESCRIPTION: SEQ ID NO:136:

```
GGTGGGGTTG GGAAGACAAC GGGCACAAGG AGGCGACTGC CAATACTTCC GACTTTTATT      60

CATAGAGATG ACGAGTCTTA TTTTCCTACT ACTATAGGGA GGATATTTGG TTGCGCGAGA     120

CGATTCATTG CGCGAAGGGA TTCTATCCTT CTTTTTTTCC GCGAAGACTT CGTTCCGGAG     180

GACGGGCTAT ATTCCCTTTA ATATTAGTCT AGCCCAGTCT AGGCCAACCA TATGGCGATG     240

CGGTAGACCT CCCAGAGATA GATACTTGAT CTTAGAGGAT TCACACGTTC AATGGTGGAA     300

ACTTAAGGAA CCGGCTAAGA GTGACTAAAC GGAAAAACCC TATTCATTCC ATAGCCTCAT     360

CCGGTCGAGG CATTAAACAA TCCATCCCAA TCCTCTTTCC TTTGGTCTAC TCTAATGATG     420

TGCCCGTTCG TTGGTGGAAT ATCTCTTTAT ACCGACGATT TATATGGGGA TTGCCACTAG     480

CGTTG                                                                485
```

(2) INFORMATION FOR SEQ ID NO:137:

(i) SEQUENCE CHARACTERISTICS:
        (A) LENGTH: 544 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..544
        (D) OTHER INFORMATION: /note= "RLG1b - Diana"

(xi) SEQUENCE DESCRIPTION: SEQ ID NO:137:

```
TACTACTACT AGAATTCGGT GTTGGTAAGA CGACTCTAGC TAGACTTTTG TATGAGGAAA      60
```

```
TGCAAGGGAA GGATCACTTC GAACTTAAGG CGTGGGTATG TGTTTCTGAT GAGTTTGATA      120

TCTTCAATAT AAGCAAAATT ATCTTACAAT CGATAGGTGG TGGAAACCAA GAATTTACGG      180

ACTTAAACCT GCTTCGAGTA GCTTTAAAAG AGAAGATCTC AAAGAAAAGA TTTCTTCTTG      240

TTCTTGATGA TGTTTGGAGT GAAAGCTATA CCGATTGGGA AATTNTAGAA CGCCCATTTC      300

TTGCAGGGGC ACCTGGAAGT AAGATTATTA TCACCACCCG GAAGCTGTCA TTGTTAAACA      360

AACTCGGTTA CAATCAACCT TACAACCTTT CGGTTTTGTC ACATGAGAAT GCTTTGTCTT      420

TATTCTGTCA GCATGCATTG GGTGAAGATA ACTTCAATTC ACATCCAACA CTTAAACCAC      480

ATGGCGNAGG TATTGTTGAA AAATGTGATG GATTGCCATT GGCATTGTCG ACATGATGAT      540

GATG                                                                  544

(2) INFORMATION FOR SEQ ID NO:138:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..273
        (D) OTHER INFORMATION: /note= "AC15-2 consensus positions
            301-600"

(xi) SEQUENCE DESCRIPTION: SEQ ID NO:138:

AAATTATAAG AGAGAATTGT TAATGGACAT GGAATCATAA ATCATTAACA CAGTTCAGTA       60

CACAAGTTGC TAATTACATT TCTTGCTGTG CAGATTGAAA TTCTATCAGA GAAAGAGACA      120

TTACAAGAAG CCACTGGCAG TATTTCTAAT GTTGTATTCC CATCCTGTCT CATGCACTCT      180

TTTCATAACC TCCATAAACT TAAATTGAAG AGATTTGAAG GAGTGGAGGT GGTGTTTGAG      240

ATAGAGAGTG AGAGTCCAAC AAGTAGAGAA TTG                                  273

(2) INFORMATION FOR SEQ ID NO:139:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:139:

CUACUACUAC UA                                                          12

(2) INFORMATION FOR SEQ ID NO:140:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:140:

CAUCAUCAUC AU                                                          12
```